US007524852B2

(12) United States Patent
Arai et al.

(10) Patent No.: US 7,524,852 B2

(45) Date of Patent: Apr. 28, 2009

(54) BICYCLIC PYRIMIDINE DERIVATIVES

(75) Inventors: Hitoshi Arai, Susono (JP); Tsutomu Matsumura, Sakai (JP); Hiroshi Ishida, Sunto-gun (JP); Yosuke Yamaura, Ichikawa (JP); Seiji Aratake, Sunto-gun (JP); Etsuo Ohshima, Nagareyama (JP); Koji Yanagawa, Sunto-gun (JP); Motoki Miyama, Sunto-gun (JP); Koji Suzuki, Mishima (JP); Ari Kawabe, Sunto-gun (JP); Satoshi Nakanishi, Yokohama (JP); Katsuya Kobayashi, Sunto-gun (JP); Takashi Sato, Sunto-gun (JP); Ichiro Miki, Sunto-gun (JP); Kimihisa Ueno, Mishima (JP); Shinya Fujii, Sanuki (JP); Miho Iwase, Sunto-gun (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 468 days.

(21) Appl. No.: 10/516,750

(22) PCT Filed: Jun. 6, 2003

(86) PCT No.: PCT/JP03/07200

§ 371 (c)(1),
(2), (4) Date: Mar. 31, 2005

(87) PCT Pub. No.: WO03/104230

PCT Pub. Date: Dec. 18, 2003

(65) Prior Publication Data

US 2007/0037834 A1 Feb. 15, 2007

(30) Foreign Application Priority Data

Jun. 7, 2002 (JP) ............................ 2002-166504

(51) Int. Cl.
*C07D 487/04* (2006.01)
*A61K 31/519* (2006.01)
*A61P 29/00* (2006.01)

(52) U.S. Cl. .................. 514/264.11; 544/279; 544/117; 544/61; 514/234.2; 514/228.5

(58) Field of Classification Search ................. 544/279; 514/264.11
See application file for complete search history.

(56) References Cited

U.S. PATENT DOCUMENTS

| | | | | |
|---|---|---|---|---|
| 3,248,395 | A * | 4/1966 | Ohnacker .................... | 544/80 |
| 2003/0018022 | A1 | 1/2003 | Collins et al. .................. | 417/2 |
| 2003/0173524 | A1 | 9/2003 | Syka .......................... | 250/396 |

FOREIGN PATENT DOCUMENTS

| | | |
|---|---|---|
| WO | WO 01/29000 | 4/2001 |
| WO | WO 01/32632 | 5/2001 |
| WO | WO 01/44246 | 6/2001 |
| WO | WO 02/22601 | 3/2002 |
| WO | WO 02/22602 | 3/2002 |
| WO | WO 02/22604 | 3/2002 |
| WO | WO 02/22606 | 3/2002 |
| WO | WO 02/22607 | 3/2002 |
| WO | WO 02/30358 | 4/2002 |
| WO | WO 02/50065 | 6/2002 |
| WO | WO 02/062789 | 8/2002 |
| WO | WO 02/087513 | 11/2002 |

OTHER PUBLICATIONS

Wikipedia, definition of derivative, http://en.wikipedia.org/wiki/Derivative_%28chemistry%29, Nov. 2006.*

* cited by examiner

*Primary Examiner*—Mark L Berch
*Assistant Examiner*—Cecilia M Jaisle
(74) *Attorney, Agent, or Firm*—Fitzpatrick, Cella, Harper & Scinto

(57) ABSTRACT

(I)

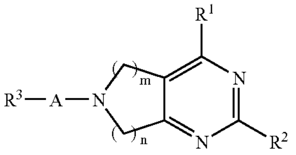

(II)

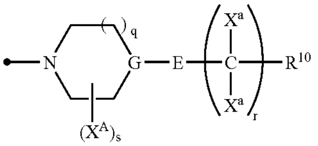

(IV)

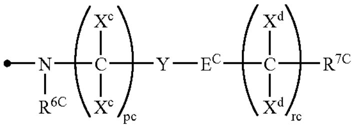

[wherein m and n may be the same or different and each represents an integer of 1 to 3 wherein m+n is 4 or less; $R^1$ represents —$NR^4R^5$ (wherein $R^4$ and $R^5$ may be the same or different and each represents a hydrogen atom, substituted or unsubstituted lower alkyl, substituted or unsubstituted aralkyl or the like); $R^2$ represents the above Formula (II), Formula (IV) or the like; A represents a single bond, —C(═O)—, —$SO_2$—, —OC(═O)— or the like; and $R^3$ represents substituted or unsubstituted lower alkyl, substituted or unsubstituted cycloalkyl, substituted or unsubstituted aralkyl or the like]

Bicyclic pyrimidine derivatives represented by the above Formula (I), or quaternary ammonium salts thereof, or pharmaceutically acceptable salts thereof, or the like, are provided. These have anti-inflammatory activities or modulation activities on the functions of TARC and/or MDC and are useful for treating and/or preventing a disease which is related to T cells, such as an allergic disease, an autoimmune disease or transplant rejection.

39 Claims, No Drawings

BICYCLIC PYRIMIDINE DERIVATIVES

TECHNICAL FIELD

The present invention relates to bicyclic pyrimidine derivatives or pharmaceutically acceptable salts thereof which have anti-inflammatory activities such as cellular infiltration inhibitory activities, and/or regulatory activities on the functions of thymus and activation-regulated chemokine [TARC; CC chemokine ligand 17 (CCL17)] and/or macrophage-derived chemokine [MDC; CC chemokine ligand 22 (CCL22)] and are useful for, for example, treating and/or preventing various diseases which are related to T cells, such as allergic diseases and autoimmune diseases.

BACKGROUND ART

Bicyclic compounds containing a pyrimidine skeleton in the structure thereof are disclosed as an antipsychotic agent in WO97/47601; as a metabotropic glutamate receptor 1 ($mGluR^1$) antagonist in WO2001/32632; as a glycogen synthase kinase 3 (GSK3) inhibitor in WO2001/44246; as a protein kinase inhibitor in WO2002/22601, WO2002/22602, WO2002/22604, WO2002/22606, WO2002/22607, WO2002/50065 and WO2002/62789; as a modulator of CC chemokine receptor 4 (CCR4) function in WO2002/30358 and US Published Patent Application No. 2003/0173524; and as a phosphodiesterase 7 (PDE7) inhibitor in WO2002/87513, respectively.

TARC was found as a T cell chemotactic factor [Journal of Biological Chemistry, vol. 271, p. 21514 (1996)], and MDC was found as a monocyte chemotactic factor [Journal of Experimental Medicine, vol. 185, p. 1595 (1997)]. Particularly, TARC is assumed to be involved in allergic diseases, since it is formed from a monocyte stimulated by Th2 cytokine [Journal of Biological Chemistry, vol. 271, p. 21514 (1996)]. Further analyses have shown that TARC and MDC are CCR4 ligands [Journal of Biological Chemistry, vol. 272, p. 15036 (1997); and Journal of Biological Chemistry, vol. 273, p. 1764 (1998)].

CCR4 has been cloned as a receptor expressed in T cells and thymocytes [Biochemical and Biophysical Research Communications, vol. 218, p. 337 (1996)], and further investigation shave reported that CCR4 is mainly expressed in "Th2" T cells [Journal of Experimental Medicine, vol. 187, p. 875 (1998); and Journal of Immunology, vol. 161, p. 5027 (1998)].

DISCLOSURE OF INVENTION

An object of the present invention is to provide bicyclic pyrimidine derivatives, or quaternary ammonium salts thereof, or pharmaceutically acceptable salts thereof, which have anti-inflammatory activities such as cellular infiltration inhibitory activities, modulating activities on TARC and/or MDC functions, such as inhibitory activities against binding of TARC and/or MDC to T cells, and are useful for treating and/or preventing, for example, a disease which is related to T cells, such as an allergic disease, an autoimmune disease or transplant rejection (graft rejection), as well as preventing cancer metastasis. Examples of such diseases are asthma, allergic rhinitis, chronic rhinitis, eosinophilic sinusitis, rhinitis with eosinophilia, pollinosis, conjunctivitis, atopic dermatitis, contact dermatitis, urticaria, psoriasis, cutaneous candidiasis, mycotic stomatitis (oral candidiasis), rheumatoid arthritis, various connective tissue diseases, systemic lupus erythematosus, Sjögren syndrome, cellular rejection in organ transplantation, cancer or carcinoma, malignant lymphoma, leukemia, adult T cell leukemia (ATL), cutaneous T cell lymphoma, interstitial cystitis, endometriosis, insulin-dependent diabetes mellitus (IDDM), Churg-Strauss syndrome, mycosis fungoides, pain, neuralgia and cutaneous itching.

The present invention relates to the following (1) to (43):

(1) A bicyclic pyrimidine derivative represented by following Formula (I):

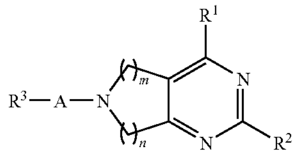

(I)

(wherein m and n may be the same or different, and each represents an integer of 1 to 3 wherein m+n is 4 or less;

$R^1$ represents
- $-NR^4R^5$ (wherein
  - $R^4$ and $R^5$ may be the same or different and each represents a hydrogen atom, substituted or unsubstituted lower alkyl, substituted or unsubstituted cycloalkyl, substituted or unsubstituted lower alkenyl, substituted or unsubstituted lower alkynyl, substituted or unsubstituted aralkyl, substituted or unsubstituted arylcarbonyl, a substituted or unsubstituted heteroaromatic group, a substituted or unsubstituted heteroalicyclic group, substituted or unsubstituted heteroaromatic-substituted alkyl or substituted or unsubstituted heteroalicyclic-substituted alkyl, or $R^4$ and $R^5$ are combined together with the adjacent nitrogen atom to form a substituted or unsubstituted heteroalicyclic group, provided that $R^4$ and $R^5$ are not simultaneously hydrogen atoms, and that when one of $R^4$ and $R^5$ is a hydrogen atom, the other of $R^4$ and $R^5$ is neither a substituted or unsubstituted pyrazol-3-yl nor a substituted or unsubstituted 1,2,4-triazol-3-yl);

$R^2$ represents
- (i) $-B-(CX_2)_p-R^7$ [wherein
  - B represents —O—, —CH═CH—, —C≡C— or phenylene;
  - p represents an integer of 1 to 4;
  - Xs may be the same or different respectively, and each represents a hydrogen atom, substituted or unsubstituted lower alkyl or halogen; and
  - $R^7$ represents
    - $-NR^8R^9$ (wherein
      - $R^8$ and $R^9$ may be the same or different and each represents a hydrogen atom, substituted or unsubstituted lower alkyl, substituted or unsubstituted cycloalkyl, substituted or unsubstituted lower alkenyl, substituted or unsubstituted lower alkynyl, substituted or unsubstituted aralkyl, substituted or unsubstituted aryl, a substituted or unsubstituted heteroaromatic group, a substituted or unsubstituted heteroalicyclic group, substituted or unsubstituted heteroaromatic-substituted alkyl or substituted or unsubstituted heteroalicyclic-substituted alkyl),
    - a substituted or unsubstituted heteroaromatic group or
    - a substituted or unsubstituted heteroalicyclic group];

(ii) Formula (II):

(II)

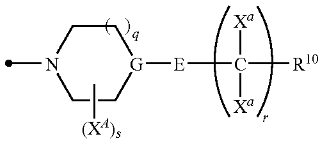

[wherein r represents an integer of 0 to 4;

s represents a number ranging from 0 to a substitutable number;

G represents a nitrogen atom, CH, C(OH), $C(CO_2H)$ or C(CN);

q represents an integer of 1 or 2 when G is a nitrogen atom, and q represents an integer of 0 to 2 when G is CH, C(OH), $C(CO_2H)$ or C(CN);

E represents a single bond, —C(═O)—, —O—, —CH(OH)—, $—CH_2CH(OH)—$, —C(═O)O—, —C(═O)$NR^6$— (wherein $R^6$ represents a hydrogen atom, substituted or unsubstituted lower alkyl or substituted or unsubstituted cycloalkyl) or

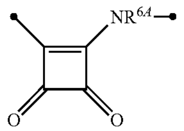

(wherein $R^{6A}$ has the same meaning as $R^6$ defined above), and E is bonded to G at the left side in each group;

$X^A$ represents substituted or unsubstituted lower alkyl or halogen, or two $X^A$s on the same carbon atom are combined together to form oxo, wherein respective $X^A$s may be the same or different when s is 2 or more;

$X^a$ has the same meaning as X defined above, where respective $X^a$s may be the same or different when r is 1 or more; and $R^{10}$ represents $—NR^{8A}R^{9A}$ (wherein $R^{8A}$ and $R^{9A}$ may be the same or different and each represents a hydrogen atom, substituted or unsubstituted lower alkyl, substituted or unsubstituted cycloalkyl, substituted or unsubstituted lower alkenyl, substituted or unsubstituted lower alkynyl, substituted or unsubstituted aralkyl, substituted or unsubstituted aryl, a substituted or unsubstituted heteroaromatic group, a substituted or unsubstituted heteroalicyclic group, substituted or unsubstituted heteroaromatic-substituted alkyl, substituted or unsubstituted heteroalicyclic-substituted alkyl, imino-(lower alkyl) or substituted or unsubstituted amidino), a hydrogen atom, substituted or unsubstituted lower alkyl, substituted or unsubstituted lower alkoxy, substituted or unsubstituted cycloalkyl, substituted or unsubstituted lower alkenyl, substituted or unsubstituted lower alkynyl, substituted or unsubstituted aryl, substituted or unsubstituted aralkyl, a substituted or unsubstituted heteroaromatic group, a substituted or unsubstituted heteroalicyclic group, substituted or unsubstituted heteroaromatic-substituted alkyl or substituted or unsubstituted heteroalicyclic-substituted alkyl];

(iii) Formula (III):

(III)

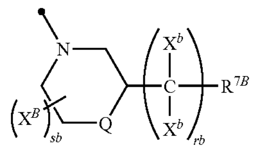

[wherein sb, rb, $X^B$, $X^b$ and $R^{7B}$ have the same meanings as s, r, $X^A$, $X^a$ and $R^7$ defined above, respectively; and Q represents —O—, —S—, $—CH_2—$ or $—NR^{6B}—$ (wherein $R^{6B}$ has the same meaning as $R^6$ defined above)] or (iv) Formula (IV):

(IV)

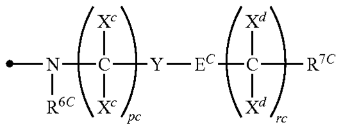

[wherein pc, rc, $E^C$, $X^C$, $X^d$ and $R^{6c}$ have the same meanings as p, r, E, X, $X^a$ and $R^6$ defined above, respectively;

$R^{7C}$ represents $—NR^8R^9$ (wherein $R^8$ and $R^9$ have the same meaning as defined above, respectively), a substituted or unsubstituted heteroaromatic group or a substituted or unsubstituted heteroalicyclic group; and Y represents a single bond, —O— or $—NR^{6D}—$ (wherein $R^{6D}$ has the same meaning as R defined above)];

A represents a single bond, —C(═O)—, $—SO_2—$, $—NR^{6D}C(═O)—$ (wherein $R^{6D}$ represents a hydrogen atom, substituted or unsubstituted lower alkyl or substituted or unsubstituted cycloalkyl, or is combined together with $R^3$ and the adjacent nitrogen atom to form a substituted or unsubstituted heterocyclic group), $—NR^{6D}C(═S)—$ (wherein $R^{6D}$ has the same meaning as defined above), —OC(═O)—, —OC(═S)—, —SC(═O)—, —SC(═S)—,

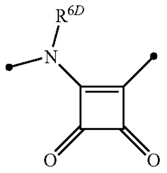

(wherein $R^{6D}$ has the same meaning as defined above),

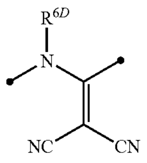

(wherein $R^{6D}$ has the same meaning as defined above) or

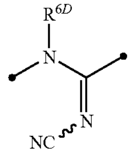

(wherein R has the same meaning as defined above), and A is bonded to $R^3$ at the left side in the each group; and (a) when A is a single bond,

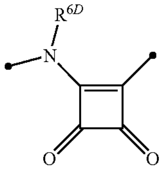

(wherein $R^{6D}$ has the same meaning as defined above),

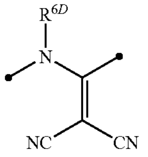

(wherein $R^{6D}$ has the same meaning as defined above) or

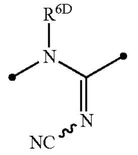

(wherein $R^{6D}$ has the same meaning as defined above), $R^3$ represents a hydrogen atom, substituted or unsubstituted lower alkyl, substituted or unsubstituted cycloalkyl, substituted or unsubstituted lower alkenyl, substituted or unsubstituted lower alkynyl, substituted or unsubstituted aralkyl, substituted or unsubstituted aryl, a substituted or unsubstituted heteroaromatic group, a substituted or unsubstituted heteroalicyclic group, substituted or unsubstituted heteroaromatic-substituted alkyl or substituted or unsubstituted heteroalicyclic-substituted alkyl, and (b) when A is —C(═O)—, —$SO_2$—, —$NR^{6D}$C(═O)— (wherein $R^{6D}$ has the same meaning as defined above), —$NR^{6D}$C(═S)—(wherein $R^{6D}$ has the same meaning as defined above), —OC(═O)—, —OC(═S)—, —SC(═O)— or —SC(═S)—, $R^3$ represents substituted or unsubstituted lower alkyl, substituted or unsubstituted cycloalkyl, substituted or unsubstituted lower alkenyl, substituted or unsubstituted lower alkynyl, substituted or unsubstituted aralkyl, substituted or unsubstituted aryl, a substituted or unsubstituted heteroaromatic group, a substituted or unsubstituted heteroalicyclic group, substituted or unsubstituted heteroaromatic-substituted alkyl, substituted or unsubstituted heteroalicyclic-substituted alkyl or —$NR^{8B}R^{9B}$ (wherein $R^{8B}$ and $R^{9B}$ have the same meanings as $R^8$ and $R^9$ defined above, respectively)}, or a quaternary ammonium salt thereof, or a pharmaceutically acceptable salt thereof.

(2) The bicyclic pyrimidine derivative, or the quaternary ammonium salt thereof, or the pharmaceutically acceptable salt thereof according to (1), wherein n is 2; and m is 1.

(3){The bicyclic pyrimidine derivative, or the quaternary ammonium salt thereof, or the pharmaceutically acceptable salt thereof according to (1), wherein n and m are 2.

(4) The bicyclic pyrimidine derivative, or the quaternary ammonium salt thereof, or the pharmaceutically acceptable salt thereof according to any of (1) to (3), wherein $R^4$ is a hydrogen atom; and $R^5$ is substituted or unsubstituted aralkyl.

(5) The bicyclic pyrimidine derivative, or the quaternary ammonium salt thereof, or the pharmaceutically acceptable salt thereof according to (1) to (3), wherein $R^4$ is a hydrogen atom; and $R^5$ is substituted or unsubstituted cycloalkyl.

(6) The bicyclic pyrimidine derivative, or the quaternary ammonium salt thereof, or the pharmaceutically acceptable salt thereof according to any of (1) to (5), wherein $R^2$ is —B—$(CX_2)_p$—$R^7$ (wherein p, X, B and $R^7$ have the same meanings as defined above, respectively).

(7) The bicyclic pyrimidine derivative, or the quaternary ammonium salt thereof, or the pharmaceutically acceptable salt thereof according to (6), wherein X is a hydrogen atom.

(8) The bicyclic pyrimidine derivative, or the quaternary ammonium salt thereof, or the pharmaceutically acceptable salt thereof according to (6) or (7), wherein A is —C(═O)— or a single bond.

(9) The bicyclic pyrimidine derivative, or the quaternary ammonium salt thereof, or the pharmaceutically acceptable salt thereof according to any of (6) to (8), wherein $R^3$ is substituted or unsubstituted cycloalkyl or substituted or unsubstituted aralkyl.

(10) The bicyclic pyrimidine derivative, or the quaternary ammonium salt thereof, or the pharmaceutically acceptable salt thereof according to any of (1) to (5), wherein $R^2$ is Formula (II):

(II)

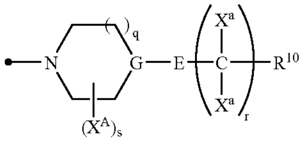

(wherein q, r, s, $X^A$, $X^a$, G, E and $R^{10}$ have the same meanings as defined above, respectively).

(11) The bicyclic pyrimidine derivative, or the quaternary ammonium salt thereof, or the pharmaceutically acceptable salt thereof according to (10), wherein s is 0.

(12) The bicyclic pyrimidine derivative, or the quaternary ammonium salt thereof, or the pharmaceutically acceptable salt thereof according to (10) or (11), wherein q is 1 or 2.

(13) The bicyclic pyrimidine derivative, or the quaternary ammonium salt thereof, or the pharmaceutically acceptable salt thereof according to any of (10) to (12), wherein $X^a$ is a hydrogen atom.

(14) The bicyclic pyrimidine derivative, or the quaternary ammonium salt thereof, or the pharmaceutically acceptable salt thereof according to any of (10) to (13), wherein $R^{10}$ is —$NR^{8A}R^{9A}$ (wherein $R^{8A}$ and $R^{9A}$ have the same meanings as defined above, respectively), a substituted or unsubstituted heteroaromatic group or a substituted or unsubstituted heteroalicyclic group.

(15) The bicyclic pyrimidine derivative, or the quaternary ammonium salt thereof, or the pharmaceutically acceptable salt thereof according to any of (10) to (14), wherein $R^3$ is substituted or unsubstituted lower alkyl, substituted or unsubstituted cycloalkyl, substituted or unsubstituted aralkyl, substituted or unsubstituted aryl or a substituted or unsubstituted heteroaromatic group.

(16) The bicyclic pyrimidine derivative, or the quaternary ammonium salt thereof, or the pharmaceutically acceptable salt thereof according to any of (1) to (5), wherein $R^2$ is Formula (III):

(III)

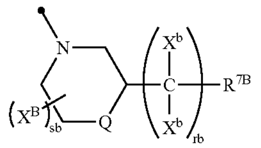

(wherein sb, rb, $X^B$, $X^b$, $R^7$ Band Q have the same meanings as defined above, respectively).

(17) The bicyclic pyrimidine derivative, or the quaternary ammonium salt thereof, or the pharmaceutically acceptable salt thereof according to (16), wherein sb is 0.

(18) The bicyclic pyrimidine derivative, or the quaternary ammonium salt thereof, or the pharmaceutically acceptable salt thereof according to (16) or (17), wherein Q is —O—.

(19) The bicyclic pyrimidine derivative, or the quaternary ammonium salt thereof, or the pharmaceutically acceptable salt thereof according to any of (16) to (18), wherein $X^b$ is a hydrogen atom.

(20) The bicyclic pyrimidine derivative, or the quaternary ammonium salt thereof, or the pharmaceutically acceptable salt thereof according to any of (16) to (19), wherein $R^{7B}$ is a substituted or unsubstituted heteroalicyclic group.

(21) The bicyclic pyrimidine derivative, or the quaternary ammonium salt thereof, or the pharmaceutically acceptable salt thereof according to any of (16) to (20), wherein A is —C(═O)— or —NHC(═O)—.

(22) The bicyclic pyrimidine derivative, or the quaternary ammonium salt thereof, or the pharmaceutically acceptable salt thereof according to any of (16) to (21), wherein $R^3$ is substituted or unsubstituted lower alkyl or substituted or unsubstituted cycloalkyl.

(23) The bicyclic pyrimidine derivative, or the quaternary ammonium salt thereof, or the pharmaceutically acceptable salt thereof according to any of (1) to (5), wherein $R^2$ is Formula (IV):

(IV)

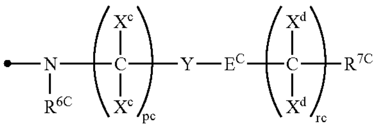

(wherein pc, rc, Y, $E^C$, $X^c$, $X^d$, $R^{6C}$ and $R^{7C}$ have the same meanings as defined above, respectively).

(24) The bicyclic pyrimidine derivative, or the quaternary ammonium salt thereof, or the pharmaceutically acceptable salt thereof according to (23), wherein $X^c$ and $X^d$ are hydrogen atoms.

(25) The bicyclic pyrimidine derivative, or the quaternary ammonium salt thereof, or the pharmaceutically acceptable salt thereof according to (23) or (24), wherein A is —C(═O)— or —$SO_2$—.

(26) The bicyclic pyrimidine derivative, or the quaternary ammonium salt thereof, or the pharmaceutically acceptable salt thereof according to any of (23) to (26), wherein $R^3$ is substituted or unsubstituted lower alkyl, substituted or unsubstituted cycloalkyl, substituted or unsubstituted aralkyl, substituted or unsubstituted aryl or a substituted or unsubstituted heteroaromatic group.

(27) The bicyclic pyrimidine derivative, or the quaternary ammonium salt thereof, or the pharmaceutically acceptable salt thereof according to any of (1) to (26), wherein the quaternary ammonium salt is a quaternary ammonium salt formed by the addition of Z-Hal (wherein Z represents substituted or unsubstituted lower alkyl or substituted or unsubstituted lower alkenyl; and Hal represents a halogen) to any nitrogen atom in $R^7$, $R^{7B}$, $R^{10}$ or $R^{7C}$.

(28) A pharmaceutical composition which comprises, as an active ingredient, the bicyclic pyrimidine derivative, or the quaternary ammonium salt thereof, or the pharmaceutically acceptable salt thereof according to any of (1) to (27).

(29) An anti-inflammatory agent which comprises, as an active ingredient, the bicyclic pyrimidine derivative, or the quaternary ammonium salt thereof, or the pharmaceutically acceptable salt thereof according to any of (1) to (27).

(30) A modulator of the function of thymus and activation-regulated chemokine [TARC; CC chemokine ligand 17 (CCL17)] and/or macrophage-derived chemokine [MDC; CC chemokine ligand 22 (CCL22)], which comprises, as an active ingredient, the bicyclic pyrimidine derivative, or the quaternary ammonium salt thereof, or the pharmaceutically acceptable salt thereof according to any of (1) to (27).

(31) A therapeutic and/or preventive agent for a disease which is related to TARC(CCL17) and/or MDC (CCL22), which comprises, as an active ingredient, the bicyclic pyrimidine derivative, or the quaternary ammonium salt thereof, or the pharmaceutically acceptable salt thereof according to any of (1) to (27).

(32) A therapeutic and/or preventive agent for a disease which is related to T cells, which comprises, as an active ingredient, the bicyclic pyrimidine derivative, or the quaternary ammonium salt thereof, or the pharmaceutically acceptable salt thereof according to any of (1) to (27).

(33) A therapeutic and/or preventive agent for an allergic disease which comprises, as an active ingredient, the bicyclic pyrimidine derivative, or the quaternary ammonium salt thereof, or the pharmaceutically acceptable salt thereof according to any of (1) to (27).

(34) Use of the bicyclic pyrimidine derivative, or the quaternary ammonium salt thereof, or the pharmaceutically acceptable salt thereof according to any of (1) to (27), for the manufacture of an anti-inflammatory agent.

(35) Use of the bicyclic pyrimidine derivative, or the quaternary ammonium salt thereof, or the pharmaceutically acceptable salt thereof according to any of (1) to (27), for the manufacture of a modulator of the function of TARC(CCL17) and/or MDC (CCL22).

(36) Use of the bicyclic pyrimidine derivative, or the quaternary ammonium salt thereof, or the pharmaceutically acceptable salt thereof according to any of (1) to (27), for the manufacture of a therapeutic and/or preventive agent for a disease which is relared to TARC(CCL17) and/or MDC (CCL22).

(37) Use of the bicyclic pyrimidine derivative, or the quaternary ammonium salt thereof, or the pharmaceutically acceptable salt thereof according to any of (1) to (27), for the manufacture of a therapeutic and/or preventive agent for a disease which is related to T cells.

(38) Use of the bicyclic pyrimidine derivative, or the quaternary ammonium salt thereof, or the pharmaceutically acceptable salt thereof according to any of (1) to (27), for the manufacture of a therapeutic and/or preventive agent for an allergic disease.

(39) A method for treating and/or preventing inflammation, which comprises administering an effective amount of the bicyclic pyrimidine derivative, or the quaternary ammonium salt thereof, or the pharmaceutically acceptable salt thereof according to any of (1) to (27).

(40) A method for modulating the function of TARC (CCL17) and/or MDC (CCL22), which comprises administering an effective amount of the bicyclic pyrimidine derivative, or the quaternary ammonium salt thereof, or the pharmaceutically acceptable salt thereof according to any of (1) to (27).

(41) A method for treating and/or preventing a disease which is related to TARC(CCL17) and/or MDC (CCL22), which comprises administering an effective amount of the bicyclic pyrimidine derivative, or the quaternary ammonium salt thereof, or the pharmaceutically acceptable salt thereof according to any of (1) to (27).

(42) A method for treating and/or preventing a disease which is related to T cells, which comprises administering an effective amount of the bicyclic pyrimidine derivative, or the quaternary ammonium salt thereof, or the pharmaceutically acceptable salt thereof according to any of (1) to (27).

(43) A method for treating and/or preventing an allergic disease, which comprises administering an effective amount of the bicyclic pyrimidine derivative, or the quaternary ammonium salt thereof, or the pharmaceutically acceptable salt thereof according to any of (1) to (27).

In the definitions of respective groups in Formulae (I) to (IV), (i) Examples of the lower alkyl and the lower alkyl moiety of the lower alkoxy include straight-chain or branched alkyl which have 1 to 10 carbon atoms, such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, isooctyl, nonyl, decyl and the like.

(ii) Examples of the cycloalkyl include cycloalkyl which have 3 to 8 carbon atoms, such as cyclopropyl, cyclobutyl, cyclopentyl, cyclohexyl, cycloheptyl, cyclooctyl and the like.

(iii) Examples of the lower alkenyl include straight-chain, branched or cyclic alkenyl which have 2 to 8 carbon atoms, such as vinyl, allyl, 1-propenyl, butenyl, pentenyl, hexenyl, heptenyl, octenyl, cyclopentenyl, cyclohexenyl, 2,6-octadienyl and the like.

(iv) Examples of the lower alkynyl include straight-chain or branched alkynyl which have 2 to 6 carbon atoms, such as ethynyl, 1-propynyl, 2-propynyl, butynyl, pentynyl, hexynyl, heptynyl, octynyl, propargyl and the like.

(v) Examples of the aryl and the aryl moiety of the arylcarbonyl include monocyclic, bicyclic or tricyclic aryl which have 6 to 14 carbon atoms, such as phenyl, naphthyl, indenyl, anthranyl and the like.

(vi) The alkylene moieties of the aralkyl, the heteroaromatic-substituted alkyl and the heteroalicyclic-substituted alkyl have the same meaning as the group formed by removing one hydrogen atom from the lower alkyl (i) defined above. The alkylidene moiety of the imino-(lower alkyl) has the same meaning as the group formed by removing two hydrogen atoms on the same carbon atom from the lower alkyl (i) defined above.

(vii) The aryl moiety of the aralkyl also includes, in addition to the definition of the aryl (v), for example, condensed bicyclic groups wherein cycloalkyl is condensed, such as indanyl, 1,2,3,4-tetrahydronaphthyl, 6,7,8,9-tetrahydro-5H-benzocycloheptyl and the like.

(viii) Examples of the heteroaromatic group and the heteroaromatic moiety of the heteroaromatic-substituted alkyl include five- or six-membered monocyclic heteroaromatic groups containing at least one atom selected from a nitrogen atom, an oxygen atom and a sulfur atom; and condensed bicyclic or tricyclic heteroaromatic groups in which 3- to 8-membered rings are condensed and containing at least one atom selected from a nitrogen atom, an oxygen atom and a sulfur atom. Specific examples thereof include pyridyl, pyrazinyl, pyrimidinyl, pyridazinyl, benzimidazolyl, 2-oxobenzimidazolyl, benzotriazolyl, benzofuryl, benzothienyl, purinyl, benzoxazolyl, benzothiazolyl, benzodioxolyl, indazolyl, indolyl, isoindolyl, quinolyl, isoquinolyl, phthalazinyl, naphthyridinyl, quinoxalinyl, pyrrolyl, pyrazolyl, quinazolinyl, cinnolinyl, triazolyl, tetrazolyl, imidazolyl, oxazolyl, isoxazolyl, thiazolyl, isothiazolyl, thienyl, furyl and the like.

(ix) Examples of the heteroalicyclic group and the heteroalicyclic moiety of the heteroalicyclic-substituted alkyl include five- or six-membered monocyclic heteroalicyclic groups containing at least one atom selected from a nitrogen atom, an oxygen atom and a sulfur atom; condensed bicyclic or tricyclic heteroalicyclic groups in which 3- to 8-membered rings are condensed and containing at least one atom selected from a nitrogen atom, an oxygen atom and a sulfur atom; and heteroalicyclic groups having a spiro structure in which 3- to 8-membered rings combine each other and containing at least one atom selected from a nitrogen atom, an oxygen atom and a sulfur atom. Specific examples thereof include pyrrolidinyl, 2-oxopyrrolidinyl, 2,5-dioxopyrrolidinyl, pyrrolinyl, thiazolidinyl, oxazolidinyl, azotidinyl, piperidyl, piperidino, 4-oxopiperidino, 2-oxopiperazinyl, perhydroazepinyl, perhydroazocinyl, piperazinyl, homopiperazinyl, homopiperidyl, homopiperidino, morpholinyl, morpholino, thiomorpholinyl, thiomorpholino, pyranyl, tetrahydropyridyl, tetrahydropyranyl, tetrahydrofuranyl, tetrahydroquinolyl, tetrahydroisoquinolyl, octahydroquinolyl, indolinyl, 1,4-dioxa-8-azaspiro [4.5]dec-8-yl and the like.

(x) Examples of the heteroalicyclic group formed together with the adjacent nitrogen atom include five- or six-membered monocyclic heteroalicyclic groups containing at least one nitrogen atom (the monocyclic heteroalicyclic groups may contain any of other nitrogen atom, an oxygen atom and a sulfur atom); and condensed bicyclic or tricyclic heteroalicyclic groups in which 3- to 8-membered rings are condensed and containing at least one nitrogen atom (the condensed heteroalicyclic groups may contain any of other nitrogen atom, an oxygen atom and a sulfur atom). Specific examples thereof include tetrahydropyridyl, indolinyl, isoindolinyl, pyrrolidinyl, thiazolidinyl, oxazolidinyl, piperidino, homopiperidino, piperazinyl, homopiperazinyl, morpholino, thiomorpholino, perhydroazepinyl, perhydroazocinyl, tetrahydroquinolyl, tetrahydroisoquinolyl, octahydroquinolyl and the like.

(xi) Examples of the heterocyclic group formed by $R^3$ and the adjacent nitrogen atom include 5- or 6-membered monocyclic heterocyclic groups containing at least one nitrogen atom (the monocyclic heterocyclic groups may contain any of other nitrogen atom, an oxygen atom and a sulfur atom); and condensed bicyclic or tricyclic heterocyclic groups in which 3- to 8-membered rings are condensed and containing at least one nitrogen atom (the condensed heterocyclic groups may contain any of other nitrogen atom, an oxygen atom and a sulfur atom). Specific examples thereof include pyridyl, tetrahydropyridyl, indolinyl, isoindolinyl, pyrrolidinyl, thiazolidinyl, oxazolidinyl, piperidino, homopiperidino, piperazinyl, homopiperazinyl, morpholino, thiomorpholino, perhydroazepinyl, perhydroazocinyl, tetrahydroquinolyl, tetrahydroisoquinolyl, octahydroquinolyl, benzimidazolyl, indazolyl, indolyl, isoindolyl, purinyl, pyrrolyl, pyrazolyl, triazolyl, tetrazolyl, imidazolyl and the like.

(xii) The halogen represents any of fluorine, chlorine, bromine and iodine atoms.

(xiii) Examples of the substituents of the substituted lower alkyl and the substituted lower alkoxy, which may be the same or different and in number of 1 to 3, include cycloalkyl, lower alkanoyl, substituted lower alkanoyl [wherein the substituent (a) of the substituted lower alkanoyl, which may be the same or different and in number of 1 to 3, include halogen and the like], lower alkoxy, substituted lower alkoxy [wherein the substituent of the substituted lower alkoxys has the same meaning as the substituent (a) of the substituted lower alkanoyl defined above], aryloxy, substituted aryloxy (wherein the substituent (b) of the substituted aryloxy, which may be the same or different and in number of 1 to 3, include cycloalkyl, lower alkanoyl, substituted lower alkanoyl [wherein the substituent of the substituted lower alkanoyl has the same meaning as the substituent (a) of the substituted lower alkanoyl defined above], lower alkoxy, substituted lower alkoxy [wherein the substituent of the substituted lower alkoxy has the same meaning as the substituent (a) of the substituted lower alkanoyl defined above], aryloxy, aralkyloxy, mono- or di-(lower alkyl)amino, substituted mono- or di-(lower alkyl)amino [wherein the substituent (c) of the lower alkyl moiety of the substituted mono- or di-(lower alkyl)amino, which may be the same or different and in number of 1 to 3, include halogen, hydroxy, carboxy, lower alkoxycarbonyl and the like], lower alkanoyloxy, lower alkoxycarbonyl, halogen, cyano, nitro, hydroxy, carboxy, carbamoyl, mercapto, amino, lower alkyl, substituted lower alkyl [wherein the substituent of the substituted lower alkyl has the same meaning as the substituent (a) of the substituted lower alkanoyl defined above], aryl, substituted aryl [wherein the substituent of the substituted aryl has the same meaning as the substituent (a) of the substituted lower alkanoyl defined above], lower alkylthio, lower alkylsulfonyl, lower alkylsulfinyl, a heteroaromatic group and a heteroalicyclic groups}, aralkyloxy, substituted aralkyloxy [wherein the substituent of the substituted aralkyloxy has the same meaning as the substituent (b) of the substituted aryloxy defined above], monoordi-(lower alkyl)amino, substituted mono- or di-(lower alkyl)amino [wherein the substituent of the lower alkyl moiety of the substituted mono- or di-(lower alkyl)amino has the same meaning as the substituent (c) of the lower alkyl moiety of the mono- or di-(lower alkyl)amino defined above], lower alkanoyloxy, lower alkoxycarbonyl, lower alkoxycarbonylamino, lower alkanoylamino, mono- or di-(lower alkyl)aminocarbonyl, mono- or di-(lower alkyl)aminocarbonyloxy, halogen, cyano, nitro, hydroxy, carboxy, carbamoyl, amino, thio, oxo, formyl, lower alkylthio, lower alkylsulfonyl and lower alkylsulfinyl.

The aryl and the aryl moieties of the aryloxy and aralkyloxy, the cycloalkyl, the halogen, the heteroaromatic group, the heteroalicyclic group, and the lower alkyl, and the lower alkyl moieties of the lower alkanoyl, the lower alkoxy, the lower alkanoyloxy, the lower alkoxycarbonyl, the lower alkoxycarbonylamino, the lower alkanoylamino, the lower alkylthio, the lower alkylsulfonyl and the lower alkylsulfinyl herein have the same meanings as the aryl (v), the cycloalkyl (ii), the halogen (xii), the heteroaromatic group (viii), the heteroalicyclic group (ix) and the lower alkyls (i), respectively. The alkylene moiety of the aralkyloxy has the same meaning as the group formed by removing one hydrogen atom from the lower alkyl (i) defined above. The lower alkyl moieties of the mono- or di-(lower alkyl)amino, the mono- or di-(lower alkyl)aminocarbonyl and the mono- or di-(lower alkyl)aminocarbonyloxy have the same meaning as the lower alkyl (i) defined above. Two lower alkyl moieties of the di(lower alkyl)amino, di(lower alkyl)aminocarbonyl and di(lower alkyl)aminocarbonyloxy may be the same or different.

(xiv) Examples of the substituents of the substituted aryl, substituted arylcarbonyl, substituted aralkyl, substituted cycloalkyl, substituted lower alkenyl, substituted lower alkynyl, substituted heteroaromatic group, substituted pyrazol-3-yl, substituted 1,2,4-triazol-3-yl, substituted heteroalicyclic group, substituted heteroaromatic-substituted alkyl, substituted heteroalicyclic-substituted alkyl, substituted heterocyclic group formed by $R^3$ and the adjacent nitrogen atom, and substituted heteroalicyclic groups formed together with the adjacent nitrogen atom include lower alkyl, substituted lower alkyl, lower alkenyl, aryl, substituted aryl, aralkyl, substituted aralkyl, a heteroaromatic group, a substituted heteroaromatic group, a heteroalicyclic group, a substituted heteroalicyclic group, heteroaromatic-substituted alkyl, substituted heteroaromatic-substituted alkyl, heteroalicyclic-substituted alkyl, substituted heteroalicyclic-substituted alkyl and the like, in addition to the groups listed in the definition of the substituents (xiii) of the substituted lower alkyl.

The lower alkyl, the lower alkenyl, the aryl, the heteroaromatic group, the heteroaromatic moiety of the heteroaromatic-substituted alkyl, the heteroalicyclic group, the heteroalicyclic moiety of the heteroalicyclic-substituted alkyl, the alkylene moieties of the aralkyl, heteroaromatic-substituted alkyl and heteroalicyclic-substituted alkyl, and the aryl moiety of the aralkyl has the same meaning as the lower alkyl (i), the lower alkenyl (iii), the aryl (v), the heteroaromatic group (viii), the heteroalicyclic group (ix), the alkylene moiety of the aralkyl(vi), and the aryl moiety of the aralkyl (vii), respectively. The substituents of the substituted aryl, substituted aralkyl, substituted heteroaromatic group, substituted heteroalicyclic group, substituted heteroaromatic-substituted alkyl and substituted heteroalicyclic-substituted alkyl, which may be the same or different and in number of 1 to 3 include lower alkyl [wherein the lower alkyl has the same meaning as the lower alkyl (i) defined above], lower alkoxy [wherein the lower alkyl moiety of the lower alkoxy has the same meaning as the lower alkyl (i) defined above] and halogen [wherein the halogen has the same meaning as the halogen (xii) defined above]. The substituents of the substituted lower alkyl, which may be the same or different, for example, in number of 1 to 3 include halogen [wherein the halogen has the same meaning as the halogen (xii) defined above], hydroxy, lower alkoxy [wherein the lower alkyl moiety of the lower alkoxy has the same meaning as the lower alkyl (i) defined above] and cyano.

(xv) The substituent of the substituted amidino, which may be the same or different, for example, in number of 1 or 2 include lower alkyl [wherein the lower alkyl has the same meaning as the lower alkyl (i) defined above] and cyano.

(xvi) The substitutable number represents a structural maximum number of the substituent that can be substituted. More specifically, s represents an integer from 0 to $[6+(q\times2)]$ (wherein q has the same meaning as defined above) and sb represents an integer of 0 to 7, respectively, of which an integer of 0 to 3 is preferred.

The compounds represented by Formula (I) are hereinafter referred to as Compound (I). The same shall apply to the compounds of the other formula numbers.

(xvii) The quaternary ammonium salts of Compounds (I) may be any quaternary ammonium salts formed by the addition of, for example, Z-Hal (wherein Z and Hal have the same meaning as defined above, respectively) to, for example, one to three nitrogen atom(s) in these structures. Specific examples of the quaternary ammonium salts include quaternary ammonium salts [—$N^+Hal^-Z$- (wherein Z and Hal have the same meanings as defined above, respectively)] each formed by the addition of Z-Hal (wherein Z and Hal have the same meanings as defined above, respectively) to any nitrogen atom in $R^7$, $R^{7B}$, $R^{10}$ or $R^{7C}$ of Compounds (I).

Among them, preferred examples are quaternary ammonium salts [—$N^+Hal^-Z$- (wherein Z and Hal have the same meanings as defined above, respectively)] formed by the addition of Z-Hal (wherein Z and Hal have the same meanings as defined above, respectively) to:

(1) nitrogen atom combined with $R^8$ and $R^9$, or $R^{8A}$ and $R^{9A}$ in —$NR^8R^9$ or —$NR^{8A}R^{9A}$, (2) nitrogen atom in the heteroalicyclic group when $R^7$, $R^{7B}$ or $R^{7C}$ is a substituted or unsubstituted heteroalicyclic group (wherein the heteroalicyclic group herein has the same meaning as the heteroalicyclic groups each containing at least one nitrogen atom in the definition of the heteroalicyclic groups (ix)), or (3) nitrogen atom in the substituted or unsubstituted heteroalicyclic group or the substituted or unsubstituted heteroalicyclic-substituted alkyl, when $R^{10}$ is a substituted or unsubstituted heteroalicyclic group (wherein the heteroalicyclic group has the same meaning as the heteroalicyclic groups each containing at least one nitrogen atom in the definition of the heteroalicyclic groups (ix)) or a substituted or unsubstituted heteroalicyclic-substituted alkyl (wherein the heteroalicyclic group moiety of the heteroalicyclic-substituted alkyl has the same meaning as the heteroalicyclic groups each containing at least one nitrogen atom in the definition of the heteroalicyclic groups (ix)).

The pharmaceutically acceptable salts of Compound (I) are preferably non-toxic and water-soluble. Specific examples include acid addition salts including inorganic acid salts such as hydrochlorides, hydrobromides, nitrates, sulfates and phosphates, and organic acid salts such as benzenesulfonates, benzoates, citrates, fumarates, gluconates, lactates, maleates, malates, oxalates, methanesulfonates and tartrates; metal salts including alkali metal salts such as sodium salts and potassium salts, alkaline earth metal salts such as magnesium salts and calcium salts, as well as aluminum salts and zinc salts; ammonium salts such as salts of ammonium and tetramethylammonium; organic amine addition salts such as morpholine addition salts and piperidine addition salts; and amino acid addition salts such as glycine addition salts, phenylalanine addition salts, lysine addition salts, aspartic acid addition salts and glutamic acid addition salts.

Preparation methods of Compounds (I) will be illustrated below.

In each of the following preparation methods, when a defined group changes under reaction conditions or is not suitable for carrying out the method, the preparation can be easily carried out by subjecting the group to a procedure conventionally employed in organic synthetic chemistry, such as protection and/or deprotection of a functional group [for example, Protective Groups in Organic Synthesis, third edition, T. W. Greene, John Wiley & Sons Inc. (1999)]. Where necessary, the order of reaction process steps such as introduction of substituents can be altered.

Compounds (I) can be prepared, for example, by any of Preparation Methods 1 to 15.

Preparation Method 1:

Of Compounds (I), Compound (IA) in which A is $A^a$ (wherein $A^a$ represents —C(=O)—, —$SO_2$—, —NHC(=O)—, —NHC(=S)—, —OC(=O)—, —OC(=S)—, —SC(=O)— or —SC(=S)— in the definition of A) can be prepared, for example, according to the following preparation method:

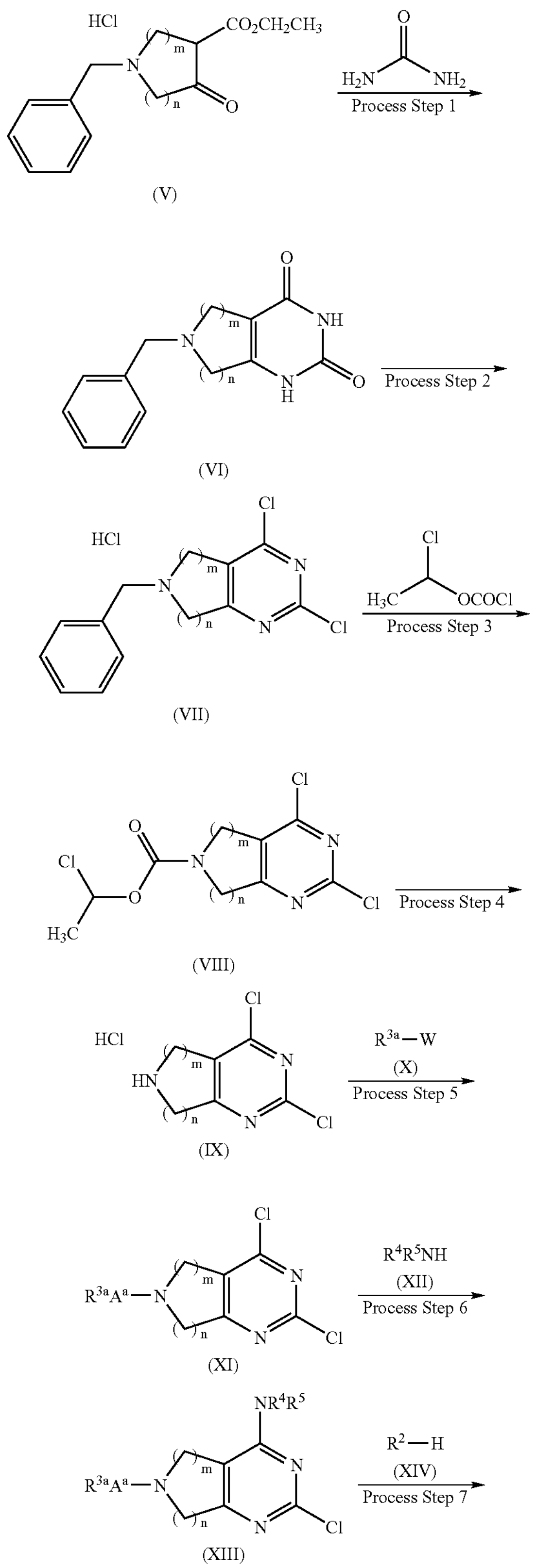

(V)
(VI)
(VII)
(VIII)
(X)
(IX)
(XII)
(XI)
(XIV)
(XIII)

-continued

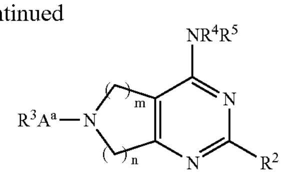

(IA)

[wherein $R^2$, $R^3$, $R^4$, $R^5$, $A^a$, m and n have the same meanings as defined above, respectively; $R^{3a}$ has the same meaning as the group formed by removing one hydrogen atom from the definition of $R^3$ defined above; and W represents —C(═O)Cl, —$CO_2COR^{3a}$ (wherein $R^{3a}$ has the same meaning defined above), —$SO_2Cl$, —NCO, —NCS, —OC(═O)Cl, —$OCO_2CO_2R^{3a}$ (wherein $R^{3a}$ is as defined above), —SC(═O)Cl, —OC(═S)Cl or —SC(═S)Cl]

[Process Step 1]

Compound (VI) can be obtained by allowing Compound (V) to react with 1 equivalent to excess and preferably 2 equivalents to 6 equivalents of urea in the presence of 2 equivalents to excess and preferably 3 equivalents to 4 equivalents of a base in a solvent inert to the reaction. Compound (V) herein is obtained as a commercially available product or prepared, for example, according to a method descried in Synthetic Communications, vol. 22, p. 1249 (1992) or Synthetic Communications, vol. 26, p. 1657 (1996).

The solvent inert to the reaction is not specifically limited, can be any solvent that is inert to the reaction and includes, for example, tetrahydrofuran, dioxane, 1,2-dimethoxyethane, benzene, toluene, xylenes, dimethylformamide, dimethylacetamide, N-methylpyrrolidone, methanol, ethanol, n-propanol and isopropyl alcohol. Each of these solvents can be used alone or in combination as a mixture. Among them, ethanol is preferred.

Examples of the base are alkoxides of alkali metals or alkaline earth metals, such as sodium methoxide, sodium ethoxide and potassium tert-butoxide, of which sodium methoxide or sodium ethoxide is preferably used.

The reaction is carried out at temperatures from room temperature to the boiling point of the used solvent and preferably from 50° C. to 100° C. generally for 1 hour to 60 hours.

[Process Step 2]

Compound (VII) can be prepared by allowing Compound (VI) prepared according to Process Step 1 to react with an excess of a chlorinating agent in the presence of or in the absence of a solvent inert to the reaction.

Examples of the chlorinating agent are phosphorus oxychloride and phosphorus pentachloride.

The solvent inert to the reaction is not specifically limited, can be any solvent that is inert to the reaction and includes, for example, 1,2-dichloroethane, tetrahydrofuran, dioxane, 1,2-dimethoxyethane, chloroform, benzene, toluene, xylene, ethyl acetate, triethylamine, pyridine and N,N-dimethylaniline. Each of these can be used alone or in combination as a mixture.

The reaction is carried out at temperatures from 0° C. to the boiling point of the solvent and preferably from 50° C. to 110° C. generally for 1 hour to 24 hours.

[Process Step 3]

Compound (VIII) can be prepared by allowing Compound (VII) prepared according to Process Step 2 to react with 1 equivalent to 6 equivalents and preferably 2 equivalents to 4 equivalents of 1-chloroethyl chloroformate in the presence of, or in the absence of, 1 equivalent to 10 equivalents of a base in a solvent inert to the reaction.

The solvent inert to the reaction is not specifically limited, can be any solvent that is inert to the reaction and includes, for example, 1,2-dichloroethane, chloroform, tetrahydrofuran, dioxane, 1,2-dimethoxyethane, benzene, toluene, xylene, ethyl acetate, dimethylformamide, dimethylacetamide, N-methylpyrrolidone, dimethyl sulfoxide and acetonitrile. Each of these can be used alone or in combination as a mixture. Among them, 1,2-dichloroethane is preferred.

Examples of the base are triethylamine and diisopropylethylamine.

The reaction is carried out at temperatures from room temperature to 120° C. and preferably from 500° C. to 100° C. generally for 1 hour to 48 hours.

[Process Step 4]

Compound (IX) can be prepared by treating Compound (VIII) prepared according to Process Step 3 with an alcohol.

Examples of the alcohol are methanol, ethanol, n-propanol, isopropyl alcohol and n-butanol. In general, these also serve as a solvent.

The reaction is carried out at temperatures from room temperature to the boiling point of the solvent and preferably from 50° C. to the boiling point of the solvent generally for 10 minutes to 10 hours.

[Process Step 5]

Compound (XI) can be prepared by allowing Compound (IX) prepared according to Process Step 4 to react with 1 equivalent to 5 equivalents and preferably 1 equivalent to 2 equivalents of $R^{3a}$—W (wherein $R^{3a}$ and W are as defined above, respectively: Compound (X)) in the presence of 1 equivalent to 10 equivalents and preferably 1 equivalent to 4 equivalents of a base in a solvent inert to the reaction.

Compound (X) can be obtained as a commercially available product or prepared, for example, according to a method described in Comprehensive Organic Transformations, second edition, R. C. Larock, John Wiley & Sons Inc. (1999).

Examples of the base are organic bases such as triethylamine, diisopropylethylamine, 1,8-diazabicyclo[5.4.0]undec-7-ene (DBU), N,N-dimethylaniline, pyridine and quinoline; inorganic bases such as potassium carbonate, sodium carbonate, sodium hydrogen carbonate, potassium hydroxide, sodium hydroxide, potassium tert-butoxide, lithium diisopropylamide (LDA), sodium hydride and potassium hydride; basic anion-exchange resins such as AMBERLYSTA-21 (available from Rhom and Haas Company) and AG1-X8 (available from Bio-Rad Laboratories, Inc.); and bases immobilized to a solid phase, such as morpholinomethyl polystyrene. Among them, triethylamine is preferred.

The solvent inert to the reaction is not specifically limited, can be any solvent that is inert to the reaction and includes, for example, dichloromethane, 1,2-dichloroethane, chloroform, tetrahydrofuran, dioxane, 1,2-dimethoxyethane, benzene, toluene, xylene, ethyl acetate, dimethylformamide, dimethylacetamide, N-methylpyrrolidone, dimethyl sulfoxide, acetonitrile and water. Each of these solvents can be alone or in combination as a mixture. Among them, dichloromethane is preferred.

The reaction is carried out at temperatures from 0° C. to 100° C. and preferably from room temperature to 50° C. generally for 1 hour to 1 week.

[Process Step 6]

Compound (XIII) can be prepared by allowing Compound (XI) prepared according to Process Step 5 to react with 1 equivalent to large excess and preferably 1 equivalent to 3 equivalents of $R^4R^5NH$ (wherein $R^4$ and $R^5$ are as defined above, respectively: Compound (XII)) in the presence of, or in the absence of, 1 equivalent to large excess and preferably 1 equivalent to 10 equivalents of a base in a solvent inert to the reaction.

Compound (XII) can be obtained as a commercially available product or prepared according to, for example, a method described in Comprehensive Organic Transformations, second edition, R. C. Larock, John Wiley & Sons Inc. (1999).

The solvent inert to the reaction is not specifically limited, can be any solvent that is inert to the reaction and includes, for example, tetrahydrofuran, dioxane, 1,2-dimethoxyethane, diethyl ether, diisopropyl ether, benzene, toluene, xylene, ethyl acetate, acetonitrile, dichloromethane, chloroform, 1,2-dichloroethane, dimethylformamide, dimethylacetamide, N-methylpyrrolidone, dimethyl sulfoxide and pyridine. Each of these solvents can be used alone or in combination as a mixture. Among them, tetrahydrofuran, dichloromethane, chloroform or a mixture of these solvents is preferred.

Examples of the base are organic bases such as triethylamine, diisopropylethylamine, DBU, N,N-dimethylaniline, pyridine and quinoline; inorganic bases such as potassium carbonate, sodium carbonate, lithium carbonate, sodium hydrogen carbonate, potassium hydroxide, sodium hydroxide, lithium hydroxide, potassium tert-butoxide, sodium hydride, potassium hydride and lithium hydride; basic anion-exchange resins such as AMBERLYST A-21 (available from Rhom and Haas Company) and AG1-X8 (available from Bio-Rad Laboratories, Inc.); and bases supported by a solid phase, such as polyvinylpyridine and morpholinomethyl polystyrene. Among them, triethylamine is preferred.

The reaction is carried out at temperatures from 0° C. to 100° C. and preferably from room temperature to 50° C. generally for 1 hour to 48 hours.

[Process Step 7]

Compound (IA) can be prepared by allowing Compound (XIII) prepared according to Process Step 6 to react with 1 equivalent to large excess and preferably 1 equivalent to 3 equivalents of Compound (XIV) in the presence of, or in the absence of, 1 equivalent to large excess and preferably 1 equivalent to 10 equivalents of a base in a solvent inert to the reaction.

Compound (XIV) can be obtained as a commercially available product or prepared, for example, according to a method described in Comprehensive Organic Transformations, second edition, R. C. Larock, John Wiley & Sons Inc. (1999).

The solvent inert to the reaction is not specifically limited, can be any solvent that is inert to the reaction and includes, for example, tetrahydrofuran, dioxane, 1,2-dimethoxyethane, diisopropyl ether, benzene, toluene, xylene, ethyl acetate, acetonitrile, chloroform, 1,2-dichloroethane, dimethylformamide, dimethylacetamide, N-methylpyrrolidone, dimethyl sulfoxide and pyridine. Each of these solvents can be used alone or in combination as a mixture. Among them, dioxane, chloroform or a mixture of these solvents is preferred.

Examples of the base are organic bases such as triethylamine, diisopropylethylamine, DBU, N,N-dimethylaniline, pyridine and quinoline; inorganic bases such as potassium carbonate, sodium carbonate, lithium carbonate, sodium hydrogen carbonate, potassium hydroxide, sodium hydroxide, lithium hydroxide, potassium tert-butoxide, sodium hydride, potassium hydride and lithium hydride; basic anion-exchange resins such as AMBERLYST A-21 (available from Rhom and Haas Company) and AG1-X8 (available from Bio-Rad Laboratories, Inc.); and bases supported by a solid phase, such as polyvinylpyridine and morpholinomethyl polystyrene. Among them, triethylamine is preferred.

The reaction is carried out at temperatures from room temperature to the boiling point of the solvent and preferably from 50° C. to 100° C. generally for 1 hour to 1 week.

Preparation Method 2:

Of Compounds (I), Compound (IB) wherein A is a single bond; and $R^3$ is $R^{3b}$ (wherein $R^{3b}$ represents a substituted or unsubstituted lower alkyl, a substituted or unsubstituted lower alkenyl, a substituted or unsubstituted lower alkynyl, a substituted or unsubstituted aralkyl, a substituted or unsubstituted heteroaromatic-substituted alkyl or a substituted or unsubstituted heteroalicyclic-substituted alkyl, each of which has —$CH_2$— at a bonding site in the definition of $R^3$) can be prepared, for example, according to the following preparation method:

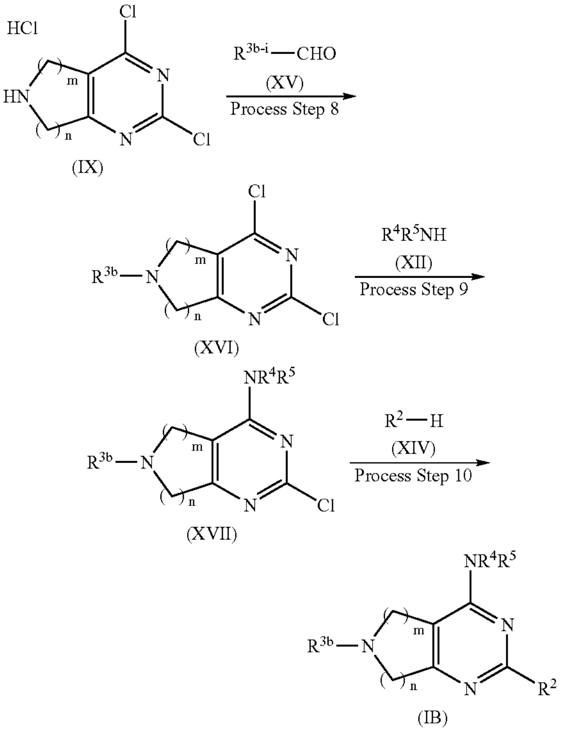

(wherein $R^2$, $R^{3b}$, $R^4$, $R^5$, m and n have the same meanings as defined above, respectively; and $R^{3b\text{-}i}$ has the same meaning as the group formed by removing the terminal —$CH_2$— from the definition of $R^{3b}$)

[Process Step 8]

Compound (XVI) can be prepared by allowing Compound (IX) prepared according to Process Step 4 of Preparation Method 1 to react with 1 equivalent to 3 equivalents of Compound (XV) in the presence of 1 equivalent to 10 equivalents of a reducing agent in a solvent inert to the reaction.

Examples of the reducing agent are sodium triacetoxyborohydride, sodium borohydride, sodium cyanoborohydride, and boron hydride supported by a solid phase.

The solvent inert to the reaction is not specifically limited, can be any solvent that is inert to the reaction and includes, for example, methanol, ethanol, n-propanol, isopropyl alcohol, n-butanol, dimethylformamide, dimethylacetamide, N-methylpyrrolidone, tetrahydrofuran, 2-methyltetrahydrofuran, dioxane, diethyl ether, benzene, toluene, xylene, ethyl acetate, acetonitrile, pyridine, dichloromethane, chloroform and 1,2-dichloroethane. Each of these can be used alone or in combination as a mixture. Among them, 1,2-dichloroethane is preferred.

The reaction is carried out at temperatures from 0° C. to 100° C. and preferably from room temperature to 50° C. generally for 10 minutes to 72 hours.

[Process Step 9]

Compound (XVII) can be prepared by allowing Compound (XVI) prepared according to Process Step 8 to react with Compound (XII) in the same way as Process Step 6 of Preparation Method 1. Preferred reaction conditions and how Compound (XII) is obtained are as in Process Step 6 of Preparation Method 1.

[Process Step 10]

Compound (IB) can be prepared by allowing Compound (XVII) prepared according to Process Step 9 to react with Compound (XIV) in the same way as Process Step 7 of Preparation Method 1. Preferred reaction conditions and how Compound (XII) is obtained are as in Process Step 7 of Preparation Method 1.

Preparation Method 3:

Of Compounds (I), Compound (IC) wherein A is a single bond; and $R^3$ is hydrogen atom can be prepared, for example, from Compound (IA-a) wherein $R^3$ is tert-butyl and $A^a$ is —OC(═O)— among Compounds

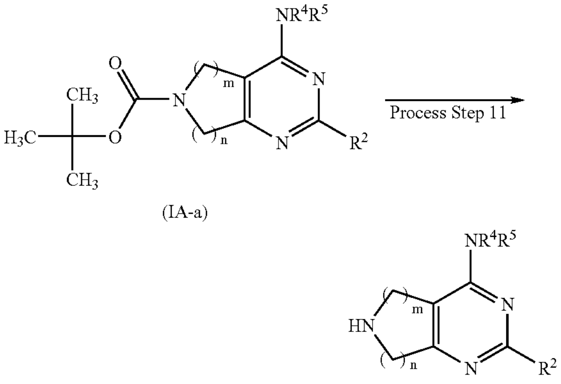

(IA-a)

(IC)

(wherein $R^2$, $R^4$, $R^5$, m and n have the same meanings as defined above, respectively)

[Process Step 11]

Compound (IC) can be prepared by treating Compound (IA-a) prepared in Preparation Method 1 with an excess of an acid in the presence of, or in the absence of, a solvent.

Examples of the acid are carboxylic acids such as trifluoroacetic acid; mineral acids such as hydrochloric acid; and sulfonic acids such as trifluoromethanesulfonic acid and benzenesulfonic acid. Among them, trifluoroacetic acid or hydrochloric acid is preferred.

The solvent is not specifically limited and includes, for example, dichloromethane, chloroform, 1,2-dichloroethane, methanol, ethanol, n-propanol, isopropyl alcohol, n-butanol, dimethylformamide, dimethylacetamide, N-methylpyrrolidone, tetrahydrofuran, 2-methyltetrahydrofuran, dioxane, diethyl ether, diisopropyl ether, benzene, toluene, xylene, formic acid and acetic acid. Each of these can be used alone or in combination as a mixture. Among them, dichloromethane is preferred.

The reaction is carried out at temperatures from 0° C. to 100° C. and preferably from 0° C. to 50° C. generally for 10 minutes to twenty-four hours.

Preparation Method 4:

Compound (IA) as prepared by Preparation Method 1 can also be prepared from Compound (IC) prepared by Preparation Method 3 according to the following preparation method:

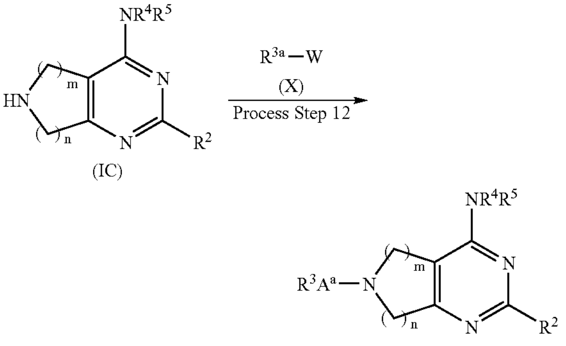

(IC)

(IA)

(wherein $R^2$, $R^3$, $R^{3a}$, $R^4$, $R^5$, $A^a$, W, m and n have the same meanings as defined above, respectively)

[Process Step 12]

Compound (IA) can be prepared by allowing Compound (IC) prepared according to Process Step 11 of Preparation Method 3 to react with Compound (X) in the same way as Process Step 5 of Preparation Method 1. Preferred reaction conditions and how Compound (X) is obtained are as in Process Step 5 of Preparation Method 1.

Preparation Method 5:

Of Compounds (I), Compound (ID), wherein A is a single bond and $R^3$ is $R^{3a}$ (wherein $R^{3a}$ is as defined above), can be prepared, for example, from Compound (IC) prepared according to Process Step 11 of Preparation Method 3 according to the following method:

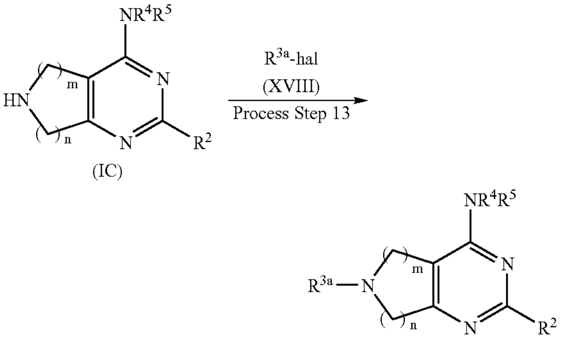

(IC)

(ID)

[wherein $R^2$, $R^{3a}$, $R^4$, $R^5$, m and n have the same meanings as defined above, respectively; and hal represents halogen (the halogen has the same meaning as the halogen (xii) defined above)]

[Process Step 13]

Compound (ID) can be prepared by allowing Compound (IC) prepared according to Process Step 11 of Preparation Method 3 to react with 1 equivalent to excess and preferably 1 equivalent to 5 equivalents of Compound (XVIII) in the presence of 1 equivalent to excess and preferably 1 equivalent to 5 equivalents of a base in a solvent inert to the reaction.

The solvent inert to the reaction is not specifically limited, can be any solvent that is inert to the reaction and includes, for example, dichloromethane, chloroform, 1,2-dichloroethane, dimethylformamide, dimethylacetamide, N-methylpyrrolidone, dimethyl sulfoxide, tetrahydrofuran, dioxane, diethyl ether, diisopropyl ether, benzene, toluene, xylene, ethyl acetate, acetone and pyridine. Each of these can be used alone or in combination as a mixture. Among them, tetrahydrofuran, dimethylformamide or dimethyl sulfoxide is preferred.

Examples of the base are inorganic bases such as potassium carbonate, sodium carbonate, lithium carbonate, potassium phosphate, potassium hydroxide, sodium hydroxide, lithium hydroxide, potassium tert-butoxide, sodium tert-butoxide and sodium methoxide; organic bases such as triethylamine, diisopropylethylamine and DBU; basic anion-exchange resins such as AMBERLYST A-21 (available from Rhom and Haas Company) and AG1-X8 (available from Bio-Rad Laboratories, Inc.); and bases each supported by a solid phase, such as morpholinomethyl polystyrene. Among them, potassium carbonate is preferred.

While the reaction temperature and reaction time vary depending typically on the reactivity of Compound (XVIII), the reaction is generally carried out at temperatures from 0° C. to the boiling point of the solvent and preferably from room temperature to 120° C. for 10 minutes to 100 hours.

When $R^{3a}$ is a substituted or unsubstituted aryl or a substituted or unsubstituted heteroaromatic group in the definition of $R^{3a}$, the reaction can be accelerated by the coexistence of a catalytic amount of a metal complex.

Examples of the metal complex are zerovalent palladium complexes such as tris(dibenzylideneacetone)dipalladium(0) ($Pd_2(dba)_3$); and divalent palladium complexes such as palladium(II) acetate ($Pd(OAc)_2$) in the presence of a ligand such as triphenylphosphine, tributylphosphine or 2,2'-bis(diphenylphosphino)-1,1'-binaphthyl (BINAP).

In this case, the solvent and the base to be used are as above, but the solvent is preferably toluene, xylene or dimethylformamide, and the base is preferably potassium tert-butoxide, sodium tert-butoxide or potassium phosphate.

The reaction is carried out at temperatures from room temperature to 150° C. and preferably from 50° C. to 120° C., generally for 1 hour to 100 hours.

Preparation Method 6:

Of Compounds (I), Compound (IF) having carboxy as substituent in $R^1$, $R^2$ or $R^3$ (wherein the position and the number of the substituted carboxy are not specifically limited but are in accordance with the definitions of the respective groups in $R^1$, $R^2$ or $R^3$) can also be prepared, in addition to the procedure in Preparation Method 1, according to the following method from Compound (IE) having a lower alkoxycarbonyl as a substituent at a corresponding position respectively in $R^1$, $R^2$ or $R^3$ (wherein the lower alkyl moiety of the lower alkoxycarbonyl has the same meaning as the lower alkyls (i), the position and number of the substituted lower alkoxycarbonyl are as in the corresponding carboxy, and when two or more lower alkoxycarbonyls are substituted, the lower alkyl moieties of the lower alkoxycarbonyls may be the same as or different from each other), among Compounds (I) prepared in the same way as Preparation Method 1, Preparation Method 2, Preparation Method 3 or Preparation Method 4.

[Process Step 14]

Compound (IF) can be prepared by treating Compound (IE) prepared by Preparation Method 1, Preparation Method 2 or Preparation Method 4 with a base in an amount of [(the number of substituted lower alkoxycarbonyls in $R^1$, R or $R^3$) times 1] equivalents to excess relative to Compound (IE) in a protic solvent.

Examples of the base are inorganic bases such as potassium carbonate, sodium carbonate, sodium hydrogen carbonate, lithium hydroxide, potassium hydroxide, sodium hydroxide and potassium tert-butoxide; and basic anion-exchange resins such as AMBERLYST A-21 (available from Rohm and Haas Company) and AG1-X8 (available from Bio-Rad Laboratories, Inc.). Among them, sodium hydroxide or AG 1-X8 is preferred.

The protic solvent is not specifically limited and includes, for example, methanol, ethanol, n-propanol, isopropyl alcohol, n-butanol and water. Each of these can be used alone or in combination as a mixture.

The reaction is carried out at temperatures from 0° C. to 100° C. and preferably from 0° C. to 50° C. generally for 10 minutes to 72 hours.

When the corresponding lower alkoxycarbonyl is tert-butoxycarbonyl in Compound (IE), the resulting compound (IF) can be prepared according to the procedure shown in Process Step 11 of Preparation Method 3 instead of the above-mentioned condition. When the corresponding lower alkoxycarbonyls are two or more different lower alkoxycarbonyls, the reaction can also be carried out by an appropriate combination of the above-mentioned two methods.

Preparation Method 7:

Of $R^2$—H (Compounds (XIV)) for use in Process Step 7 or Process Step 10, Compound (XIV-a) represented by:

(XIV-a)

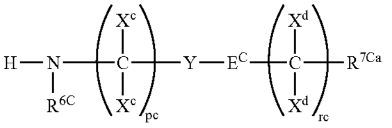

[wherein pc, rc, Y, $E^C$, $X^c$, $X^d$ and $R^{6C}$ have the same meanings as defined above, respectively; and $R^{7Ca}$ represents —$NR^8R^9$ (wherein $R^8$ and $R^9$ have the same meanings as defined above, respectively) or a substituted or unsubstituted heteroalicyclic group combined with the adjacent group at nitrogen atom, in the definition of $R^{7C}$] and Compound (XIV-b) represented by:

(XIV-b)

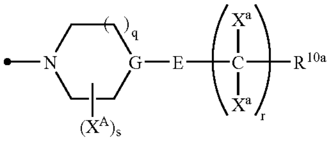

(wherein $R^{10a}$ has the same meaning as $R^{7Ca}$; and q, r, s, $X^A$, $X^a$, G and E have the same meanings as defined above, respectively) can be obtained as commercially available products or prepared, for example, according to a method described in Comprehensive Organic Transformations, second edition, R. C. Larock, John Wiley & Sons Inc. (1999). These compounds can also be prepared by the following method:

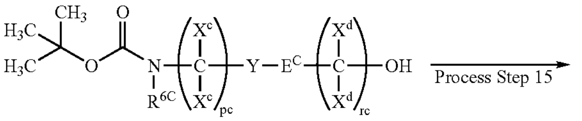

(XIX-a)

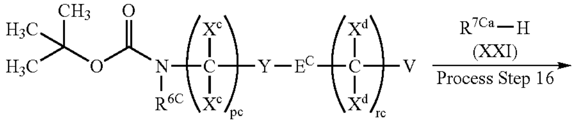

(XX-a)

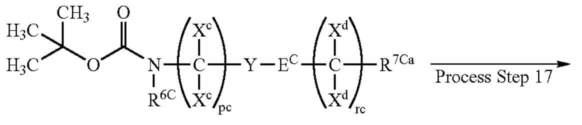

(XXII-a)

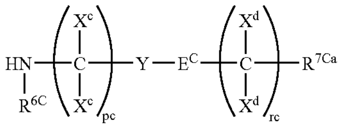

(XIV-a)

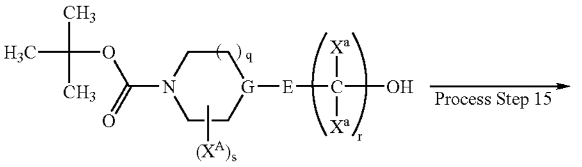

(XIX-b)

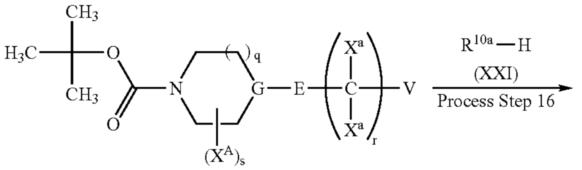

(XX-b)

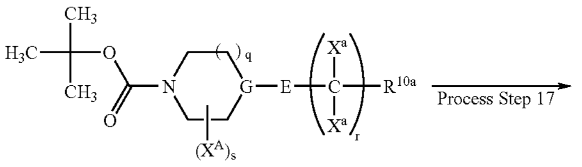

(XXII-b)

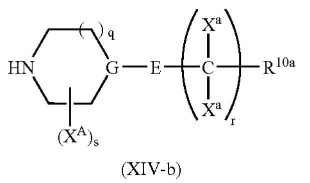

(XIV-b)

{wherein pc, q, r, rc, s, $X^A$, $X^a$, $X^c$, $X^d$, G, E, $E^C$, Y, $R^{6C}$, $R^{7Ca}$ and $R^{10a}$ have the same meanings as defined above, respectively; V represents lower alkylsulfonyloxy (the lower alkyl moiety of the lower alkylsulfonyloxy has the same meaning as the lower alkyl (i) defined above), substituted or unsubstituted arylsulfonyloxy [the aryl moiety of the arylsulfonyloxy has the same meaning as the aryl (v) defined above; and the substituent for the substituted arylsulfonyloxy, which may be the same or different, for example, in number of 1 to 3 include halogen (the halogen has the same meaning as the halogen (xii) defined above) and lower alkyl (the lower alkyl has the same meaning as the lower alkyl (i) defined above] or halogen (wherein the halogen has the same meaning as the halogen (xii) defined above)}

[Process Step 15]

Compound (XX-a) or Compound (XX-b) can be prepared by allowing Compound (XIX-a) or Compound (XIX-b) to react with 1 equivalent to large excess and preferably 1 equivalent to 10 equivalents of a sulfonyl halide or sulfonic anhydride, respectively, in the presence of 1 equivalent to large excess and preferably 1 equivalent to 3 equivalents of a base in a solvent inert to the reaction.

The solvent inert to the reaction is not specifically limited, can be any solvent that is inert to the reaction and includes, for example, tetrahydrofuran, dioxane, diethyl ether, diisopropyl ether, benzene, toluene, xylene, ethyl acetate, acetonitrile, dichloromethane, chloroform, dichloroethane, dimethylformamide, dimethylacetamide-, N-methylpyrrolidone, dimethyl sulfoxide and pyridine. Each of these can be used alone or in combination as a mixture. Among them, dichloromethane is preferred.

Examples of the base are organic bases such as triethylamine, diisopropylethylamine, DBU, N,N-dimethylaniline, pyridine and quinoline; inorganic bases such as potassium carbonate, sodium carbonate, lithium carbonate, sodium hydrogen carbonate, potassium hydroxide, sodium hydroxide, lithium hydroxide and potassium tert-butoxide; basic anion-exchange resins such as AMBERLYST A-21 (available from Rhom and Haas Company) and AG1-X8 (available from Bio-Rad Laboratories, Inc.); and bases supported by a solid phase, such as polyvinylpyridine and morpholinomethyl polystyrene. Among them, triethylamine is preferred.

Examples of the sulfonyl halide are methanesulfonyl chloride, benzenesulfonyl chloride and p-toluenesulfonyl chloride, and examples of the sulfonic anhydride are methanesulfonic anhydride and toluenesulfonic anhydride, of which methanesulfonyl chloride is preferred.

The reaction is carried out at temperatures from 0° C. to 150° C. and preferably from 0° C. to 50° C. generally for 1 hour to 48 hours.

Compound (XIX-a) and Compound (XIX-b) can be obtained as commercially available products or prepared, for example, according to a method described in Comprehensive Organic Transformations, second edition, R. C. Larock, John Wiley & Sons Inc. (1999) or Protective Groups in Organic Synthesis, third edition, T. W. Greene, John Wiley & Sons Inc. (1999).

[Process Step 16]

Compound (XXII-a) or Compound (XXII-b) can be prepared by allowing Compound (XX-a) or Compound (XX-b) prepared according to Process Step 15 to react with 1 equivalent to 10 equivalents and preferably 2 equivalents to 5 equivalents of Compound (XXI), respectively, in the presence of, or in the absence of, 1 equivalent to large excess and preferably 1 equivalent to 10 equivalents of a base in a solvent inert to the reaction.

The solvent inert to the reaction is not specifically limited, can be any solvent that is inert to the reaction and includes, for example, tetrahydrofuran, dioxane, diethyl ether, diisopropyl ether, benzene, toluene, xylene, ethyl acetate, acetonitrile, dichloromethane, chloroform, dichloroethane, dimethylformamide, dimethylacetamide, N-methylpyrrolidone, dimethyl sulfoxide and pyridine. Each of these can be used alone or in combination as a mixture. Among them, tetrahydrofuran, chloroform or a mixture of these solvents is preferred.

Examples of the base are organic bases such as triethylamine, diisopropylethylamine, DBU, N,N-dimethylaniline, pyridine and quinoline; inorganic bases such as potassium carbonate, sodium carbonate, lithium carbonate, sodium hydrogen carbonate, potassium hydroxide, sodium hydroxide, lithium hydroxide and potassium tert-butoxide; basic anion-exchange resins such as AMBERLYST A-21 (available from Rhom and Haas Company) and AG1-X8 (available from Bio-Rad Laboratories, Inc.); and bases supported by a solid phase, such as polyvinylpyridine and morpholinomethyl polystyrene. Among them, polyvinylpyridine is preferred.

The reaction is carried out at temperatures from room temperature to 200° C. and preferably from 50° C. to 100° C. generally for 1 hour to 100 hours.

[Process Step 17]

Compound (XIV-a) or Compound (XIV-b) can be prepared by treating Compound (XXII-a) or Compound (XXII-b) prepared according to Process Step 16 with 1 equivalent to large excess and preferably 1 equivalent to 10 equivalents of an acid in a solvent inert to the reaction.

The solvent inert to the reaction is not specifically limited, can be any solvent that is inert to the reaction and includes, for example, dichloromethane, chloroform, dichloroethane, dimethylformamide, dimethylacetamide, N-methylpyrrolidone, dimethyl sulfoxide, tetrahydrofuran, dioxane, diethyl ether, diisopropyl ether, benzene, toluene, xylene, ethyl acetate, acetonitrile and water. Each of these can be used alone or in combination as a mixture. Among them, dichloromethane is preferred.

Examples of the acid are carboxylic acids such as trifluoroacetic acid; mineral acids such as hydrochloric acid; and sulfonic acids such as trifluoromethanesulfonic acid and benzenesulfonic acid. Among them, trifluoroacetic acid or hydrochloric acid is preferred.

The reaction is carried out at temperatures from 0° C. to 150° C. and preferably from 0° C. to 50° C. generally for about 1 hour to about 48 hours.

Preparation Method 8:

Of Compounds (XIV) for use in Process Step 7 or Process Step 10, Compound (XIV-c) represented by:

(XIV-c)

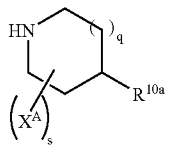

(wherein q, s, $X^A$ and $R^{10a}$ have the same meanings as defined above, respectively) can be prepared, for example, in the same way as Preparation Method 7 or as Journal of Organic Chemistry, vol. 55, No. 8, p. 2552 (1990). The compound can also be prepared, for example, by the following method:

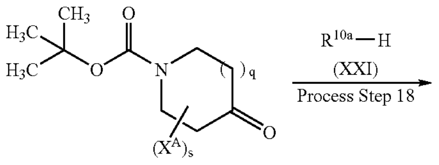

(XXIII)

-continued

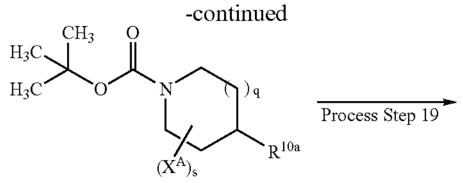

(XXIV)

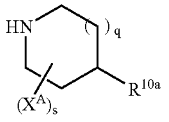

(XIV-c)

(wherein q, s, $X^A$ and $R^{10a}$ have the same meanings as defined above, respectively)

[Process Step 18]

Compound (XXIV) can be obtained as a commercially available product or prepared by allowing Compound (XXIII) to react with 1 equivalent to 10 equivalents of Compound (XXI) in the presence of 1 equivalent to 10 equivalents of a reducing agent and in the presence of, or in the absence of, 1 equivalent to 10 equivalents of a Lewis acid in a solvent inert to the reaction. Compound (XXIII) can be obtained as a commercially available product or prepared according to the method described in Journal of Chemical Society, Perkin Transactions I, p. 641 (1990).

The solvent inert to the reaction is not specifically limited, can be any solvent that is inert to the reaction and includes, for example, dichloromethane, chloroform, dichloroethane, dimethylformamide, dimethylacetamide, N-methylpyrrolidone, dimethyl sulfoxide, tetrahydrofuran, dioxane, diethyl ether, diisopropyl ether, benzene, toluene, xylene, ethyl acetate, acetonitrile and water. Each of these can be used alone or in combination as a mixture. Among them, dichloroethane is preferred.

Examples of the reducing agent are sodium triacetoxyborohydride, sodium borohydride and sodium cyanoborohydride, or any of these reducing agents supported by a solid phase. Among them, sodium triacetoxyborohydride is preferred.

Examples of the Lewis acid are titanium tetraisopropoxide, titanium tetrachloride and boron trifluoride, of which titanium tetraisopropoxide is preferred.

The reaction is carried out at temperatures from 0° C. to 100° C. and preferably from 0° C. to 50° C., generally for 1 hour to 48 hours.

[Process Step 19]

Compound (XIV-c) can be prepared by treating Compound (XXIV) prepared according to Process Step 18 with 1 equivalent to large excess and preferably 1 equivalent to 10 equivalents of an acid in a solvent inert to the reaction.

The solvent inert to the reaction is not specifically limited, can be any solvent that is inert to the reaction and includes, for example, dichloromethane, chloroform, dichloroethane, dimethylformamide, dimethylacetamide, N-methylpyrrolidone, dimethyl sulfoxide, tetrahydrofuran, dioxane, diethyl ether, diisopropyl ether, benzene, toluene, xylene, ethyl acetate, acetonitrile and water. Each of these can be used alone or in combination as a mixture. Among them, dichloromethane is preferred.

Examples of the acid are carboxylic acids such as trifluoroacetic acid; mineral acids such as hydrochloric acid; and sulfonic acids such as trifluoromethanesulfonic acid and benzenesulfonic acid, of which trifluoroacetic acid or hydrochloric acid is preferred.

The reaction is carried out at temperatures from 0° C. to 150° C. and preferably from 0° C. to 50° C., generally for 1 hour to 48 hours.

Preparation Method 9:

Of Compounds (XIV) for use in Process Step 7 or Process Step 10, Compound (XIV-d) represented by:

(XIV-d)

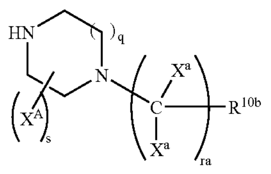

(wherein q, s, $X^A$ and $X^a$ have the same meanings as defined above, respectively; $R^{10b}$ represents substituted or unsubstituted lower alkyl, substituted or unsubstituted cycloalkyl, substituted or unsubstituted lower alkenyl, substituted or unsubstituted lower alkynyl, substituted or unsubstituted aryl, substituted or unsubstituted aralkyl, a substituted or unsubstituted heteroaromatic group, a substituted or unsubstituted heteroalicyclic group, substituted or unsubstituted heteroaromatic-substituted alkyl or substituted or unsubstituted heteroalicyclic-substituted alkyl, in the definition of $R^{10}$; and ra represents an integer of 1 to 4) and Compound (XIV-e) represented by:

(XIV-e)

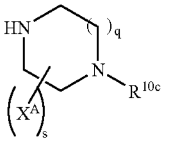

(wherein q, s and $X^A$ have the same meanings as defined above, respectively; and $R^{10c}$ represents substituted or unsubstituted lower alkyl, substituted or unsubstituted lower alkenyl, substituted or unsubstituted lower alkynyl, substituted or unsubstituted aralkyl, substituted or unsubstituted heteroaromatic-substituted alkyl or substituted or unsubstituted heteroalicyclic-substituted alkyl, in the definition of $R^{10}$) can be obtained as commercially available products or prepared, for example, according to the method described in Comprehensive Organic Transformations, second edition, R. C. Larock, John Wiley & Sons Inc. (1999). These compounds can also be prepared, for example, by the following method:

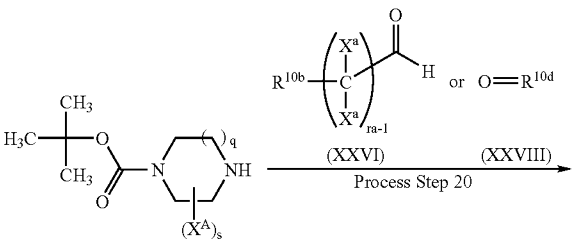

(XXV)

-continued

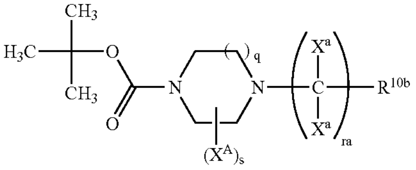

or (XXVII-d)

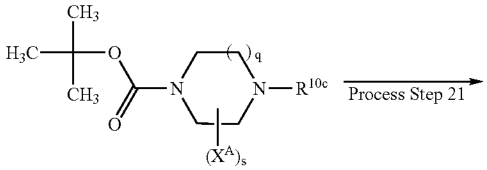

(XXVII-e)

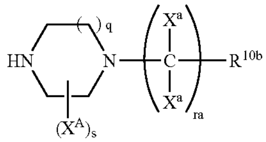

or

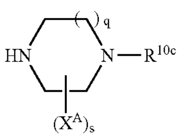

(XIV-d) (XIV-e)

(wherein q, s, ra, $X^A$, $X^a$, $R^{10b}$ and $R^{10c}$ have the same meanings as defined above, respectively; and $R^{10d}$ has the same meaning as the group formed by removing one hydrogen atom on the carbon atom at the bonding site of the respective alkylene moiety in the definition of $R^{10c}$)

[Process Step 20]

Compound (XXVII-d) or Compound (XXVII-e) can be prepared by allowing Compound (XXV) to react with 1 equivalent to 5 equivalents of Compound (XXVI) or Compound (XXVIII), respectively, in the presence of 1 equivalent to 10 equivalents of a reducing agent in a solvent inert to the reaction.

The solvent inert to the reaction is not specifically limited, can be any solvent that is inert to the reaction and includes, for example, dichloromethane, chloroform, dichloroethane, tetrahydrofuran, dioxane, diethyl ether, diisopropyl ether, benzene, toluene and xylene. Each of these can be used alone or in combination as a mixture. Among them, dichloroethane is preferred.

Examples of the reducing agent are sodium triacetoxyborohydride, sodium borohydride and sodium cyanoborohydride or any of these reducing agents supported by a solid phase, of which sodium triacetoxyborohydride is preferred.

The reaction is carried out at temperatures from 0° C. to 100° C. and preferably from 0° C. to 50° C., generally for 1 hour to 48 hours.

Compound (XXV) can be obtained as a commercially available product or prepared, for example, according to a method described in Comprehensive Organic Transformations, second edition, R. C. Larock, John Wiley & Sons Inc. (1999) or Protective Groups in Organic Synthesis, third edition, T. W. Greene, John Wiley & Sons Inc. (1999).

[Process Step 21]

Compound (XIV-d) or Compound (XIV-e) can be prepared by treating Compound (XXVII-d) or Compound (XXVII-e) prepared according to Process Step 20, respectively, with 1 equivalent to large excess and preferably 1 equivalent to 10 equivalents of an acid in a solvent inert to the reaction.

The solvent inert to the reaction is not specifically limited, can be any solvent that is inert to the reaction and includes, for example, dichloromethane, chloroform, dichloroethane, dimethylformamide, dimethylacetamide, N-methylpyrrolidone, dimethyl sulfoxide, tetrahydrofuran, dioxane, diethyl ether, diisopropyl ether, benzene, toluene, xylene, ethyl acetate, acetonitrile and water. Each of these can be used alone or in combination as a mixture. Among them, dichloromethane is preferred.

Examples of the acid are carboxylic acids such as trifluoroacetic acid; mineral acids such as hydrochloric acid; and sulfonic acids such as trifluoromethanesulfonic acid and benzenesulfonic acid, of which trifluoroacetic acid or hydrochloric acid is preferred.

The reaction is carried out at temperatures from 0° C. to 150° C. and preferably from 0° C. to 50° C., generally for 1 hour to 48 hours.

Preparation Method 10:

Of Compounds (XIV) for use in Process Step 7 or Process Step 10, Compound (XIV-f) represented by:

(XIV-f)

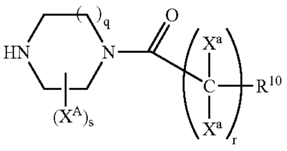

(wherein q, r, s, $X^A$, $X^a$ and $R^{10}$ have the same meanings as defined above, respectively) can be obtained as a commercially available product or prepared, for example, according to a method described in Comprehensive Organic Transformations, second edition, R. C. Larock, John Wiley & Sons Inc. (1999). The compound can also be prepared, for example, by the following method:

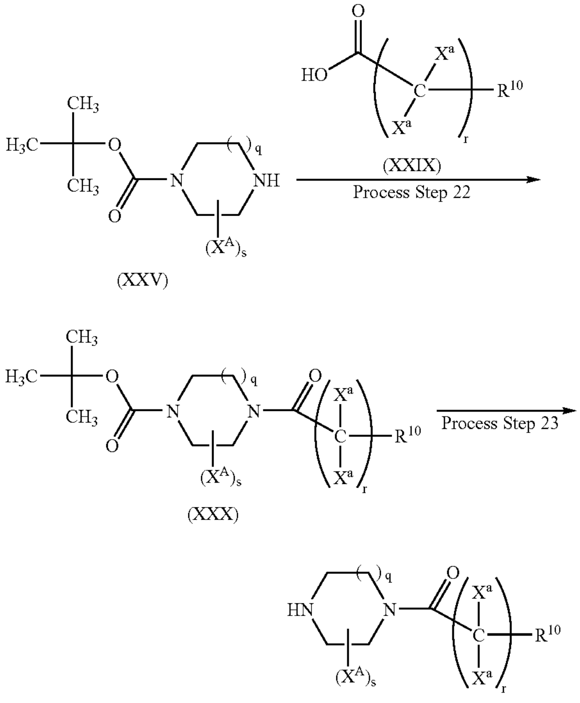

(XXV) (XXIX) (XXX) (XIV-f)

(wherein q, r, s, $X^A$, $X^a$ and $R^{10}$ have the same meanings as defined above, respectively)

[Process Step 22]

Compound (XXX) can be prepared by allowing Compound (XXV) to react with 1 to 5 equivalents of Compound (XXIX) in the presence of 1 to 10 equivalents of a condensing agent in a solvent inert to the reaction.

Examples of the condensing agent are dicyclohexylcarbodiimide, diisopropylcarbodiimide, N-ethyl-N'-(3-dimethylaminopropyl)carbodiimide or a hydrochloride thereof, N-ethyl-N'-(3-dimethylaminopropyl)carbodiimide supported by polystyrene, N-benzyl-N'-cyclohexylcarbodiimide supported by polystyrene, benzotriazol-1-yloxytris(dimethylamino)phosphonium hexafluorophosphate and diphenylphosphorylazide. Among them, N-ethyl-N'-(3-dimethylaminopropyl)carbodiimide or a hydrochloride thereof, or N-ethyl-N'-(3-dimethylaminopropyl)carbodiimide supported by polystyrene is preferred.

This reaction is carried out appropriately in the coexistence of 1 to 5 equivalents of an additive. Examples of the additive are N-hydroxysuccinimide, 1-hydroxybenzotriazole and 3-hydroxy-4-oxo-3,4-dihydro-1,2,3-benzotriazine, of which 1-hydroxybenzotriazole is preferred.

The solvent inert to the reaction is not specifically limited, can be any solvent that is inert to the reaction and includes, for example, dichloromethane, chloroform, dichloroethane, dimethylformamide, dimethylacetamide, N-methylpyrrolidone, dimethyl sulfoxide, tetrahydrofuran, 2-methyltetrahydrofuran, dioxane, diethyl ether, benzene, toluene, xylene, ethyl acetate and acetonitrile. Each of these can be used alone or in combination as a mixture. Among them, chloroform, tetrahydrofuran, or a mixture of these solvents is preferred.

The reaction is carried out at temperatures from 0° C. to 150° C. and preferably from room temperature to 80° C., generally for 1 to 120 hours.

Compound (XXIX) can be obtained as a commercially available product or prepared, for example, according to a method described in Comprehensive Organic Transformations, second edition, R. C. Larock, John Wiley & Sons Inc. (1999).

[Process Step 23]

Compound (XIV-f) can be prepared by treating Compound (XXX) prepared according to Process Step 22 with 1 equivalent to large excess and preferably 1 equivalent to 10 equivalents of an acid in a solvent inert to the reaction.

The solvent inert to the reaction is not specifically limited, can be any solvent that is inert to the reaction and includes, for example, dichloromethane, chloroform, dichloroethane, dimethylformamide, dimethylacetamide, N-methylpyrrolidone, dimethyl sulfoxide, tetrahydrofuran, dioxane, diethyl ether, diisopropyl ether, benzene, toluene, xylene, ethyl acetate, acetonitrile and water. Each of these can be used alone or in combination as a mixture. Among them, dichloromethane is preferred.

Examples of the acid are carboxylic acids such as trifluoroacetic acid; mineral acids such as hydrochloric acid; and sulfonic acids such as trifluoromethanesulfonic acid and benzenesulfonic acid, of which trifluotoacetic acid or hydrochloric acid is preferred.

The reaction is carried out at temperatures from 0° C. to 150° C. and preferably from 0° C. to 50° C., generally for 1 hour to 48 hours.

Preparation Method 11:

Of Compounds (XIV) for use in Process Step 7 or Process Step 10, Compound (XIV-g) represented by:

(XIV-g)

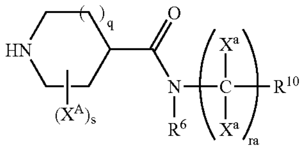

(wherein q, ra, s, $X^A$, $X^a$, $R^6$ and $R^{10}$ have the same meanings as defined above, respectively) and Compound (XIV-h) represented by:

(XIV-h)

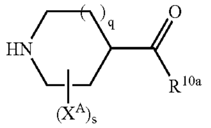

(wherein q, s, $X^A$ and $R^{10a}$ have the same meanings as defined above, respectively) can be obtained as commercially available products or prepared, for example, according to a method described in Comprehensive Organic Transformations, second edition, R. C. Larock, John Wiley & Sons Inc. (1999). These compounds can also be prepared, for example, by the following method:

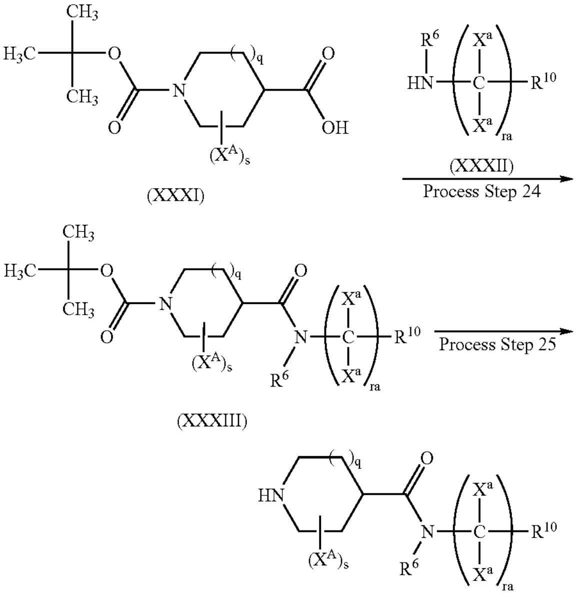

(XXXI) (XXXII) (XXXIII) (XIV-g)

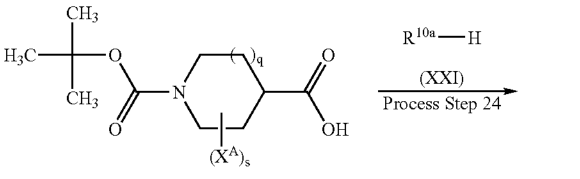

(XXXI) (XXI)

-continued

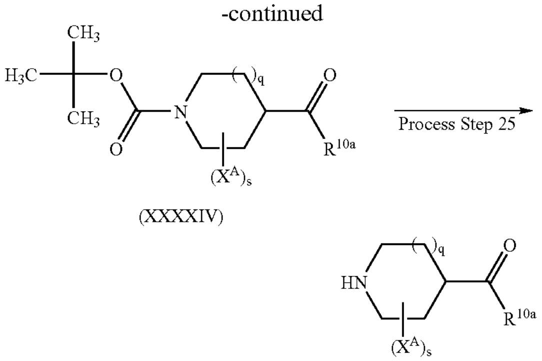

(XXXXIV) (XIV-h)

(wherein q, r, ra, s, $X^A$, $X^a$, $R^6$, $R^{10a}$ and $R^{10}$ have the same meanings as defined above, respectively)

[Process Step 24]

Compound (XXXIII) or Compound (XXXXIV) can be prepared by allowing Compound (XXXI) to react with 1 to 5 equivalents of Compound (XXXII) or Compound (XXI), respectively, in the presence of 1 to 10 equivalents of a condensing agent in a solvent inert to the reaction.

Examples of the condensing agent are dicyclohexylcarbodiimide, diisopropylcarbodiimide, N-ethyl-N'-(3-dimethylaminopropyl)carbodiimide or a hydrochloride thereof, N-ethyl-N'-(3-dimethylaminopropyl)carbodiimide supported by polystyrene, N-benzyl-N'-cyclohexylcarbodiimide supported by polystyrene, benzotriazol-1-yloxytris(dimethylamino)phosphonium hexafluorophosphate and diphenylphosphorylazide. Among them, N-ethyl-N'-(3-dimethylaminopropyl)carbodiimide or a hydrochloride thereof, or N-ethyl-N'-(3-dimethylaminopropyl)carbodiimide supported by polystyrene is preferred.

This reaction is appropriately carried out in the coexistence of 1 to 5 equivalents of an additive. Examples of the additive are N-hydroxysuccinimide, 1-hydroxybenzotriazole and 3-hydroxy-4-oxo-3,4-dihydro-1,2,3-benzotriazine, of which 1-hydroxybenzotriazole is preferred.

The solvent inert to the reaction is not specifically limited, can be any solvent that is inert to the reaction and includes, for example, dichloromethane, chloroform, dichloroethane, dimethylformamide, dimethylacetamide, N-methylpyrrolidone, dimethyl sulfoxide, tetrahydrofuran, 2-methyltetrahydrofuran, dioxane, diethyl ether, benzene, toluene, xylene, ethyl acetate and acetonitrile. Each of these can be used alone or in combination as a mixture. Among them, chloroform, tetrahydrofuran or a mixture of these solvents is preferred.

The reaction is carried out at temperatures from 0° C. to 150° C. and preferably from room temperature to 80° C., generally for 1 to 120 hours.

Compound (XXXI) and Compound (XXXII) can be obtained as commercially available products or prepared, for example, according to a method described in Comprehensive Organic Transformations, second edition, R. C. Larock, John Wiley & Sons Inc. (1999) or Protective Groups in Organic Synthesis, third edition, T. W. Greene, John Wiley & Sons Inc. (1999).

[Process Step 25]

Compound (XIV-g) or Compound (XIV-h) can be prepared by treating Compound (XXXIII) or Compound (XXXXIV) prepared according to Process Step 24, respectively, with 1 equivalent to large excess and preferably 1 equivalent to 10 equivalents of an acid in a solvent inert to the reaction.

The solvent inert to the reaction is not specifically limited, can be any solvent that is inert to the reaction and includes, for example, dichloromethane, chloroform, dichloroethane, dimethylformamide, dimethylacetamide, N-methylpyrrolidone, dimethyl sulfoxide, tetrahydrofuran, dioxane, diethyl ether, diisopropyl ether, benzene, toluene, xylene, ethyl acetate, acetonitrile and water. Each of these can be used alone or in combination as a mixture. Among them, dichloromethane is preferred.

Examples of the acid are carboxylic acids such as trifluoroacetic acid; mineral acids such as hydrochloric acid; and sulfonic acids such as trifluoromethanesulfonic acid and benzenesulfonic acid, of which trifluoroacetic acid or hydrochloric acid is preferred.

The reaction is carried out at temperatures from 0° C. to 150° C. and preferably from 0° C. to 500° C., generally for 1 hour to 48 hours.

Preparation Method 12:

Compound (XXVII-d) as an intermediate in the synthesis of Compound (XIV-d) in Preparation Method 9 can also be synthetically prepared by the following method:

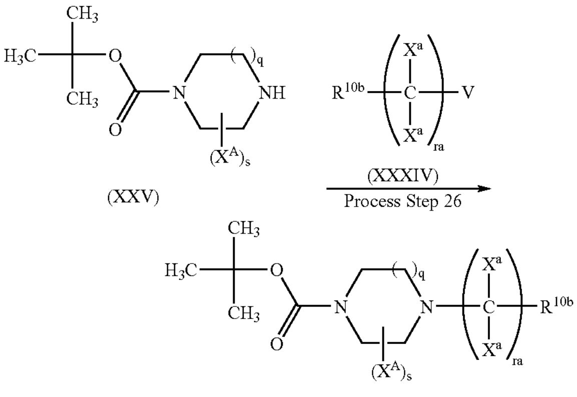

(XXVII-d)

(wherein q, s, ra, V, $X^A$, $X^a$ and $R^{10b}$ have the same meanings as defined above, respectively)

[Process Step 26]

Compound (XXVII-d) can be prepared by allowing Compound (XXV) to react with 1 equivalent to 10 equivalents and preferably 1 equivalent to 5 equivalents of Compound (XXXIV) in the presence of, or in the absence of, 1 equivalent to large excess and preferably 1 equivalent to 10 equivalents of a base in a solvent inert to the reaction, by the procedure of Process Step 16 of Preparation Method 7.

Compound (XXXIV) can be obtained as a commercially available product or prepared, for example, according to a method described in Comprehensive Organic Transformations, second edition, R. C. Larock, John Wiley & Sons Inc. (1999) or Protective Groups in Organic Synthesis, third edition, T. W. Greene, John Wiley & Sons Inc. (1999).

Preparation Method 13:

Of Compounds (XIV) for use in Process Step 7 or Process Step 10, Compound (XIV-i) represented by:

(XIV-i)

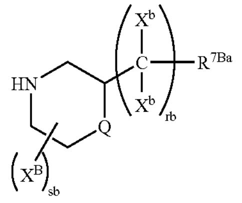

(wherein rb, sb, Q, $X^B$ and $X^b$ have the same meanings as defined above, respectively; and $R^{7Ba}$ has the same meaning as $R^{7Ca}$ defined above) can be obtained as a commercially available product or prepared, for example, according to a method described in Comprehensive Organic Transformations, second edition, R. C. Larock, John Wiley & Sons Inc. (1999). The compound can also be prepared, for example, by the following method:

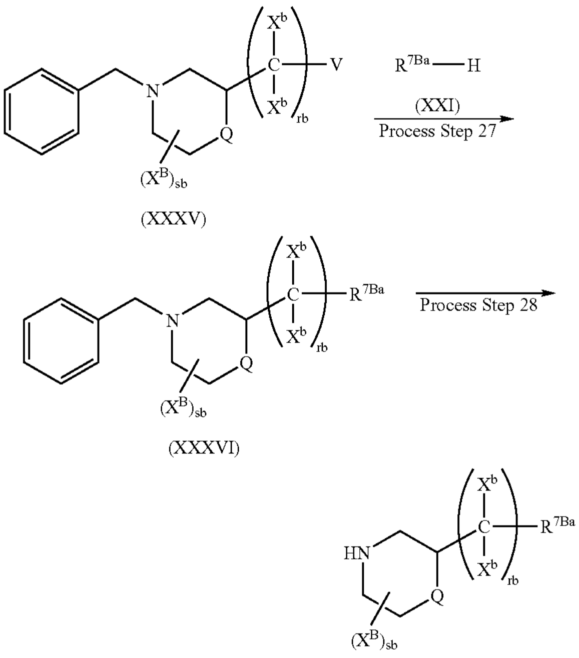

(wherein rb, sb, V, Q, $X^B$, $X^b$ and $R^{7Ba}$ have the same meanings as defined above, respectively)

[Process Step 27]

Compound (XXXVI) can be prepared by allowing Compound (XXXV) to react with 1 equivalent to large excess and preferably 1 equivalent to 10 equivalents of Compound (XXI) in the presence of, or in the absence of, 1 equivalent to large excess and preferably 1 equivalent to 3 equivalents of a base in a solvent inert to the reaction in the same way as Process Step 16 of Preparation Method 7.

Compound (XXXV) can be prepared, for example, according to a method described in Journal of Medicinal Chemistry, vol. 33, p. 1406 (1990) or Comprehensive Organic Transformations, second edition, R. C. Larock, John Wiley & Sons Inc. (1999). Alternatively, Compound (XXXV) can be introduced from the following compound (XXXVII):

(XXXVII)

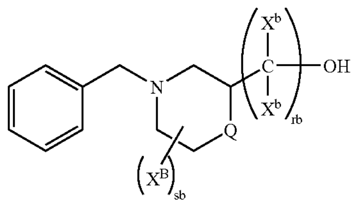

in the same way as Process Step 15 of Preparation Method 7. Compound (XXXVII) herein can be prepared by the method described in above-mentioned literatures or in a manner similar to the method.

[Process Step 28]

Compound (XIV-i) can be prepared from Compound (XXXVI) prepared according to Process-Step 27, for example, according to a method described in Protective Groups in Organic Synthesis, third edition, pp. 579-580, T. W. Greene, John Wiley & Sons Inc. (1999).

Preparation Method 14:

Of Compounds (XIV) for use in Process Step 7 or Process Step 10, Compound (XIV-j) represented by:

(XIV-j)

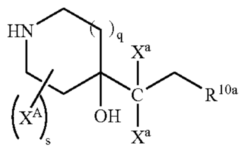

(wherein q, s, $X^a$, $X^A$ and $R^{10a}$ have the same meanings as defined above, respectively) can be obtained as a commercially available product or prepared, for example, according to a method described in Comprehensive Organic Transformations, second edition, R. C. Larock, John Wiley & Sons Inc. (1999). The compound can also be prepared, for example, by the following method:

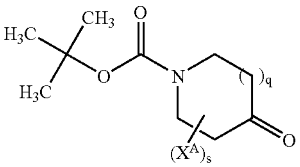

(XXIII)

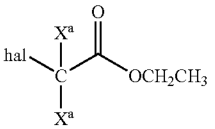

(XXXVIII)

Process Step 29

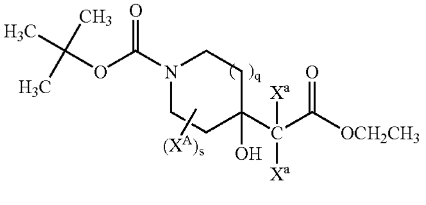

(XXXIX)

Process Step 30

-continued

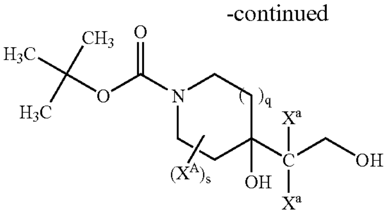

(XXXX)

Process Step 31

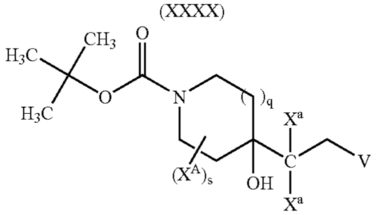

(XXXXI)

$R^{10a}$—H (XXI)

Process Step 32

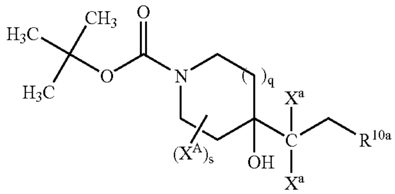

(XXXXII)

Process Step 33

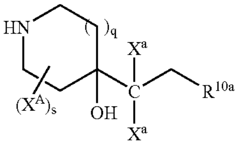

(XIV-j)

(wherein q, s, $X^A$, $X^a$, $R^{10a}$, V and hal have the same meanings as defined above, respectively)

[Process. Step 29]

Compound (XXXIX) can be prepared by allowing Compound (XXIII) to react with 1 equivalent to 10 equivalents of Compound (XXXVIII) in the presence of 1 equivalent to 10 equivalents of zinc in a solvent inert to the reaction. Compound (XXIII) can be obtained as a commercially available product or prepared, for example, according to a method described in Journal of Chemical Society Perkin Transactions I, p. 641 (1990).

The solvent inert to the reaction is not specifically limited, can be any solvent that is inert to the reaction and includes, for example, dimethylformamide, dimethylacetamide, N-methylpyrrolidone, tetrahydrofuran, 2-methyltetrahydrofuran, dioxane, diethyl ether, benzene, toluene and xylene. Each of these can be used alone or in combination as a mixture. Among them, tetrahydrofuran is preferred.

The reaction is carried out at temperatures from 0° C. to the boiling point of the solvent and preferably from room temperature to the boiling point of the solvent, generally for 1 to 120 hours.

Compound (XXXVIII) can be obtained as a commercially available product or prepared, for example, according to a method described in Comprehensive Organic Transformations, second edition, R. C. Larock, John Wiley & Sons Inc. (1999) or Protective Groups in Organic Synthesis, third edition, T. W. Greene, John Wiley & Sons Inc. (1999).

[Process Step 30]

Compound (XXXX) can be prepared by treating Compound (XXXIX) prepared according to Process Step 29 with 1 equivalent to 10 equivalents of a reducing agent in a solvent inert to the reaction.

Examples of the reducing agent are lithium aluminum hydride, diborane and various complexes thereof. The solvent inert to the reaction is not specifically limited, can be any solvent that is inert to the reaction and includes, for example, tetrahydrofuran, 2-methyltetrahydrofuran, dioxane, diethyl ether, benzene, toluene and xylene. Each of these can be used alone or in combination as a mixture. Among them, tetrahydrofuran is preferred.

The reaction is carried out at temperatures from −80° C. to the boiling point of the solvent and preferably from 0° C. to room temperature, generally for 10 minutes to 10 hours.

The conversion can also be carried out, for example, according to a method described in Comprehensive Organic Transformations, second edition, R. C. Larock, John Wiley & Sons Inc. (1999), instead of the above-mentioned reaction conditions.

[Process Step 31]

Compound (XXXXI) can be prepared by allowing Compound (XXXX) prepared according to Process Step 30 to react with 1 equivalent to large excess and preferably 1 equivalent to 10 equivalents of a sulfonyl halide or sulfonic anhydride in the presence of, or in the absence of, 1 equivalent to large excess and preferably 1 equivalent to 3 equivalents of a base in a solvent inert to the reaction in the same way as Process Step 15 of Preparation Method 7.

[Process Step 32]

Compound (XXXXII) can be prepared by allowing Compound (XXXXI) prepared according to Process Step 31 to react with 1 equivalent to 10 equivalents and preferably 2 equivalents to 5 equivalents of Compound (XXI) in the presence of, or in the absence of, 1 equivalent to large excess and preferably 1 equivalent to 10 equivalents of a base in a solvent inert to the reaction in the same way as Process Step 16 of Preparation Method 7.

[Process Step 33]

Compound (XIV-j) can be prepared by treating Compound (XXXXII) prepared according to Process Step 32 with 1 equivalent to large excess and preferably 1 equivalent to 10 equivalents of an acid in a solvent inert to the reaction in the same way as Process Step 17 of Preparation Method 7.

Preparation Method 15:

Target Compounds (I) can be obtained as Compound (IA), (IB), (IC), (ID), (IE) and (IF) prepared in Preparation Methods 1 to 6 or, alternatively, be prepared from compounds prepared in a manner similar to the preparation methods by further converting a functional group in R in the same way as the preparation methods of Compounds (VIV-a), (VIV-b), (VIV-c), (VIV-d), ((VIV-e), (VIV-f), (VIV-g), (VIV-h), (VIV-i) and (VIV-j) and intermediates thereof in Preparation Methods 7 to 14.

Of Compounds (I), for example, a compound wherein $R^2$ is:

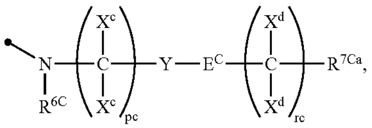

-continued

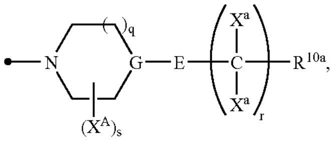

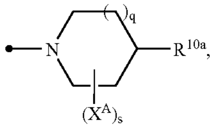

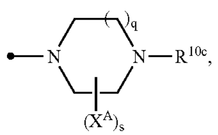

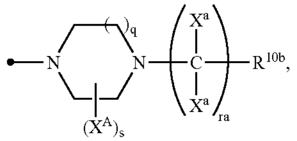

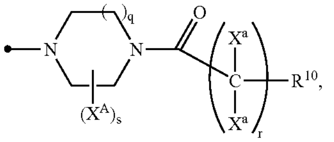

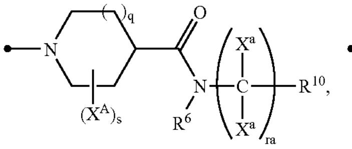

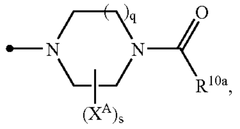

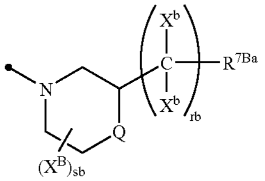

(wherein $R^6$, $R^{6C}$, $R^{7Ba}$, $R^{7Ca}$, $R^{10}$, $R^{10a}$, $R^{10b}$, $R^{10c}$, $X^A$, $X^B$, $X^a$, $X^b$, $X^c$, $X^d$, Y, $E^C$, G, E, Q, pc, q, r, ra, rb, rc, s and sb have the same meanings as defined above, respectively) can be prepared from Compound (A) represented by:

(A)

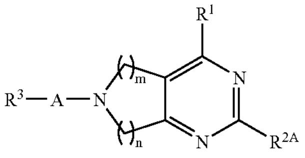

[wherein $R^1$, $R^3$, A, n and m have the same meanings as defined above, respectively; and $R^{2A}$ represents, for example:

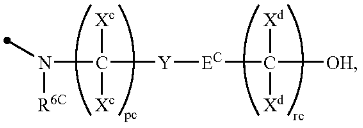

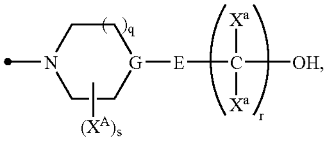

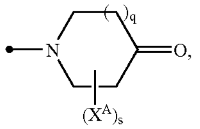

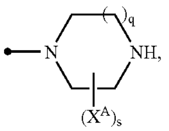

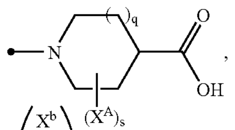

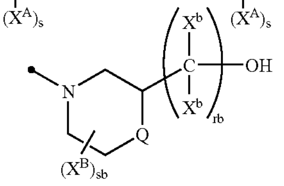

(wherein $R^{6C}$, $X^{A}$, $X^{B}$, $X^{a}$, $X^{b}$, $X^{c}$, $X^{d}$, Y, $E^{C}$, G, E, Q, pc, q, r, rb, rc, sand sb have the same meanings as defined above, respectively)], in the same way as, for example, Process Steps 15 and 16, 18, 20, 22, 24, 26 and 27 of Preparation Methods 7 to 13.

Compound (A) for use in Preparation Method 12 can be obtained as any of Compounds (IA), (IB), (IC), (ID), (IE) and (IF) described in Preparation Methods 1 to 6 or prepared in a manner similar to these preparation methods.

Compound (A), for example, can be prepared from Compound (XXXXIII) which is prepared in the same way as Process Step 6 of Preparation Method 1 or Process Step 9 of Preparation Method 2, and $R^{2A}$—H (wherein $R^{2A}$ is as defined above) in the same way as Process Step 7 of Preparation Method 1:

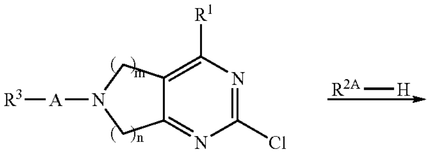

(XXXXIII)

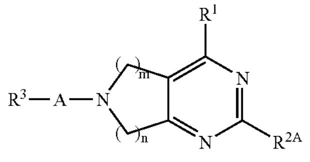

(A)

(wherein $R^{1}$, $R^{2A}$, $R^{3}$, A, m and n have the same meanings as defined above, respectively)

Preferred reaction conditions and how $R^{2A}$—H is available are similar to the conditions and how Compound (XIV) is available, respectively, described in Process Step 7 of Preparation Method 1.

Of Compounds (I), for example, Compound (IM), wherein G is nitrogen atom; E is a single bond; r is 0; and $R^{10}$ is hydrogen atom, can be prepared from Compound (IR), wherein G is nitrogen atom; E is —C(═O)O—; r is 0; and $R^{10}$ is tert-butyl among Compounds (I), in the same way as Process Step 21 of Preparation Method 9:

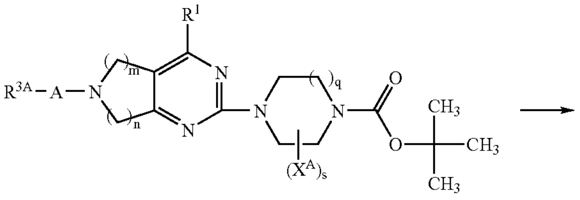

(IR)

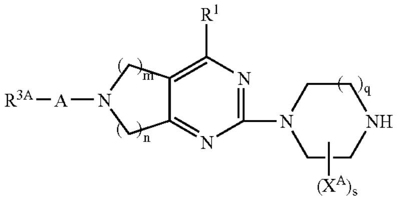

(IM)

(wherein $R^{2}$, $R^{3A}$, A, $X^{A}$, m, n, q and s have the same meanings as defined above, respectively)

The conversion of respective functional groups in Compounds (I) and starting material and the conversion of functional groups contained in the substituents can also be carried out, for example, any other methods than the above-mentioned process steps, such as a method described in Comprehensive Organic Transformations, second edition, R. C. Larock, John Wiley & Sons Inc. (1999).

Compounds (I) each having one or more desired functional groups at desired positions can be prepared by carrying out, for example, a suitable combination of the above-mentioned methods or procedures.

The intermediates and products in the above-mentioned preparation methods can be isolated and purified, for example, according to any suitable combination of procedures generally used in organic syntheses, such as filtration, extraction, washing, drying, concentration, crystallization and various chromatography. Further, a purification procedure generally used in regular parallel synthesis methods including combinatorial chemistry, such as a procedure using a resin such as an ion-exchange resin can also be employed. Examples of the ion-exchange resin are scavenger resins including benzoyl chloride polymer-bound, poly-4-vinylpyridine, benzaldehyde polymer-bound and trityl chloride polymer-bound, such as AG 1-X8 OH-resin (available from Bio-Rad Laboratories, Inc.). The intermediates can also be subjected to a subsequent reaction without purification.

In the above-mentioned preparation methods, some of starting material and intermediates may exist in the form of a salt such as hydrochloride under some reaction conditions. Such salts can be used as intact or as a free compound. To use or obtain a starting material or intermediate in the form of a salt, a salt of the starting material or intermediate as obtained can be used or obtained as intact. When the starting material or intermediate is prepared in the form of a salt but should be used or obtained as a free compound, the salt can be converted into a free compound by dissolving or suspending the salt in an appropriate solvent and then neutralizing the same with, for example, a base such as an aqueous solution of sodium hydrogen carbonate.

In some of Compounds (I), there can be isomers such as regioisomers, geometrical isomers or optical isomers. All possible isomers including these isomers, and mixtures of the isomers in any proportions are within the scope of the present invention.

To obtain a salt of any of Compounds (I), the salt, if prepared, can be purified as intact. When Compound (I) is prepared in the form of a free compound, the corresponding salt can be obtained, for example, by dissolving or suspending Compound (I) in an appropriate solvent and adding an acid or a base thereto to thereby form the salt.

Some of Compounds (I) or pharmacologically acceptable salts thereof may exist in the form of adducts with water or solvents. These adducts are also within the scope of the present invention.

Specific examples of Compounds (I) are shown in Tables 1 to 25. The compounds of the present invention, however, are not limited to these compounds.

TABLE 1
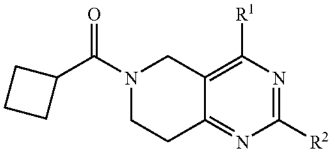
| Compound Number | •—$R^1$ | •—$R^2$ | Spectrum Data |
|---|---|---|---|
| 1-1 | 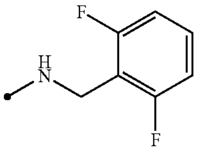 | 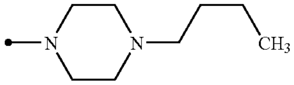 | MS m/z 499 $(M + H)^+$ |
| 1-2 | 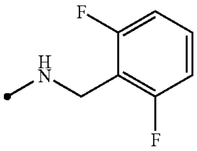 | 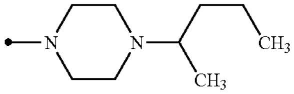 | MS m/z 513 $(M + H)^+$ |
| 1-3 | 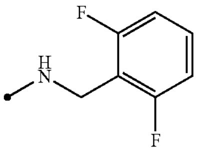 | 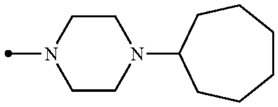 | MS m/z 539 $(M + H)^+$ |
| 1-4 | 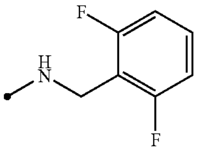 | 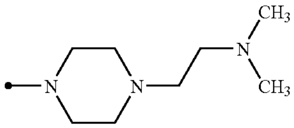 | MS m/z 514 $(M + H)^+$ |
| 1-5 | 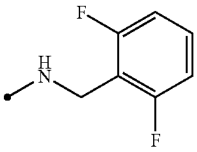 | 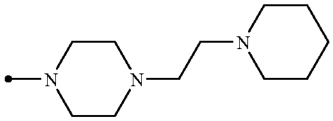 | MS m/z 554 $(M + H)^+$ |
| 1-6 | 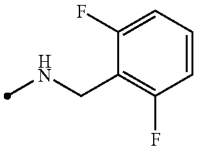 | 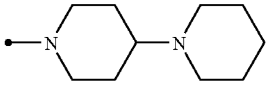 | MS m/z 525 $(M + H)^+$ |
| 1-7 | 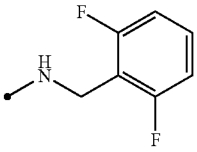 | 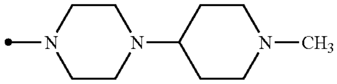 | MS m/z 540 $(M + H)^+$ |

TABLE 2
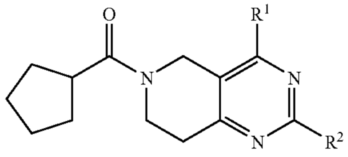
| Compound Number | •—$R^1$ | •—$R^2$ | Spectrum Data |
|---|---|---|---|
| 2-1 | 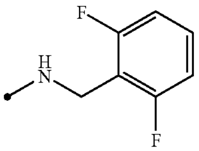 | 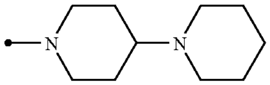 | MS m/z 539 $(M + H)^+$ |
| 2-2 | 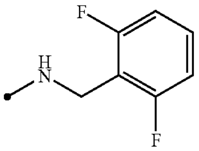 | 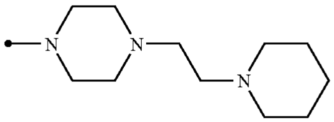 | MS m/z 568 $(M + H)^+$ |
| 2-3 | 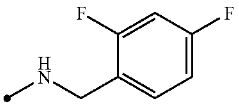 | 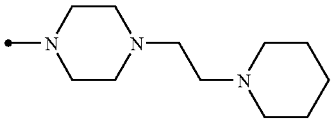 | MS m/z 568 $(M + H)^+$ |
| 2-4 | 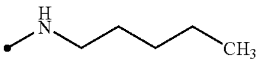 | 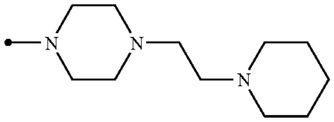 | MS m/z 512 $(M + H)^+$ |
TABLE 3
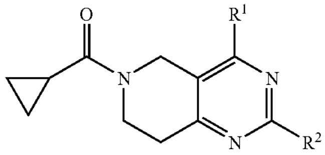
| Compound Number | •—$R^1$ | •—$R^2$ | Spectrum Data |
|---|---|---|---|
| 3-1 | 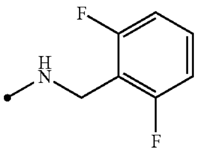 | 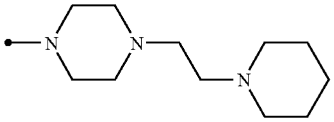 | MS m/z 540 $(M + H)^+$ |
| 3-2 | 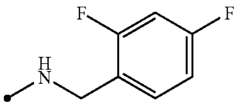 | 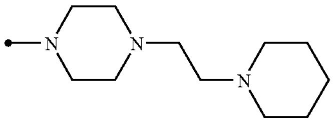 | MS m/z 540 $(M + H)^+$ |
| 3-3 | 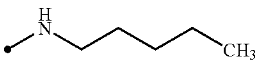 | 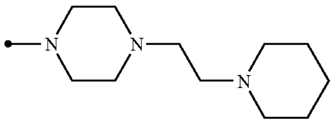 | MS m/z 484 $(M + H)^+$ |

TABLE 3-continued
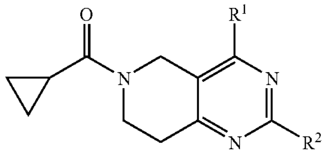
| Compound Number | •—$R^1$ | •—$R^2$ | Spectrum Data |
|---|---|---|---|
| 3-4 | 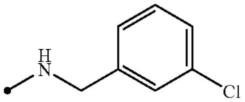 | 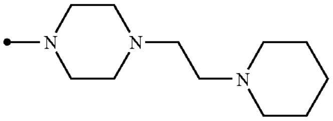 | MS m/z 538 $(M + H)^+$ |
| 3-5 | 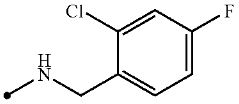 | 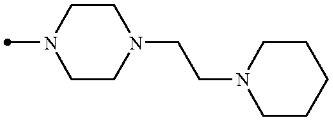 | MS m/z 556 $(M + H)^+$ |
| 3-6 | 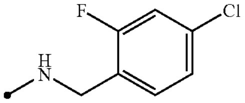 | 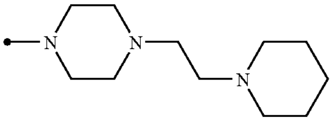 | MS m/z 556 $(M + H)^+$ |
| 3-7 | 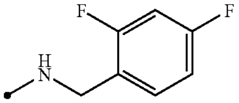 | 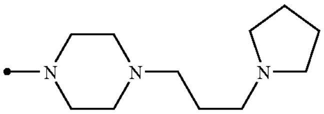 | MS m/z 540 $(M + H)^+$ |
| 3-8 | 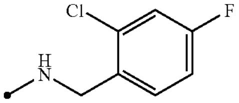 | 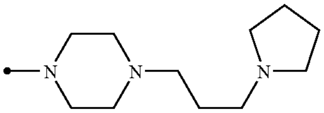 | MS m/z 556 $(M + H)^+$ |
| 3-9 | 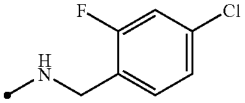 | 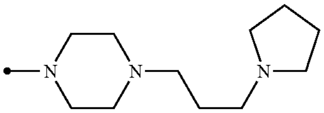 | MS m/z 556 $(M + H)^+$ |
| 3-10 | 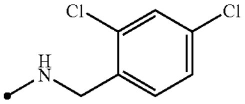 | 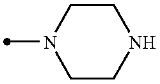 | MS m/z 461 $(M + H)^+$ |
| 3-11 | 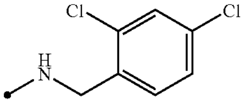 | 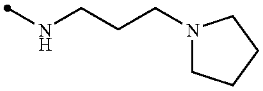 | MS m/z 503 $(M + H)^+$ |
| 3-12 | 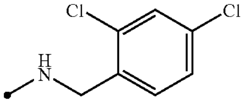 | 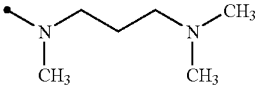 | MS m/z 491 $(M + H)^+$ |
| 3-13 | 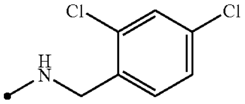 | 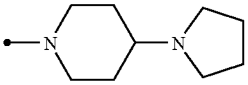 | MS m/z 529 $(M + H)^+$ |
| 3-14 | 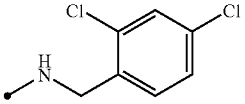 | 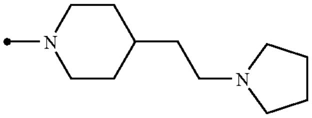 | MS m/z 577 $(M + H)^+$ |

TABLE 3-continued
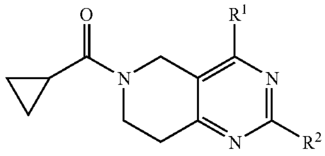
| Compound Number | •—$R^1$ | •—$R^2$ | Spectrum Data |
|---|---|---|---|
| 3-15 | 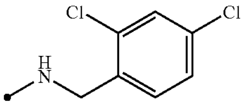 | 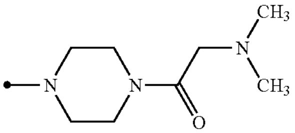 | MS m/z 546 $(M + H)^+$ |
| 3-16 | 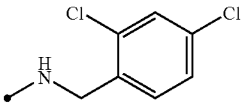 | 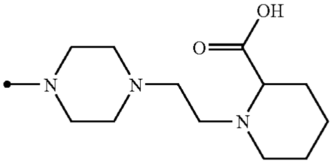 | MS m/z 616 $(M + H)^+$ |
| 3-17 | 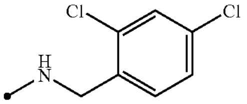 | 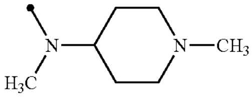 | MS m/z 503 $(M + H)^+$ |
| 3-18 | 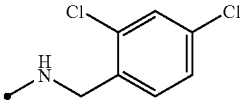 | 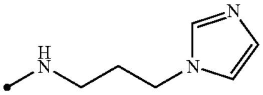 | MS m/z 500 $(M + H)^+$ |
| 3-19 | 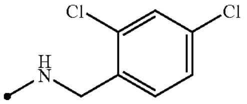 | 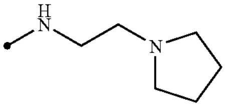 | MS m/z 489 $(M + H)^+$ |
| 3-20 | 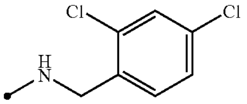 | 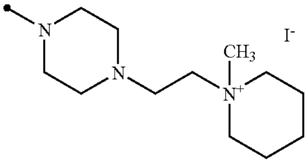 | MS m/z 586 $M^+$ |
| 3-21 | 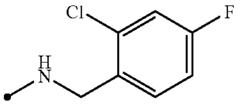 | 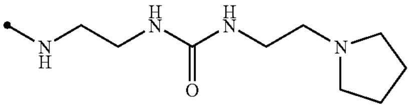 | MS m/z 557 $(M + H)^-$ |
| 3-22 | 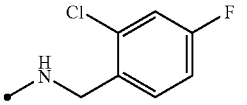 | 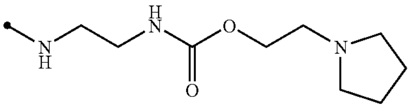 | MS m/z 560 $(M + H)^+$ |
| 3-23 | 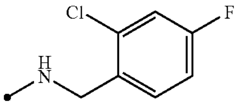 | 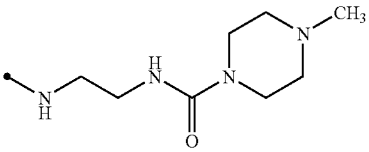 | MS m/z 545 $(M + H)^+$ |

TABLE 3-continued
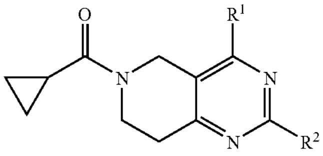
| Compound Number | •—$R^1$ | •—$R^2$ | Spectrum Data |
|---|---|---|---|
| 3-24 | 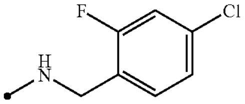 | 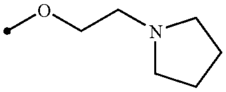 | MS m/z 474 $(M + H)^+$ |
| 3-25 | 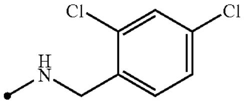 | 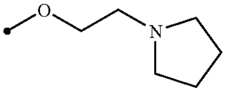 | MS m/z 490 $(M + H)^+$ |
| 3-26 | 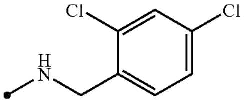 | 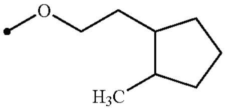 | MS m/z 504 $(M + H)^+$ |
| 3-27 | 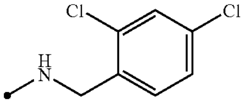 | 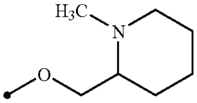 | MS m/z 504 $(M + H)^+$ |
| 3-28 | 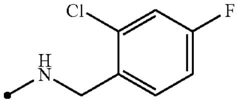 | 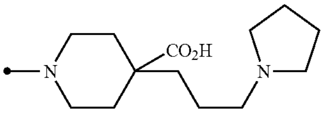 | MS m/z 599 $(M + H)^+$ |
| 3-29 | 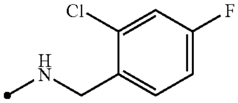 | 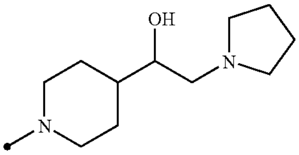 | MS m/z 557 $(M + H)^+$ |
| 3-30 | 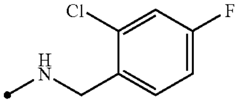 | 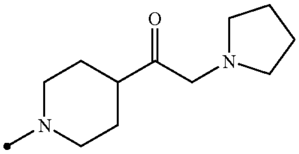 | MS m/z 555 $(M + H)^+$ |
| 3-31 | 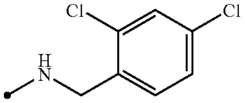 | 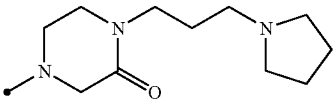 | MS m/z 586 $(M + H)^+$ |
| 3-32 | 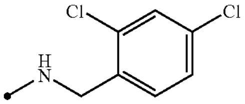 | 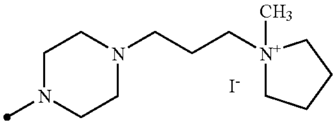 | MS m/z 586 $M^+$ |
| 3-33 | 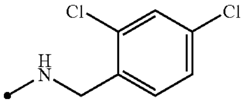 | 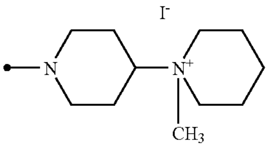 | MS m/z 577 $M^+$ |

TABLE 4
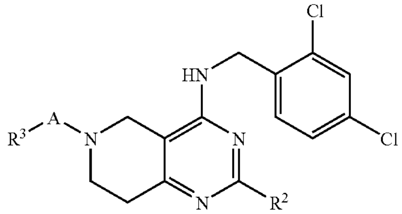
| Compound Number | •—A—$R^3$ | •—$R^2$ | Spectrum Data |
|---|---|---|---|
| 4-1 | 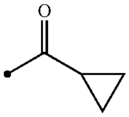 | 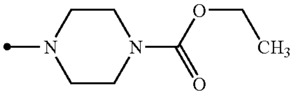 | MS m/z 533 $(M + H)^+$ |
| 4-2 | 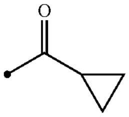 | 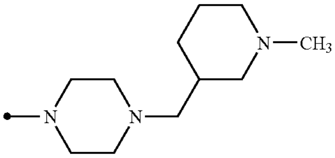 | MS m/z 572 $(M + H)^+$ |
| 4-3 | 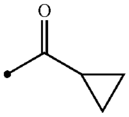 | 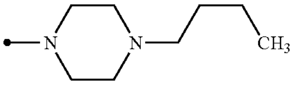 | MS m/z 517 $(M + H)^+$ |
| 4-4 | 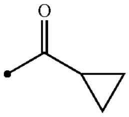 | 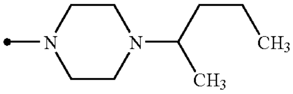 | MS m/z 531 $(M + H)^+$ |
| 4-5 | 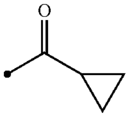 | 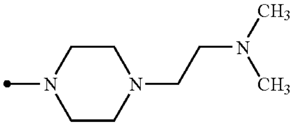 | MS m/z 532 $(M + H)^+$ |
| 4-6 | 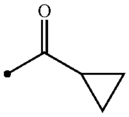 | 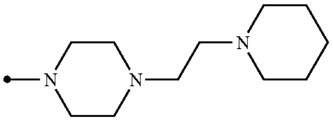 | MS m/z 572 $(M + H)^+$ |
| 4-7 | 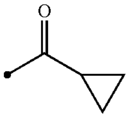 | 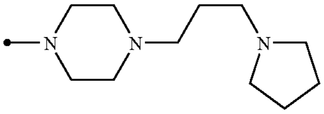 | MS m/z 572 $(M + H)^+$ |
| 4-8 | 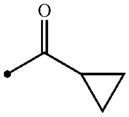 | 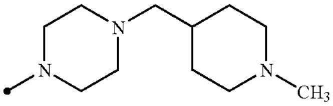 | MS m/z 572 $(M + H)^+$ |
| 4-9 | 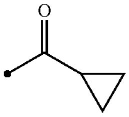 | 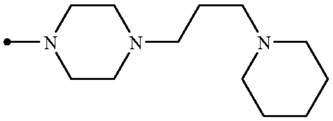 | MS m/z 586 $(M + H)^+$ |

TABLE 4-continued
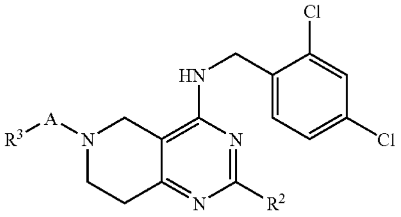
| Compound Number | •—A—$R^3$ | •—$R^2$ | Spectrum Data |
|---|---|---|---|
| 4-10 | 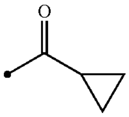 | 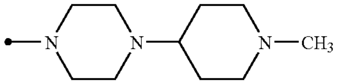 | MS m/z 558 $(M + H)^+$ |
| 4-11 | 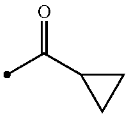 | 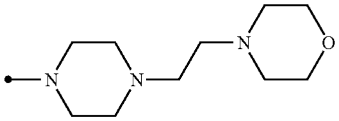 | MS m/z 574 $(M + H)^+$ |
| 4-12 | 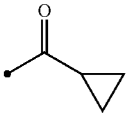 | 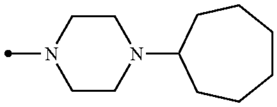 | MS m/z 557 $(M + H)^+$ |
| 4-13 | 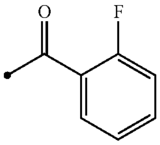 | 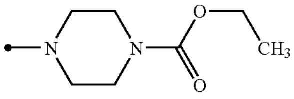 | MS m/z 587 $(M + H)^+$ |
| 4-14 | 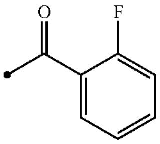 | 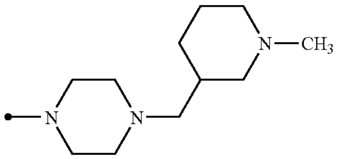 | MS m/z 626 $(M + H)^+$ |
| 4-15 | 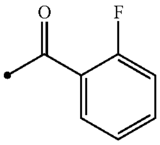 | 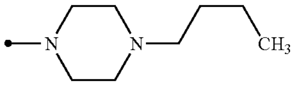 | MS m/z 571 $(M + H)^+$ |
| 4-16 | 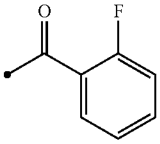 | 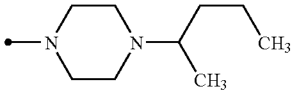 | MS m/z 585 $(M + H)^+$ |
| 4-17 | 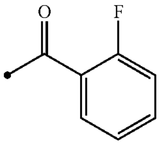 | 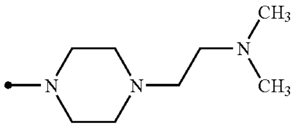 | MS m/z 586 $(M + H)^+$ |

TABLE 4-continued
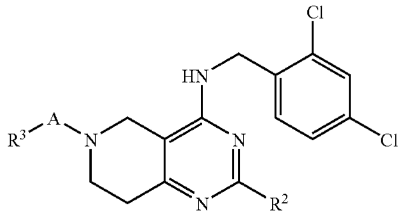
| Compound Number | •—A—$R^3$ | •—$R^2$ | Spectrum Data |
|---|---|---|---|
| 4-18 | 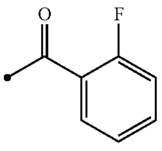 | 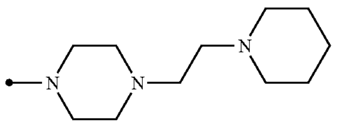 | MS m/z 626 $(M + H)^+$ |
| 4-19 | 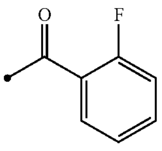 | 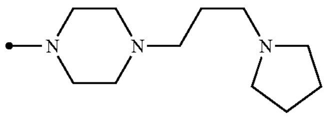 | MS m/z 626 $(M + H)^+$ |
| 4-20 | 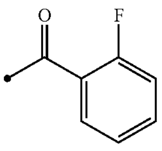 | 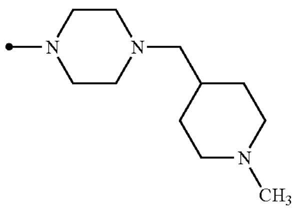 | MS m/z 626 $(M + H)^+$ |
| 4-21 | 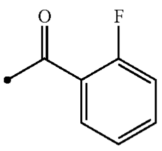 | 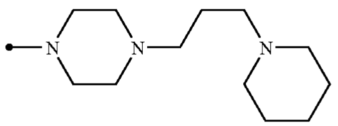 | MS m/z 640 $(M + H)^+$ |
| 4-22 | 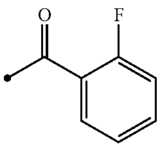 | 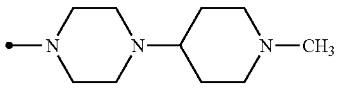 | MS m/z 612 $(M + H)^+$ |
| 4-23 | 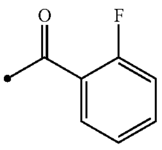 | 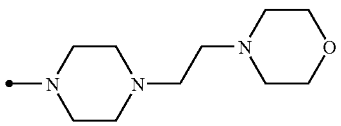 | MS m/z 628 $(M + H)^+$ |
| 4-24 | 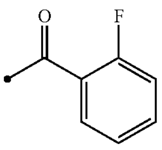 | 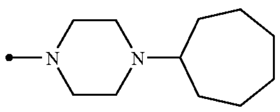 | MS m/z 611 $(M + H)^+$ |
| 4-25 | 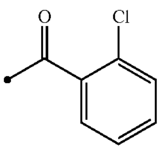 | 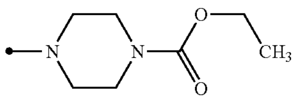 | MS m/z 603 $(M + H)^+$ |

TABLE 4-continued
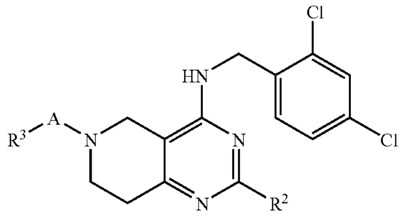
| Compound Number | •—A—$R^3$ | •—$R^2$ | Spectrum Data |
|---|---|---|---|
| 4-26 | 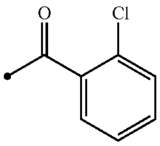 | 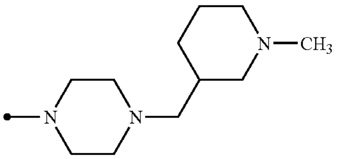 | MS m/z 642 $(M + H)^+$ |
| 4-27 | 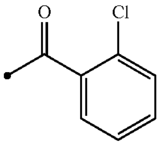 | 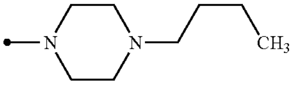 | MS m/z 587 $(M + H)^+$ |
| 4-28 | 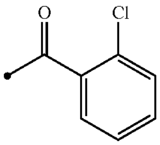 | 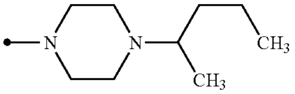 | MS m/z 601 $(M + H)^+$ |
| 4-29 | 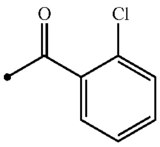 | 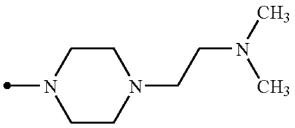 | MS m/z 602 $(M + H)^+$ |
| 4-30 | 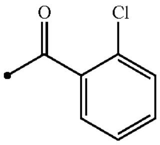 | 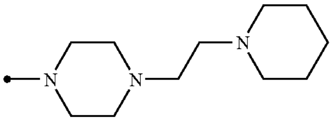 | MS m/z 642 $(M + H)^+$ |
| 4-31 | 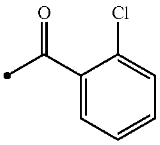 | 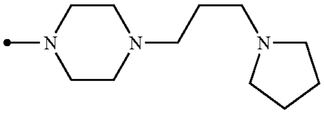 | MS m/z 642 $(M + H)^+$ |
| 4-32 | 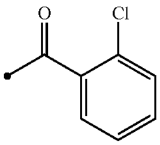 | 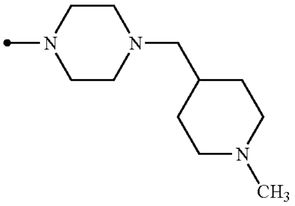 | MS m/z 642 $(M + H)^+$ |
| 4-33 | 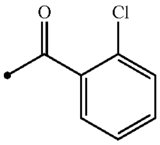 | 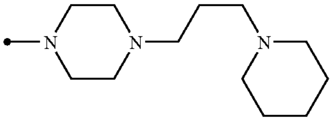 | MS m/z 656 $(M + H)^+$ |

TABLE 4-continued
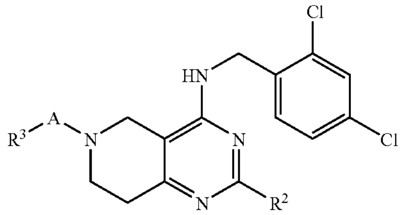
| Compound Number | •—A—$R^3$ | •—$R^2$ | Spectrum Data |
|---|---|---|---|
| 4-34 | 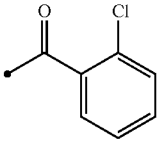 | 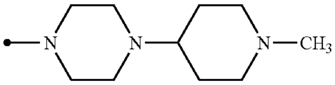 | MS m/z 628 (M + H)$^+$ |
| 4-35 | 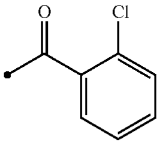 | 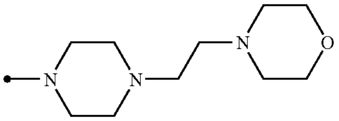 | MS m/z 644 (M + H)$^+$ |
| 4-36 | 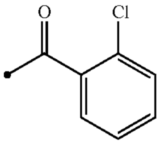 | 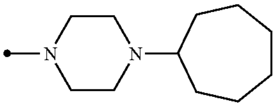 | MS m/z 627 (M + H)$^+$ |
| 4-37 | 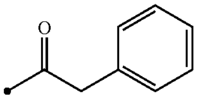 | 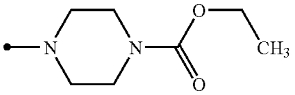 | MS m/z 583 (M + H)$^+$ |
| 4-38 | 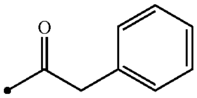 | 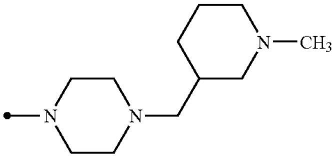 | MS m/z 622 (M + H)$^+$ |
| 4-39 | 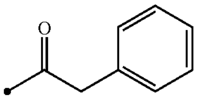 | 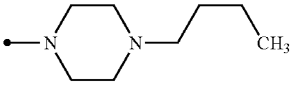 | MS m/z 567 (M + H)$^+$ |
| 4-40 | 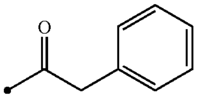 | 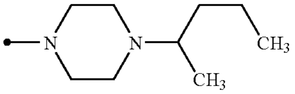 | MS m/z 581 (M + H)$^+$ |
| 4-41 | 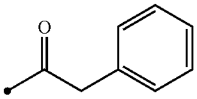 | 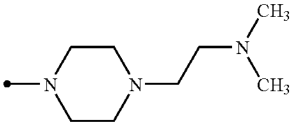 | MS m/z 582 (M + H)$^+$ |
| 4-42 | 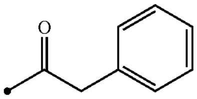 | 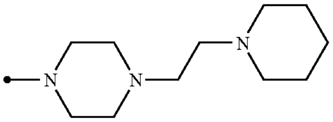 | MS m/z 622 (M + H)$^+$ |

TABLE 4-continued
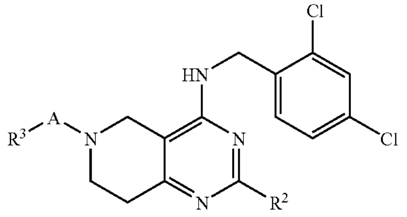
| Compound Number | •—A—$R^3$ | •—$R^2$ | Spectrum Data |
|---|---|---|---|
| 4-43 | 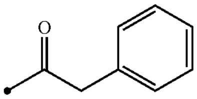 | 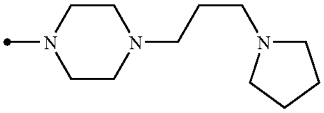 | MS m/z 622 $(M + H)^+$ |
| 4-44 | 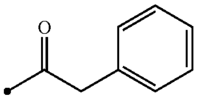 | 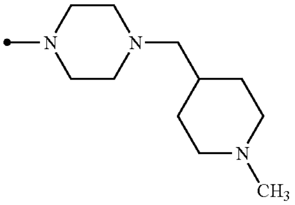 | MS m/z 622 $(M + H)^+$ |
| 4-45 | 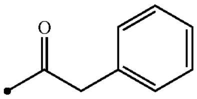 | 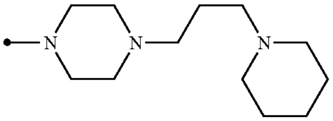 | MS m/z 636 $(M + H)^+$ |
| 4-46 | 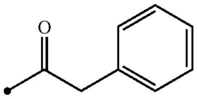 | 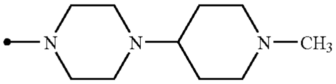 | MS m/z 608 $(M + H)^+$ |
| 4-47 | 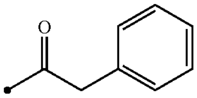 | 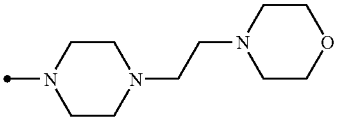 | MS m/z 624 $(M + H)^+$ |
| 4-48 | 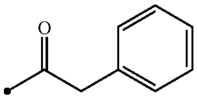 | 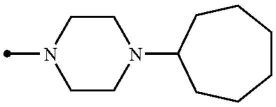 | MS m/z 607 $(M + H)^+$ |
| 4-49 | 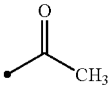 | 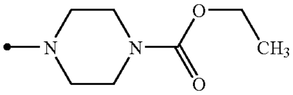 | MS m/z 507 $(M + H)^+$ |
| 4-50 | 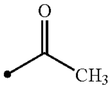 | 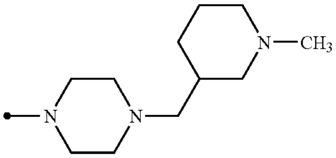 | MS m/z 546 $(M + H)^+$ |
| 4-51 | 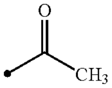 | 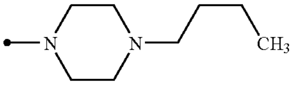 | MS m/z 491 $(M + H)^+$ |

TABLE 4-continued
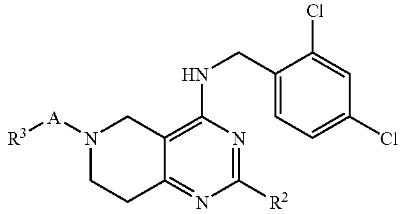
| Compound Number | •—A—$R^3$ | •—$R^2$ | Spectrum Data |
|---|---|---|---|
| 4-52 | 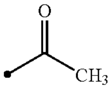 | 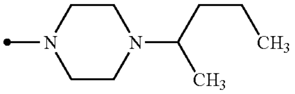 | MS m/z 505 $(M + H)^+$ |
| 4-53 | 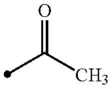 | 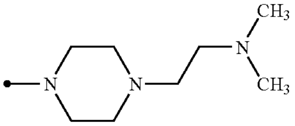 | MS m/z 506 $(M + H)^+$ |
| 4-54 | 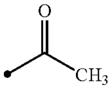 | 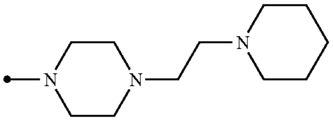 | MS m/z 546 $(M + H)^+$ |
| 4-55 | 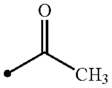 | 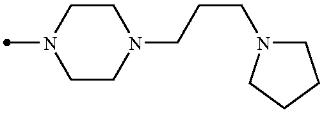 | MS m/z 546 $(M + H)^+$ |
| 4-56 | 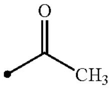 | 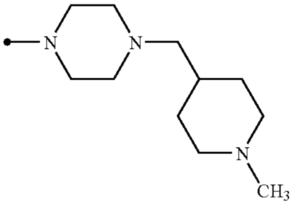 | MS m/z 546 $(M + H)^+$ |
| 4-57 | 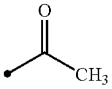 | 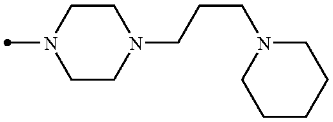 | MS m/z 560 $(M + H)^+$ |
| 4-58 | 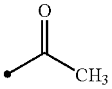 | 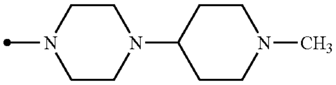 | MS m/z 532 $(M + H)^+$ |
| 4-59 | 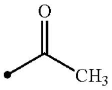 | 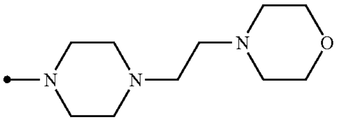 | MS m/z 548 $(M + H)^+$ |
| 4-60 | 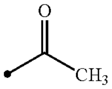 | 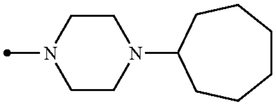 | MS m/z 531 $(M + H)^+$ |

TABLE 4-continued
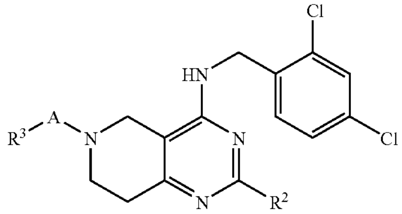
| Compound Number | •—A—$R^3$ | •—$R^2$ | Spectrum Data |
|---|---|---|---|
| 4-61 | 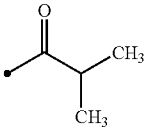 | 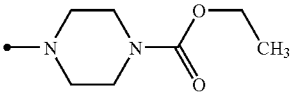 | MS m/z 535 $(M + H)^+$ |
| 4-62 | 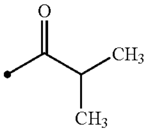 | 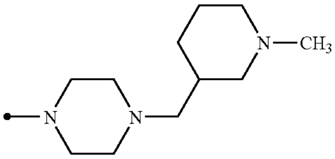 | MS m/z 574 $(M + H)^+$ |
| 4-63 | 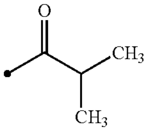 | 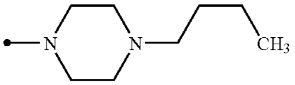 | MS m/z 519 $(M + H)^+$ |
| 4-64 | 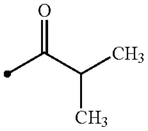 | 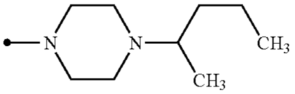 | MS m/z 533 $(M + H)^+$ |
| 4-65 | 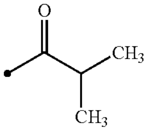 | 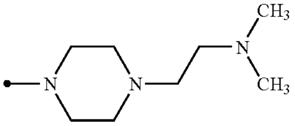 | MS m/z 534 $(M + H)^+$ |
| 4-66 | 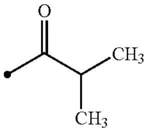 | 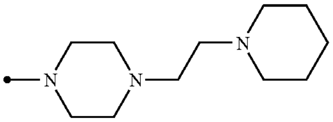 | MS m/z 574 $(M + H)^+$ |
| 4-67 | 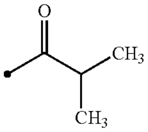 | 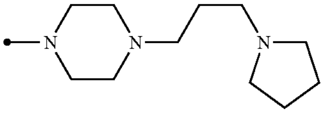 | MS m/z 574 $(M + H)^+$ |
| 4-68 | 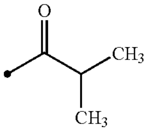 | 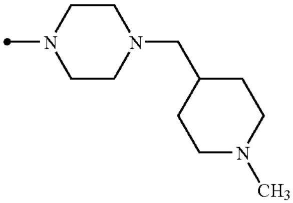 | MS m/z 574 $(M + H)^+$ |

TABLE 4-continued
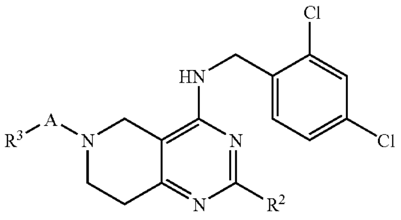
| Compound Number | •—A—$R^3$ | •—$R^2$ | Spectrum Data |
|---|---|---|---|
| 4-69 | 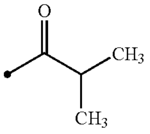 | 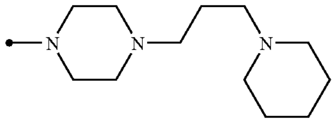 | MS m/z 588 $(M + H)^+$ |
| 4-70 | 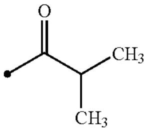 | 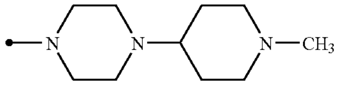 | MS m/z 560 $(M + H)^+$ |
| 4-71 | 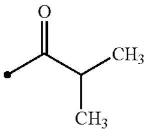 | 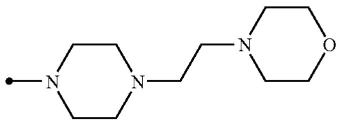 | MS m/z 576 $(M + H)^+$ |
| 4-72 | 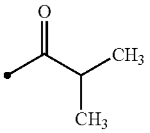 | 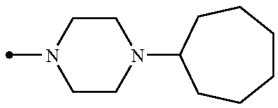 | MS m/z 559 $(M + H)^+$ |
| 4-73 | 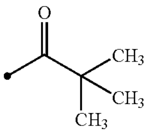 | 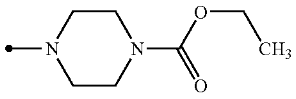 | MS m/z 549 $(M + H)^+$ |
| 4-74 | 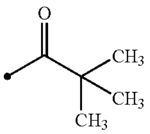 | 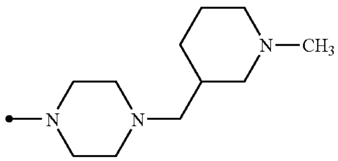 | MS m/z 588 $(M + H)^+$ |
| 4-75 | 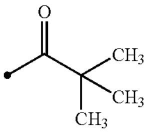 | 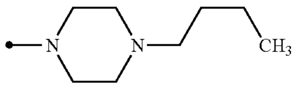 | MS m/z 533 $(M + H)^+$ |
| 4-76 | 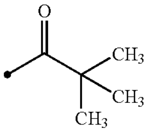 | 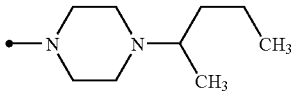 | MS m/z 547 $(M + H)^+$ |

TABLE 4-continued
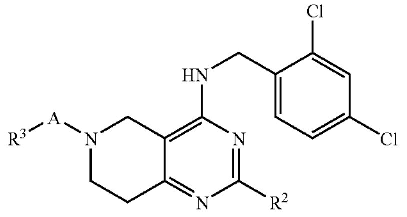
| Compound Number | •—A—$R^3$ | •—$R^2$ | Spectrum Data |
|---|---|---|---|
| 4-77 | 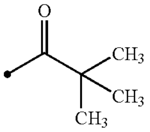 | 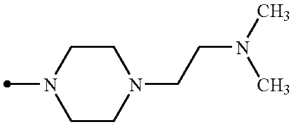 | MS m/z 548 $(M + H)^+$ |
| 4-78 | 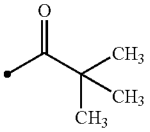 | 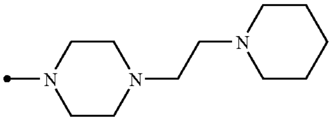 | MS m/z 588 $(M + H)^+$ |
| 4-79 | 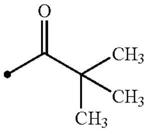 | 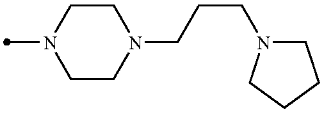 | MS m/z 588 $(M + H)^+$ |
| 4-80 | 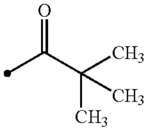 | 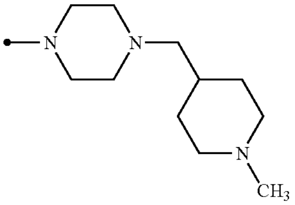 | MS m/z 588 $(M + H)^+$ |
| 4-81 | 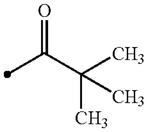 | 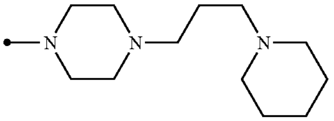 | MS m/z 602 $(M + H)^+$ |
| 4-82 | 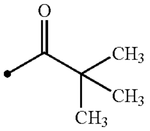 | 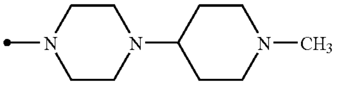 | MS m/z 574 $(M + H)^+$ |
| 4-83 | 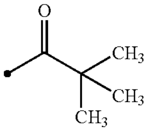 | 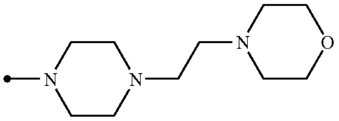 | MS m/z 590 $(M + H)^+$ |
| 4-84 | 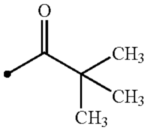 | 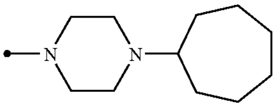 | MS m/z 573 $(M + H)^+$ |

TABLE 4-continued
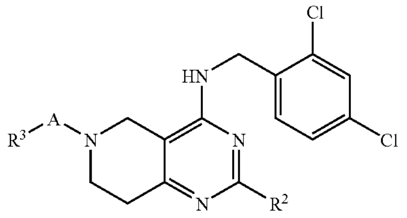
| Compound Number | •—A—$R^3$ | •—$R^2$ | Spectrum Data |
|---|---|---|---|
| 4-85 | 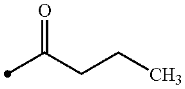 | 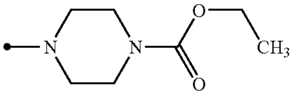 | MS m/z 535 $(M + H)^+$ |
| 4-86 | 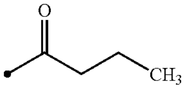 | 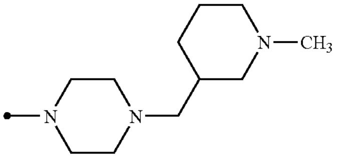 | MS m/z 574 $(M + H)^+$ |
| 4-87 | 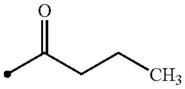 | 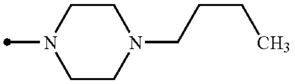 | MS m/z 519 $(M + H)^+$ |
| 4-88 | 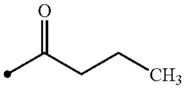 | 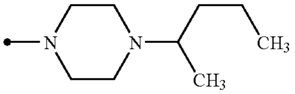 | MS m/z 533 $(M + H)^+$ |
| 4-89 | 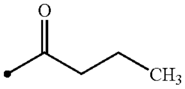 | 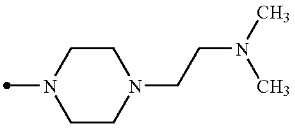 | MS m/z 534 $(M + H)^+$ |
| 4-90 | 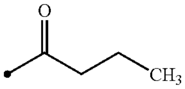 | 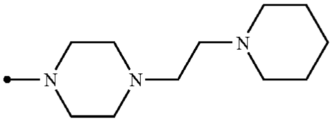 | MS m/z 574 $(M + H)^+$ |
| 4-91 | 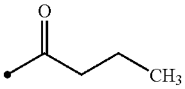 | 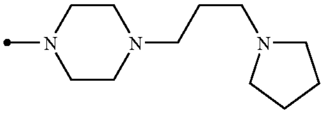 | MS m/z 574 $(M + H)^+$ |
| 4-92 | 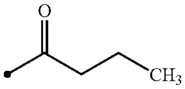 | 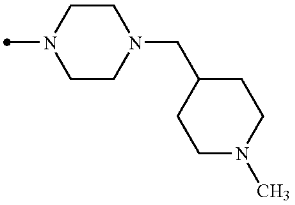 | MS m/z 574 $(M + H)^+$ |
| 4-93 | 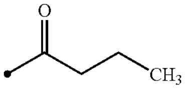 | 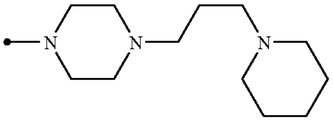 | MS m/z 588 $(M + H)^+$ |

TABLE 4-continued
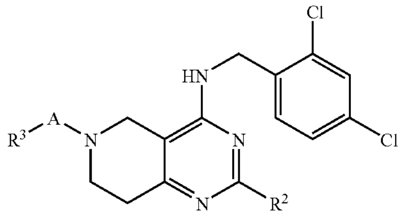
| Compound Number | •—A—R$^3$ | •—R$^2$ | Spectrum Data |
|---|---|---|---|
| 4-94 | 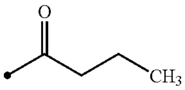 | 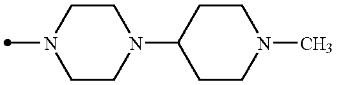 | MS m/z 560 (M + H)$^+$ |
| 4-95 | 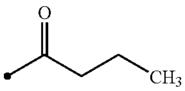 | 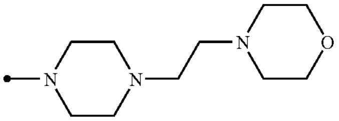 | MS m/z 576 (M + H)$^+$ |
| 4-96 | 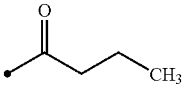 | 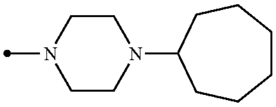 | MS m/z 559 (M + H)$^+$ |
| 4-97 | 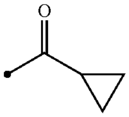 | 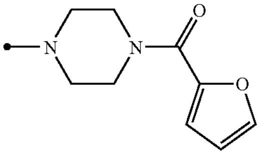 | MS m/z 555 (M + H)$^+$ |
| 4-98 | 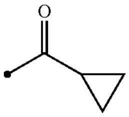 | 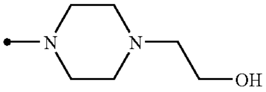 | MS m/z 505 (M + H)$^+$ |
| 4-99 | 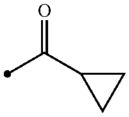 | 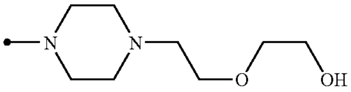 | MS m/z 549 (M + H)$^+$ |
| 4-100 | 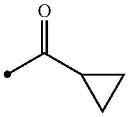 | 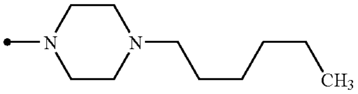 | MS m/z 545 (M + H)$^+$ |
| 4-101 | 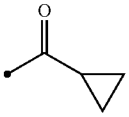 | 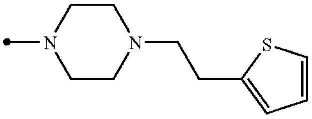 | MS m/z 571 (M + H)$^+$ |
| 4-102 | 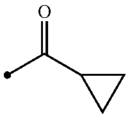 | 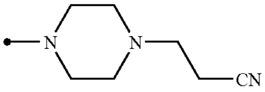 | MS m/z 514 (M + H)$^+$ |
| 4-103 | 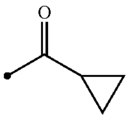 | 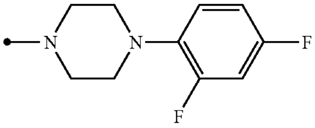 | MS m/z 573 (M + H)$^+$ |

TABLE 4-continued
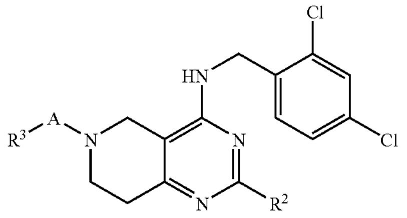
| Compound Number | •—A—$R^3$ | •—$R^2$ | Spectrum Data |
|---|---|---|---|
| 4-104 | 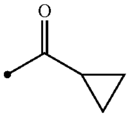 | 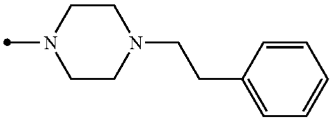 | MS m/z 565 $(M + H)^+$ |
| 4-105 | 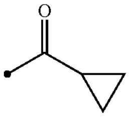 | 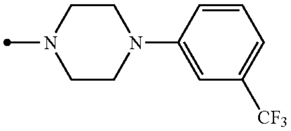 | MS m/z 605 $(M + H)^+$ |
| 4-106 | 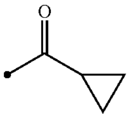 | 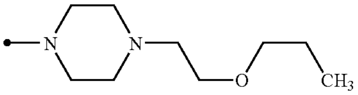 | MS m/z 533 $(M + H)^+$ |
| 4-107 | 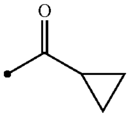 | 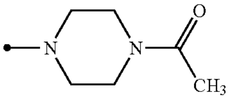 | MS m/z 503 $(M + H)^+$ |
| 4-108 | 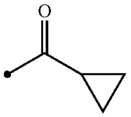 | 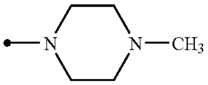 | MS m/z 475 $(M + H)^+$ |
| 4-109 | 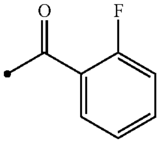 | 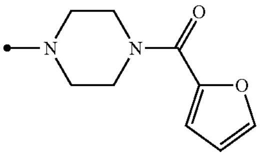 | MS m/z 609 $(M + H)^+$ |
| 4-110 | 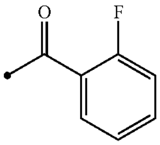 | 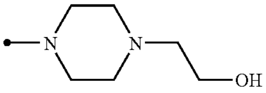 | MS m/z 559 $(M + H)^+$ |
| 4-111 | 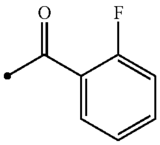 | 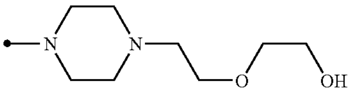 | MS m/z 603 $(M + H)^+$ |
| 4-112 | 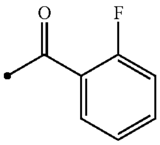 | 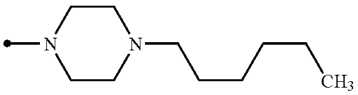 | MS m/z 599 $(M + H)^+$ |

TABLE 4-continued
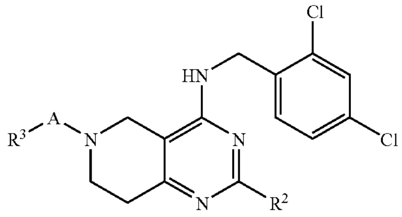
| Compound Number | •—A—$R^3$ | •—$R^2$ | Spectrum Data |
|---|---|---|---|
| 4-113 | 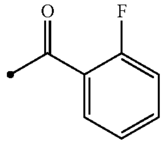 | 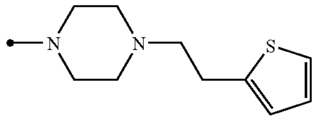 | MS m/z 625 $(M + H)^+$ |
| 4-114 | 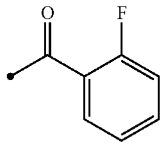 | 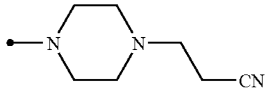 | MS m/z 568 $(M + H)^+$ |
| 4-115 | 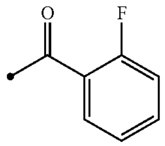 | 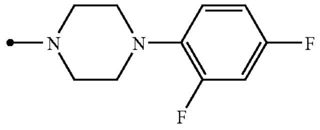 | MS m/z 627 $(M + H)^+$ |
| 4-116 | 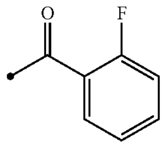 | 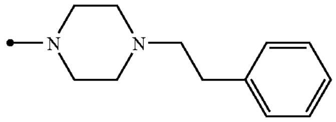 | MS m/z 619 $(M + H)^+$ |
| 4-117 | 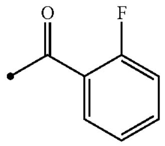 | 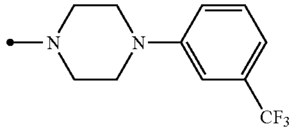 | MS m/z 659 $(M + H)^+$ |
| 4-118 | 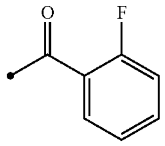 | 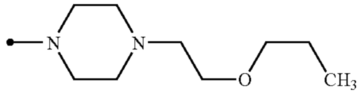 | MS m/z 587 $(M + H)^+$ |
| 4-119 | 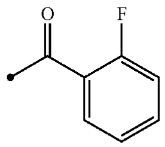 | 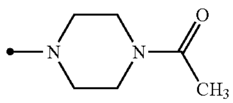 | MS m/z 557 $(M + H)^+$ |
| 4-120 | 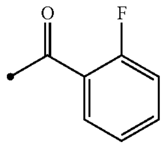 | 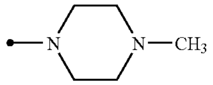 | MS m/z 529 $(M + H)^+$ |

TABLE 4-continued
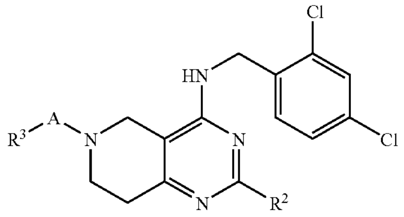
| Compound Number | •—A—$R^3$ | •—$R^2$ | Spectrum Data |
|---|---|---|---|
| 4-121 | 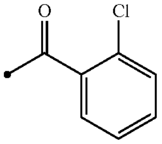 | 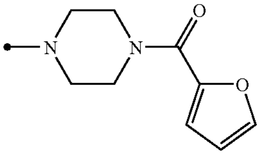 | MS m/z 625 $(M + H)^+$ |
| 4-122 | 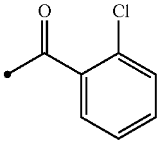 | 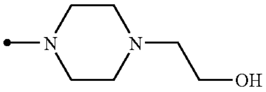 | MS m/z 575 $(M + H)^+$ |
| 4-123 | 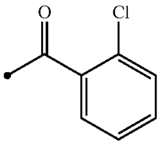 | 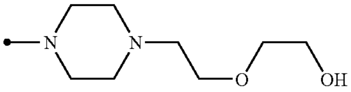 | MS m/z 619 $(M + H)^+$ |
| 4-124 | 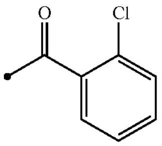 | 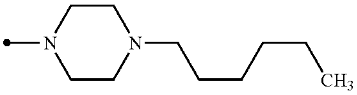 | MS m/z 615 $(M + H)^+$ |
| 4-125 | 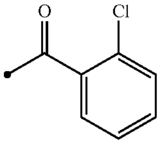 | 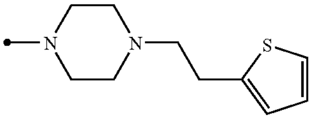 | MS m/z 641 $(M + H)^+$ |
| 4-126 | 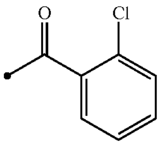 | 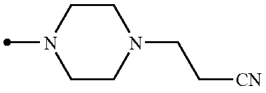 | MS m/z 584 $(M + H)^+$ |
| 4-127 | 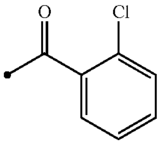 | 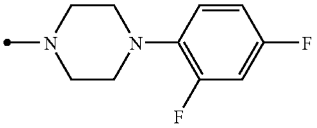 | MS m/z 643 $(M + H)^+$ |
| 4-128 | 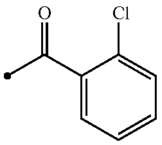 | 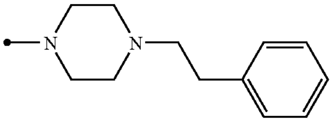 | MS m/z 635 $(M + H)^+$ |

TABLE 4-continued
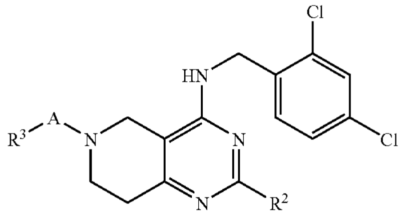
| Compound Number | •—A—$R^3$ | •—$R^2$ | Spectrum Data |
|---|---|---|---|
| 4-129 | 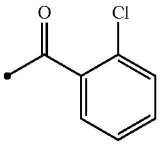 | 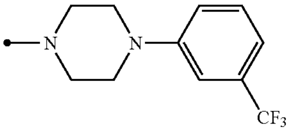 | MS m/z 675 $(M + H)^+$ |
| 4-130 | 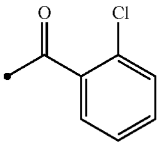 | 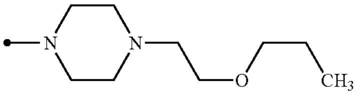 | MS m/z 603 $(M + H)^+$ |
| 4-131 | 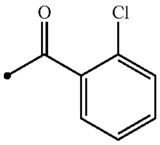 | 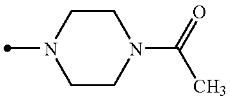 | MS m/z 573 $(M + H)^+$ |
| 4-132 | 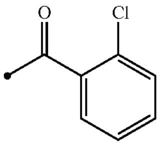 | 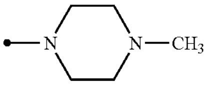 | MS m/z 545 $(M + H)^+$ |
| 4-133 | 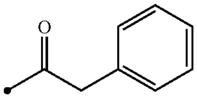 | 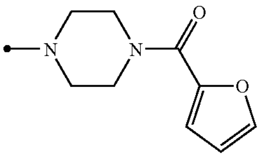 | MS m/z 605 $(M + H)^+$ |
| 4-134 | 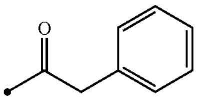 | 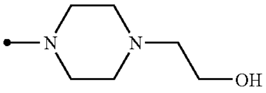 | MS m/z 555 $(M + H)^+$ |
| 4-135 | 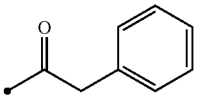 | 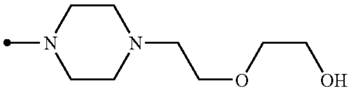 | MS m/z 599 $(M + H)^+$ |
| 4-136 | 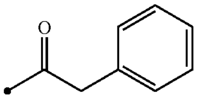 | 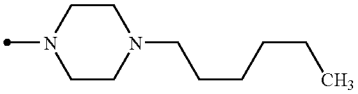 | MS m/z 595 $(M + H)^+$ |
| 4-137 | 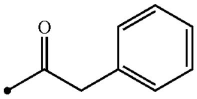 | 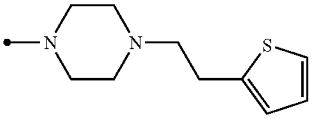 | MS m/z 621 $(M + H)^+$ |

TABLE 4-continued
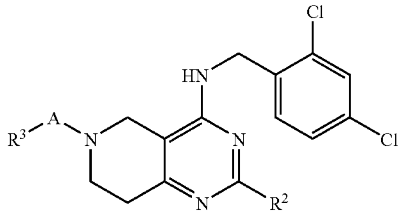
| Compound Number | •—A—$R^3$ | •—$R^2$ | Spectrum Data |
|---|---|---|---|
| 4-138 | 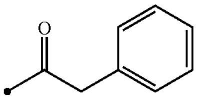 | 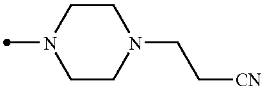 | MS m/z 564 $(M + H)^+$ |
| 4-139 | 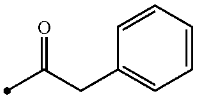 | 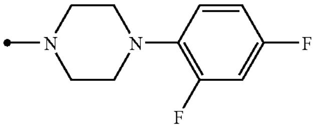 | MS m/z 623 $(M + H)^+$ |
| 4-140 | 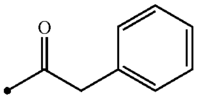 | 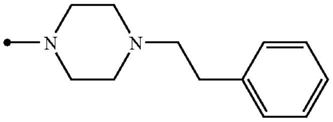 | MS m/z 615 $(M + H)^+$ |
| 4-141 | 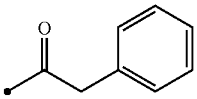 | 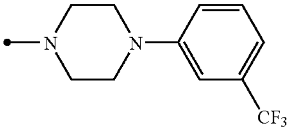 | MS m/z 655 $(M + H)^+$ |
| 4-142 | 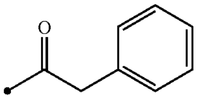 | 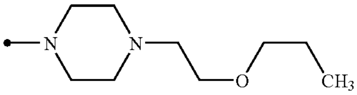 | MS m/z 583 $(M + H)^+$ |
| 4-143 | 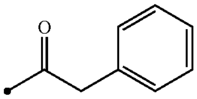 | 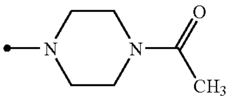 | MS m/z 553 $(M + H)^+$ |
| 4-144 | 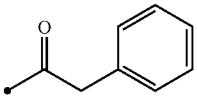 | 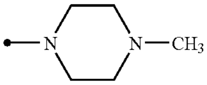 | MS m/z 525 $(M + H)^+$ |
| 4-145 | 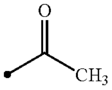 | 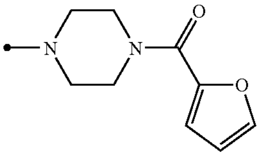 | MS m/z 529 $(M + H)^+$ |
| 4-146 | 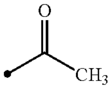 | 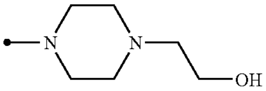 | MS m/z 479 $(M + H)^+$ |
| 4-147 | 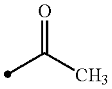 | 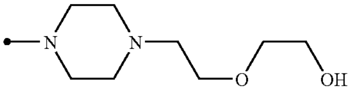 | MS m/z 523 $(M + H)^+$ |

TABLE 4-continued
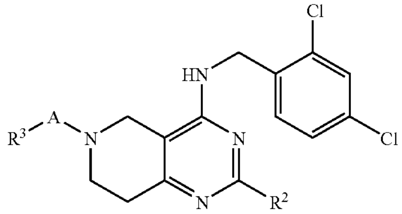
| Compound Number | •—A—$R^3$ | •—$R^2$ | Spectrum Data |
|---|---|---|---|
| 4-148 | 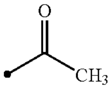 | 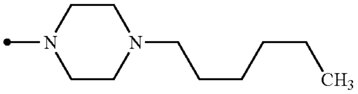 | MS m/z 519 $(M + H)^+$ |
| 4-149 | 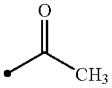 | 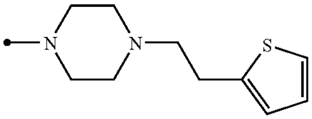 | MS m/z 545 $(M + H)^+$ |
| 4-150 | 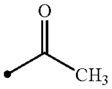 | 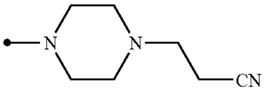 | MS m/z 488 $(M + H)^+$ |
| 4-151 | 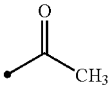 | 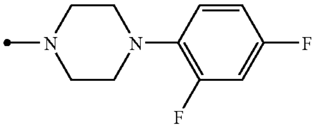 | MS m/z 547 $(M + H)^+$ |
| 4-152 | 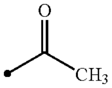 | 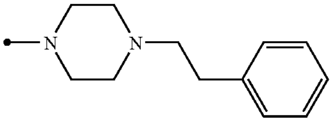 | MS m/z 539 $(M + H)^+$ |
| 4-153 | 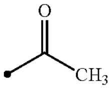 | 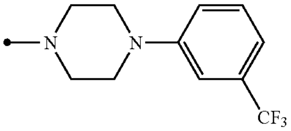 | MS m/z 579 $(M + H)^+$ |
| 4-154 | 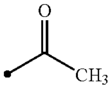 | 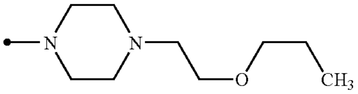 | MS m/z 507 $(M + H)^+$ |
| 4-155 | 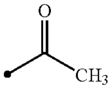 | 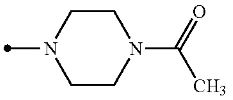 | MS m/z 477 $(M + H)^+$ |
| 4-156 | 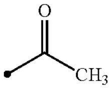 | 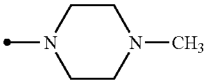 | MS m/z 449 $(M + H)^+$ |
| 4-157 | 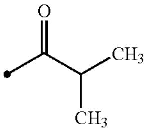 | 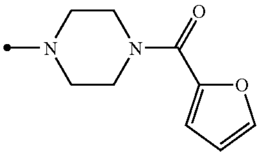 | MS m/z 557 $(M + H)^+$ |

TABLE 4-continued
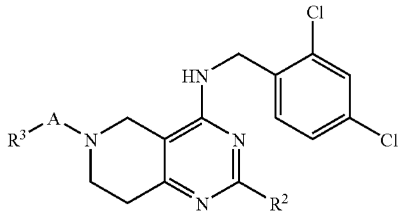
| Compound Number | •—A—$R^3$ | •—$R^2$ | Spectrum Data |
|---|---|---|---|
| 4-158 | 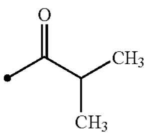 | 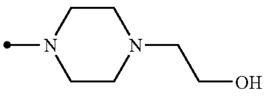 | MS m/z 507 $(M + H)^+$ |
| 4-159 | 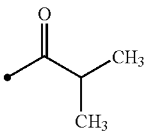 | 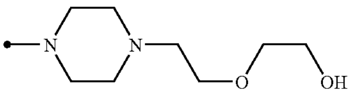 | MS m/z 551 $(M + H)^+$ |
| 4-160 | 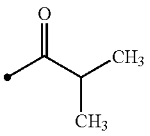 | 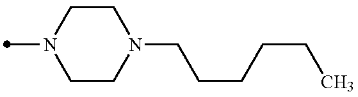 | MS m/z 547 $(M + H)^+$ |
| 4-161 | 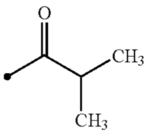 | 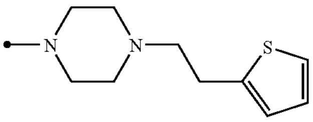 | MS m/z 573 $(M + H)^+$ |
| 4-162 | 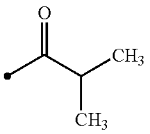 | 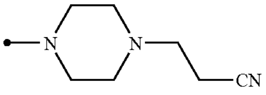 | MS m/z 516 $(M + H)^+$ |
| 4-163 | 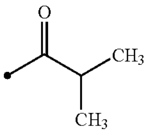 | 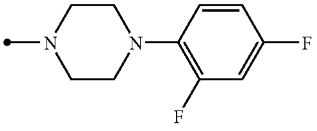 | MS m/z 575 $(M + H)^+$ |
| 4-164 | 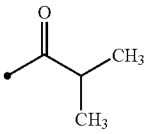 | 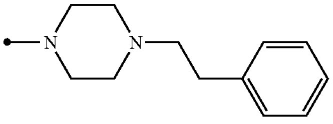 | MS m/z 567 $(M + H)^+$ |
| 4-165 | 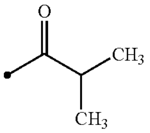 | 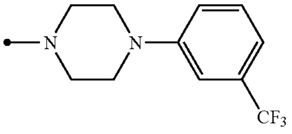 | MS m/z 607 $(M + H)^+$ |
| 4-166 | 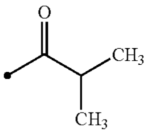 | 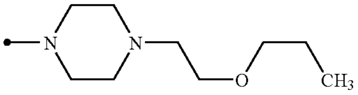 | MS m/z 535 $(M + H)^+$ |

TABLE 4-continued
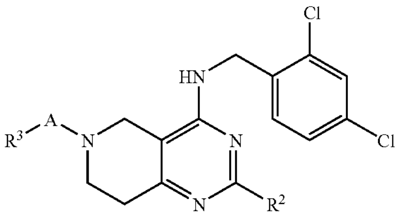
| Compound Number | •—A—$R^3$ | •—$R^2$ | Spectrum Data |
|---|---|---|---|
| 4-167 | 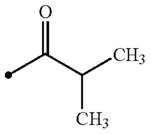 | 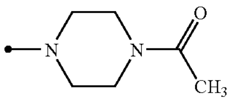 | MS m/z 505 $(M + H)^+$ |
| 4-168 | 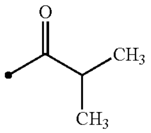 | 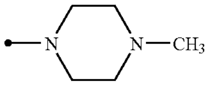 | MS m/z 477 $(M + H)^+$ |
| 4-169 | 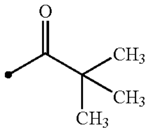 | 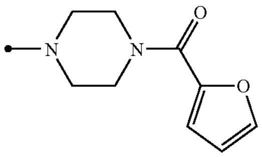 | MS m/z 571 $(M + H)^+$ |
| 4-170 | 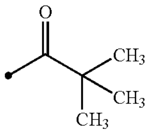 | 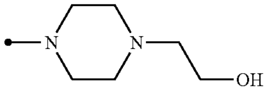 | MS m/z 521 $(M + H)^+$ |
| 4-171 | 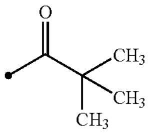 | 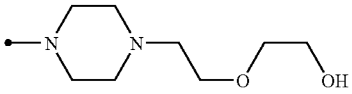 | MS m/z 565 $(M + H)^+$ |
| 4-172 | 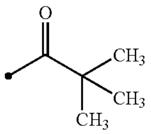 | 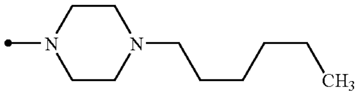 | MS m/z 561 $(M + H)^+$ |
| 4-173 | 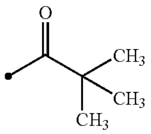 | 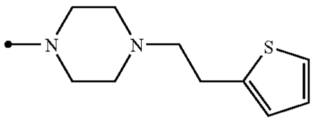 | MS m/z 587 $(M + H)^+$ |
| 4-174 | 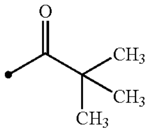 | 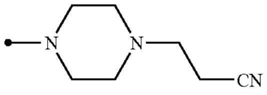 | MS m/z 530 $(M + H)^+$ |

TABLE 4-continued
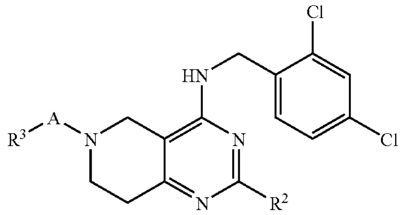
| Compound Number | •—A—$R^3$ | •—$R^2$ | Spectrum Data |
|---|---|---|---|
| 4-175 | 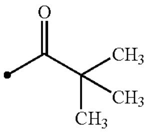 | 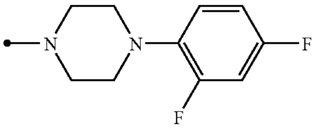 | MS m/z 589 $(M + H)^+$ |
| 4-176 | 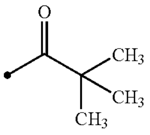 | 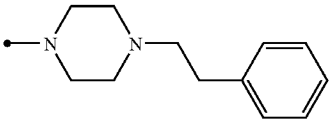 | MS m/z 581 $(M + H)^+$ |
| 4-177 | 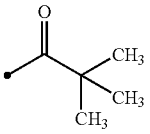 | 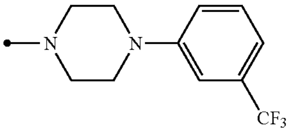 | MS m/z 621 $(M + H)^+$ |
| 4-178 | 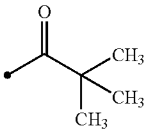 | 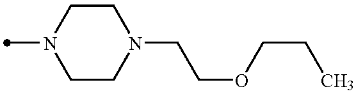 | MS m/z 549 $(M + H)^+$ |
| 4-179 | 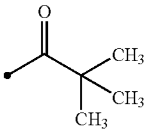 | 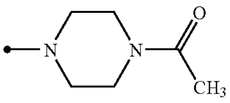 | MS m/z 519 $(M + H)^+$ |
| 4-180 | 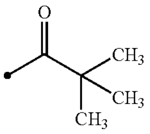 | 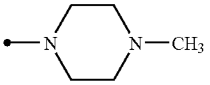 | MS m/z 491 $(M + H)^+$ |
| 4-181 | 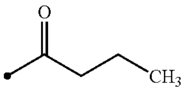 | 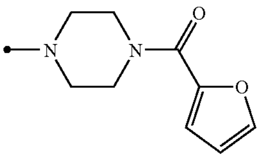 | MS m/z 557 $(M + H)^+$ |
| 4-182 | 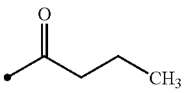 | 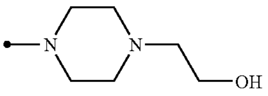 | MS m/z 507 $(M + H)^+$ |
| 4-183 | 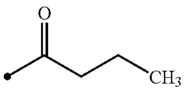 | 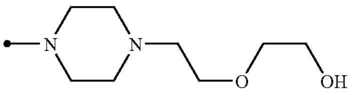 | MS m/z 551 $(M + H)^+$ |

TABLE 4-continued
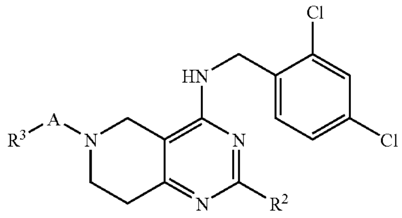
| Compound Number | •—A—$R^3$ | •—$R^2$ | Spectrum Data |
|---|---|---|---|
| 4-184 | 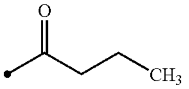 | 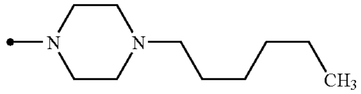 | MS m/z 547 $(M + H)^+$ |
| 4-185 | 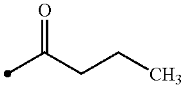 | 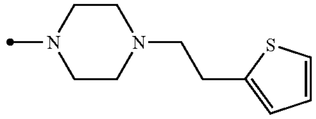 | MS m/z 573 $(M + H)^+$ |
| 4-186 | 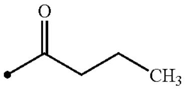 | 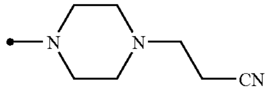 | MS m/z 516 $(M + H)^+$ |
| 4-187 | 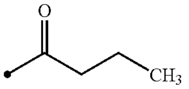 | 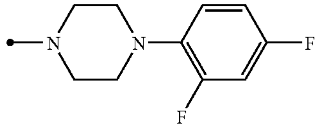 | MS m/z 575 $(M + H)^+$ |
| 4-188 | 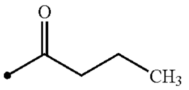 | 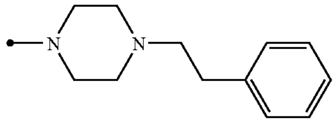 | MS m/z 567 $(M + H)^+$ |
| 4-189 | 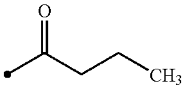 | 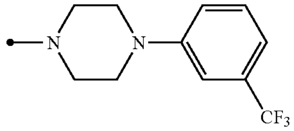 | MS m/z 607 $(M + H)^+$ |
| 4-190 | 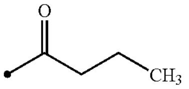 | 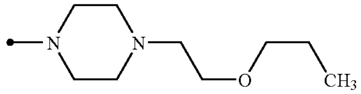 | MS m/z 535 $(M + H)^+$ |
| 4-191 | 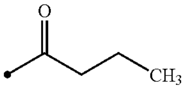 | 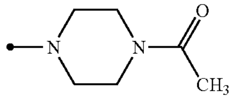 | MS m/z 505 $(M + H)^+$ |
| 4-192 | 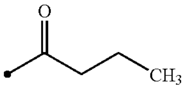 | 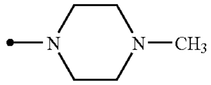 | MS m/z 477 $(M + H)^+$ |
| 4-193 | 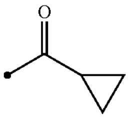 | 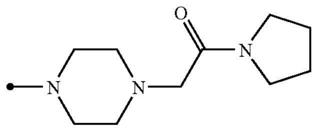 | MS m/z 572 $(M + H)^+$ |

TABLE 4-continued
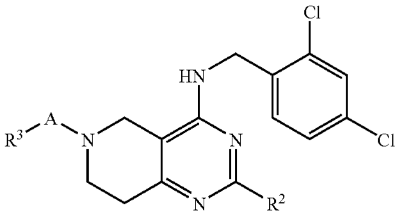
| Compound Number | •—A—$R^3$ | •—$R^2$ | Spectrum Data |
|---|---|---|---|
| 4-194 | 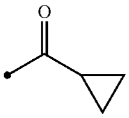 | 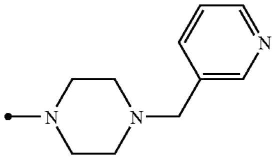 | MS m/z 552 $(M + H)^+$ |
| 4-195 | 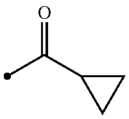 | 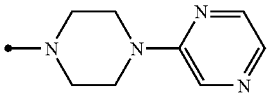 | MS m/z 539 $(M + H)^+$ |
| 4-196 | 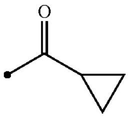 | 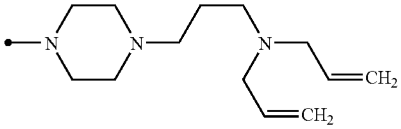 | MS m/z 598 $(M + H)^+$ |
| 4-197 | 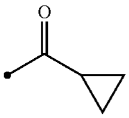 | 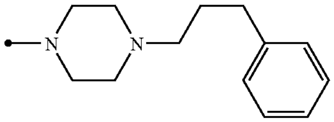 | MS m/z 579 $(M + H)^+$ |
| 4-198 | 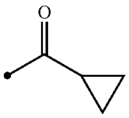 | 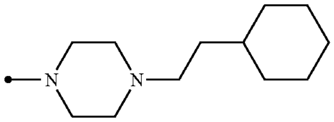 | MS m/z 571 $(M + H)^+$ |
| 4-199 | 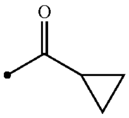 | 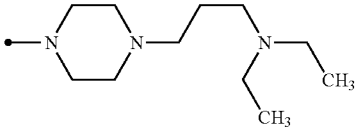 | MS m/z 574 $(M + H)^+$ |
| 4-200 | 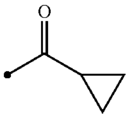 | 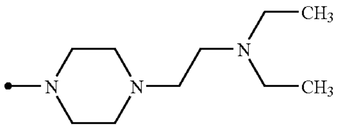 | MS m/z 560 $(M + H)^+$ |
| 4-201 | 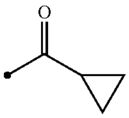 | 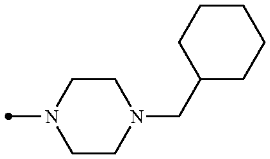 | MS m/z 557 $(M + H)^+$ |
| 4-202 | 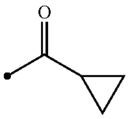 | 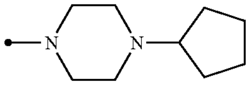 | MS m/z 529 $(M + H)^+$ |

TABLE 4-continued
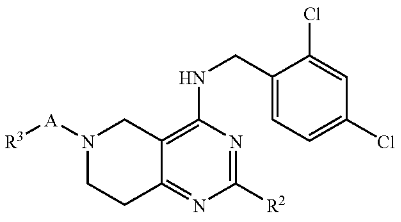
| Compound Number | •—A—$R^3$ | •—$R^2$ | Spectrum Data |
|---|---|---|---|
| 4-203 | 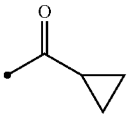 | 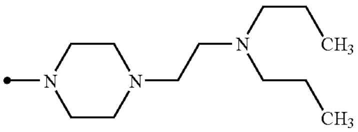 | MS m/z 588 $(M + H)^+$ |
| 4-204 | 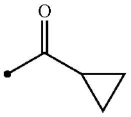 | 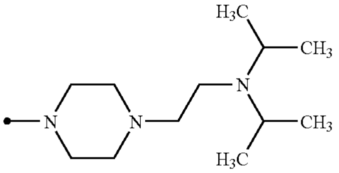 | MS m/z 588 $(M + H)^+$ |
| 4-205 | 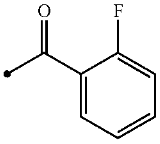 | 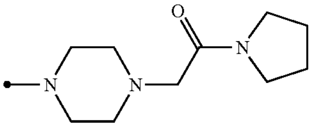 | MS m/z 626 $(M + H)^+$ |
| 4-206 | 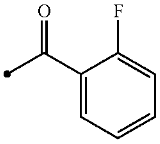 | 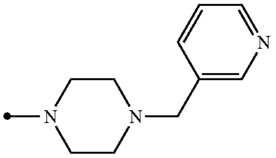 | MS m/z 606 $(M + H)^+$ |
| 4-207 | 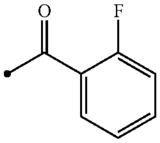 | 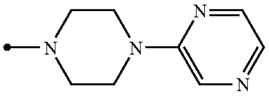 | MS m/z 593 $(M + H)^+$ |
| 4-208 | 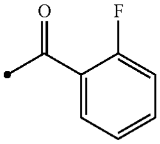 | 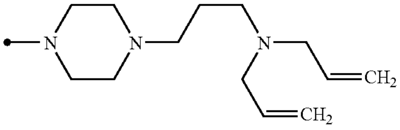 | MS m/z 652 $(M + H)^+$ |
| 4-209 | 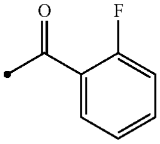 | 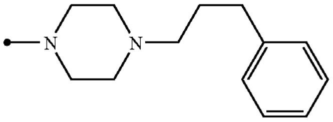 | MS m/z 633 $(M + H)^+$ |
| 4-210 | 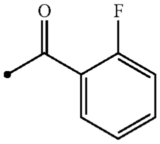 | 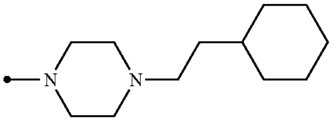 | MS m/z 625 $(M + H)^+$ |

TABLE 4-continued
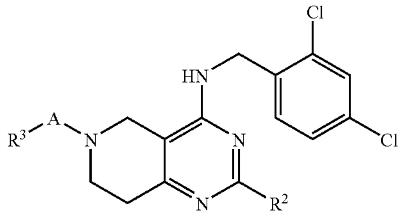
| Compound Number | •—A—$R^3$ | •—$R^2$ | Spectrum Data |
|---|---|---|---|
| 4-211 | 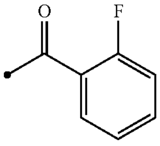 | 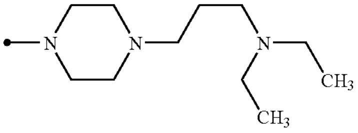 | MS m/z 628 (M + H)$^+$ |
| 4-212 | 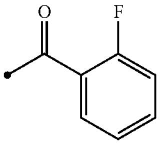 | 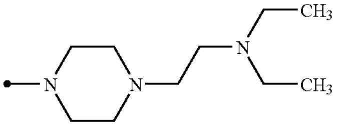 | MS m/z 614 (M + H)$^+$ |
| 4-213 | 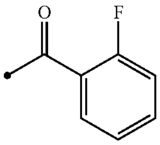 | 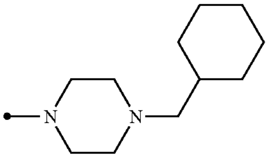 | MS m/z 611 (M + H)$^+$ |
| 4-214 | 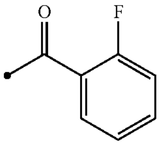 | 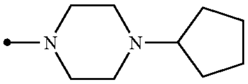 | MS m/z 583 (M + H)$^+$ |
| 4-215 | 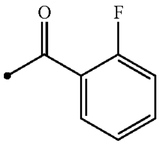 | 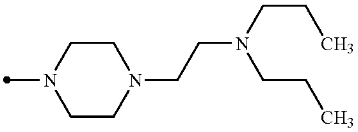 | MS m/z 642 (M + H)$^+$ |
| 4-216 | 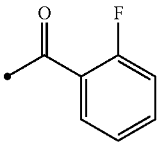 | 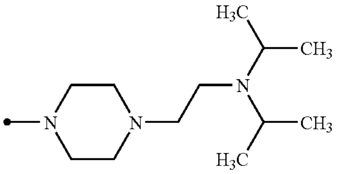 | MS m/z 642 (M + H)$^+$ |
| 4-217 | 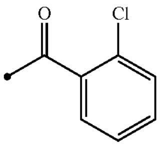 | 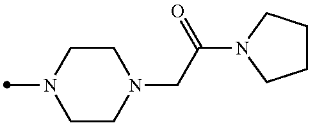 | MS m/z 642 (M + H)$^+$ |
| 4-218 | 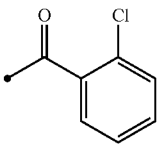 | 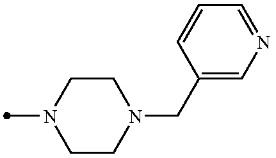 | MS m/z 622 (M + H)$^+$ |

TABLE 4-continued
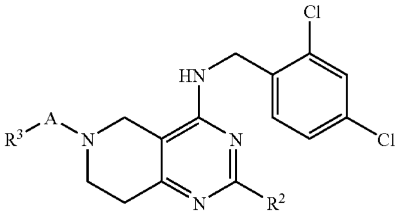
| Compound Number | •—A—$R^3$ | •—$R^2$ | Spectrum Data |
|---|---|---|---|
| 4-219 | 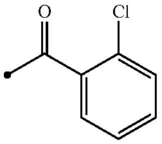 | 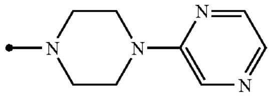 | MS m/z 609 $(M + H)^+$ |
| 4-220 | 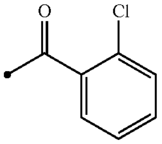 | 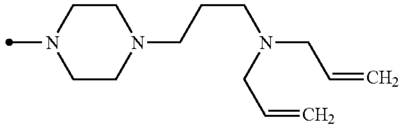 | MS m/z 668 $(M + H)^+$ |
| 4-221 | 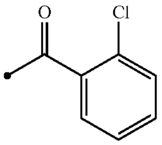 | 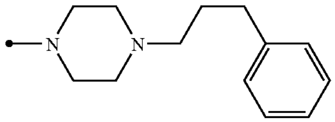 | MS m/z 649 $(M + H)^+$ |
| 4-222 | 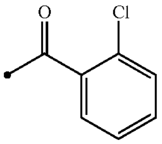 | 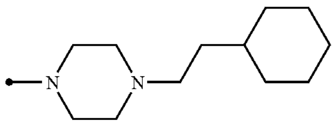 | MS m/z 641 $(M + H)^+$ |
| 4-223 | 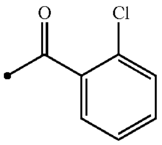 | 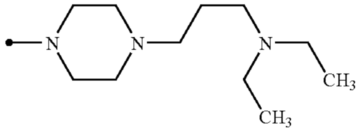 | MS m/z 644 $(M + H)^+$ |
| 4-224 | 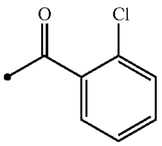 | 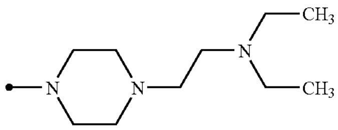 | MS m/z 630 $(M + H)^+$ |
| 4-225 | 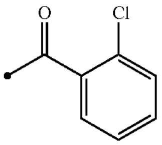 | 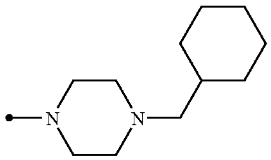 | MS m/z 627 $(M + H)^+$ |
| 4-226 | 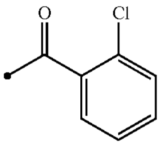 | 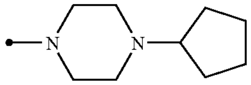 | MS m/z 599 $(M + H)^+$ |

TABLE 4-continued
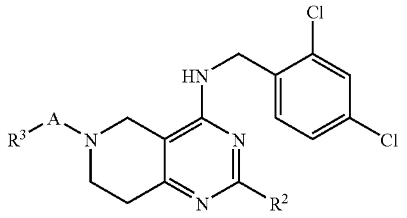
| Compound Number | •—A—$R^3$ | •—$R^2$ | Spectrum Data |
|---|---|---|---|
| 4-227 | 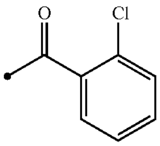 | 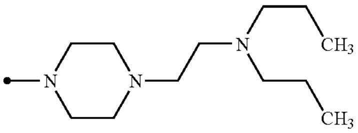 | MS m/z 658 $(M + H)^+$ |
| 4-228 | 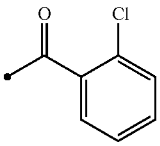 | 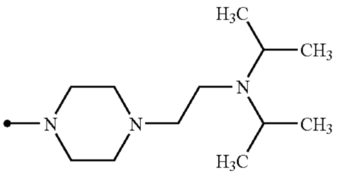 | MS m/z 658 $(M + H)^+$ |
| 4-229 | 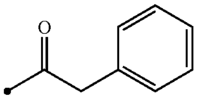 | 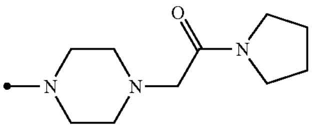 | MS m/z 622 $(M + H)^+$ |
| 4-230 | 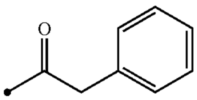 | 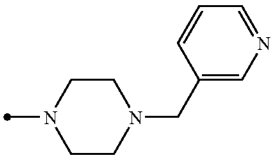 | MS m/z 602 $(M + H)^+$ |
| 4-231 | 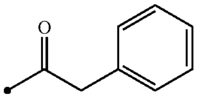 | 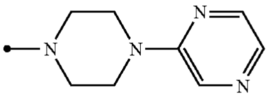 | MS m/z 589 $(M + H)^+$ |
| 4-232 | 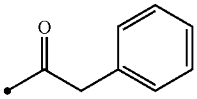 | 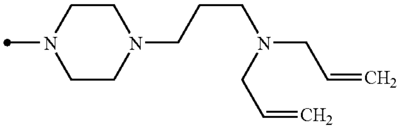 | MS m/z 648 $(M + H)^+$ |
| 4-233 | 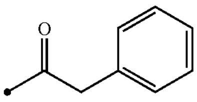 | 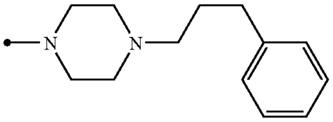 | MS m/z 629 $(M + H)^+$ |
| 4-234 | 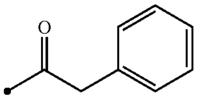 | 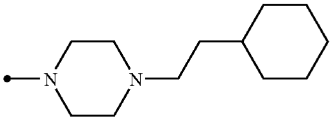 | MS m/z 621 $(M + H)^+$ |
| 4-235 | 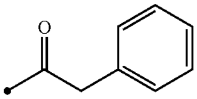 | 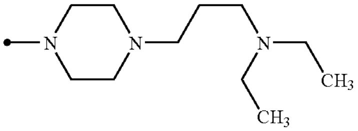 | MS m/z 624 $(M + H)^+$ |

TABLE 4-continued
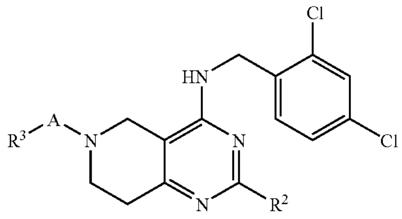
| Compound Number | •—A—$R^3$ | •—$R^2$ | Spectrum Data |
|---|---|---|---|
| 4-236 | 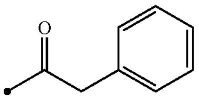 | 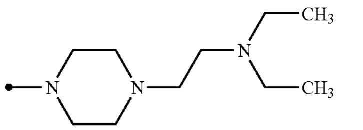 | MS m/z 610 (M + H)$^+$ |
| 4-237 | 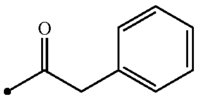 | 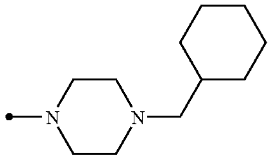 | MS m/z 607 (M + H)$^+$ |
| 4-238 | 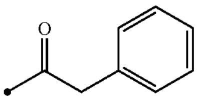 | 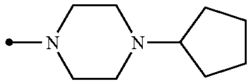 | MS m/z 579 (M + H)$^+$ |
| 4-239 | 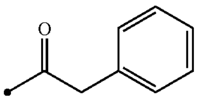 | 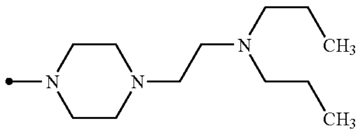 | MS m/z 638 (M + H)$^+$ |
| 4-240 | 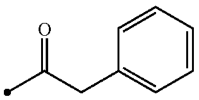 | 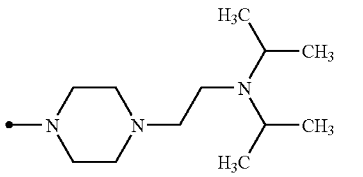 | MS m/z 638 (M + H)$^+$ |
| 4-241 | 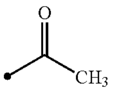 | 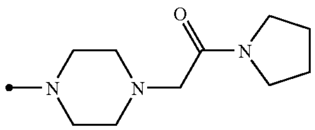 | MS m/z 546 (M + H)$^+$ |
| 4-242 | 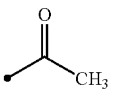 | 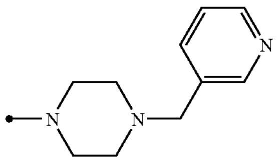 | MS m/z 526 (M + H)$^+$ |
| 4-243 | 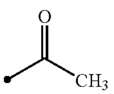 | 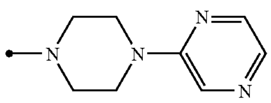 | MS m/z 513 (M + H)$^+$ |

TABLE 4-continued
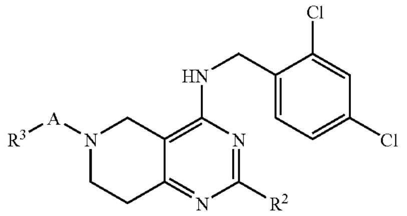
| Compound Number | •—A—R$^3$ | •—R$^2$ | Spectrum Data |
|---|---|---|---|
| 4-244 | 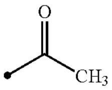 | 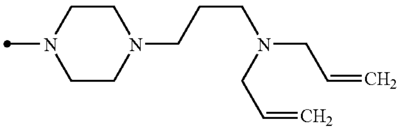 | MS m/z 572 $(M + H)^+$ |
| 4-245 | 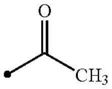 | 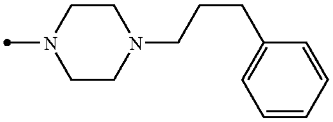 | MS m/z 553 $(M + H)^+$ |
| 4-246 | 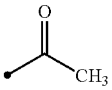 | 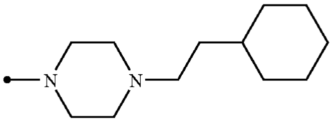 | MS m/z 545 $(M + H)^+$ |
| 4-247 | 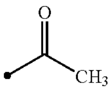 | 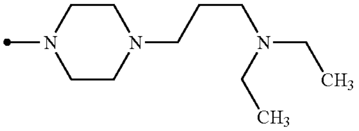 | MS m/z 548 $(M + H)^+$ |
| 4-248 | 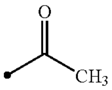 | 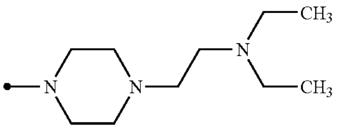 | MS m/z 534 $(M + H)^+$ |
| 4-249 | 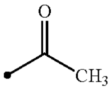 | 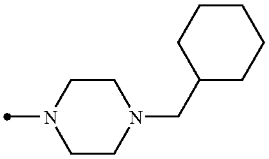 | MS m/z 531 $(M + H)^+$ |
| 4-250 | 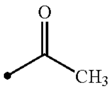 | 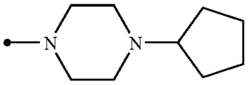 | MS m/z 503 $(M + H)^+$ |
| 4-251 | 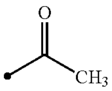 | 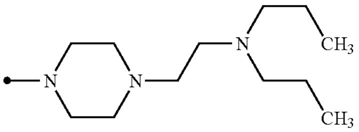 | MS m/z 562 $(M + H)^+$ |
| 4-252 | 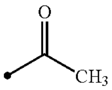 | 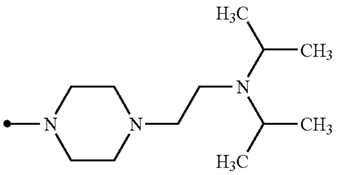 | MS m/z 562 $(M + H)^+$ |

TABLE 4-continued
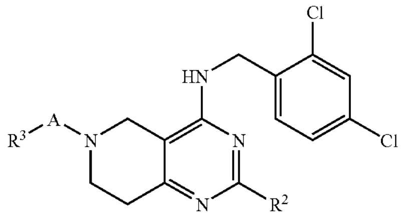
| Compound Number | •—A—$R^3$ | •—$R^2$ | Spectrum Data |
| --- | --- | --- | --- |
| 4-253 | 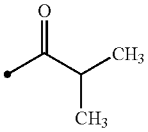 | 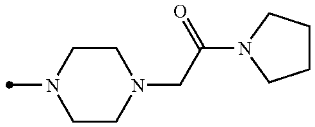 | MS m/z 574 $(M + H)^+$ |
| 4-254 | 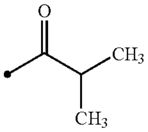 | 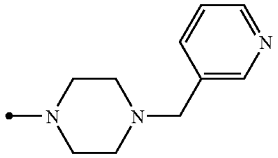 | MS m/z 554 $(M + H)^+$ |
| 4-255 | 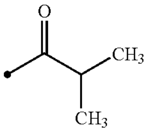 | 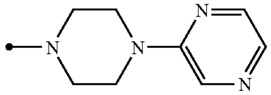 | MS m/z 541 $(M + H)^+$ |
| 4-256 | 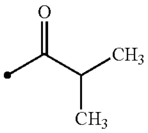 | 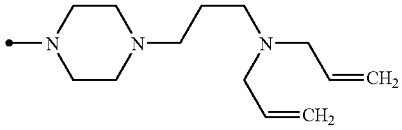 | MS m/z 600 $(M + H)^+$ |
| 4-257 | 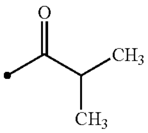 | 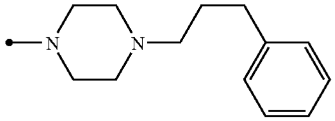 | MS m/z 581 $(M + H)^+$ |
| 4-258 | 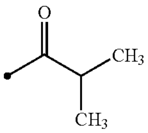 | 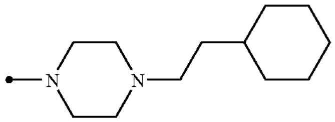 | MS m/z 573 $(M + H)^+$ |
| 4-259 | 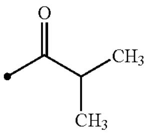 | 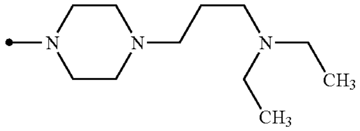 | MS m/z 576 $(M + H)^+$ |
| 4-260 | 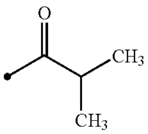 | 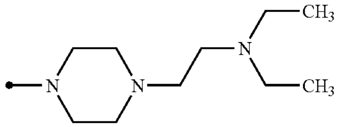 | MS m/z 562 $(M + H)^+$ |

TABLE 4-continued
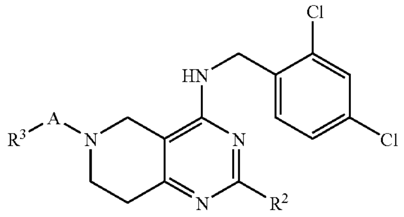
| Compound Number | •—A—$R^3$ | •—$R^2$ | Spectrum Data |
|---|---|---|---|
| 4-261 | 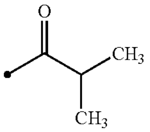 | 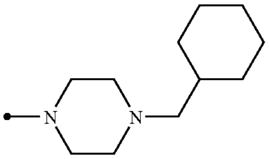 | MS m/z 559 $(M + H)^+$ |
| 4-262 | 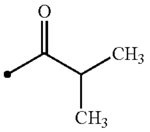 | 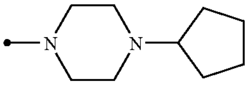 | MS m/z 531 $(M + H)^+$ |
| 4-263 | 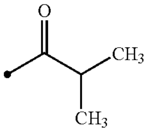 | 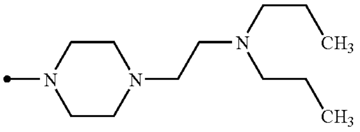 | MS m/z 590 $(M + H)^+$ |
| 4-264 | 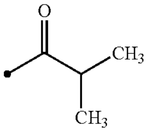 | 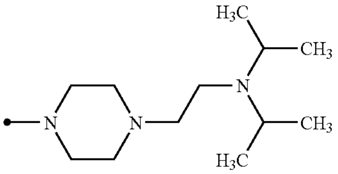 | MS m/z 590 $(M + H)^+$ |
| 4-265 | 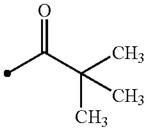 | 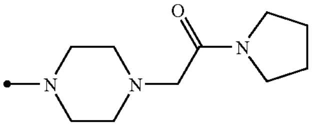 | MS m/z 588 $(M + H)^+$ |
| 4-266 | 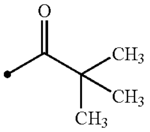 | 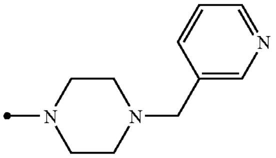 | MS m/z 568 $(M + H)^+$ |
| 4-267 | 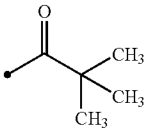 | 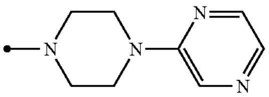 | MS m/z 555 $(M + H)^+$ |
| 4-268 | 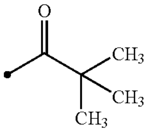 | 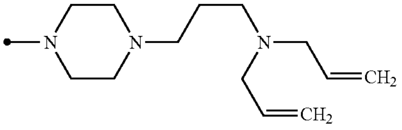 | MS m/z 614 $(M + H)^+$ |

TABLE 4-continued
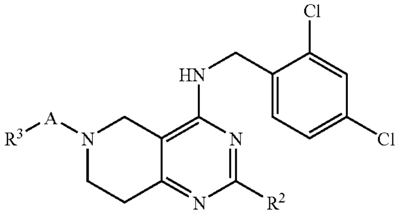
| Compound Number | •—A—$R^3$ | •—$R^2$ | Spectrum Data |
|---|---|---|---|
| 4-269 | 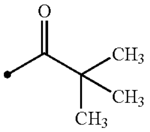 | 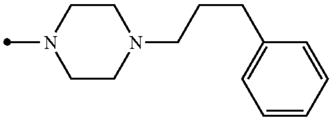 | MS m/z 595 $(M + H)^+$ |
| 4-270 | 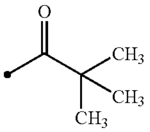 | 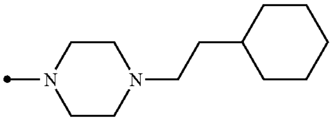 | MS m/z 587 $(M + H)^+$ |
| 4-271 | 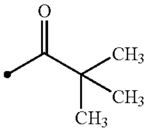 | 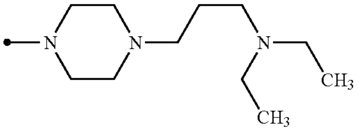 | MS m/z 590 $(M + H)^+$ |
| 4-272 | 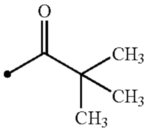 | 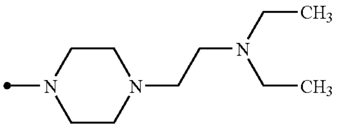 | MS m/z 576 $(M + H)^+$ |
| 4-273 | 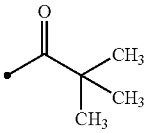 | 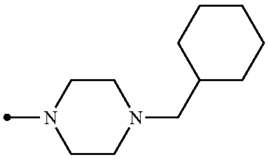 | MS m/z 573 $(M + H)^+$ |
| 4-274 | 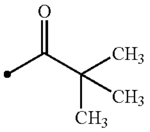 | 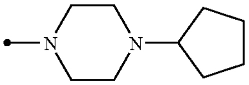 | MS m/z 545 $(M + H)^+$ |
| 4-275 | 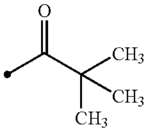 | 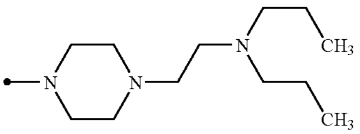 | MS m/z 604 $(M + H)^+$ |
| 4-276 | 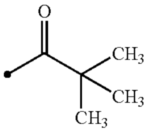 | 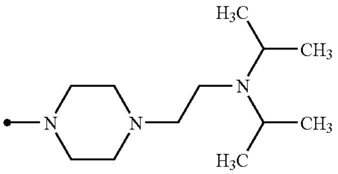 | MS m/z 604 $(M + H)^+$ |

TABLE 4-continued
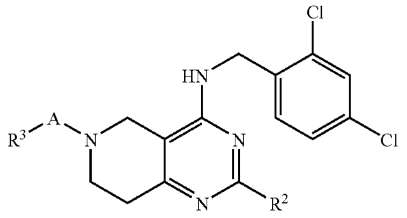
| Compound Number | •—A—$R^3$ | •—$R^2$ | Spectrum Data |
|---|---|---|---|
| 4-277 | 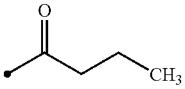 | 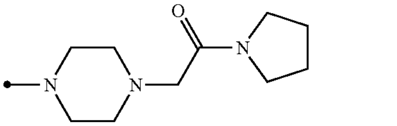 | MS m/z 574 $(M + H)^+$ |
| 4-278 | 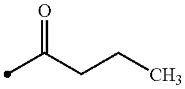 | 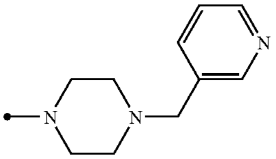 | MS m/z 554 $(M + H)^+$ |
| 4-279 | 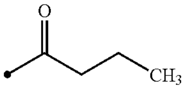 | 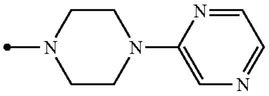 | MS m/z 541 $(M + H)^+$ |
| 4-280 | 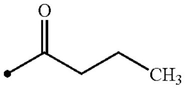 | 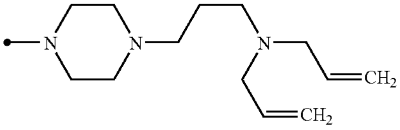 | MS m/z 600 $(M + H)^+$ |
| 4-281 | 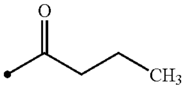 | 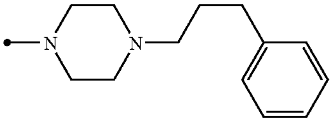 | MS m/z 581 $(M + H)^+$ |
| 4-282 | 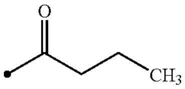 | 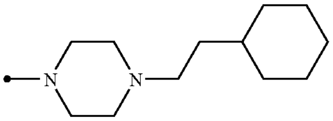 | MS m/z 573 $(M + H)^+$ |
| 4-283 | 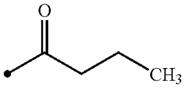 | 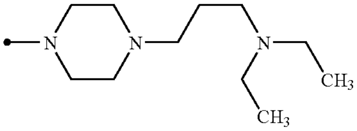 | MS m/z 576 $(M + H)^+$ |
| 4-284 | 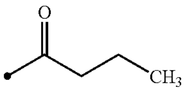 | 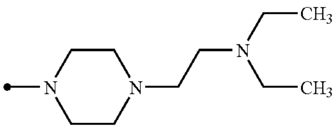 | MS m/z 562 $(M + H)^+$ |
| 4-285 | 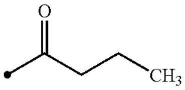 | 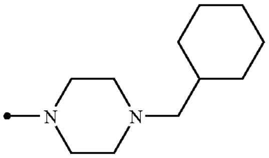 | MS m/z 559 $(M + H)^+$ |

TABLE 4-continued
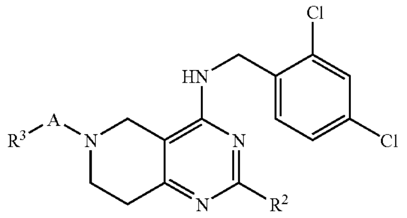
| Compound Number | •—A—$R^3$ | •—$R^2$ | Spectrum Data |
|---|---|---|---|
| 4-286 | 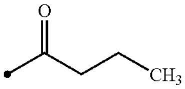 | 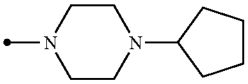 | MS m/z 531 $(M + H)^+$ |
| 4-287 | 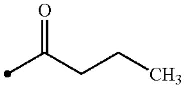 | 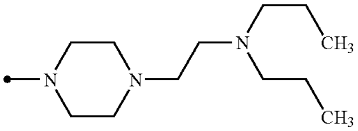 | MS m/z 590 $(M + H)^+$ |
| 4-288 | 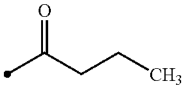 | 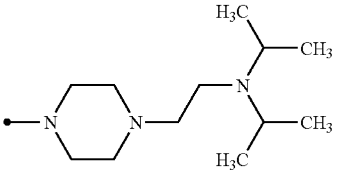 | MS m/z 590 $(M + H)^+$ |
| 4-289 | 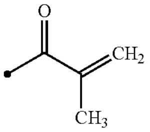 | 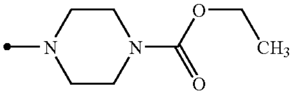 | MS m/z 533 $(M + H)^+$ |
| 4-290 | 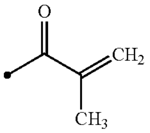 | 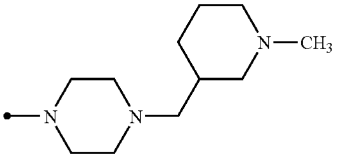 | MS m/z 572 $(M + H)^+$ |
| 4-291 | 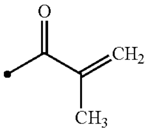 | 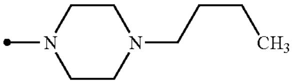 | MS m/z 517 $(M + H)^+$ |
| 4-292 | 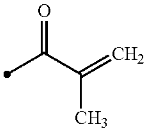 | 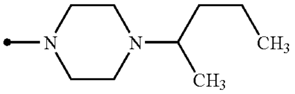 | MS m/z 531 $(M + H)^+$ |
| 4-293 | 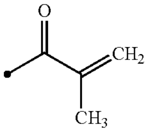 | 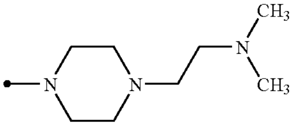 | MS m/z 532 $(M + H)^+$ |

TABLE 4-continued
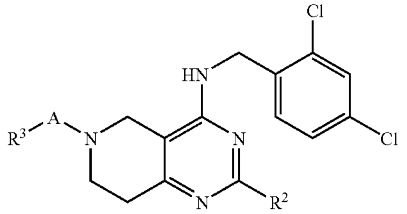
| Compound Number | •—A—R³ | •—R² | Spectrum Data |
|---|---|---|---|
| 4-294 | 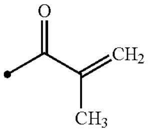 | 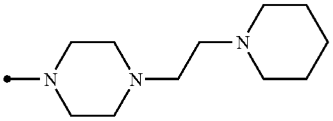 | MS m/z 572 (M + H)+ |
| 4-295 | 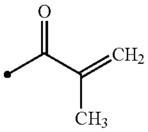 | 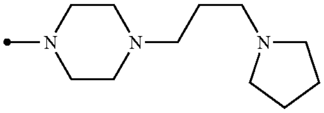 | MS m/z 572 (M + H)+ |
| 4-296 | 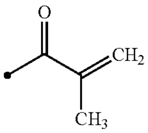 | 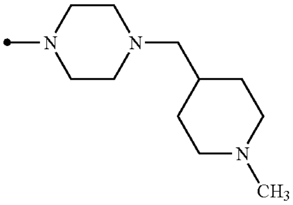 | MS m/z 572 (M + H)+ |
| 4-297 | 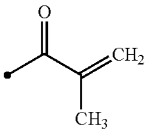 | 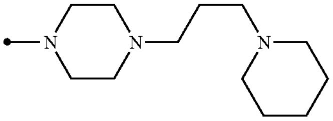 | MS m/z 586 (M + H)+ |
| 4-298 | 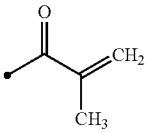 | 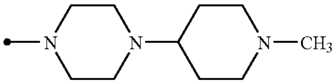 | MS m/z 558 (M + H)+ |
| 4-299 | 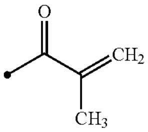 | 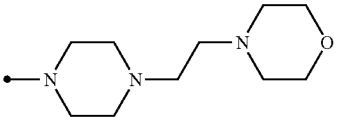 | MS m/z 574 (M + H)+ |
| 4-300 | 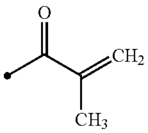 | 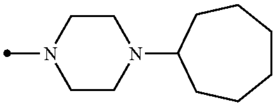 | MS m/z 557 (M + H)+ |
| 4-301 | 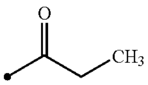 | 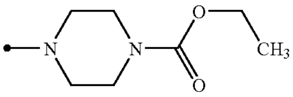 | MS m/z 521 (M + H)+ |

TABLE 4-continued
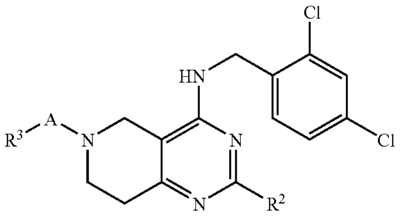
| Compound Number | •—A—$R^3$ | •—$R^2$ | Spectrum Data |
|---|---|---|---|
| 4-302 | 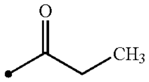 | 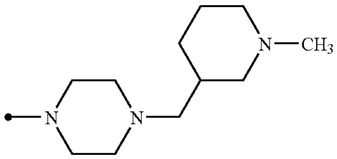 | MS m/z 560 $(M + H)^+$ |
| 4-303 | 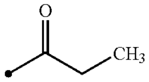 | 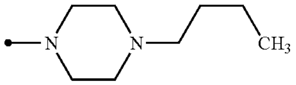 | MS m/z 505 $(M + H)^+$ |
| 4-304 | 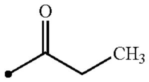 | 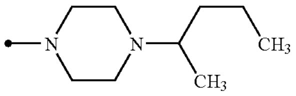 | MS m/z 519 $(M + H)^+$ |
| 4-305 | 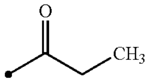 | 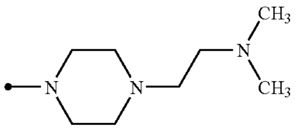 | MS m/z 520 $(M + H)^+$ |
| 4-306 | 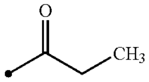 | 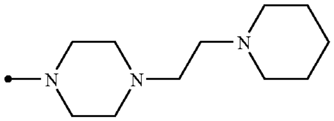 | MS m/z 560 $(M + H)^+$ |
| 4-307 | 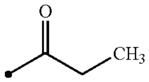 | 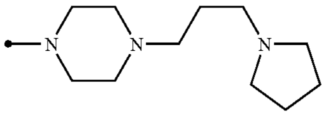 | MS m/z 560 $(M + H)^+$ |
| 4-308 | 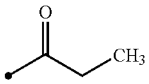 | 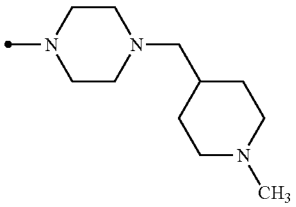 | MS m/z 560 $(M + H)^+$ |
| 4-309 | 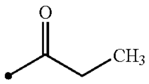 | 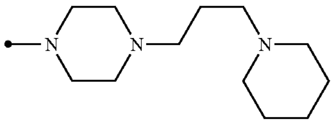 | MS m/z 574 $(M + H)^+$ |
| 4-310 | 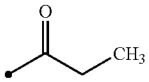 | 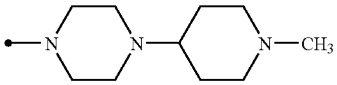 | MS m/z 546 $(M + H)^+$ |

TABLE 4-continued
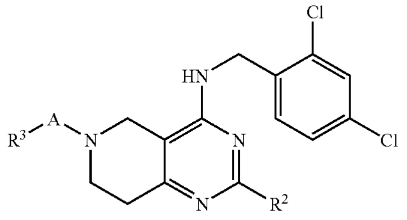
| Compound Number | •—A—$R^3$ | •—$R^2$ | Spectrum Data |
|---|---|---|---|
| 4-311 | 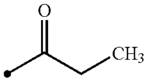 | 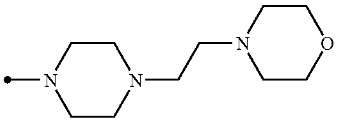 | MS m/z 562 $(M + H)^+$ |
| 4-312 | 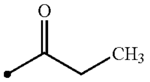 | 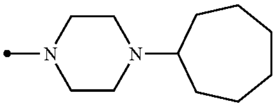 | MS m/z 545 $(M + H)^+$ |
| 4-313 | 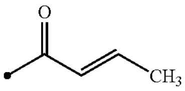 | 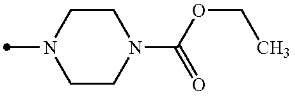 | MS m/z 533 $(M + H)^+$ |
| 4-314 | 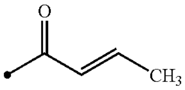 | 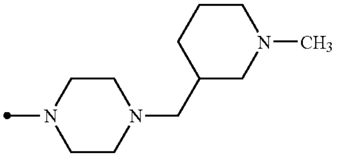 | MS m/z 572 $(M + H)^+$ |
| 4-315 | 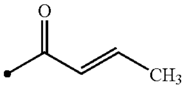 | 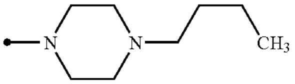 | MS m/z 517 $(M + H)^+$ |
| 4-316 | 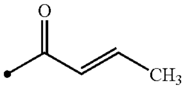 | 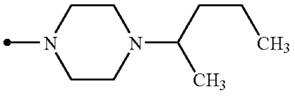 | MS m/z 531 $(M + H)^+$ |
| 4-317 | 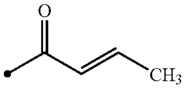 | 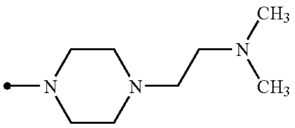 | MS m/z 532 $(M + H)^+$ |
| 4-318 | 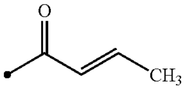 | 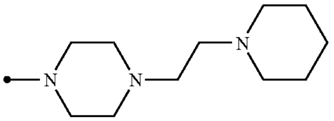 | MS m/z 572 $(M + H)^+$ |
| 4-319 | 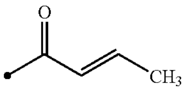 | 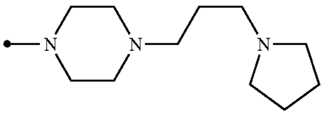 | MS m/z 572 $(M + H)^+$ |

TABLE 4-continued
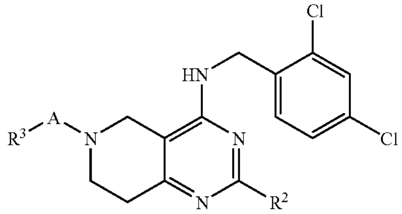
| Compound Number | •—A—$R^3$ | •—$R^2$ | Spectrum Data |
|---|---|---|---|
| 4-320 | 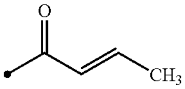 | 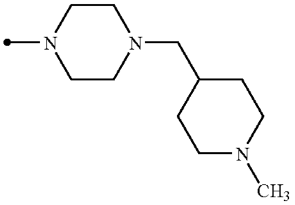 | MS m/z 572 $(M + H)^+$ |
| 4-321 | 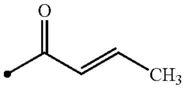 | 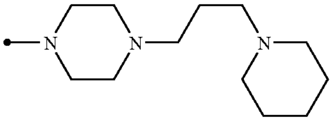 | MS m/z 586 $(M + H)^+$ |
| 4-322 | 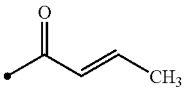 | 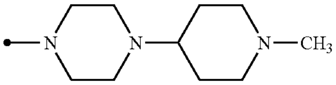 | MS m/z 558 $(M + H)^+$ |
| 4-323 | 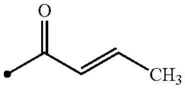 | 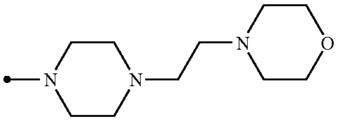 | MS m/z 574 $(M + H)^+$ |
| 4-324 | 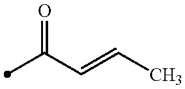 | 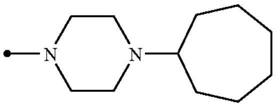 | MS m/z 557 $(M + H)^+$ |
| 4-325 | 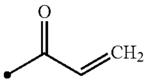 | 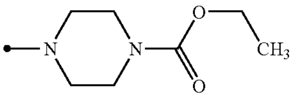 | MS m/z 519 $(M + H)^+$ |
| 4-326 | 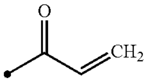 | 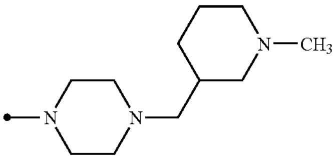 | MS m/z 558 $(M + H)^+$ |
| 4-327 | 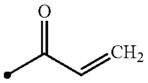 | 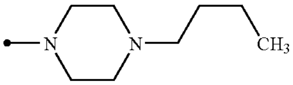 | MS m/z 503 $(M + H)^+$ |
| 4-328 | 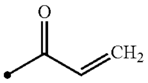 | 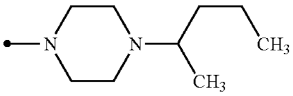 | MS m/z 517 $(M + H)^+$ |

TABLE 4-continued
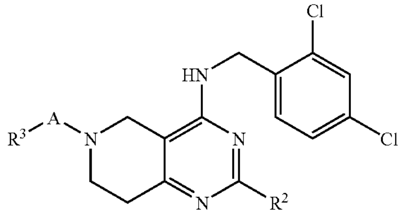
| Compound Number | •—A—$R^3$ | •—$R^2$ | Spectrum Data |
|---|---|---|---|
| 4-329 | 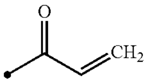 | 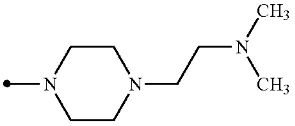 | MS m/z 518 (M + H)+ |
| 4-330 | 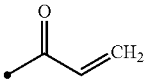 | 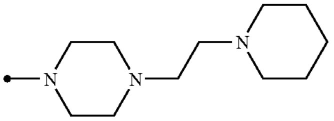 | MS m/z 558 (M + H)+ |
| 4-331 | 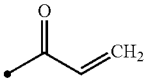 | 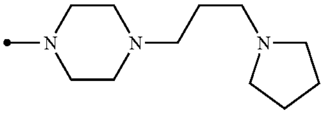 | MS m/z 558 (M + H)+ |
| 4-332 | 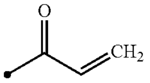 | 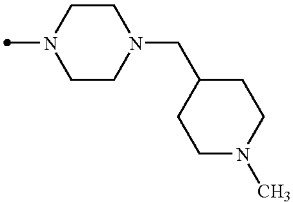 | MS m/z 558 (M + H)+ |
| 4-333 | 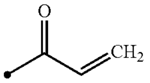 | 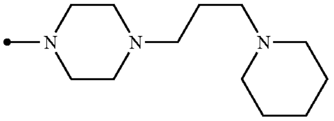 | MS m/z 572 (M + H)+ |
| 4-334 | 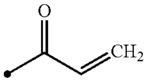 | 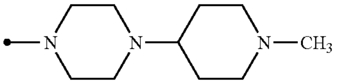 | MS m/z 544 (M + H)+ |
| 4-335 | 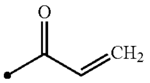 | 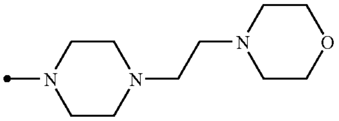 | MS m/z 560 (M + H)+ |
| 4-336 | 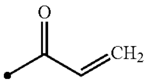 | 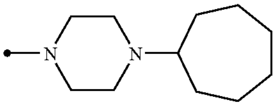 | MS m/z 543 (M + H)+ |
| 4-337 | 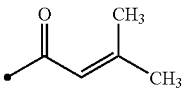 | 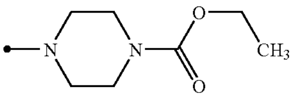 | MS m/z 547 (M + H)+ |

TABLE 4-continued
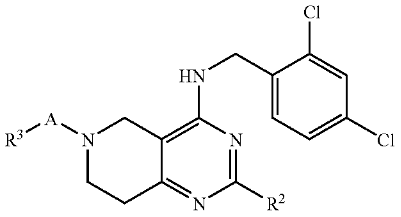
| Compound Number | •—A—$R^3$ | •—$R^2$ | Spectrum Data |
|---|---|---|---|
| 4-338 | 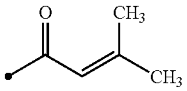 | 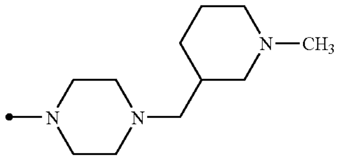 | MS m/z 586 $(M + H)^+$ |
| 4-339 | 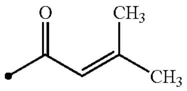 | 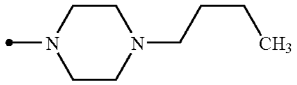 | MS m/z 531 $(M + H)^+$ |
| 4-340 | 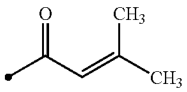 | 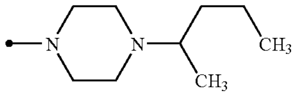 | MS m/z 545 $(M + H)^+$ |
| 4-341 | 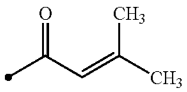 | 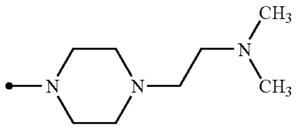 | MS m/z 546 $(M + H)^+$ |
| 4-342 | 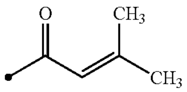 | 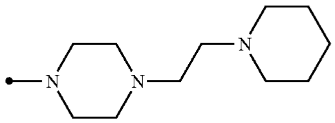 | MS m/z 586 $(M + H)^+$ |
| 4-343 | 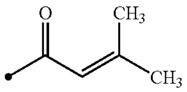 | 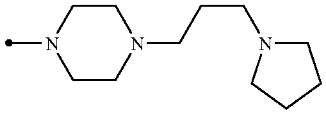 | MS m/z 586 $(M + H)^+$ |
| 4-344 | 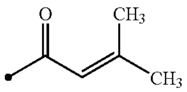 | 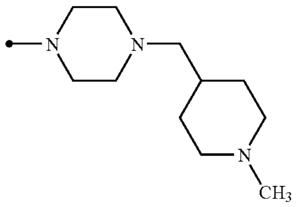 | MS m/z 586 $(M + H)^+$ |
| 4-345 | 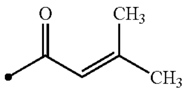 | 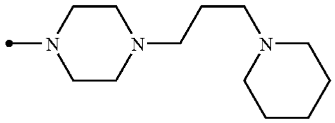 | MS m/z 600 $(M + H)^+$ |
| 4-346 | 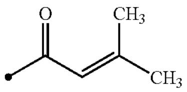 | 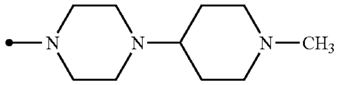 | MS m/z 572 $(M + H)^+$ |

TABLE 4-continued
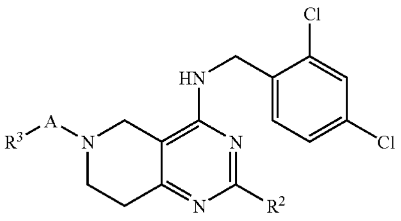
| Compound Number | •—A—$R^3$ | •—$R^2$ | Spectrum Data |
|---|---|---|---|
| 4-347 | 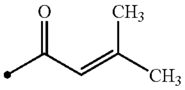 | 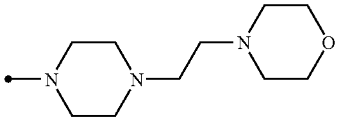 | MS m/z 588 $(M + H)^+$ |
| 4-348 | 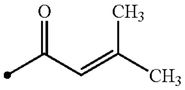 | 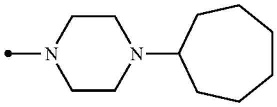 | MS m/z 571 $(M + H)^+$ |
| 4-349 | 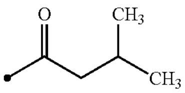 | 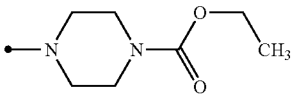 | MS m/z 549 $(M + H)^+$ |
| 4-350 | 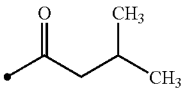 | 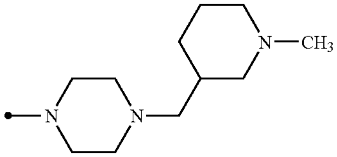 | MS m/z 588 $(M + H)^+$ |
| 4-351 | 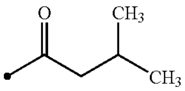 | 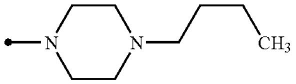 | MS m/z 533 $(M + H)^+$ |
| 4-352 | 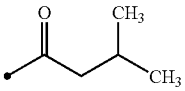 | 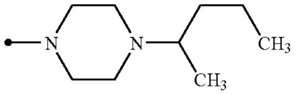 | MS m/z 547 $(M + H)^+$ |
| 4-353 | 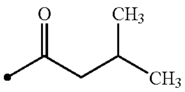 | 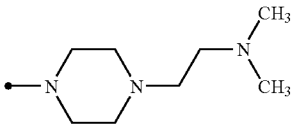 | MS m/z 548 $(M + H)^+$ |
| 4-354 | 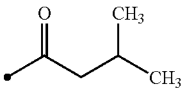 | 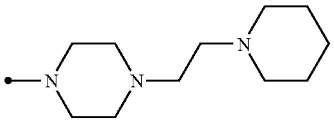 | MS m/z 588 $(M + H)^+$ |
| 4-355 | 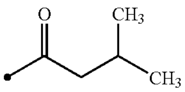 | 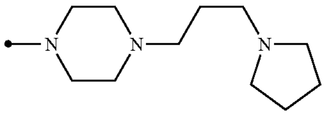 | MS m/z 588 $(M + H)^+$ |

TABLE 4-continued
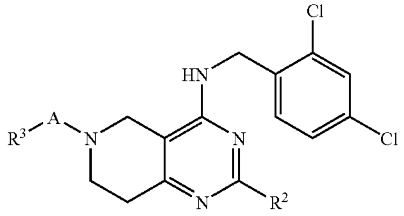
| Compound Number | •—A—$R^3$ | •—$R^2$ | Spectrum Data |
|---|---|---|---|
| 4-356 | 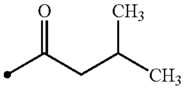 | 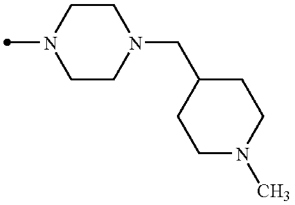 | MS m/z 588 $(M + H)^+$ |
| 4-357 | 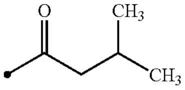 | 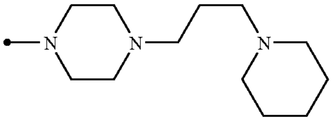 | MS m/z 602 $(M + H)^+$ |
| 4-358 | 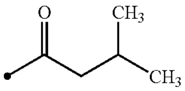 | 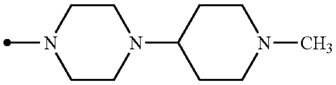 | MS m/z 574 $(M + H)^+$ |
| 4-359 | 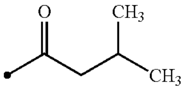 | 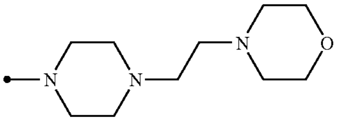 | MS m/z 590 $(M + H)^+$ |
| 4-360 | 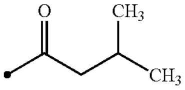 | 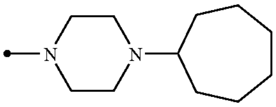 | MS m/z 573 $(M + H)^+$ |
| 4-361 | 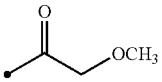 | 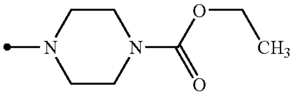 | MS m/z 537 $(M + H)^+$ |
| 4-362 | 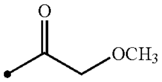 | 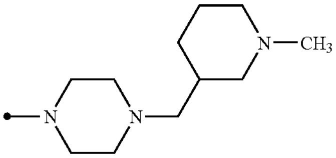 | MS m/z 576 $(M + H)^+$ |
| 4-363 | 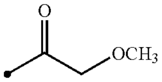 | 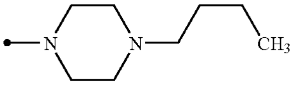 | MS m/z 521 $(M + H)^+$ |
| 4-364 | 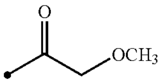 | 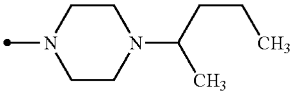 | MS m/z 535 $(M + H)^+$ |

TABLE 4-continued
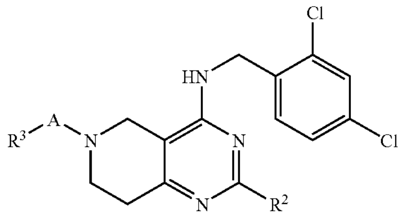
| Compound Number | •—A—$R^3$ | •—$R^2$ | Spectrum Data |
|---|---|---|---|
| 4-365 | 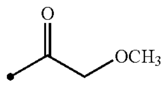 | 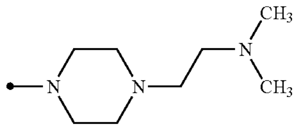 | MS m/z 536 $(M+H)^+$ |
| 4-366 | 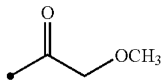 | 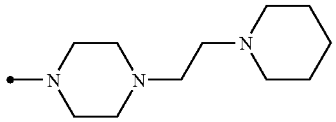 | MS m/z 576 $(M+H)^+$ |
| 4-367 | 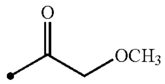 | 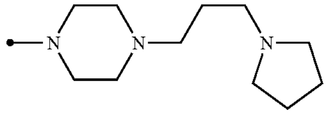 | MS m/z 576 $(M+H)^+$ |
| 4-368 | 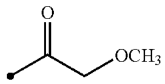 | 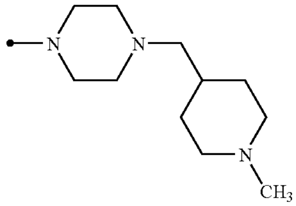 | MS m/z 576 $(M+H)^+$ |
| 4-369 | 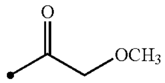 | 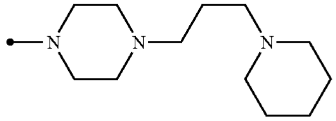 | MS m/z 590 $(M+H)^+$ |
| 4-370 | 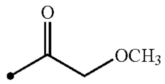 | 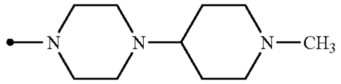 | MS m/z 562 $(M+H)^+$ |
| 4-371 | 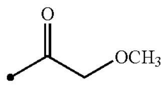 | 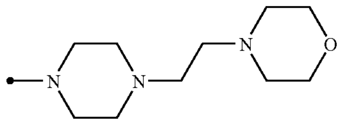 | MS m/z 578 $(M+H)^+$ |
| 4-372 | 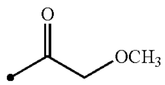 | 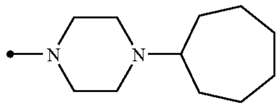 | MS m/z 561 $(M+H)^+$ |
| 4-373 | 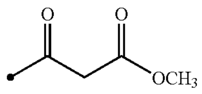 | 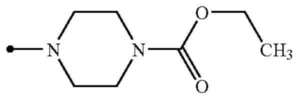 | MS m/z 565 $(M+H)^+$ |

TABLE 4-continued
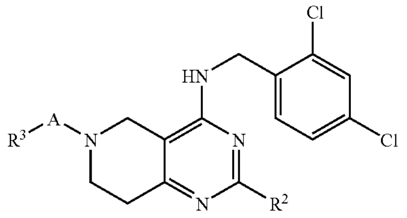
| Compound Number | •—A—$R^3$ | •—$R^2$ | Spectrum Data |
|---|---|---|---|
| 4-374 | 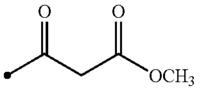 | 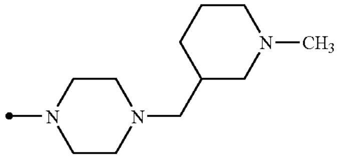 | MS m/z 604 (M + H)$^+$ |
| 4-375 | 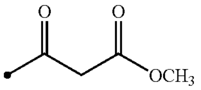 | 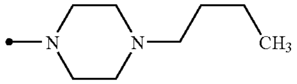 | MS m/z 549 (M + H)$^+$ |
| 4-376 | 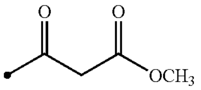 | 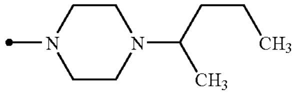 | MS m/z 563 (M + H)$^+$ |
| 4-377 | 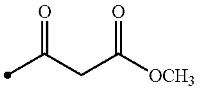 | 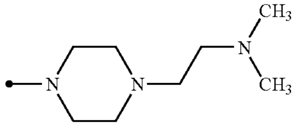 | MS m/z 564 (M + H)$^+$ |
| 4-378 | 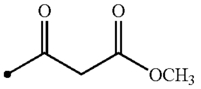 | 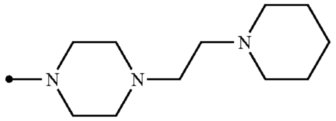 | MS m/z 604 (M + H)$^+$ |
| 4-379 | 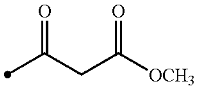 | 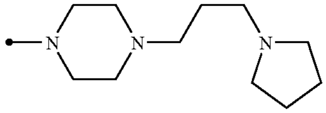 | MS m/z 604 (M + H)$^+$ |
| 4-380 | 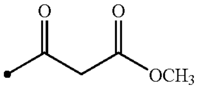 | 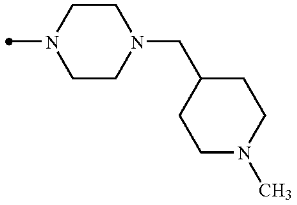 | MS m/z 604 (M + H)$^+$ |
| 4-381 | 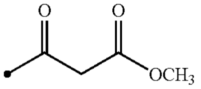 | 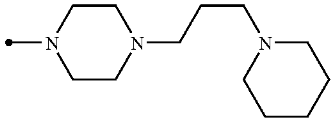 | MS m/z 618 (M + H)$^+$ |
| 4-382 | 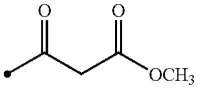 | 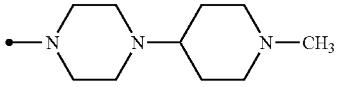 | MS m/z 590 (M + H)$^+$ |

TABLE 4-continued
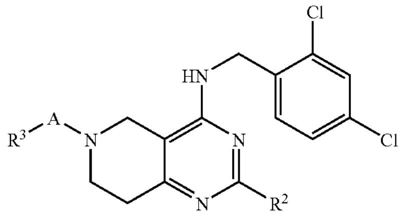
| Compound Number | •—A—$R^3$ | •—$R^2$ | Spectrum Data |
|---|---|---|---|
| 4-383 | 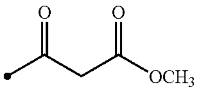 | 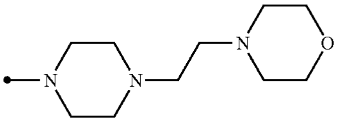 | MS m/z 606 (M + H)$^+$ |
| 4-384 | 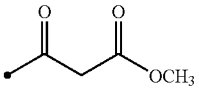 | 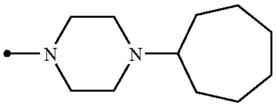 | MS m/z 589 (M + H)$^+$ |
| 4-385 | 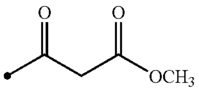 | 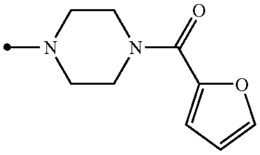 | MS m/z 555 (M + H)$^+$ |
| 4-386 | 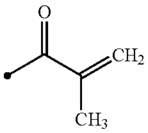 | 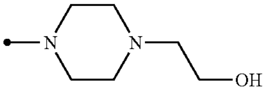 | MS m/z 505 (M + H)$^+$ |
| 4-387 | 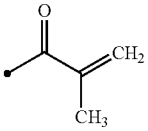 | 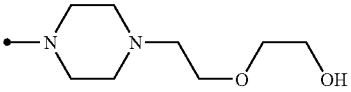 | MS m/z 549 (M + H)$^+$ |
| 4-388 | 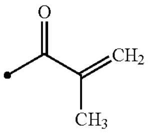 | 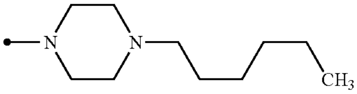 | MS m/z 545 (M + H)$^+$ |
| 4-389 | 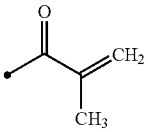 | 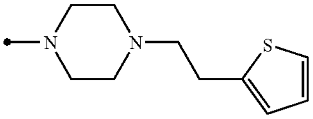 | MS m/z 571 (M + H)$^+$ |
| 4-390 | 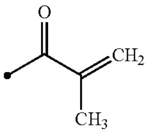 | 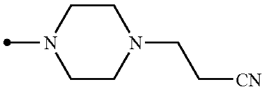 | MS m/z 514 (M + H)$^+$ |
| 4-391 | 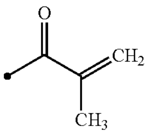 | 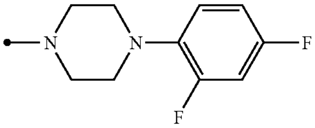 | MS m/z 573 (M + H)$^+$ |

TABLE 4-continued
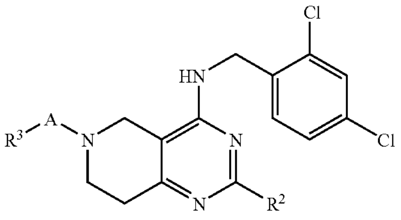
| Compound Number | •—A—$R^3$ | •—$R^2$ | Spectrum Data |
|---|---|---|---|
| 4-392 | 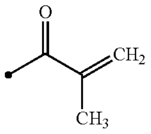 | 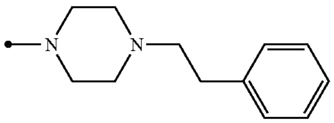 | MS m/z 565 $(M + H)^+$ |
| 4-393 | 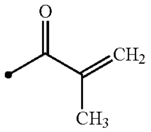 | 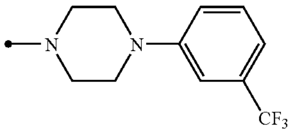 | MS m/z 605 $(M + H)^+$ |
| 4-394 | 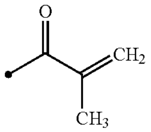 | 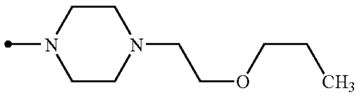 | MS m/z 533 $(M + H)^+$ |
| 4-395 | 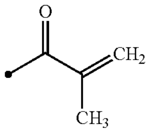 | 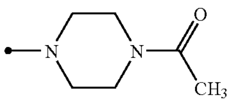 | MS m/z 503 $(M + H)^+$ |
| 4-396 | 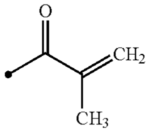 | 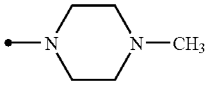 | MS m/z 475 $(M + H)^+$ |
| 4-397 | 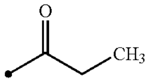 | 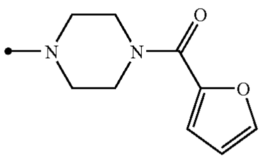 | MS m/z 543 $(M + H)^+$ |
| 4-398 | 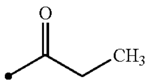 | 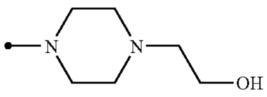 | MS m/z 493 $(M + H)^+$ |
| 4-399 | 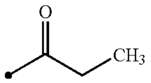 | 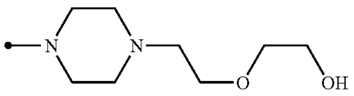 | MS m/z 537 $(M + H)^+$ |
| 4-400 | 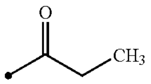 | 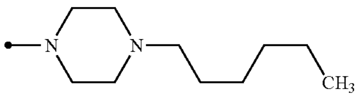 | MS m/z 533 $(M + H)^+$ |

TABLE 4-continued
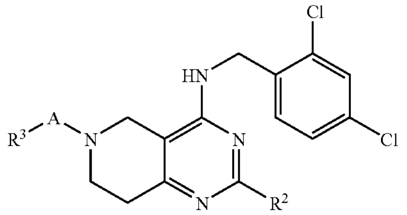
| Compound Number | •—A—$R^3$ | •—$R^2$ | Spectrum Data |
|---|---|---|---|
| 4-401 | 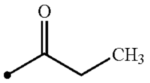 | 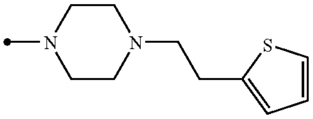 | MS m/z 559 (M + H)$^+$ |
| 4-402 | 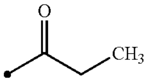 | 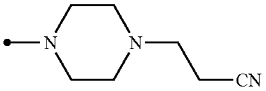 | MS m/z 502 (M + H)$^+$ |
| 4-403 | 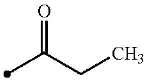 | 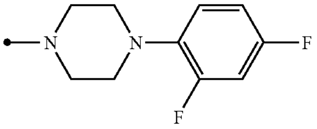 | MS m/z 561 (M + H)$^+$ |
| 4-404 | 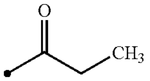 | 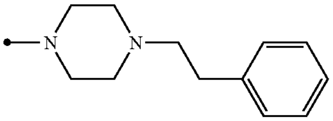 | MS m/z 553 (M + H)$^+$ |
| 4-405 | 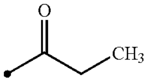 | 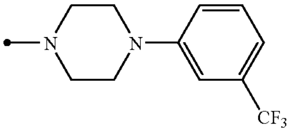 | MS m/z 593 (M + H)$^+$ |
| 4-406 | 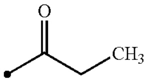 | 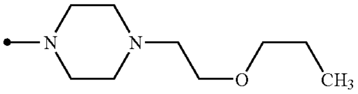 | MS m/z 521 (M + H)$^+$ |
| 4-407 | 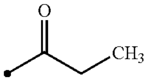 | 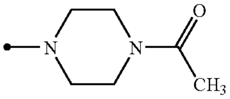 | MS m/z 491 (M + H)$^+$ |
| 4-408 | 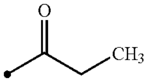 | 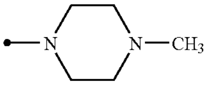 | MS m/z 463 (M + H)$^+$ |
| 4-409 | 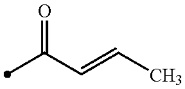 | 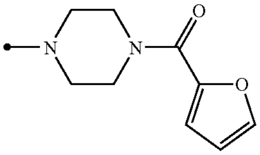 | MS m/z 555 (M + H)$^+$ |
| 4-410 | 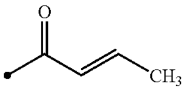 | 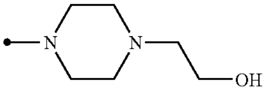 | MS m/z 505 (M + H)$^+$ |

TABLE 4-continued
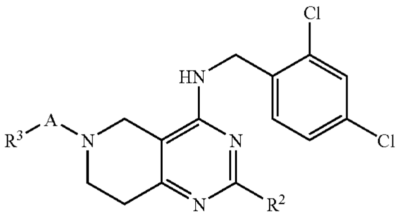
| Compound Number | •—A—$R^3$ | •—$R^2$ | Spectrum Data |
|---|---|---|---|
| 4-411 | 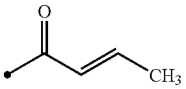 | 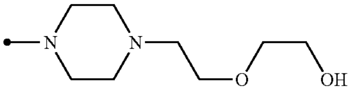 | MS m/z 549 $(M + H)^+$ |
| 4-412 | 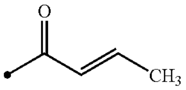 | 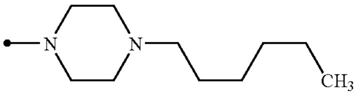 | MS m/z 545 $(M + H)^+$ |
| 4-413 | 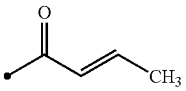 | 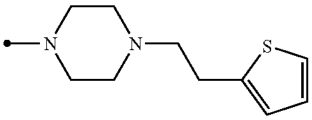 | MS m/z 571 $(M + H)^+$ |
| 4-414 | 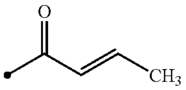 | 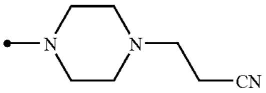 | MS m/z 514 $(M + H)^+$ |
| 4-415 | 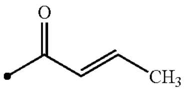 | 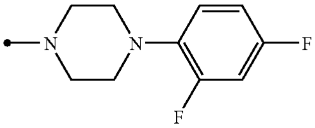 | MS m/z 573 $(M + H)^+$ |
| 4-416 | 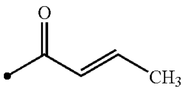 | 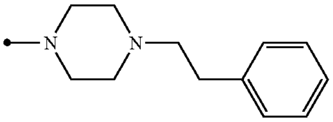 | MS m/z 565 $(M + H)^+$ |
| 4-417 | 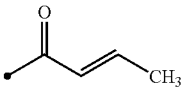 | 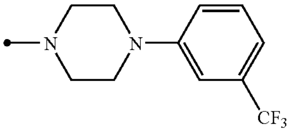 | MS m/z 605 $(M + H)^+$ |
| 4-418 | 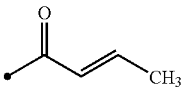 | 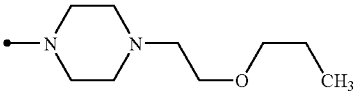 | MS m/z 533 $(M + H)^+$ |
| 4-419 | 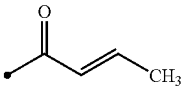 | 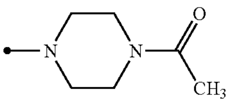 | MS m/z 503 $(M + H)^+$ |
| 4-420 | 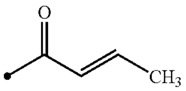 | 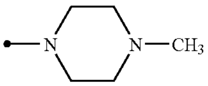 | MS m/z 475 $(M + H)^+$ |

TABLE 4-continued
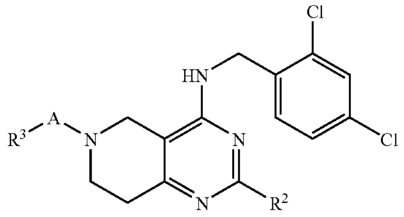
| Compound Number | •—A—R$^3$ | •—R$^2$ | Spectrum Data |
|---|---|---|---|
| 4-421 | 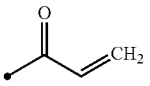 | 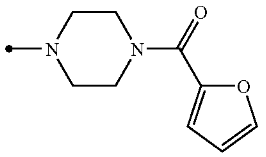 | MS m/z 541 (M + H)$^+$ |
| 4-422 | 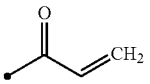 | 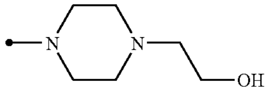 | MS m/z 491 (M + H)$^+$ |
| 4-423 | 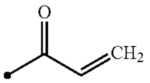 | 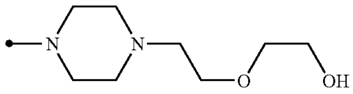 | MS m/z 535 (M + H)$^+$ |
| 4-424 | 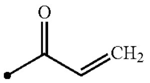 | 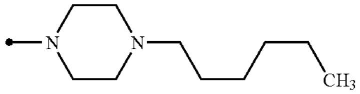 | MS m/z 531 (M + H)$^+$ |
| 4-425 | 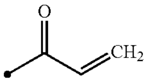 | 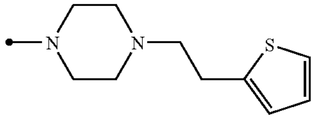 | MS m/z 557 (M + H)$^+$ |
| 4-426 | 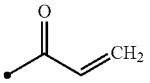 | 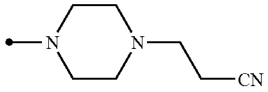 | MS m/z 500 (M + H)$^+$ |
| 4-427 | 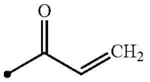 | 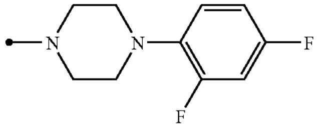 | MS m/z 559 (M + H)$^+$ |
| 4-428 | 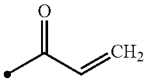 | 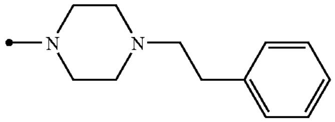 | MS m/z 551 (M + H)$^+$ |
| 4-429 | 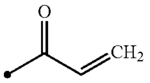 | 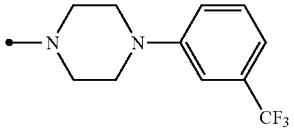 | MS m/z 591 (M + H)$^+$ |
| 4-430 | 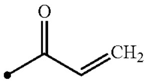 | 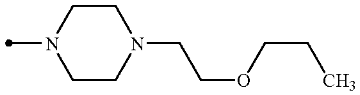 | MS m/z 519 (M + H)$^+$ |

TABLE 4-continued
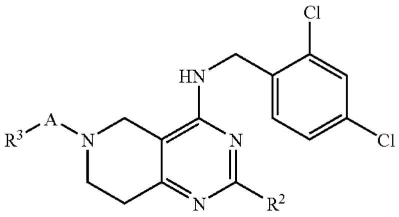
| Compound Number | •—A—$R^3$ | •—$R^2$ | Spectrum Data |
|---|---|---|---|
| 4-431 | 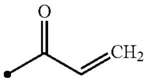 | 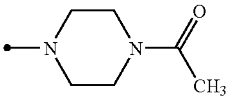 | MS m/z 489 $(M + H)^+$ |
| 4-432 | 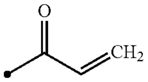 | 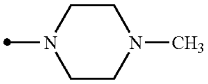 | MS m/z 461 $(M + H)^+$ |
| 4-433 | 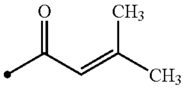 | 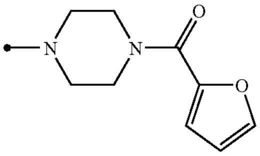 | MS m/z 569 $(M + H)^+$ |
| 4-434 | 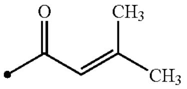 | 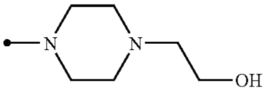 | MS m/z 519 $(M + H)^+$ |
| 4-435 | 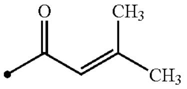 | 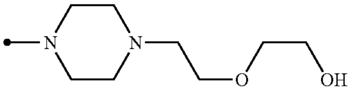 | MS m/z 563 $(M + H)^+$ |
| 4-436 | 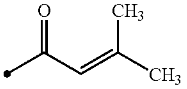 | 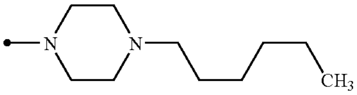 | MS m/z 559 $(M + H)^+$ |
| 4-437 | 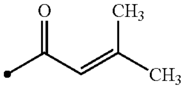 | 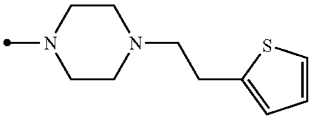 | MS m/z 585 $(M + H)^+$ |
| 4-438 | 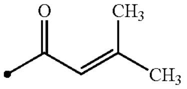 | 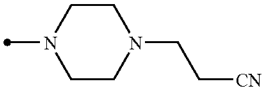 | MS m/z 528 $(M + H)^+$ |
| 4-439 | 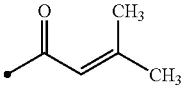 | 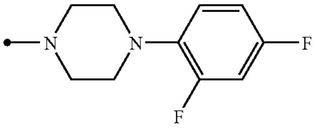 | MS m/z 587 $(M + H)^+$ |
| 4-440 | 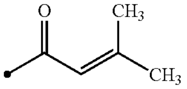 | 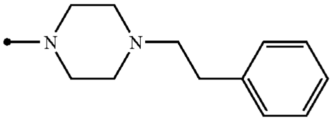 | MS m/z 579 $(M + H)^+$ |

TABLE 4-continued
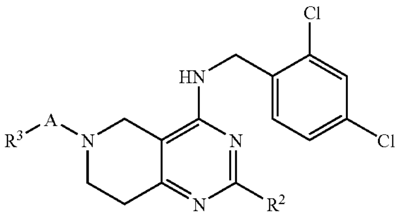
| Compound Number | •—A—$R^3$ | •—$R^2$ | Spectrum Data |
|---|---|---|---|
| 4-441 | 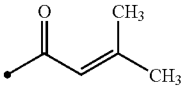 | 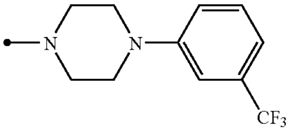 | MS m/z 619 $(M + H)^+$ |
| 4-442 | 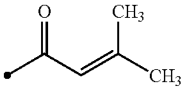 | 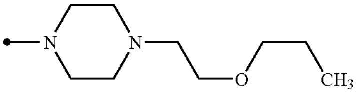 | MS m/z 547 $(M + H)^+$ |
| 4-443 | 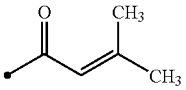 | 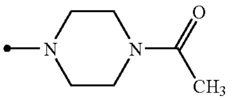 | MS m/z 517 $(M + H)^+$ |
| 4-444 | 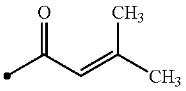 | 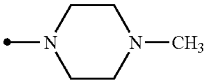 | MS m/z 489 $(M + H)^+$ |
| 4-445 | 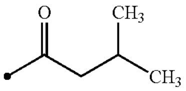 | 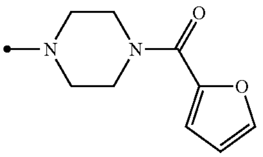 | MS m/z 571 $(M + H)^+$ |
| 4-446 | 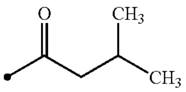 | 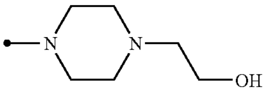 | MS m/z 521 $(M + H)^+$ |
| 4-447 | 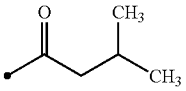 | 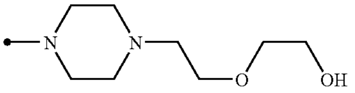 | MS m/z 565 $(M + H)^+$ |
| 4-448 | 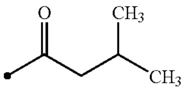 | 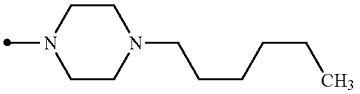 | MS m/z 561 $(M + H)^+$ |
| 4-449 | 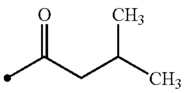 | 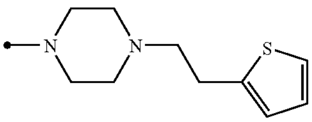 | MS m/z 587 $(M + H)^+$ |
| 4-450 | 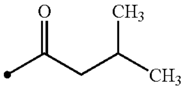 | 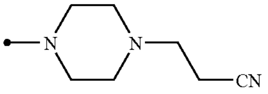 | MS m/z 530 $(M + H)^+$ |

TABLE 4-continued
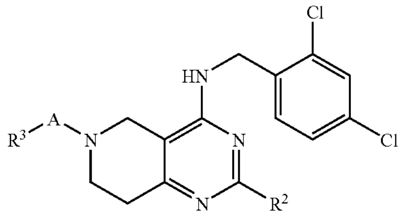
| Compound Number | •—A—$R^3$ | •—$R^2$ | Spectrum Data |
|---|---|---|---|
| 4-451 | 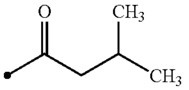 | 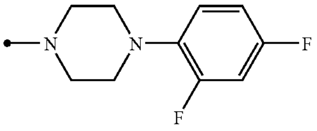 | MS m/z 589 $(M + H)^+$ |
| 4-452 | 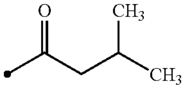 | 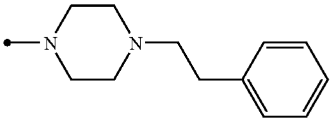 | MS m/z 581 $(M + H)^+$ |
| 4-453 | 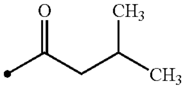 | 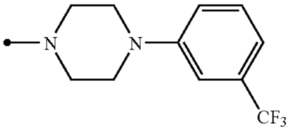 | MS m/z 621 $(M + H)^+$ |
| 4-454 | 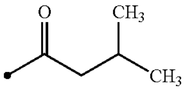 | 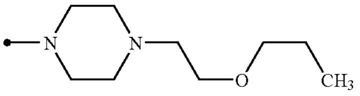 | MS m/z 549 $(M + H)^+$ |
| 4-455 | 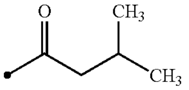 | 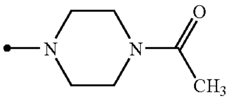 | MS m/z 519 $(M + H)^+$ |
| 4-456 | 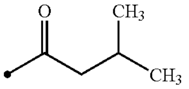 | 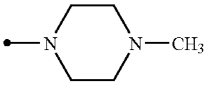 | MS m/z 491 $(M + H)^+$ |
| 4-457 | 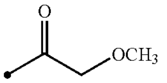 | 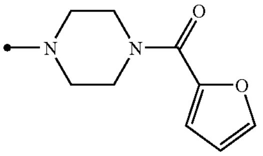 | MS m/z 559 $(M + H)^+$ |
| 4-458 | 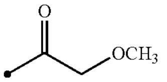 | 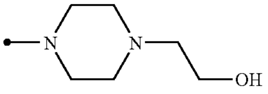 | MS m/z 509 $(M + H)^+$ |
| 4-459 | 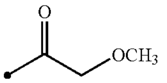 | 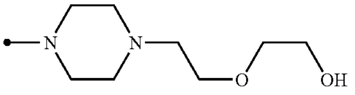 | MS m/z 553 $(M + H)^+$ |
| 4-460 | 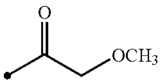 | 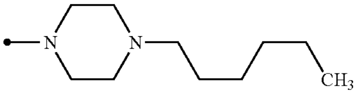 | MS m/z 549 $(M + H)^+$ |

TABLE 4-continued
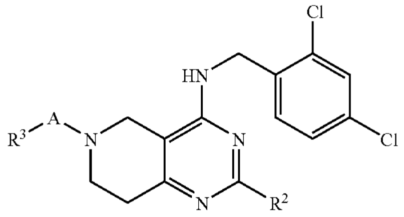
| Compound Number | •—A—$R^3$ | •—$R^2$ | Spectrum Data |
|---|---|---|---|
| 4-461 | 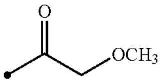 | 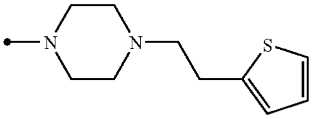 | MS m/z 575 $(M + H)^+$ |
| 4-462 | 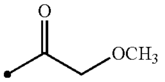 | 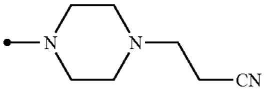 | MS m/z 518 $(M + H)^+$ |
| 4-463 | 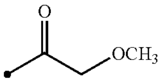 | 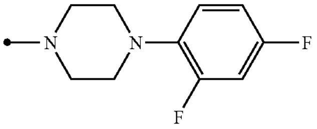 | MS m/z 577 $(M + H)^+$ |
| 4-464 | 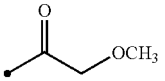 | 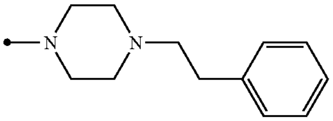 | MS m/z 569 $(M + H)^+$ |
| 4-465 | 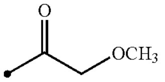 | 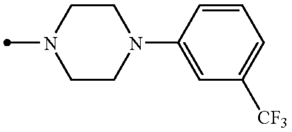 | MS m/z 609 $(M + H)^+$ |
| 4-466 | 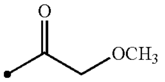 | 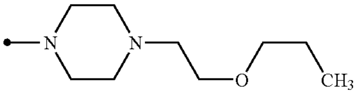 | MS m/z 537 $(M + H)^+$ |
| 4-467 | 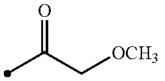 | 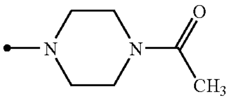 | MS m/z 507 $(M + H)^+$ |
| 4-468 | 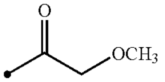 | 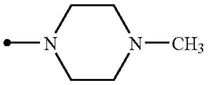 | MS m/z 479 $(M + H)^+$ |
| 4-469 | 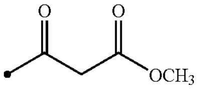 | 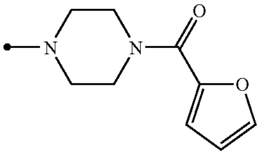 | MS m/z 587 $(M + H)^+$ |
| 4-470 | 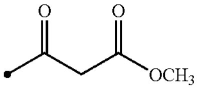 | 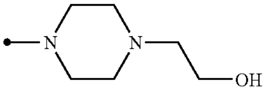 | MS m/z 537 $(M + H)^+$ |

TABLE 4-continued
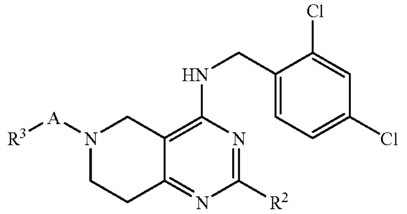
| Compound Number | •—A—$R^3$ | •—$R^2$ | Spectrum Data |
|---|---|---|---|
| 4-471 | 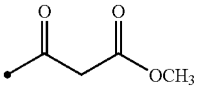 | 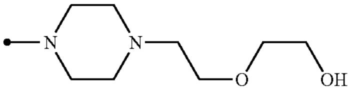 | MS m/z 581 $(M + H)^+$ |
| 4-472 | 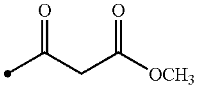 | 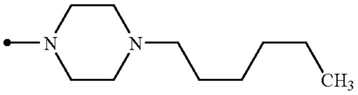 | MS m/z 577 $(M + H)^+$ |
| 4-473 | 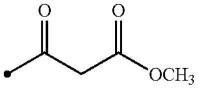 | 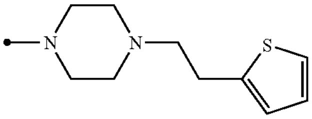 | MS m/z 603 $(M + H)^+$ |
| 4-474 | 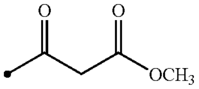 | 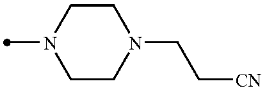 | MS m/z 546 $(M + H)^+$ |
| 4-475 | 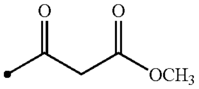 | 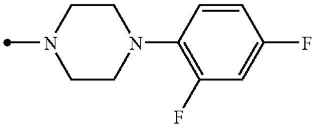 | MS m/z 605 $(M + H)^+$ |
| 4-476 | 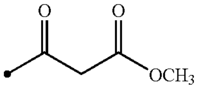 | 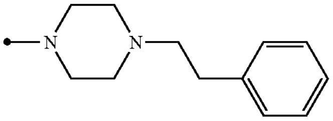 | MS m/z 597 $(M + H)^+$ |
| 4-477 | 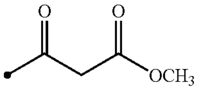 | 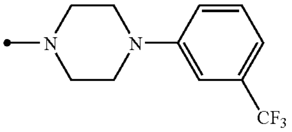 | MS m/z 637 $(M + H)^+$ |
| 4-478 | 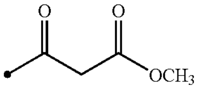 | 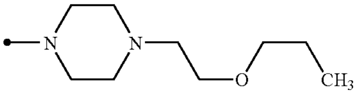 | MS m/z 565 $(M + H)^+$ |
| 4-479 | 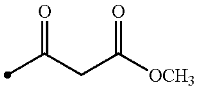 | 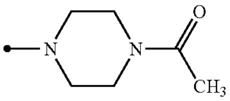 | MS m/z 535 $(M + H)^+$ |
| 4-480 | 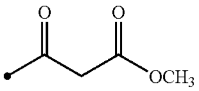 | 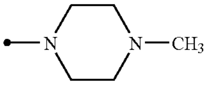 | MS m/z 507 $(M + H)^+$ |

TABLE 4-continued
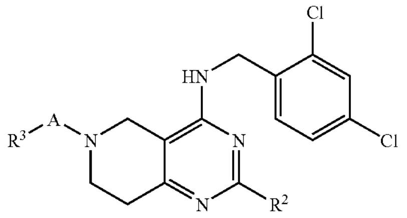
| Compound Number | •—A—$R^3$ | •—$R^2$ | Spectrum Data |
|---|---|---|---|
| 4-481 | 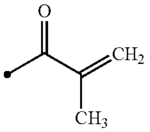 | 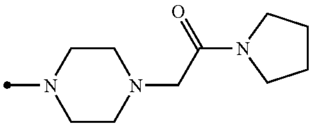 | MS m/z 572 $(M + H)^+$ |
| 4-482 | 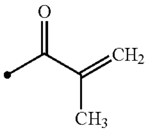 | 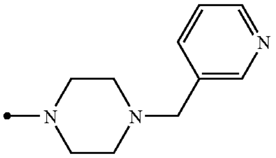 | MS m/z 552 $(M + H)^+$ |
| 4-483 | 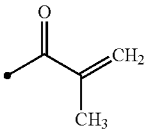 | 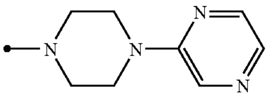 | MS m/z 539 $(M + H)^+$ |
| 4-484 | 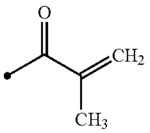 | 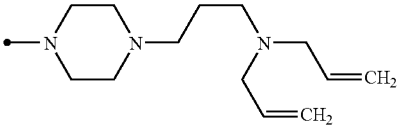 | MS m/z 598 $(M + H)^+$ |
| 4-485 | 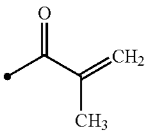 | 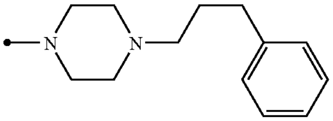 | MS m/z 579 $(M + H)^+$ |
| 4-486 | 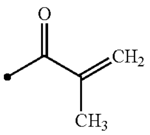 | 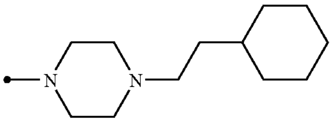 | MS m/z 571 $(M + H)^+$ |
| 4-487 | 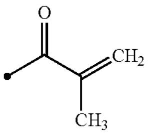 | 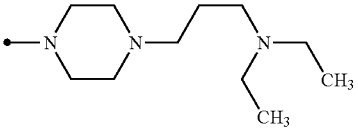 | MS m/z 574 $(M + H)^+$ |
| 4-488 | 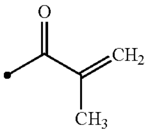 | 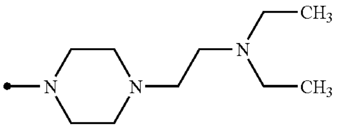 | MS m/z 560 $(M + H)^+$ |

TABLE 4-continued
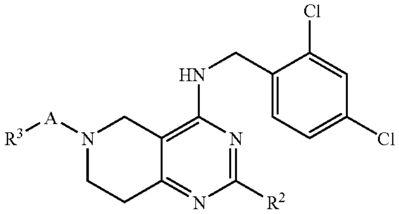
| Compound Number | •—A—$R^3$ | •—$R^2$ | Spectrum Data |
|---|---|---|---|
| 4-489 | 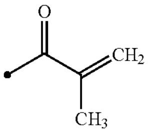 | 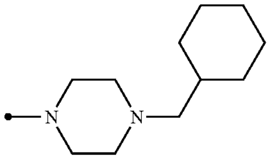 | MS m/z 557 (M + H)$^+$ |
| 4-490 | 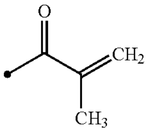 | 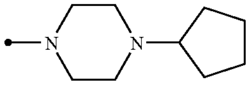 | MS m/z 529 (M + H)$^+$ |
| 4-491 | 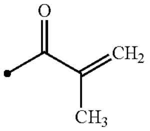 | 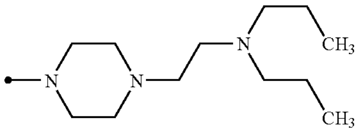 | MS m/z 588 (M + H)$^+$ |
| 4-492 | 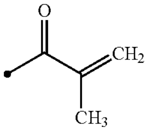 | 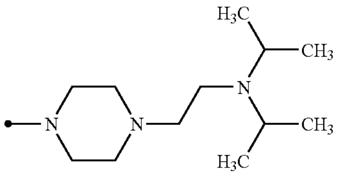 | MS m/z 588 (M + H)$^+$ |
| 4-493 | 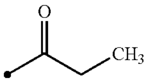 | 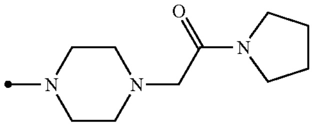 | MS m/z 560 (M + H)$^+$ |
| 4-494 | 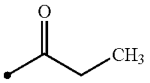 | 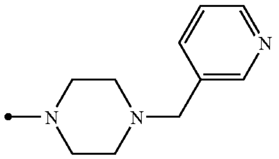 | MS m/z 540 (M + H)$^+$ |
| 4-495 | 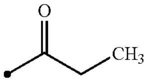 | 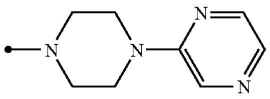 | MS m/z 527 (M + H)$^+$ |
| 4-496 | 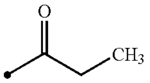 | 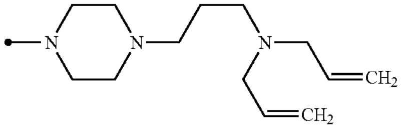 | MS m/z 586 (M + H)$^+$ |

TABLE 4-continued
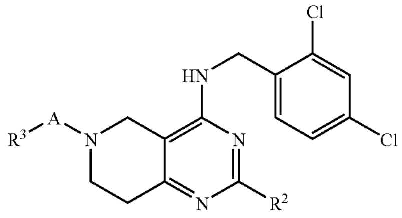
| Compound Number | •—A—$R^3$ | •—$R^2$ | Spectrum Data |
|---|---|---|---|
| 4-497 | 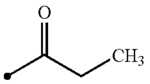 | 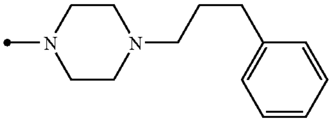 | MS m/z 567 $(M + H)^+$ |
| 4-498 | 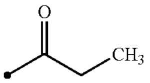 | 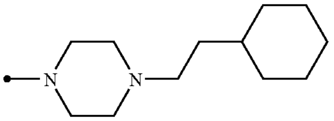 | MS m/z 559 $(M + H)^+$ |
| 4-499 | 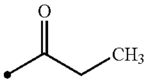 | 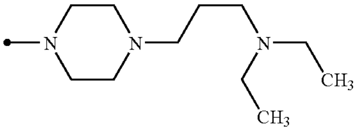 | MS m/z 562 $(M + H)^+$ |
| 4-500 | 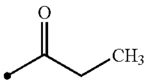 | 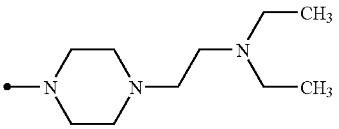 | MS m/z 548 $(M + H)^+$ |
| 4-501 | 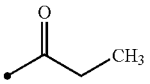 | 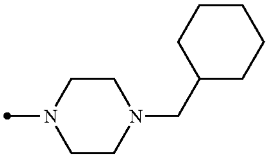 | MS m/z 545 $(M + H)^+$ |
| 4-502 | 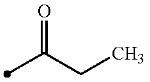 | 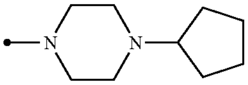 | MS m/z 517 $(M + H)^+$ |
| 4-503 | 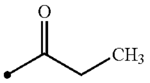 | 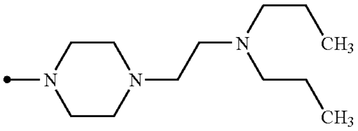 | MS m/z 576 $(M + H)^+$ |
| 4-504 | 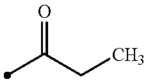 | 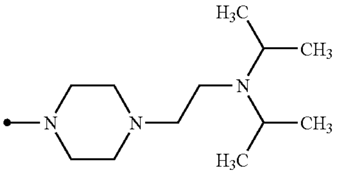 | MS m/z 576 $(M + H)^+$ |
| 4-505 | 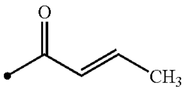 | 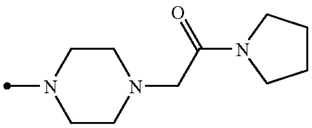 | MS m/z 572 $(M + H)^+$ |

TABLE 4-continued
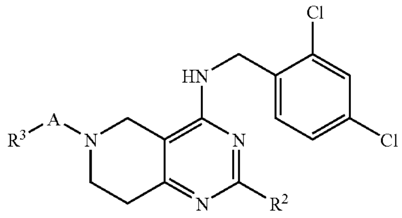
| Compound Number | •—A—$R^3$ | •—$R^2$ | Spectrum Data |
| --- | --- | --- | --- |
| 4-506 | 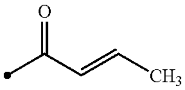 | 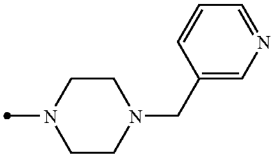 | MS m/z 552 $(M + H)^+$ |
| 4-507 | 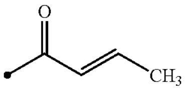 | 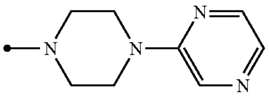 | MS m/z 539 $(M + H)^+$ |
| 4-508 | 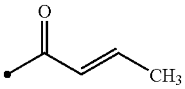 | 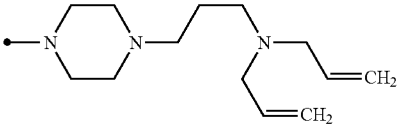 | MS m/z 598 $(M + H)^+$ |
| 4-509 | 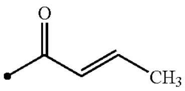 | 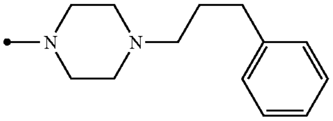 | MS m/z 579 $(M + H)^+$ |
| 4-510 | 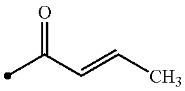 | 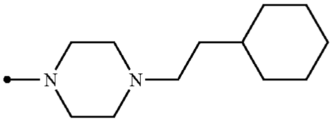 | MS m/z 571 $(M + H)^+$ |
| 4-511 | 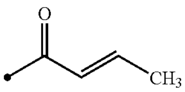 | 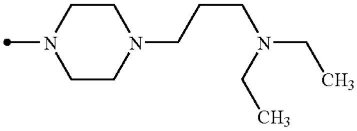 | MS m/z 574 $(M + H)^+$ |
| 4-512 | 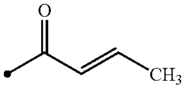 | 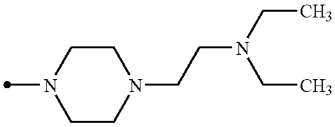 | MS m/z 560 $(M + H)^+$ |
| 4-513 | 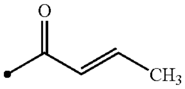 | 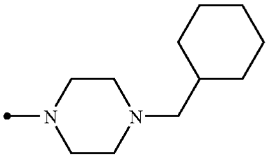 | MS m/z 557 $(M + H)^+$ |
| 4-514 | 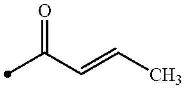 | 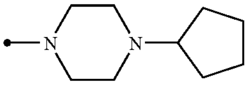 | MS m/z 529 $(M + H)^+$ |

TABLE 4-continued
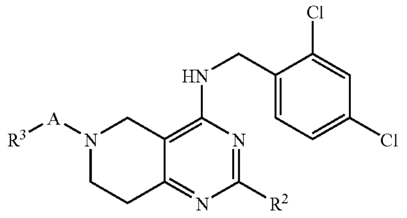
| Compound Number | •—A—$R^3$ | •—$R^2$ | Spectrum Data |
|---|---|---|---|
| 4-515 | 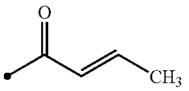 | 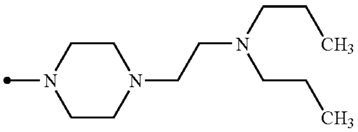 | MS m/z 588 $(M + H)^+$ |
| 4-516 | 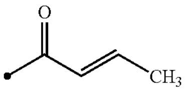 | 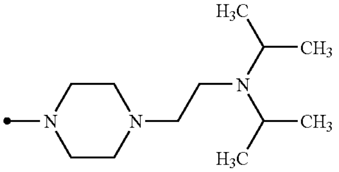 | MS m/z 588 $(M + H)^+$ |
| 4-517 | 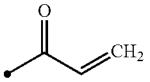 | 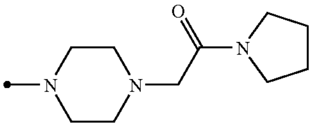 | MS m/z 558 $(M + H)^+$ |
| 4-518 | 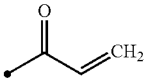 | 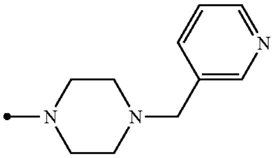 | MS m/z 538 $(M + H)^+$ |
| 4-519 | 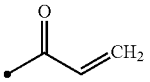 | 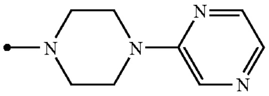 | MS m/z 525 $(M + H)^+$ |
| 4-520 | 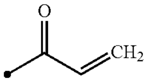 | 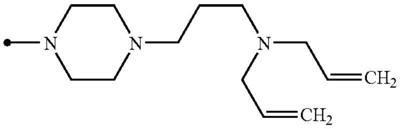 | MS m/z 584 $(M + H)^+$ |
| 4-521 | 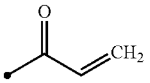 | 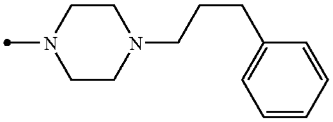 | MS m/z 565 $(M + H)^+$ |
| 4-522 | 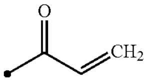 | 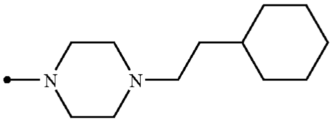 | MS m/z 557 $(M + H)^+$ |
| 4-523 | 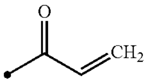 | 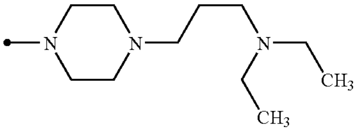 | MS m/z 560 $(M + H)^+$ |

TABLE 4-continued
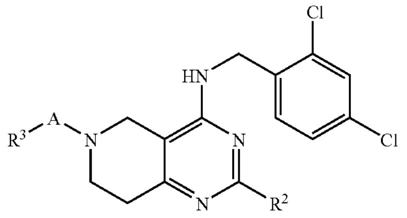
| Compound Number | •—A—$R^3$ | •—$R^2$ | Spectrum Data |
|---|---|---|---|
| 4-524 | 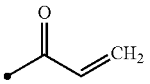 | 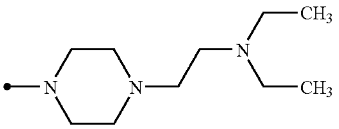 | MS m/z 546 (M + H)$^+$ |
| 4-525 | 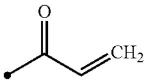 | 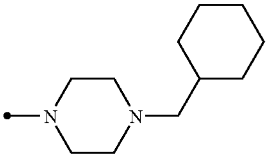 | MS m/z 543 (M + H)$^+$ |
| 4-526 | 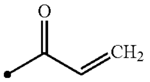 | 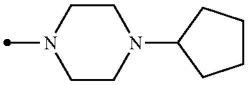 | MS m/z 515 (M + H)$^+$ |
| 4-527 | 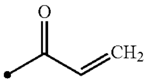 | 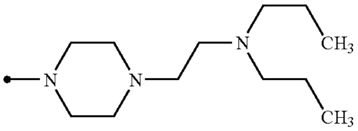 | MS m/z 574 (M + H)$^+$ |
| 4-528 | 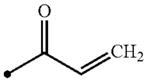 | 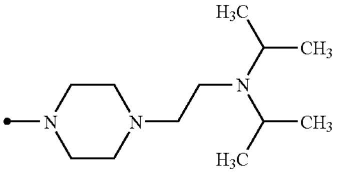 | MS m/z 574 (M + H)$^+$ |
| 4-529 | 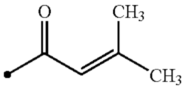 | 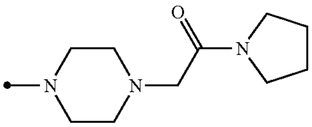 | MS m/z 586 (M + H)$^+$ |
| 4-530 | 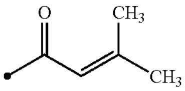 | 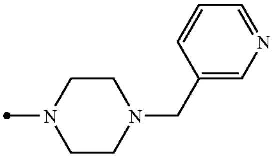 | MS m/z 566 (M + H)$^+$ |
| 4-531 | 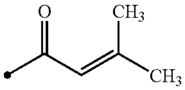 | 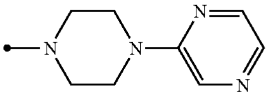 | MS m/z 553 (M + H)$^+$ |
| 4-532 | 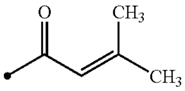 | 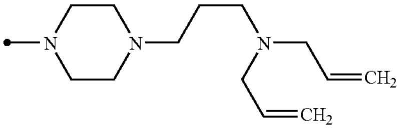 | MS m/z 612 (M + H)$^+$ |

TABLE 4-continued
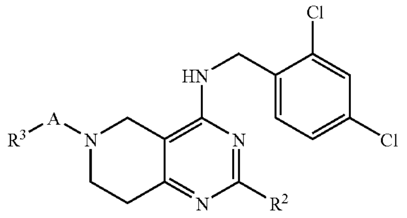
| Compound Number | •—A—$R^3$ | •—$R^2$ | Spectrum Data |
|---|---|---|---|
| 4-533 | 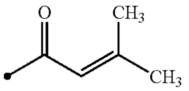 | 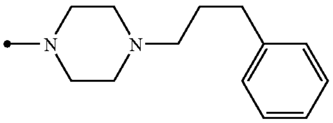 | MS m/z 593 (M + H)$^+$ |
| 4-534 | 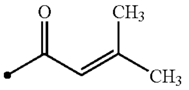 | 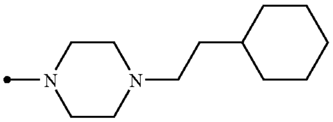 | MS m/z 585 (M + H)$^+$ |
| 4-535 | 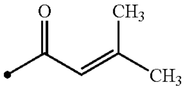 | 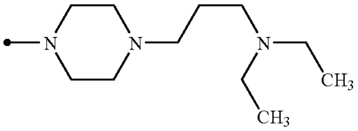 | MS m/z 588 (M + H)$^+$ |
| 4-536 | 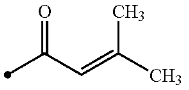 | 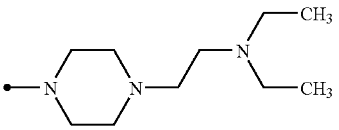 | MS m/z 574 (M + H)$^+$ |
| 4-537 | 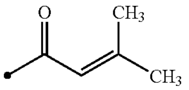 | 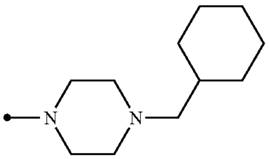 | MS m/z 571 (M + H)$^+$ |
| 4-538 | 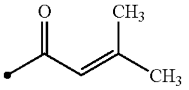 | 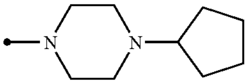 | MS m/z 543 (M + H)$^+$ |
| 4-539 | 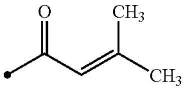 | 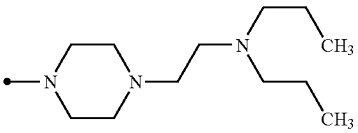 | MS m/z 602 (M + H)$^+$ |
| 4-540 | 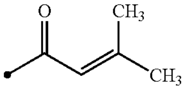 | 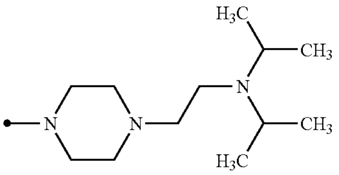 | MS m/z 602 (M + H)$^+$ |
| 4-541 | 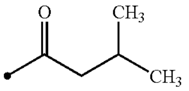 | 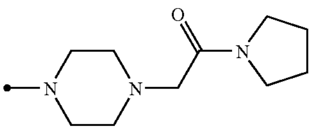 | MS m/z 588 (M + H)$^+$ |

TABLE 4-continued
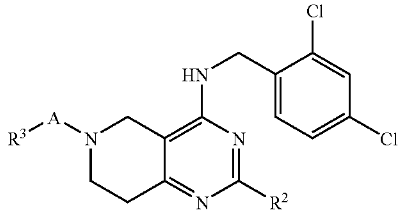
| Compound Number | •—A—$R^3$ | •—$R^2$ | Spectrum Data |
|---|---|---|---|
| 4-542 | 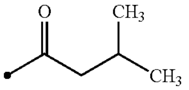 | 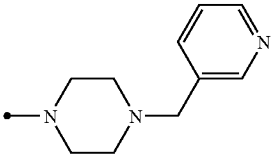 | MS m/z 568 $(M + H)^+$ |
| 4-543 | 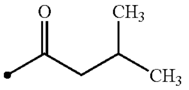 | 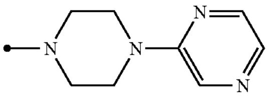 | MS m/z 555 $(M + H)^+$ |
| 4-544 | 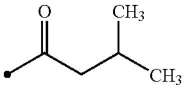 | 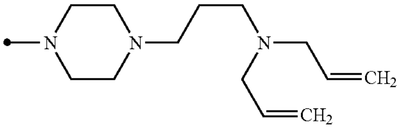 | MS m/z 614 $(M + H)^+$ |
| 4-545 | 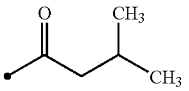 | 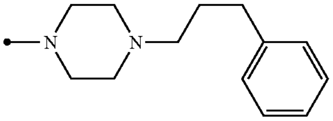 | MS m/z 595 $(M + H)^+$ |
| 4-546 | 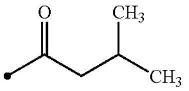 | 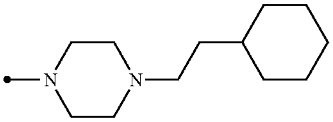 | MS m/z 587 $(M + H)^+$ |
| 4-547 | 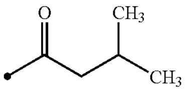 | 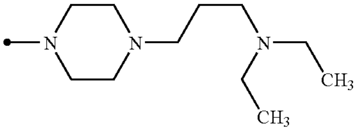 | MS m/z 590 $(M + H)^+$ |
| 4-548 | 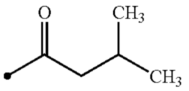 | 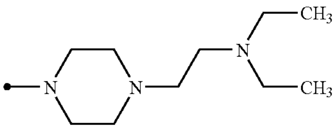 | MS m/z 576 $(M + H)^+$ |
| 4-549 | 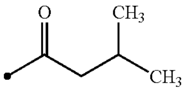 | 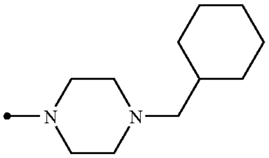 | MS m/z 573 $(M + H)^+$ |
| 4-550 | 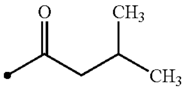 | 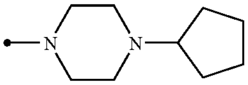 | MS m/z 545 $(M + H)^+$ |

TABLE 4-continued
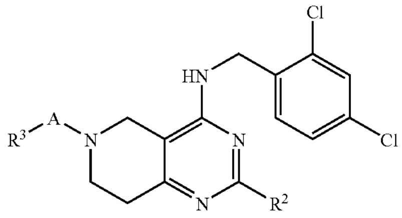
| Compound Number | •—A—$R^3$ | •—$R^2$ | Spectrum Data |
|---|---|---|---|
| 4-551 | 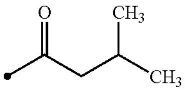 | 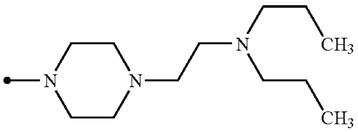 | MS m/z 604 $(M + H)^+$ |
| 4-552 | 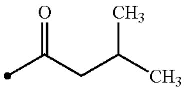 | 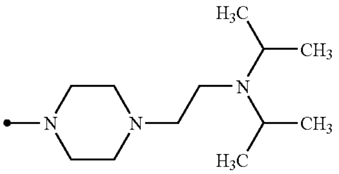 | MS m/z 604 $(M + H)^+$ |
| 4-553 | 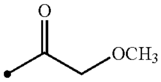 | 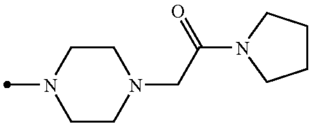 | MS m/z 576 $(M + H)^+$ |
| 4-554 | 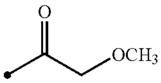 | 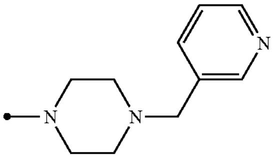 | MS m/z 556 $(M + H)^+$ |
| 4-555 | 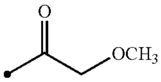 | 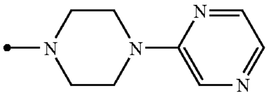 | MS m/z 543 $(M + H)^+$ |
| 4-556 | 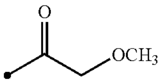 | 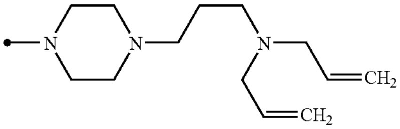 | MS m/z 602 $(M + H)^+$ |
| 4-557 | 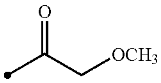 | 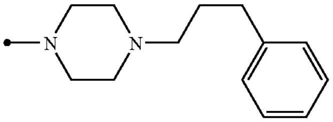 | MS m/z 583 $(M + H)^+$ |
| 4-558 | 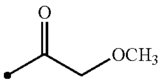 | 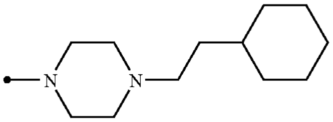 | MS m/z 575 $(M + H)^+$ |
| 4-559 | 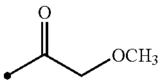 | 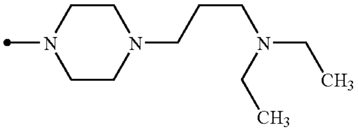 | MS m/z 578 $(M + H)^+$ |

TABLE 4-continued
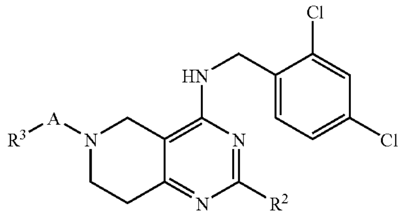
| Compound Number | •—A—$R^3$ | •—$R^2$ | Spectrum Data |
|---|---|---|---|
| 4-560 | 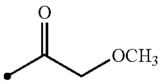 | 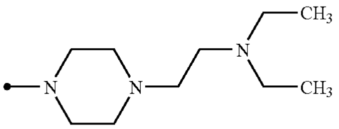 | MS m/z 564 $(M + H)^+$ |
| 4-561 | 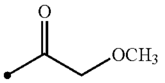 | 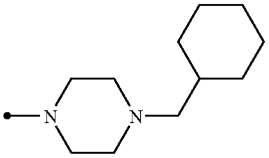 | MS m/z 561 $(M + H)^+$ |
| 4-562 | 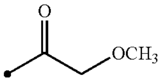 | 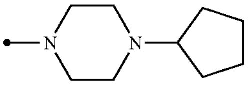 | MS m/z 533 $(M + H)^+$ |
| 4-563 | 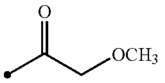 | 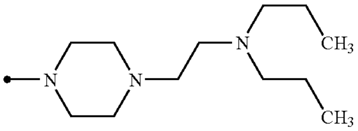 | MS m/z 592 $(M + H)^+$ |
| 4-564 | 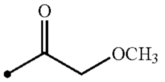 | 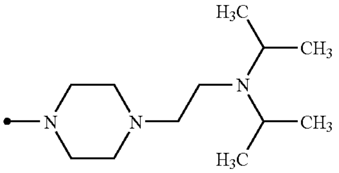 | MS m/z 592 $(M + H)^+$ |
| 4-565 | 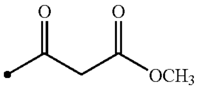 | 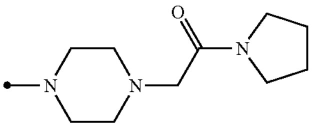 | MS m/z 604 $(M + H)^+$ |
| 4-566 | 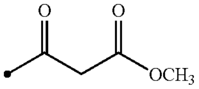 | 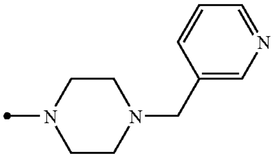 | MS m/z 584 $(M + H)^+$ |
| 4-567 | 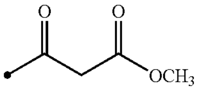 | 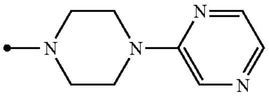 | MS m/z 571 $(M + H)^+$ |
| 4-568 | 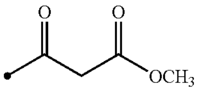 | 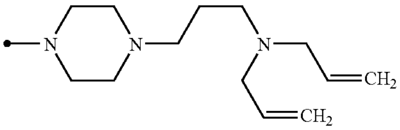 | MS m/z 630 $(M + H)^+$ |

TABLE 4-continued
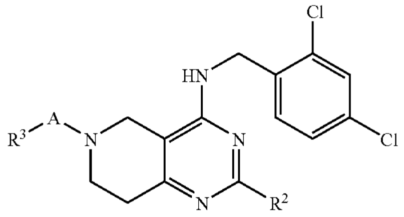
| Compound Number | •—A—$R^3$ | •—$R^2$ | Spectrum Data |
|---|---|---|---|
| 4-569 | 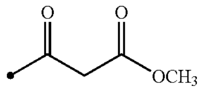 | 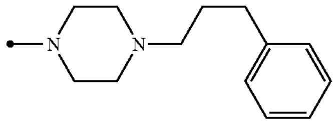 | MS m/z 611 (M + H)$^+$ |
| 4-570 | 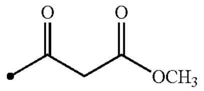 | 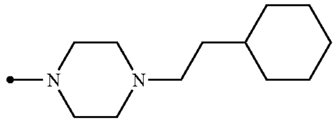 | MS m/z 603 (M + H)$^+$ |
| 4-571 | 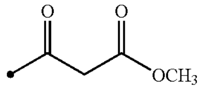 | 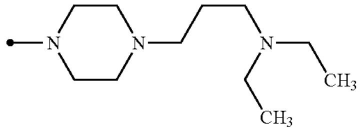 | MS m/z 606 (M + H)$^+$ |
| 4-572 | 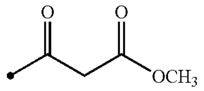 | 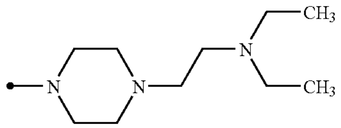 | MS m/z 592 (M + H)$^+$ |
| 4-573 | 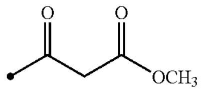 | 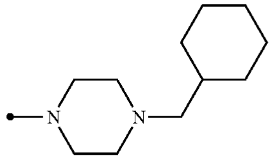 | MS m/z 589 (M + H)$^+$ |
| 4-574 | 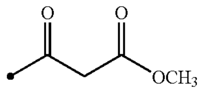 | 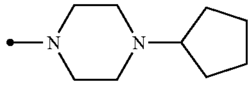 | MS m/z 561 (M + H)$^+$ |
| 4-575 | 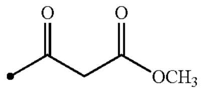 | 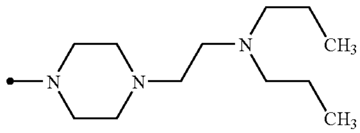 | MS m/z 620 (M + H)$^+$ |
| 4-576 | 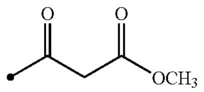 | 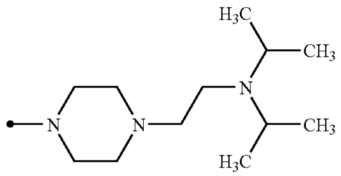 | MS m/z 620 (M + H)$^+$ |
| 4-577 | 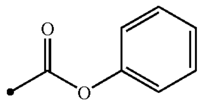 | 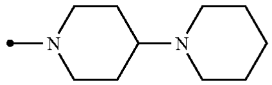 | MS m/z 595 (M + H)$^+$ |

TABLE 4-continued
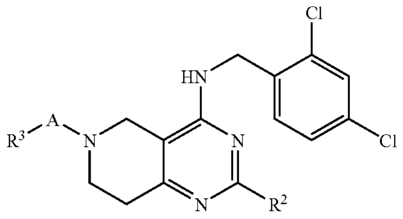
| Compound Number | •—A—$R^3$ | •—$R^2$ | Spectrum Data |
| --- | --- | --- | --- |
| 4-578 | 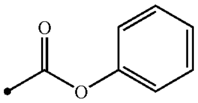 | 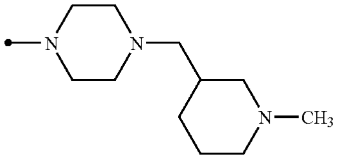 | MS m/z 624 $(M + H)^+$ |
| 4-579 | 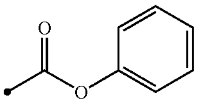 | 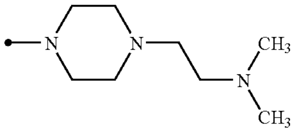 | MS m/z 584 $(M + H)^+$ |
| 4-580 | 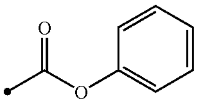 | 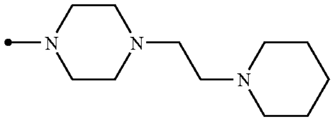 | MS m/z 624 $(M + H)^+$ |
| 4-581 | 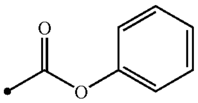 | 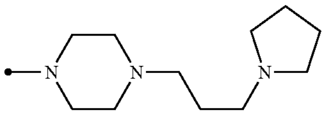 | MS m/z 624 $(M + H)^+$ |
| 4-582 | 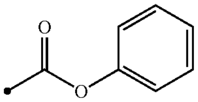 | 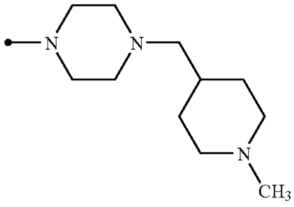 | MS m/z 624 $(M + H)^+$ |
| 4-583 | 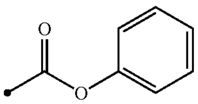 | 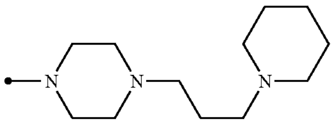 | MS m/z 638 $(M + H)^+$ |
| 4-584 | 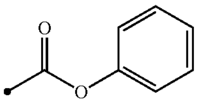 | 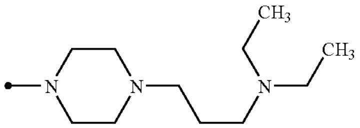 | MS m/z 626 $(M + H)^+$ |
| 4-585 | 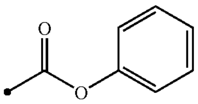 | 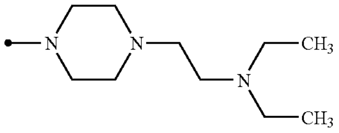 | MS m/z 612 $(M + H)^+$ |

TABLE 4-continued
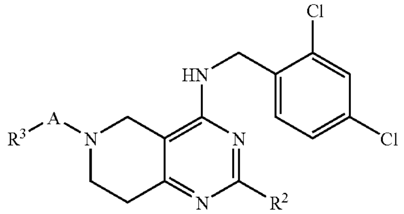
| Compound Number | •—A—$R^3$ | •—$R^2$ | Spectrum Data |
|---|---|---|---|
| 4-586 | 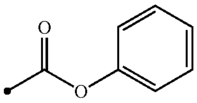 | 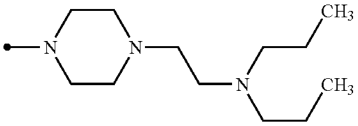 | MS m/z 640 $(M + H)^+$ |
| 4-587 | 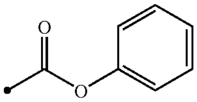 | 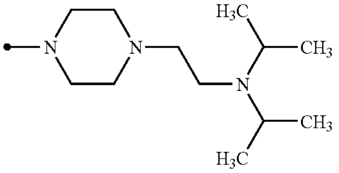 | MS m/z 640 $(M + H)^+$ |
| 4-588 | 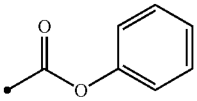 | 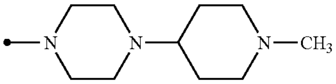 | MS m/z 610 $(M + H)^+$ |
| 4-589 | 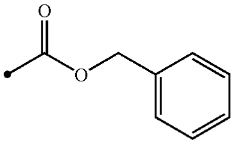 | 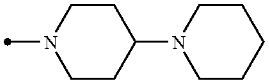 | MS m/z 609 $(M + H)^+$ |
| 4-590 | 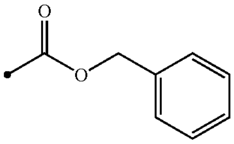 | 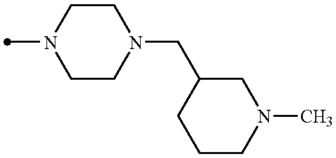 | MS m/z 638 $(M + H)^+$ |
| 4-591 | 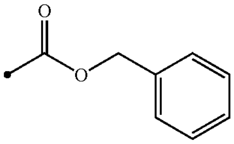 | 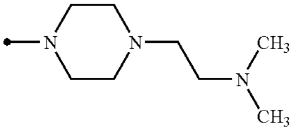 | MS m/z 598 $(M + H)^+$ |
| 4-592 | 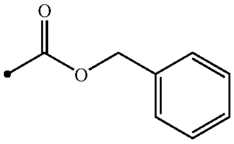 | 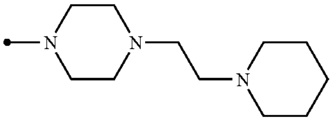 | MS m/z 638 $(M + H)^+$ |
| 4-593 | 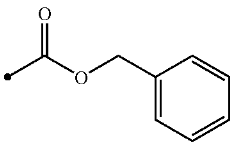 | 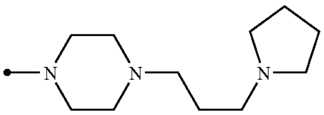 | MS m/z 638 $(M + H)^+$ |

TABLE 4-continued
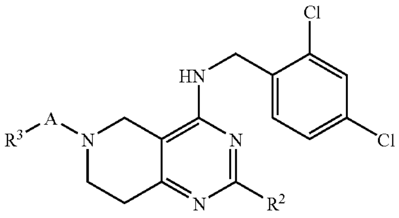
| Compound Number | •—A—R$^3$ | •—R$^2$ | Spectrum Data |
|---|---|---|---|
| 4-594 | 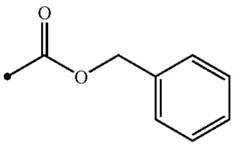 | 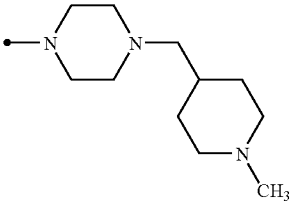 | MS m/z 638 (M + H)$^+$ |
| 4-595 | 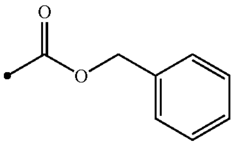 | 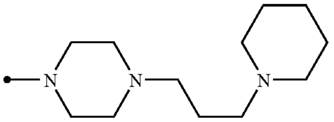 | MS m/z 652 (M + H)$^+$ |
| 4-596 | 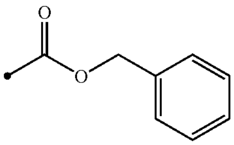 | 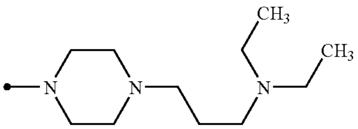 | MS m/z 640 (M + H)$^+$ |
| 4-597 | 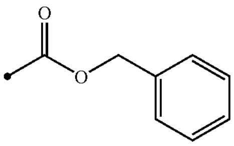 | 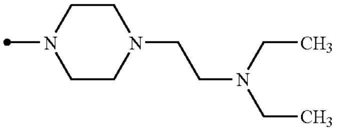 | MS m/z 626 (M + H)$^+$ |
| 4-598 | 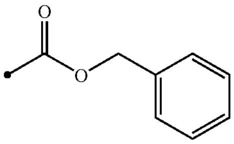 | 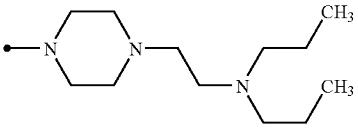 | MS m/z 654 (M + H)$^+$ |
| 4-599 | 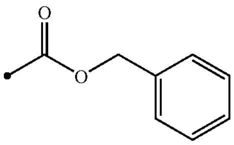 | 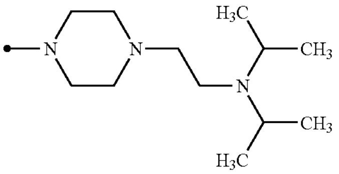 | MS m/z 654 (M + H)$^+$ |
| 4-600 | 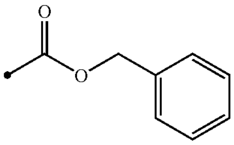 | 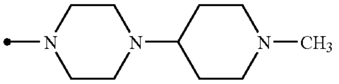 | MS m/z 624 (M + H)$^+$ |
| 4-601 | 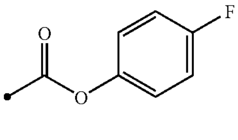 | 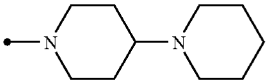 | MS m/z 613 (M + H)$^+$ |

TABLE 4-continued
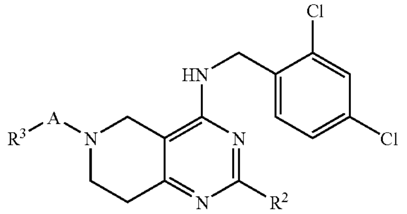
| Compound Number | •—A—$R^3$ | •—$R^2$ | Spectrum Data |
|---|---|---|---|
| 4-602 | 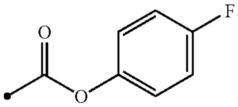 | 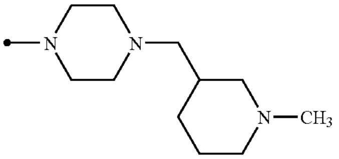 | MS m/z 642 $(M + H)^+$ |
| 4-603 | 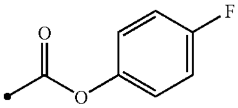 | 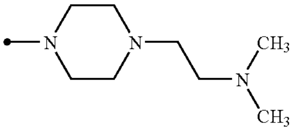 | MS m/z 602 $(M + H)^+$ |
| 4-604 | 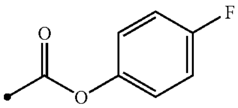 | 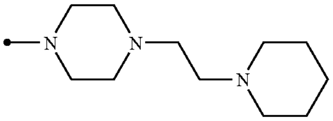 | MS m/z 642 $(M + H)^+$ |
| 4-605 | 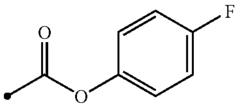 | 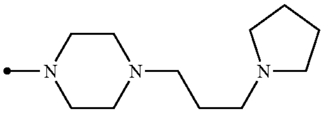 | MS m/z 642 $(M + H)^+$ |
| 4-606 | 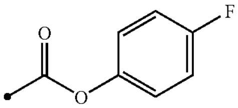 | 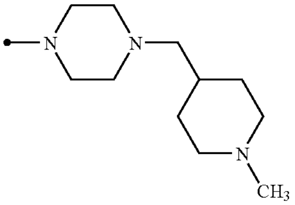 | MS m/z 642 $(M + H)^+$ |
| 4-607 | 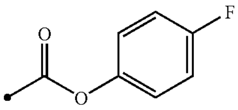 | 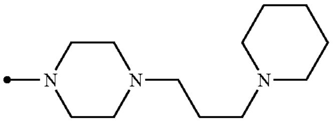 | MS m/z 656 $(M + H)^+$ |
| 4-608 | 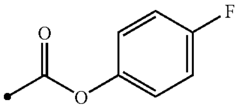 | 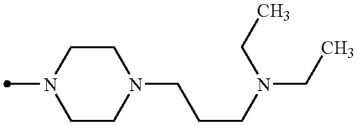 | MS m/z 644 $(M + H)^+$ |
| 4-609 | 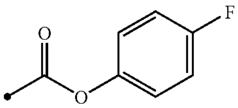 | 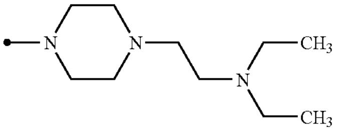 | MS m/z 630 $(M + H)^+$ |

TABLE 4-continued
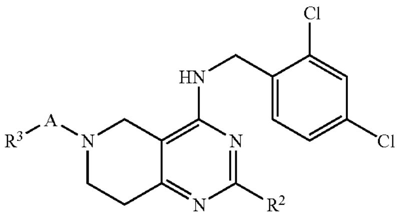
| Compound Number | •—A—$R^3$ | •—$R^2$ | Spectrum Data |
|---|---|---|---|
| 4-610 | 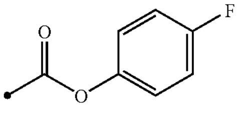 | 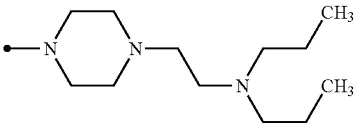 | MS m/z 658 $(M + H)^+$ |
| 4-611 | 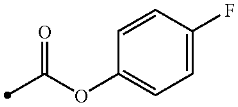 | 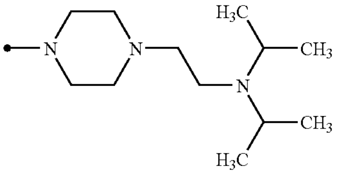 | MS m/z 658 $(M + H)^+$ |
| 4-612 | 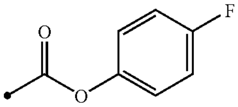 | 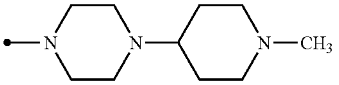 | MS m/z 628 $(M + H)^+$ |
| 4-613 | 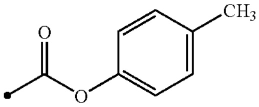 | 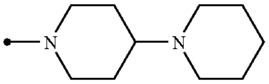 | MS m/z 609 $(M + H)^+$ |
| 4-614 | 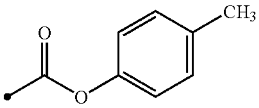 | 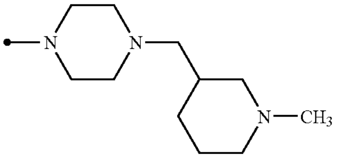 | MS m/z 638 $(M + H)^+$ |
| 4-615 | 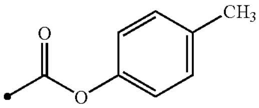 | 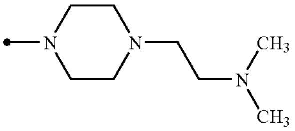 | MS m/z 598 $(M + H)^+$ |
| 4-616 | 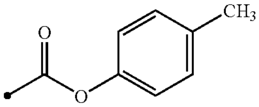 | 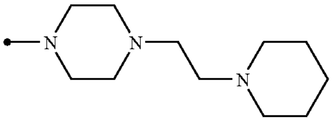 | MS m/z 638 $(M + H)^+$ |
| 4-617 | 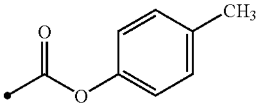 | 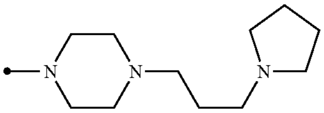 | MS m/z 638 $(M + H)^+$ |

TABLE 4-continued
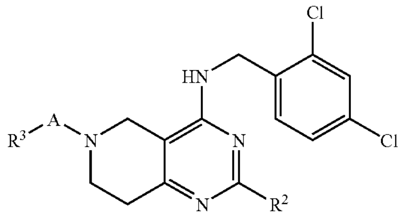
| Compound Number | •—A—$R^3$ | •—$R^2$ | Spectrum Data |
|---|---|---|---|
| 4-618 | 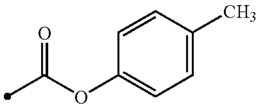 | 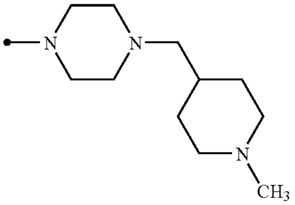 | MS m/z 638 $(M + H)^+$ |
| 4-619 | 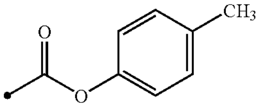 | 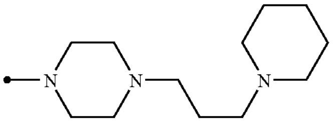 | MS m/z 652 $(M + H)^+$ |
| 4-620 | 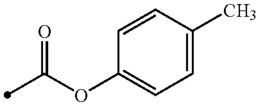 | 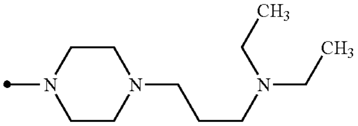 | MS m/z 640 $(M + H)^+$ |
| 4-621 | 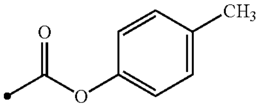 | 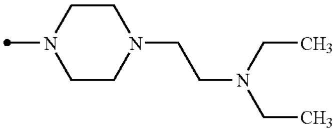 | MS m/z 626 $(M + H)^+$ |
| 4-622 | 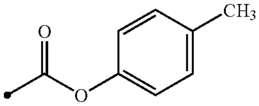 | 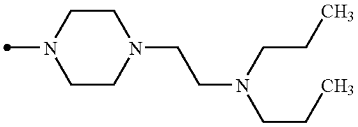 | MS m/z 654 $(M + H)^+$ |
| 4-623 | 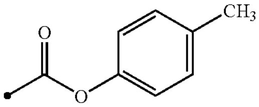 | 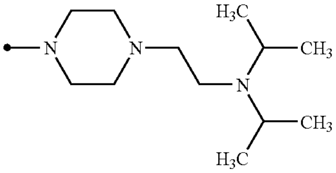 | MS m/z 654 $(M + H)^+$ |
| 4-624 | 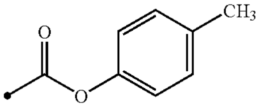 | 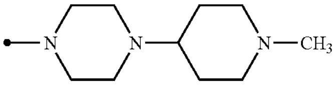 | MS m/z 624 $(M + H)^+$ |
| 4-625 | 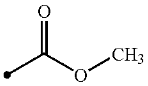 | 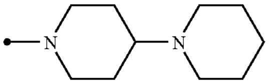 | MS m/z 533 $(M + H)^+$ |

TABLE 4-continued
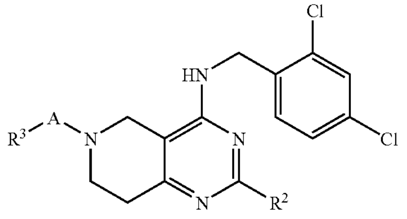
| Compound Number | •—A—$R^3$ | •—$R^2$ | Spectrum Data |
| --- | --- | --- | --- |
| 4-626 | 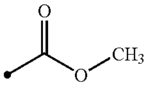 | 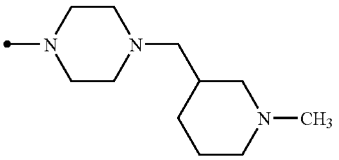 | MS m/z 562 $(M + H)^+$ |
| 4-627 | 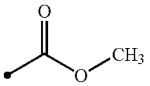 | 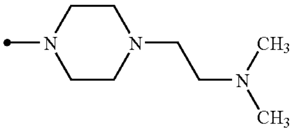 | MS m/z 522 $(M + H)^+$ |
| 4-628 | 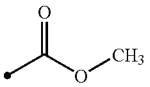 | 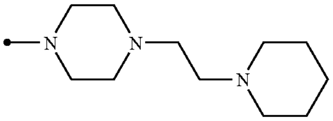 | MS m/z 562 $(M + H)^+$ |
| 4-629 | 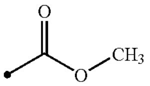 | 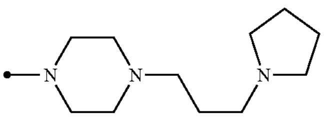 | MS m/z 562 $(M + H)^+$ |
| 4-630 | 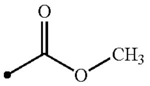 | 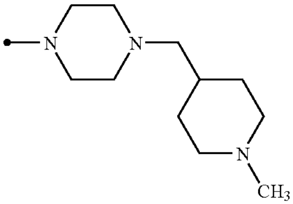 | MS m/z 562 $(M + H)^+$ |
| 4-631 | 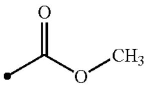 | 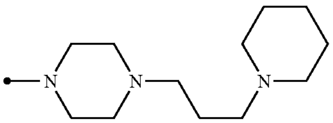 | MS m/z 576 $(M + H)^+$ |
| 4-632 | 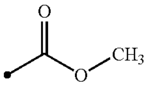 | 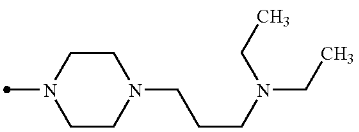 | MS m/z 564 $(M + H)^+$ |
| 4-633 | 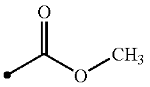 | 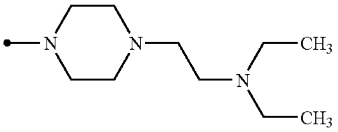 | MS m/z 550 $(M + H)^+$ |

TABLE 4-continued
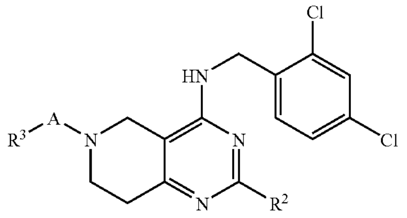
| Compound Number | •—A—$R^3$ | •—$R^2$ | Spectrum Data |
|---|---|---|---|
| 4-634 | 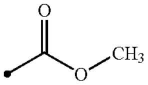 | 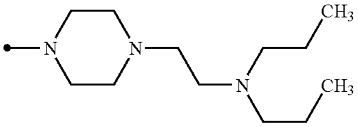 | MS m/z 578 $(M + H)^+$ |
| 4-635 | 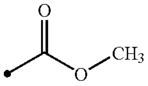 | 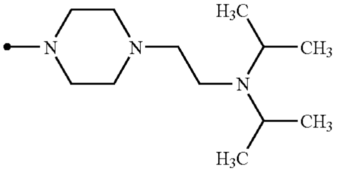 | MS m/z 578 $(M + H)^+$ |
| 4-636 | 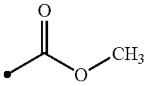 | 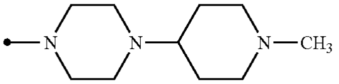 | MS m/z 548 $(M + H)^+$ |
| 4-637 | 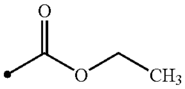 | 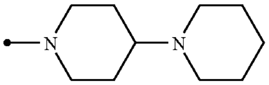 | MS m/z 547 $(M + H)^+$ |
| 4-638 | 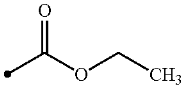 | 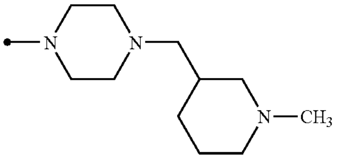 | MS m/z 576 $(M + H)^+$ |
| 4-639 | 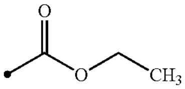 | 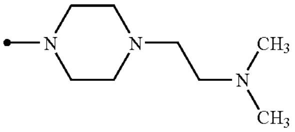 | MS m/z 536 $(M + H)^+$ |
| 4-640 | 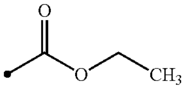 | 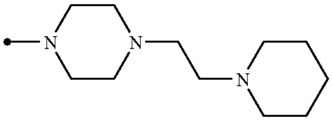 | MS m/z 576 $(M + H)^+$ |
| 4-641 | 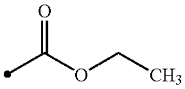 | 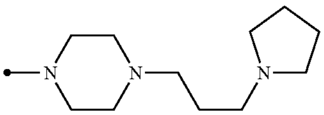 | MS m/z 576 $(M + H)^+$ |
| 4-642 | 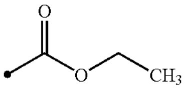 | 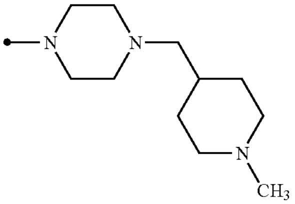 | MS m/z 576 $(M + H)^+$ |

TABLE 4-continued
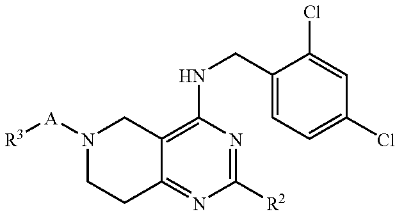
| Compound Number | •—A—$R^3$ | •—$R^2$ | Spectrum Data |
|---|---|---|---|
| 4-643 | 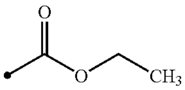 | 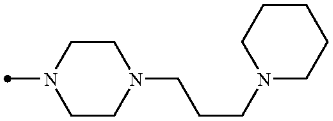 | MS m/z 590 $(M + H)^+$ |
| 4-644 | 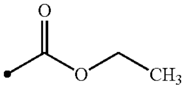 | 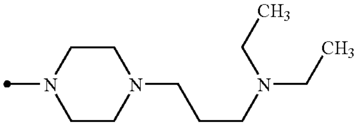 | MS m/z 578 $(M + H)^+$ |
| 4-645 | 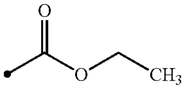 | 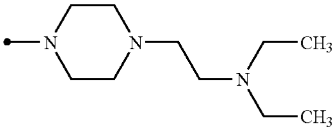 | MS m/z 564 $(M + H)^+$ |
| 4-646 | 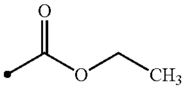 | 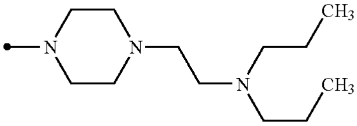 | MS m/z 592 $(M + H)^+$ |
| 4-647 | 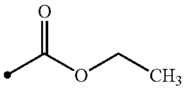 | 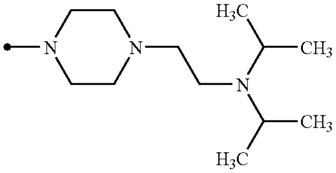 | MS m/z 592 $(M + H)^+$ |
| 4-648 | 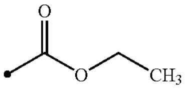 | 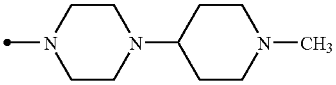 | MS m/z 562 $(M + H)^+$ |
| 4-649 | 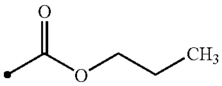 | 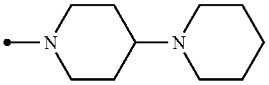 | MS m/z 561 $(M + H)^+$ |
| 4-650 | 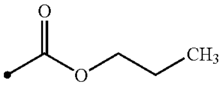 | 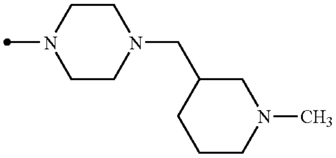 | MS m/z 590 $(M + H)^+$ |
| 4-651 | 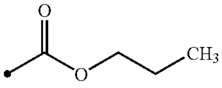 | 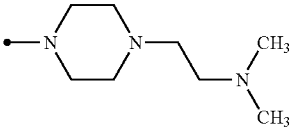 | MS m/z 550 $(M + H)^+$ |

TABLE 4-continued
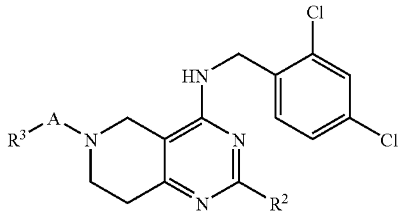
| Compound Number | •—A—$R^3$ | •—$R^2$ | Spectrum Data |
|---|---|---|---|
| 4-652 | 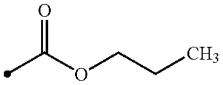 | 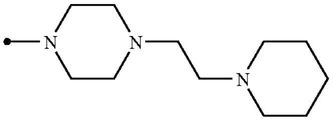 | MS m/z 590 $(M + H)^+$ |
| 4-653 | 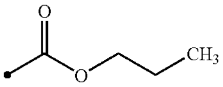 | 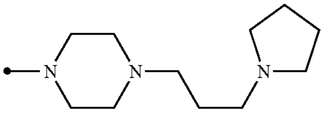 | MS m/z 590 $(M + H)^+$ |
| 4-654 | 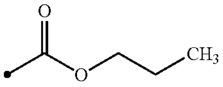 | 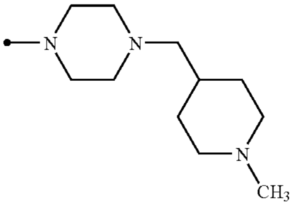 | MS m/z 590 $(M + H)^+$ |
| 4-655 | 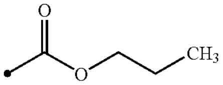 | 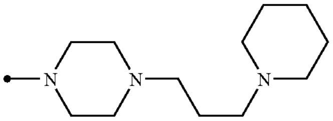 | MS m/z 604 $(M + H)^+$ |
| 4-656 | 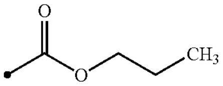 | 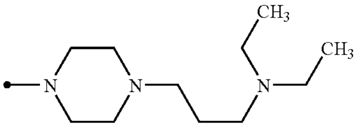 | MS m/z 592 $(M + H)^+$ |
| 4-657 | 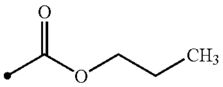 | 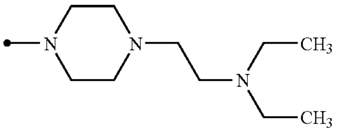 | MS m/z 578 $(M + H)^+$ |
| 4-658 | 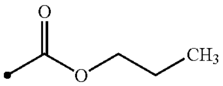 | 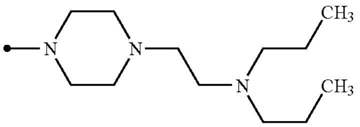 | MS m/z 606 $(M + H)^+$ |
| 4-659 | 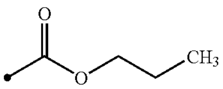 | 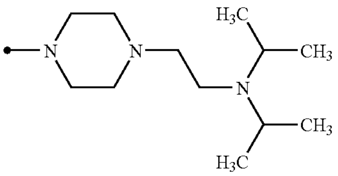 | MS m/z 606 $(M + H)^+$ |
| 4-660 | 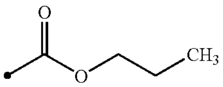 | 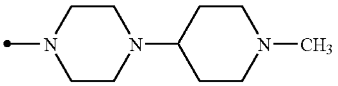 | MS m/z 576 $(M + H)^+$ |

TABLE 4-continued
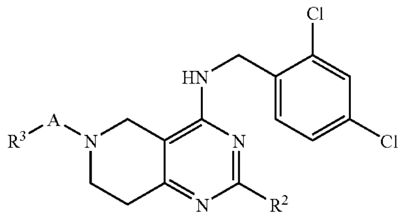
| Compound Number | •—A—$R^3$ | •—$R^2$ | Spectrum Data |
|---|---|---|---|
| 4-661 | 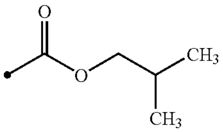 | 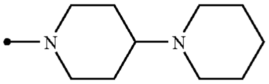 | MS m/z 575 $(M + H)^+$ |
| 4-662 | 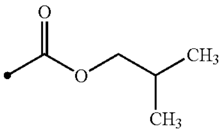 | 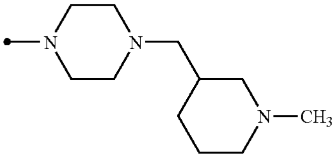 | MS m/z 604 $(M + H)^+$ |
| 4-663 | 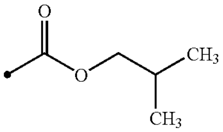 | 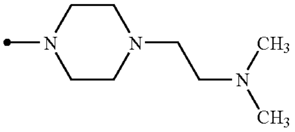 | MS m/z 564 $(M + H)^+$ |
| 4-664 | 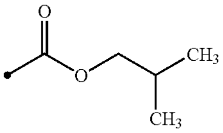 | 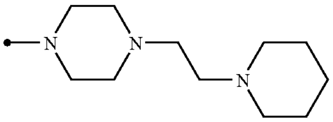 | MS m/z 604 $(M + H)^+$ |
| 4-665 | 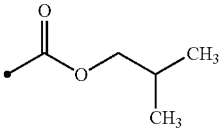 | 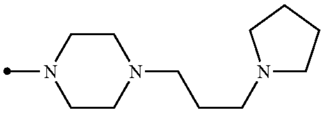 | MS m/z 604 $(M + H)^+$ |
| 4-666 | 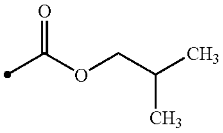 | 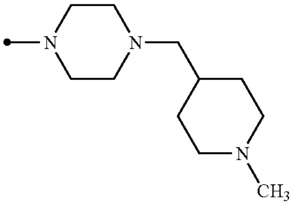 | MS m/z 604 $(M + H)^+$ |
| 4-667 | 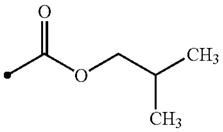 | 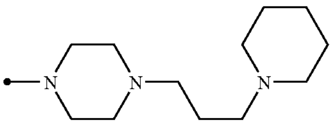 | MS m/z 618 $(M + H)^+$ |
| 4-668 | 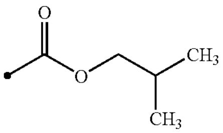 | 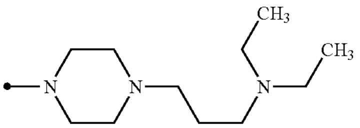 | MS m/z 606 $(M + H)^+$ |

TABLE 4-continued
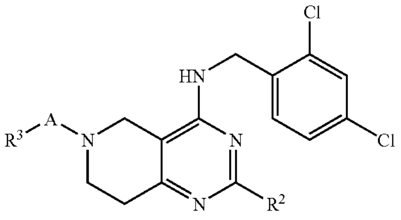
| Compound Number | •—A—$R^3$ | •—$R^2$ | Spectrum Data |
|---|---|---|---|
| 4-669 | 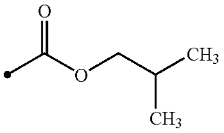 | 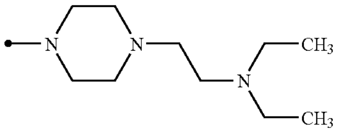 | MS m/z 592 $(M + H)^+$ |
| 4-670 | 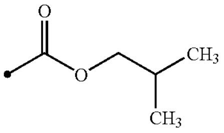 | 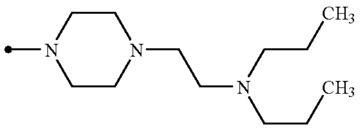 | MS m/z 620 $(M + H)^+$ |
| 4-671 | 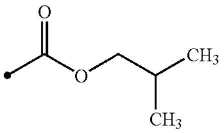 | 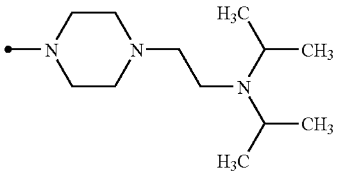 | MS m/z 620 $(M + H)^+$ |
| 4-672 | 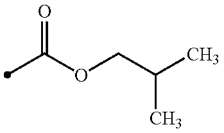 | 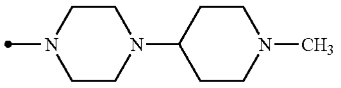 | MS m/z 590 $(M + H)^+$ |
TABLE 5
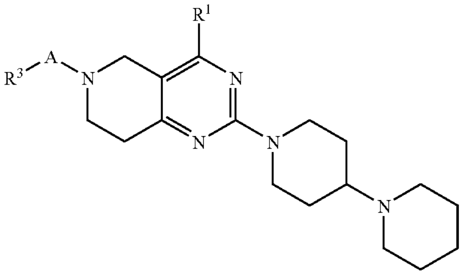
| Compound Number | •—A—$R^3$ | •—$R^1$ | Spectrum Data |
|---|---|---|---|
| 5-1 | 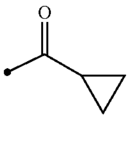 | 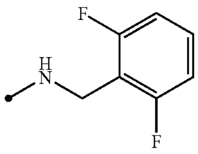 | MS m/z 511 $(M + H)^+$ |

TABLE 5-continued
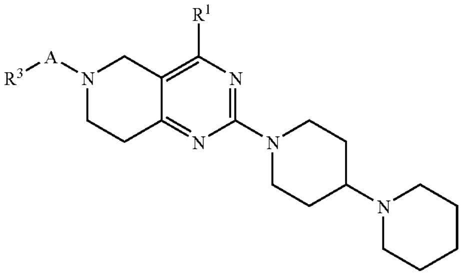
| Compound Number | •—A—$R^3$ | •—$R^1$ | Spectrum Data |
|---|---|---|---|
| 5-2 | 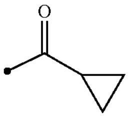 | 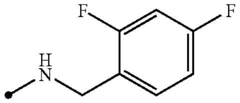 | MS m/z 511 $(M + H)^+$ |
| 5-3 | 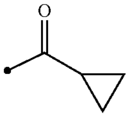 | 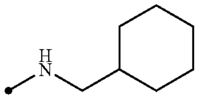 | MS m/z 481 $(M + H)^+$ |
| 5-4 | 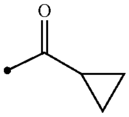 | 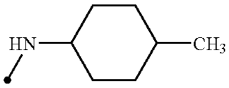 | MS m/z 481 $(M + H)^+$ |
| 5-5 | 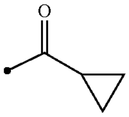 | 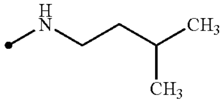 | MS m/z 455 $(M + H)^+$ |
| 5-6 | 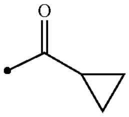 | 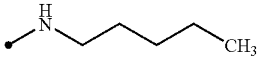 | MS m/z 455 $(M + H)^+$ |
| 5-7 | 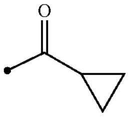 | 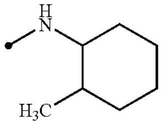 | MS m/z 481 $(M + H)^+$ |
| 5-8 | 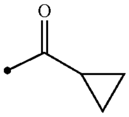 | 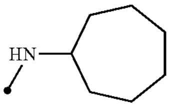 | MS m/z 481 $(M + H)^+$ |
| 5-9 | 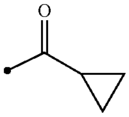 | 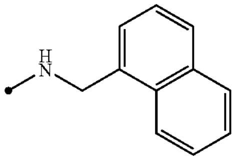 | MS m/z 525 $(M + H)^+$ |
| 5-10 | 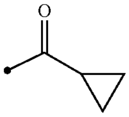 | 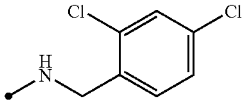 | MS m/z 543 $(M + H)^+$ |

TABLE 5-continued
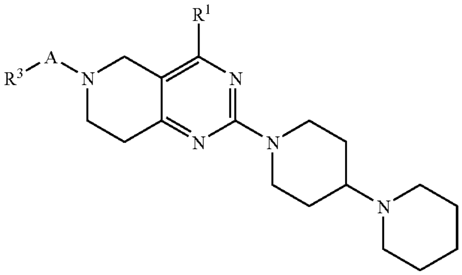
| Compound Number | •—A—$R^3$ | •—$R^1$ | Spectrum Data |
|---|---|---|---|
| 5-11 | 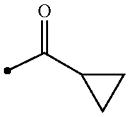 | 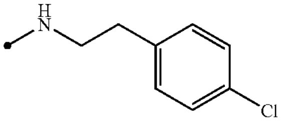 | MS m/z 523 $(M + H)^+$ |
| 5-12 | 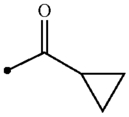 | 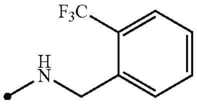 | MS m/z 543 $(M + H)^+$ |
| 5-13 | 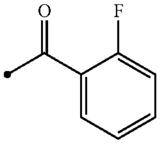 | 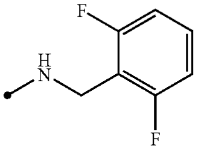 | MS m/z 565 $(M + H)^+$ |
| 5-14 | 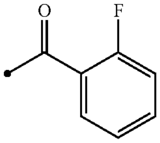 | 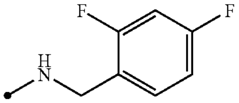 | MS m/z 565 $(M + H)^+$ |
| 5-15 | 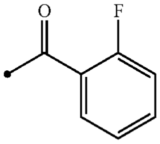 | 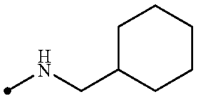 | MS m/z 535 $(M + H)^+$ |
| 5-16 | 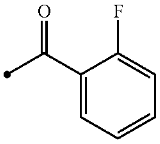 | 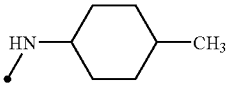 | MS m/z 535 $(M + H)^+$ |
| 5-17 | 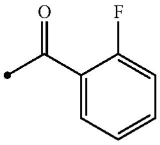 | 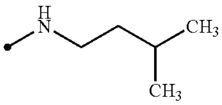 | MS m/z 509 $(M + H)^+$ |
| 5-18 | 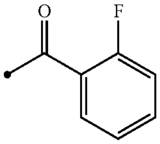 | 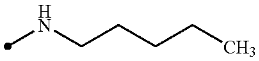 | MS m/z 509 $(M + H)^+$ |

TABLE 5-continued
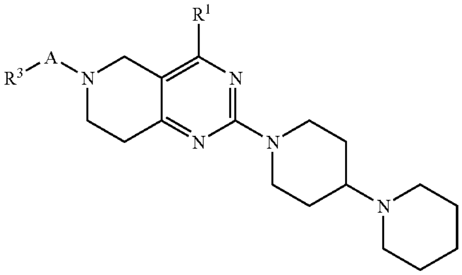
| Compound Number | •—A—$R^3$ | •—$R^1$ | Spectrum Data |
|---|---|---|---|
| 5-19 | 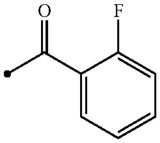 | 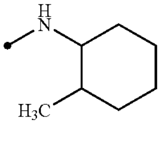 | MS m/z 535 $(M + H)^+$ |
| 5-20 | 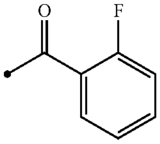 | 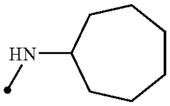 | MS m/z 535 $(M + H)^+$ |
| 5-21 | 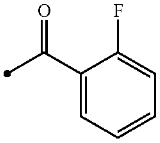 | 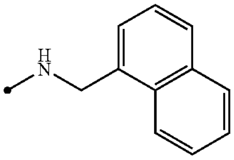 | MS m/z 579 $(M + H)^+$ |
| 5-22 | 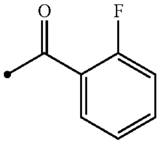 | 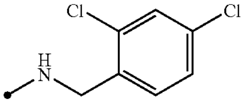 | MS m/z 597 $(M + H)^+$ |
| 5-23 | 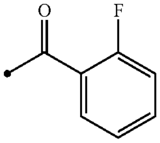 | 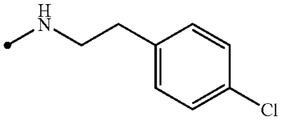 | MS m/z 577 $(M + H)^+$ |
| 5-24 | 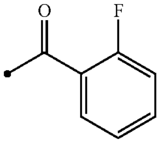 | 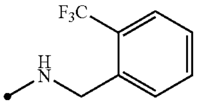 | MS m/z 597 $(M + H)^+$ |
| 5-25 | 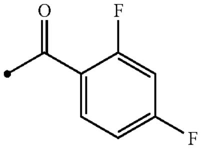 | 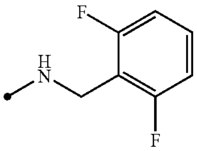 | MS m/z 583 $(M + H)^+$ |

TABLE 5-continued
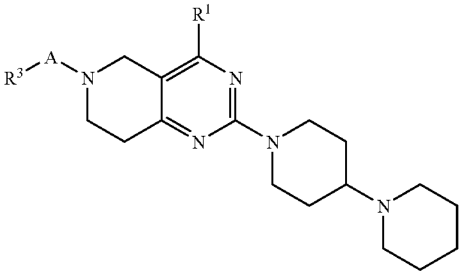
| Compound Number | •—A—$R^3$ | •—$R^1$ | Spectrum Data |
| --- | --- | --- | --- |
| 5-26 | 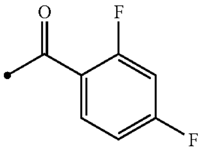 | 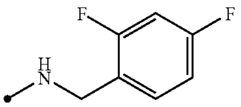 | MS m/z 583 $(M + H)^+$ |
| 5-27 | 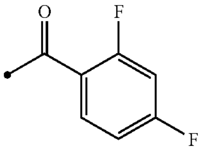 | 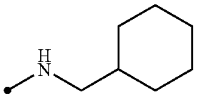 | MS m/z 553 $(M + H)^+$ |
| 5-28 | 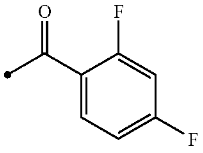 | 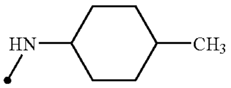 | MS m/z 553 $(M + H)^+$ |
| 5-29 | 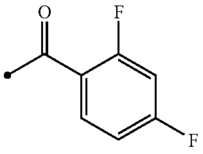 | 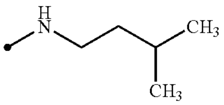 | MS m/z 527 $(M + H)^+$ |
| 5-30 | 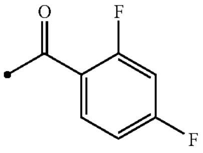 | 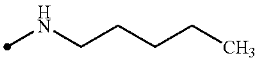 | MS m/z 527 $(M + H)^+$ |
| 5-31 | 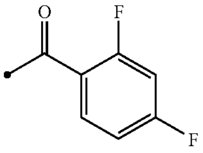 | 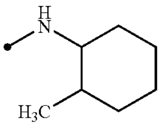 | MS m/z 553 $(M + H)^+$ |
| 5-32 | 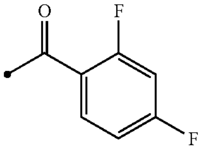 | 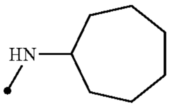 | MS m/z 553 $(M + H)^+$ |

TABLE 5-continued
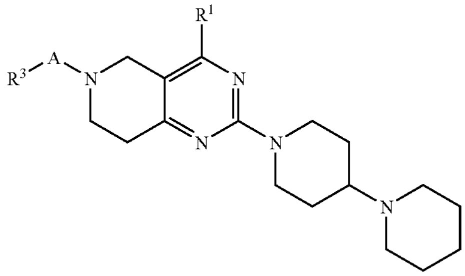
| Compound Number | •—A—$R^3$ | •—$R^1$ | Spectrum Data |
|---|---|---|---|
| 5-33 | 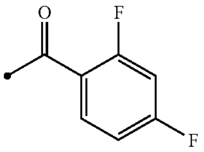 | 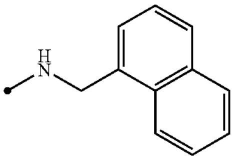 | MS m/z 597 $(M + H)^+$ |
| 5-34 | 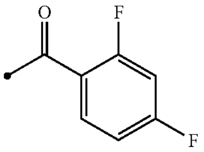 | 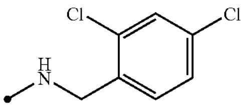 | MS m/z 615 $(M + H)^+$ |
| 5-35 | 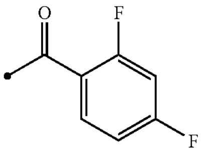 | 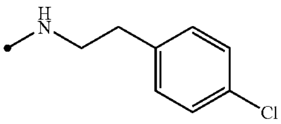 | MS m/z 595 $(M + H)^+$ |
| 5-36 | 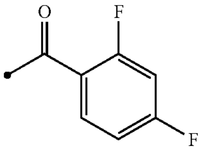 | 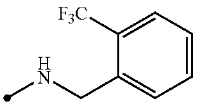 | MS m/z 615 $(M + H)^+$ |
| 5-37 | 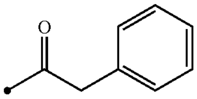 | 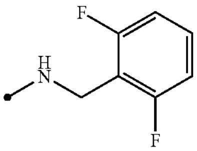 | MS m/z 561 $(M + H)^+$ |
| 5-38 | 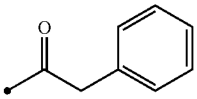 | 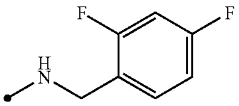 | MS m/z 561 $(M + H)^+$ |
| 5-39 | 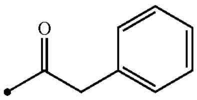 | 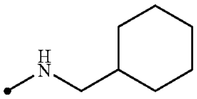 | MS m/z 531 $(M + H)^+$ |
| 5-40 | 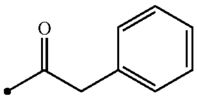 | 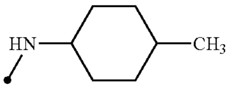 | MS m/z 531 $(M + H)^+$ |

TABLE 5-continued
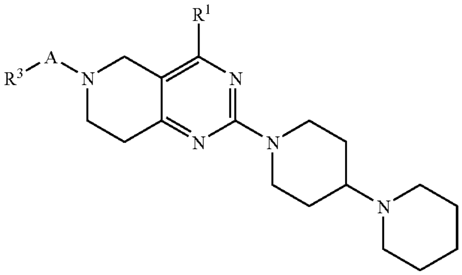
| Compound Number | •—A—$R^3$ | •—$R^1$ | Spectrum Data |
|---|---|---|---|
| 5-41 | 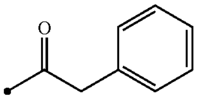 | 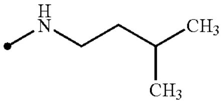 | MS m/z 505 $(M + H)^+$ |
| 5-42 | 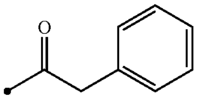 | 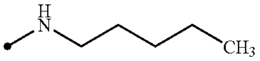 | MS m/z 505 $(M + H)^+$ |
| 5-43 | 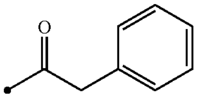 | 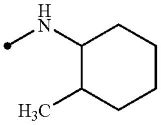 | MS m/z 531 $(M + H)^+$ |
| 5-44 | 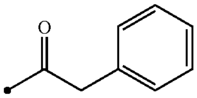 | 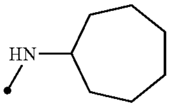 | MS m/z 531 $(M + H)^+$ |
| 5-45 | 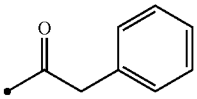 | 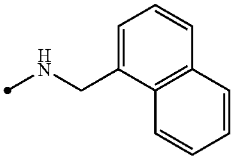 | MS m/z 575 $(M + H)^+$ |
| 5-46 | 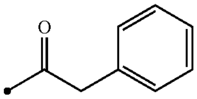 | 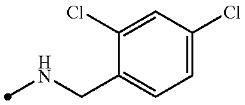 | MS m/z 593 $(M + H)^+$ |
| 5-47 | 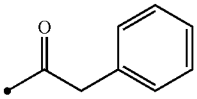 | 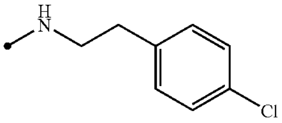 | MS m/z 573 $(M + H)^+$ |
| 5-48 | 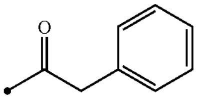 | 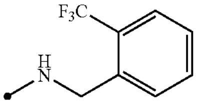 | MS m/z 593 $(M + H)^+$ |
| 5-49 | 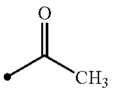 | 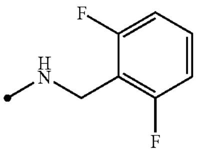 | MS m/z 485 $(M + H)^+$ |

TABLE 5-continued
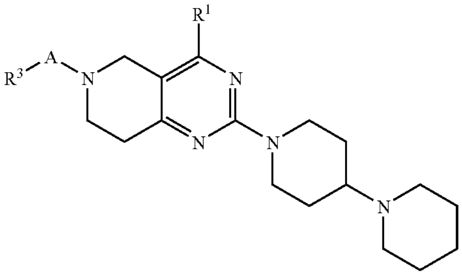
| Compound Number | •—A—$R^3$ | •—$R^1$ | Spectrum Data |
|---|---|---|---|
| 5-50 | 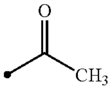 | 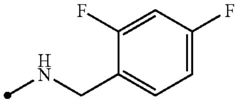 | MS m/z 485 $(M + H)^+$ |
| 5-51 | 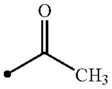 | 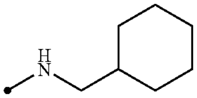 | MS m/z 455 $(M + H)^+$ |
| 5-52 | 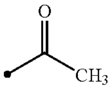 | 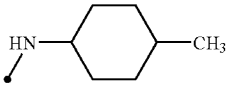 | MS m/z 455 $(M + H)^+$ |
| 5-53 | 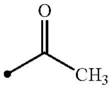 | 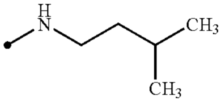 | MS m/z 429 $(M + H)^+$ |
| 5-54 | 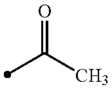 | 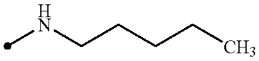 | MS m/z 429 $(M + H)^+$ |
| 5-55 | 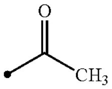 | 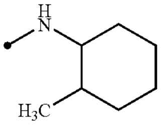 | MS m/z 455 $(M + H)^+$ |
| 5-56 | 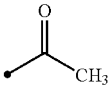 | 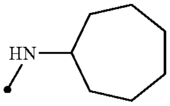 | MS m/z 455 $(M + H)^+$ |
| 5-57 | 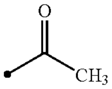 | 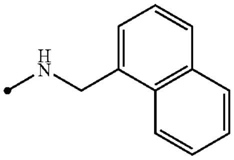 | MS m/z 499 $(M + H)^+$ |
| 5-58 | 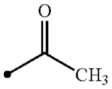 | 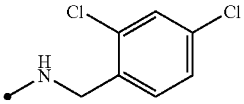 | MS m/z 517 $(M + H)^+$ |
| 5-59 | 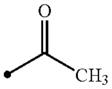 | 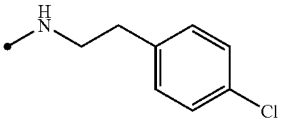 | MS m/z 497 $(M + H)^+$ |

TABLE 5-continued
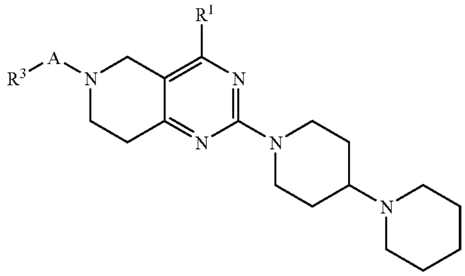
| Compound Number | •—A—$R^3$ | •—$R^1$ | Spectrum Data |
|---|---|---|---|
| 5-60 | 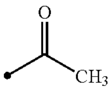 | 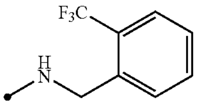 | MS m/z 517 $(M + H)^+$ |
| 5-61 | 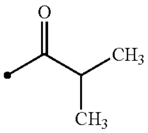 | 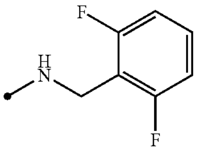 | MS m/z 513 $(M + H)^+$ |
| 5-62 | 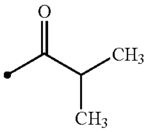 | 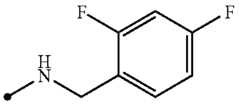 | MS m/z 513 $(M + H)^+$ |
| 5-63 | 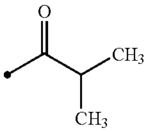 | 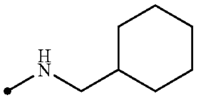 | MS m/z 483 $(M + H)^+$ |
| 5-64 | 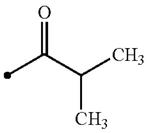 | 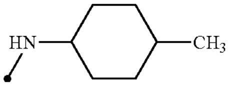 | MS m/z 483 $(M + H)^+$ |
| 5-65 | 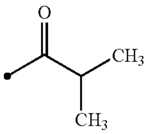 | 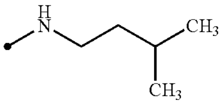 | MS m/z 457 $(M + H)^+$ |
| 5-66 | 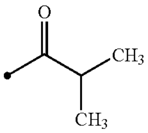 | 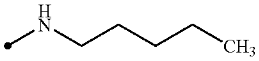 | MS m/z 457 $(M + H)^+$ |
| 5-67 | 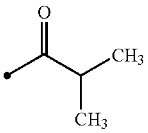 | 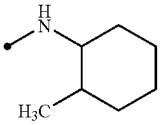 | MS m/z 483 $(M + H)^+$ |

TABLE 5-continued
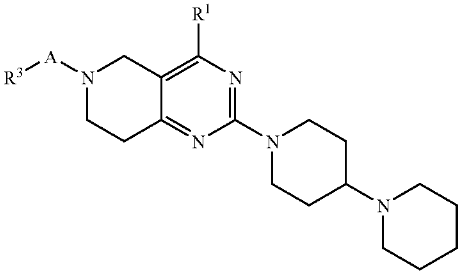
| Compound Number | •—A—$R^3$ | •—$R^1$ | Spectrum Data |
|---|---|---|---|
| 5-68 | 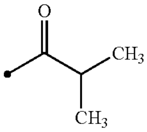 | 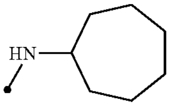 | MS m/z 483 $(M+H)^+$ |
| 5-69 | 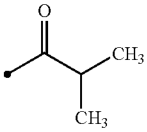 | 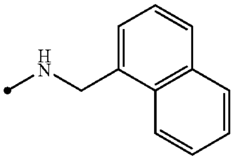 | MS m/z 527 $(M+H)^+$ |
| 5-70 | 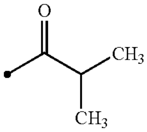 | 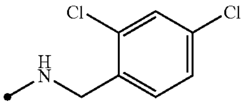 | MS m/z 545 $(M+H)^+$ |
| 5-71 | 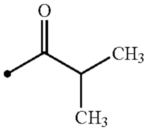 | 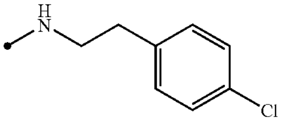 | MS m/z 525 $(M+H)^+$ |
| 5-72 | 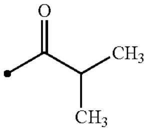 | 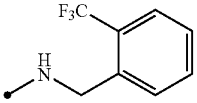 | MS m/z 545 $(M+H)^+$ |
| 5-73 | 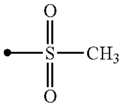 | 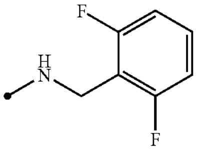 | MS m/z 521 $(M+H)^+$ |
| 5-74 | 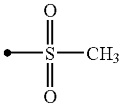 | 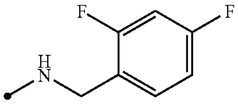 | MS m/z 521 $(M+H)^+$ |
| 5-75 | 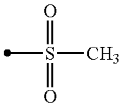 | 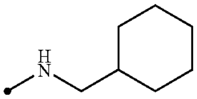 | MS m/z 491 $(M+H)^+$ |

TABLE 5-continued
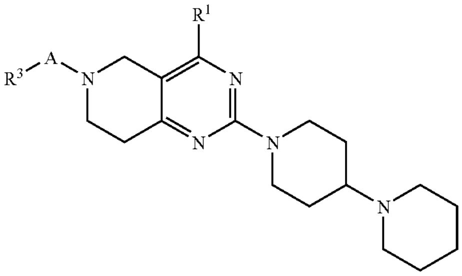
| Compound Number | •—A—$R^3$ | •—$R^1$ | Spectrum Data |
|---|---|---|---|
| 5-76 | 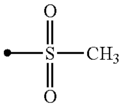 | 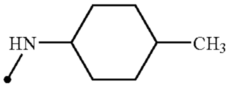 | MS m/z 491 $(M + H)^+$ |
| 5-77 | 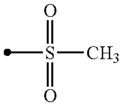 | 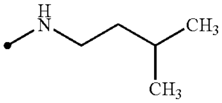 | MS m/z 465 $(M + H)^+$ |
| 5-78 | 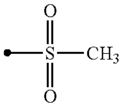 | 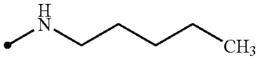 | MS m/z 465 $(M + H)^+$ |
| 5-79 | 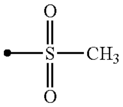 | 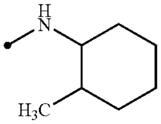 | MS m/z 491 $(M + H)^+$ |
| 5-80 | 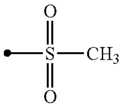 | 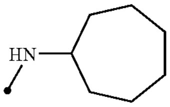 | MS m/z 491 $(M + H)^+$ |
| 5-81 | 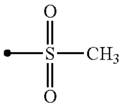 | 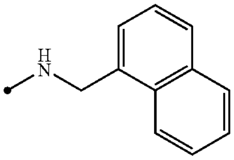 | MS m/z 535 $(M + H)^+$ |
| 5-82 | 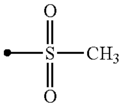 | 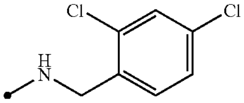 | MS m/z 553 $(M + H)^+$ |
| 5-83 | 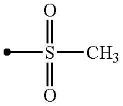 | 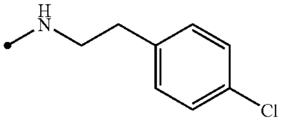 | MS m/z 533 $(M + H)^+$ |
| 5-84 | 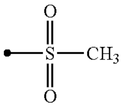 | 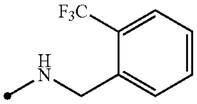 | MS m/z 553 $(M + H)^+$ |

TABLE 5-continued
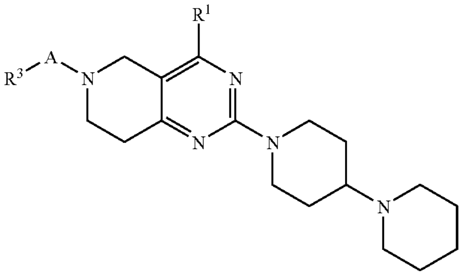
| Compound Number | •—A—$R^3$ | •—$R^1$ | Spectrum Data |
|---|---|---|---|
| 5-85 | 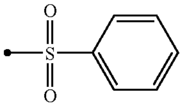 | 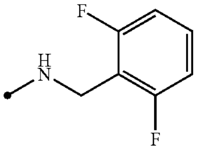 | MS m/z 583 $(M + H)^+$ |
| 5-86 | 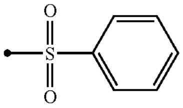 | 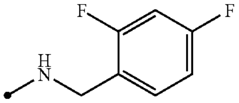 | MS m/z 583 $(M + H)^+$ |
| 5-87 | 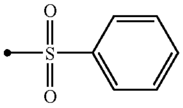 | 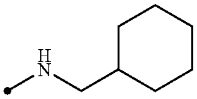 | MS m/z 553 $(M + H)^+$ |
| 5-88 | 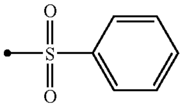 | 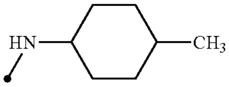 | MS m/z 553 $(M + H)^+$ |
| 5-89 | 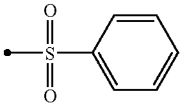 | 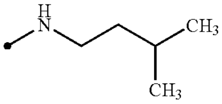 | MS m/z 527 $(M + H)^+$ |
| 5-90 | 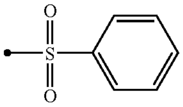 | 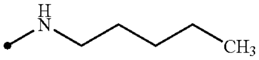 | MS m/z 527 $(M + H)^+$ |
| 5-91 | 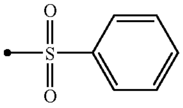 | 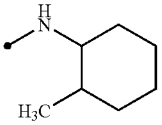 | MS m/z 553 $(M + H)^+$ |
| 5-92 | 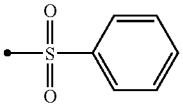 | 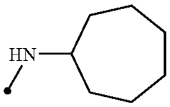 | MS m/z 553 $(M + H)^+$ |
| 5-93 | 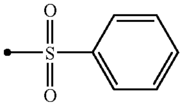 | 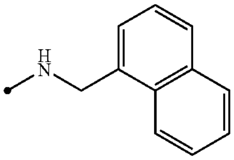 | MS m/z 597 $(M + H)^+$ |

TABLE 5-continued
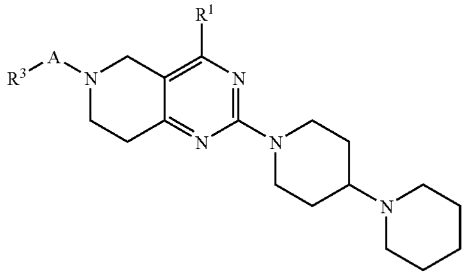
| Compound Number | •—A—$R^3$ | •—$R^1$ | Spectrum Data |
|---|---|---|---|
| 5-94 | 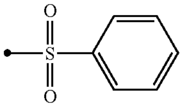 | 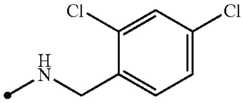 | MS m/z 615 (M + H)+ |
| 5-95 | 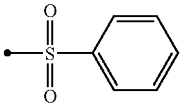 | 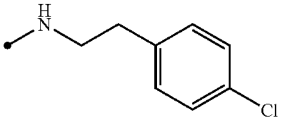 | MS m/z 595 (M + H)+ |
| 5-96 | 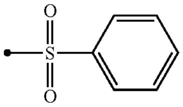 | 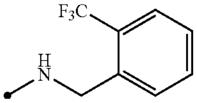 | MS m/z 615 (M + H)+ |
| 5-97 | 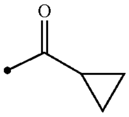 | 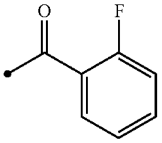 | MS m/z 509 (M + H)+ |
| 5-98 | 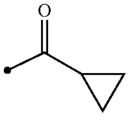 | 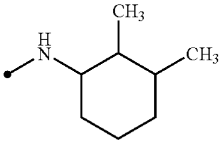 | MS m/z 495 (M + H)+ |
| 5-99 | 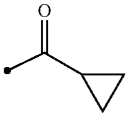 | 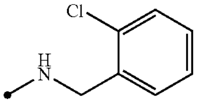 | MS m/z 509 (M + H)+ |
| 5-100 | 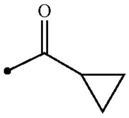 | 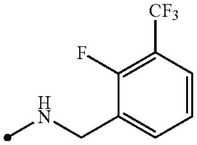 | MS m/z 561 (M + H)+ |
| 5-101 | 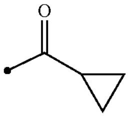 | 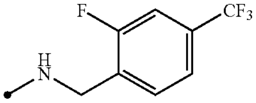 | MS m/z 561 (M + H)+ |
| 5-102 | 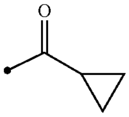 | 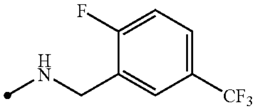 | MS m/z 561 (M + H)+ |

TABLE 5-continued
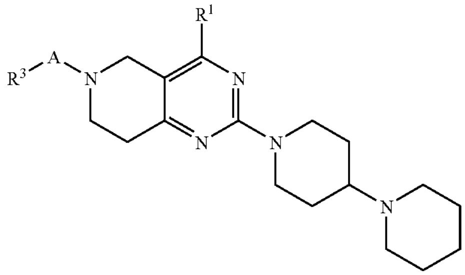
| Compound Number | •—A—$R^3$ | •—$R^1$ | Spectrum Data |
|---|---|---|---|
| 5-103 | 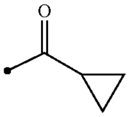 | 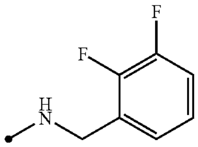 | MS m/z 511 $(M + H)^+$ |
| 5-104 | 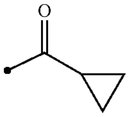 | 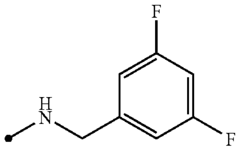 | MS m/z 511 $(M + H)^+$ |
| 5-105 | 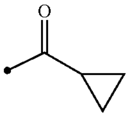 | 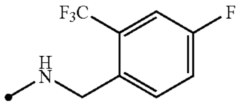 | MS m/z 561 $(M + H)^+$ |
| 5-106 | 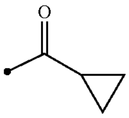 | 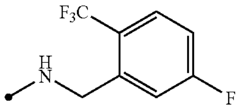 | MS m/z 561 $(M + H)^+$ |
| 5-107 | 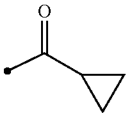 | 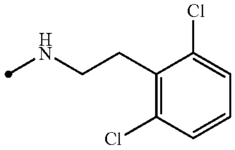 | MS m/z 557 $(M + H)^+$ |
| 5-108 | 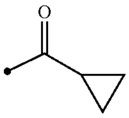 | 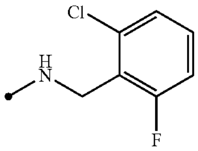 | MS m/z 527 $(M + H)^+$ |
| 5-109 | 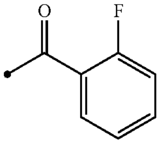 | 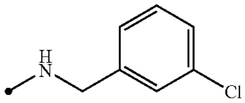 | MS m/z 563 $(M + H)^+$ |
| 5-110 | 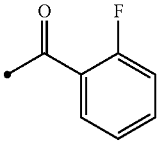 | 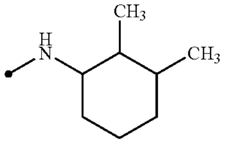 | MS m/z 549 $(M + H)^+$ |

TABLE 5-continued
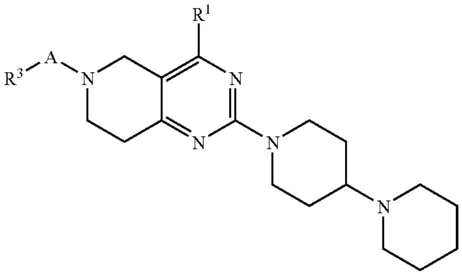
| Compound Number | •—A—R³ | •—R¹ | Spectrum Data |
|---|---|---|---|
| 5-111 | 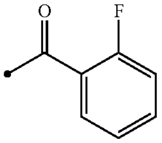 | 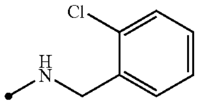 | MS m/z 563 (M + H)⁺ |
| 5-112 | 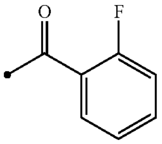 | 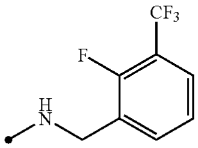 | MS m/z 615 (M + H)⁺ |
| 5-113 | 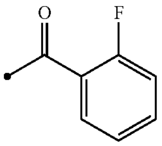 | 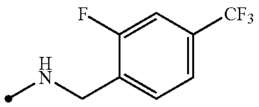 | MS m/z 615 (M + H)⁺ |
| 5-114 | 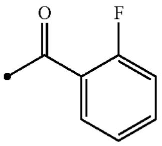 | 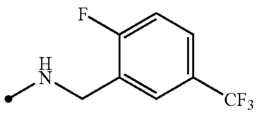 | MS m/z 615 (M + H)⁺ |
| 5-115 | 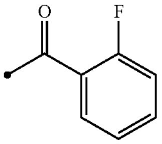 | 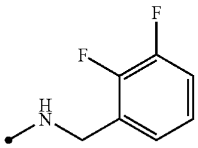 | MS m/z 565 (M + H)⁺ |
| 5-116 | 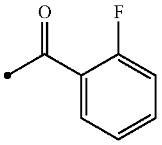 | 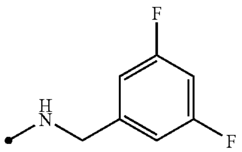 | MS m/z 565 (M + H)⁺ |
| 5-117 | 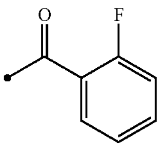 | 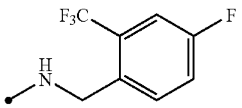 | MS m/z 615 (M + H)⁺ |
| 5-118 | 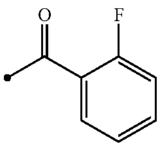 | 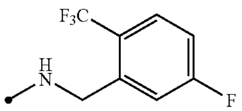 | MS m/z 615 (M + H)⁺ |

TABLE 5-continued
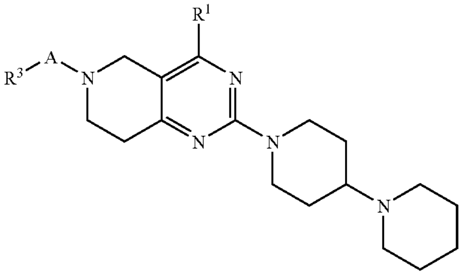
| Compound Number | •—A—R$^3$ | •—R$^1$ | Spectrum Data |
|---|---|---|---|
| 5-119 | 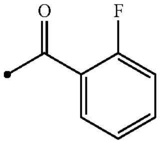 | 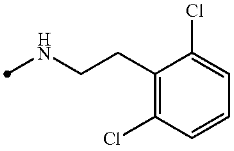 | MS m/z 611 (M + H)$^+$ |
| 5-120 | 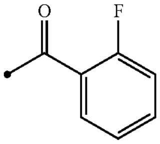 | 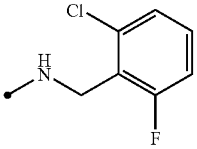 | MS m/z 581 (M + H)$^+$ |
| 5-121 | 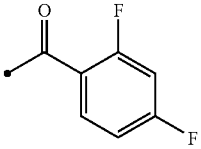 | 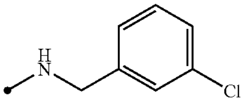 | MS m/z 581 (M + H)$^+$ |
| 5-122 | 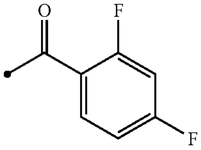 | 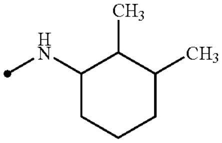 | MS m/z 567 (M + H)$^+$ |
| 5-123 | 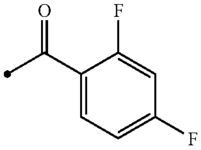 | 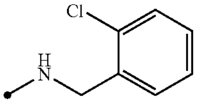 | MS m/z 581 (M + H)$^+$ |
| 5-124 | 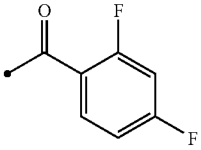 | 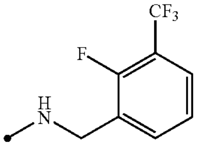 | MS m/z 633 (M + H)$^+$ |
| 5-125 | 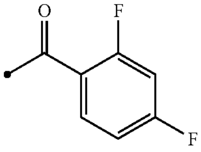 | 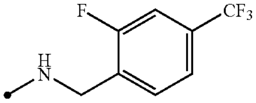 | MS m/z 633 (M + H)$^+$ |

TABLE 5-continued
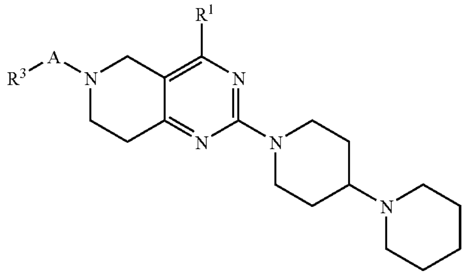
| Compound Number | •—A—$R^3$ | •—$R^1$ | Spectrum Data |
|---|---|---|---|
| 5-126 | 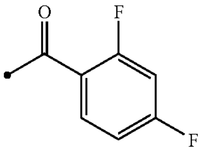 | 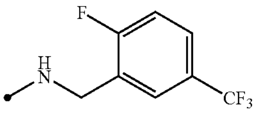 | MS m/z 633 $(M + H)^+$ |
| 5-127 | 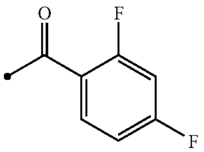 | 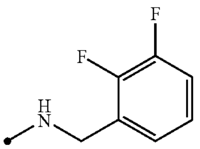 | MS m/z 583 $(M + H)^+$ |
| 5-128 | 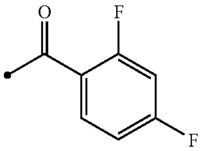 | 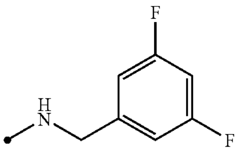 | MS m/z 583 $(M + H)^+$ |
| 5-129 | 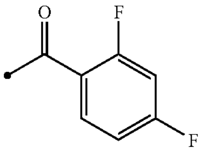 | 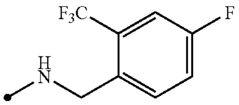 | MS m/z 633 $(M + H)^+$ |
| 5-130 | 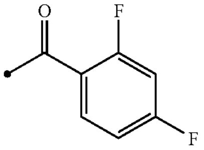 | 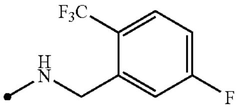 | MS m/z 633 $(M + H)^+$ |
| 5-131 | 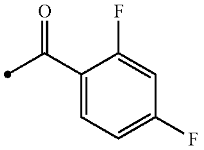 | 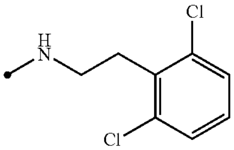 | MS m/z 629 $(M + H)^+$ |
| 5-132 | 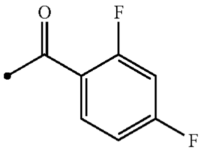 | 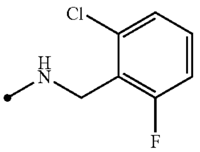 | MS m/z 599 $(M + H)^+$ |
| 5-133 | 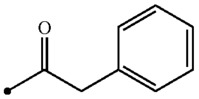 | 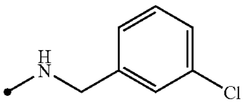 | MS m/z 559 $(M + H)^+$ |

TABLE 5-continued
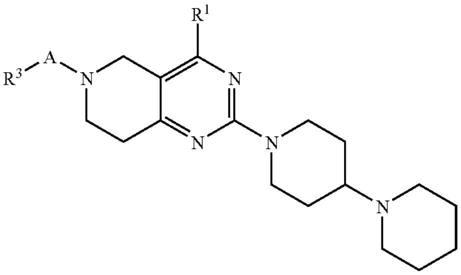
| Compound Number | •—A—$R^3$ | •—$R^1$ | Spectrum Data |
|---|---|---|---|
| 5-134 | 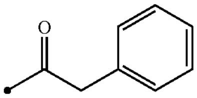 | 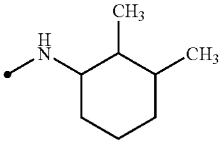 | MS m/z 545 $(M + H)^+$ |
| 5-135 | 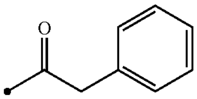 | 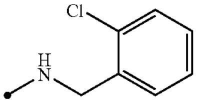 | MS m/z 559 $(M + H)^+$ |
| 5-136 | 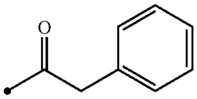 | 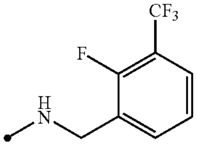 | MS m/z 611 $(M + H)^+$ |
| 5-137 | 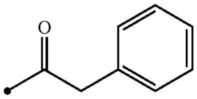 | 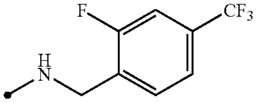 | MS m/z 611 $(M + H)^+$ |
| 5-138 | 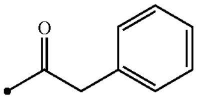 | 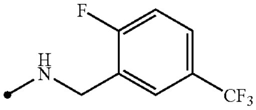 | MS m/z 611 $(M + H)^+$ |
| 5-139 | 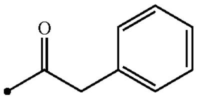 | 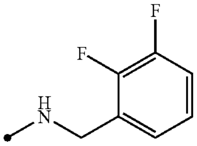 | MS m/z 561 $(M + H)^+$ |
| 5-140 | 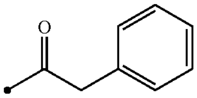 | 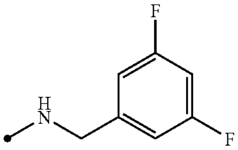 | MS m/z 561 $(M + H)^+$ |
| 5-141 | 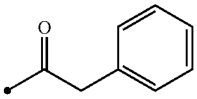 | 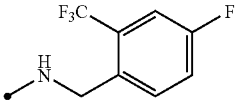 | MS m/z 611 $(M + H)^+$ |
| 5-142 | 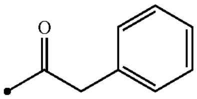 | 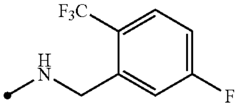 | MS m/z 611 $(M + H)^+$ |

TABLE 5-continued
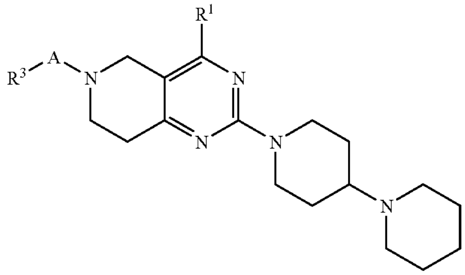
| Compound Number | •—A—$R^3$ | •—$R^1$ | Spectrum Data |
|---|---|---|---|
| 5-143 | 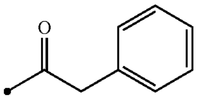 | 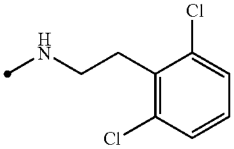 | MS m/z 607 $(M + H)^+$ |
| 5-144 | 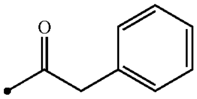 | 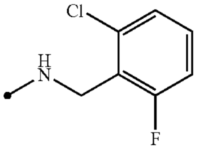 | MS m/z 577 $(M + H)^+$ |
| 5-145 | 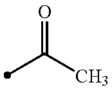 | 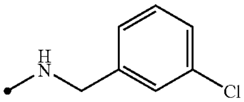 | MS m/z 483 $(M + H)^+$ |
| 5-146 | 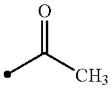 | 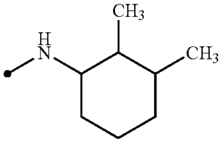 | MS m/z 469 $(M + H)^+$ |
| 5-147 | 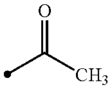 | 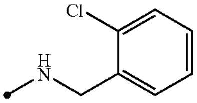 | MS m/z 483 $(M + H)^+$ |
| 5-148 | 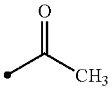 | 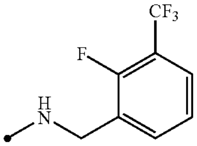 | MS m/z 535 $(M + H)^+$ |
| 5-149 | 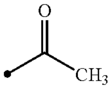 | 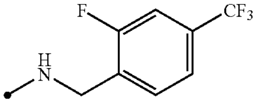 | MS m/z 535 $(M + H)^+$ |
| 5-150 | 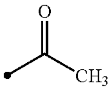 | 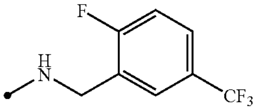 | MS m/z 535 $(M + H)^+$ |

TABLE 5-continued
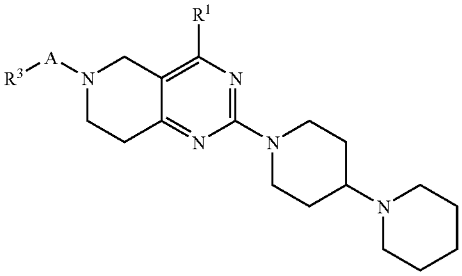
| Compound Number | •—A—$R^3$ | •—$R^1$ | Spectrum Data |
|---|---|---|---|
| 5-151 | 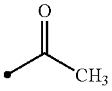 | 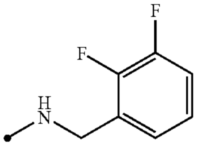 | MS m/z 485 $(M + H)^+$ |
| 5-152 | 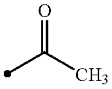 | 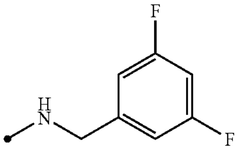 | MS m/z 485 $(M + H)^+$ |
| 5-153 | 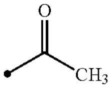 | 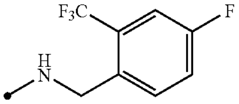 | MS m/z 535 $(M + H)^+$ |
| 5-154 | 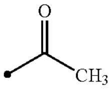 | 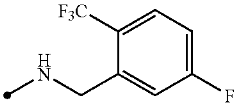 | MS m/z 535 $(M + H)^+$ |
| 5-155 | 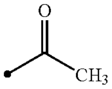 | 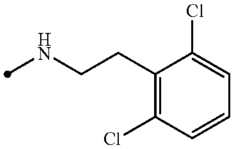 | MS m/z 531 $(M + H)^+$ |
| 5-156 | 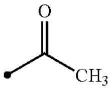 | 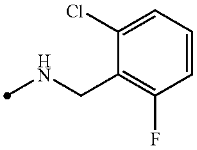 | MS m/z 501 $(M + H)^+$ |
| 5-157 | 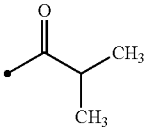 | 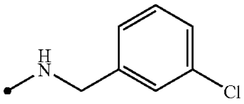 | MS m/z 511 $(M + H)^+$ |
| 5-158 | 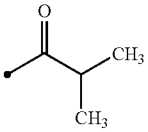 | 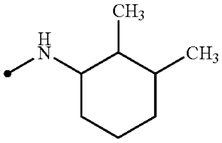 | MS m/z 497 $(M + H)^+$ |

TABLE 5-continued
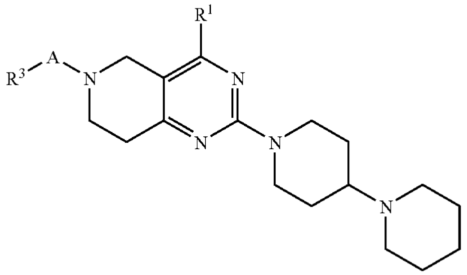
| Compound Number | •—A—$R^3$ | •—$R^1$ | Spectrum Data |
|---|---|---|---|
| 5-159 | 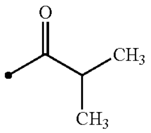 | 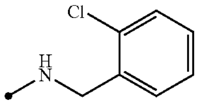 | MS m/z 511 $(M + H)^+$ |
| 5-160 | 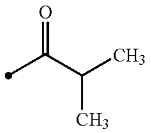 | 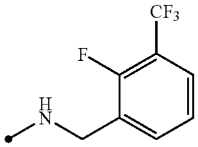 | MS m/z 563 $(M + H)^+$ |
| 5-161 | 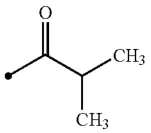 | 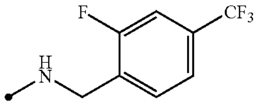 | MS m/z 563 $(M + H)^+$ |
| 5-162 | 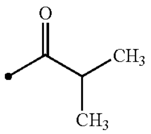 | 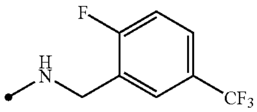 | MS m/z 563 $(M + H)^+$ |
| 5-163 | 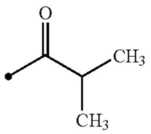 | 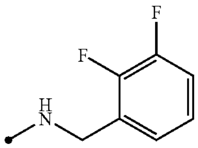 | MS m/z 513 $(M + H)^+$ |
| 5-164 | 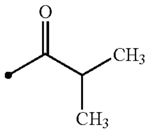 | 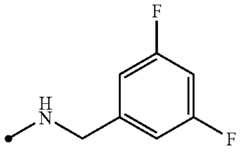 | MS m/z 513 $(M + H)^+$ |
| 5-165 | 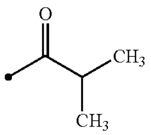 | 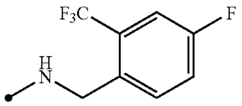 | MS m/z 563 $(M + H)^+$ |
| 5-166 | 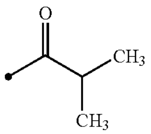 | 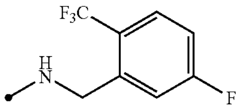 | MS m/z 563 $(M + H)^+$ |

TABLE 5-continued
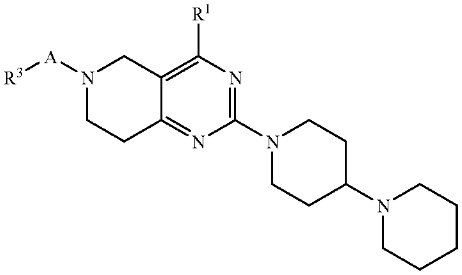
| Compound Number | •—A—$R^3$ | •—$R^1$ | Spectrum Data |
|---|---|---|---|
| 5-167 | 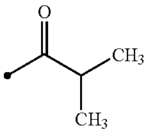 | 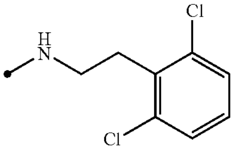 | MS m/z 529 (M + H)+ |
| 5-168 | 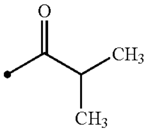 | 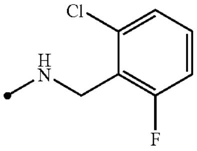 | MS m/z 529 (M + H)+ |
| 5-169 | 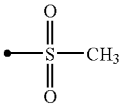 | 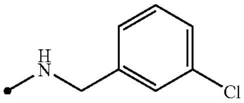 | MS m/z 519 (M + H)+ |
| 5-170 | 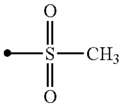 | 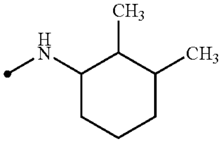 | MS m/z 505 (M + H)+ |
| 5-171 | 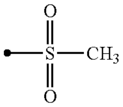 | 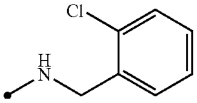 | MS m/z 519 (M + H)+ |
| 5-172 | 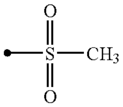 | 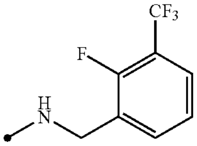 | MS m/z 571 (M + H)+ |
| 5-173 | 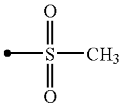 | 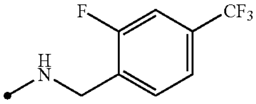 | MS m/z 571 (M + H)+ |
| 5-174 | 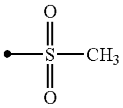 | 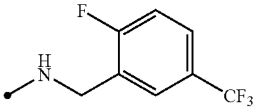 | MS m/z 571 (M + H)+ |

TABLE 5-continued
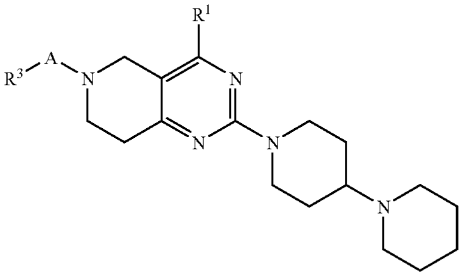
| Compound Number | •—A—$R^3$ | •—$R^1$ | Spectrum Data |
|---|---|---|---|
| 5-175 | 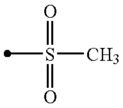 | 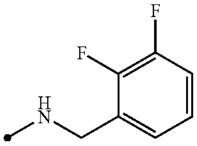 | MS m/z 521 $(M + H)^+$ |
| 5-176 | 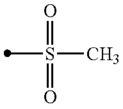 | 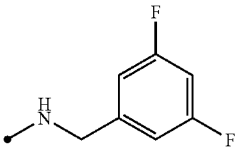 | MS m/z 521 $(M + H)^+$ |
| 5-177 | 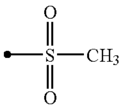 | 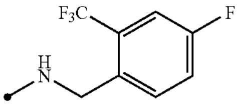 | MS m/z 571 $(M + H)^+$ |
| 5-178 | 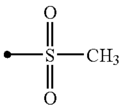 | 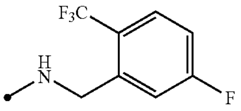 | MS m/z 571 $(M + H)^+$ |
| 5-179 | 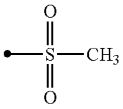 | 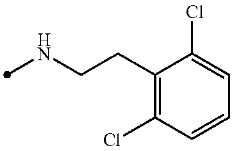 | MS m/z 567 $(M + H)^+$ |
| 5-180 | 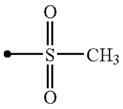 | 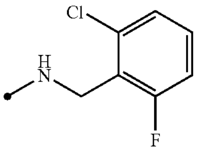 | MS m/z 537 $(M + H)^+$ |
| 5-181 | 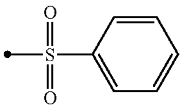 | 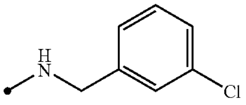 | MS m/z 581 $(M + H)^+$ |
| 5-182 | 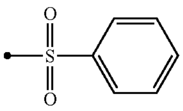 | 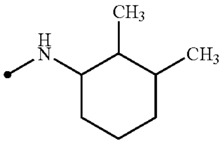 | MS m/z 567 $(M + H)^+$ |

TABLE 5-continued
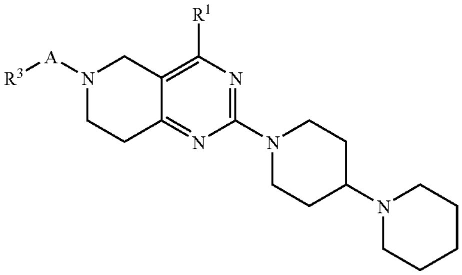
| Compound Number | •—A—$R^3$ | •—$R^1$ | Spectrum Data |
|---|---|---|---|
| 5-183 | 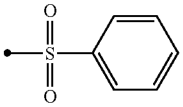 | 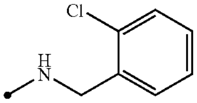 | MS m/z 581 $(M + H)^+$ |
| 5-184 | 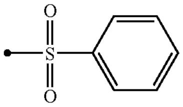 | 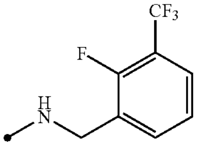 | MS m/z 633 $(M + H)^+$ |
| 5-185 | 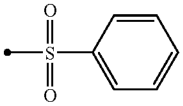 | 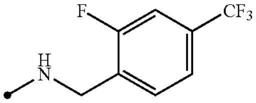 | MS m/z 633 $(M + H)^+$ |
| 5-186 | 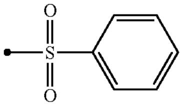 | 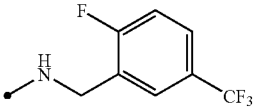 | MS m/z 633 $(M + H)^+$ |
| 5-187 | 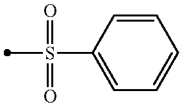 | 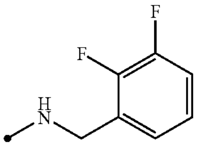 | MS m/z 583 $(M + H)^+$ |
| 5-188 | 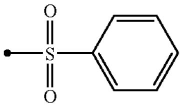 | 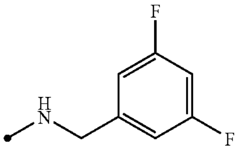 | MS m/z 583 $(M + H)^+$ |
| 5-189 | 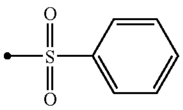 | 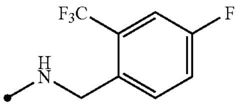 | MS m/z 633 $(M + H)^+$ |
| 5-190 | 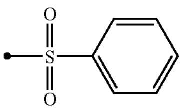 | 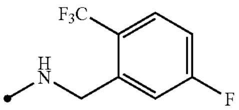 | MS m/z 633 $(M + H)^+$ |
| 5-191 | 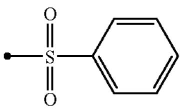 | 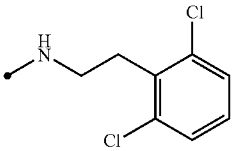 | MS m/z 629 $(M + H)^+$ |

TABLE 5-continued
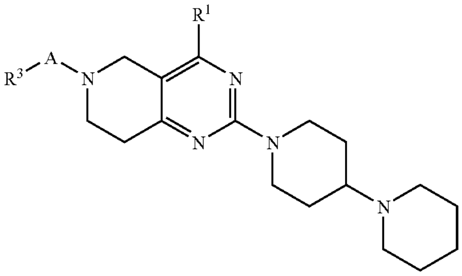
| Compound Number | •—A—$R^3$ | •—$R^1$ | Spectrum Data |
|---|---|---|---|
| 5-192 | 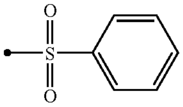 | 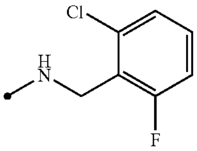 | MS m/z 599 $(M + H)^+$ |
| 5-193 | 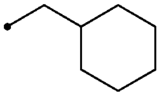 | 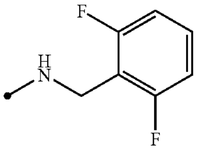 | MS m/z 539 $(M + H)^+$ |
| 5-194 | 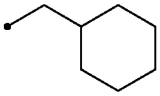 | 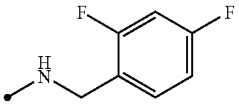 | MS m/z 539 $(M + H)^+$ |
| 5-195 | 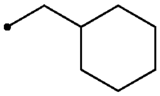 | 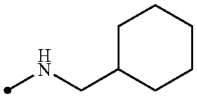 | MS m/z 509 $(M + H)^+$ |
| 5-196 | 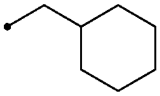 | 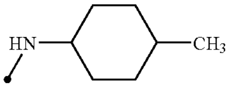 | MS m/z 509 $(M + H)^+$ |
| 5-197 | 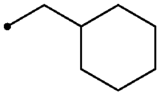 | 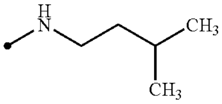 | MS m/z 483 $(M + H)^+$ |
| 5-198 | 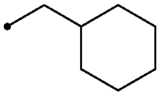 | 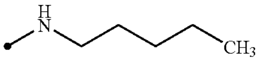 | MS m/z 483 $(M + H)^+$ |
| 5-199 | 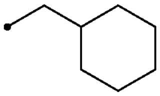 | 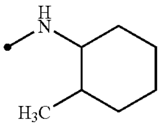 | MS m/z 509 $(M + H)^+$ |
| 5-200 | 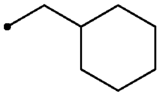 | 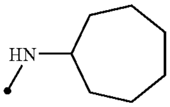 | MS m/z 509 $(M + H)^+$ |

TABLE 5-continued
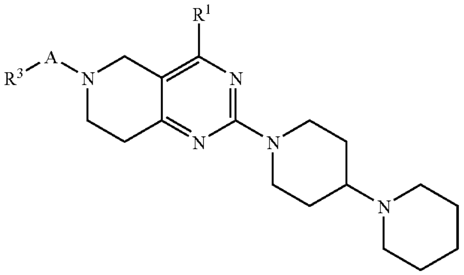
| Compound Number | •—A—R$^3$ | •—R$^1$ | Spectrum Data |
|---|---|---|---|
| 5-201 | 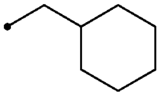 | 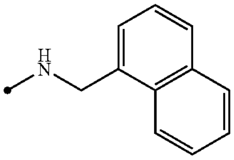 | MS m/z 553 (M + H)$^+$ |
| 5-202 | 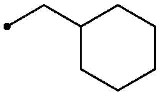 | 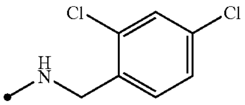 | MS m/z 571 (M + H)$^+$ |
| 5-203 | 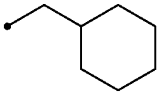 | 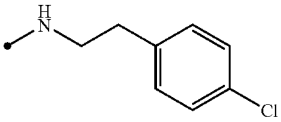 | MS m/z 551 (M + H)$^+$ |
| 5-204 | 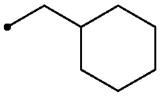 | 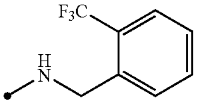 | MS m/z 571 (M + H)$^+$ |
| 5-205 | 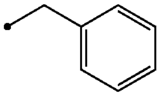 | 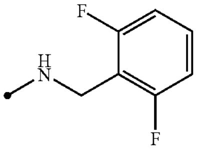 | MS m/z 533 (M + H)$^+$ |
| 5-206 | 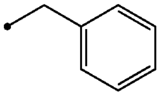 | 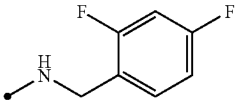 | MS m/z 533 (M + H)$^+$ |
| 5-207 | 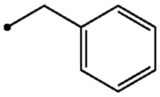 | 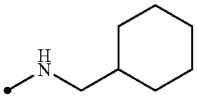 | MS m/z 503 (M + H)$^+$ |
| 5-208 | 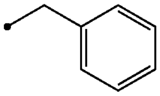 | 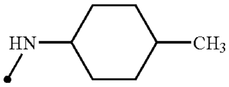 | MS m/z 503 (M + H)$^+$ |
| 5-209 | 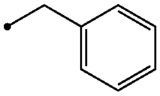 | 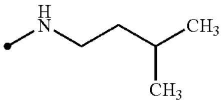 | MS m/z 477 (M + H)$^+$ |
| 5-210 | 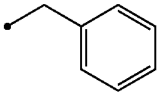 | 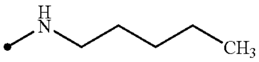 | MS m/z 477 (M + H)$^+$ |

TABLE 5-continued
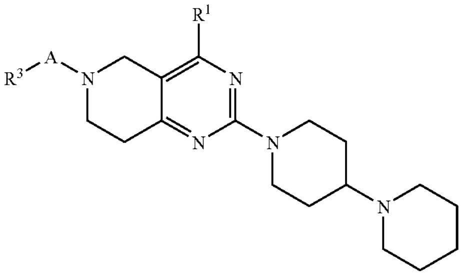
| Compound Number | •—A—$R^3$ | •—$R^1$ | Spectrum Data |
|---|---|---|---|
| 5-211 | 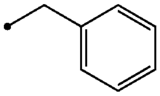 | 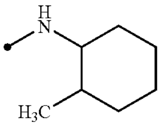 | MS m/z 503 $(M + H)^+$ |
| 5-212 | 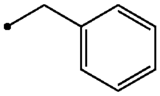 | 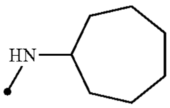 | MS m/z 503 $(M + H)^+$ |
| 5-213 | 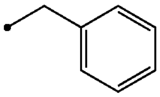 | 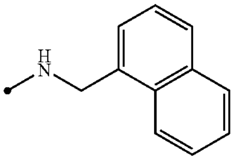 | MS m/z 547 $(M + H)^+$ |
| 5-214 | 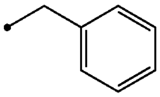 | 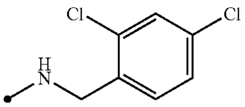 | MS m/z 565 $(M + H)^+$ |
| 5-215 | 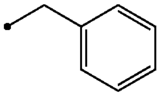 | 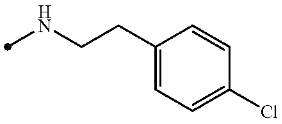 | MS m/z 545 $(M + H)^+$ |
| 5-216 | 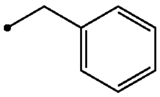 | 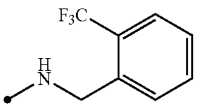 | MS m/z 565 $(M + H)^+$ |
| 5-217 | 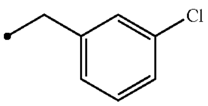 | 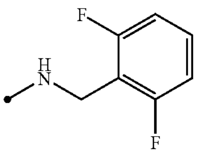 | MS m/z 567 $(M + H)^+$ |
| 5-218 | 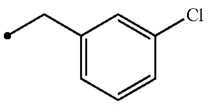 | 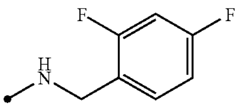 | MS m/z 567 $(M + H)^+$ |
| 5-219 | 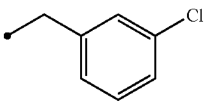 | 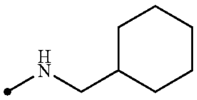 | MS m/z 537 $(M + H)^+$ |

TABLE 5-continued
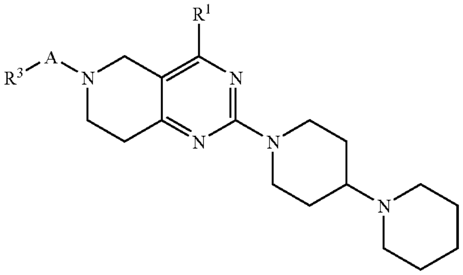
| Compound Number | •—A—$R^3$ | •—$R^1$ | Spectrum Data |
|---|---|---|---|
| 5-220 | 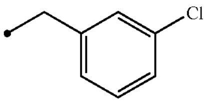 | 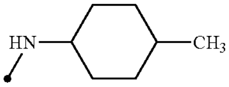 | MS m/z 537 $(M + H)^+$ |
| 5-221 | 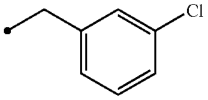 | 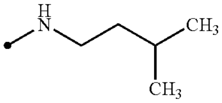 | MS m/z 511 $(M + H)^+$ |
| 5-222 | 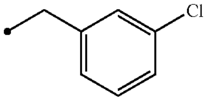 | 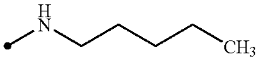 | MS m/z 511 $(M + H)^+$ |
| 5-223 | 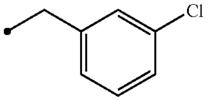 | 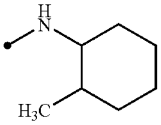 | MS m/z 537 $(M + H)^+$ |
| 5-224 | 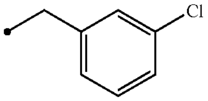 | 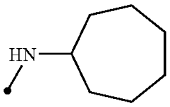 | MS m/z 537 $(M + H)^+$ |
| 5-225 | 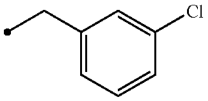 | 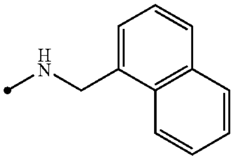 | MS m/z 581 $(M + H)^+$ |
| 5-226 | 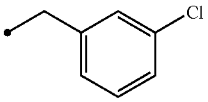 | 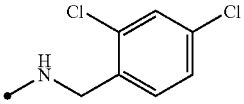 | MS m/z 599 $(M + H)^+$ |
| 5-227 | 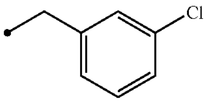 | 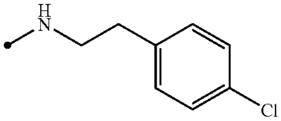 | MS m/z 579 $(M + H)^+$ |
| 5-228 | 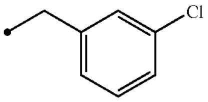 | 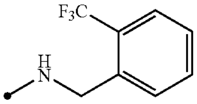 | MS m/z 599 $(M + H)^+$ |

TABLE 5-continued
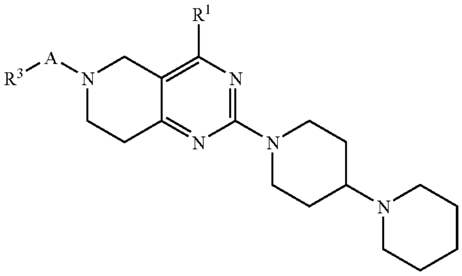
| Compound Number | •—A—$R^3$ | •—$R^1$ | Spectrum Data |
|---|---|---|---|
| 5-229 | 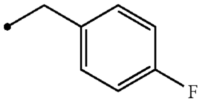 | 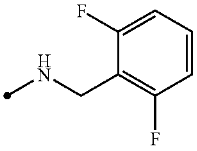 | MS m/z 551 $(M + H)^+$ |
| 5-230 | 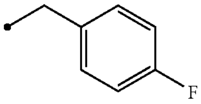 | 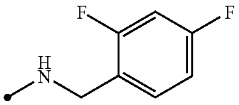 | MS m/z 551 $(M + H)^+$ |
| 5-231 | 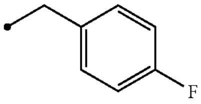 | 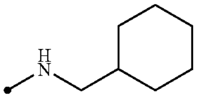 | MS m/z 521 $(M + H)^+$ |
| 5-232 | 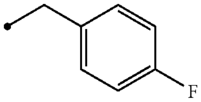 | 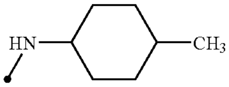 | MS m/z 521 $(M + H)^+$ |
| 5-233 | 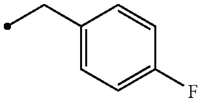 | 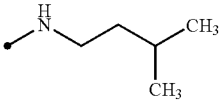 | MS m/z 495 $(M + H)^+$ |
| 5-234 | 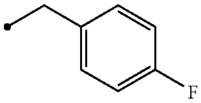 | 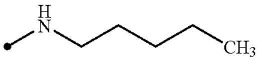 | MS m/z 495 $(M + H)^+$ |
| 5-235 | 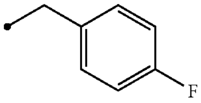 | 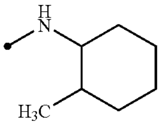 | MS m/z 521 $(M + H)^+$ |
| 5-236 | 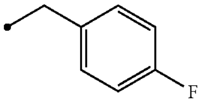 | 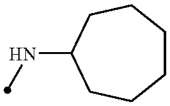 | MS m/z 521 $(M + H)^+$ |
| 5-237 | 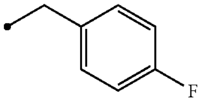 | 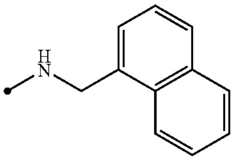 | MS m/z 565 $(M + H)^+$ |

TABLE 5-continued
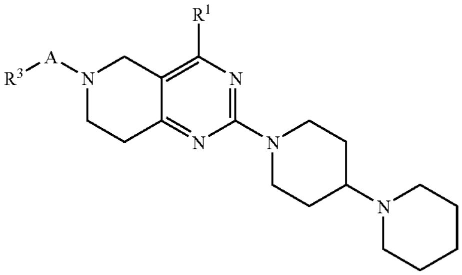
| Compound Number | •—A—$R^3$ | •—$R^1$ | Spectrum Data |
|---|---|---|---|
| 5-238 | 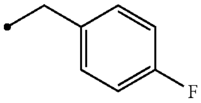 | 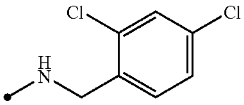 | MS m/z 583 $(M+H)^+$ |
| 5-239 | 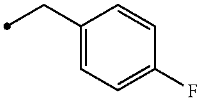 | 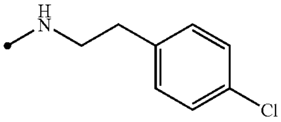 | MS m/z 563 $(M+H)^+$ |
| 5-240 | 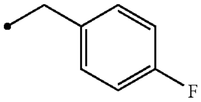 | 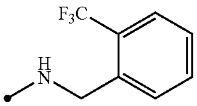 | MS m/z 583 $(M+H)^+$ |
| 5-241 | 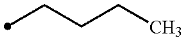 | 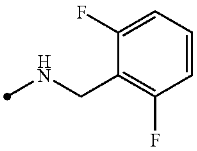 | MS m/z 499 $(M+H)^+$ |
| 5-242 | 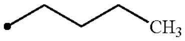 | 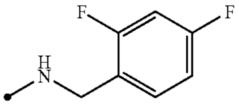 | MS m/z 499 $(M+H)^+$ |
| 5-243 | 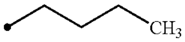 | 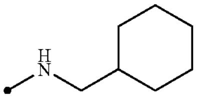 | MS m/z 469 $(M+H)^+$ |
| 5-244 | 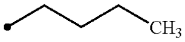 | 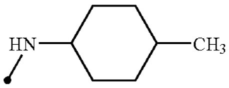 | MS m/z 469 $(M+H)^+$ |
| 5-245 | 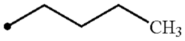 | 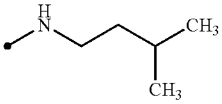 | MS m/z 443 $(M+H)^+$ |
| 5-246 | 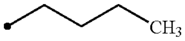 | 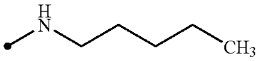 | MS m/z 443 $(M+H)^+$ |
| 5-247 | 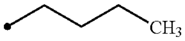 | 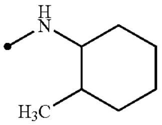 | MS m/z 469 $(M+H)^+$ |

TABLE 5-continued
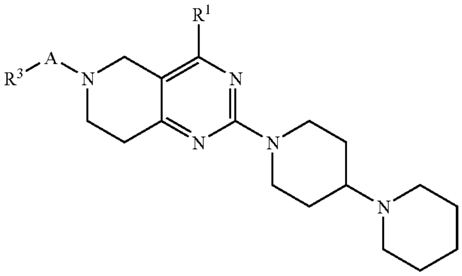
| Compound Number | •—A—$R^3$ | •—$R^1$ | Spectrum Data |
|---|---|---|---|
| 5-248 | 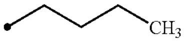 | 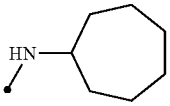 | MS m/z 469 $(M+H)^+$ |
| 5-249 | 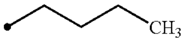 | 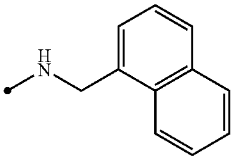 | MS m/z 513 $(M+H)^+$ |
| 5-250 | 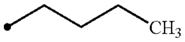 | 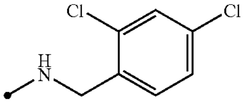 | MS m/z 531 $(M+H)^+$ |
| 5-251 | 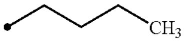 | 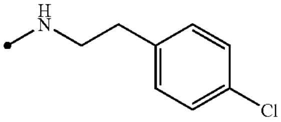 | MS m/z 511 $(M+H)^+$ |
| 5-252 | 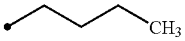 | 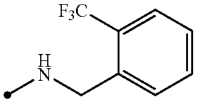 | MS m/z 531 $(M+H)^+$ |
| 5-253 | 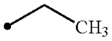 | 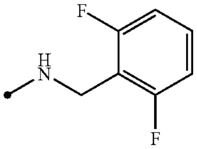 | MS m/z 471 $(M+H)^+$ |
| 5-254 | 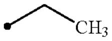 | 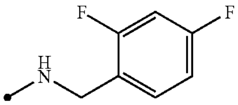 | MS m/z 471 $(M+H)^+$ |
| 5-255 | 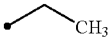 | 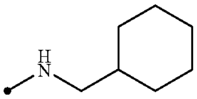 | MS m/z 441 $(M+H)^+$ |
| 5-256 | 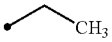 | 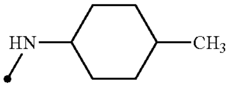 | MS m/z 441 $(M+H)^+$ |

TABLE 5-continued
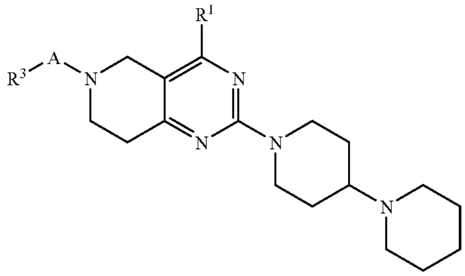
| Compound Number | •—A—$R^3$ | •—$R^1$ | Spectrum Data |
|---|---|---|---|
| 5-257 | 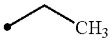 | 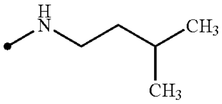 | MS m/z 415 $(M + H)^+$ |
| 5-258 | 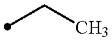 | 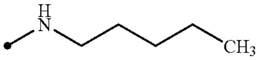 | MS m/z 415 $(M + H)^+$ |
| 5-259 | 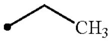 | 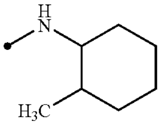 | MS m/z 441 $(M + H)^+$ |
| 5-260 | 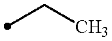 | 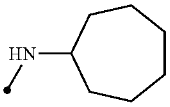 | MS m/z 441 $(M + H)^+$ |
| 5-261 | 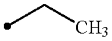 | 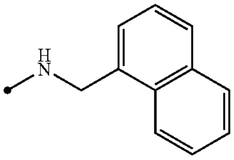 | MS m/z 485 $(M + H)^+$ |
| 5-262 | 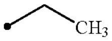 | 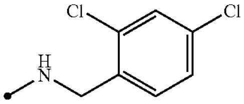 | MS m/z 503 $(M + H)^+$ |
| 5-263 | 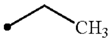 | 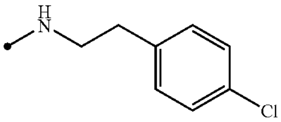 | MS m/z 483 $(M + H)^+$ |
| 5-264 | 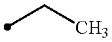 | 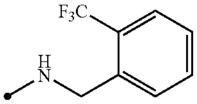 | MS m/z 503 $(M + H)^+$ |
| 5-265 | 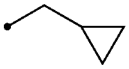 | 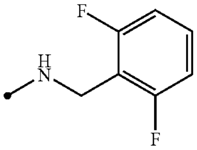 | MS m/z 497 $(M + H)^+$ |

TABLE 5-continued
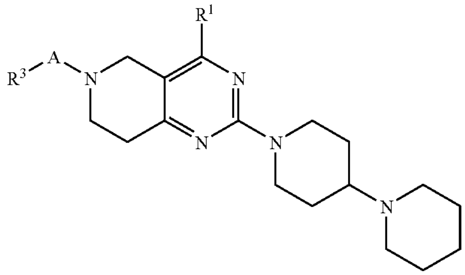
| Compound Number | •—A—$R^3$ | •—$R^1$ | Spectrum Data |
|---|---|---|---|
| 5-266 | 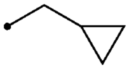 | 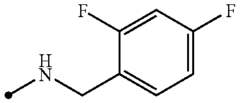 | MS m/z 497 $(M + H)^+$ |
| 5-267 | 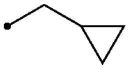 | 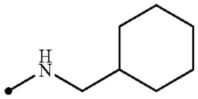 | MS m/z 467 $(M + H)^+$ |
| 5-268 | 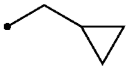 | 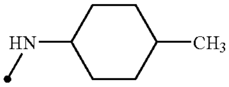 | MS m/z 467 $(M + H)^+$ |
| 5-269 | 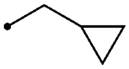 | 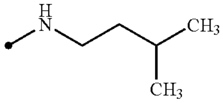 | MS m/z 441 $(M + H)^+$ |
| 5-270 | 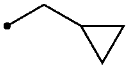 | 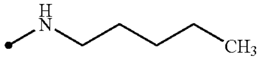 | MS m/z 441 $(M + H)^+$ |
| 5-271 | 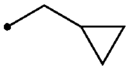 | 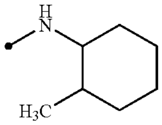 | MS m/z 467 $(M + H)^+$ |
| 5-272 | 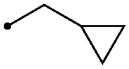 | 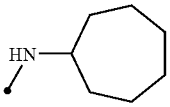 | MS m/z 467 $(M + H)^+$ |
| 5-273 | 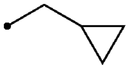 | 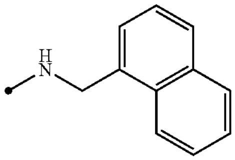 | MS m/z 511 $(M + H)^+$ |
| 5-274 | 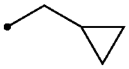 | 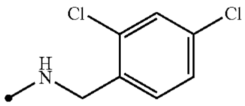 | MS m/z 529 $(M + H)^+$ |
| 5-275 | 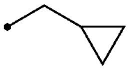 | 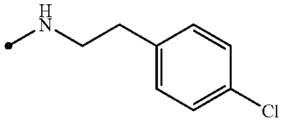 | MS m/z 509 $(M + H)^+$ |

TABLE 5-continued
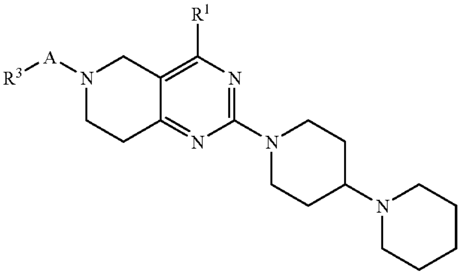
| Compound Number | •—A—$R^3$ | •—$R^1$ | Spectrum Data |
|---|---|---|---|
| 5-276 | 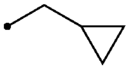 | 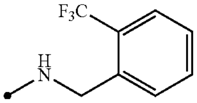 | MS m/z 529 $(M + H)^+$ |
| 5-277 | 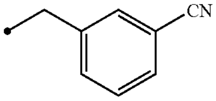 | 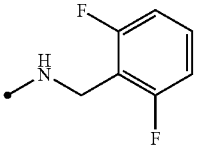 | MS m/z 558 $(M + H)^+$ |
| 5-278 | 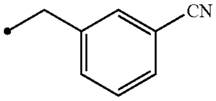 | 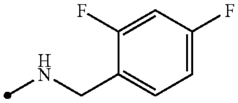 | MS m/z 558 $(M + H)^+$ |
| 5-279 | 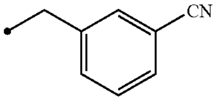 | 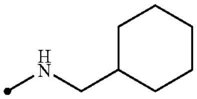 | MS m/z 528 $(M + H)^+$ |
| 5-280 | 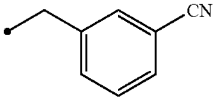 | 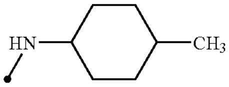 | MS m/z 528 $(M + H)^+$ |
| 5-281 | 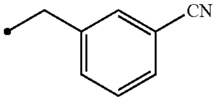 | 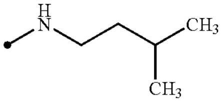 | MS m/z 502 $(M + H)^+$ |
| 5-282 | 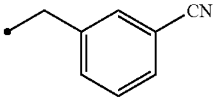 | 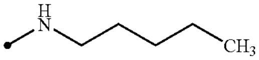 | MS m/z 502 $(M + H)^+$ |
| 5-283 | 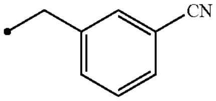 | 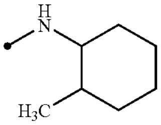 | MS m/z 528 $(M + H)^+$ |
| 5-284 | 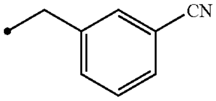 | 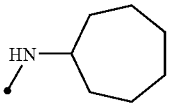 | MS m/z 528 $(M + H)^+$ |

TABLE 5-continued
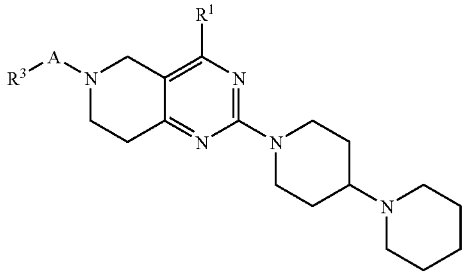
| Compound Number | •—A—$R^3$ | •—$R^1$ | Spectrum Data |
|---|---|---|---|
| 5-285 | 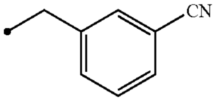 | 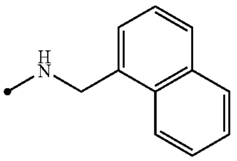 | MS m/z 572 $(M + H)^+$ |
| 5-286 | 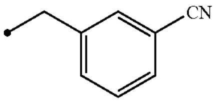 | 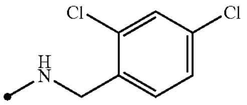 | MS m/z 590 $(M + H)^+$ |
| 5-287 | 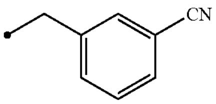 | 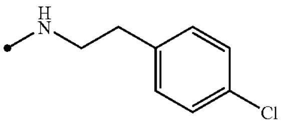 | MS m/z 570 $(M + H)^+$ |
| 5-288 | 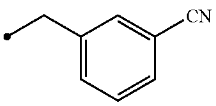 | 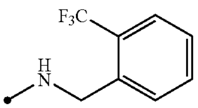 | MS m/z 590 $(M + H)^+$ |
| 5-289 | 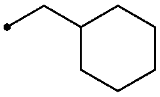 | 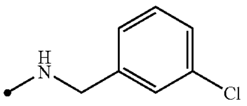 | MS m/z 537 $(M + H)^+$ |
| 5-290 | 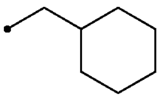 | 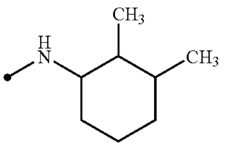 | MS m/z 523 $(M + H)^+$ |
| 5-291 | 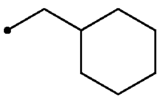 | 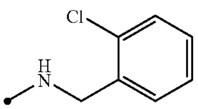 | MS m/z 537 $(M + H)^+$ |
| 5-292 | 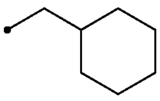 | 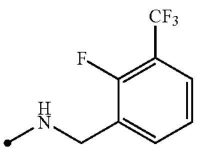 | MS m/z 589 $(M + H)^+$ |
| 5-293 | 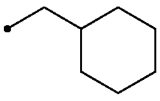 | 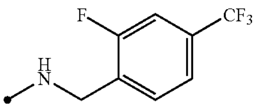 | MS m/z 589 $(M + H)^+$ |

TABLE 5-continued
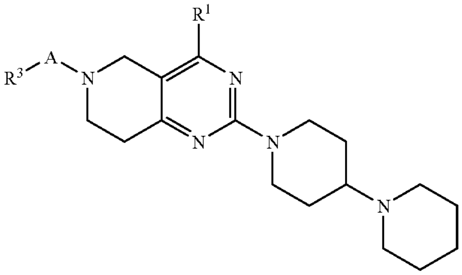
| Compound Number | •—A—$R^3$ | •—$R^1$ | Spectrum Data |
|---|---|---|---|
| 5-294 | 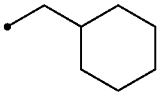 | 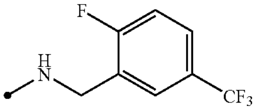 | MS m/z 589 (M + H)+ |
| 5-295 | 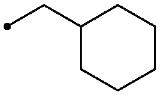 | 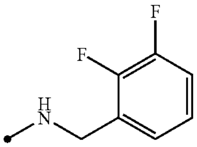 | MS m/z 539 (M + H)+ |
| 5-296 | 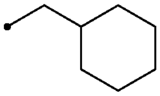 | 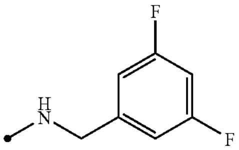 | MS m/z 539 (M + H)+ |
| 5-297 | 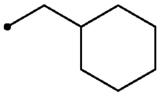 | 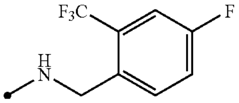 | MS m/z 589 (M + H)+ |
| 5-298 | 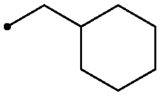 | 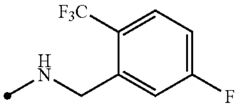 | MS m/z 589 (M + H)+ |
| 5-299 | 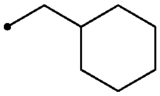 | 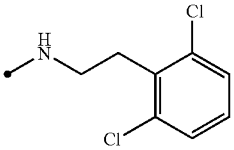 | MS m/z 585 (M + H)+ |
| 5-300 | 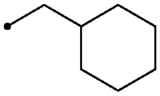 | 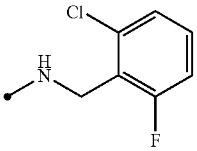 | MS m/z 585 (M + H)+ |
| 5-301 | 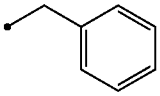 | 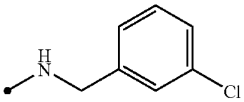 | MS m/z 531 (M + H)+ |

TABLE 5-continued
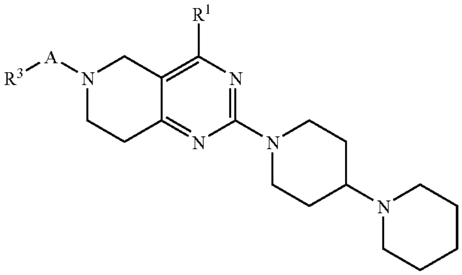
| Compound Number | •—A—$R^3$ | •—$R^1$ | Spectrum Data |
|---|---|---|---|
| 5-302 | 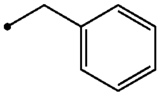 | 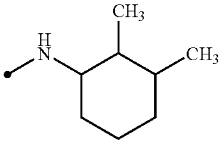 | MS m/z 517 (M + H)$^+$ |
| 5-303 | 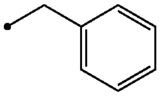 | 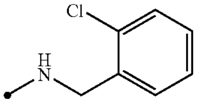 | MS m/z 531 (M + H)$^+$ |
| 5-304 | 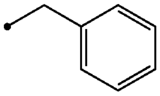 | 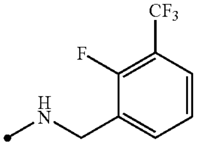 | MS m/z 583 (M + H)$^+$ |
| 5-305 | 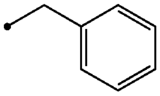 | 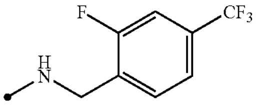 | MS m/z 583 (M + H)$^+$ |
| 5-306 | 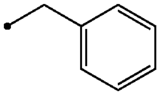 | 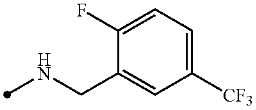 | MS m/z 583 (M + H)$^+$ |
| 5-307 | 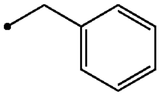 | 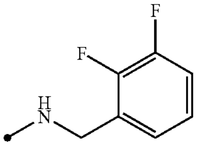 | MS m/z 533 (M + H)$^+$ |
| 5-308 | 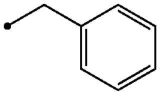 | 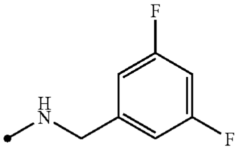 | MS m/z 533 (M + H)$^+$ |
| 5-309 | 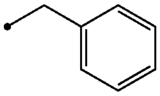 | 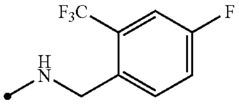 | MS m/z 583 (M + H)$^+$ |
| 5-310 | 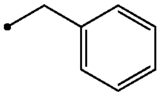 | 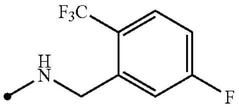 | MS m/z 583 (M + H)$^+$ |

TABLE 5-continued
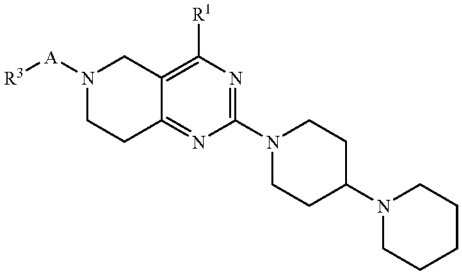
| Compound Number | •—A—$R^3$ | •—$R^1$ | Spectrum Data |
|---|---|---|---|
| 5-311 | 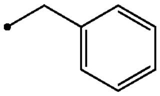 | 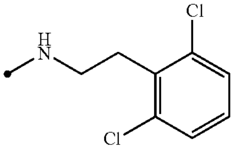 | MS m/z 579 $(M + H)^+$ |
| 5-312 | 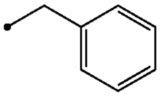 | 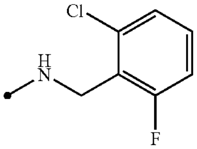 | MS m/z 549 $(M + H)^+$ |
| 5-313 | 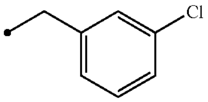 | 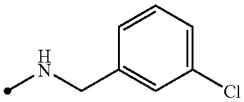 | MS m/z 565 $(M + H)^+$ |
| 5-314 | 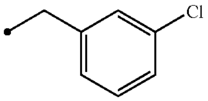 | 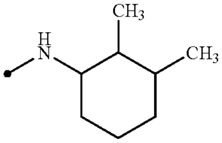 | MS m/z 551 $(M + H)^+$ |
| 5-315 | 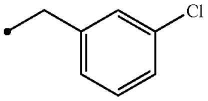 | 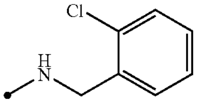 | MS m/z 565 $(M + H)^+$ |
| 5-316 | 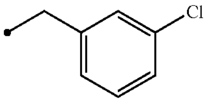 | 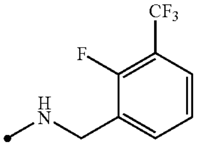 | MS m/z 617 $(M + H)^+$ |
| 5-317 | 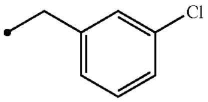 | 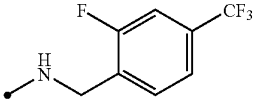 | MS m/z 617 $(M + H)^+$ |
| 5-318 | 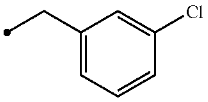 | 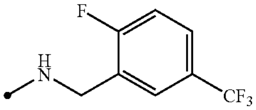 | MS m/z 617 $(M + H)^+$ |

TABLE 5-continued
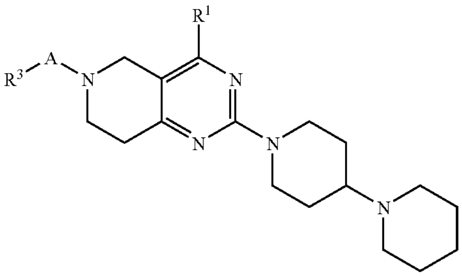
| Compound Number | •—A—R3 | •—R1 | Spectrum Data |
|---|---|---|---|
| 5-319 | 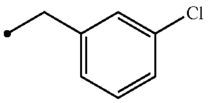 | 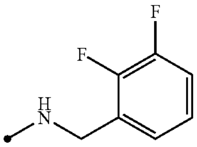 | MS m/z 567 $(M + H)^+$ |
| 5-320 | 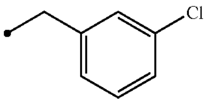 | 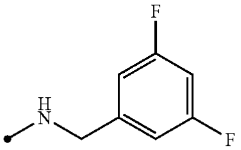 | MS m/z 567 $(M + H)^+$ |
| 5-321 | 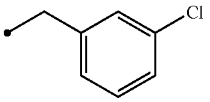 | 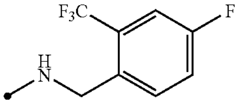 | MS m/z 617 $(M + H)^+$ |
| 5-322 | 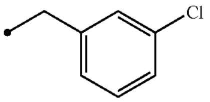 | 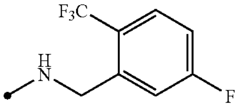 | MS m/z 617 $(M + H)^+$ |
| 5-323 | 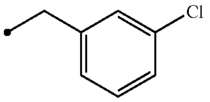 | 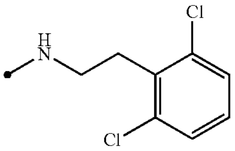 | MS m/z 613 $(M + H)^+$ |
| 5-324 | 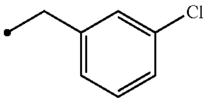 | 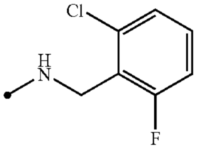 | MS m/z 583 $(M + H)^+$ |
| 5-325 | 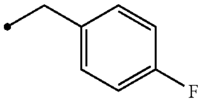 | 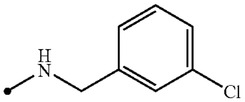 | MS m/z 549 $(M + H)^+$ |
| 5-326 | 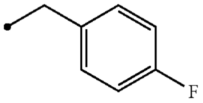 | 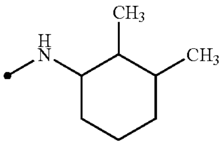 | MS m/z 535 $(M + H)^+$ |
| 5-327 | 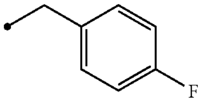 | 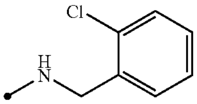 | MS m/z 549 $(M + H)^+$ |

TABLE 5-continued
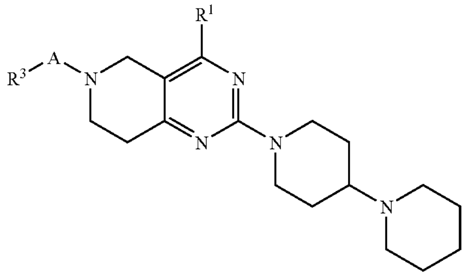
| Compound Number | •—A—$R^3$ | •—$R^1$ | Spectrum Data |
|---|---|---|---|
| 5-328 | 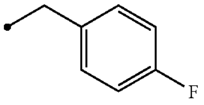 | 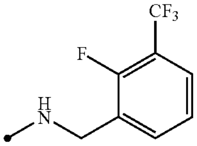 | MS m/z 601 $(M+H)^+$ |
| 5-329 | 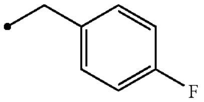 | 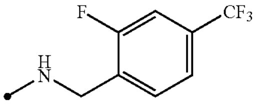 | MS m/z 601 $(M+H)^+$ |
| 5-330 | 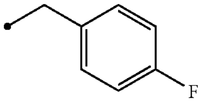 | 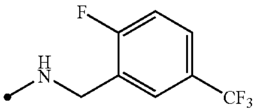 | MS m/z 601 $(M+H)^+$ |
| 5-331 | 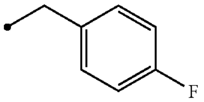 | 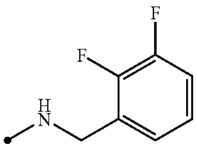 | MS m/z 551 $(M+H)^+$ |
| 5-332 | 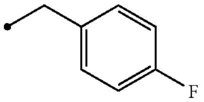 | 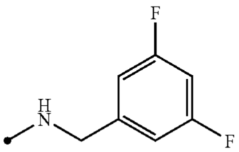 | MS m/z 551 $(M+H)^+$ |
| 5-333 | 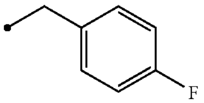 | 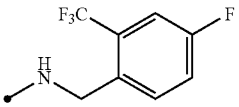 | MS m/z 601 $(M+H)^+$ |
| 5-334 | 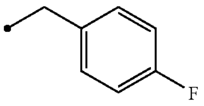 | 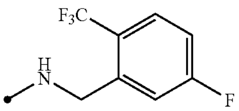 | MS m/z 601 $(M+H)^+$ |
| 5-335 | 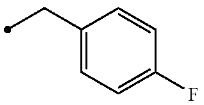 | 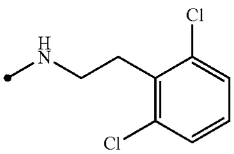 | MS m/z 597 $(M+H)^+$ |

TABLE 5-continued
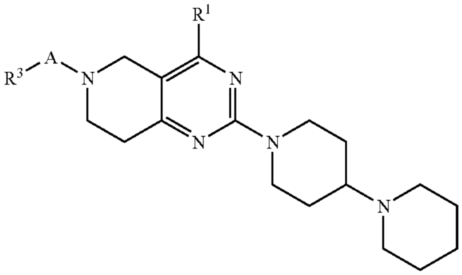
| Compound Number | •—A—$R^3$ | •—$R^1$ | Spectrum Data |
|---|---|---|---|
| 5-336 | 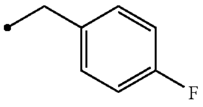 | 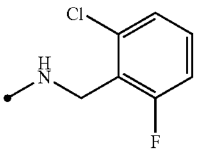 | MS m/z 567 $(M + H)^+$ |
| 5-337 | 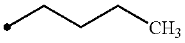 | 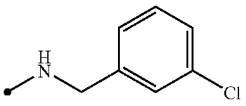 | MS m/z 497 $(M + H)^+$ |
| 5-338 | 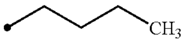 | 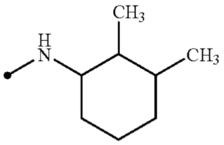 | MS m/z 483 $(M + H)^+$ |
| 5-339 | 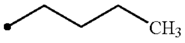 | 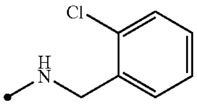 | MS m/z 497 $(M + H)^+$ |
| 5-340 | 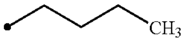 | 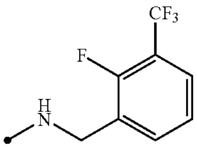 | MS m/z 549 $(M + H)^+$ |
| 5-341 | 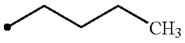 | 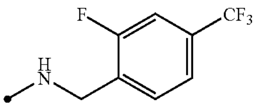 | MS m/z 549 $(M + H)^+$ |
| 5-342 | 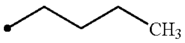 | 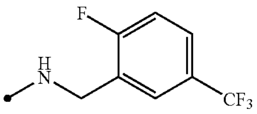 | MS m/z 549 $(M + H)^+$ |
| 5-343 | 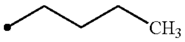 | 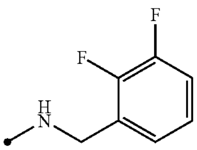 | MS m/z 499 $(M + H)^+$ |

TABLE 5-continued
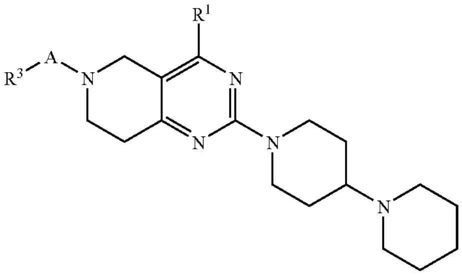
| Compound Number | •—A—$R^3$ | •—$R^1$ | Spectrum Data |
|---|---|---|---|
| 5-344 | 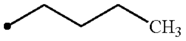 | 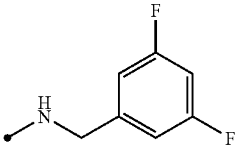 | MS m/z 499 $(M + H)^+$ |
| 5-345 | 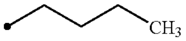 | 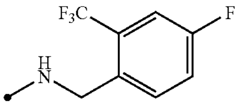 | MS m/z 549 $(M + H)^+$ |
| 5-346 | 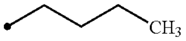 | 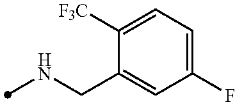 | MS m/z 549 $(M + H)^+$ |
| 5-347 | 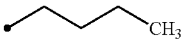 | 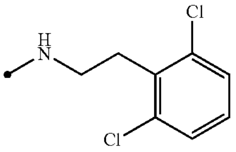 | MS m/z 545 $(M + H)^+$ |
| 5-348 | 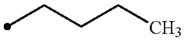 | 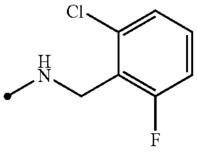 | MS m/z 515 $(M + H)^+$ |
| 5-349 | 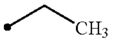 | 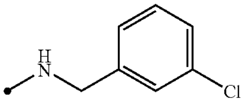 | MS m/z 469 $(M + H)^+$ |
| 5-350 | 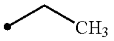 | 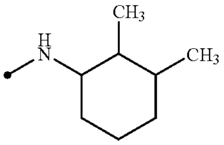 | MS m/z 455 $(M + H)^+$ |
| 5-351 | 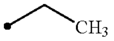 | 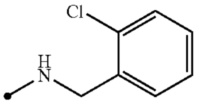 | MS m/z 469 $(M + H)^+$ |
| 5-352 | 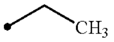 | 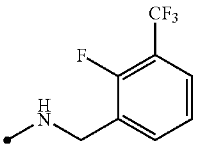 | MS m/z 521 $(M + H)^+$ |

TABLE 5-continued
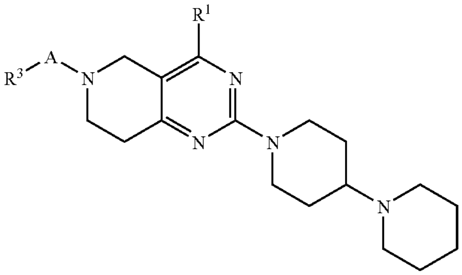
| Compound Number | •—A—$R^3$ | •—$R^1$ | Spectrum Data |
|---|---|---|---|
| 5-353 | 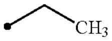 | 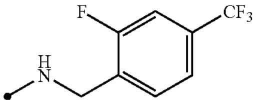 | MS m/z 521 $(M + H)^+$ |
| 5-354 | 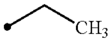 | 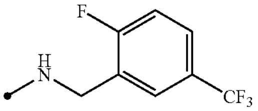 | MS m/z 521 $(M + H)^+$ |
| 5-355 | 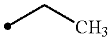 | 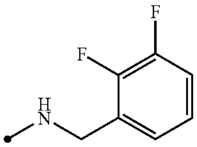 | MS m/z 471 $(M + H)^+$ |
| 5-356 | 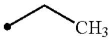 | 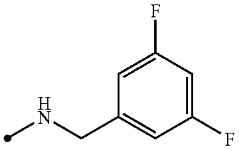 | MS m/z 471 $(M + H)^+$ |
| 5-357 | 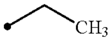 | 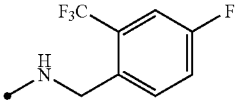 | MS m/z 521 $(M + H)^+$ |
| 5-358 | 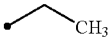 | 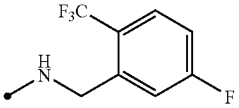 | MS m/z 521 $(M + H)^+$ |
| 5-359 | 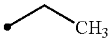 | 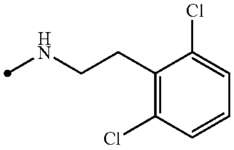 | MS m/z 517 $(M + H)^+$ |
| 5-360 | 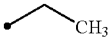 | 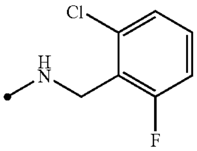 | MS m/z 487 $(M + H)^+$ |
| 5-361 | 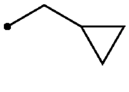 | 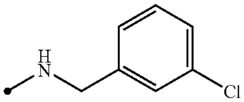 | MS m/z 495 $(M + H)^+$ |

TABLE 5-continued
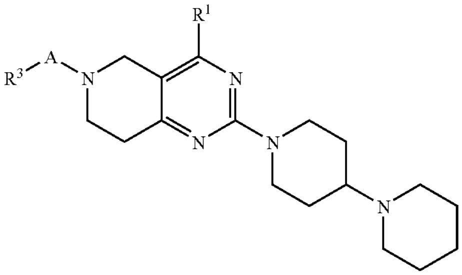
| Compound Number | •—A—$R^3$ | •—$R^1$ | Spectrum Data |
|---|---|---|---|
| 5-362 | 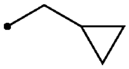 | 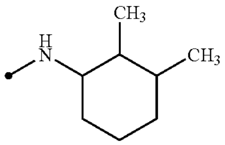 | MS m/z 481 $(M + H)^+$ |
| 5-363 | 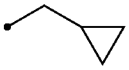 | 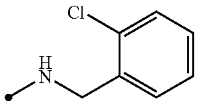 | MS m/z 495 $(M + H)^+$ |
| 5-364 | 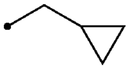 | 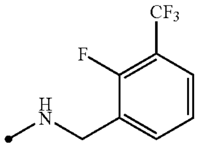 | MS m/z 547 $(M + H)^+$ |
| 5-365 | 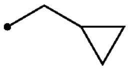 | 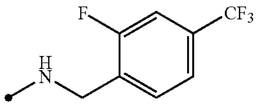 | MS m/z 547 $(M + H)^+$ |
| 5-366 | 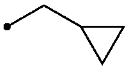 | 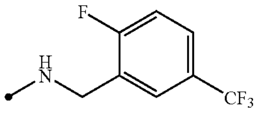 | MS m/z 547 $(M + H)^+$ |
| 5-367 | 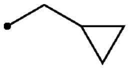 | 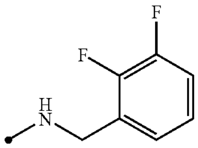 | MS m/z 497 $(M + H)^+$ |
| 5-368 | 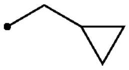 | 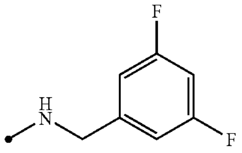 | MS m/z 497 $(M + H)^+$ |
| 5-369 | 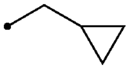 | 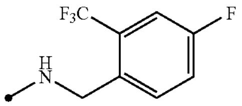 | MS m/z 547 $(M + H)^+$ |
| 5-370 | 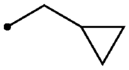 | 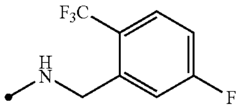 | MS m/z 547 $(M + H)^+$ |

TABLE 5-continued
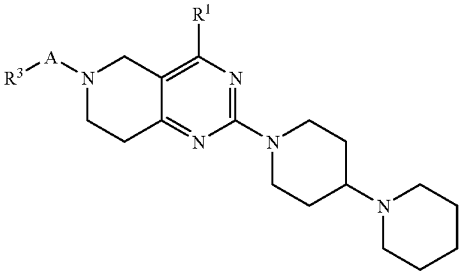
| Compound Number | •—A—$R^3$ | •—$R^1$ | Spectrum Data |
|---|---|---|---|
| 5-371 | 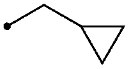 | 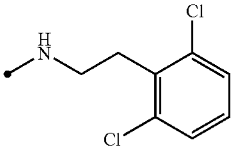 | MS m/z 543 $(M + H)^+$ |
| 5-372 | 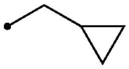 | 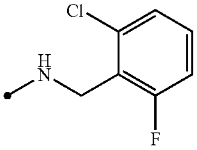 | MS m/z 513 $(M + H)^+$ |
| 5-373 | 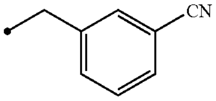 | 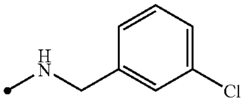 | MS m/z 556 $(M + H)^+$ |
| 5-374 | 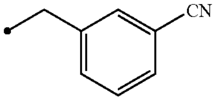 | 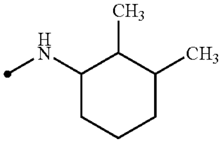 | MS m/z 542 $(M + H)^+$ |
| 5-375 | 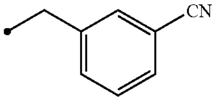 | 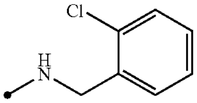 | MS m/z 556 $(M + H)^+$ |
| 5-376 | 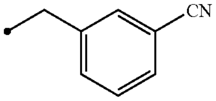 | 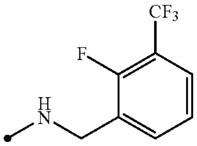 | MS m/z 608 $(M + H)^+$ |
| 5-377 | 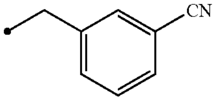 | 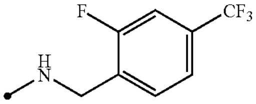 | MS m/z 608 $(M + H)^+$ |
| 5-378 | 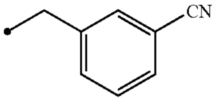 | 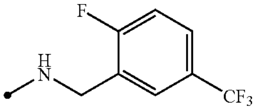 | MS m/z 608 $(M + H)^+$ |

TABLE 5-continued
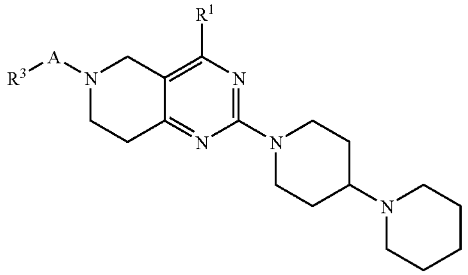
| Compound Number | •—A—$R^3$ | •—$R^1$ | Spectrum Data |
|---|---|---|---|
| 5-379 | 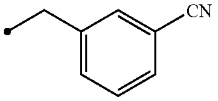 | 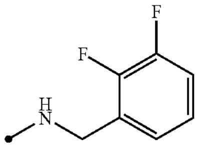 | MS m/z 558 $(M + H)^+$ |
| 5-380 | 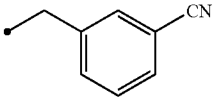 | 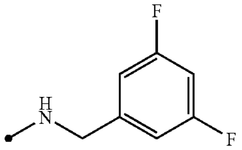 | MS m/z 558 $(M + H)^+$ |
| 5-381 | 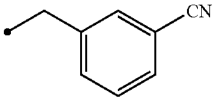 | 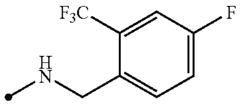 | MS m/z 608 $(M + H)^+$ |
| 5-382 | 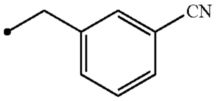 | 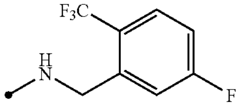 | MS m/z 608 $(M + H)^+$ |
| 5-383 | 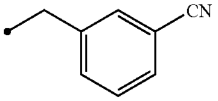 | 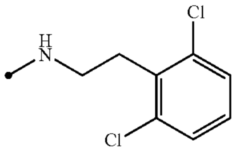 | MS m/z 604 $(M + H)^+$ |
| 5-384 | 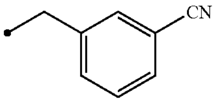 | 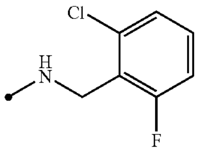 | MS m/z 574 $(M + H)^+$ |
| 5-385 | 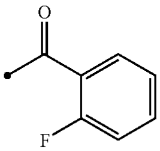 | 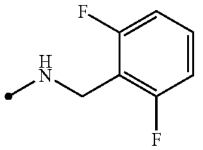 | MS m/z 565 $(M + H)^+$ |
| 5-386 | 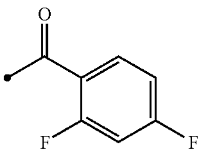 | 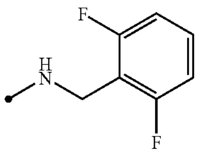 | MS m/z 583 $(M + H)^+$ |

TABLE 5-continued
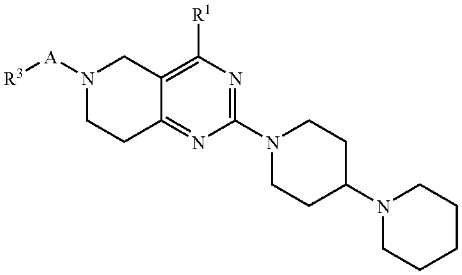
| Compound Number | •—A—R$^3$ | •—R$^1$ | Spectrum Data |
|---|---|---|---|
| 5-387 | 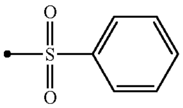 | 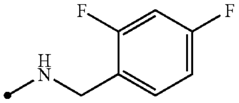 | MS m/z 583 (M + H)$^+$ |
| 5-388 | 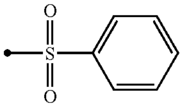 | 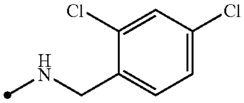 | MS m/z 615 (M + H)$^+$ |
| 5-389 | 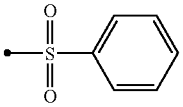 | 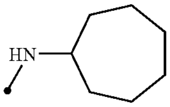 | MS m/z 553 (M + H)$^+$ |
| 5-390 | 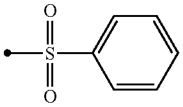 | 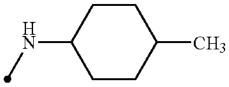 | MS m/z 553 (M + H)$^+$ |
| 5-391 | 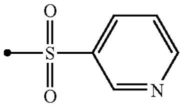 | 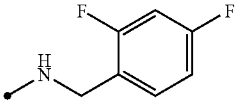 | MS m/z 584 (M + H)$^+$ |
| 5-392 | 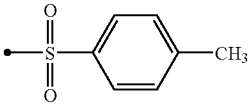 | 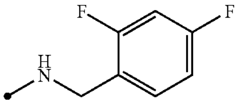 | MS m/z 597 (M + H)$^+$ |
| 5-393 | 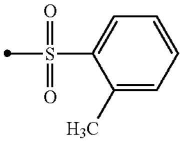 | 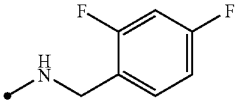 | MS m/z 597 (M + H)$^+$ |
| 5-394 | 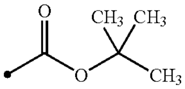 | 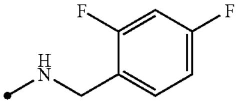 | MS m/z 543 (M + H)$^+$ |
| 5-395 | •—H | 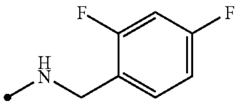 | MS m/z 443 (M + H)$^+$ |
| 5-396 | 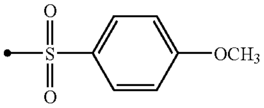 | 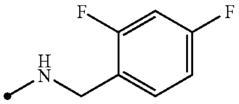 | MS m/z 613 (M + H)$^+$ |

TABLE 5-continued
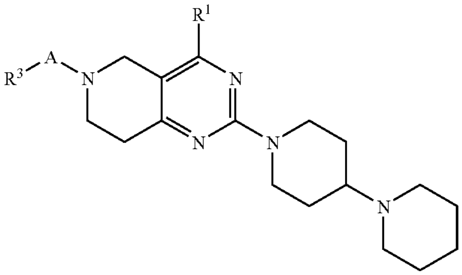
| Compound Number | •—A—$R^3$ | •—$R^1$ | Spectrum Data |
|---|---|---|---|
| 5-397 | 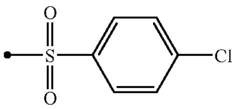 | 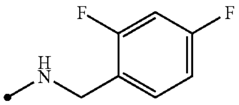 | MS m/z 617 $(M + H)^+$ |
| 5-398 | 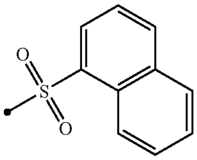 | 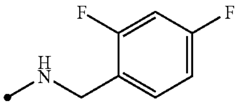 | MS m/z 633 $(M + H)^+$ |
| 5-399 | 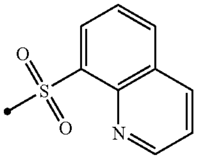 | 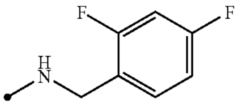 | MS m/z 634 $(M + H)^+$ |
| 5-400 | 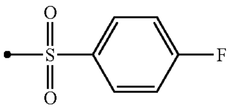 | 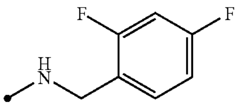 | MS m/z 601 $(M + H)^+$ |
| 5-401 | 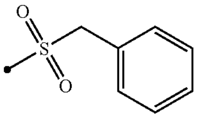 | 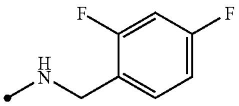 | MS m/z 597 $(M + H)^+$ |
| 5-402 | 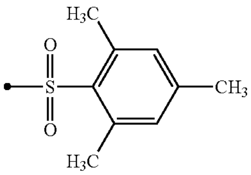 | 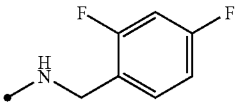 | MS m/z 625 $(M + H)^+$ |
| 5-403 | 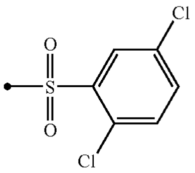 | 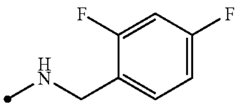 | MS m/z 651 $(M + H)^+$ |
| 5-404 | 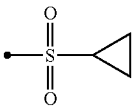 | 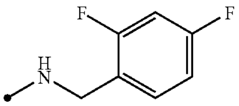 | MS m/z 547 $(M + H)^+$ |

TABLE 5-continued
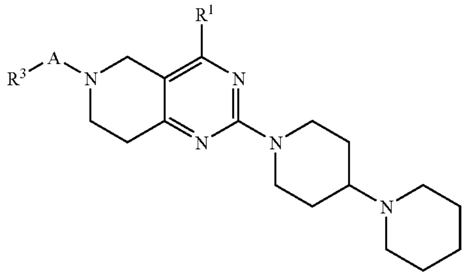
| Compound Number | •—A—$R^3$ | •—$R^1$ | Spectrum Data |
|---|---|---|---|
| 5-405 | 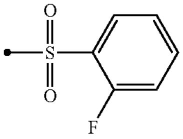 | 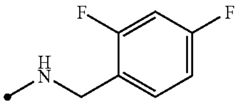 | MS m/z 601 $(M + H)^+$ |
| 5-406 | 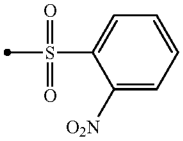 | 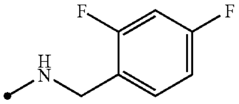 | MS m/z 628 $(M + H)^+$ |
| 5-407 | 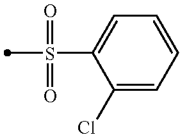 | 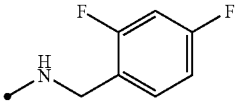 | MS m/z 617 $(M + H)^+$ |
| 5-408 | 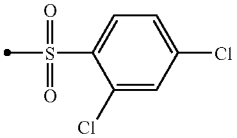 | 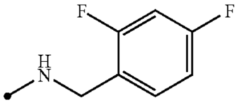 | MS m/z 651 $(M + H)^+$ |
| 5-409 | 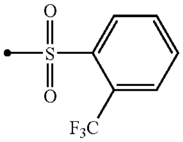 | 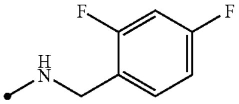 | MS m/z 651 $(M + H)^+$ |
| 5-410 | 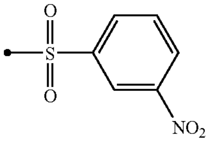 | 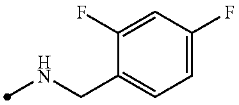 | MS m/z 628 $(M + H)^+$ |
| 5-411 | 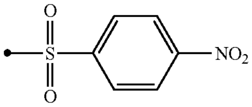 | 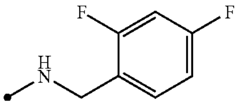 | MS m/z 628 $(M + H)^+$ |
| 5-412 | 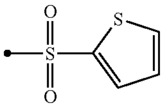 | 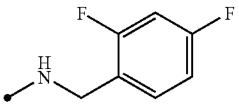 | MS m/z 589 $(M + H)^+$ |

TABLE 5-continued
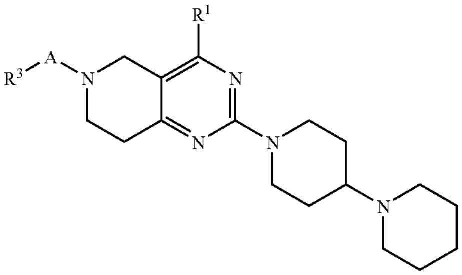
| Compound Number | •—A—$R^3$ | •—$R^1$ | Spectrum Data |
|---|---|---|---|
| 5-413 | 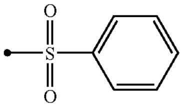 | 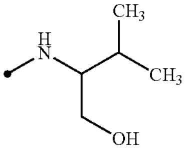 | MS m/z 543 $(M + H)^+$ |
| 5-414 | 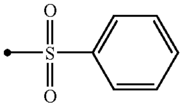 | 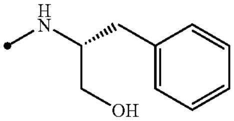 | MS m/z 591 $(M + H)^+$ |
| 5-415 | 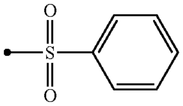 | 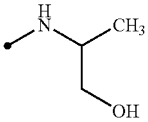 | MS m/z 515 $(M + H)^+$ |
| 5-416 | 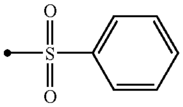 | 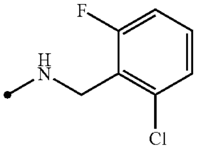 | MS m/z 599 $(M + H)^+$ |
| 5-417 | 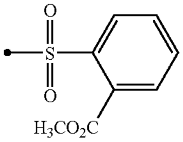 | 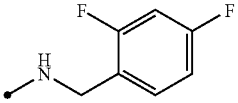 | MS m/z 641 $(M + H)^+$ |
| 5-418 | 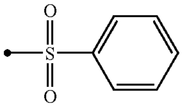 | 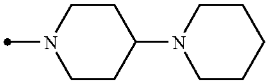 | MS m/z 608 $(M + H)^+$ |
| 5-419 | 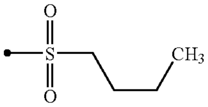 | 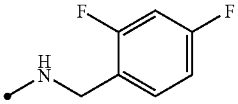 | MS m/z 563 $(M + H)^+$ |
| 5-420 | 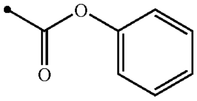 | 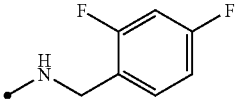 | MS m/z 563 $(M + H)^+$ |
| 5-421 | 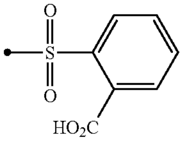 | 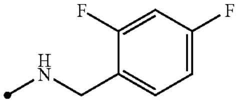 | MS m/z 627 $(M + H)^+$ |

TABLE 5-continued
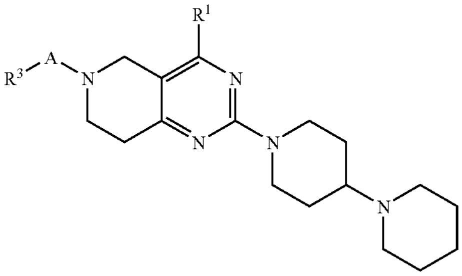
| Compound Number | •—A—$R^3$ | •—$R^1$ | Spectrum Data |
|---|---|---|---|
| 5-422 | 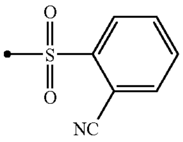 | 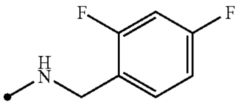 | MS m/z 608 $(M + H)^+$ |
| 5-423 | 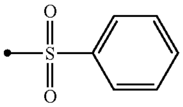 | 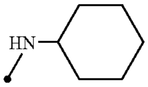 | MS m/z 539 $(M + H)^+$ |
| 5-424 | 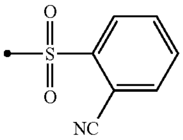 | 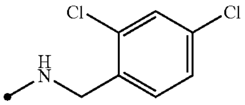 | MS m/z 649 $(M + H)^+$ |
| 5-425 | 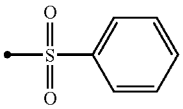 | 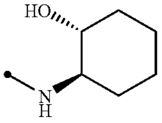 | MS m/z 555 $(M + H)^+$ |
| 5-426 | 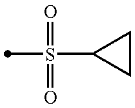 | 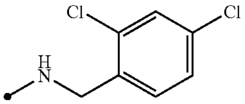 | MS m/z 579 $(M + H)^+$ |
| 5-427 | 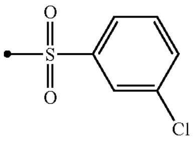 | 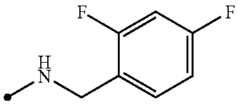 | MS m/z 617 $(M + H)^+$ |
| 5-428 | 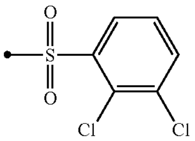 | 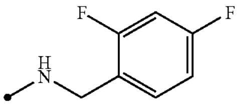 | MS m/z 651 $(M + H)^+$ |
| 5-429 | 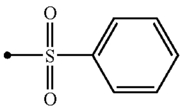 | 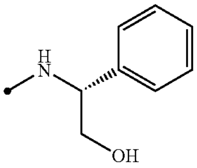 | MS m/z 577 $(M + H)^+$ |

TABLE 5-continued
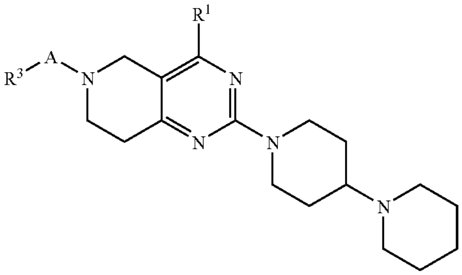
| Compound Number | •—A—$R^3$ | •—$R^1$ | Spectrum Data |
|---|---|---|---|
| 5-430 | 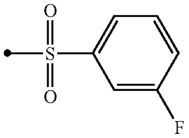 | 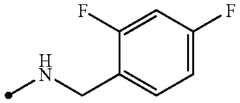 | MS m/z 601 $(M + H)^+$ |
| 5-431 | 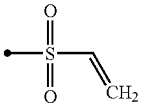 | 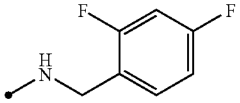 | MS m/z 533 $(M + H)^+$ |
| 5-432 | 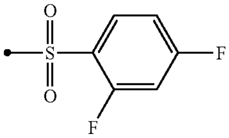 | 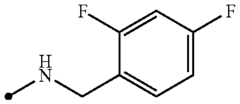 | MS m/z 619 $(M + H)^+$ |
| 5-433 | 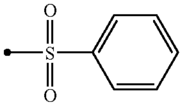 | 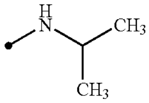 | MS m/z 499 $(M + H)^+$ |
| 5-434 | 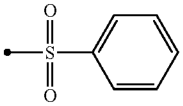 | 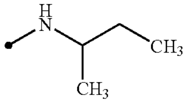 | MS m/z 513 $(M + H)^+$ |
| 5-435 | 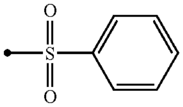 | 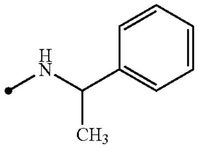 | MS m/z 561 $(M + H)^+$ |
| 5-436 | 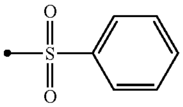 | 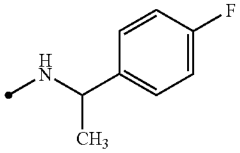 | MS m/z 579 $(M + H)^+$ |
| 5-437 | 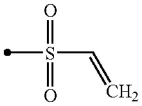 | 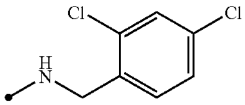 | MS m/z 565 $(M + H)^+$ |
| 5-438 | 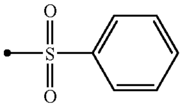 | 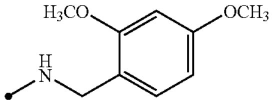 | MS m/z 607 $(M + H)^+$ |

TABLE 5-continued
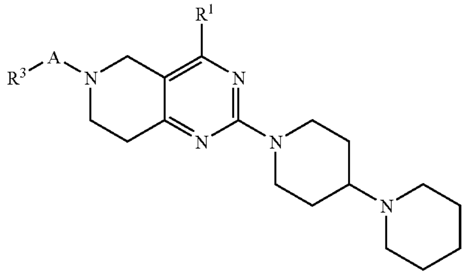
| Compound Number | •—A—$R^3$ | •—$R^1$ | Spectrum Data |
|---|---|---|---|
| 5-439 | 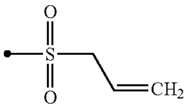 | 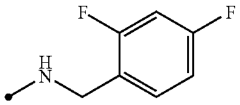 | MS m/z 547 $(M + H)^+$ |
| 5-440 | 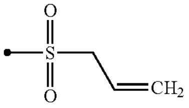 | 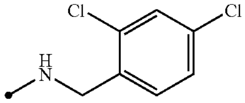 | MS m/z 579 $(M + H)^+$ |
| 5-441 | 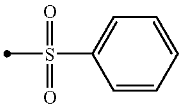 | 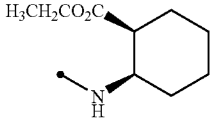 | MS m/z 611 $(M + H)^+$ |
| 5-442 | 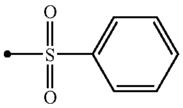 | 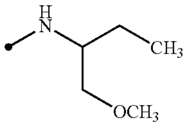 | MS m/z 543 $(M + H)^+$ |
| 5-443 | 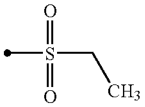 | 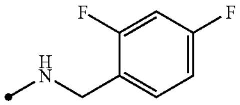 | MS m/z 535 $(M + H)^+$ |
| 5-444 | 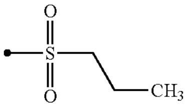 | 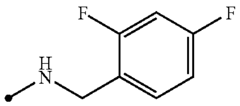 | MS m/z 549 $(M + H)^+$ |
| 5-445 | 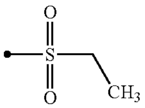 | 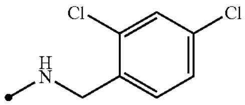 | MS m/z 567 $(M + H)^+$ |
| 5-446 | 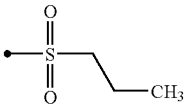 | 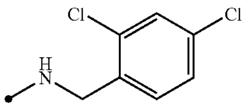 | MS m/z 581 $(M + H)^+$ |
| 5-447 | 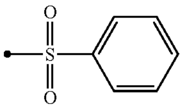 | 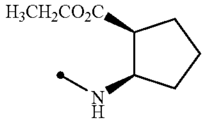 | MS m/z 597 $(M + H)^+$ |

TABLE 5-continued
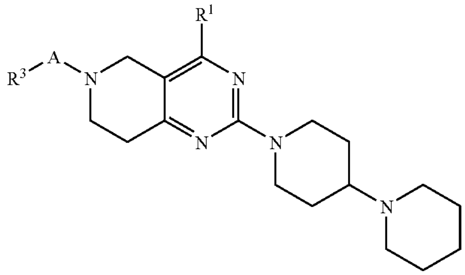
| Compound Number | •—A—$R^3$ | •—$R^1$ | Spectrum Data |
|---|---|---|---|
| 5-448 | 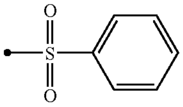 | 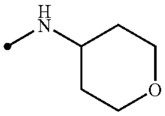 | MS m/z 541 $(M + H)^+$ |
| 5-449 | 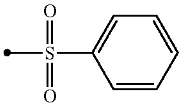 | 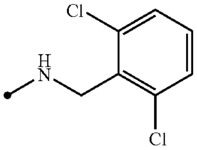 | MS m/z 615 $(M + H)^+$ |
| 5-450 | 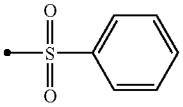 | 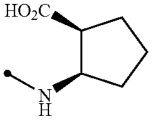 | MS m/z 569 $(M + H)^+$ |
| 5-451 | 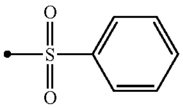 | 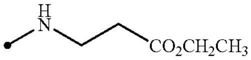 | MS m/z 557 $(M + H)^+$ |
| 5-452 | 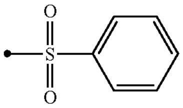 | 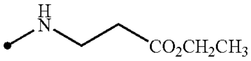 | MS m/z 571 $(M + H)^+$ |
| 5-453 | 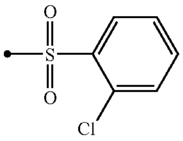 | 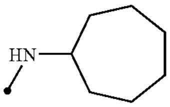 | MS m/z 588 $(M + H)^+$ |
| 5-454 | 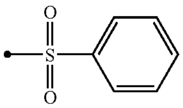 | 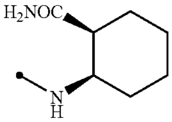 | MS m/z 582 $(M + H)^+$ |
| 5-455 | 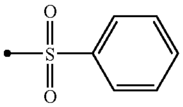 | 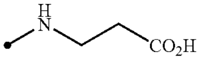 | MS m/z 529 $(M + H)^+$ |
| 5-456 | 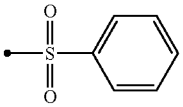 | 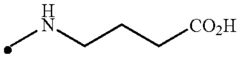 | MS m/z 543 $(M + H)^+$ |

TABLE 5-continued
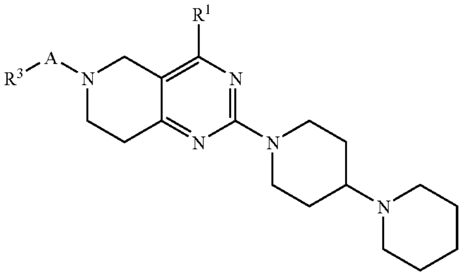
| Compound Number | •—A—$R^3$ | •—$R^1$ | Spectrum Data |
|---|---|---|---|
| 5-457 | 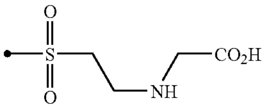 | 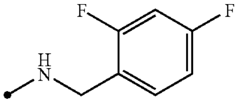 | MS m/z 608 $(M + H)^+$ |
| 5-458 | 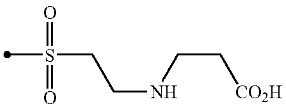 | 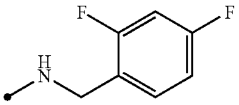 | MS m/z 621 $(M + H)^+$ |
TABLE 6
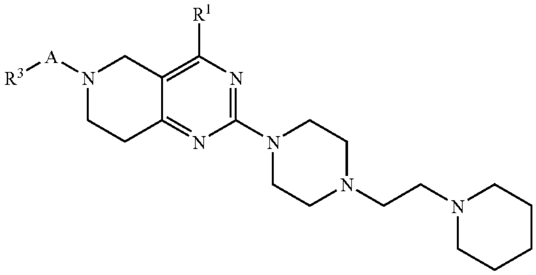
| Compound Number | •—A—$R^3$ | •—$R^1$ | Spectrum Data |
|---|---|---|---|
| 6-1 | 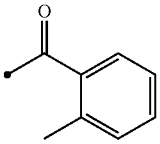 | 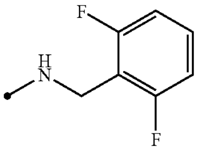 | MS m/z 594 $(M + H)^+$ |
| 6-2 | 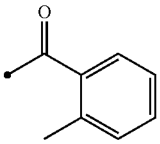 | 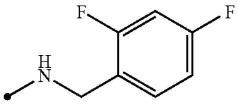 | MS m/z 594 $(M + H)^+$ |
| 6-3 | 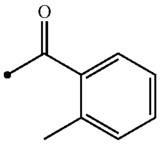 | 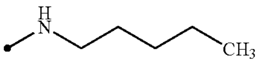 | MS m/z 538 $(M + H)^+$ |

TABLE 6-continued
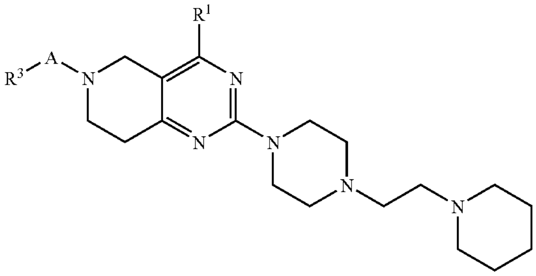
| Compound Number | •—A—$R^3$ | •—$R^1$ | Spectrum Data |
|---|---|---|---|
| 6-4 | 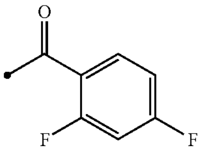 | 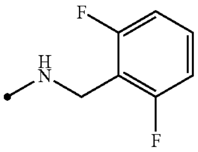 | MS m/z 612 $(M + H)^+$ |
| 6-5 | 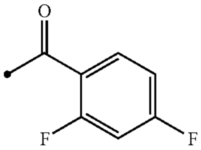 | 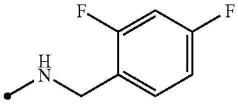 | MS m/z 612 $(M + H)^+$ |
| 6-6 | 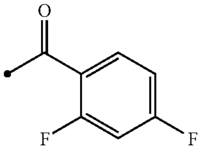 | 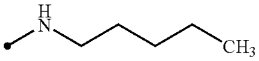 | MS m/z 556 $(M + H)^+$ |
| 6-7 | 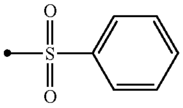 | 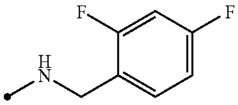 | MS m/z 612 $(M + H)^+$ |
| 6-8 | 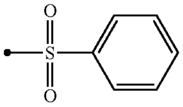 | 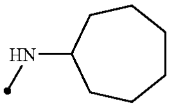 | MS m/z 582 $(M + H)^+$ |
| 6-9 | •—H | 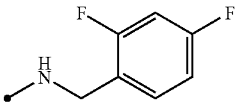 | MS m/z 472 $(M + H)^+$ |
| 6-10 | 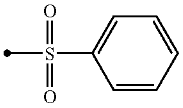 | 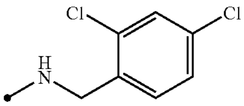 | MS m/z 644 $(M + H)^+$ |
| 6-11 | 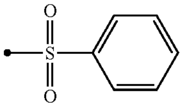 | 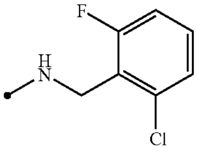 | MS m/z 628 $(M + H)^+$ |

TABLE 6-continued
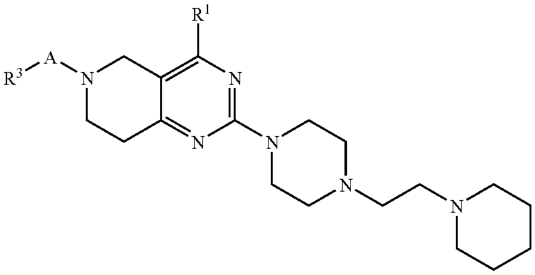
| Compound Number | •—A—$R^3$ | •—$R^1$ | Spectrum Data |
|---|---|---|---|
| 6-12 | 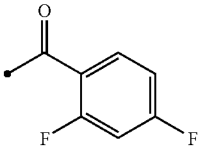 | 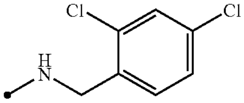 | MS m/z 678 $(M + H)^+$ |
| 6-13 | 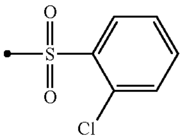 | 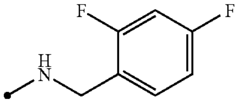 | MS m/z 646 $(M + H)^+$ |
| 6-14 | 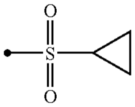 | 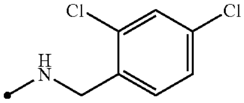 | MS m/z 608 $(M + H)^+$ |
| 6-15 | 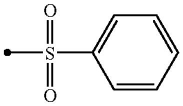 | 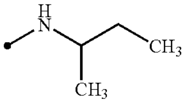 | MS m/z 528 $(M + H)^+$ |
| 6-16 | 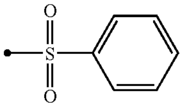 | 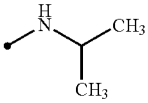 | MS m/z 542 $(M + H)^+$ |
| 6-17 | 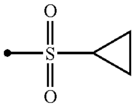 | 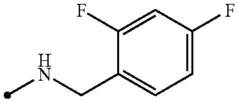 | MS m/z 576 $(M + H)^+$ |
| 6-18 | 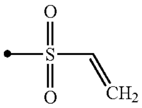 | 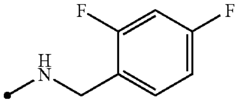 | MS m/z 562 $(M + H)^+$ |
| 6-19 | 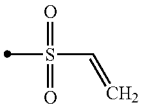 | 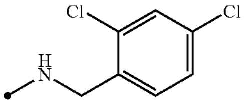 | MS m/z 594 $(M + H)^+$ |
| 6-20 | 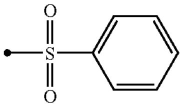 | 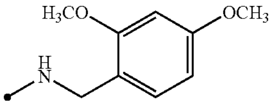 | MS m/z 636 $(M + H)^+$ |

TABLE 6-continued
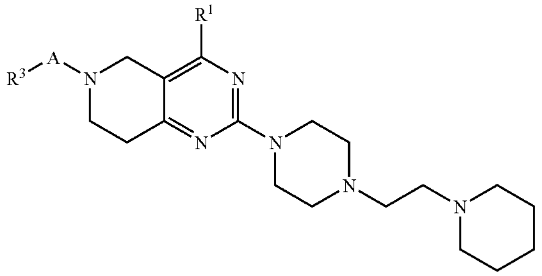
| Compound Number | •—A—$R^3$ | •—$R^1$ | Spectrum Data |
|---|---|---|---|
| 6-21 | •—H | 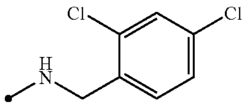 | MS m/z 504 $(M + H)^+$ |
| 6-22 | 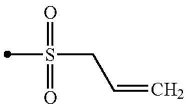 | 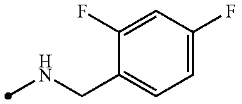 | MS m/z 576 $(M + H)^+$ |
| 6-23 | 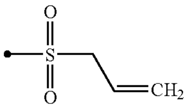 | 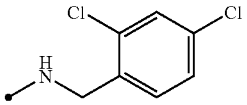 | MS m/z 608 $(M + H)^+$ |
| 6-24 | 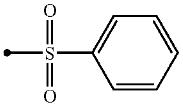 | 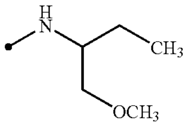 | MS m/z 572 $(M + H)^+$ |
| 6-25 | 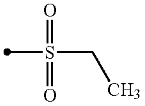 | 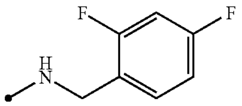 | MS m/z 564 $(M + H)^+$ |
| 6-26 | 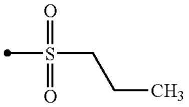 | 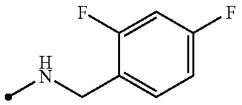 | MS m/z 578 $(M + H)^+$ |
| 6-27 | 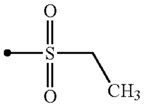 | 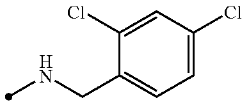 | MS m/z 596 $(M + H)^+$ |
| 6-28 | 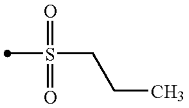 | 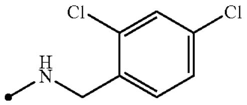 | MS m/z 610 $(M + H)^+$ |
| 6-29 | 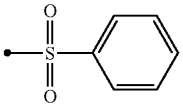 | 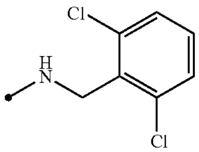 | MS m/z 644 $(M + H)^+$ |
| 6-30 | 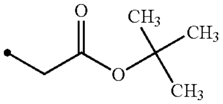 | 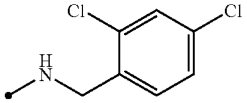 | MS m/z 618 $(M + H)^+$ |

TABLE 6-continued
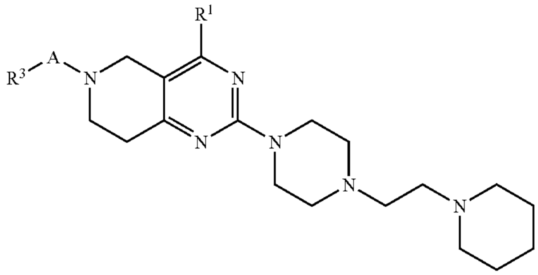
| Compound Number | •—A—$R^3$ | •—$R^1$ | Spectrum Data |
|---|---|---|---|
| 6-31 | 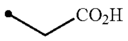 | 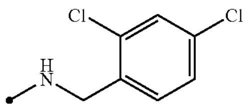 | MS m/z 562 $(M + H)^+$ |
| 6-32 | 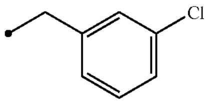 | 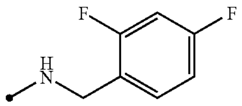 | MS m/z 596 $(M + H)^+$ |
| 6-33 | 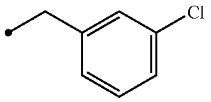 | 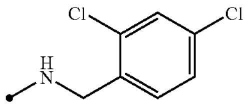 | MS m/z 628 $(M + H)^+$ |
| 6-34 | 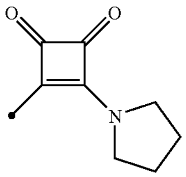 | 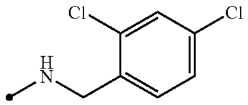 | MS m/z 653 $(M + H)^+$ |
| 6-35 | 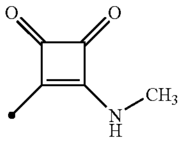 | 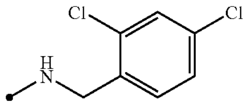 | MS m/z 613 $(M + H)^+$ |
| 6-36 | 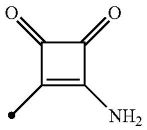 | 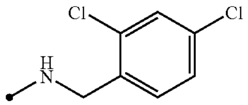 | MS m/z 599 $(M + H)^+$ |
| 6-37 | 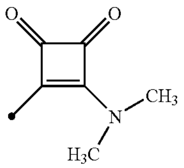 | 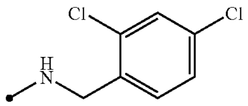 | MS m/z 627 $(M + H)^+$ |

TABLE 7
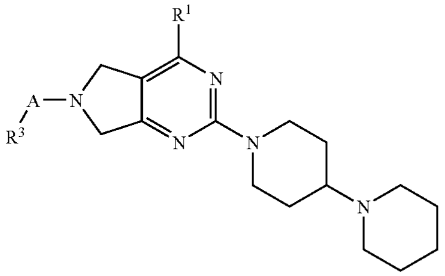
| Compound Number | •—A—$R^3$ | •—$R^1$ | Spectrum Data |
|---|---|---|---|
| 7-1 | 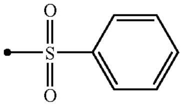 | 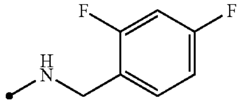 | MS m/z 597 $(M + H)^+$ |
TABLE 8
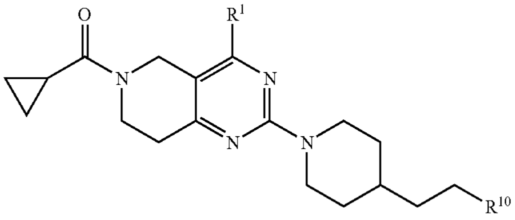
| Compound Number | •—$R^1$ | •—$R^{10}$ | Spectrum Data |
|---|---|---|---|
| 8-1 | 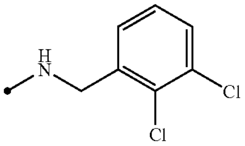 | 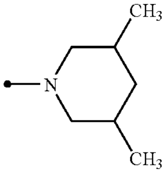 | MS m/z 599 $(M + H)^+$ |
| 8-2 | 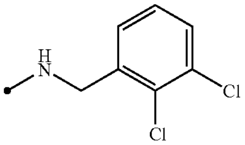 | 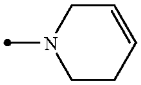 | MS m/z 569 $(M + H)^+$ |
| 8-3 | 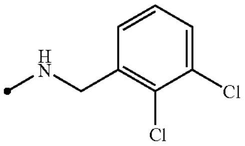 | 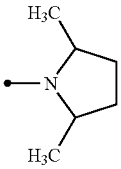 | MS m/z 585 $(M + H)^+$ |
| 8-4 | 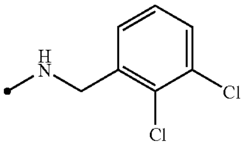 | 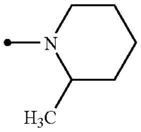 | MS m/z 585 $(M + H)^+$ |

TABLE 8-continued
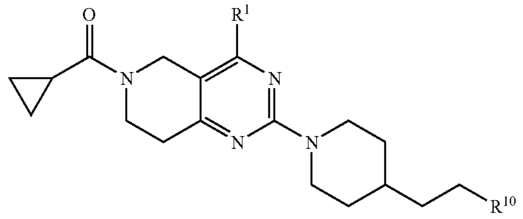
| Compound Number | •—$R^1$ | •—$R^{10}$ | Spectrum Data |
|---|---|---|---|
| 8-5 | 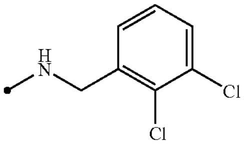 | 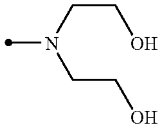 | MS m/z 591 $(M + H)^+$ |
| 8-6 | 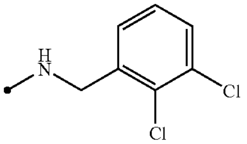 | 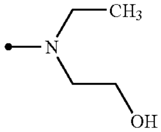 | MS m/z 575 $(M + H)^+$ |
| 8-7 | 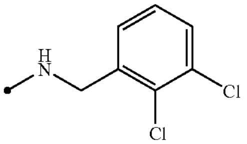 | 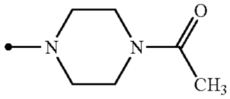 | MS m/z 614 $(M + H)^+$ |
| 8-8 | 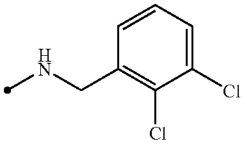 | 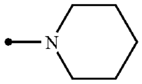 | MS m/z 571 $(M + H)^+$ |
| 8-9 | 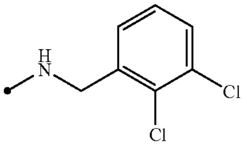 | 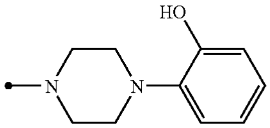 | MS m/z 664 $(M + H)^+$ |
| 8-10 | 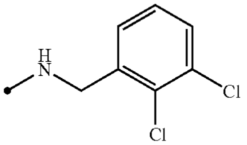 | 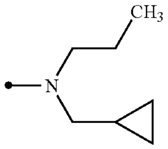 | MS m/z 599 $(M + H)^+$ |
| 8-11 | 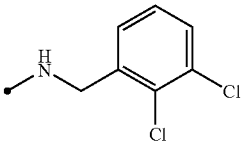 | 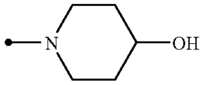 | MS m/z 587 $(M + H)^+$ |
| 8-12 | 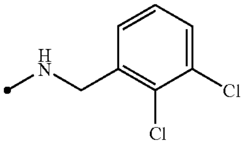 | 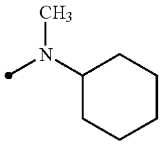 | MS m/z 599 $(M + H)^+$ |

TABLE 8-continued
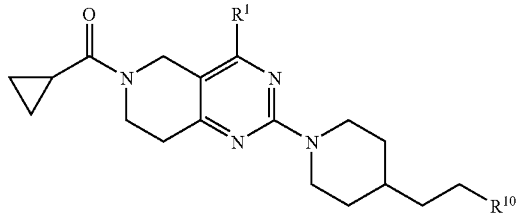
| Compound Number | •—R¹ | •—R¹⁰ | Spectrum Data |
|---|---|---|---|
| 8-13 | 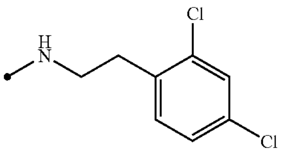 | 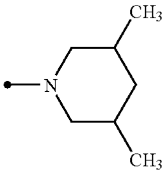 | MS m/z 613 $(M + H)^+$ |
| 8-14 | 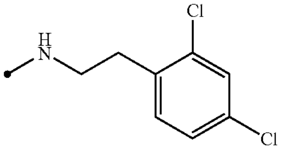 | 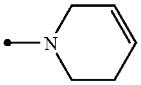 | MS m/z 583 $(M + H)^+$ |
| 8-15 | 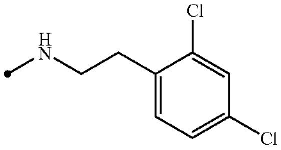 | 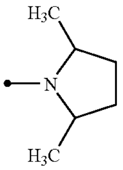 | MS m/z 599 $(M + H)^+$ |
| 8-16 | 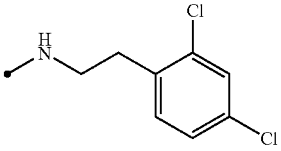 | 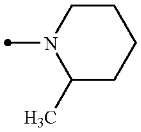 | MS m/z 599 $(M + H)^+$ |
| 8-17 | 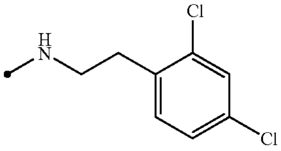 | 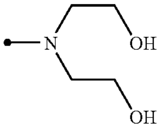 | MS m/z 605 $(M + H)^+$ |
| 8-18 | 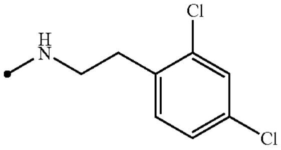 | 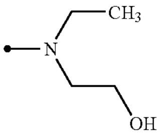 | MS m/z 589 $(M + H)^+$ |
| 8-19 | 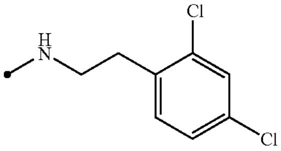 | 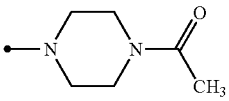 | MS m/z 628 $(M + H)^+$ |

TABLE 8-continued
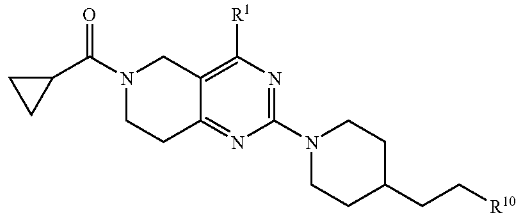
| Compound Number | •—$R^1$ | •—$R^{10}$ | Spectrum Data |
|---|---|---|---|
| 8-20 | 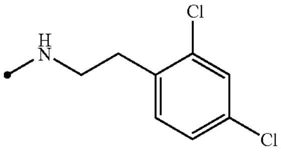 | 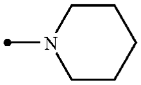 | MS m/z 585 $(M + H)^+$ |
| 8-21 | 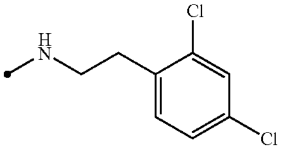 | 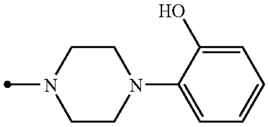 | MS m/z 678 $(M + H)^+$ |
| 8-22 | 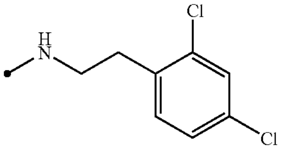 | 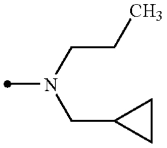 | MS m/z 613 $(M + H)^+$ |
| 8-23 | 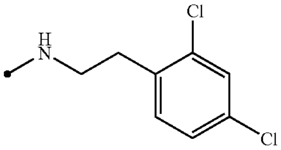 | 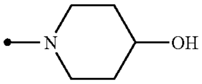 | MS m/z 601 $(M + H)^+$ |
| 8-24 | 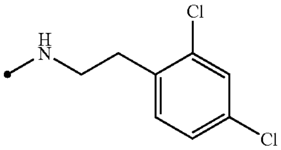 | 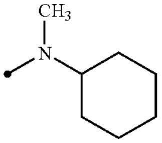 | MS m/z 613 $(M + H)^+$ |
| 8-25 | 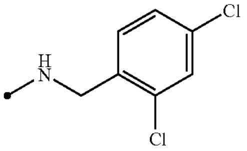 | 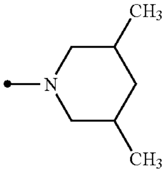 | MS m/z 599 $(M + H)^+$ |
| 8-26 | 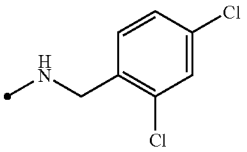 | 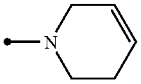 | MS m/z 569 $(M + H)^+$ |

TABLE 8-continued
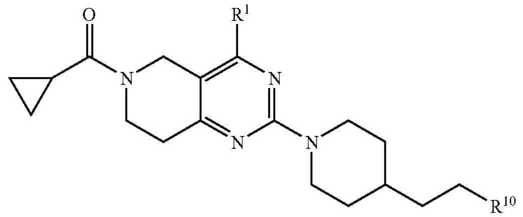
| Compound Number | •—$R^1$ | •—$R^{10}$ | Spectrum Data |
|---|---|---|---|
| 8-27 | 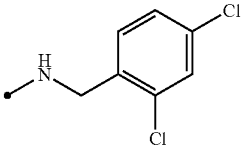 | 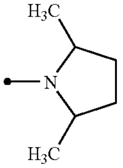 | MS m/z 585 $(M+H)^+$ |
| 8-28 | 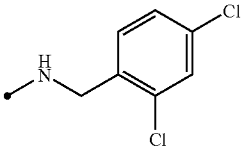 | 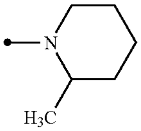 | MS m/z 585 $(M+H)^+$ |
| 8-29 | 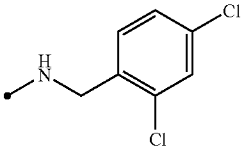 | 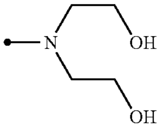 | MS m/z 591 $(M+H)^+$ |
| 8-30 | 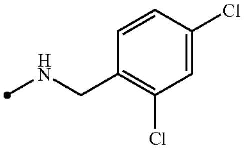 | 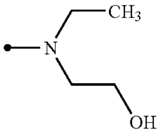 | MS m/z 575 $(M+H)^+$ |
| 8-31 | 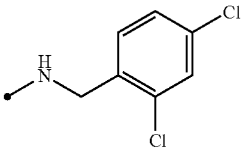 | 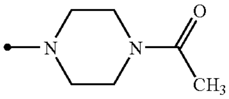 | MS m/z 614 $(M+H)^+$ |
| 8-32 | 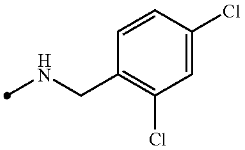 | 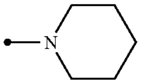 | MS m/z 571 $(M+H)^+$ |
| 8-33 | 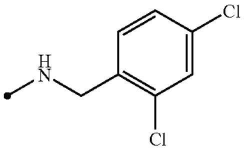 | 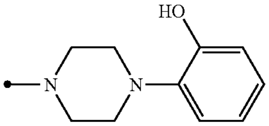 | MS m/z 664 $(M+H)^+$ |
| 8-34 | 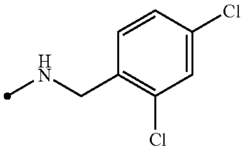 | 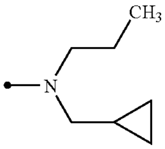 | MS m/z 599 $(M+H)^+$ |

TABLE 8-continued
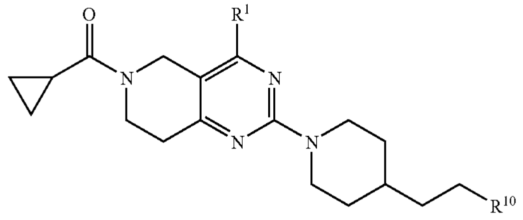
| Compound Number | •—$R^1$ | •—$R^{10}$ | Spectrum Data |
|---|---|---|---|
| 8-35 | 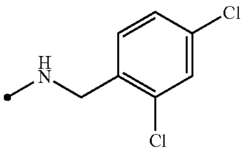 | 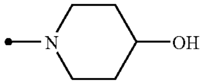 | MS m/z 587 $(M+H)^+$ |
| 8-36 | 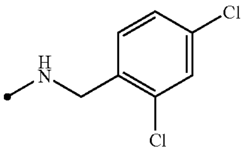 | 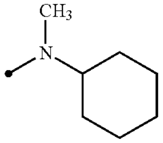 | MS m/z 599 $(M+H)^+$ |
| 8-37 | 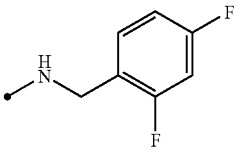 | 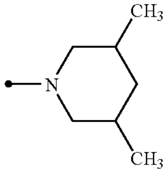 | MS m/z 567 $(M+H)^+$ |
| 8-38 | 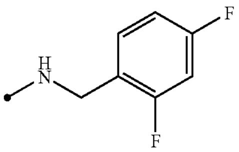 | 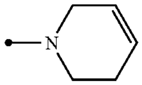 | MS m/z 537 $(M+H)^+$ |
| 8-39 | 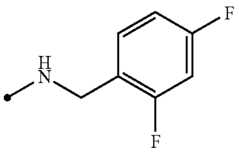 | 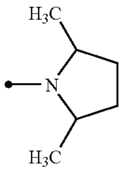 | MS m/z 553 $(M+H)^+$ |
| 8-40 | 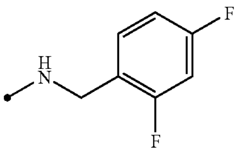 | 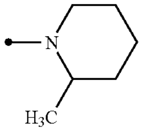 | MS m/z 553 $(M+H)^+$ |
| 8-41 | 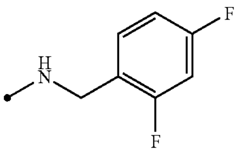 | 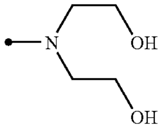 | MS m/z 559 $(M+H)^+$ |

TABLE 8-continued
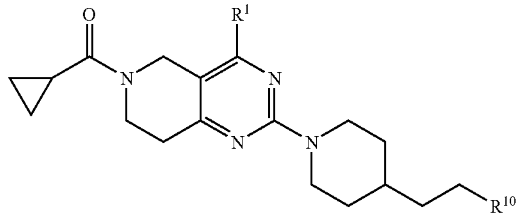
| Compound Number | •—$R^1$ | •—$R^{10}$ | Spectrum Data |
|---|---|---|---|
| 8-42 | 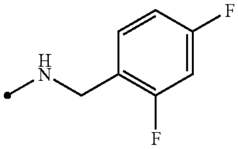 | 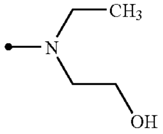 | MS m/z 543 $(M + H)^+$ |
| 8-43 | 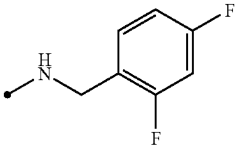 | 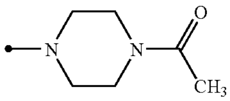 | MS m/z 582 $(M + H)^+$ |
| 8-44 | 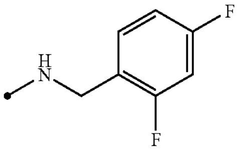 | 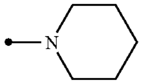 | MS m/z 539 $(M + H)^+$ |
| 8-45 | 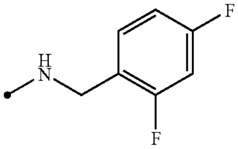 | 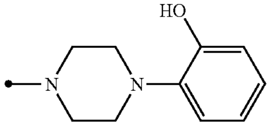 | MS m/z 632 $(M + H)^+$ |
| 8-46 | 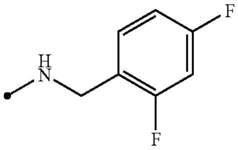 | 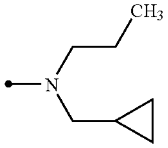 | MS m/z 567 $(M + H)^+$ |
| 8-47 | 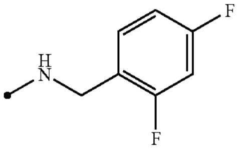 | 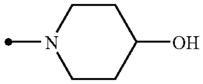 | MS m/z 555 $(M + H)^+$ |
| 8-48 | 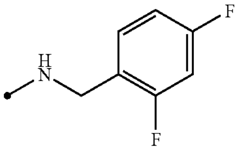 | 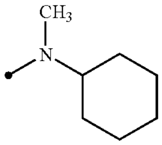 | MS m/z 567 $(M + H)^+$ |
| 8-49 | 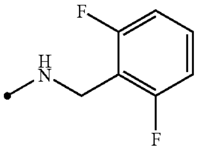 | 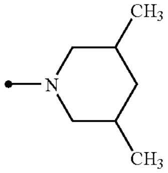 | MS m/z 567 $(M + H)^+$ |

TABLE 8-continued
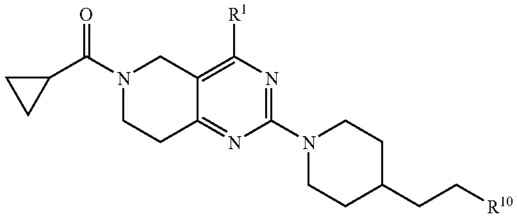
| Compound Number | •—$R^1$ | •—$R^{10}$ | Spectrum Data |
|---|---|---|---|
| 8-50 | 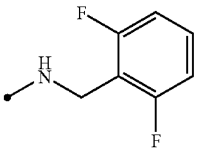 | 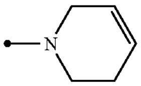 | MS m/z 537 $(M + H)^+$ |
| 8-51 | 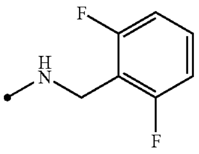 | 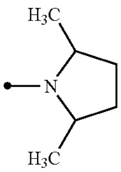 | MS m/z 553 $(M + H)^+$ |
| 8-52 | 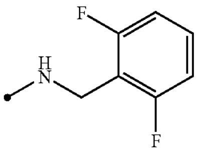 | 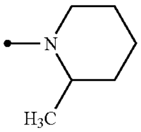 | MS m/z 553 $(M + H)^+$ |
| 8-53 | 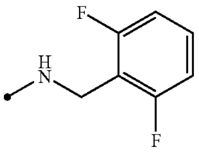 | 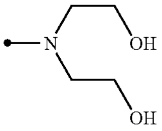 | MS m/z 559 $(M + H)^+$ |
| 8-54 | 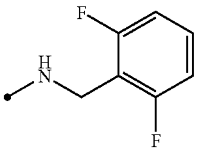 | 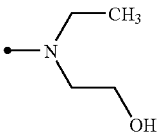 | MS m/z 543 $(M + H)^+$ |
| 8-55 | 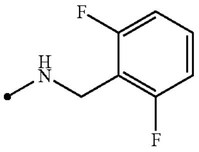 | 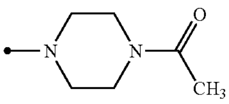 | MS m/z 582 $(M + H)^+$ |
| 8-56 | 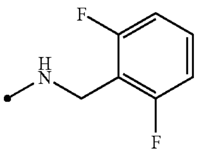 | 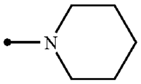 | MS m/z 539 $(M + H)^+$ |

TABLE 8-continued
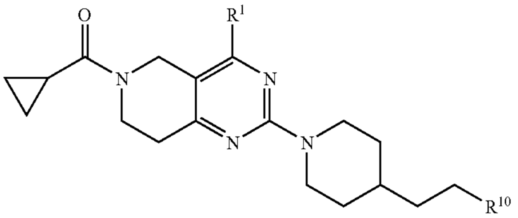
| Compound Number | •—R¹ | •—R¹⁰ | Spectrum Data |
|---|---|---|---|
| 8-57 | 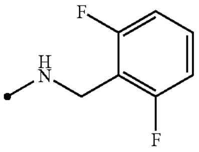 | 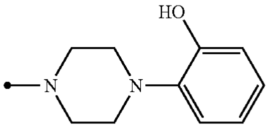 | MS m/z 632 $(M + H)^+$ |
| 8-58 | 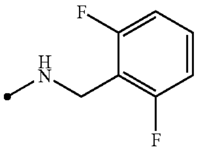 | 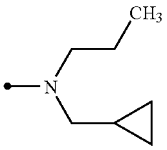 | MS m/z 567 $(M + H)^+$ |
| 8-59 | 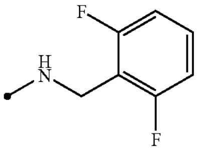 | 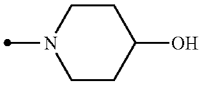 | MS m/z 555 $(M + H)^+$ |
| 8-60 | 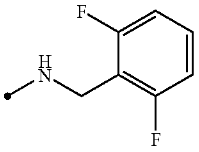 | 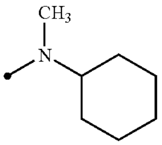 | MS m/z 567 $(M + H)^+$ |
| 8-61 | 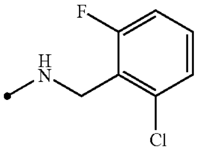 | 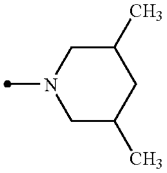 | MS m/z 583 $(M + H)^+$ |
| 8-62 | 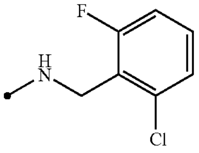 | 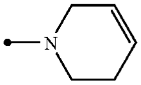 | MS m/z 553 $(M + H)^+$ |
| 8-63 | 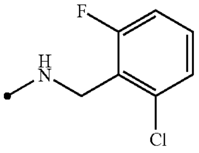 | 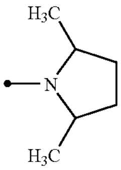 | MS m/z 569 $(M + H)^+$ |

TABLE 8-continued
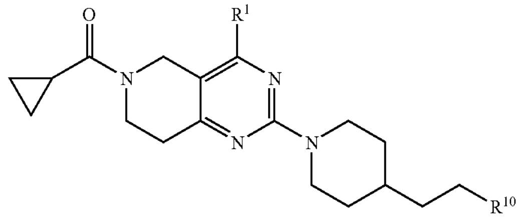
| Compound Number | •—$R^1$ | •—$R^{10}$ | Spectrum Data |
|---|---|---|---|
| 8-64 | 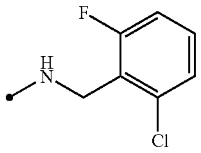 | 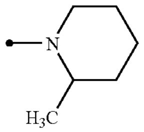 | MS m/z 569 $(M + H)^+$ |
| 8-65 | 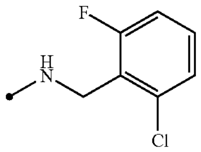 | 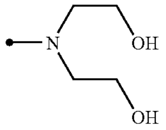 | MS m/z 575 $(M + H)^+$ |
| 8-66 | 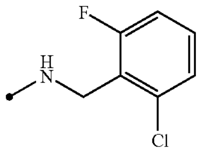 | 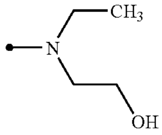 | MS m/z 559 $(M + H)^+$ |
| 8-67 | 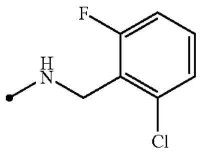 | 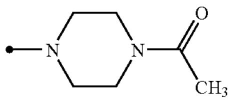 | MS m/z 598 $(M + H)^+$ |
| 8-68 | 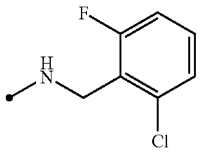 | 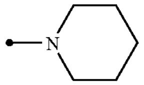 | MS m/z 555 $(M + H)^+$ |
| 8-69 | 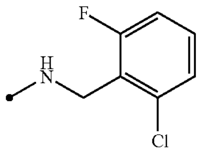 | 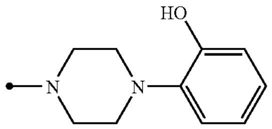 | MS m/z 648 $(M + H)^+$ |
| 8-70 | 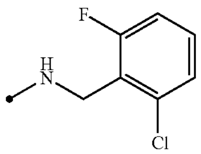 | 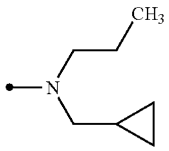 | MS m/z 583 $(M + H)^+$ |
| 8-71 | 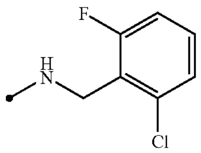 | 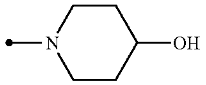 | MS m/z 571 $(M + H)^+$ |

TABLE 8-continued
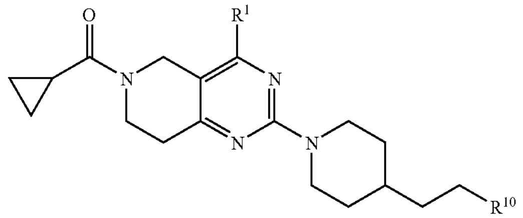
| Compound Number | •—$R^1$ | •—$R^{10}$ | Spectrum Data |
|---|---|---|---|
| 8-72 | 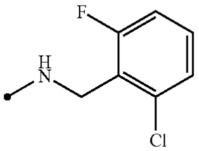 | 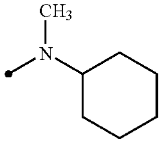 | MS m/z 583 $(M+H)^+$ |
| 8-73 | 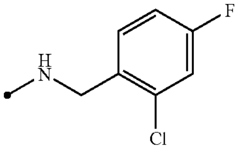 | 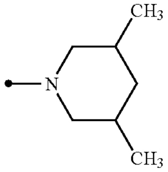 | MS m/z 583 $(M+H)^+$ |
| 8-74 | 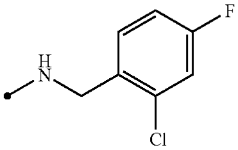 | 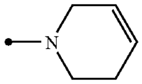 | MS m/z 553 $(M+H)^+$ |
| 8-75 | 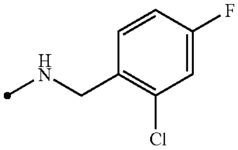 | 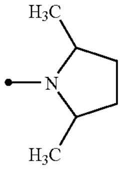 | MS m/z 569 $(M+H)^+$ |
| 8-76 | 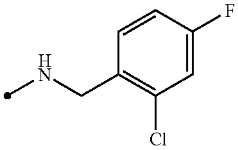 | 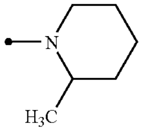 | MS m/z 569 $(M+H)^+$ |
| 8-77 | 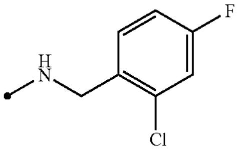 | 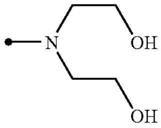 | MS m/z 575 $(M+H)^+$ |
| 8-78 | 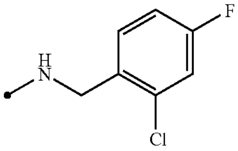 | 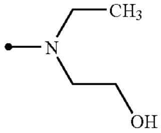 | MS m/z 559 $(M+H)^+$ |

TABLE 8-continued
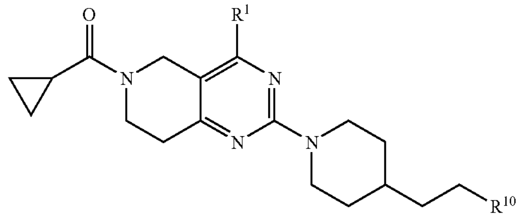
| Compound Number | •—$R^1$ | •—$R^{10}$ | Spectrum Data |
|---|---|---|---|
| 8-79 | 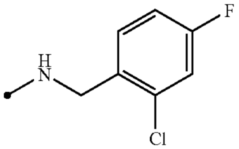 | 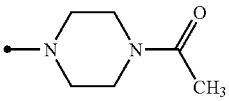 | MS m/z 598 $(M + H)^+$ |
| 8-80 | 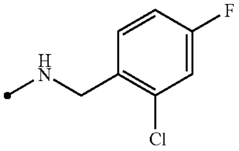 | 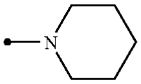 | MS m/z 555 $(M + H)^+$ |
| 8-81 | 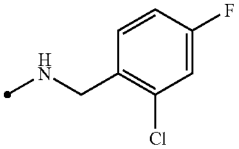 | 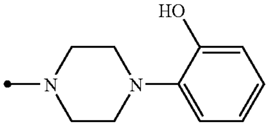 | MS m/z 648 $(M + H)^+$ |
| 8-82 | 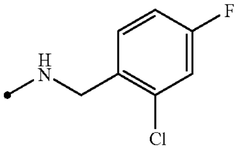 | 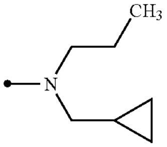 | MS m/z 583 $(M + H)^+$ |
| 8-83 | 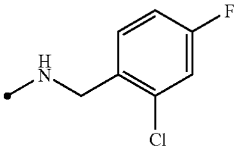 | 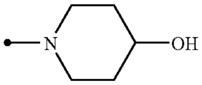 | MS m/z 571 $(M + H)^+$ |
| 8-84 | 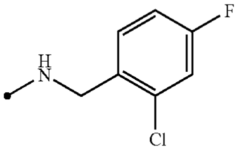 | 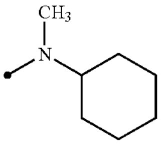 | MS m/z 583 $(M + H)^+$ |
| 8-85 | 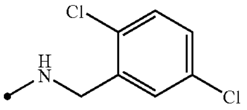 | 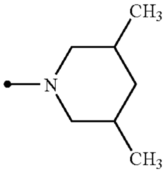 | MS m/z 599 $(M + H)^+$ |
| 8-86 | 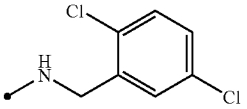 | 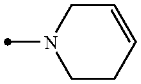 | MS m/z 569 $(M + H)^+$ |

TABLE 8-continued
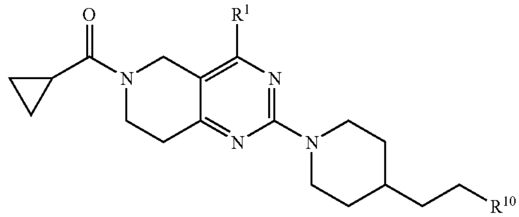
| Compound Number | •—$R^1$ | •—$R^{10}$ | Spectrum Data |
|---|---|---|---|
| 8-87 | 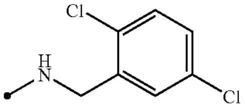 | 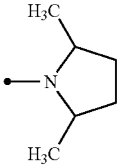 | MS m/z 585 $(M+H)^+$ |
| 8-88 | 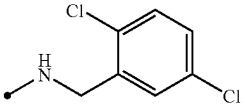 | 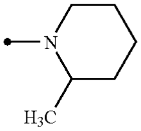 | MS m/z 585 $(M+H)^+$ |
| 8-89 | 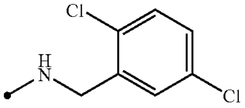 | 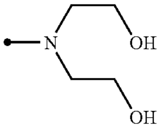 | MS m/z 591 $(M+H)^+$ |
| 8-90 | 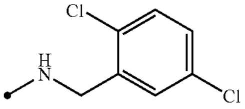 | 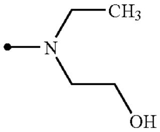 | MS m/z 575 $(M+H)^+$ |
| 8-91 | 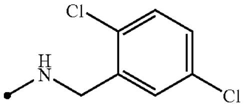 | 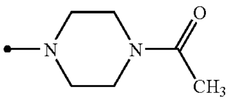 | MS m/z 614 $(M+H)^+$ |
| 8-92 | 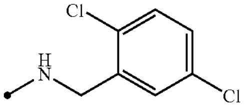 | 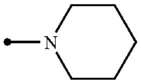 | MS m/z 571 $(M+H)^+$ |
| 8-93 | 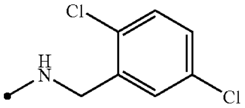 | 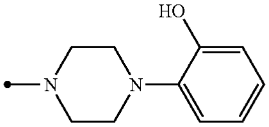 | MS m/z 664 $(M+H)^+$ |
| 8-94 | 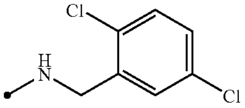 | 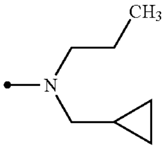 | MS m/z 599 $(M+H)^+$ |
| 8-95 | 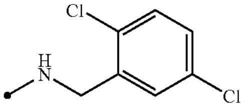 | 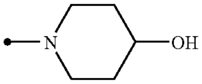 | MS m/z 587 $(M+H)^+$ |

TABLE 8-continued
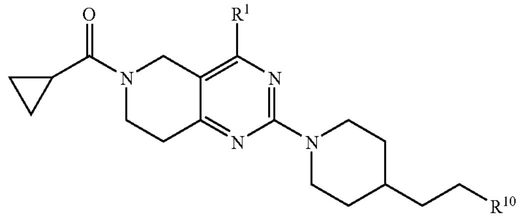
| Compound Number | •—$R^1$ | •—$R^{10}$ | Spectrum Data |
|---|---|---|---|
| 8-96 | 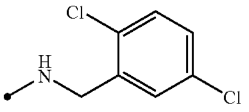 | 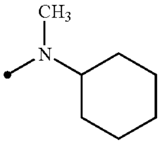 | MS m/z 599 $(M + H)^+$ |
| 8-97 | 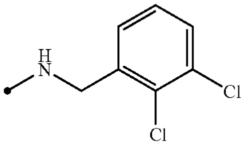 | 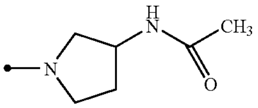 | MS m/z 614 $(M + H)^+$ |
| 8-98 | 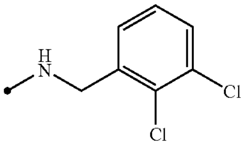 | 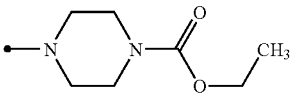 | MS m/z 644 $(M + H)^+$ |
| 8-99 | 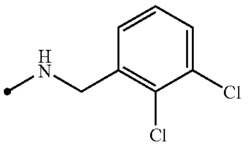 | 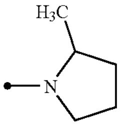 | MS m/z 571 $(M + H)^+$ |
| 8-100 | 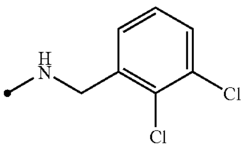 | 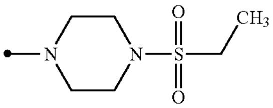 | MS m/z 664 $(M + H)^+$ |
| 8-101 | 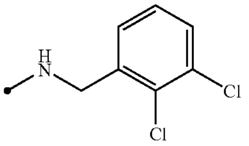 | 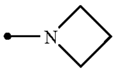 | MS m/z 543 $(M + H)^+$ |
| 8-102 | 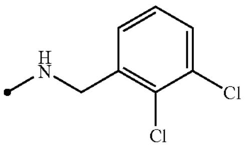 | 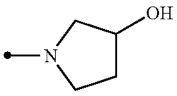 | MS m/z 573 $(M + H)^+$ |
| 8-103 | 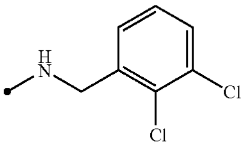 | 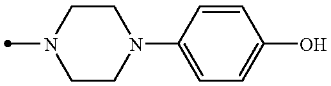 | MS m/z 664 $(M + H)^+$ |

TABLE 8-continued
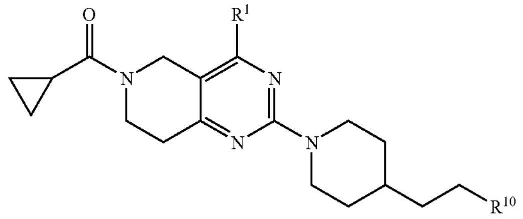
| Compound Number | •—$R^1$ | •—$R^{10}$ | Spectrum Data |
|---|---|---|---|
| 8-104 | 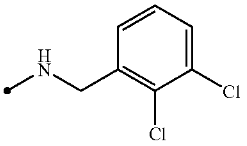 | 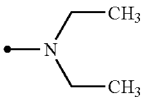 | MS m/z 559 $(M + H)^+$ |
| 8-105 | 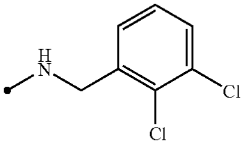 | 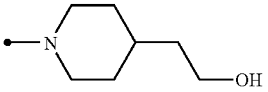 | MS m/z 615 $(M + H)^+$ |
| 8-106 | 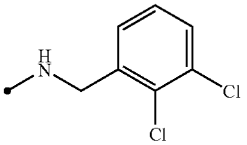 | 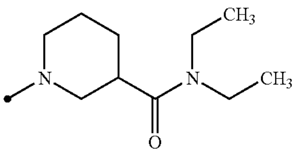 | MS m/z 670 $(M + H)^+$ |
| 8-107 | 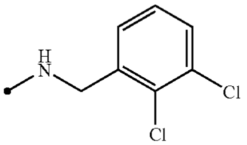 | 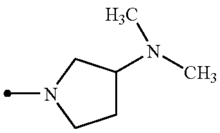 | MS m/z 600 $(M + H)^+$ |
| 8-108 | 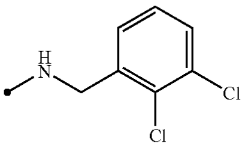 | 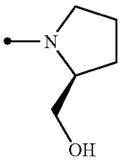 | MS m/z 587 $(M + H)^+$ |
| 8-109 | 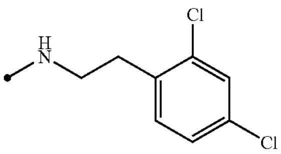 | 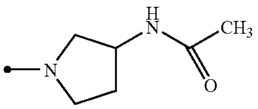 | MS m/z 628 $(M + H)^+$ |
| 8-110 | 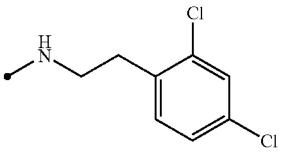 | 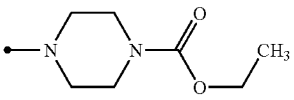 | MS m/z 658 $(M + H)^+$ |
| 8-111 | 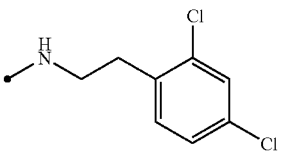 | 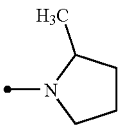 | MS m/z 585 $(M + H)^+$ |

TABLE 8-continued
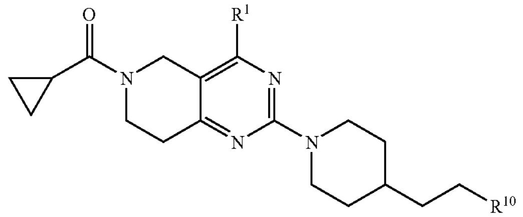
| Compound Number | •—$R^1$ | •—$R^{10}$ | Spectrum Data |
|---|---|---|---|
| 8-112 | 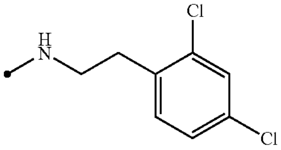 | 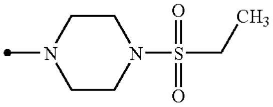 | MS m/z 678 $(M + H)^+$ |
| 8-113 | 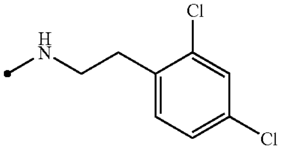 | 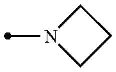 | MS m/z 557 $(M + H)^+$ |
| 8-114 | 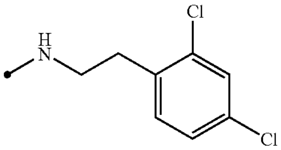 | 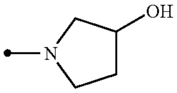 | MS m/z 587 $(M + H)^+$ |
| 8-115 | 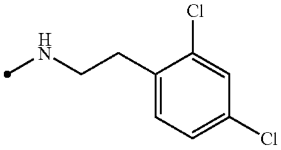 | 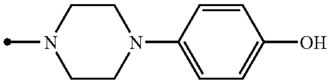 | MS m/z 678 $(M + H)^+$ |
| 8-116 | 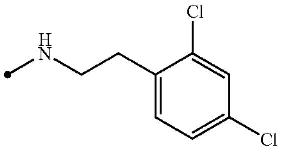 | 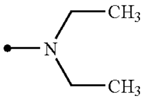 | MS m/z 573 $(M + H)^+$ |
| 8-117 | 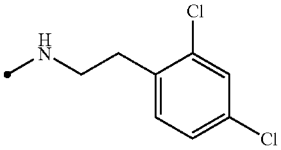 | 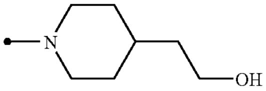 | MS m/z 629 $(M + H)^+$ |
| 8-118 | 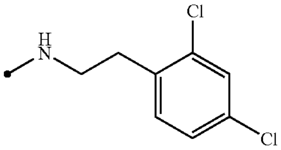 | 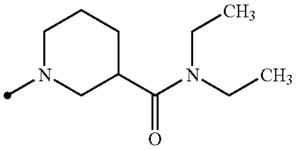 | MS m/z 684 $(M + H)^+$ |
| 8-119 | 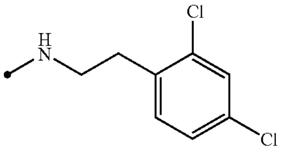 | 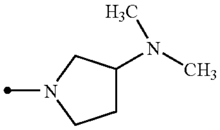 | MS m/z 614 $(M + H)^+$ |

TABLE 8-continued
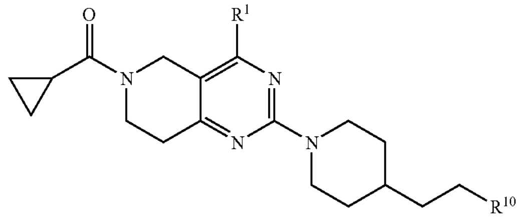
| Compound Number | •—$R^1$ | •—$R^{10}$ | Spectrum Data |
|---|---|---|---|
| 8-120 | 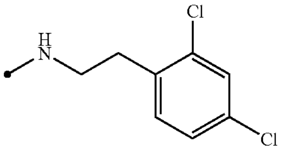 | 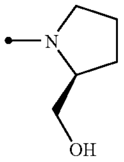 | MS m/z 601 $(M+H)^+$ |
| 8-121 | 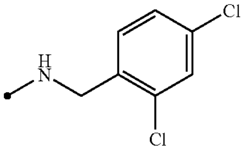 | 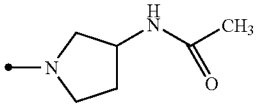 | MS m/z 614 $(M+H)^+$ |
| 8-122 | 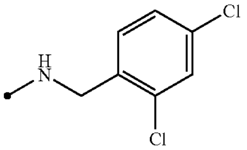 | 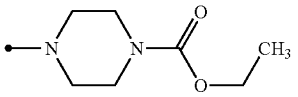 | MS m/z 644 $(M+H)^+$ |
| 8-123 | 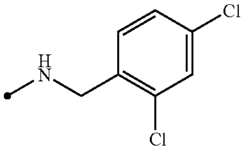 | 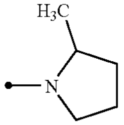 | MS m/z 571 $(M+H)^+$ |
| 8-124 | 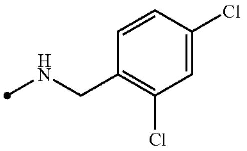 | 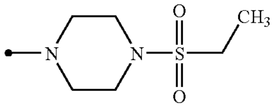 | MS m/z 664 $(M+H)^+$ |
| 8-125 | 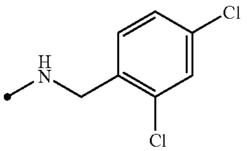 | 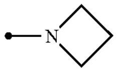 | MS m/z 543 $(M+H)^+$ |
| 8-126 | 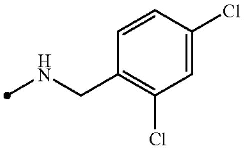 | 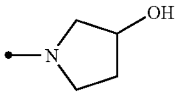 | MS m/z 573 $(M+H)^+$ |
| 8-127 | 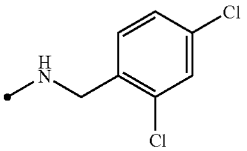 | 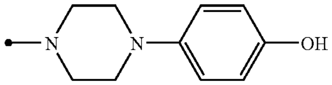 | MS m/z 664 $(M+H)^+$ |

TABLE 8-continued
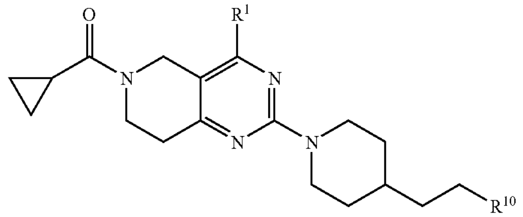
| Compound Number | •—$R^1$ | •—$R^{10}$ | Spectrum Data |
|---|---|---|---|
| 8-128 | 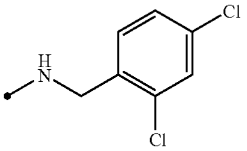 | 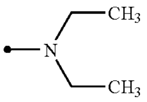 | MS m/z 559 $(M + H)^+$ |
| 8-129 | 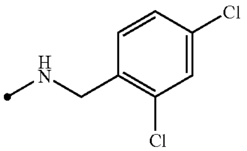 | 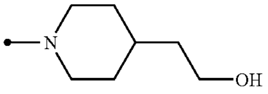 | MS m/z 615 $(M + H)^+$ |
| 8-130 | 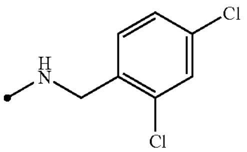 | 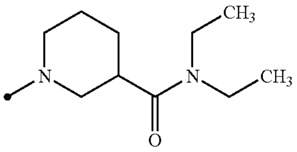 | MS m/z 670 $(M + H)^+$ |
| 8-131 | 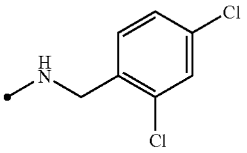 | 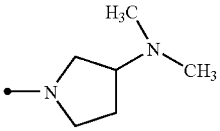 | MS m/z 600 $(M + H)^+$ |
| 8-132 | 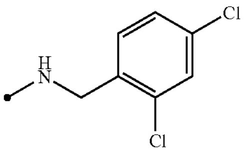 | 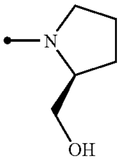 | MS m/z 587 $(M + H)^+$ |
| 8-133 | 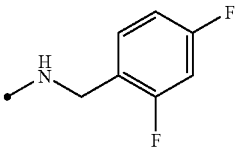 | 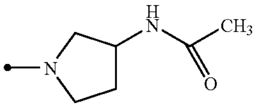 | MS m/z 582 $(M + H)^+$ |
| 8-134 | 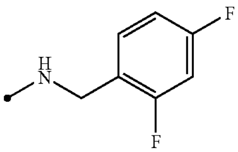 | 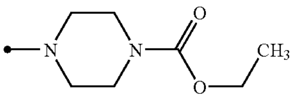 | MS m/z 612 $(M + H)^+$ |
| 8-135 | 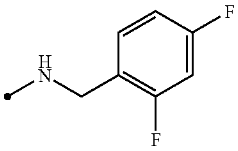 | 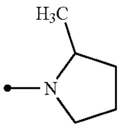 | MS m/z 539 $(M + H)^+$ |

TABLE 8-continued
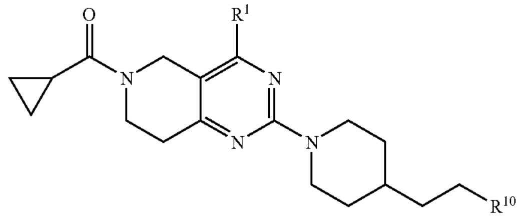
| Compound Number | •—$R^1$ | •—$R^{10}$ | Spectrum Data |
|---|---|---|---|
| 8-136 | 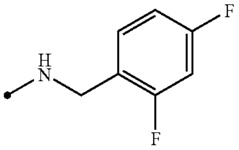 | 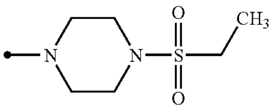 | MS m/z 632 $(M + H)^+$ |
| 8-137 | 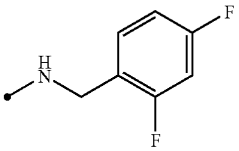 | 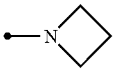 | MS m/z 511 $(M + H)^+$ |
| 8-138 | 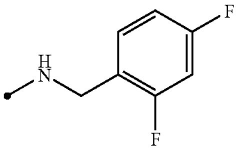 | 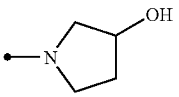 | MS m/z 541 $(M + H)^+$ |
| 8-139 | 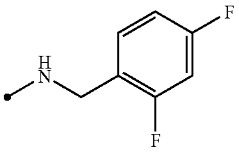 | 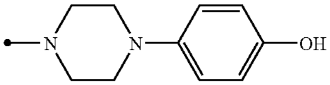 | MS m/z 632 $(M + H)^+$ |
| 8-140 | 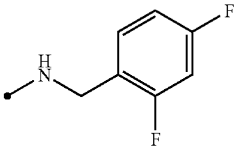 | 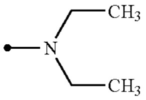 | MS m/z 527 $(M + H)^+$ |
| 8-141 | 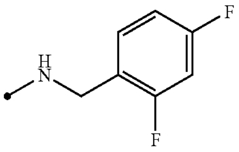 | 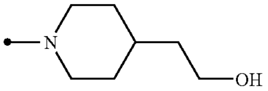 | MS m/z 583 $(M + H)^+$ |
| 8-142 | 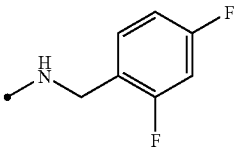 | 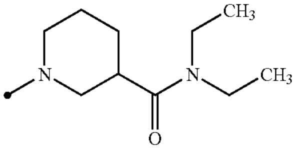 | MS m/z 638 $(M + H)^+$ |
| 8-143 | 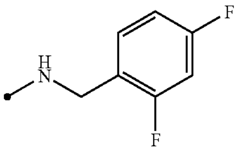 | 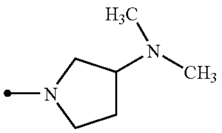 | MS m/z 568 $(M + H)^+$ |

TABLE 8-continued
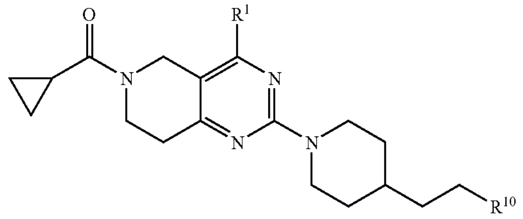
| Compound Number | •—$R^1$ | •—$R^{10}$ | Spectrum Data |
| --- | --- | --- | --- |
| 8-144 | 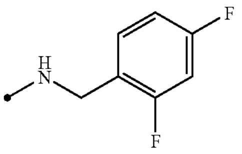 | 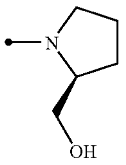 | MS m/z 555 $(M + H)^+$ |
| 8-145 | 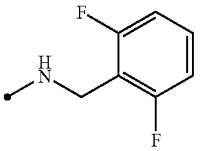 | 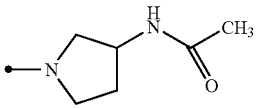 | MS m/z 582 $(M + H)^+$ |
| 8-146 | 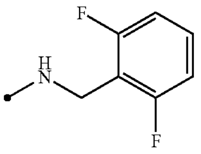 | 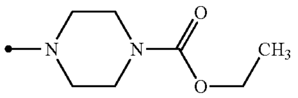 | MS m/z 612 $(M + H)^+$ |
| 8-147 | 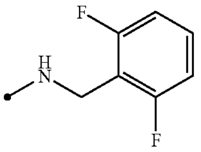 | 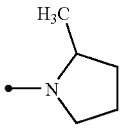 | MS m/z 539 $(M + H)^+$ |
| 8-148 | 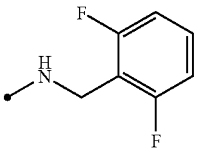 | 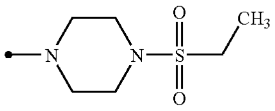 | MS m/z 632 $(M + H)^+$ |
| 8-149 | 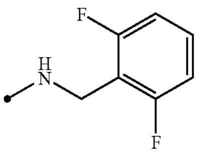 | 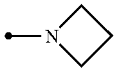 | MS m/z 511 $(M + H)^+$ |
| 8-150 | 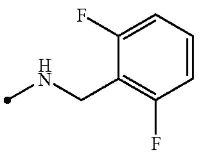 | 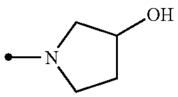 | MS m/z 541 $(M + H)^+$ |
| 8-151 | 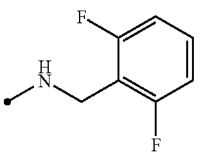 | 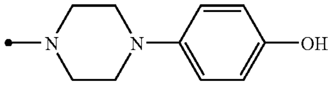 | MS m/z 632 $(M + H)^+$ |

TABLE 8-continued
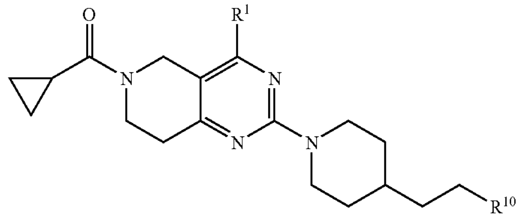
| Compound Number | •—R¹ | •—R¹⁰ | Spectrum Data |
|---|---|---|---|
| 8-152 | 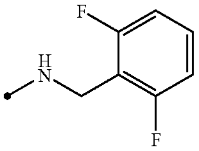 | 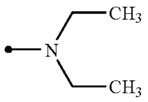 | MS m/z 527 $(M + H)^+$ |
| 8-153 | 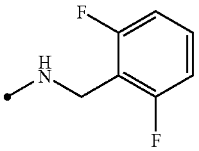 | 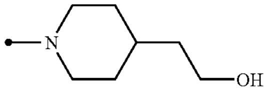 | MS m/z 583 $(M + H)^+$ |
| 8-154 | 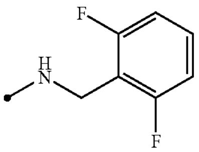 | 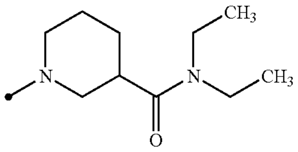 | MS m/z 638 $(M + H)^+$ |
| 8-155 | 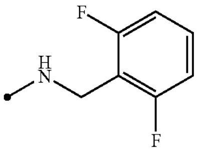 | 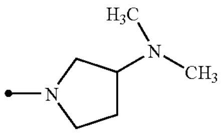 | MS m/z 568 $(M + H)^+$ |
| 8-156 | 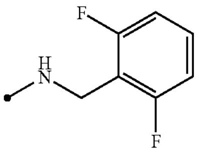 | 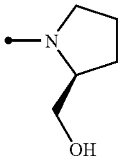 | MS m/z 555 $(M + H)^+$ |
| 8-157 | 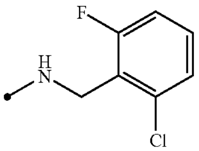 | 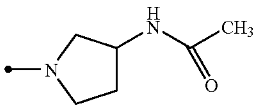 | MS m/z 598 $(M + H)^+$ |
| 8-158 | 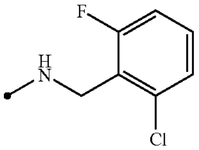 | 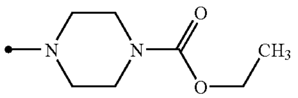 | MS m/z 628 $(M + H)^+$ |
| 8-159 | 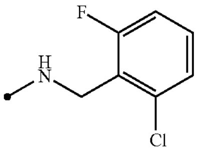 | 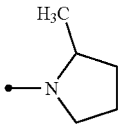 | MS m/z 555 $(M + H)^+$ |

TABLE 8-continued
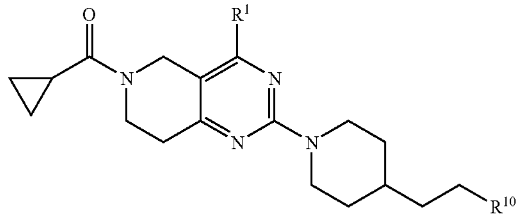
| Compound Number | •—R1 | •—R10 | Spectrum Data |
| --- | --- | --- | --- |
| 8-160 | 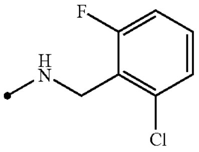 | 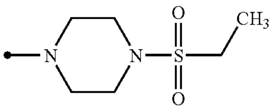 | MS m/z 648 $(M + H)^+$ |
| 8-161 | 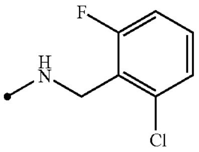 | 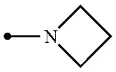 | MS m/z 527 $(M + H)^+$ |
| 8-162 | 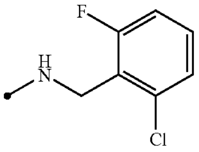 | 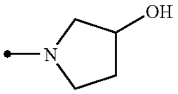 | MS m/z 557 $(M + H)^+$ |
| 8-163 | 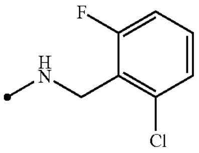 | 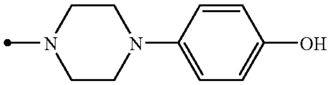 | MS m/z 648 $(M + H)^+$ |
| 8-164 | 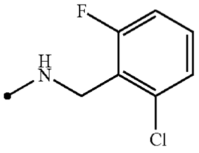 | 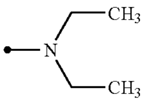 | MS m/z 543 $(M + H)^+$ |
| 8-165 | 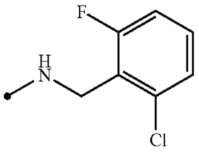 | 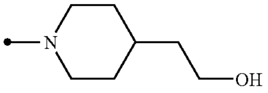 | MS m/z 599 $(M + H)^+$ |
| 8-166 | 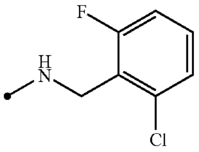 | 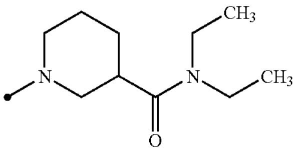 | MS m/z 554 $(M + H)^+$ |
| 8-167 | 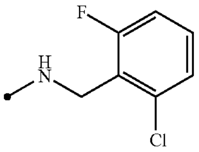 | 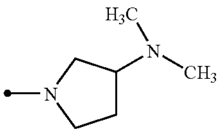 | MS m/z 584 $(M + H)^+$ |

TABLE 8-continued
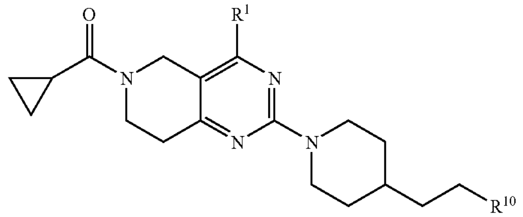
| Compound Number | •—$R^1$ | •—$R^{10}$ | Spectrum Data |
|---|---|---|---|
| 8-168 | 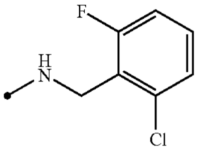 | 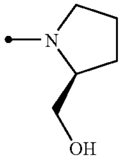 | MS m/z 571 $(M + H)^+$ |
| 8-169 | 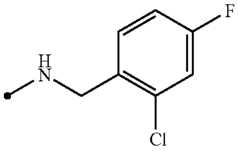 | 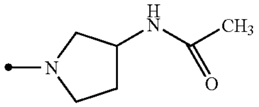 | MS m/z 598 $(M + H)^+$ |
| 8-170 | 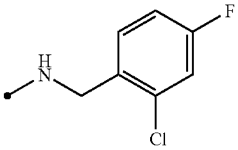 | 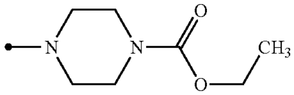 | MS m/z 628 $(M + H)^+$ |
| 8-171 | 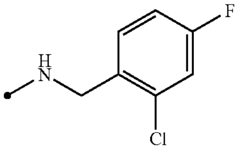 | 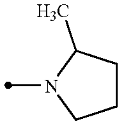 | MS m/z 555 $(M + H)^+$ |
| 8-172 | 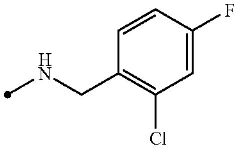 | 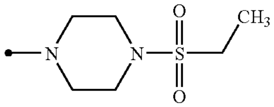 | MS m/z 648 $(M + H)^+$ |
| 8-173 | 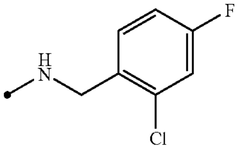 | 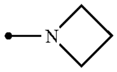 | MS m/z 527 $(M + H)^+$ |
| 8-174 | 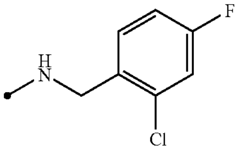 | 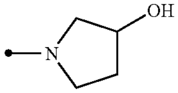 | MS m/z 557 $(M + H)^+$ |
| 8-175 | 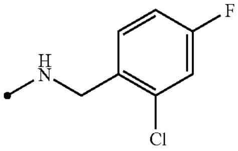 | 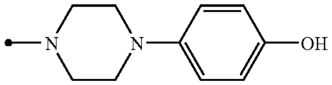 | MS m/z 648 $(M + H)^+$ |

TABLE 8-continued
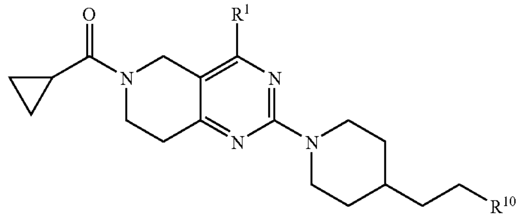
| Compound Number | •—$R^1$ | •—$R^{10}$ | Spectrum Data |
|---|---|---|---|
| 8-176 | 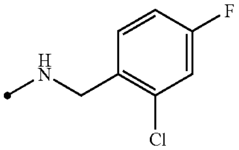 | 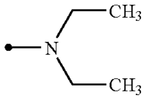 | MS m/z 543 $(M + H)^+$ |
| 8-177 | 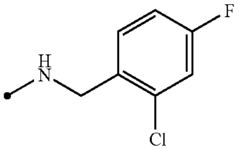 | 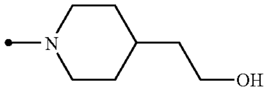 | MS m/z 599 $(M + H)^+$ |
| 8-178 | 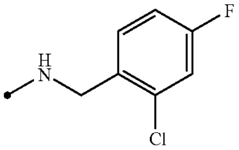 | 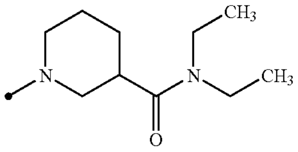 | MS m/z 654 $(M + H)^+$ |
| 8-179 | 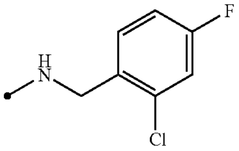 | 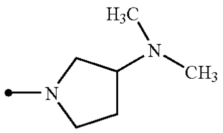 | MS m/z 584 $(M + H)^+$ |
| 8-180 | 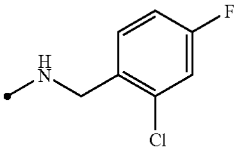 | 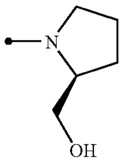 | MS m/z 571 $(M + H)^+$ |
| 8-181 | 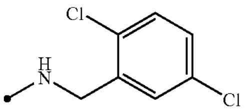 | 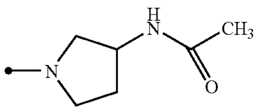 | MS m/z 614 $(M + H)^+$ |
| 8-182 | 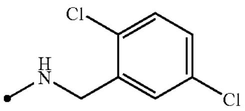 | 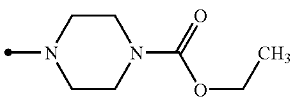 | MS m/z 644 $(M + H)^+$ |
| 8-183 | 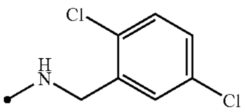 | 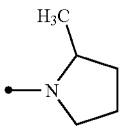 | MS m/z 571 $(M + H)^+$ |

TABLE 8-continued
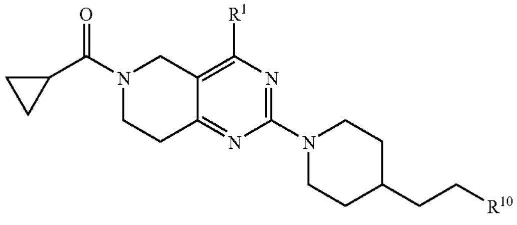
| Compound Number | •—$R^1$ | •—$R^{10}$ | Spectrum Data |
|---|---|---|---|
| 8-184 | 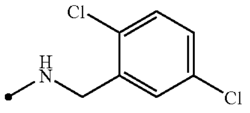 | 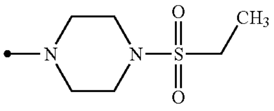 | MS m/z 664 $(M + H)^+$ |
| 8-185 | 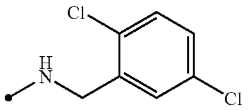 | 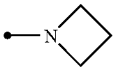 | MS m/z 543 $(M + H)^+$ |
| 8-186 | 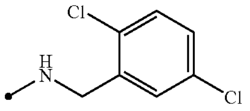 | 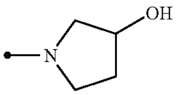 | MS m/z 573 $(M + H)^+$ |
| 8-187 | 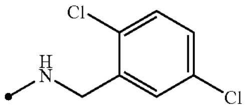 | 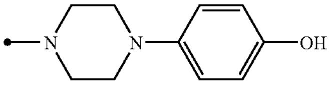 | MS m/z 664 $(M + H)^+$ |
| 8-188 | 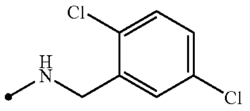 | 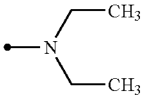 | MS m/z 559 $(M + H)^+$ |
| 8-189 | 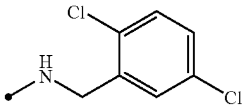 | 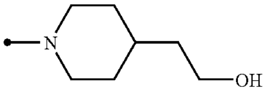 | MS m/z 615 $(M + H)^+$ |
| 8-190 | 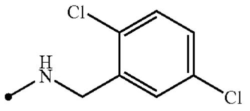 | 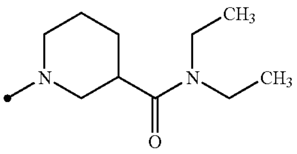 | MS m/z 670 $(M + H)^+$ |
| 8-191 | 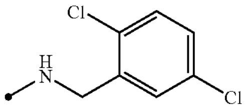 | 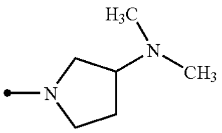 | MS m/z 600 $(M + H)^+$ |
| 8-192 | 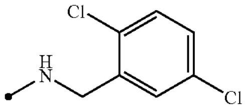 | 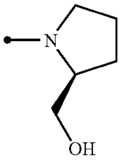 | MS m/z 587 $(M + H)^+$ |

TABLE 8-continued
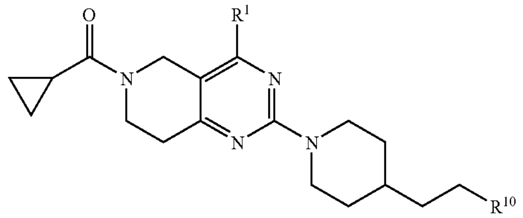
| Compound Number | •—$R^1$ | •—$R^{10}$ | Spectrum Data |
|---|---|---|---|
| 8-193 | 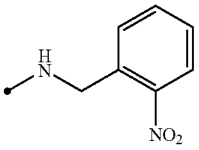 | 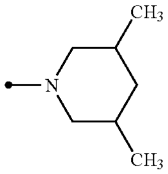 | MS m/z 576 $(M+H)^+$ |
| 8-194 | 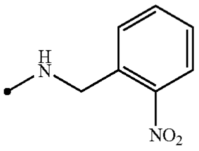 | 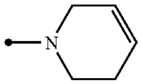 | MS m/z 546 $(M+H)^+$ |
| 8-195 | 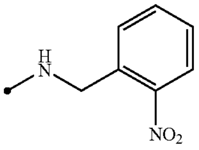 | 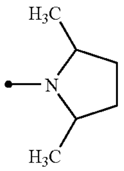 | MS m/z 562 $(M+H)^+$ |
| 8-196 | 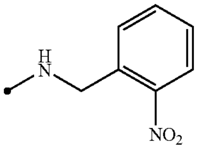 | 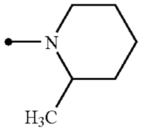 | MS m/z 562 $(M+H)^+$ |
| 8-197 | 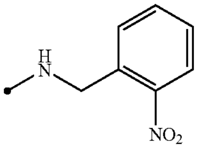 | 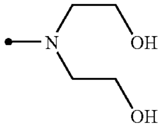 | MS m/z 568 $(M+H)^+$ |
| 8-198 | 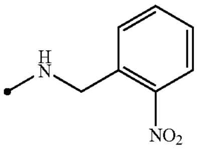 | 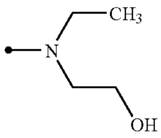 | MS m/z 552 $(M+H)^+$ |
| 8-199 | 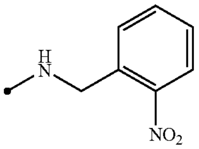 | 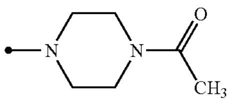 | MS m/z 591 $(M+H)^+$ |

TABLE 8-continued
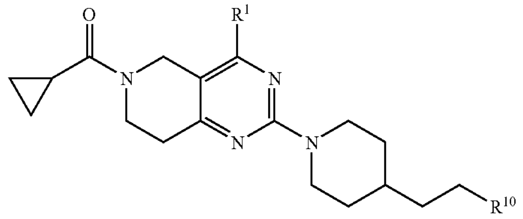
| Compound Number | •—$R^1$ | •—$R^{10}$ | Spectrum Data |
|---|---|---|---|
| 8-200 | 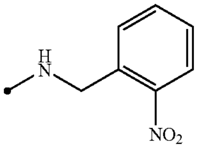 | 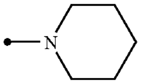 | MS m/z 548 $(M + H)^+$ |
| 8-201 | 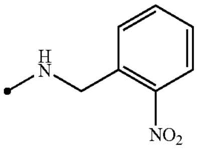 | 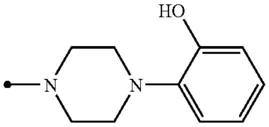 | MS m/z 641 $(M + H)^+$ |
| 8-202 | 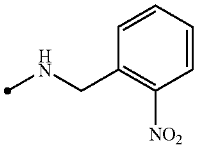 | 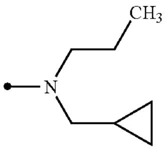 | MS m/z 576 $(M + H)^+$ |
| 8-203 | 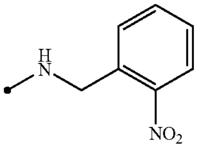 | 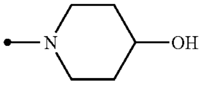 | MS m/z 564 $(M + H)^+$ |
| 8-204 | 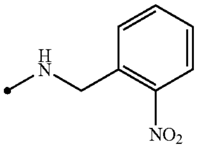 | 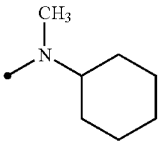 | MS m/z 576 $(M + H)^+$ |
| 8-205 | 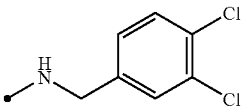 | 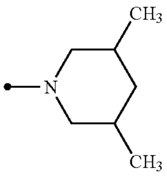 | MS m/z 599 $(M + H)^+$ |
| 8-206 | 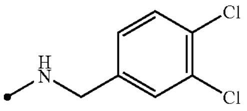 | 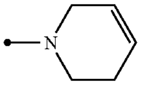 | MS m/z 569 $(M + H)^+$ |
| 8-207 | 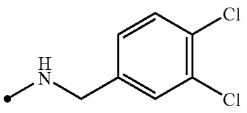 | 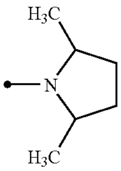 | MS m/z 585 $(M + H)^+$ |

TABLE 8-continued
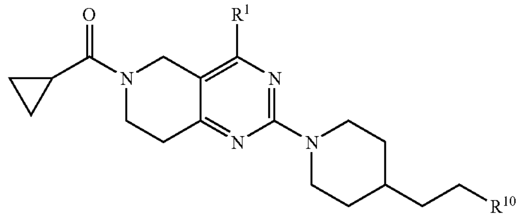
| Compound Number | •—$R^1$ | •—$R^{10}$ | Spectrum Data |
|---|---|---|---|
| 8-208 | 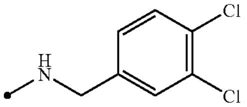 | 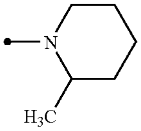 | MS m/z 585 $(M + H)^+$ |
| 8-209 | 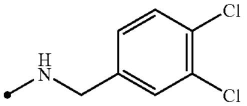 | 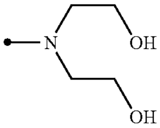 | MS m/z 591 $(M + H)^+$ |
| 8-210 | 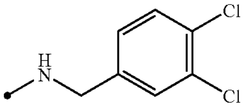 | 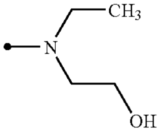 | MS m/z 575 $(M + H)^+$ |
| 8-211 | 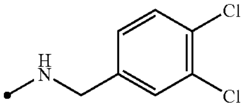 | 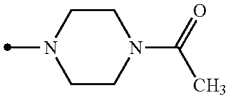 | MS m/z 614 $(M + H)^+$ |
| 8-212 | 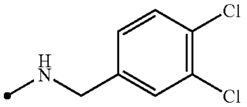 | 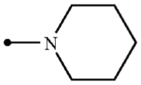 | MS m/z 571 $(M + H)^+$ |
| 8-213 | 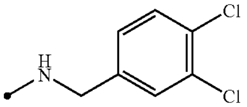 | 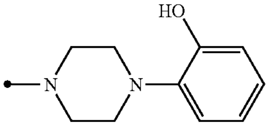 | MS m/z 664 $(M + H)^+$ |
| 8-214 | 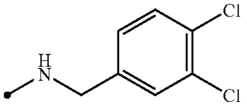 | 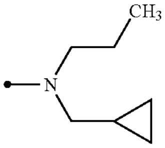 | MS m/z 599 $(M + H)^+$ |
| 8-215 | 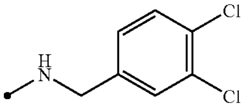 | 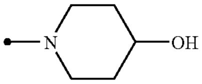 | MS m/z 587 $(M + H)^+$ |
| 8-216 | 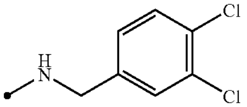 | 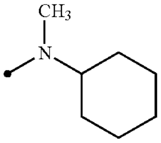 | MS m/z 599 $(M + H)^+$ |

TABLE 8-continued
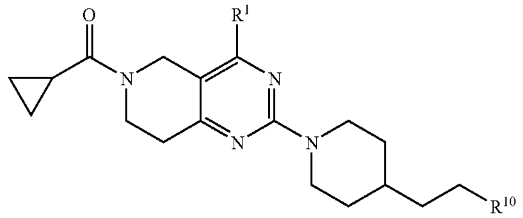
| Compound Number | •—R¹ | •—R¹⁰ | Spectrum Data |
|---|---|---|---|
| 8-217 | 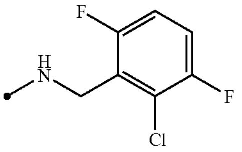 | 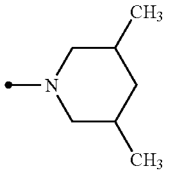 | MS m/z 601 $(M + H)^+$ |
| 8-218 | 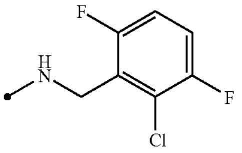 | 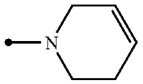 | MS m/z 571 $(M + H)^+$ |
| 8-219 | 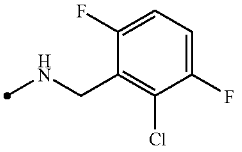 | 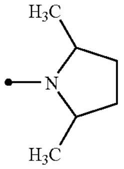 | MS m/z 587 $(M + H)^+$ |
| 8-220 | 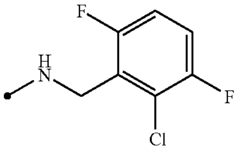 | 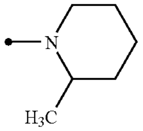 | MS m/z 587 $(M + H)^+$ |
| 8-221 | 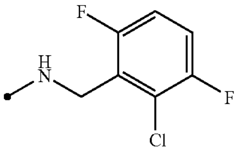 | 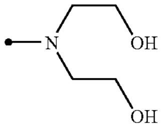 | MS m/z 593 $(M + H)^+$ |
| 8-222 | 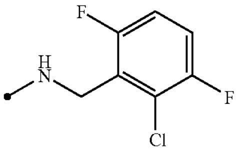 | 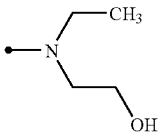 | MS m/z 577 $(M + H)^+$ |
| 8-223 | 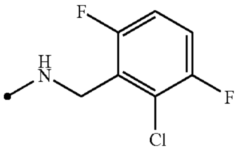 | 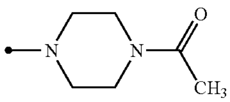 | MS m/z 616 $(M + H)^+$ |

TABLE 8-continued
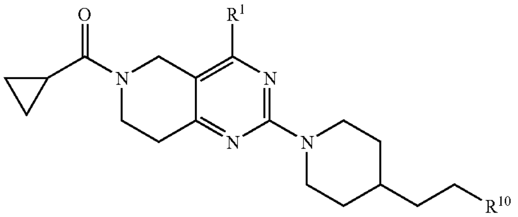
| Compound Number | •—R[1] | •—R[10] | Spectrum Data |
|---|---|---|---|
| 8-224 | 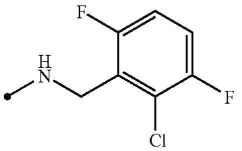 | 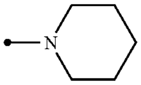 | MS m/z 573 $(M+H)^+$ |
| 8-225 | 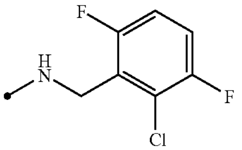 | 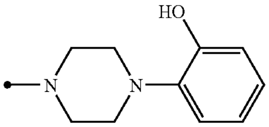 | MS m/z 666 $(M+H)^+$ |
| 8-226 | 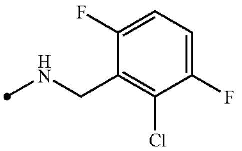 | 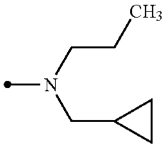 | MS m/z 601 $(M+H)^+$ |
| 8-227 | 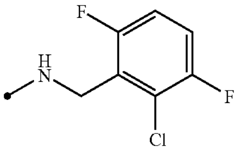 | 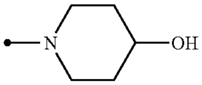 | MS m/z 589 $(M+H)^+$ |
| 8-228 | 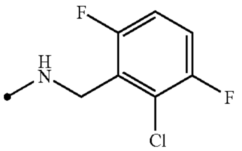 | 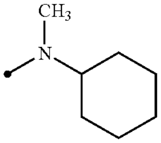 | MS m/z 601 $(M+H)^+$ |
| 8-229 | 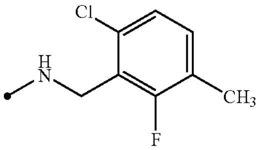 | 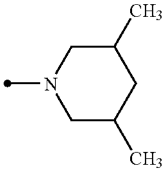 | MS m/z 597 $(M+H)^+$ |
| 8-230 | 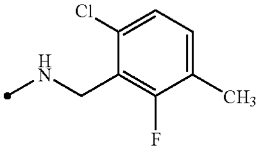 | 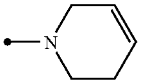 | MS m/z 567 $(M+H)^+$ |

TABLE 8-continued
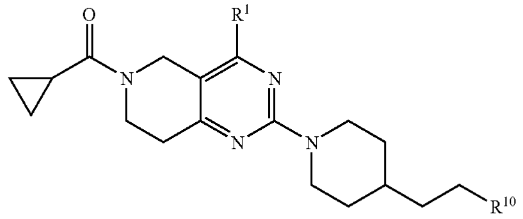
| Compound Number | •—$R^1$ | •—$R^{10}$ | Spectrum Data |
| --- | --- | --- | --- |
| 8-231 | 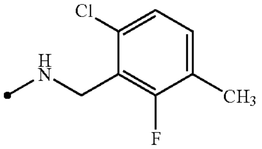 | 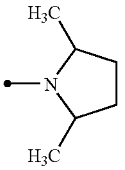 | MS m/z 583 $(M + H)^+$ |
| 8-232 | 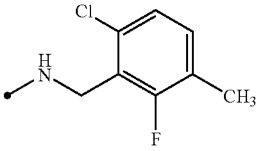 | 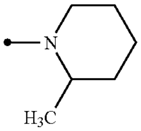 | MS m/z 583 $(M + H)^+$ |
| 8-233 | 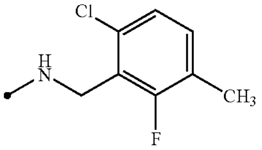 | 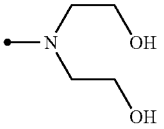 | MS m/z 589 $(M + H)^+$ |
| 8-234 | 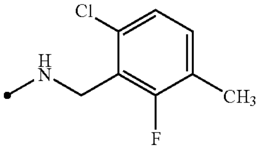 | 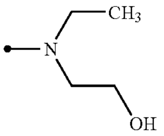 | MS m/z 573 $(M + H)^+$ |
| 8-235 | 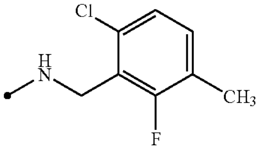 | 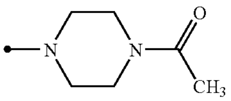 | MS m/z 612 $(M + H)^+$ |
| 8-236 | 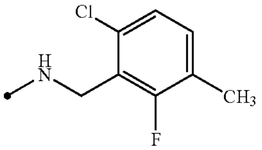 | 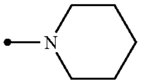 | MS m/z 569 $(M + H)^+$ |
| 8-237 | 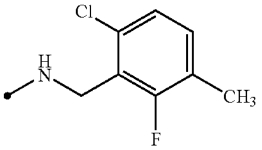 | 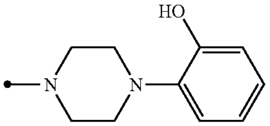 | MS m/z 662 $(M + H)^+$ |
| 8-238 | 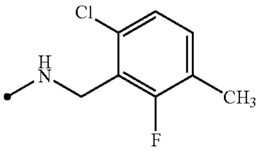 | 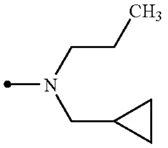 | MS m/z 597 $(M + H)^+$ |

TABLE 8-continued
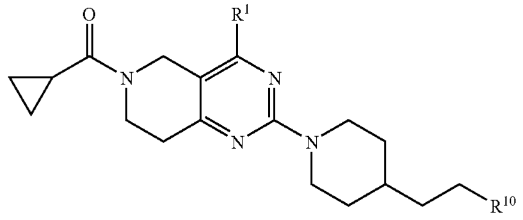
| Compound Number | •—$R^1$ | •—$R^{10}$ | Spectrum Data |
|---|---|---|---|
| 8-239 | 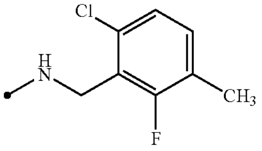 | 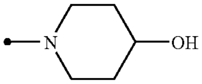 | MS m/z 585 $(M + H)^+$ |
| 8-240 | 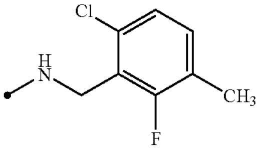 | 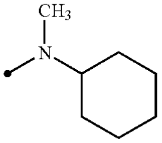 | MS m/z 597 $(M + H)^+$ |
| 8-241 | 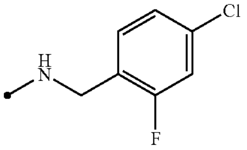 | 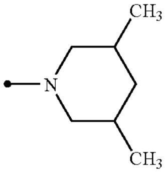 | MS m/z 583 $(M + H)^+$ |
| 8-242 | 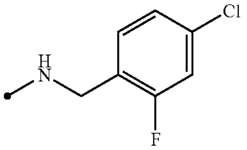 | 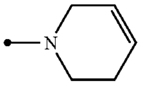 | MS m/z 553 $(M + H)^+$ |
| 8-243 | 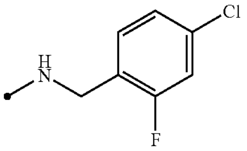 | 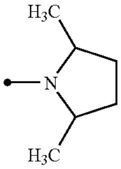 | MS m/z 569 $(M + H)^+$ |
| 8-244 | 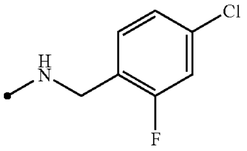 | 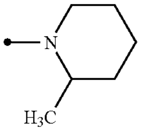 | MS m/z 569 $(M + H)^+$ |
| 8-245 | 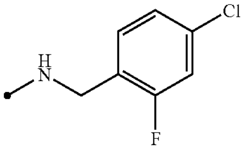 | 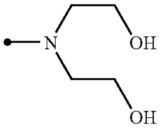 | MS m/z 575 $(M + H)^+$ |

TABLE 8-continued
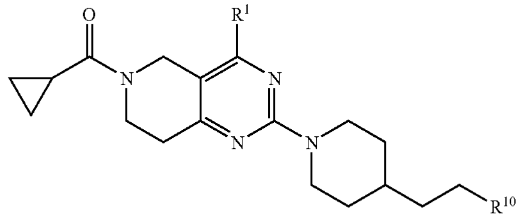
| Compound Number | •—$R^1$ | •—$R^{10}$ | Spectrum Data |
|---|---|---|---|
| 8-246 | 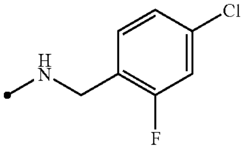 | 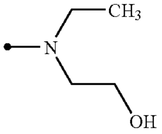 | MS m/z 559 $(M + H)^+$ |
| 8-247 | 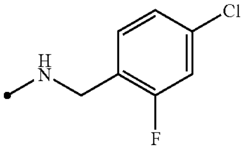 | 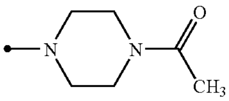 | MS m/z 598 $(M + H)^+$ |
| 8-248 | 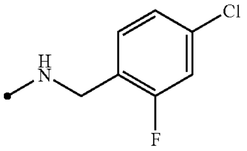 | 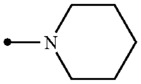 | MS m/z 555 $(M + H)^+$ |
| 8-249 | 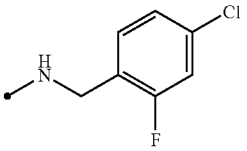 | 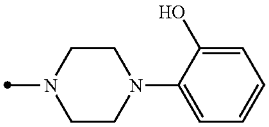 | MS m/z 648 $(M + H)^+$ |
| 8-250 | 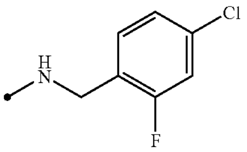 | 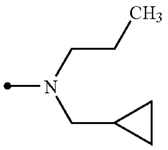 | MS m/z 583 $(M + H)^+$ |
| 8-251 | 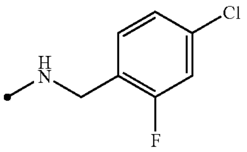 | 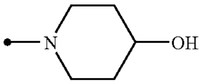 | MS m/z 571 $(M + H)^+$ |
| 8-252 | 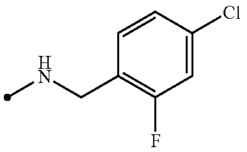 | 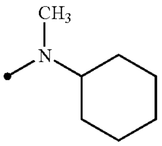 | MS m/z 583 $(M + H)^+$ |
| 8-253 | 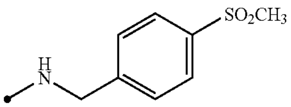 | 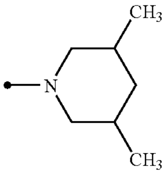 | MS m/z 609 $(M + H)^+$ |

TABLE 8-continued
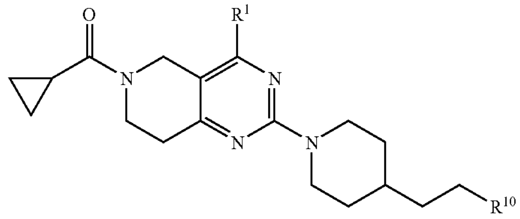
| Compound Number | •—$R^1$ | •—$R^{10}$ | Spectrum Data |
|---|---|---|---|
| 8-254 | 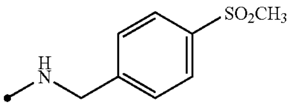 | 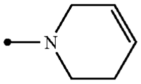 | MS m/z 579 $(M + H)^+$ |
| 8-255 | 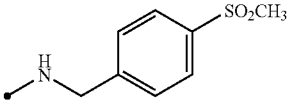 | 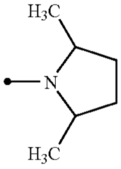 | MS m/z 595 $(M + H)^+$ |
| 8-256 | 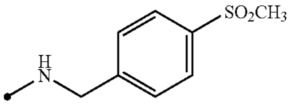 | 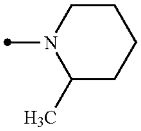 | MS m/z 595 $(M + H)^+$ |
| 8-257 | 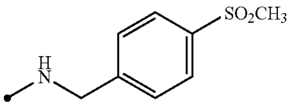 | 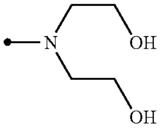 | MS m/z 601 $(M + H)^+$ |
| 8-258 | 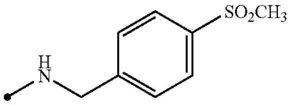 | 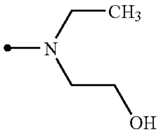 | MS m/z 585 $(M + H)^+$ |
| 8-259 | 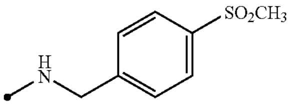 | 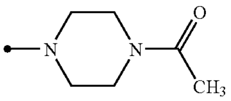 | MS m/z 624 $(M + H)^+$ |
| 8-260 | 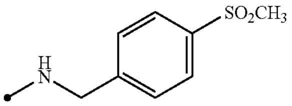 | 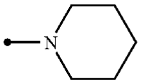 | MS m/z 581 $(M + H)^+$ |
| 8-261 | 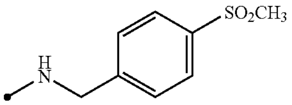 | 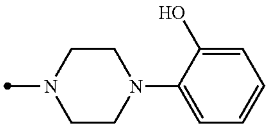 | MS m/z 674 $(M + H)^+$ |
| 8-262 | 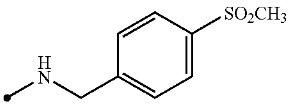 | 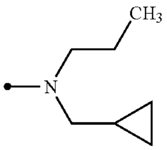 | MS m/z 609 $(M + H)^+$ |

TABLE 8-continued
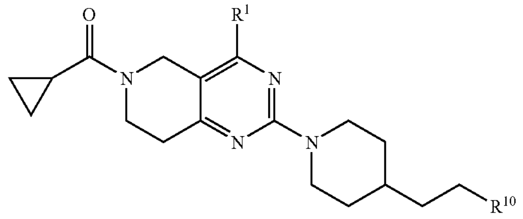
| Compound Number | •—R$^1$ | •—R$^{10}$ | Spectrum Data |
|---|---|---|---|
| 8-263 | 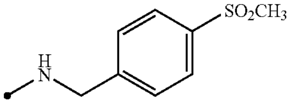 | 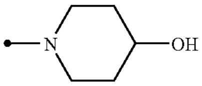 | MS m/z 597 $(M + H)^+$ |
| 8-264 | 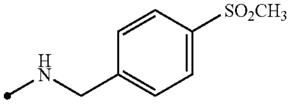 | 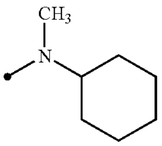 | MS m/z 609 $(M + H)^+$ |
| 8-265 | 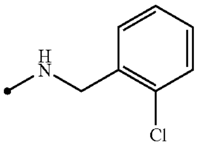 | 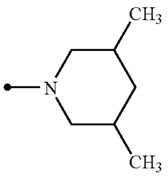 | MS m/z 565 $(M + H)^+$ |
| 8-266 | 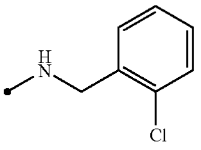 | 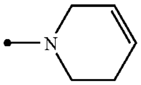 | MS m/z 535 $(M + H)^+$ |
| 8-267 | 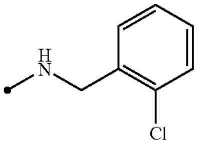 | 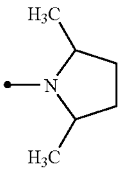 | MS m/z 551 $(M + H)^+$ |
| 8-268 | 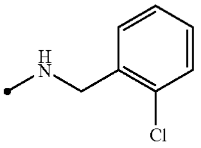 | 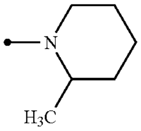 | MS m/z 551 $(M + H)^+$ |
| 8-269 | 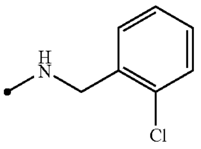 | 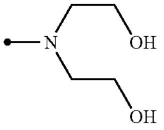 | MS m/z 557 $(M + H)^+$ |
| 8-270 | 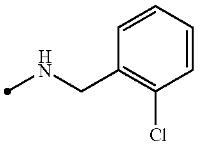 | 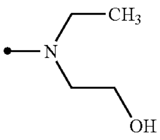 | MS m/z 541 $(M + H)^+$ |

TABLE 8-continued
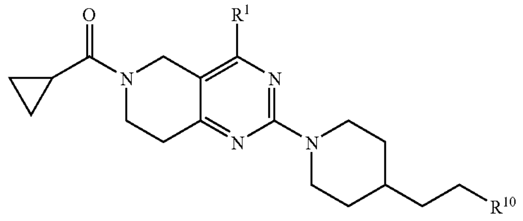
| Compound Number | •—$R^1$ | •—$R^{10}$ | Spectrum Data |
|---|---|---|---|
| 8-271 | 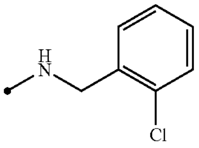 | 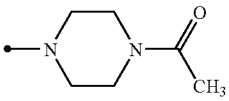 | MS m/z 580 $(M + H)^+$ |
| 8-272 | 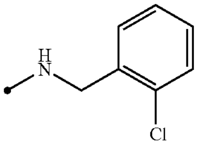 | 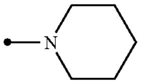 | MS m/z 537 $(M + H)^+$ |
| 8-273 | 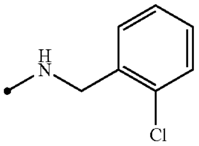 | 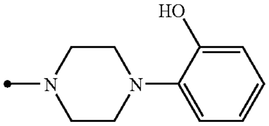 | MS m/z 630 $(M + H)^+$ |
| 8-274 | 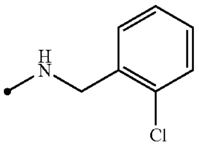 | 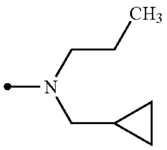 | MS m/z 565 $(M + H)^+$ |
| 8-275 | 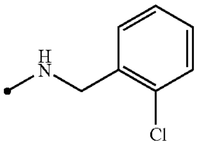 | 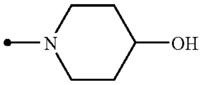 | MS m/z 553 $(M + H)^+$ |
| 8-276 | 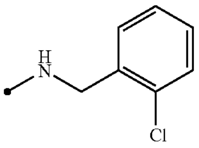 | 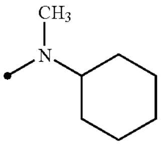 | MS m/z 565 $(M + H)^+$ |
| 8-277 | 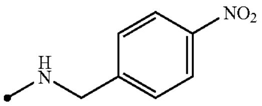 | 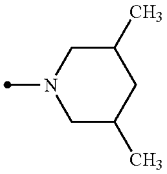 | MS m/z 576 $(M + H)^+$ |
| 8-278 | 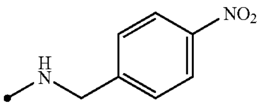 | 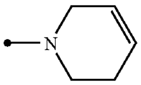 | MS m/z 546 $(M + H)^+$ |

TABLE 8-continued
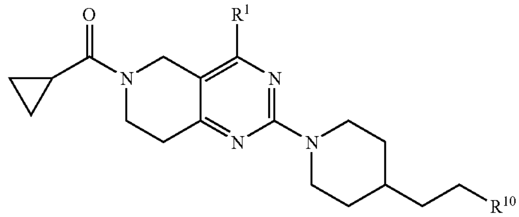
| Compound Number | •—$R^1$ | •—$R^{10}$ | Spectrum Data |
| --- | --- | --- | --- |
| 8-279 | 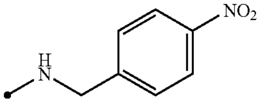 | 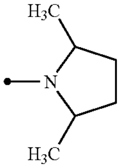 | MS m/z 562 $(M + H)^+$ |
| 8-280 | 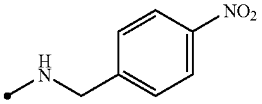 | 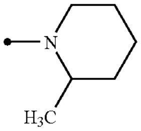 | MS m/z 562 $(M + H)^+$ |
| 8-281 | 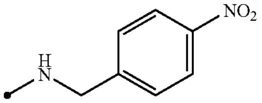 | 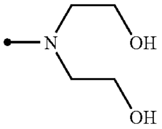 | MS m/z 568 $(M + H)^+$ |
| 8-282 | 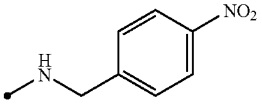 | 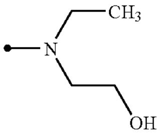 | MS m/z 552 $(M + H)^+$ |
| 8-283 | 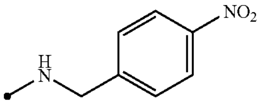 | 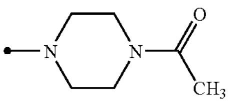 | MS m/z 591 $(M + H)^+$ |
| 8-284 | 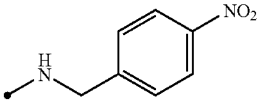 | 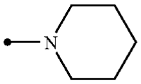 | MS m/z 548 $(M + H)^+$ |
| 8-285 | 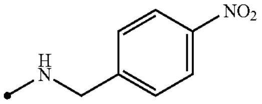 | 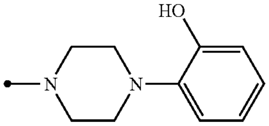 | MS m/z 641 $(M + H)^+$ |
| 8-286 | 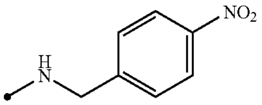 | 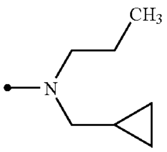 | MS m/z 576 $(M + H)^+$ |
| 8-287 | 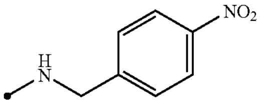 | 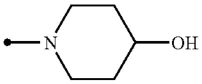 | MS m/z 564 $(M + H)^+$ |

TABLE 8-continued
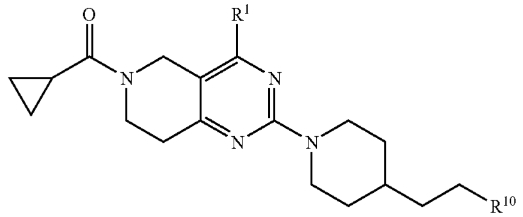
| Compound Number | •—R1 | •—R10 | Spectrum Data |
| --- | --- | --- | --- |
| 8-288 | 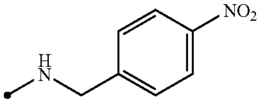 | 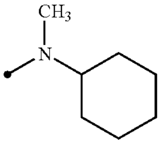 | MS m/z 576 (M + H)+ |
| 8-289 | 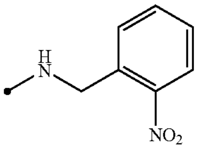 | 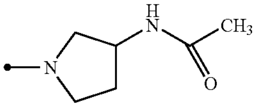 | MS m/z 591 (M + H)+ |
| 8-290 | 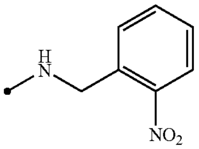 | 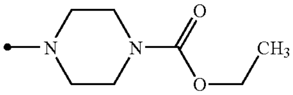 | MS m/z 621 (M + H)+ |
| 8-291 | 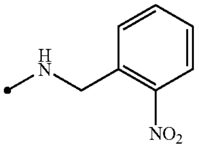 | 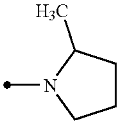 | MS m/z 548 (M + H)+ |
| 8-292 | 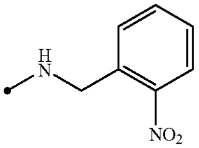 | 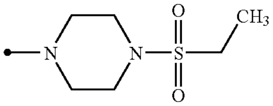 | MS m/z 641 (M + H)+ |
| 8-293 | 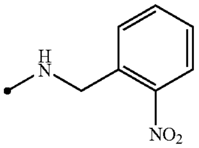 | 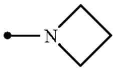 | MS m/z 520 (M + H)+ |
| 8-294 | 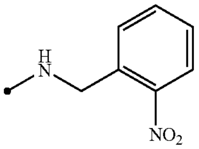 | 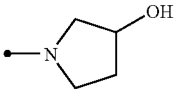 | MS m/z 550 (M + H)+ |
| 8-295 | 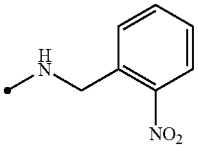 | 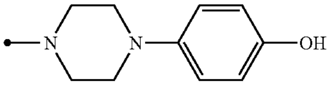 | MS m/z 641 (M + H)+ |

TABLE 8-continued
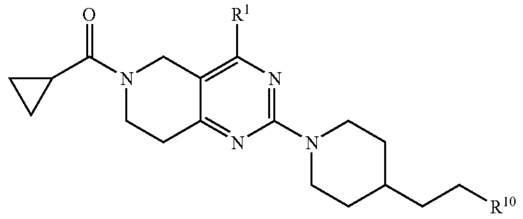
| Compound Number | •—$R^1$ | •—$R^{10}$ | Spectrum Data |
|---|---|---|---|
| 8-296 | 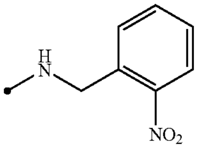 | 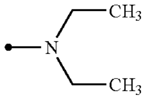 | MS m/z 536 $(M+H)^+$ |
| 8-297 | 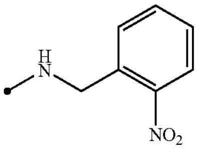 | 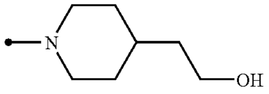 | MS m/z 592 $(M+H)^+$ |
| 8-298 | 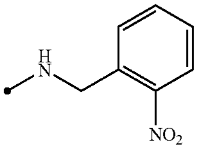 | 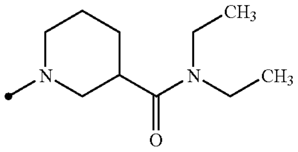 | MS m/z 647 $(M+H)^+$ |
| 8-299 | 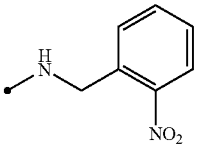 | 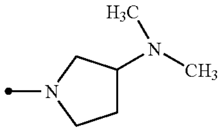 | MS m/z 577 $(M+H)^+$ |
| 8-300 | 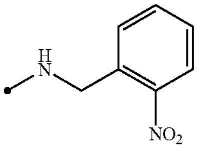 | 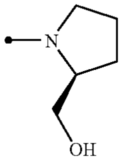 | MS m/z 564 $(M+H)^+$ |
| 8-301 | 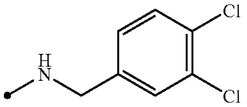 | 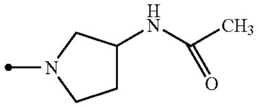 | MS m/z 614 $(M+H)^+$ |
| 8-302 | 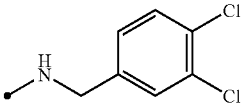 | 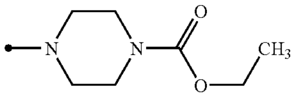 | MS m/z 644 $(M+H)^+$ |
| 8-303 | 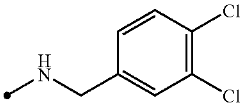 | 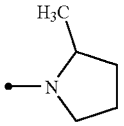 | MS m/z 571 $(M+H)^+$ |
| 8-304 | 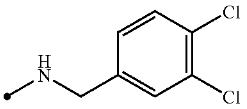 | 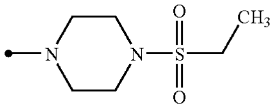 | MS m/z 664 $(M+H)^+$ |

TABLE 8-continued
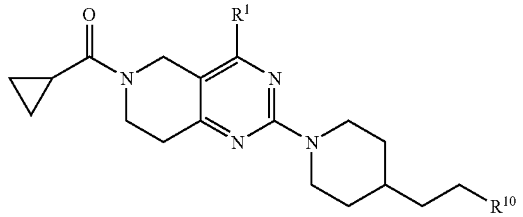
| Compound Number | •—R¹ | •—R¹⁰ | Spectrum Data |
| --- | --- | --- | --- |
| 8-305 | 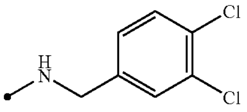 | 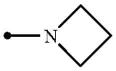 | MS m/z 543 $(M + H)^+$ |
| 8-306 | 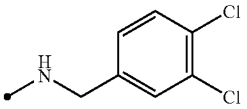 | 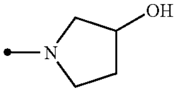 | MS m/z 573 $(M + H)^+$ |
| 8-307 | 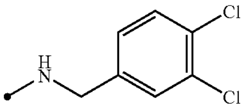 | 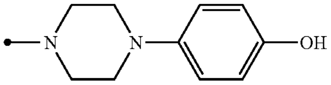 | MS m/z 664 $(M + H)^+$ |
| 8-308 | 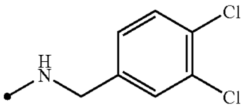 | 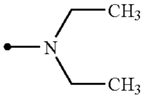 | MS m/z 559 $(M + H)^+$ |
| 8-309 | 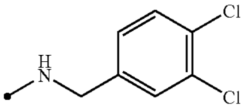 | 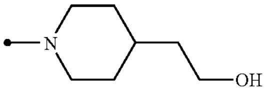 | MS m/z 615 $(M + H)^+$ |
| 8-310 | 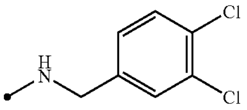 | 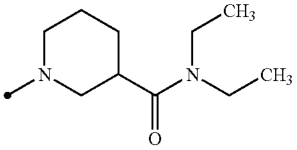 | MS m/z 670 $(M + H)^+$ |
| 8-311 | 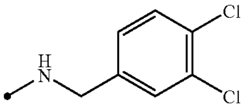 | 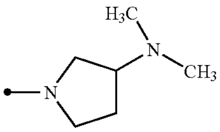 | MS m/z 600 $(M + H)^+$ |
| 8-312 | 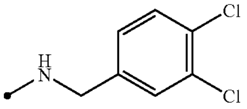 | 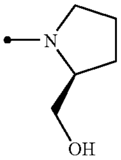 | MS m/z 587 $(M + H)^+$ |
| 8-313 | 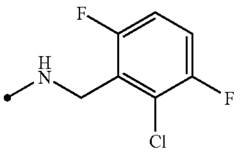 | 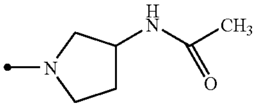 | MS m/z 616 $(M + H)^+$ |

TABLE 8-continued
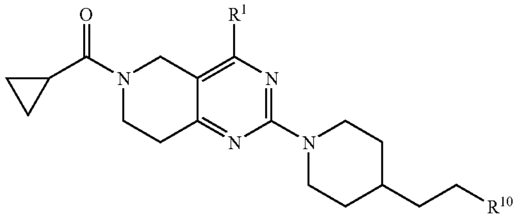
| Compound Number | •—$R^1$ | •—$R^{10}$ | Spectrum Data |
|---|---|---|---|
| 8-314 | 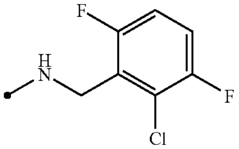 | 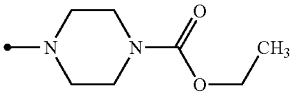 | MS m/z 646 $(M + H)^+$ |
| 8-315 | 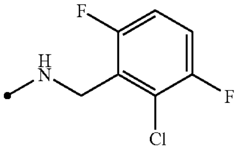 | 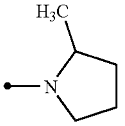 | MS m/z 573 $(M + H)^+$ |
| 8-316 | 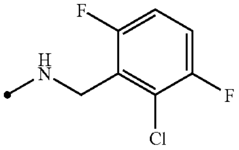 | 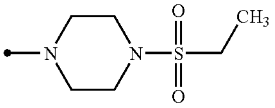 | MS m/z 666 $(M + H)^+$ |
| 8-317 | 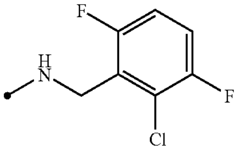 | 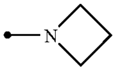 | MS m/z 545 $(M + H)^+$ |
| 8-318 | 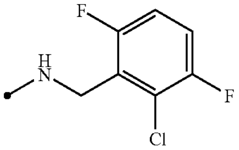 | 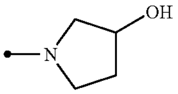 | MS m/z 575 $(M + H)^+$ |
| 8-319 | 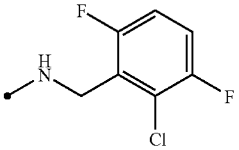 | 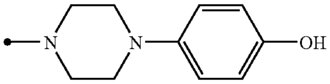 | MS m/z 666 $(M + H)^+$ |
| 8-320 | 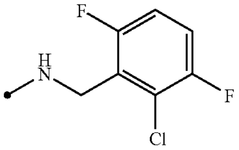 | 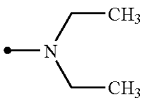 | MS m/z 561 $(M + H)^+$ |
| 8-321 | 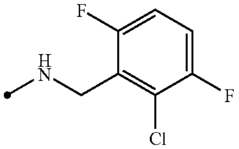 | 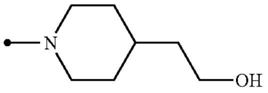 | MS m/z 617 $(M + H)^+$ |

TABLE 8-continued
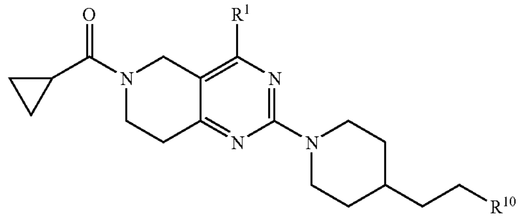
| Compound Number | •—$R^1$ | •—$R^{10}$ | Spectrum Data |
|---|---|---|---|
| 8-322 | 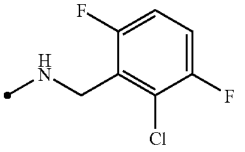 | 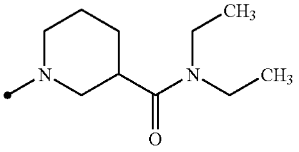 | MS m/z 672 $(M + H)^+$ |
| 8-323 | 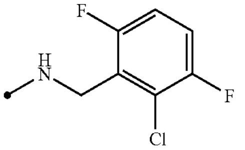 | 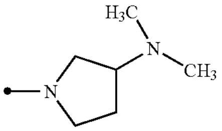 | MS m/z 602 $(M + H)^+$ |
| 8-324 | 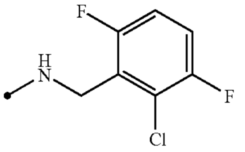 | 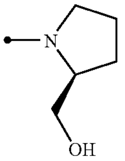 | MS m/z 589 $(M + H)^+$ |
| 8-325 | 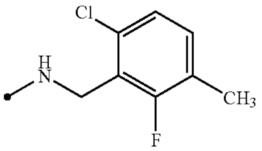 | 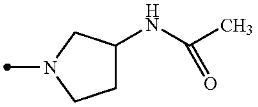 | MS m/z 612 $(M + H)^+$ |
| 8-326 | 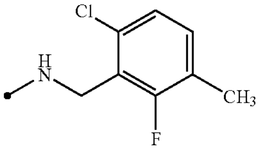 | 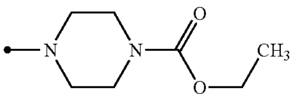 | MS m/z 642 $(M + H)^+$ |
| 8-327 | 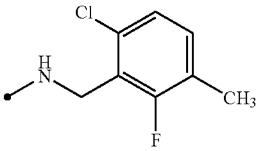 | 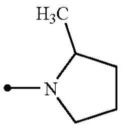 | MS m/z 569 $(M + H)^+$ |
| 8-328 | 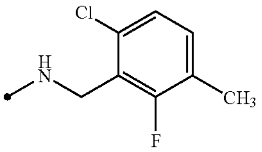 | 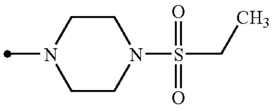 | MS m/z 662 $(M + H)^+$ |
| 8-329 | 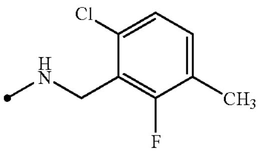 | 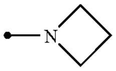 | MS m/z 541 $(M + H)^+$ |

TABLE 8-continued
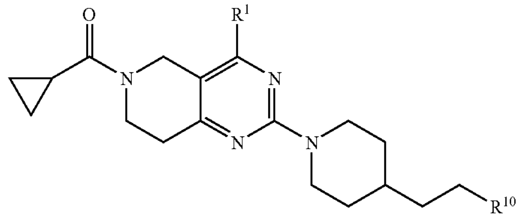
| Compound Number | •—$R^1$ | •—$R^{10}$ | Spectrum Data |
|---|---|---|---|
| 8-330 | 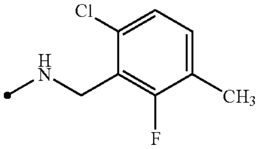 | 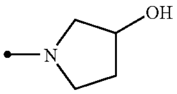 | MS m/z 571 $(M + H)^+$ |
| 8-331 | 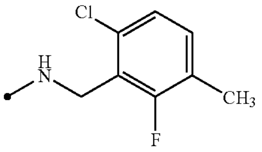 | 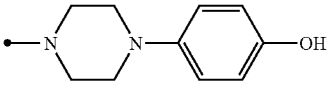 | MS m/z 662 $(M + H)^+$ |
| 8-332 | 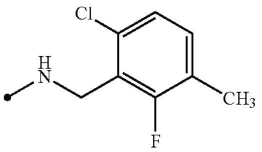 | 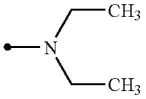 | MS m/z 557 $(M + H)^+$ |
| 8-333 | 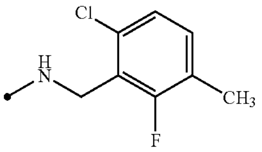 | 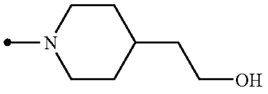 | MS m/z 613 $(M + H)^+$ |
| 8-334 | 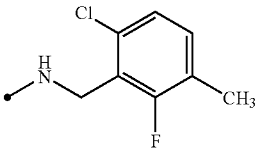 | 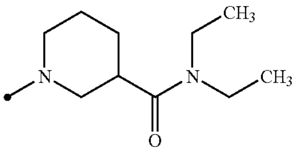 | MS m/z 668 $(M + H)^+$ |
| 8-335 | 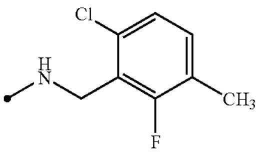 | 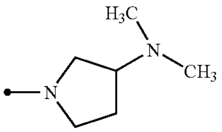 | MS m/z 598 $(M + H)^+$ |
| 8-336 | 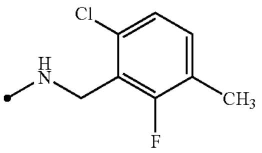 | 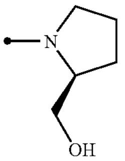 | MS m/z 585 $(M + H)^+$ |
| 8-337 | 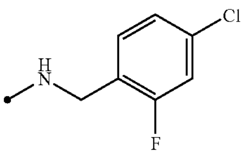 | 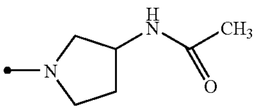 | MS m/z 598 $(M + H)^+$ |

TABLE 8-continued
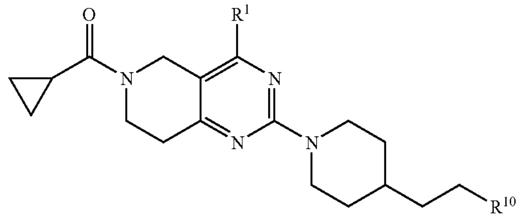
| Compound Number | •—$R^1$ | •—$R^{10}$ | Spectrum Data |
| --- | --- | --- | --- |
| 8-338 | 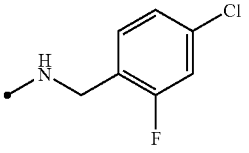 | 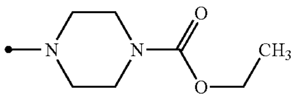 | MS m/z 628 $(M + H)^+$ |
| 8-339 | 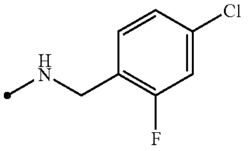 | 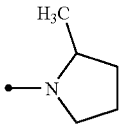 | MS m/z 555 $(M + H)^+$ |
| 8-340 | 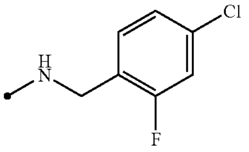 | 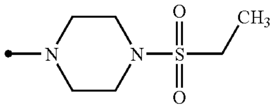 | MS m/z 648 $(M + H)^+$ |
| 8-341 | 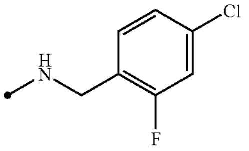 | 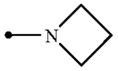 | MS m/z 527 $(M + H)^+$ |
| 8-342 | 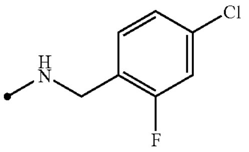 | 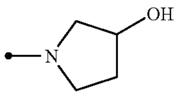 | MS m/z 557 $(M + H)^+$ |
| 8-343 | 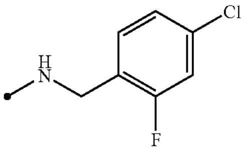 | 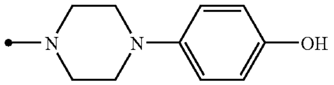 | MS m/z 648 $(M + H)^+$ |
| 8-344 | 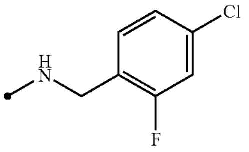 | 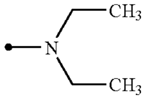 | MS m/z 543 $(M + H)^+$ |
| 8-345 | 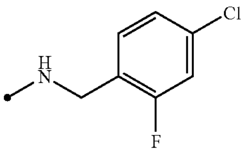 | 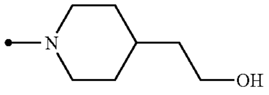 | MS m/z 599 $(M + H)^+$ |

TABLE 8-continued
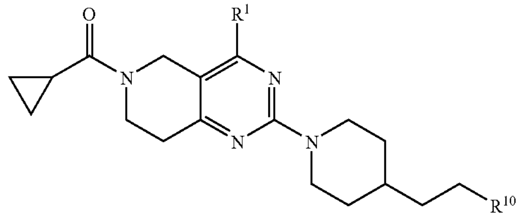
| Compound Number | •—$R^1$ | •—$R^{10}$ | Spectrum Data |
|---|---|---|---|
| 8-346 | 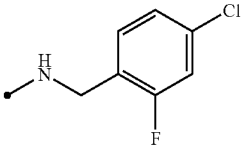 | 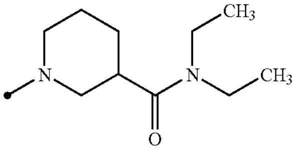 | MS m/z 654 $(M + H)^+$ |
| 8-347 | 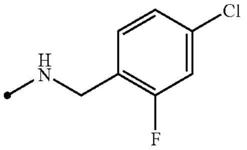 | 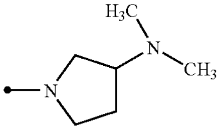 | MS m/z 584 $(M + H)^+$ |
| 8-348 | 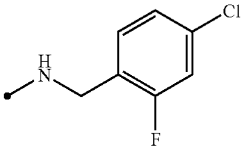 | 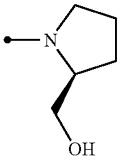 | MS m/z 571 $(M + H)^+$ |
| 8-349 | 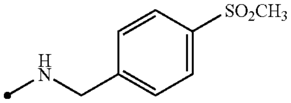 | 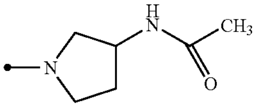 | MS m/z 624 $(M + H)^+$ |
| 8-350 | 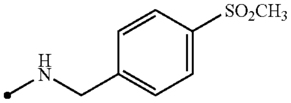 | 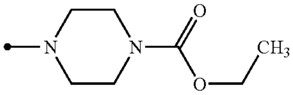 | MS m/z 654 $(M + H)^+$ |
| 8-351 | 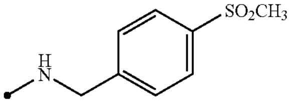 | 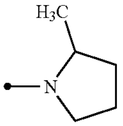 | MS m/z 581 $(M + H)^+$ |
| 8-352 | 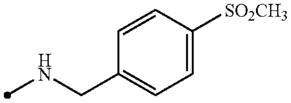 | 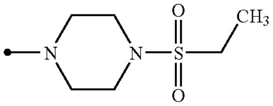 | MS m/z 674 $(M + H)^+$ |
| 8-353 | 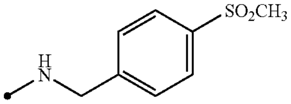 | 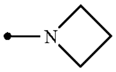 | MS m/z 553 $(M + H)^+$ |
| 8-354 | 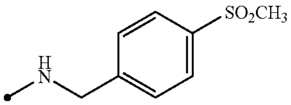 | 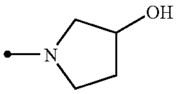 | MS m/z 583 $(M + H)^+$ |

TABLE 8-continued
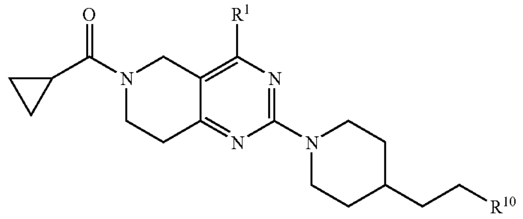
| Compound Number | •—$R^1$ | •—$R^{10}$ | Spectrum Data |
|---|---|---|---|
| 8-355 | 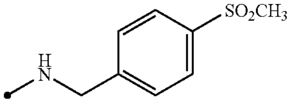 | 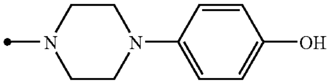 | MS m/z 674 $(M + H)^+$ |
| 8-356 | 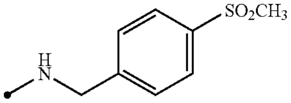 | 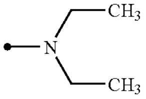 | MS m/z 569 $(M + H)^+$ |
| 8-357 | 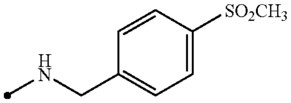 | 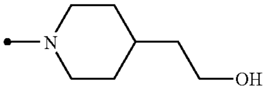 | MS m/z 625 $(M + H)^+$ |
| 8-358 | 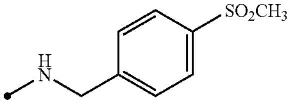 | 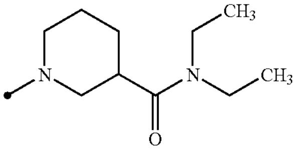 | MS m/z 680 $(M + H)^+$ |
| 8-359 | 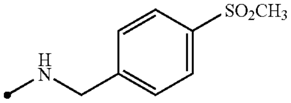 | 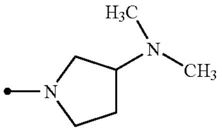 | MS m/z 610 $(M + H)^+$ |
| 8-360 | 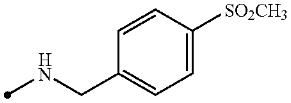 | 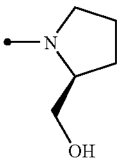 | MS m/z 597 $(M + H)^+$ |
| 8-361 | 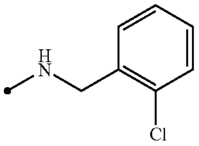 | 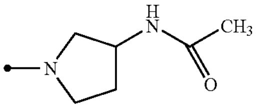 | MS m/z 580 $(M + H)^+$ |
| 8-362 | 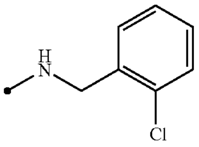 | 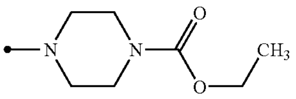 | MS m/z 610 $(M + H)^+$ |
| 8-363 | 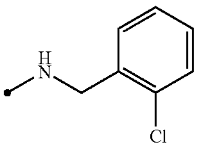 | 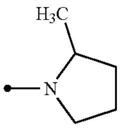 | MS m/z 537 $(M + H)^+$ |

TABLE 8-continued
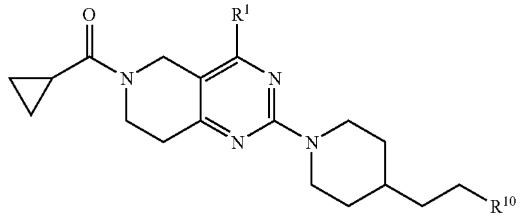
| Compound Number | •—R¹ | •—R¹⁰ | Spectrum Data |
|---|---|---|---|
| 8-364 | 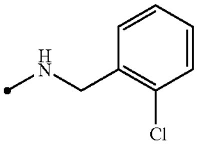 | 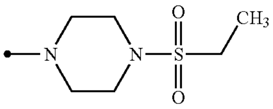 | MS m/z 630 $(M + H)^+$ |
| 8-365 | 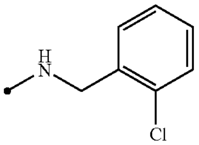 | 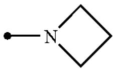 | MS m/z 509 $(M + H)^+$ |
| 8-366 | 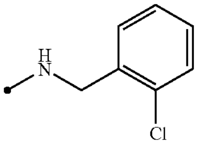 | 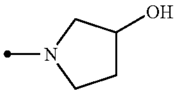 | MS m/z 539 $(M + H)^+$ |
| 8-367 | 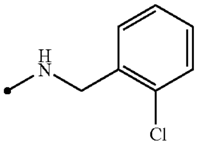 | 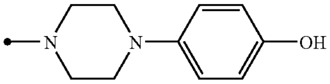 | MS m/z 630 $(M + H)^+$ |
| 8-368 | 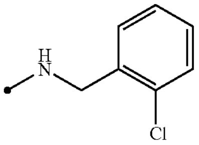 | 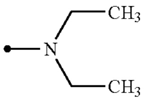 | MS m/z 525 $(M + H)^+$ |
| 8-369 | 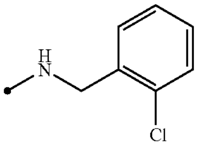 | 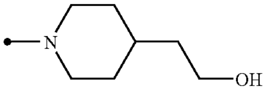 | MS m/z 581 $(M + H)^+$ |
| 8-370 | 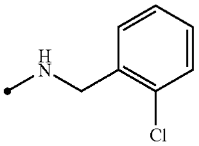 | 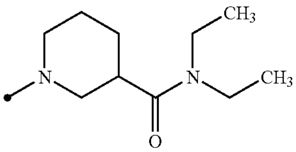 | MS m/z 636 $(M + H)^+$ |
| 8-371 | 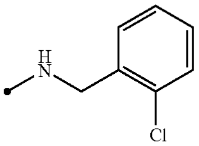 | 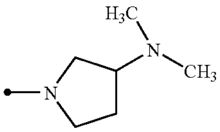 | MS m/z 566 $(M + H)^+$ |

TABLE 8-continued
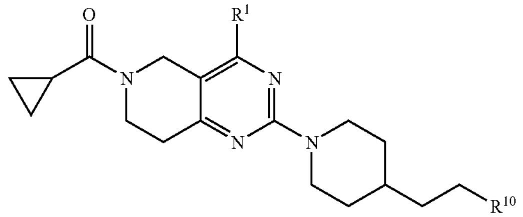
| Compound Number | •—$R^1$ | •—$R^{10}$ | Spectrum Data |
|---|---|---|---|
| 8-372 | 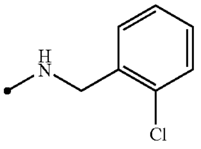 | 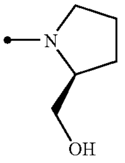 | MS m/z 553 $(M + H)^+$ |
| 8-373 | 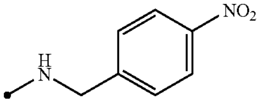 | 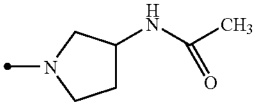 | MS m/z 591 $(M + H)^+$ |
| 8-374 | 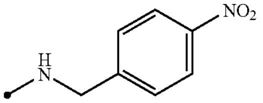 | 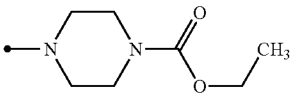 | MS m/z 621 $(M + H)^+$ |
| 8-375 | 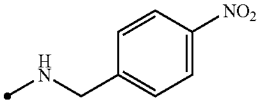 | 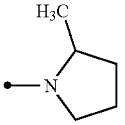 | MS m/z 548 $(M + H)^+$ |
| 8-376 | 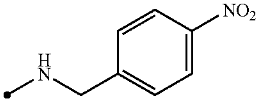 | 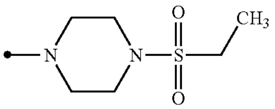 | MS m/z 641 $(M + H)^+$ |
| 8-377 | 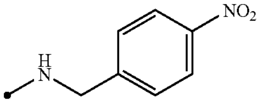 | 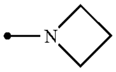 | MS m/z 520 $(M + H)^+$ |
| 8-378 | 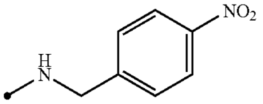 | 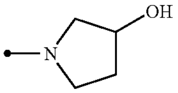 | MS m/z 550 $(M + H)^+$ |
| 8-379 | 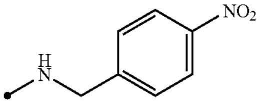 | 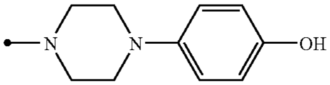 | MS m/z 641 $(M + H)^+$ |
| 8-380 | 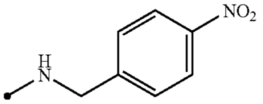 | 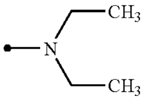 | MS m/z 536 $(M + H)^+$ |
| 8-381 | 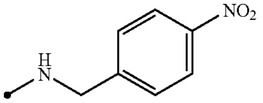 | 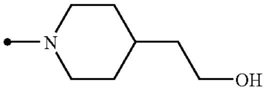 | MS m/z 592 $(M + H)^+$ |

TABLE 8-continued
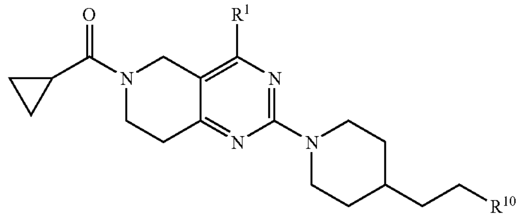
| Compound Number | •—R¹ | •—R¹⁰ | Spectrum Data |
|---|---|---|---|
| 8-382 | 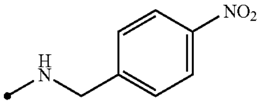 | 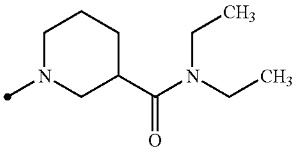 | MS m/z 647 $(M+H)^+$ |
| 8-383 | 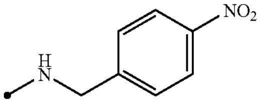 | 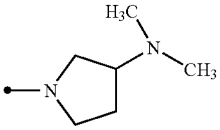 | MS m/z 577 $(M+H)^+$ |
| 8-384 | 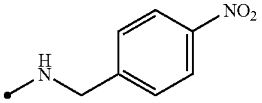 | 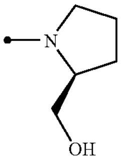 | MS m/z 564 $(M+H)^+$ |
| 8-385 | 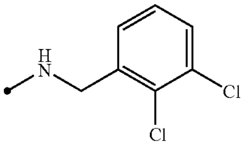 | 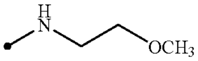 | MS m/z 561 $(M+H)^+$ |
| 8-386 | 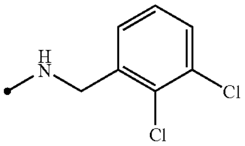 | 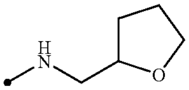 | MS m/z 587 $(M+H)^+$ |
| 8-387 | 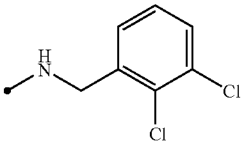 | 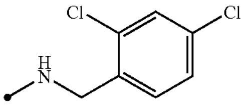 | MS m/z 661 $(M+H)^+$ |
| 8-388 | 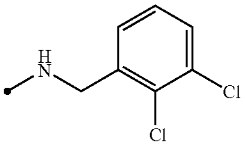 | 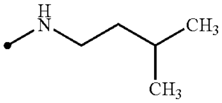 | MS m/z 573 $(M+H)^+$ |
| 8-389 | 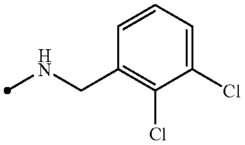 | 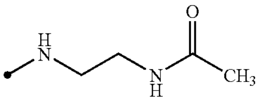 | MS m/z 588 $(M+H)^+$ |

TABLE 8-continued
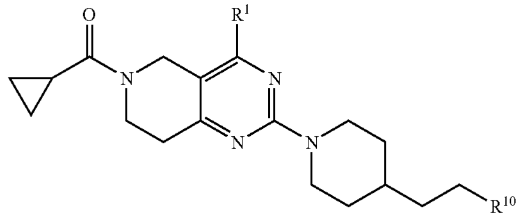
| Compound Number | •—R¹ | •—R¹⁰ | Spectrum Data |
|---|---|---|---|
| 8-390 | 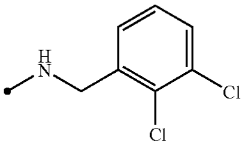 | 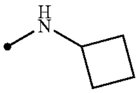 | MS m/z 557 $(M+H)^+$ |
| 8-391 | 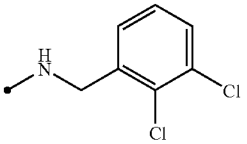 | 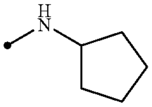 | MS m/z 571 $(M+H)^+$ |
| 8-392 | 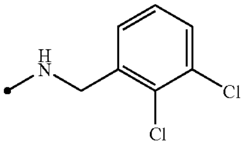 | 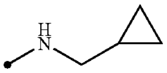 | MS m/z 557 $(M+H)^+$ |
| 8-393 | 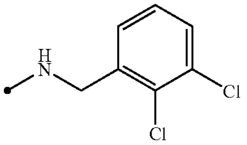 | 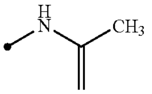 | MS m/z 557 $(M+H)^+$ |
| 8-394 | 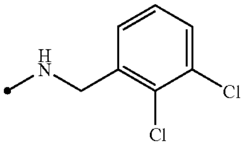 | 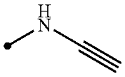 | MS m/z 541 $(M+H)^+$ |
| 8-395 | 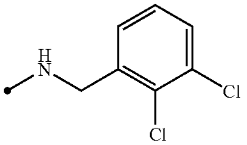 | 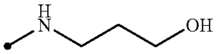 | MS m/z 561 $(M+H)^+$ |
| 8-396 | 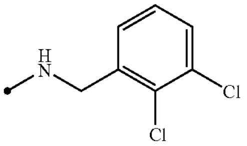 | 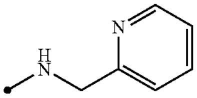 | MS m/z 594 $(M+H)^+$ |
| 8-397 | 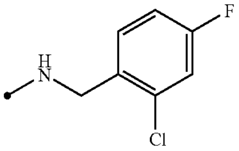 | 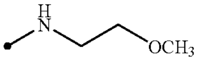 | MS m/z 545 $(M+H)^+$ |

TABLE 8-continued
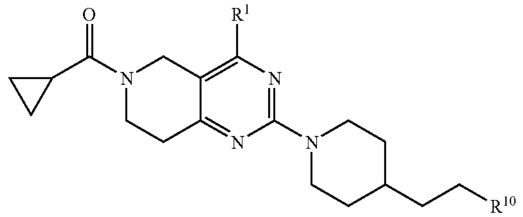
| Compound Number | •—$R^1$ | •—$R^{10}$ | Spectrum Data |
|---|---|---|---|
| 8-398 | 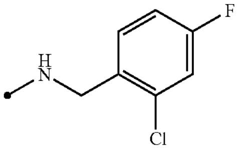 | 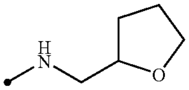 | MS m/z 571 $(M+H)^+$ |
| 8-399 | 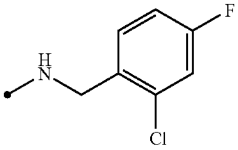 | 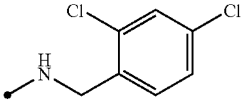 | MS m/z 645 $(M+H)^+$ |
| 8-400 | 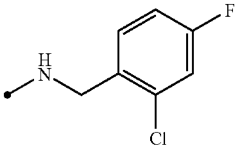 | 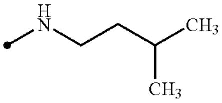 | MS m/z 557 $(M+H)^+$ |
| 8-401 | 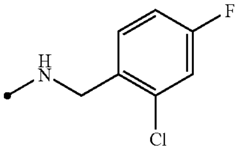 | 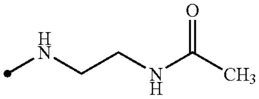 | MS m/z 572 $(M+H)^+$ |
| 8-402 | 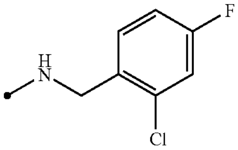 | 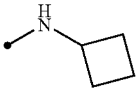 | MS m/z 541 $(M+H)^+$ |
| 8-403 | 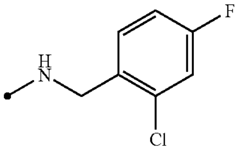 | 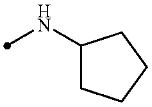 | MS m/z 555 $(M+H)^+$ |
| 8-404 | 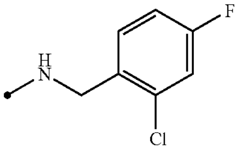 | 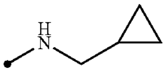 | MS m/z 541 $(M+H)^+$ |
| 8-405 | 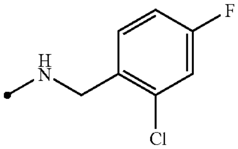 | 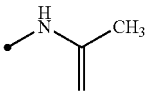 | MS m/z 541 $(M+H)^+$ |

TABLE 8-continued
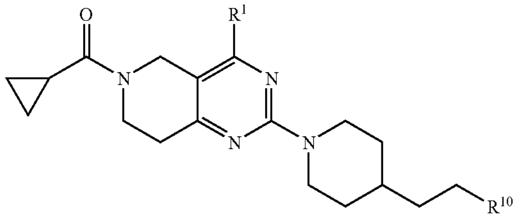
| Compound Number | •—$R^1$ | •—$R^{10}$ | Spectrum Data |
|---|---|---|---|
| 8-406 | 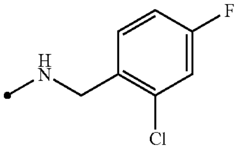 | 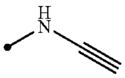 | MS m/z 525 $(M + H)^+$ |
| 8-407 | 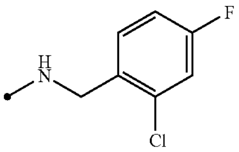 | 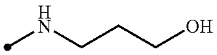 | MS m/z 545 $(M + H)^+$ |
| 8-408 | 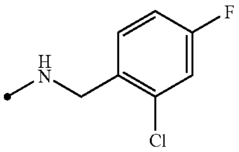 | 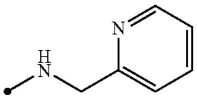 | MS m/z 578 $(M + H)^+$ |
| 8-409 | 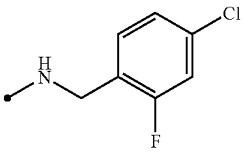 | 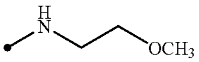 | MS m/z 545 $(M + H)^+$ |
| 8-410 | 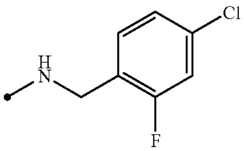 | 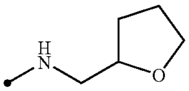 | MS m/z 571 $(M + H)^+$ |
| 8-411 | 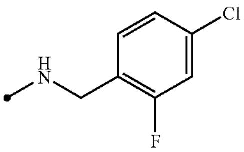 | 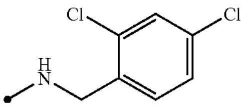 | MS m/z 645 $(M + H)^+$ |
| 8-412 | 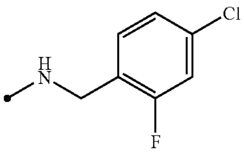 | 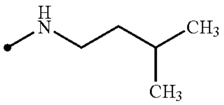 | MS m/z 557 $(M + H)^+$ |
| 8-413 | 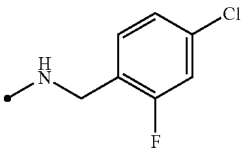 | 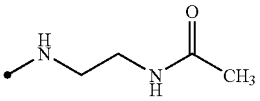 | MS m/z 572 $(M + H)^+$ |

TABLE 8-continued
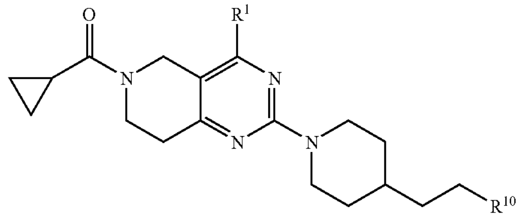
| Compound Number | •—$R^1$ | •—$R^{10}$ | Spectrum Data |
|---|---|---|---|
| 8-414 | 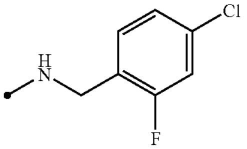 | 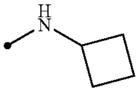 | MS m/z 541 $(M + H)^+$ |
| 8-415 | 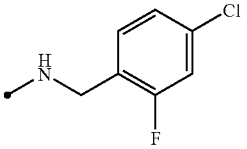 | 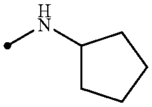 | MS m/z 555 $(M + H)^+$ |
| 8-416 | 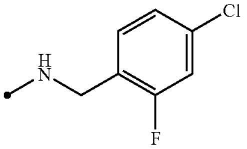 | 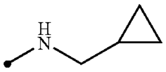 | MS m/z 541 $(M + H)^+$ |
| 8-417 | 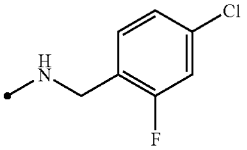 | 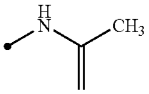 | MS m/z 541 $(M + H)^+$ |
| 8-418 | 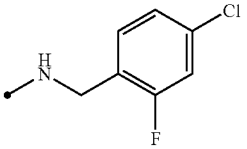 | 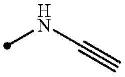 | MS m/z 525 $(M + H)^+$ |
| 8-419 | 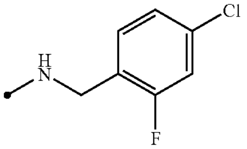 | 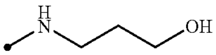 | MS m/z 545 $(M + H)^+$ |
| 8-420 | 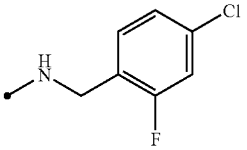 | 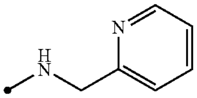 | MS m/z 578 $(M + H)^+$ |
| 8-421 | 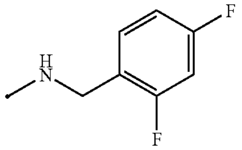 | 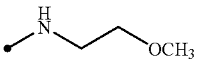 | MS m/z 529 $(M + H)^+$ |

TABLE 8-continued
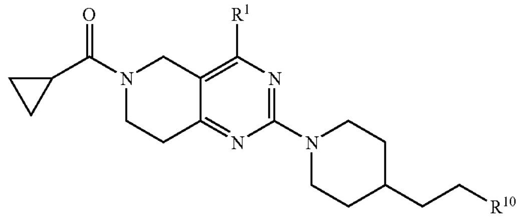
| Compound Number | •—R¹ | •—R¹⁰ | Spectrum Data |
|---|---|---|---|
| 8-422 | 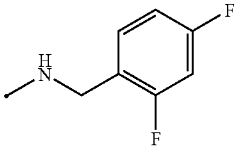 | 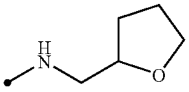 | MS m/z 555 $(M + H)^+$ |
| 8-423 | 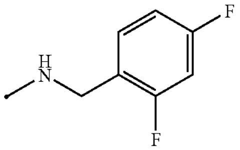 | 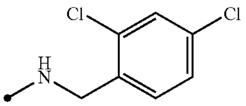 | MS m/z 629 $(M + H)^+$ |
| 8-424 | 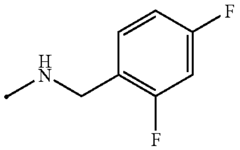 | 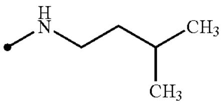 | MS m/z 541 $(M + H)^+$ |
| 8-425 | 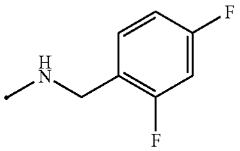 | 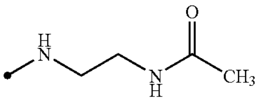 | MS m/z 556 $(M + H)^+$ |
| 8-426 | 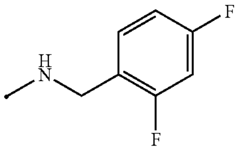 | 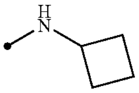 | MS m/z 525 $(M + H)^+$ |
| 8-427 | 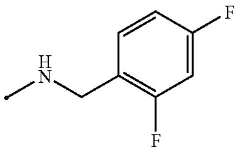 | 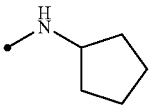 | MS m/z 539 $(M + H)^+$ |
| 8-428 | 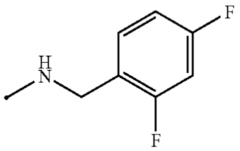 | 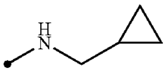 | MS m/z 525 $(M + H)^+$ |
| 8-429 | 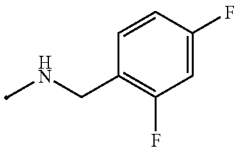 | 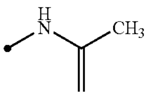 | MS m/z 525 $(M + H)^+$ |

TABLE 8-continued
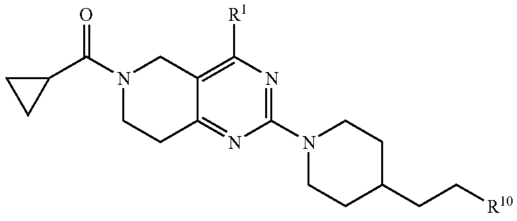
| Compound Number | •—$R^1$ | •—$R^{10}$ | Spectrum Data |
|---|---|---|---|
| 8-430 | 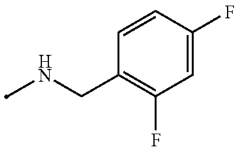 | 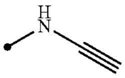 | MS m/z 509 $(M + H)^+$ |
| 8-431 | 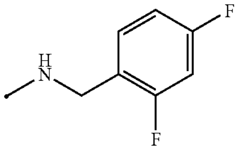 | 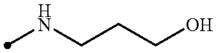 | MS m/z 529 $(M + H)^+$ |
| 8-432 | 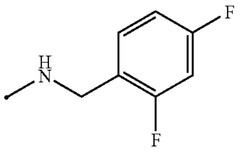 | 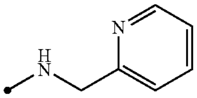 | MS m/z 562 $(M + H)^+$ |
| 8-433 | 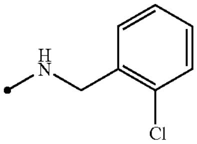 | 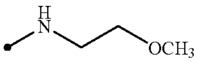 | MS m/z 527 $(M + H)^+$ |
| 8-434 | 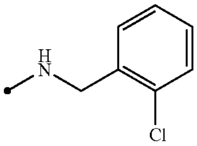 | 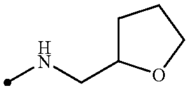 | MS m/z 553 $(M + H)^+$ |
| 8-435 | 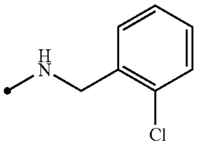 | 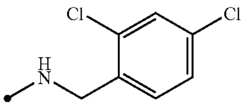 | MS m/z 627 $(M + H)^+$ |
| 8-436 | 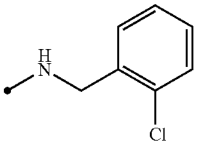 | 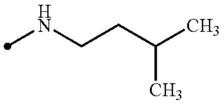 | MS m/z 539 $(M + H)^+$ |
| 8-437 | 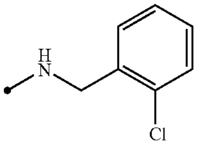 | 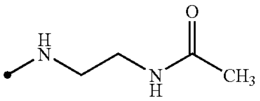 | MS m/z 554 $(M + H)^+$ |

TABLE 8-continued
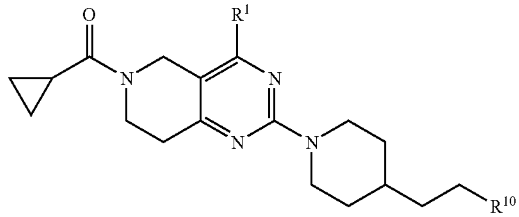
| Compound Number | •—$R^1$ | •—$R^{10}$ | Spectrum Data |
|---|---|---|---|
| 8-438 | 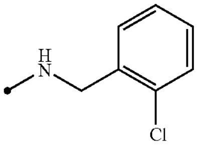 | 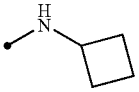 | MS m/z 523 $(M + H)^+$ |
| 8-439 | 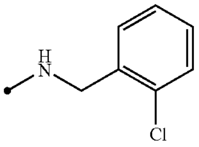 | 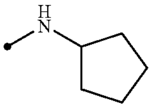 | MS m/z 537 $(M + H)^+$ |
| 8-440 | 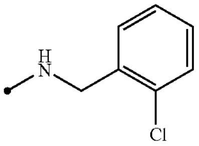 | 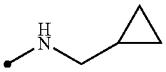 | MS m/z 523 $(M + H)^+$ |
| 8-441 | 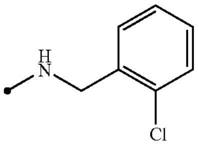 | 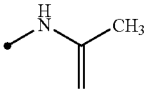 | MS m/z 523 $(M + H)^+$ |
| 8-442 | 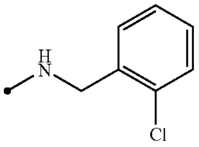 | 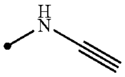 | MS m/z 507 $(M + H)^+$ |
| 8-443 | 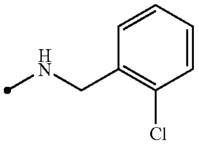 | 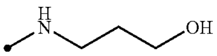 | MS m/z 527 $(M + H)^+$ |
| 8-444 | 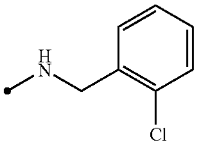 | 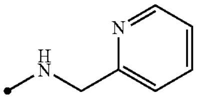 | MS m/z 560 $(M + H)^+$ |
| 8-445 | 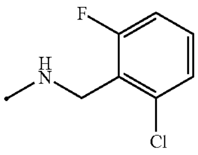 | 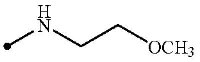 | MS m/z 545 $(M + H)^+$ |

TABLE 8-continued
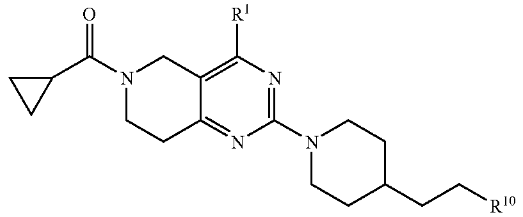
| Compound Number | •—$R^1$ | •—$R^{10}$ | Spectrum Data |
|---|---|---|---|
| 8-446 | 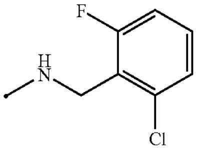 | 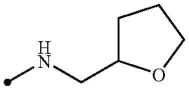 | MS m/z 571 $(M + H)^+$ |
| 8-447 | 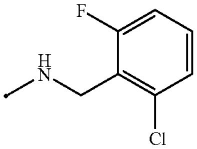 | 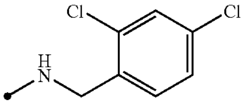 | MS m/z 645 $(M + H)^+$ |
| 8-448 | 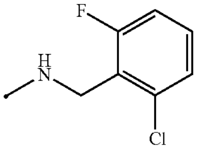 | 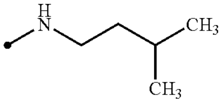 | MS m/z 557 $(M + H)^+$ |
| 8-449 | 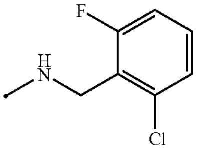 | 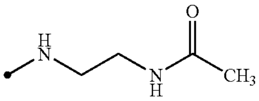 | MS m/z 572 $(M + H)^+$ |
| 8-450 | 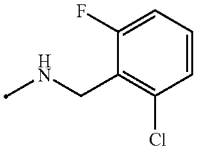 | 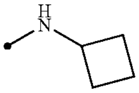 | MS m/z 541 $(M + H)^+$ |
| 8-451 | 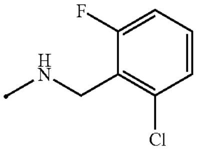 | 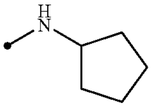 | MS m/z 555 $(M + H)^+$ |
| 8-452 | 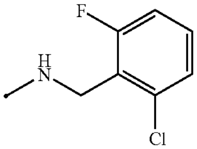 | 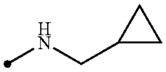 | MS m/z 541 $(M + H)^+$ |
| 8-453 | 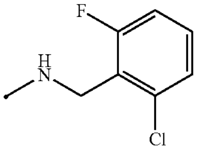 | 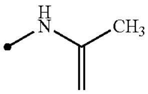 | MS m/z 541 $(M + H)^+$ |

TABLE 8-continued
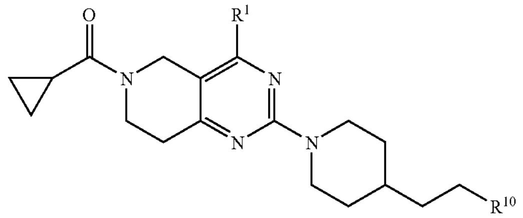
| Compound Number | •—$R^1$ | •—$R^{10}$ | Spectrum Data |
|---|---|---|---|
| 8-454 | 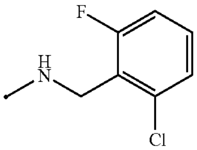 | 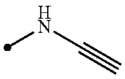 | MS m/z 525 $(M+H)^+$ |
| 8-455 | 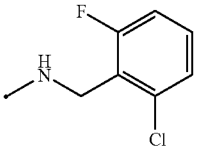 | 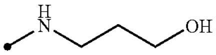 | MS m/z 545 $(M+H)^+$ |
| 8-456 | 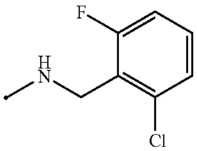 | 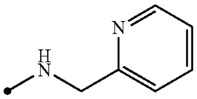 | MS m/z 578 $(M+H)^+$ |
| 8-457 | 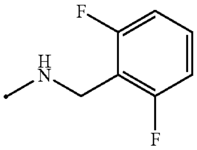 | 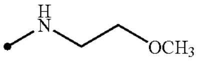 | MS m/z 529 $(M+H)^+$ |
| 8-458 | 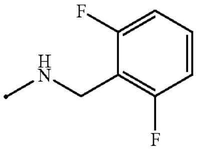 | 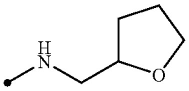 | MS m/z 555 $(M+H)^+$ |
| 8-459 | 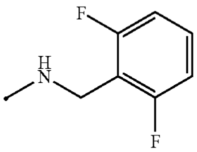 | 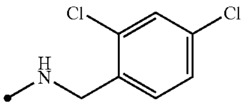 | MS m/z 629 $(M+H)^+$ |
| 8-460 | 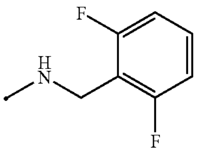 | 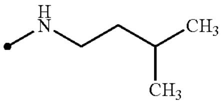 | MS m/z 541 $(M+H)^+$ |

TABLE 8-continued
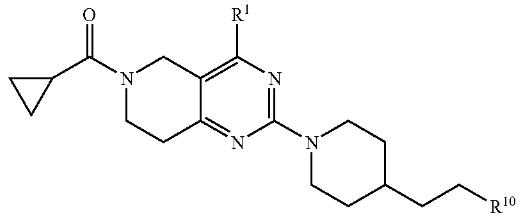
| Compound Number | •—$R^1$ | •—$R^{10}$ | Spectrum Data |
|---|---|---|---|
| 8-461 | 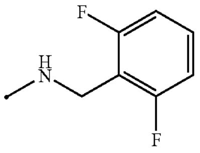 | 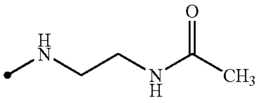 | MS m/z 556 $(M+H)^+$ |
| 8-462 | 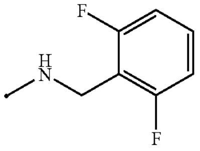 | 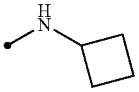 | MS m/z 525 $(M+H)^+$ |
| 8-463 | 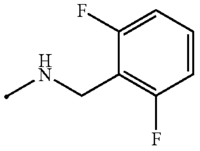 | 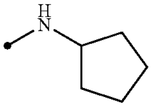 | MS m/z 539 $(M+H)^+$ |
| 8-464 | 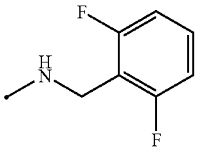 | 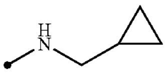 | MS m/z 525 $(M+H)^+$ |
| 8-465 | 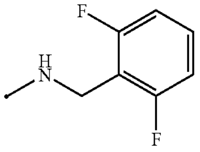 | 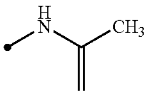 | MS m/z 525 $(M+H)^+$ |
| 8-466 | 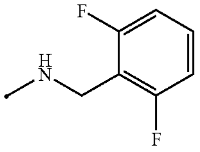 | 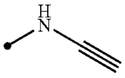 | MS m/z 509 $(M+H)^+$ |
| 8-467 | 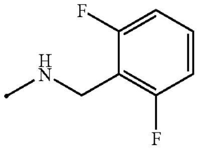 | 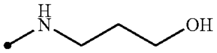 | MS m/z 529 $(M+H)^+$ |
| 8-468 | 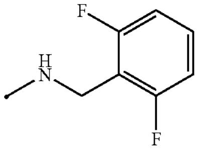 | 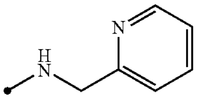 | MS m/z 562 $(M+H)^+$ |

TABLE 8-continued
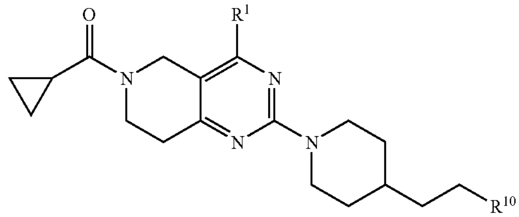
| Compound Number | •—$R^1$ | •—$R^{10}$ | Spectrum Data |
|---|---|---|---|
| 8-469 | 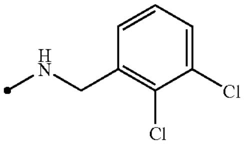 | 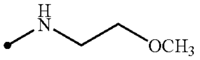 | MS m/z 561 $(M + H)^+$ |
| 8-470 | 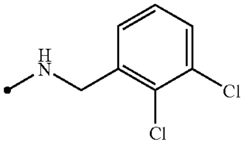 | 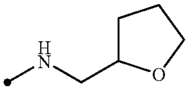 | MS m/z 587 $(M + H)^+$ |
| 8-471 | 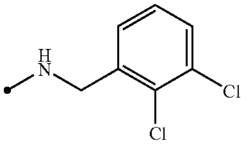 | 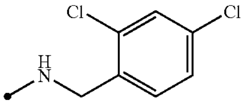 | MS m/z 661 $(M + H)^+$ |
| 8-472 | 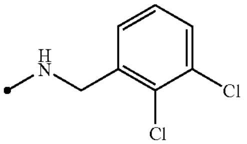 | 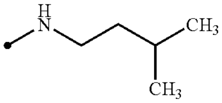 | MS m/z 573 $(M + H)^+$ |
| 8-473 | 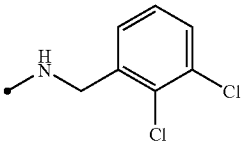 | 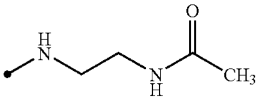 | MS m/z 588 $(M + H)^+$ |
| 8-474 | 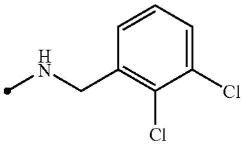 | 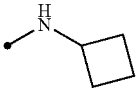 | MS m/z 557 $(M + H)^+$ |
| 8-475 | 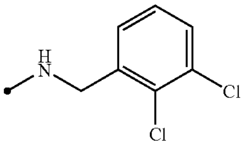 | 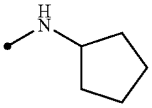 | MS m/z 571 $(M + H)^+$ |
| 8-476 | 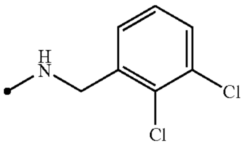 | 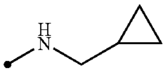 | MS m/z 557 $(M + H)^+$ |

TABLE 8-continued
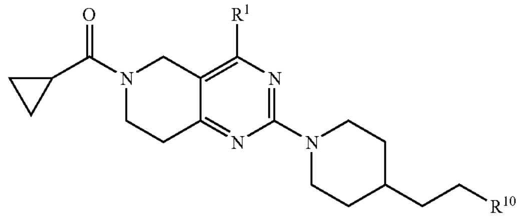
| Compound Number | •—$R^1$ | •—$R^{10}$ | Spectrum Data |
|---|---|---|---|
| 8-477 | 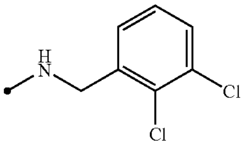 | 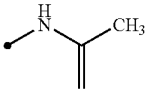 | MS m/z 557 $(M + H)^+$ |
| 8-478 | 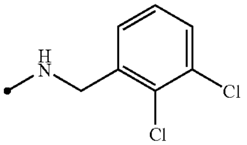 | 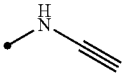 | MS m/z 541 $(M + H)^+$ |
| 8-479 | 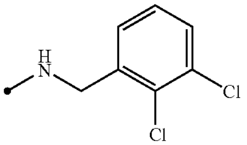 | 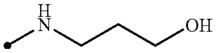 | MS m/z 561 $(M + H)^+$ |
| 8-480 | 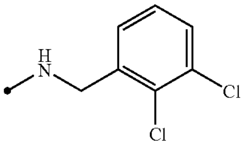 | 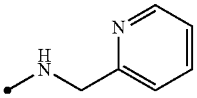 | MS m/z 594 $(M + H)^+$ |
| 8-481 | 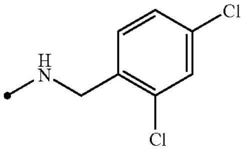 | 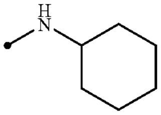 | MS m/z 585 $(M + H)^+$ |
| 8-482 | 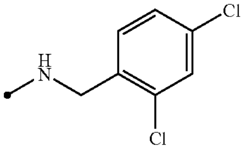 | 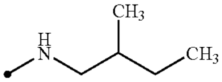 | MS m/z 573 $(M + H)^+$ |
| 8-483 | 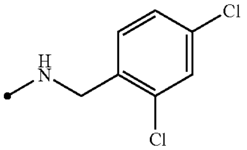 | 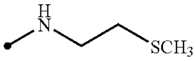 | MS m/z 577 $(M + H)^+$ |
| 8-484 | 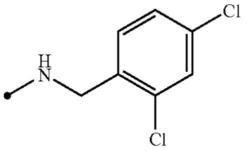 | 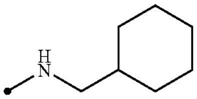 | MS m/z 599 $(M + H)^+$ |

TABLE 8-continued
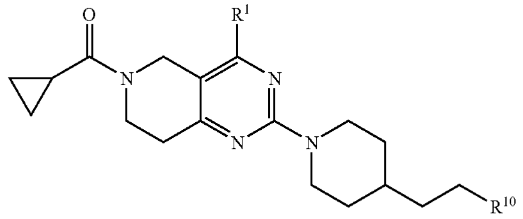
| Compound Number | •—$R^1$ | •—$R^{10}$ | Spectrum Data |
|---|---|---|---|
| 8-485 | 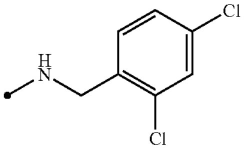 | 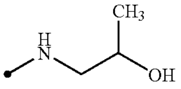 | MS m/z 561 $(M + H)^+$ |
| 8-486 | 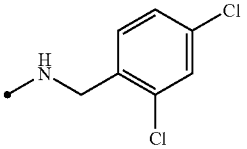 | 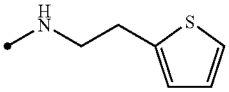 | MS m/z 613 $(M + H)^+$ |
| 8-487 | 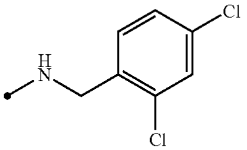 | 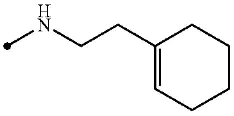 | MS m/z 611 $(M + H)^+$ |
| 8-488 | 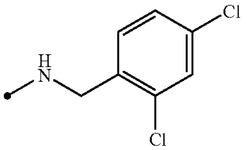 | 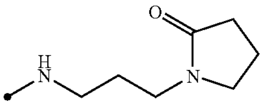 | MS m/z 628 $(M + H)^+$ |
| 8-489 | 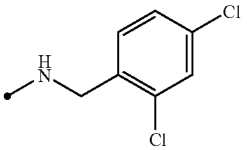 | 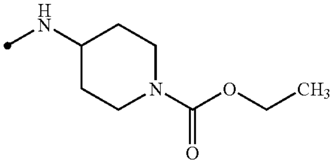 | MS m/z 658 $(M + H)^+$ |
| 8-490 | 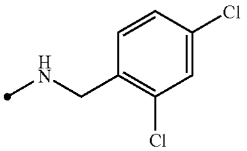 | 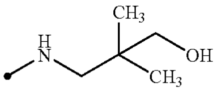 | MS m/z 589 $(M + H)^+$ |
| 8-491 | 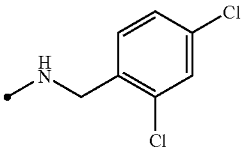 | 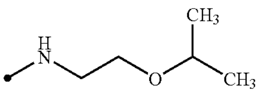 | MS m/z 589 $(M + H)^+$ |
| 8-492 | 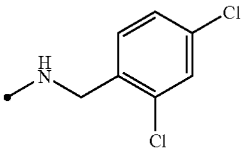 | 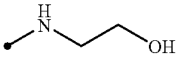 | MS m/z 547 $(M + H)^+$ |

TABLE 8-continued
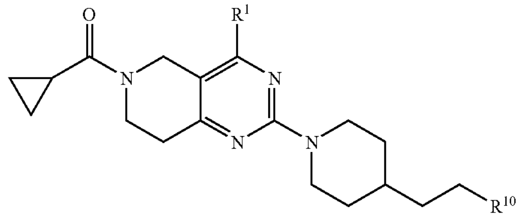
| Compound Number | •—$R^1$ | •—$R^{10}$ | Spectrum Data |
|---|---|---|---|
| 8-493 | 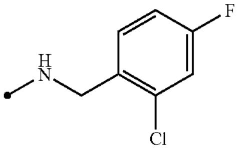 | 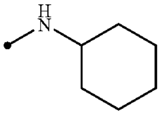 | MS m/z 569 $(M + H)^+$ |
| 8-494 | 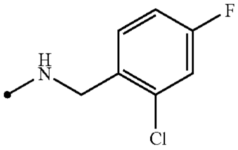 | 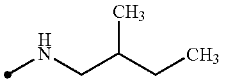 | MS m/z 557 $(M + H)^+$ |
| 8-495 | 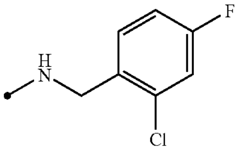 | 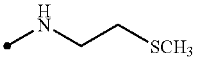 | MS m/z 561 $(M + H)^+$ |
| 8-496 | 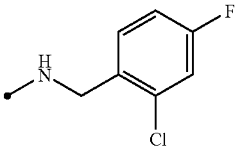 | 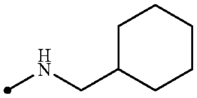 | MS m/z 583 $(M + H)^+$ |
| 8-497 | 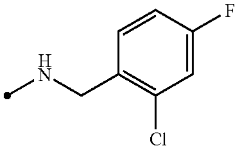 | 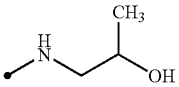 | MS m/z 545 $(M + H)^+$ |
| 8-498 | 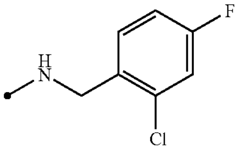 | 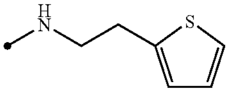 | MS m/z 597 $(M + H)^+$ |
| 8-499 | 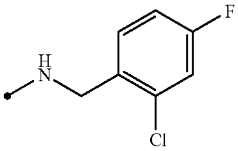 | 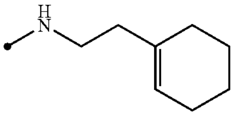 | MS m/z 595 $(M + H)^+$ |
| 8-500 | 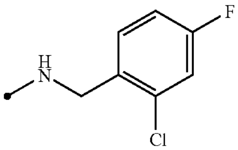 | 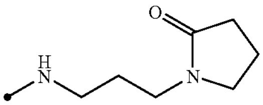 | MS m/z 612 $(M + H)^+$ |

TABLE 8-continued
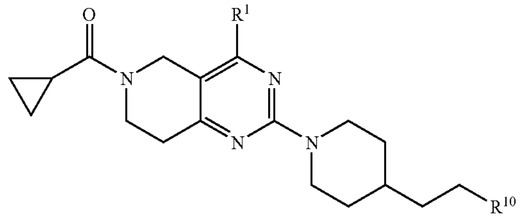
| Compound Number | •—$R^1$ | •—$R^{10}$ | Spectrum Data |
|---|---|---|---|
| 8-501 | 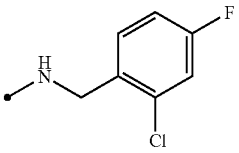 | 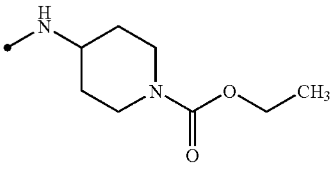 | MS m/z 642 $(M+H)^+$ |
| 8-502 | 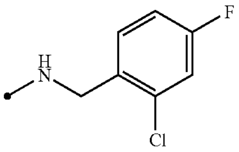 | 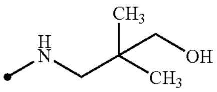 | MS m/z 573 $(M+H)^+$ |
| 8-503 | 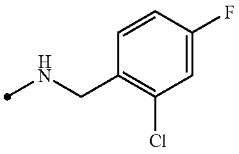 | 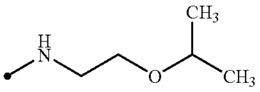 | MS m/z 573 $(M+H)^+$ |
| 8-504 | 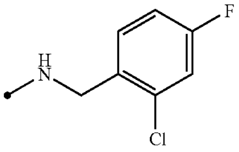 | 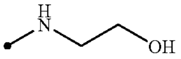 | MS m/z 531 $(M+H)^+$ |
| 8-505 | 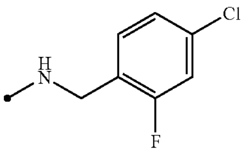 | 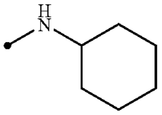 | MS m/z 569 $(M+H)^+$ |
| 8-506 | 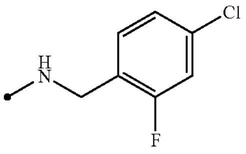 | 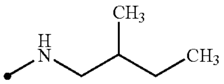 | MS m/z 557 $(M+H)^+$ |
| 8-507 | 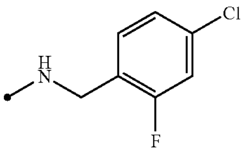 | 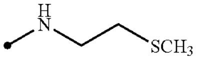 | MS m/z 561 $(M+H)^+$ |
| 8-508 | 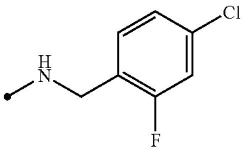 | 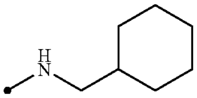 | MS m/z 583 $(M+H)^+$ |

TABLE 8-continued
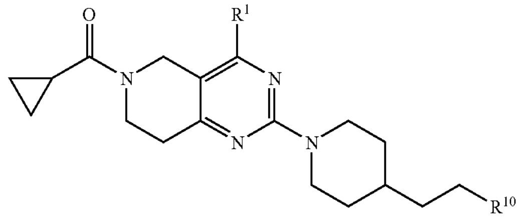
| Compound Number | •—$R^1$ | •—$R^{10}$ | Spectrum Data |
|---|---|---|---|
| 8-509 | 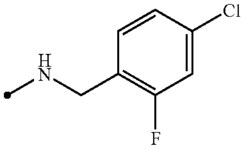 | 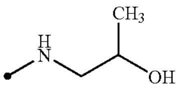 | MS m/z 545 $(M + H)^+$ |
| 8-510 | 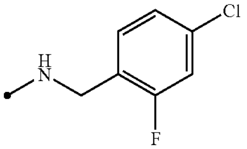 | 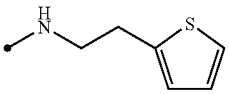 | MS m/z 597 $(M + H)^+$ |
| 8-511 | 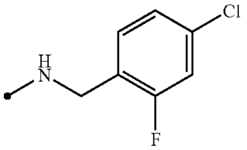 | 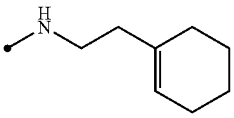 | MS m/z 595 $(M + H)^+$ |
| 8-512 | 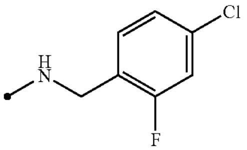 | 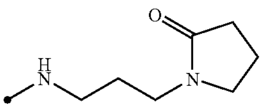 | MS m/z 612 $(M + H)^+$ |
| 8-513 | 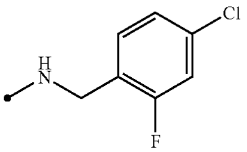 | 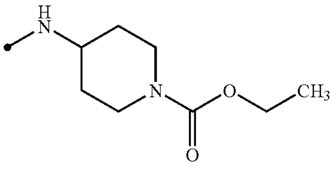 | MS m/z 642 $(M + H)^+$ |
| 8-514 | 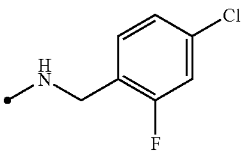 | 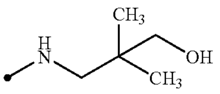 | MS m/z 573 $(M + H)^+$ |
| 8-515 | 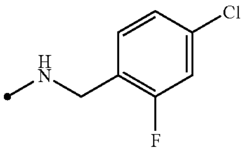 | 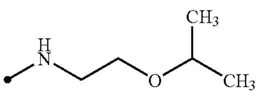 | MS m/z 573 $(M + H)^+$ |
| 8-516 | 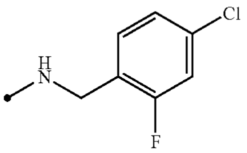 | 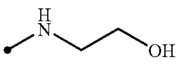 | MS m/z 531 $(M + H)^+$ |

TABLE 8-continued
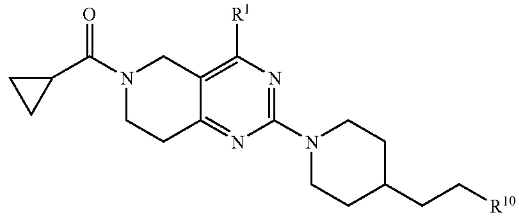
| Compound Number | •—$R^1$ | •—$R^{10}$ | Spectrum Data |
|---|---|---|---|
| 8-517 | 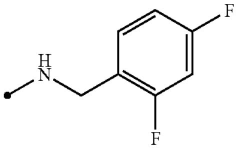 | 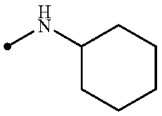 | MS m/z 553 $(M + H)^+$ |
| 8-518 | 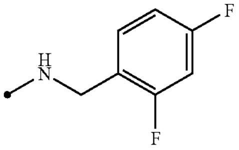 | 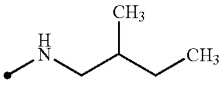 | MS m/z 541 $(M + H)^+$ |
| 8-519 | 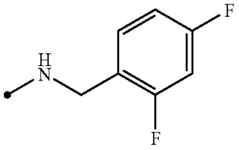 | 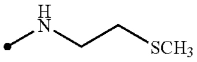 | MS m/z 545 $(M + H)^+$ |
| 8-520 | 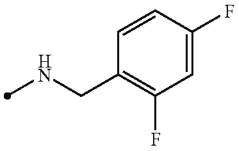 | 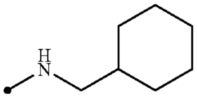 | MS m/z 567 $(M + H)^+$ |
| 8-521 | 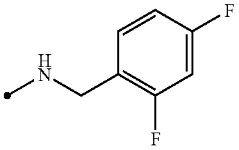 | 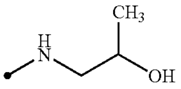 | MS m/z 529 $(M + H)^+$ |
| 8-522 | 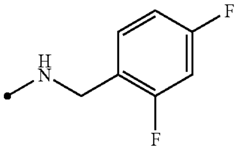 | 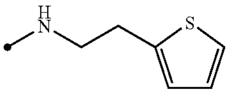 | MS m/z 581 $(M + H)^+$ |
| 8-523 | 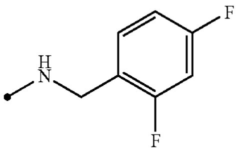 | 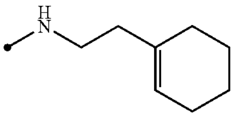 | MS m/z 579 $(M + H)^+$ |
| 8-524 | 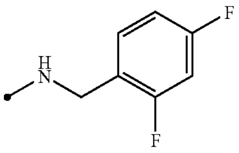 | 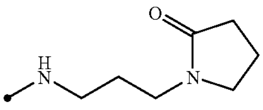 | MS m/z 596 $(M + H)^+$ |

TABLE 8-continued
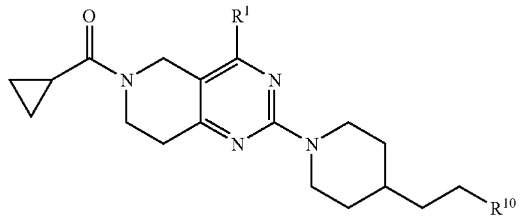
| Compound Number | •—R¹ | •—R¹⁰ | Spectrum Data |
|---|---|---|---|
| 8-525 | 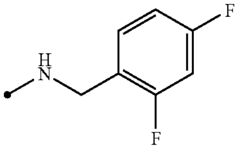 | 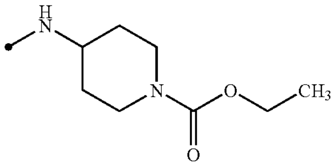 | MS m/z 626 $(M + H)^+$ |
| 8-526 | 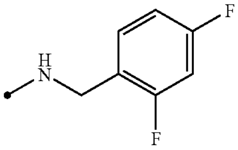 | 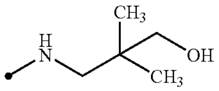 | MS m/z 557 $(M + H)^+$ |
| 8-527 | 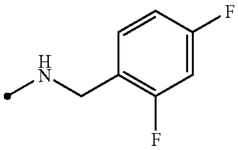 | 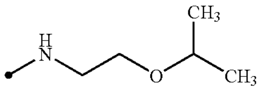 | MS m/z 557 $(M + H)^+$ |
| 8-528 | 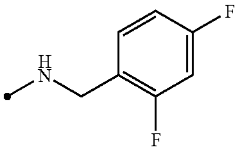 | 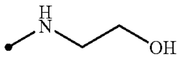 | MS m/z 515 $(M + H)^+$ |
| 8-529 | 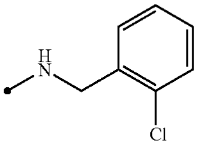 | 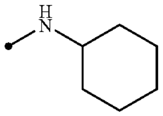 | MS m/z 551 $(M + H)^+$ |
| 8-530 | 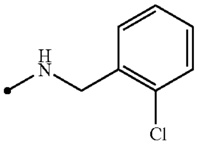 | 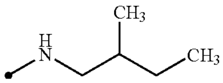 | MS m/z 539 $(M + H)^+$ |
| 8-531 | 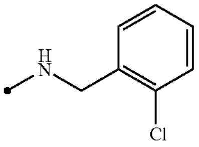 | 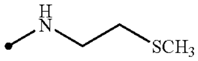 | MS m/z 543 $(M + H)^+$ |
| 8-532 | 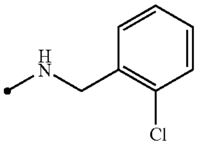 | 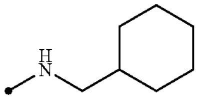 | MS m/z 565 $(M + H)^+$ |

TABLE 8-continued
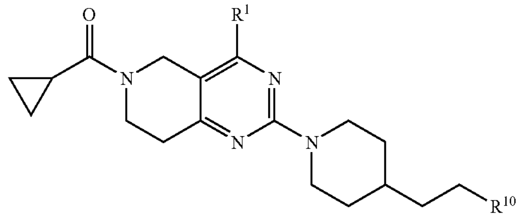
| Compound Number | •—$R^1$ | •—$R^{10}$ | Spectrum Data |
|---|---|---|---|
| 8-533 | 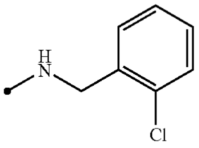 | 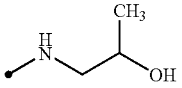 | MS m/z 527 $(M+H)^+$ |
| 8-534 | 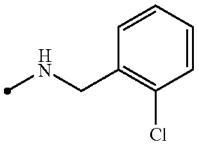 | 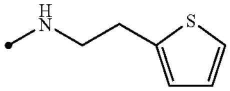 | MS m/z 579 $(M+H)^+$ |
| 8-535 | 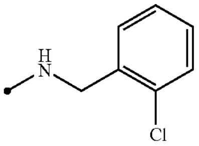 | 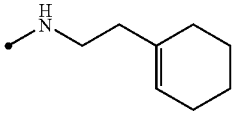 | MS m/z 577 $(M+H)^+$ |
| 8-536 | 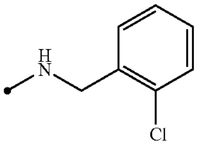 | 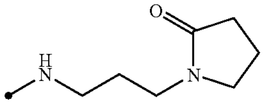 | MS m/z 594 $(M+H)^+$ |
| 8-537 | 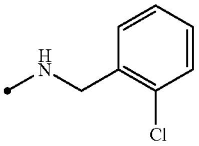 | 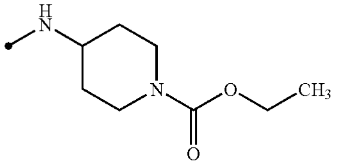 | MS m/z 624 $(M+H)^+$ |
| 8-538 | 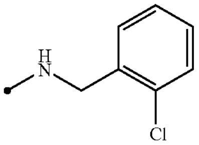 | 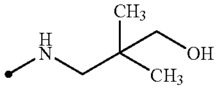 | MS m/z 555 $(M+H)^+$ |
| 8-539 | 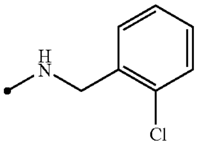 | 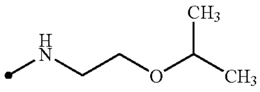 | MS m/z 555 $(M+H)^+$ |
| 8-540 | 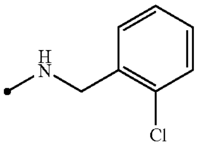 | 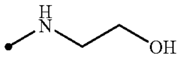 | MS m/z 513 $(M+H)^+$ |

TABLE 8-continued
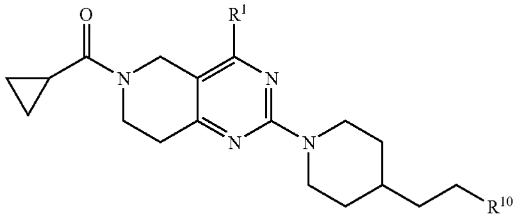
| Compound Number | •—$R^1$ | •—$R^{10}$ | Spectrum Data |
|---|---|---|---|
| 8-541 | 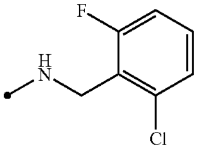 | 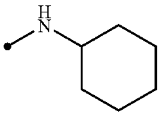 | MS m/z 569 $(M + H)^+$ |
| 8-542 | 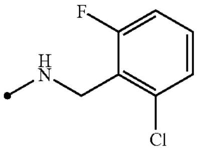 | 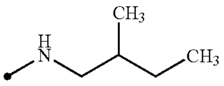 | MS m/z 557 $(M + H)^+$ |
| 8-543 | 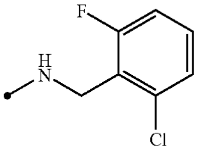 | 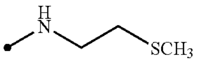 | MS m/z 561 $(M + H)^+$ |
| 8-544 | 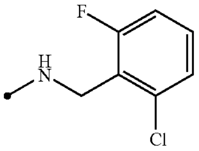 | 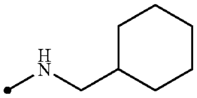 | MS m/z 583 $(M + H)^+$ |
| 8-545 | 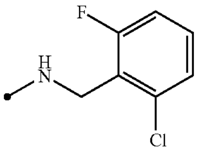 | 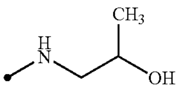 | MS m/z 545 $(M + H)^+$ |
| 8-546 | 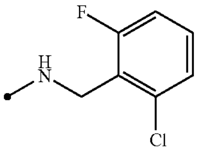 | 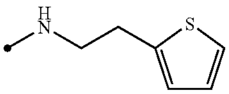 | MS m/z 597 $(M + H)^+$ |
| 8-547 | 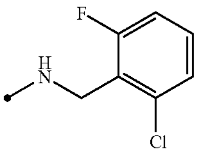 | 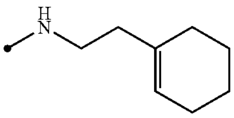 | MS m/z 595 $(M + H)^+$ |
| 8-548 | 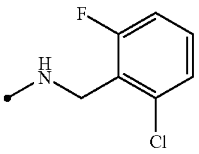 | 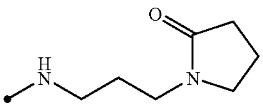 | MS m/z 612 $(M + H)^+$ |

TABLE 8-continued
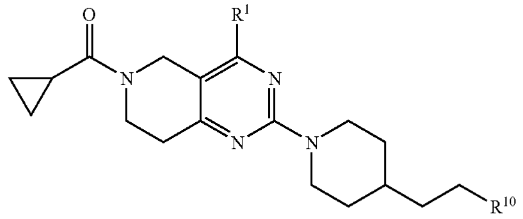
| Compound Number | •—$R^1$ | •—$R^{10}$ | Spectrum Data |
|---|---|---|---|
| 8-549 | 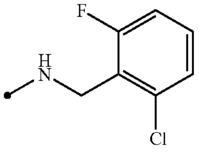 | 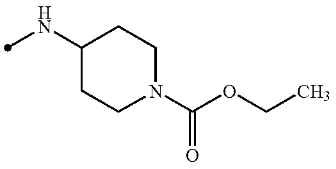 | MS m/z 642 $(M + H)^+$ |
| 8-550 | 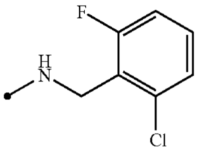 | 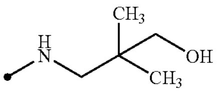 | MS m/z 573 $(M + H)^+$ |
| 8-551 | 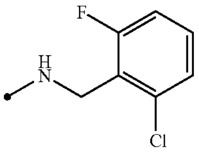 | 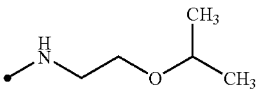 | MS m/z 573 $(M + H)^+$ |
| 8-552 | 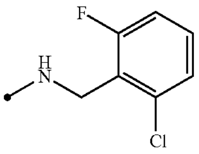 | 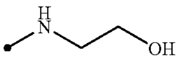 | MS m/z 531 $(M + H)^+$ |
| 8-553 | 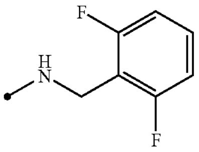 | 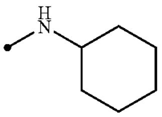 | MS m/z 553 $(M + H)^+$ |
| 8-554 | 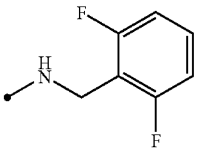 | 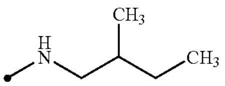 | MS m/z 541 $(M + H)^+$ |
| 8-555 | 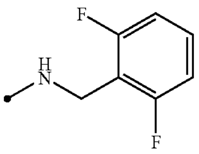 | 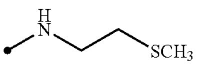 | MS m/z 545 $(M + H)^+$ |
| 8-556 | 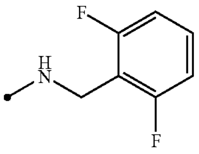 | 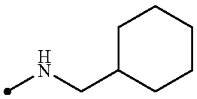 | MS m/z 567 $(M + H)^+$ |

TABLE 8-continued
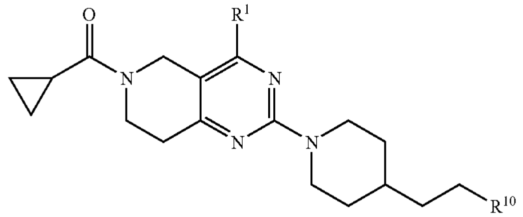
| Compound Number | •—$R^1$ | •—$R^{10}$ | Spectrum Data |
|---|---|---|---|
| 8-557 | 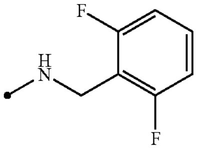 | 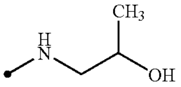 | MS m/z 529 $(M + H)^+$ |
| 8-558 | 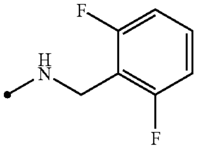 | 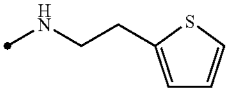 | MS m/z 581 $(M + H)^+$ |
| 8-559 | 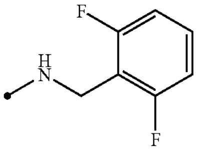 | 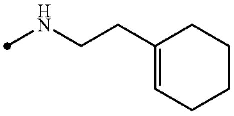 | MS m/z 579 $(M + H)^+$ |
| 8-560 | 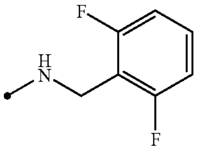 | 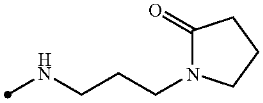 | MS m/z 596 $(M + H)^+$ |
| 8-561 | 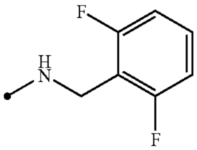 | 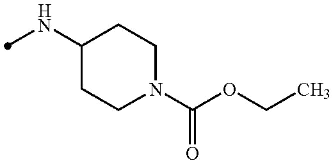 | MS m/z 626 $(M + H)^+$ |
| 8-562 | 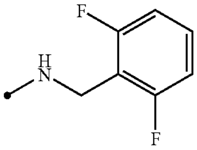 | 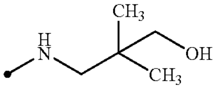 | MS m/z 557 $(M + H)^+$ |
| 8-563 | 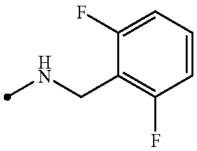 | 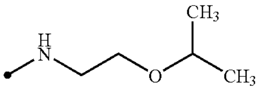 | MS m/z 557 $(M + H)^+$ |
| 8-564 | 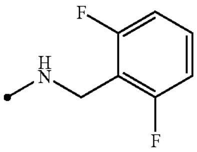 | 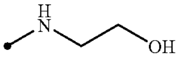 | MS m/z 515 $(M + H)^+$ |

TABLE 8-continued
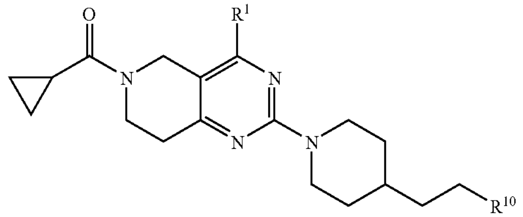
| Compound Number | •—$R^1$ | •—$R^{10}$ | Spectrum Data |
|---|---|---|---|
| 8-565 | 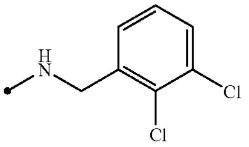 | 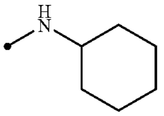 | MS m/z 585 $(M + H)^+$ |
| 8-566 | 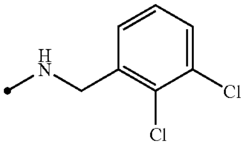 | 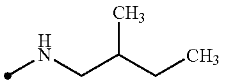 | MS m/z 573 $(M + H)^+$ |
| 8-567 | 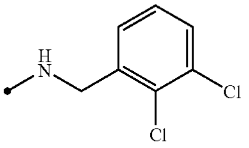 | 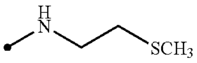 | MS m/z 577 $(M + H)^+$ |
| 8-568 | 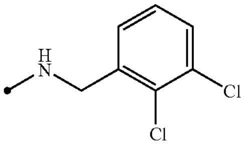 | 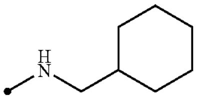 | MS m/z 599 $(M + H)^+$ |
| 8-569 | 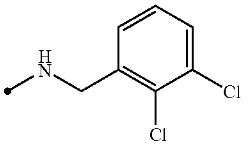 | 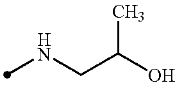 | MS m/z 561 $(M + H)^+$ |
| 8-570 | 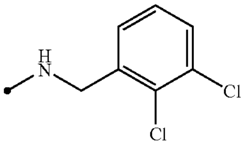 | 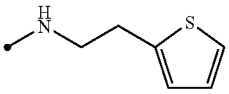 | MS m/z 613 $(M + H)^+$ |
| 8-571 | 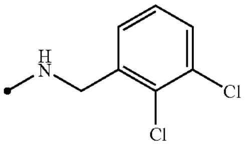 | 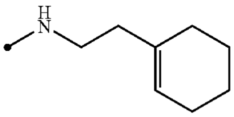 | MS m/z 611 $(M + H)^+$ |
| 8-572 | 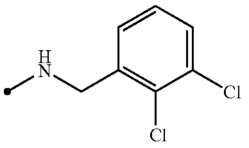 | 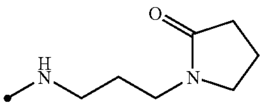 | MS m/z 628 $(M + H)^+$ |

TABLE 8-continued
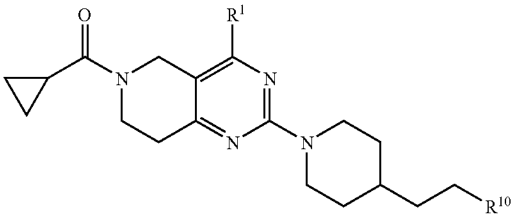
| Compound Number | •—$R^1$ | •—$R^{10}$ | Spectrum Data |
|---|---|---|---|
| 8-573 | 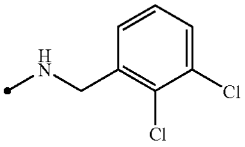 | 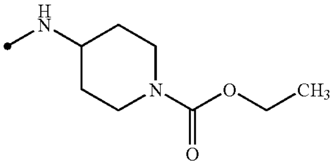 | MS m/z 658 $(M + H)^+$ |
| 8-574 | 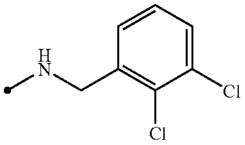 | 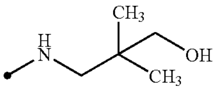 | MS m/z 589 $(M + H)^+$ |
| 8-575 | 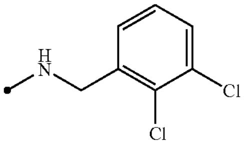 | 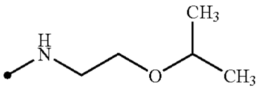 | MS m/z 589 $(M + H)^+$ |
| 8-576 | 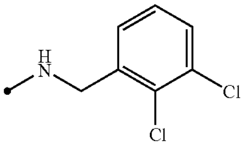 | 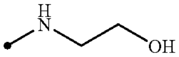 | MS m/z 547 $(M + H)^+$ |
TABLE 9
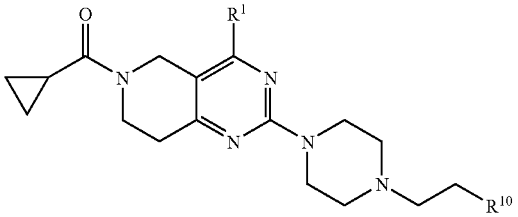
| Compound Number | •—$R^1$ | •—$R^{10}$ | Spectrum Data |
|---|---|---|---|
| 9-1 | 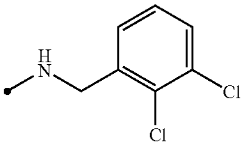 | 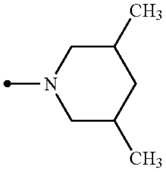 | MS m/z 600 $(M + H)^+$ |

TABLE 9-continued
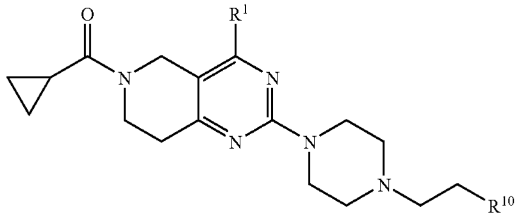
| Compound Number | •—$R^1$ | •—$R^{10}$ | Spectrum Data |
|---|---|---|---|
| 9-2 | 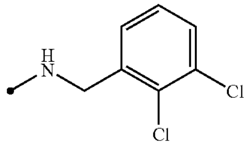 | 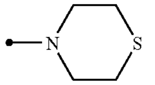 | MS m/z 590 $(M + H)^+$ |
| 9-3 | 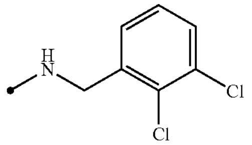 | 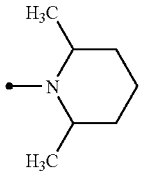 | MS m/z 600 $(M + H)^+$ |
| 9-4 | 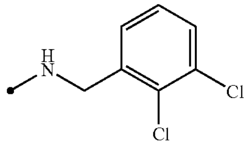 | 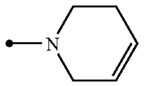 | MS m/z 570 $(M + H)^+$ |
| 9-5 | 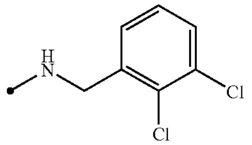 | 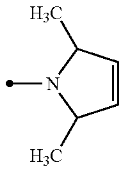 | MS m/z 584 $(M + H)^+$ |
| 9-6 | 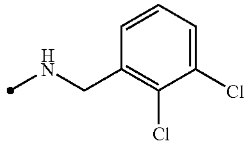 | 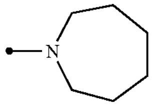 | MS m/z 586 $(M + H)^+$ |
| 9-7 | 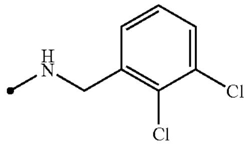 | 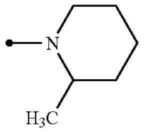 | MS m/z 586 $(M + H)^+$ |
| 9-8 | 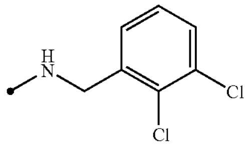 | 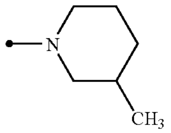 | MS m/z 586 $(M + H)^+$ |
| 9-9 | 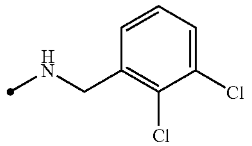 | 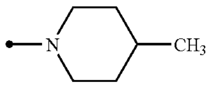 | MS m/z 586 $(M + H)^+$ |

TABLE 9-continued
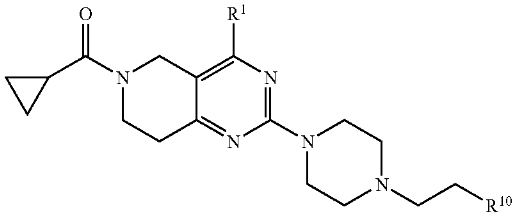
| Compound Number | •—R¹ | •—R¹⁰ | Spectrum Data |
|---|---|---|---|
| 9-10 | 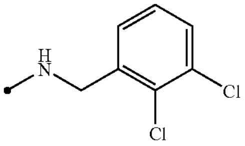 | 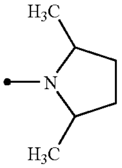 | MS m/z 586 (M + H)+ |
| 9-11 | 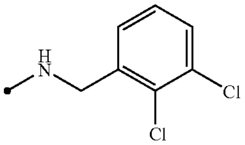 | 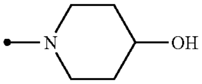 | MS m/z 588 (M + H)+ |
| 9-12 | 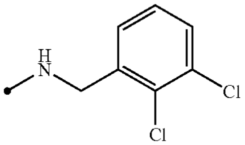 | 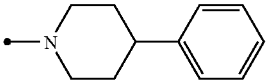 | MS m/z 648 (M + H)+ |
| 9-13 | 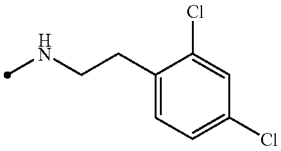 | 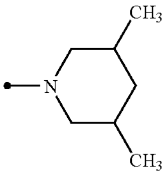 | MS m/z 614 (M + H)+ |
| 9-14 | 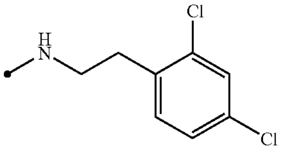 | 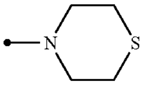 | MS m/z 604 (M + H)+ |
| 9-15 | 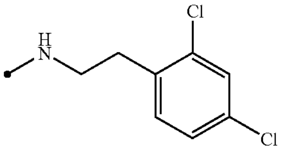 | 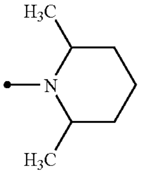 | MS m/z 614 (M + H)+ |
| 9-16 | 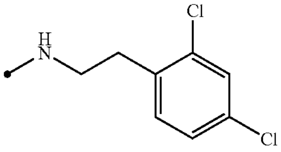 | 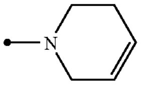 | MS m/z 584 (M + H)+ |

TABLE 9-continued
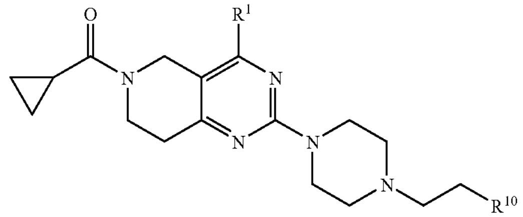
| Compound Number | •—$R^1$ | •—$R^{10}$ | Spectrum Data |
|---|---|---|---|
| 9-17 | 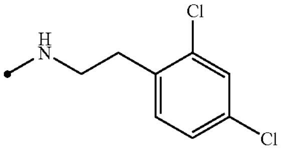 | 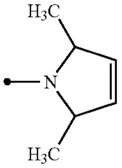 | MS m/z 598 $(M + H)^+$ |
| 9-18 | 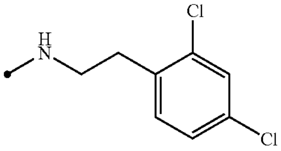 | 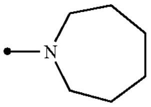 | MS m/z 600 $(M + H)^+$ |
| 9-19 | 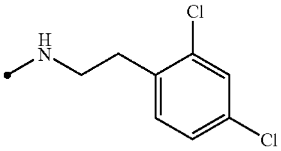 | 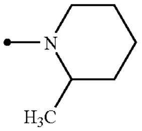 | MS m/z 600 $(M + H)^+$ |
| 9-20 | 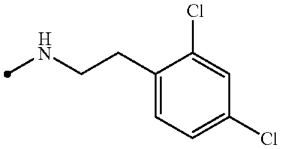 | 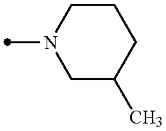 | MS m/z 600 $(M + H)^+$ |
| 9-21 | 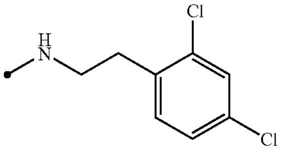 | 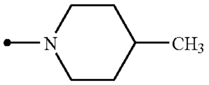 | MS m/z 600 $(M + H)^+$ |
| 9-22 | 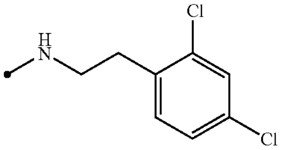 | 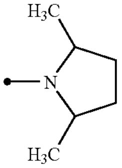 | MS m/z 600 $(M + H)^+$ |
| 9-23 | 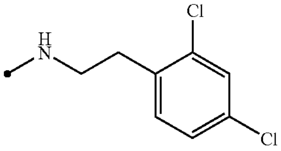 | 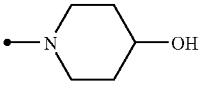 | MS m/z 602 $(M + H)^+$ |
| 9-24 | 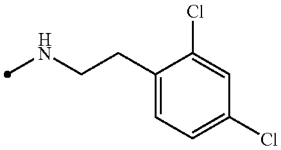 | 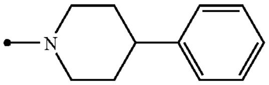 | MS m/z 662 $(M + H)^+$ |

TABLE 9-continued
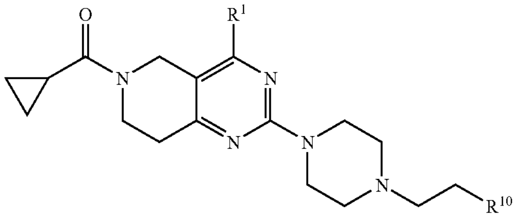
| Compound Number | •—$R^1$ | •—$R^{10}$ | Spectrum Data |
|---|---|---|---|
| 9-25 | 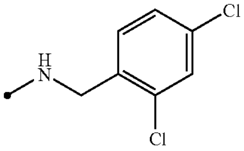 | 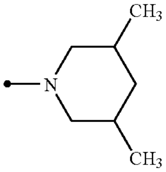 | MS m/z 600 $(M + H)^+$ |
| 9-26 | 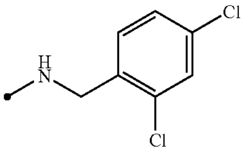 | 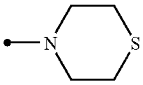 | MS m/z 590 $(M + H)^+$ |
| 9-27 | 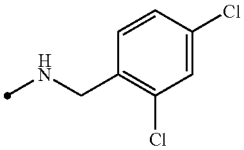 | 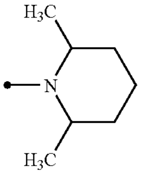 | MS m/z 600 $(M + H)^+$ |
| 9-28 | 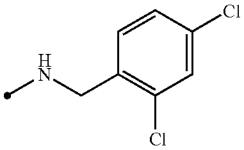 | 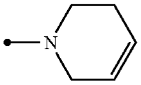 | MS m/z 570 $(M + H)^+$ |
| 9-29 | 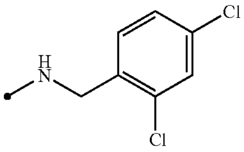 | 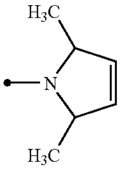 | MS m/z 584 $(M + H)^+$ |
| 9-30 | 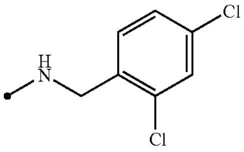 | 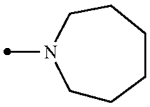 | MS m/z 586 $(M + H)^+$ |
| 9-31 | 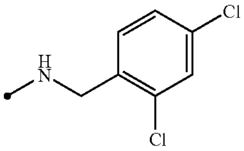 | 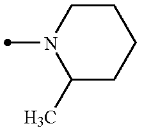 | MS m/z 586 $(M + H)^+$ |

TABLE 9-continued
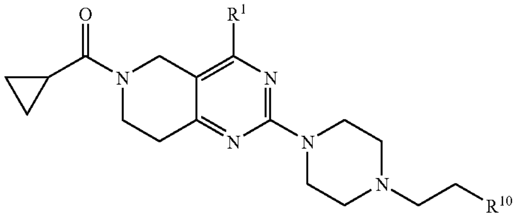
| Compound Number | •—$R^1$ | •—$R^{10}$ | Spectrum Data |
|---|---|---|---|
| 9-32 | 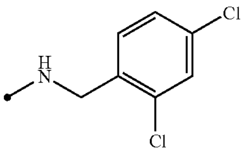 | 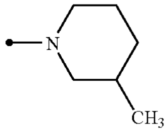 | MS m/z 586 $(M + H)^+$ |
| 9-33 | 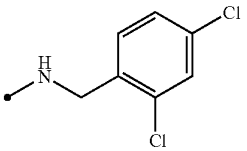 | 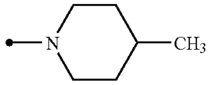 | MS m/z 586 $(M + H)^+$ |
| 9-34 | 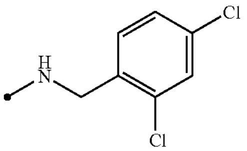 | 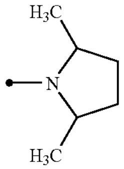 | MS m/z 586 $(M + H)^+$ |
| 9-35 | 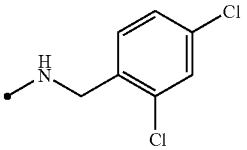 | 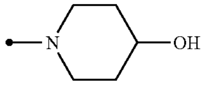 | MS m/z 588 $(M + H)^+$ |
| 9-36 | 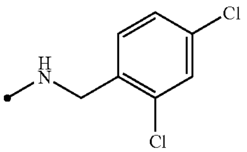 | 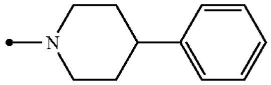 | MS m/z 648 $(M + H)^+$ |
| 9-37 | 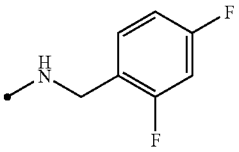 | 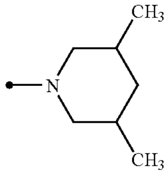 | MS m/z 568 $(M + H)^+$ |
| 9-38 | 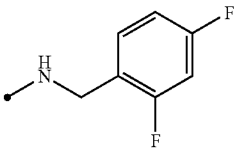 | 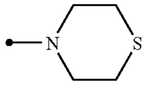 | MS m/z 590 $(M + H)^+$ |

TABLE 9-continued
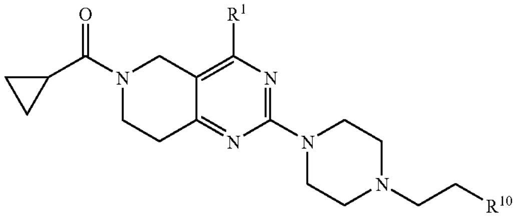
| Compound Number | •—$R^1$ | •—$R^{10}$ | Spectrum Data |
| --- | --- | --- | --- |
| 9-39 | 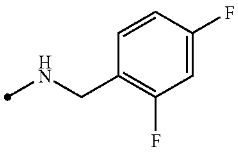 | 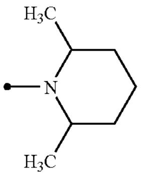 | MS m/z 568 $(M + H)^+$ |
| 9-40 | 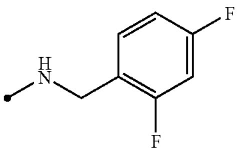 | 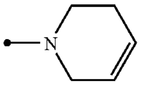 | MS m/z 538 $(M + H)^+$ |
| 9-41 | 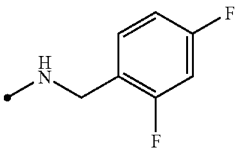 | 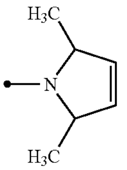 | MS m/z 552 $(M + H)^+$ |
| 9-42 | 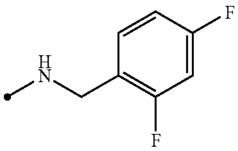 | 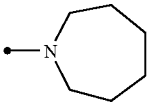 | MS m/z 554 $(M + H)^+$ |
| 9-43 | 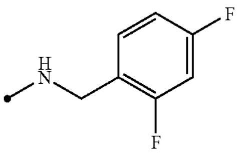 | 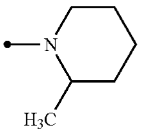 | MS m/z 554 $(M + H)^+$ |
| 9-44 | 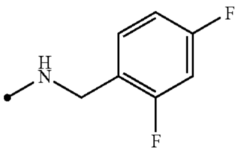 | 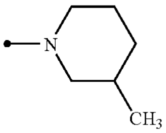 | MS m/z 554 $(M + H)^+$ |
| 9-45 | 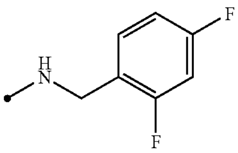 | 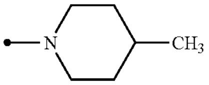 | MS m/z 554 $(M + H)^+$ |

TABLE 9-continued
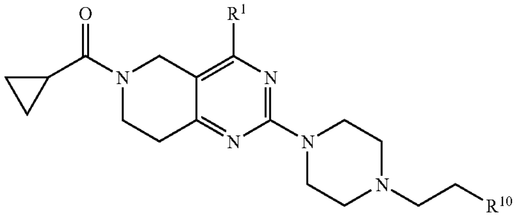
| Compound Number | •—$R^1$ | •—$R^{10}$ | Spectrum Data |
| --- | --- | --- | --- |
| 9-46 | 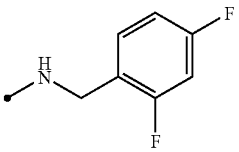 | 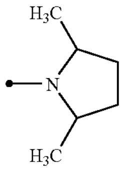 | MS m/z 554 $(M + H)^+$ |
| 9-47 | 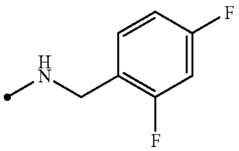 | 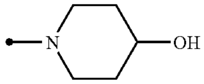 | MS m/z 556 $(M + H)^+$ |
| 9-48 | 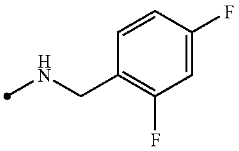 | 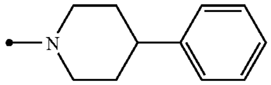 | MS m/z 616 $(M + H)^+$ |
| 9-49 | 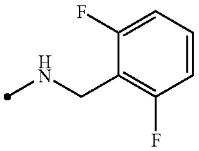 | 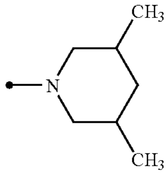 | MS m/z 568 $(M + H)^+$ |
| 9-50 | 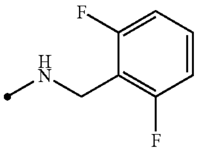 | 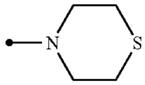 | MS m/z 558 $(M + H)^+$ |
| 9-51 | 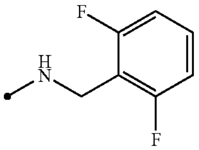 | 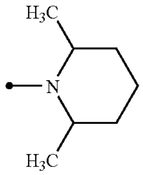 | MS m/z 568 $(M + H)^+$ |
| 9-52 | 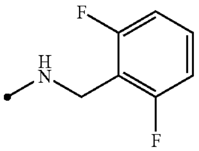 | 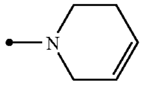 | MS m/z 538 $(M + H)^+$ |

TABLE 9-continued
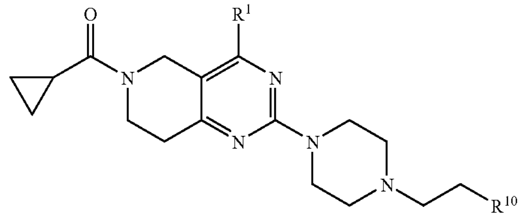
| Compound Number | •—$R^1$ | •—$R^{10}$ | Spectrum Data |
|---|---|---|---|
| 9-53 | 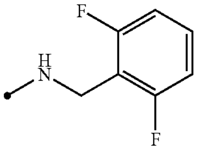 | 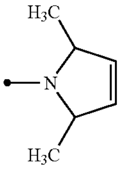 | MS m/z 552 $(M + H)^+$ |
| 9-54 | 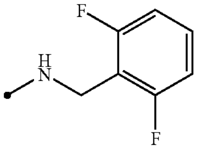 | 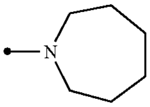 | MS m/z 554 $(M + H)^+$ |
| 9-55 | 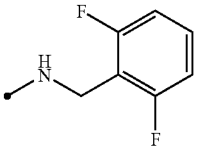 | 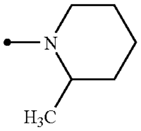 | MS m/z 554 $(M + H)^+$ |
| 9-56 | 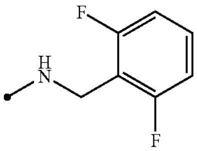 | 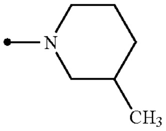 | MS m/z 554 $(M + H)^+$ |
| 9-57 | 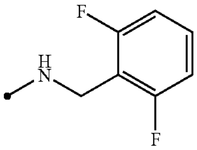 | 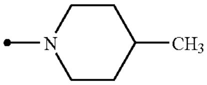 | MS m/z 554 $(M + H)^+$ |
| 9-58 | 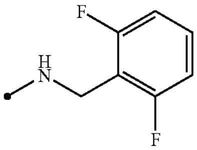 | 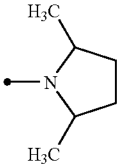 | MS m/z 554 $(M + H)^+$ |
| 9-59 | 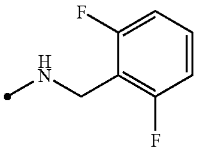 | 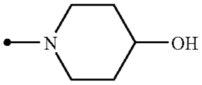 | MS m/z 556 $(M + H)^+$ |
| 9-60 | 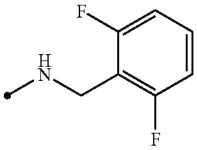 | 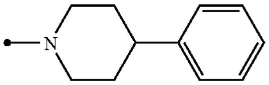 | MS m/z 616 $(M + H)^+$ |

TABLE 9-continued
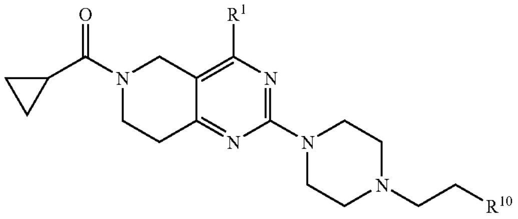
| Compound Number | •—$R^1$ | •—$R^{10}$ | Spectrum Data |
|---|---|---|---|
| 9-61 | 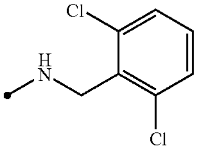 | 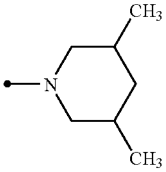 | MS m/z 600 $(M + H)^+$ |
| 9-62 | 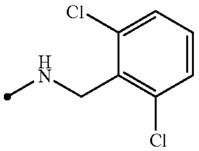 | 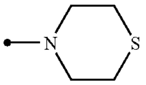 | MS m/z 590 $(M + H)^+$ |
| 9-63 | 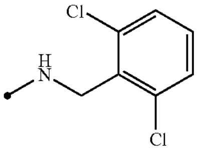 | 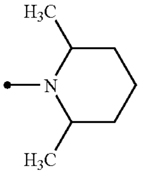 | MS m/z 600 $(M + H)^+$ |
| 9-64 | 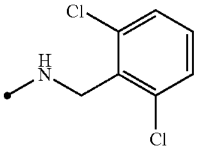 | 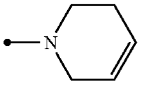 | MS m/z 570 $(M + H)^+$ |
| 9-65 | 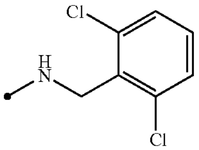 | 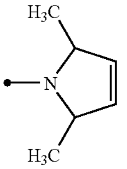 | MS m/z 584 $(M + H)^+$ |
| 9-66 | 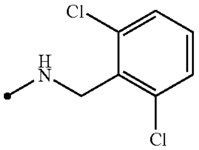 | 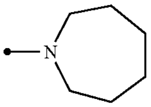 | MS m/z 586 $(M + H)^+$ |
| 9-67 | 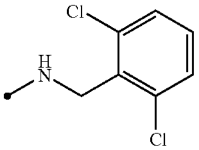 | 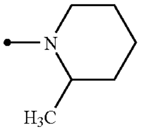 | MS m/z 586 $(M + H)^+$ |

TABLE 9-continued
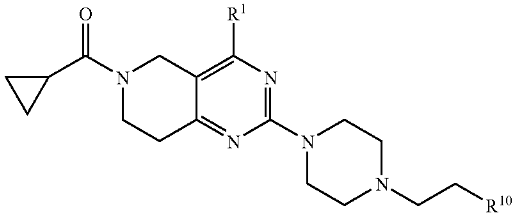
| Compound Number | •—$R^1$ | •—$R^{10}$ | Spectrum Data |
| --- | --- | --- | --- |
| 9-68 | 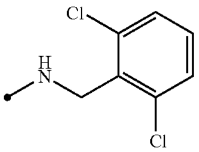 | 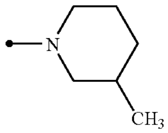 | MS m/z 586 $(M + H)^+$ |
| 9-69 | 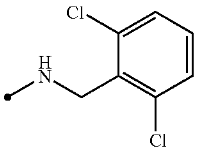 | 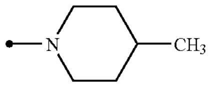 | MS m/z 586 $(M + H)^+$ |
| 9-70 | 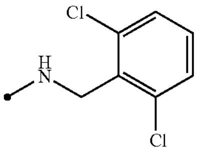 | 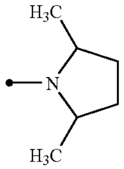 | MS m/z 586 $(M + H)^+$ |
| 9-71 | 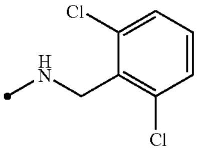 | 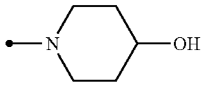 | MS m/z 588 $(M + H)^+$ |
| 9-72 | 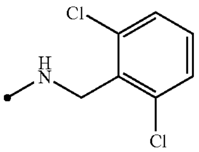 | 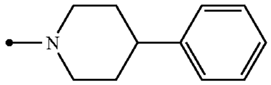 | MS m/z 648 $(M + H)^+$ |
| 9-73 | 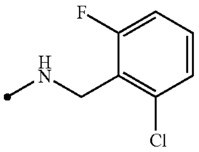 | 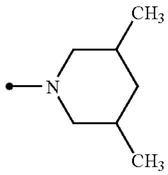 | MS m/z 584 $(M + H)^+$ |
| 9-74 | 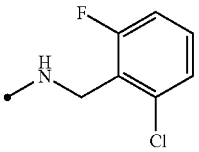 | 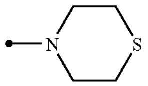 | MS m/z 574 $(M + H)^+$ |

TABLE 9-continued
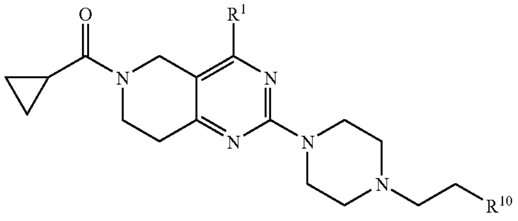
| Compound Number | •—$R^1$ | •—$R^{10}$ | Spectrum Data |
|---|---|---|---|
| 9-75 | 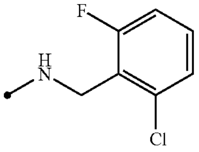 | 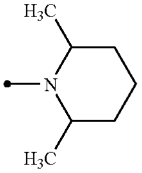 | MS m/z 584 $(M+H)^+$ |
| 9-76 | 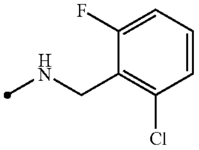 | 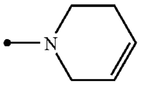 | MS m/z 554 $(M+H)^+$ |
| 9-77 | 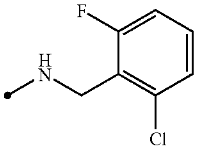 | 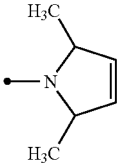 | MS m/z 568 $(M+H)^+$ |
| 9-78 | 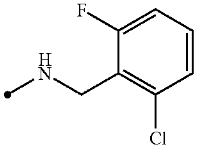 | 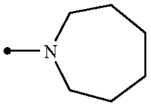 | MS m/z 570 $(M+H)^+$ |
| 9-79 | 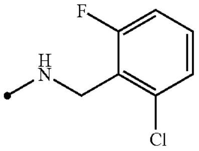 | 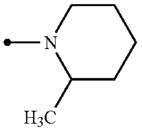 | MS m/z 570 $(M+H)^+$ |
| 9-80 | 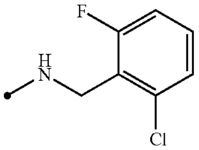 | 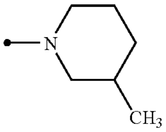 | MS m/z 570 $(M+H)^+$ |
| 9-81 | 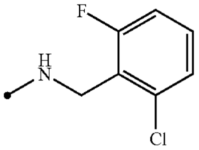 | 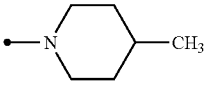 | MS m/z 570 $(M+H)^+$ |

TABLE 9-continued
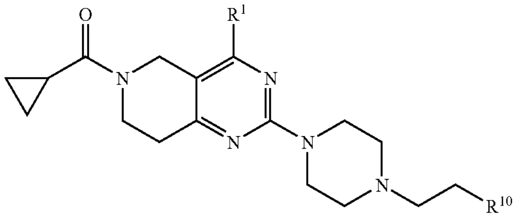
| Compound Number | •—$R^1$ | •—$R^{10}$ | Spectrum Data |
| --- | --- | --- | --- |
| 9-82 | 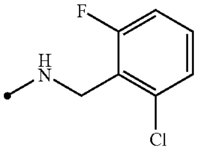 | 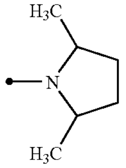 | MS m/z 570 $(M + H)^+$ |
| 9-83 | 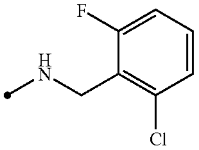 | 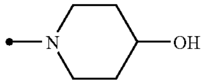 | MS m/z 572 $(M + H)^+$ |
| 9-84 | 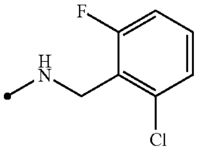 | 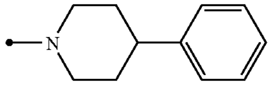 | MS m/z 632 $(M + H)^+$ |
| 9-85 | 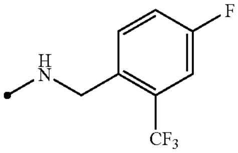 | 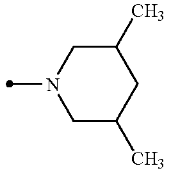 | MS m/z 618 $(M + H)^+$ |
| 9-86 | 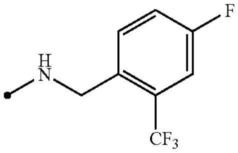 | 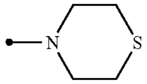 | MS m/z 608 $(M + H)^+$ |
| 9-87 | 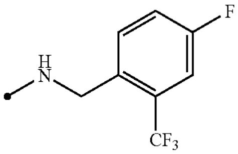 | 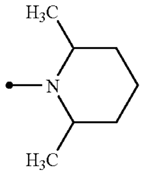 | MS m/z 618 $(M + H)^+$ |
| 9-88 | 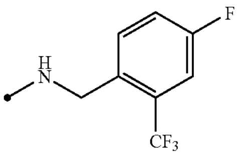 | 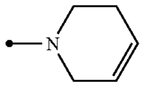 | MS m/z 588 $(M + H)^+$ |

TABLE 9-continued
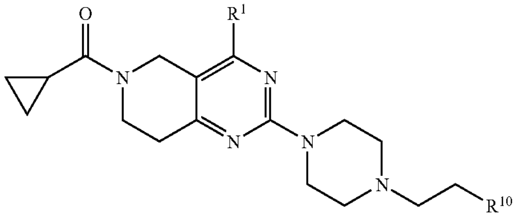
| Compound Number | •—$R^1$ | •—$R^{10}$ | Spectrum Data |
|---|---|---|---|
| 9-89 | 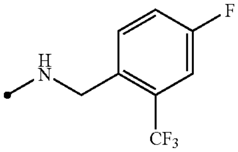 | 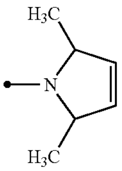 | MS m/z 602 $(M + H)^+$ |
| 9-90 | 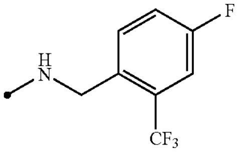 | 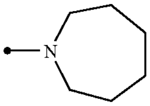 | MS m/z 604 $(M + H)^+$ |
| 9-91 | 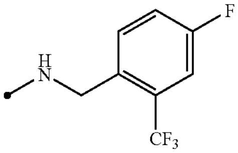 | 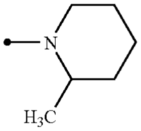 | MS m/z 604 $(M + H)^+$ |
| 9-92 | 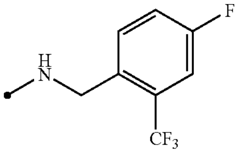 | 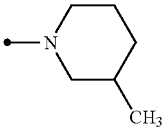 | MS m/z 604 $(M + H)^+$ |
| 9-93 | 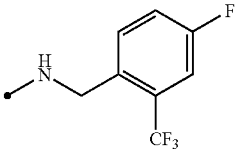 | 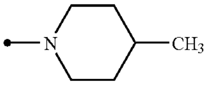 | MS m/z 604 $(M + H)^+$ |
| 9-94 | 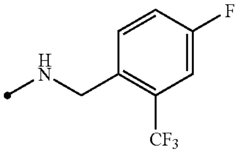 | 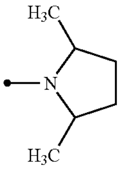 | MS m/z 604 $(M + H)^+$ |
| 9-95 | 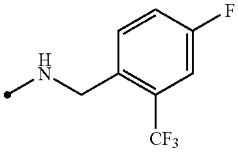 | 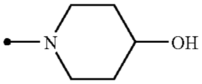 | MS m/z 606 $(M + H)^+$ |

TABLE 9-continued
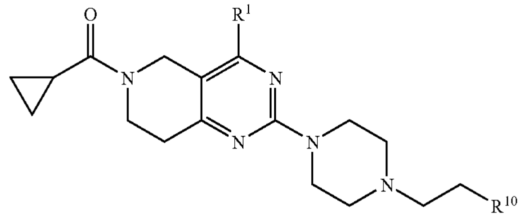
| Compound Number | •—$R^1$ | •—$R^{10}$ | Spectrum Data |
|---|---|---|---|
| 9-96 | 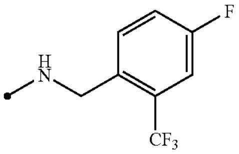 | 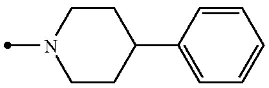 | MS m/z 666 $(M + H)^+$ |
| 9-97 | 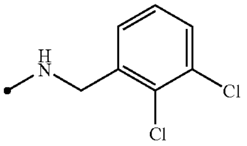 | 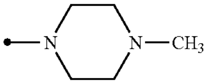 | MS m/z 587 $(M + H)^+$ |
| 9-98 | 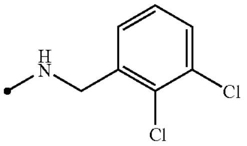 | 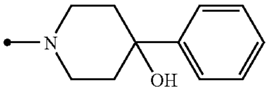 | MS m/z 664 $(M + H)^+$ |
| 9-99 | 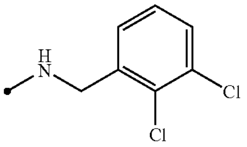 | 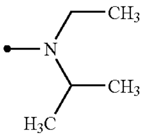 | MS m/z 574 $(M + H)^+$ |
| 9-100 | 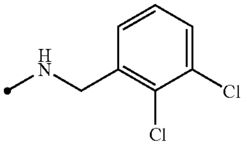 | 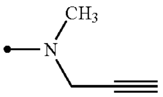 | MS m/z 556 $(M + H)^+$ |
| 9-101 | 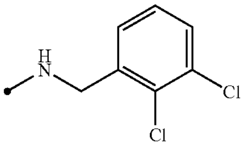 | 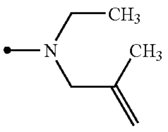 | MS m/z 586 $(M + H)^+$ |
| 9-102 | 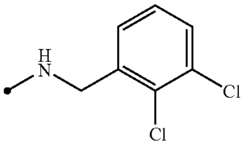 | 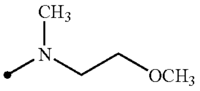 | MS m/z 576 $(M + H)^+$ |
| 9-103 | 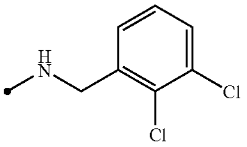 | 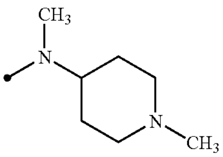 | MS m/z 615 $(M + H)^+$ |

TABLE 9-continued
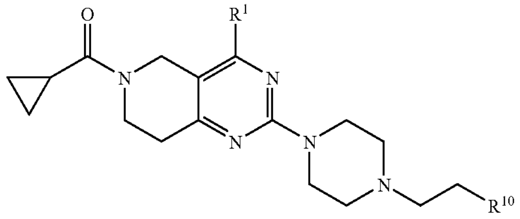
| Compound Number | •—$R^1$ | •—$R^{10}$ | Spectrum Data |
|---|---|---|---|
| 9-104 | 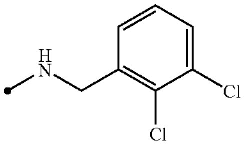 | 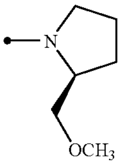 | MS m/z 602 $(M + H)^+$ |
| 9-105 | 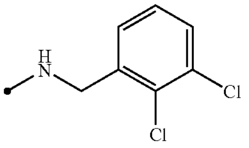 | 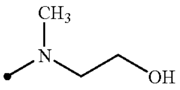 | MS m/z 562 $(M + H)^+$ |
| 9-106 | 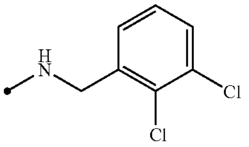 | 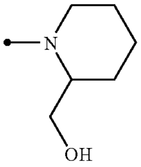 | MS m/z 602 $(M + H)^+$ |
| 9-107 | 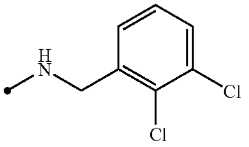 | 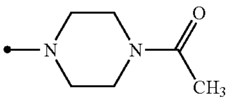 | MS m/z 615 $(M + H)^+$ |
| 9-108 | 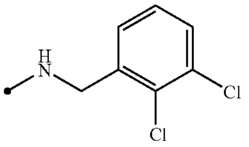 | 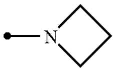 | MS m/z 544 $(M + H)^+$ |
| 9-109 | 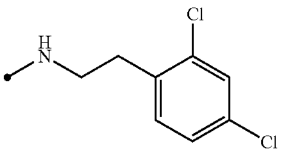 | 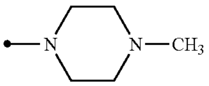 | MS m/z 601 $(M + H)^+$ |
| 9-110 | 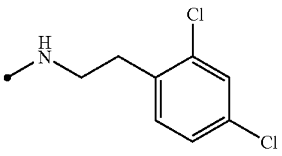 | 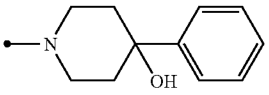 | MS m/z 678 $(M + H)^+$ |
| 9-111 | 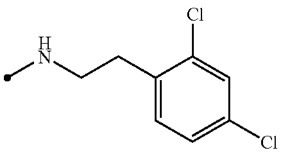 | 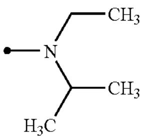 | MS m/z 588 $(M + H)^+$ |

TABLE 9-continued
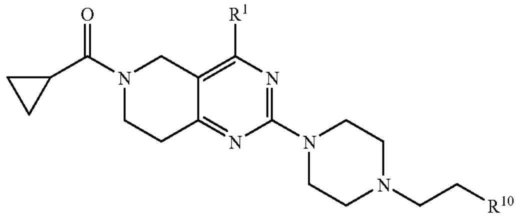
| Compound Number | •—$R^1$ | •—$R^{10}$ | Spectrum Data |
|---|---|---|---|
| 9-112 | 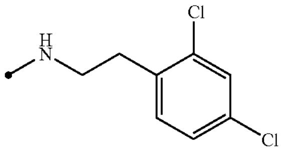 | 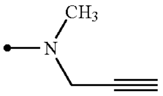 | MS m/z 570 $(M + H)^+$ |
| 9-113 | 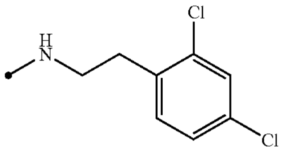 | 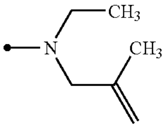 | MS m/z 600 $(M + H)^+$ |
| 9-114 | 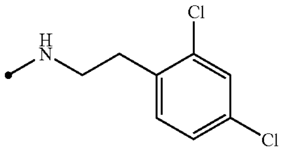 | 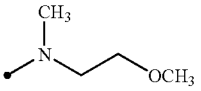 | MS m/z 590 $(M + H)^+$ |
| 9-115 | 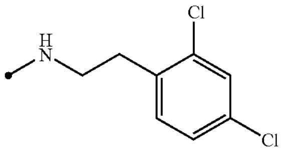 | 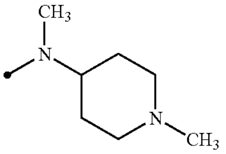 | MS m/z 629 $(M + H)^+$ |
| 9-116 | 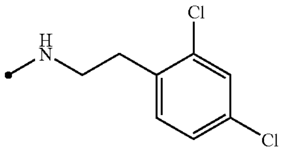 | 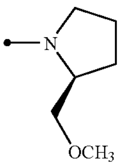 | MS m/z 616 $(M + H)^+$ |
| 9-117 | 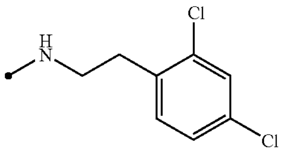 | 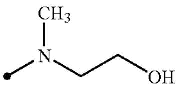 | MS m/z 576 $(M + H)^+$ |
| 9-118 | 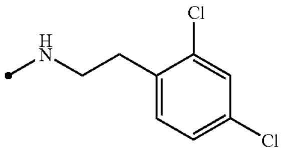 | 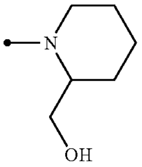 | MS m/z 616 $(M + H)^+$ |
| 9-119 | 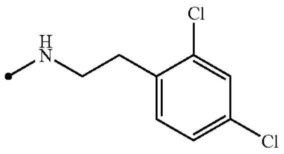 | 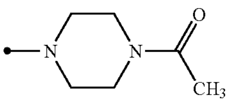 | MS m/z 629 $(M + H)^+$ |

TABLE 9-continued
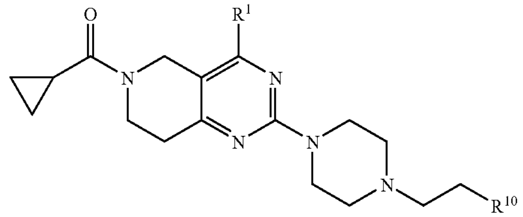
| Compound Number | •—$R^1$ | •—$R^{10}$ | Spectrum Data |
|---|---|---|---|
| 9-120 | 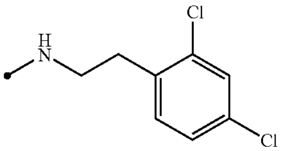 | 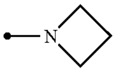 | MS m/z 558 $(M + H)^+$ |
| 9-121 | 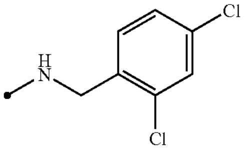 | 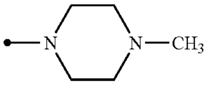 | MS m/z 587 $(M + H)^+$ |
| 9-122 | 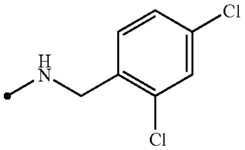 | 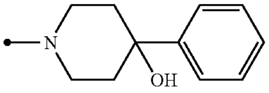 | MS m/z 664 $(M + H)^+$ |
| 9-123 | 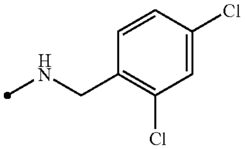 | 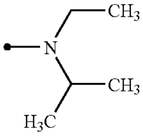 | MS m/z 574 $(M + H)^+$ |
| 9-124 | 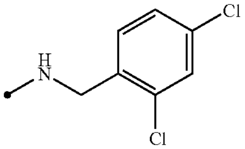 | 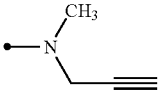 | MS m/z 556 $(M + H)^+$ |
| 9-125 | 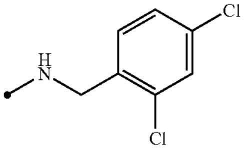 | 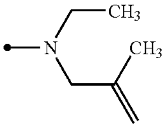 | MS m/z 586 $(M + H)^+$ |
| 9-126 | 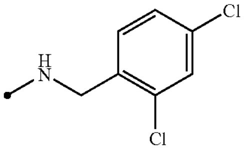 | 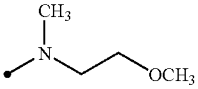 | MS m/z 576 $(M + H)^+$ |
| 9-127 | 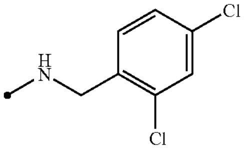 | 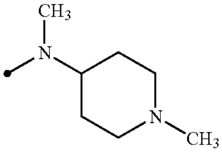 | MS m/z 615 $(M + H)^+$ |

TABLE 9-continued
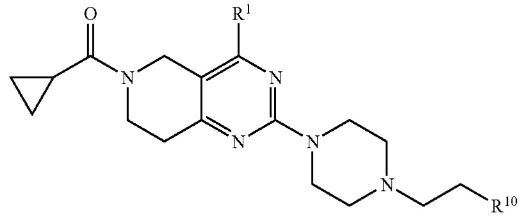
| Compound Number | •—$R^1$ | •—$R^{10}$ | Spectrum Data |
| --- | --- | --- | --- |
| 9-128 | 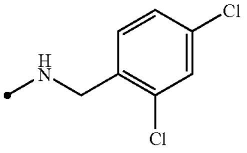 | 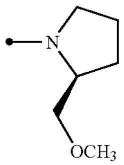 | MS m/z 602 $(M + H)^+$ |
| 9-129 | 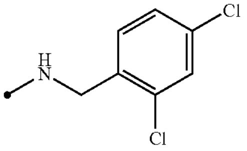 | 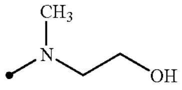 | MS m/z 562 $(M + H)^+$ |
| 9-130 | 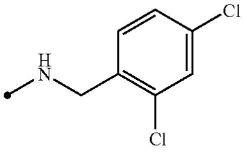 | 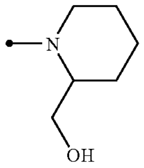 | MS m/z 602 $(M + H)^+$ |
| 9-131 | 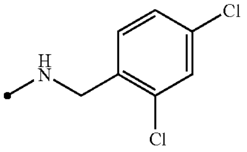 | 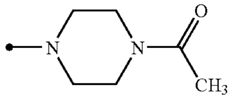 | MS m/z 615 $(M + H)^+$ |
| 9-132 | 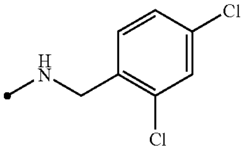 | 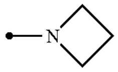 | MS m/z 544 $(M + H)^+$ |
| 9-133 | 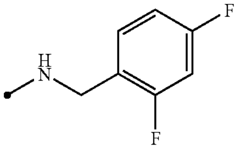 | 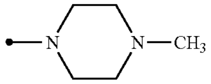 | MS m/z 555 $(M + H)^+$ |
| 9-134 | 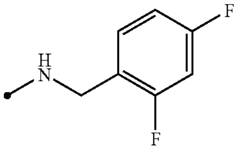 | 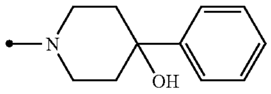 | MS m/z 632 $(M + H)^+$ |

TABLE 9-continued
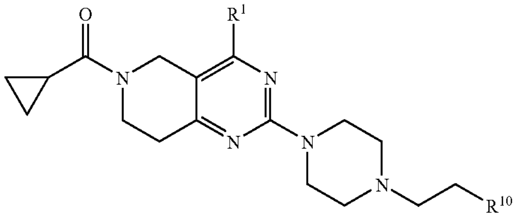
| Compound Number | •—R¹ | •—R¹⁰ | Spectrum Data |
|---|---|---|---|
| 9-135 | 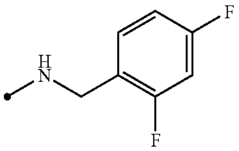 | 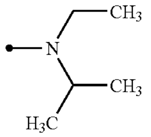 | MS m/z 542 $(M + H)^+$ |
| 9-136 | 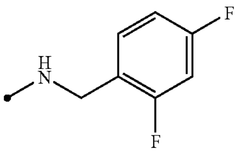 | 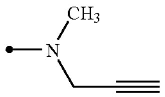 | MS m/z 524 $(M + H)^+$ |
| 9-137 | 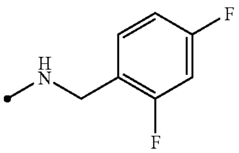 | 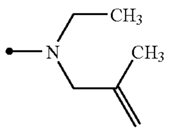 | MS m/z 554 $(M + H)^+$ |
| 9-138 | 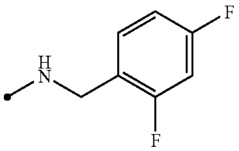 | 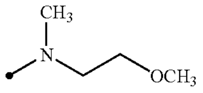 | MS m/z 544 $(M + H)^+$ |
| 9-139 | 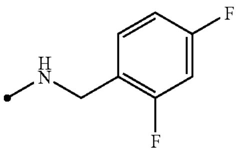 | 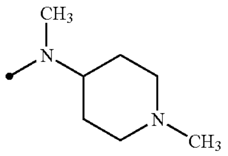 | MS m/z 583 $(M + H)^+$ |
| 9-140 | 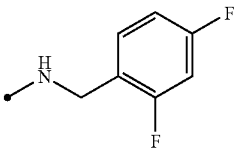 | 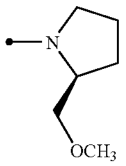 | MS m/z 570 $(M + H)^+$ |
| 9-141 | 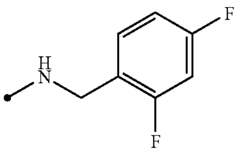 | 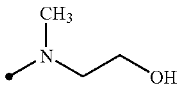 | MS m/z 530 $(M + H)^+$ |
| 9-142 | 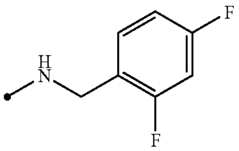 | 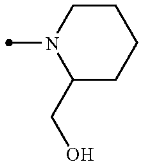 | MS m/z 570 $(M + H)^+$ |

TABLE 9-continued
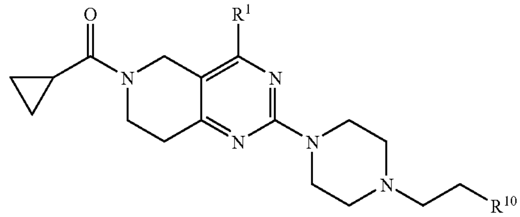
| Compound Number | •—$R^1$ | •—$R^{10}$ | Spectrum Data |
|---|---|---|---|
| 9-143 | 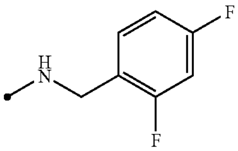 | 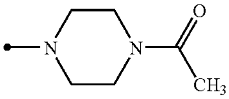 | MS m/z 583 $(M + H)^+$ |
| 9-144 | 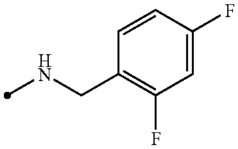 | 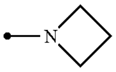 | MS m/z 512 $(M + H)^+$ |
| 9-145 | 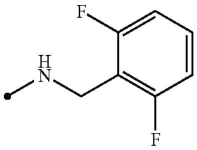 | 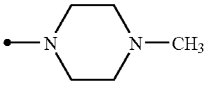 | MS m/z 555 $(M + H)^+$ |
| 9-146 | 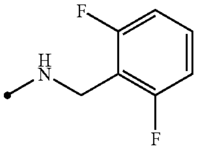 | 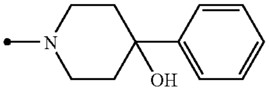 | MS m/z 632 $(M + H)^+$ |
| 9-147 | 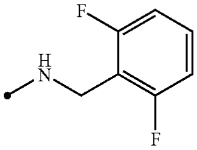 | 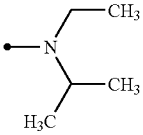 | MS m/z 542 $(M + H)^+$ |
| 9-148 | 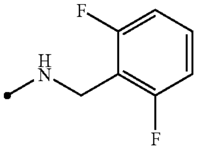 | 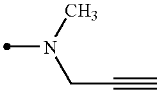 | MS m/z 524 $(M + H)^+$ |
| 9-149 | 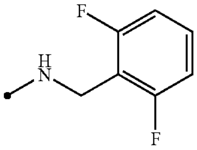 | 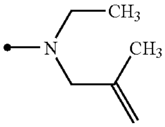 | MS m/z 554 $(M + H)^+$ |
| 9-150 | 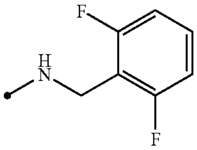 | 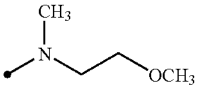 | MS m/z 544 $(M + H)^+$ |

TABLE 9-continued
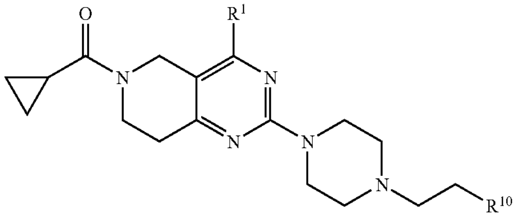
| Compound Number | •—$R^1$ | •—$R^{10}$ | Spectrum Data |
|---|---|---|---|
| 9-151 | 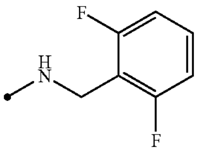 | 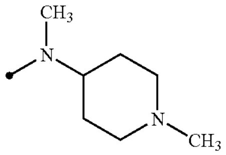 | MS m/z 583 $(M + H)^+$ |
| 9-152 | 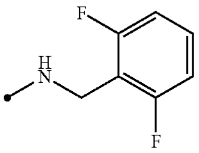 | 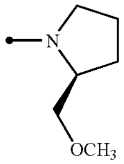 | MS m/z 570 $(M + H)^+$ |
| 9-153 | 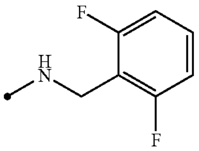 | 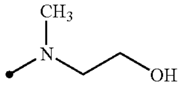 | MS m/z 530 $(M + H)^+$ |
| 9-154 | 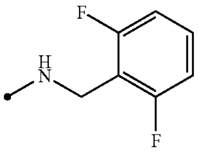 | 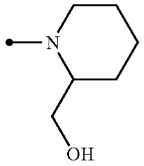 | MS m/z 570 $(M + H)^+$ |
| 9-155 | 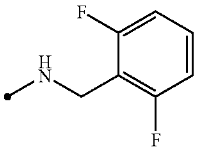 | 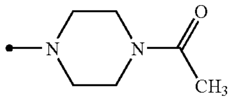 | MS m/z 583 $(M + H)^+$ |
| 9-156 | 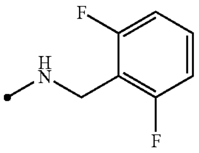 | 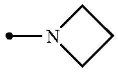 | MS m/z 512 $(M + H)^+$ |
| 9-157 | 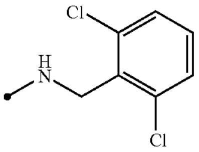 | 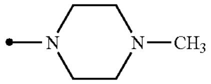 | MS m/z 587 $(M + H)^+$ |

TABLE 9-continued
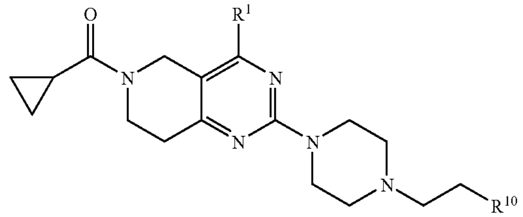
| Compound Number | •—$R^1$ | •—$R^{10}$ | Spectrum Data |
|---|---|---|---|
| 9-158 | 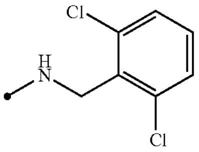 | 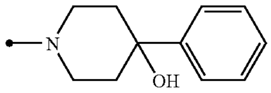 | MS m/z 664 $(M + H)^+$ |
| 9-159 | 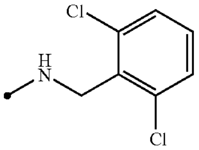 | 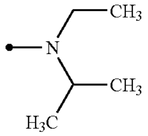 | MS m/z 574 $(M + H)^+$ |
| 9-160 | 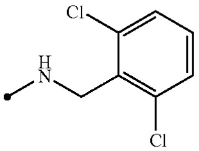 | 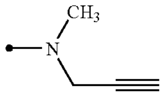 | MS m/z 556 $(M + H)^+$ |
| 9-161 | 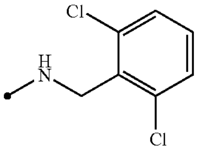 | 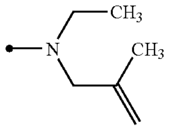 | MS m/z 586 $(M + H)^+$ |
| 9-162 | 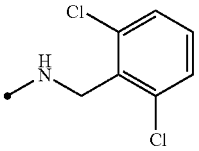 | 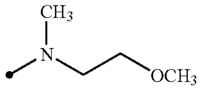 | MS m/z 576 $(M + H)^+$ |
| 9-163 | 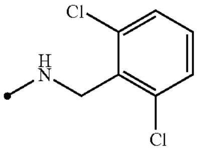 | 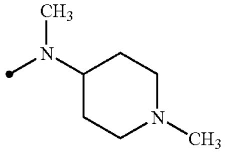 | MS m/z 615 $(M + H)^+$ |
| 9-164 | 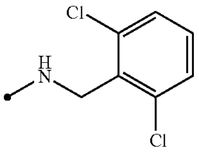 | 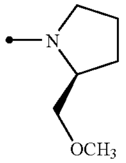 | MS m/z 602 $(M + H)^+$ |
| 9-165 | 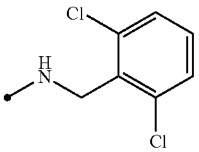 | 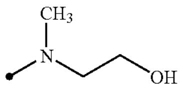 | MS m/z 562 $(M + H)^+$ |

TABLE 9-continued
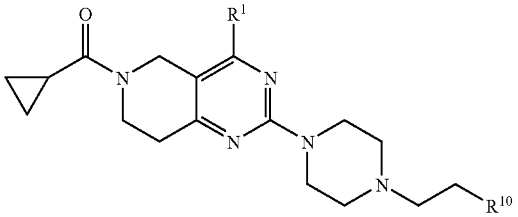
| Compound Number | •—R1 | •—R10 | Spectrum Data |
|---|---|---|---|
| 9-166 | 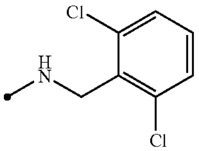 | 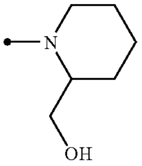 | MS m/z 602 $(M + H)^+$ |
| 9-167 | 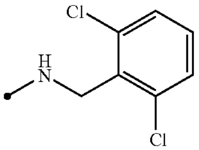 | 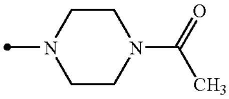 | MS m/z 615 $(M + H)^+$ |
| 9-168 | 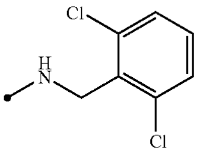 | 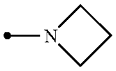 | MS m/z 544 $(M + H)^+$ |
| 9-169 | 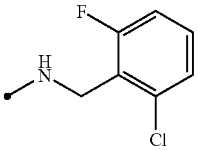 | 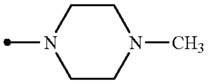 | MS m/z 571 $(M + H)^+$ |
| 9-170 | 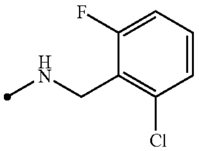 | 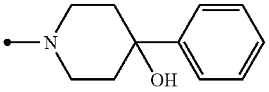 | MS m/z 648 $(M + H)^+$ |
| 9-171 | 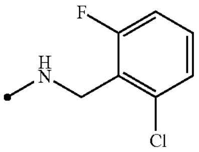 | 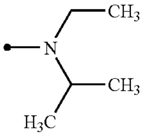 | MS m/z 558 $(M + H)^+$ |
| 9-172 | 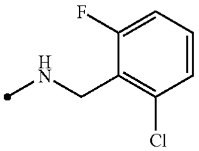 | 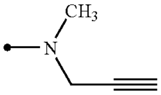 | MS m/z 540 $(M + H)^+$ |
| 9-173 | 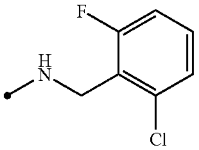 | 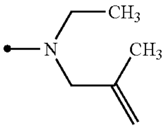 | MS m/z 570 $(M + H)^+$ |

TABLE 9-continued
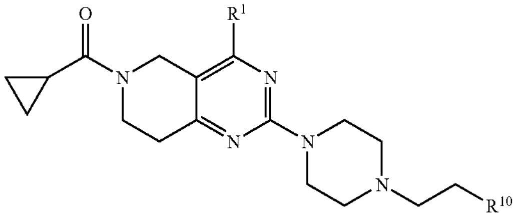
| Compound Number | •—$R^1$ | •—$R^{10}$ | Spectrum Data |
|---|---|---|---|
| 9-174 | 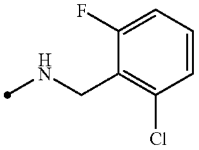 | 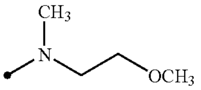 | MS m/z 560 $(M + H)^+$ |
| 9-175 | 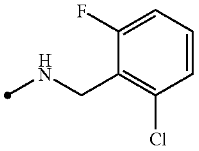 | 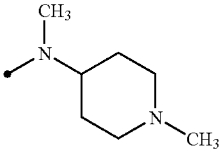 | MS m/z 599 $(M + H)^+$ |
| 9-176 | 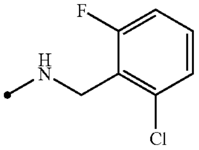 | 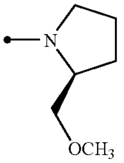 | MS m/z 586 $(M + H)^+$ |
| 9-177 | 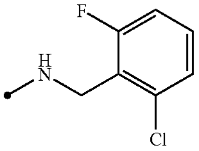 | 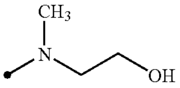 | MS m/z 546 $(M + H)^+$ |
| 9-178 | 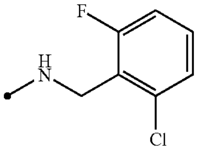 | 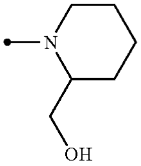 | MS m/z 586 $(M + H)^+$ |
| 9-179 | 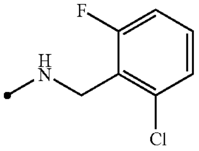 | 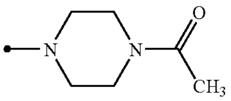 | MS m/z 599 $(M + H)^+$ |
| 9-180 | 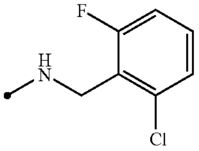 | 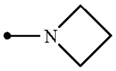 | MS m/z 528 $(M + H)^+$ |

TABLE 9-continued
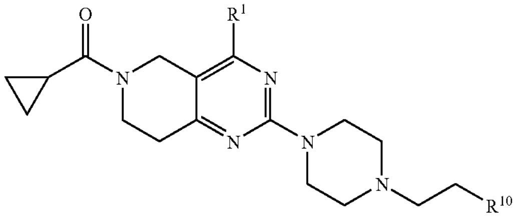
| Compound Number | •—$R^1$ | •—$R^{10}$ | Spectrum Data |
|---|---|---|---|
| 9-181 | 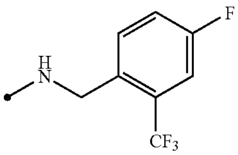 | 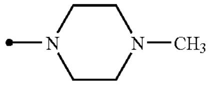 | MS m/z 605 $(M + H)^+$ |
| 9-182 | 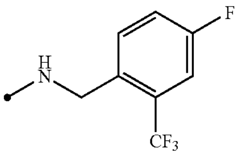 | 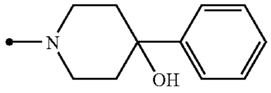 | MS m/z 682 $(M + H)^+$ |
| 9-183 | 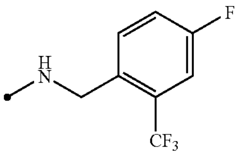 | 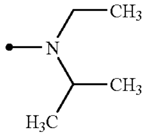 | MS m/z 592 $(M + H)^+$ |
| 9-184 | 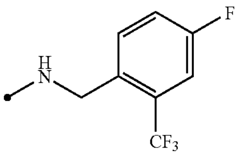 | 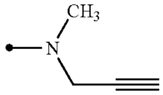 | MS m/z 574 $(M + H)^+$ |
| 9-185 | 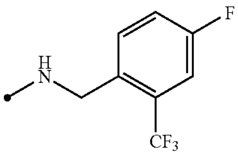 | 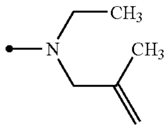 | MS m/z 604 $(M + H)^+$ |
| 9-186 | 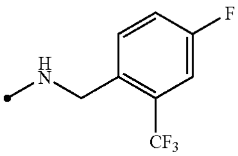 | 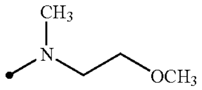 | MS m/z 594 $(M + H)^+$ |
| 9-187 | 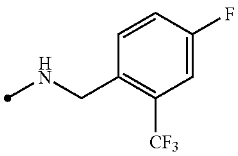 | 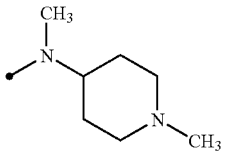 | MS m/z 633 $(M + H)^+$ |

TABLE 9-continued
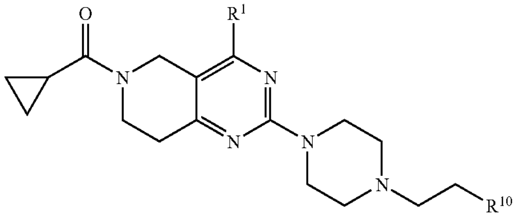
| Compound Number | •—$R^1$ | •—$R^{10}$ | Spectrum Data |
|---|---|---|---|
| 9-188 | 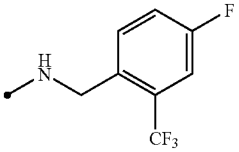 | 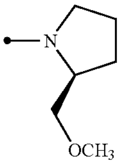 | MS m/z 620 $(M + H)^+$ |
| 9-189 | 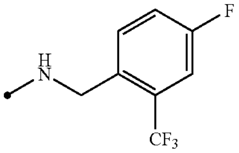 | 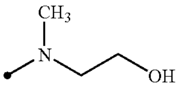 | MS m/z 580 $(M + H)^+$ |
| 9-190 | 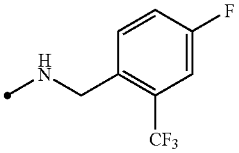 | 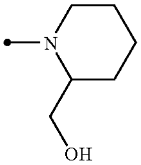 | MS m/z 620 $(M + H)^+$ |
| 9-191 | 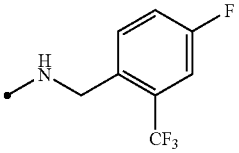 | 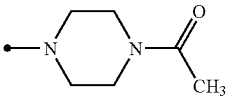 | MS m/z 633 $(M + H)^+$ |
| 9-192 | 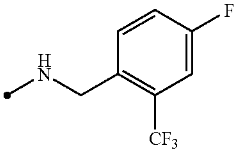 | 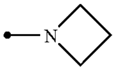 | MS m/z 562 $(M + H)^+$ |
| 9-193 | 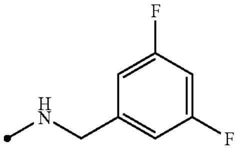 | 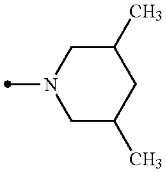 | MS m/z 568 $(M + H)^+$ |
| 9-194 | 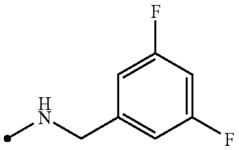 | 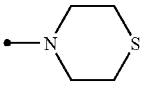 | MS m/z 558 $(M + H)^+$ |

TABLE 9-continued
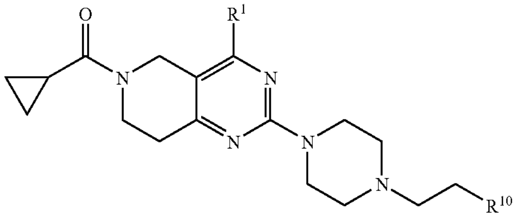
| Compound Number | •—$R^1$ | •—$R^{10}$ | Spectrum Data |
|---|---|---|---|
| 9-195 | 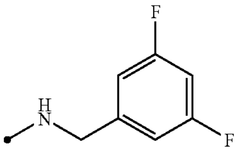 | 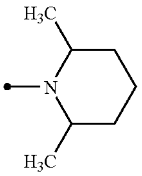 | MS m/z 568 $(M + H)^+$ |
| 9-196 | 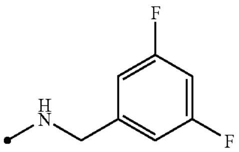 | 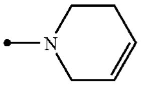 | MS m/z 538 $(M + H)^+$ |
| 9-197 | 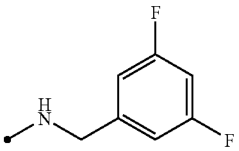 | 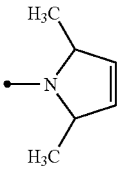 | MS m/z 552 $(M + H)^+$ |
| 9-198 | 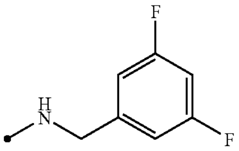 | 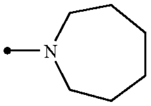 | MS m/z 554 $(M + H)^+$ |
| 9-199 | 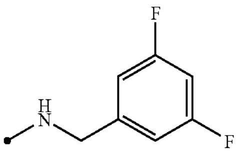 | 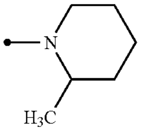 | MS m/z 554 $(M + H)^+$ |
| 9-200 | 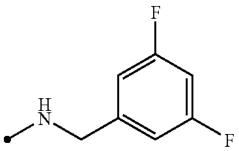 | 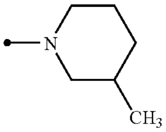 | MS m/z 554 $(M + H)^+$ |
| 9-201 | 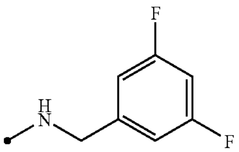 | 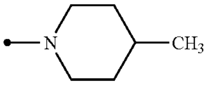 | MS m/z 554 $(M + H)^+$ |

TABLE 9-continued
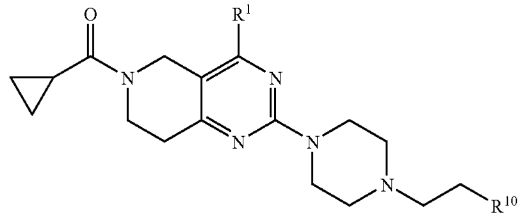
| Compound Number | •—$R^1$ | •—$R^{10}$ | Spectrum Data |
|---|---|---|---|
| 9-202 | 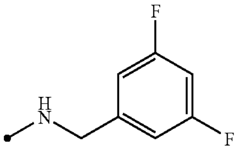 | 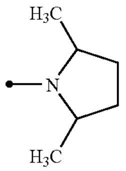 | MS m/z 554 $(M+H)^+$ |
| 9-203 | 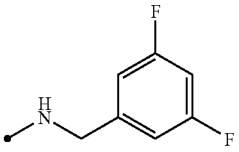 | 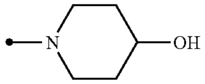 | MS m/z 556 $(M+H)^+$ |
| 9-204 | 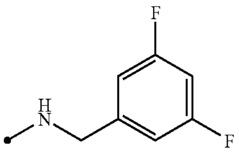 | 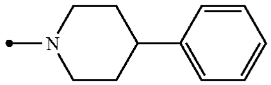 | MS m/z 616 $(M+H)^+$ |
| 9-205 | 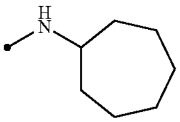 | 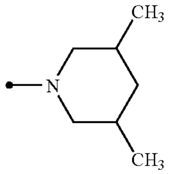 | MS m/z 538 $(M+H)^+$ |
| 9-206 | 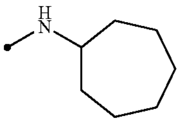 | 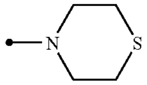 | MS m/z 528 $(M+H)^+$ |
| 9-207 | 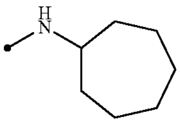 | 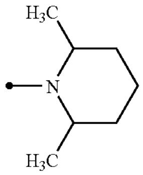 | MS m/z 538 $(M+H)^+$ |
| 9-208 | 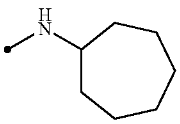 | 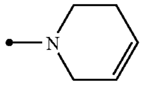 | MS m/z 508 $(M+H)^+$ |
| 9-209 | 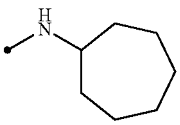 | 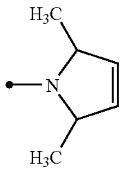 | MS m/z 522 $(M+H)^+$ |

TABLE 9-continued
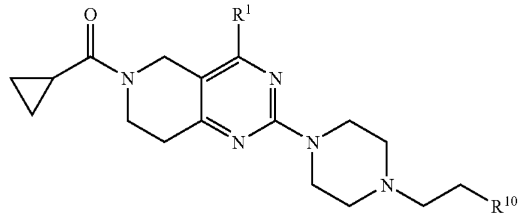
| Compound Number | •—$R^1$ | •—$R^{10}$ | Spectrum Data |
| --- | --- | --- | --- |
| 9-210 | 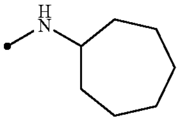 | 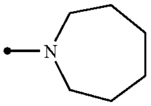 | MS m/z 524 (M + H)$^+$ |
| 9-211 | 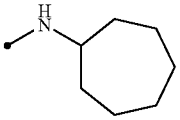 | 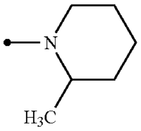 | MS m/z 524 (M + H)$^+$ |
| 9-212 | 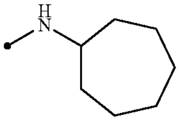 | 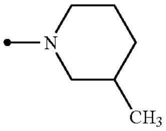 | MS m/z 524 (M + H)$^+$ |
| 9-213 | 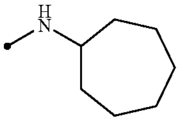 | 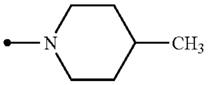 | MS m/z 524 (M + H)$^+$ |
| 9-214 | 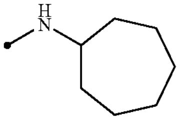 | 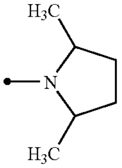 | MS m/z 524 (M + H)$^+$ |
| 9-215 | 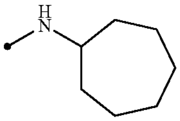 | 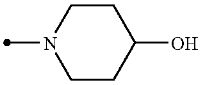 | MS m/z 526 (M + H)$^+$ |
| 9-216 | 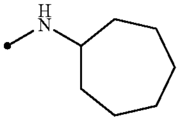 | 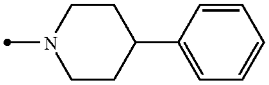 | MS m/z 586 (M + H)$^+$ |
| 9-217 | 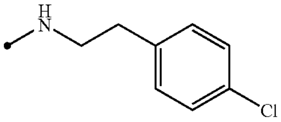 | 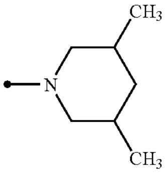 | MS m/z 580 (M + H)$^+$ |

TABLE 9-continued
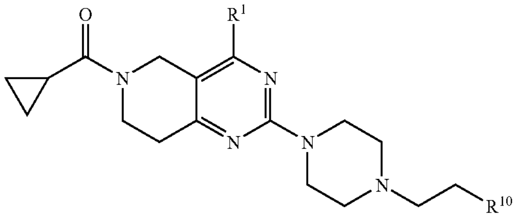
| Compound Number | •—$R^1$ | •—$R^{10}$ | Spectrum Data |
|---|---|---|---|
| 9-218 | 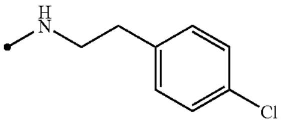 | 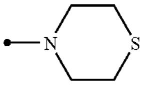 | MS m/z 570 $(M + H)^+$ |
| 9-219 | 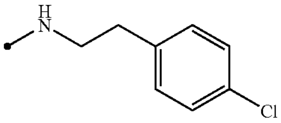 | 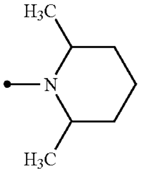 | MS m/z 580 $(M + H)^+$ |
| 9-220 | 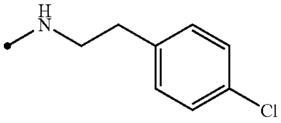 | 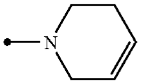 | MS m/z 550 $(M + H)^+$ |
| 9-221 | 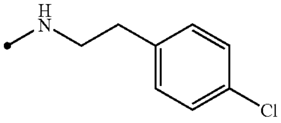 | 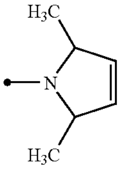 | MS m/z 564 $(M + H)^+$ |
| 9-222 | 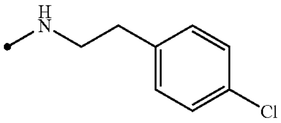 | 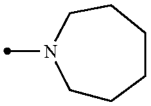 | MS m/z 566 $(M + H)^+$ |
| 9-223 | 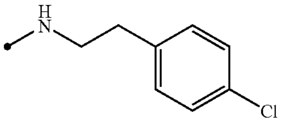 | 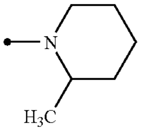 | MS m/z 566 $(M + H)^+$ |
| 9-224 | 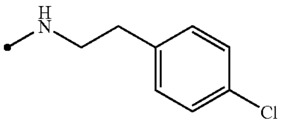 | 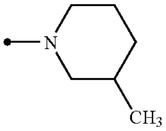 | MS m/z 566 $(M + H)^+$ |
| 9-225 | 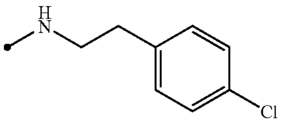 | 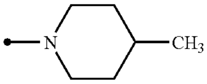 | MS m/z 566 $(M + H)^+$ |

TABLE 9-continued
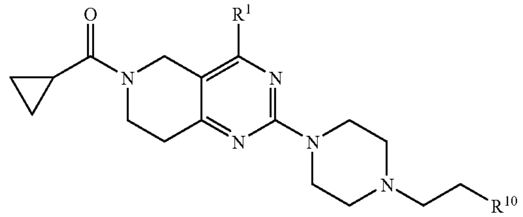
| Compound Number | •—$R^1$ | •—$R^{10}$ | Spectrum Data |
|---|---|---|---|
| 9-226 | 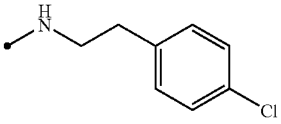 | 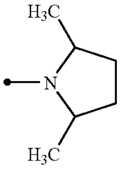 | MS m/z 566 $(M + H)^+$ |
| 9-227 | 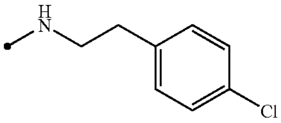 | 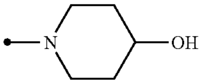 | MS m/z 568 $(M + H)^+$ |
| 9-228 | 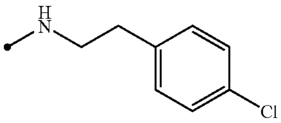 | 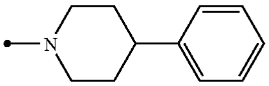 | MS m/z 628 $(M + H)^+$ |
| 9-229 | 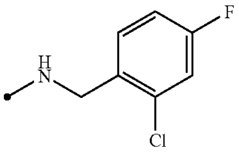 | 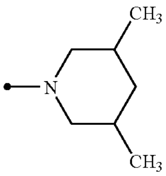 | MS m/z 584 $(M + H)^+$ |
| 9-230 | 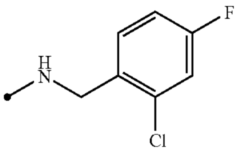 | 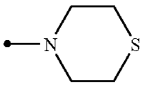 | MS m/z 574 $(M + H)^+$ |
| 9-231 | 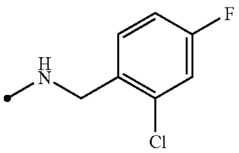 | 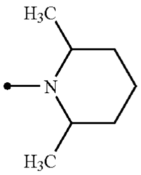 | MS m/z 584 $(M + H)^+$ |
| 9-232 | 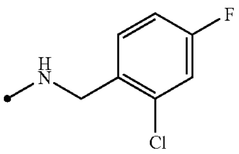 | 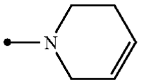 | MS m/z 554 $(M + H)^+$ |
| 9-233 | 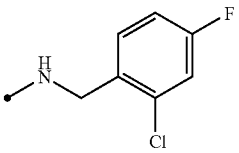 | 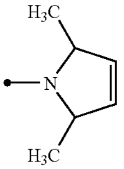 | MS m/z 568 $(M + H)^+$ |

TABLE 9-continued
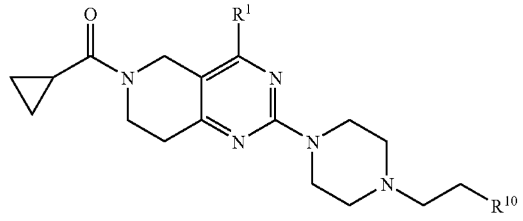
| Compound Number | •—$R^1$ | •—$R^{10}$ | Spectrum Data |
| --- | --- | --- | --- |
| 9-234 | 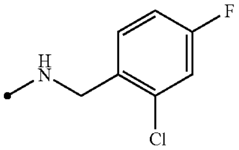 | 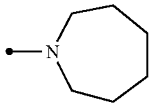 | MS m/z 570 $(M + H)^+$ |
| 9-235 | 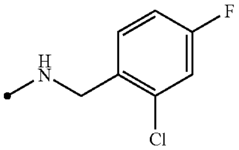 | 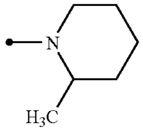 | MS m/z 570 $(M + H)^+$ |
| 9-236 | 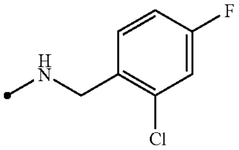 | 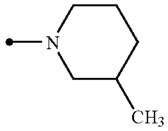 | MS m/z 570 $(M + H)^+$ |
| 9-237 | 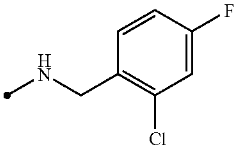 | 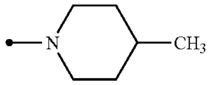 | MS m/z 570 $(M + H)^+$ |
| 9-238 | 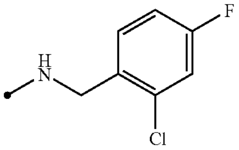 | 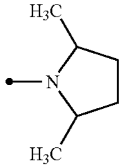 | MS m/z 570 $(M + H)^+$ |
| 9-239 | 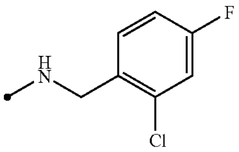 | 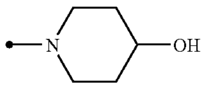 | MS m/z 572 $(M + H)^+$ |
| 9-240 | 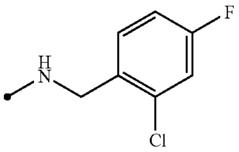 | 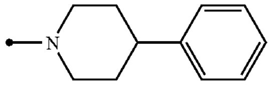 | MS m/z 632 $(M + H)^+$ |

TABLE 9-continued
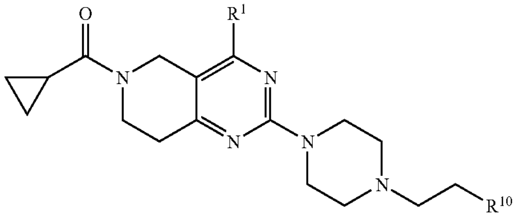
| Compound Number | •—$R^1$ | •—$R^{10}$ | Spectrum Data |
|---|---|---|---|
| 9-241 | 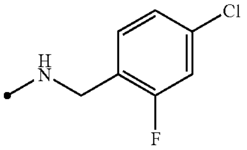 | 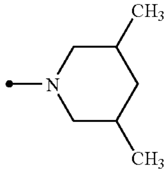 | MS m/z 600 $(M + H)^+$ |
| 9-242 | 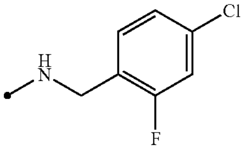 | 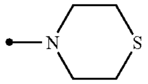 | MS m/z 574 $(M + H)^+$ |
| 9-243 | 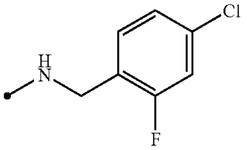 | 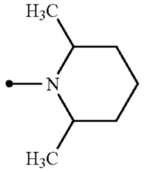 | MS m/z 584 $(M + H)^+$ |
| 9-244 | 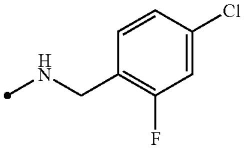 | 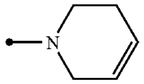 | MS m/z 554 $(M + H)^+$ |
| 9-245 | 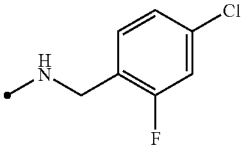 | 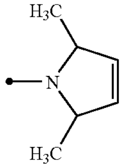 | MS m/z 568 $(M + H)^+$ |
| 9-246 | 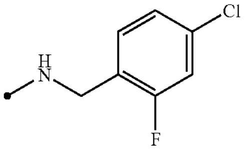 | 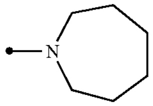 | MS m/z 570 $(M + H)^+$ |
| 9-247 | 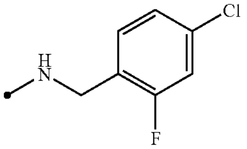 | 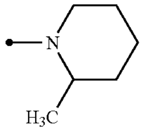 | MS m/z 570 $(M + H)^+$ |

TABLE 9-continued
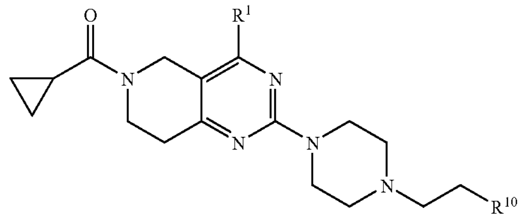
| Compound Number | •—$R^1$ | •—$R^{10}$ | Spectrum Data |
| --- | --- | --- | --- |
| 9-248 | 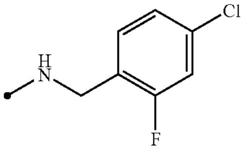 | 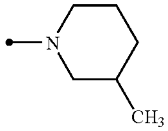 | MS m/z 570 $(M + H)^+$ |
| 9-249 | 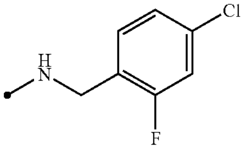 | 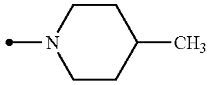 | MS m/z 570 $(M + H)^+$ |
| 9-250 | 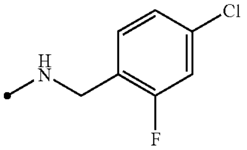 | 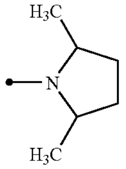 | MS m/z 570 $(M + H)^+$ |
| 9-251 | 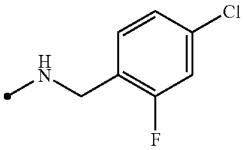 | 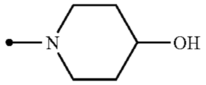 | MS m/z 572 $(M + H)^+$ |
| 9-252 | 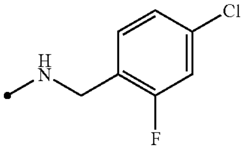 | 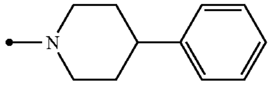 | MS m/z 632 $(M + H)^+$ |
| 9-253 | 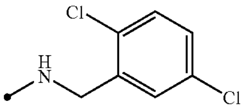 | 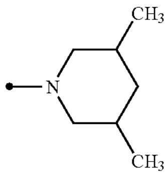 | MS m/z 600 $(M + H)^+$ |
| 9-254 | 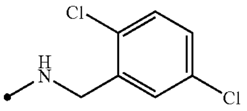 | 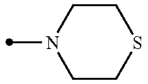 | MS m/z 590 $(M + H)^+$ |
| 9-255 | 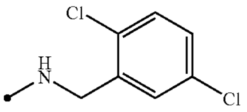 | 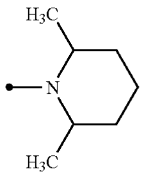 | MS m/z 600 $(M + H)^+$ |

TABLE 9-continued
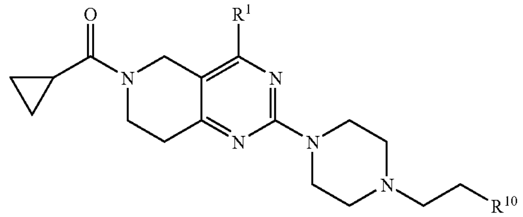
| Compound Number | •—$R^1$ | •—$R^{10}$ | Spectrum Data |
|---|---|---|---|
| 9-256 | 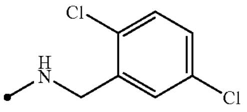 | 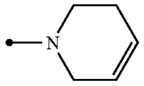 | MS m/z 570 $(M + H)^+$ |
| 9-257 | 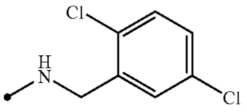 | 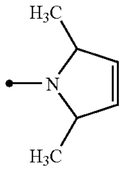 | MS m/z 584 $(M + H)^+$ |
| 9-258 | 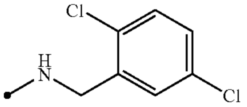 | 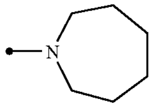 | MS m/z 586 $(M + H)^+$ |
| 9-259 | 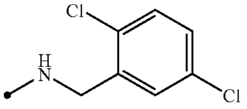 | 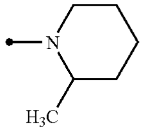 | MS m/z 586 $(M + H)^+$ |
| 9-260 | 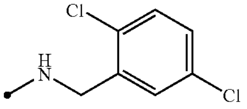 | 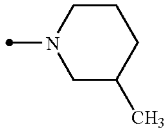 | MS m/z 586 $(M + H)^+$ |
| 9-261 | 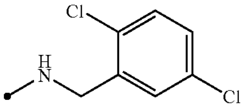 | 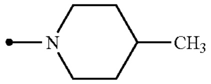 | MS m/z 586 $(M + H)^+$ |
| 9-262 | 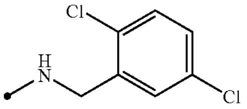 | 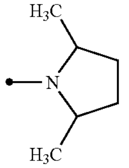 | MS m/z 586 $(M + H)^+$ |
| 9-263 | 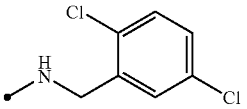 | 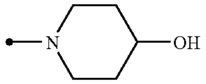 | MS m/z 588 $(M + H)^+$ |
| 9-264 | 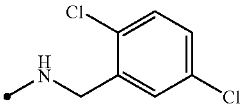 | 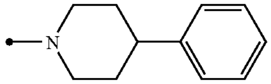 | MS m/z 648 $(M + H)^+$ |

TABLE 9-continued
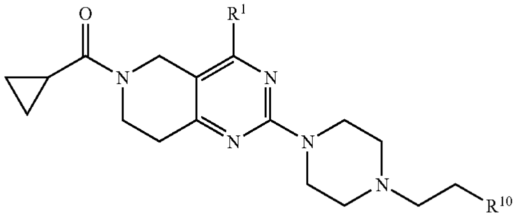
| Compound Number | •—$R^1$ | •—$R^{10}$ | Spectrum Data |
| --- | --- | --- | --- |
| 9-265 | 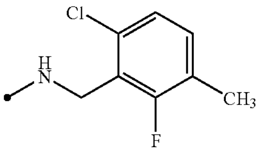 | 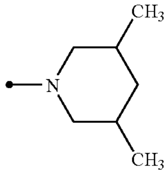 | MS m/z 598 $(M + H)^+$ |
| 9-266 | 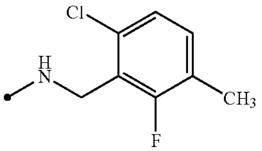 | 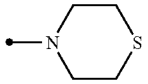 | MS m/z 588 $(M + H)^+$ |
| 9-267 | 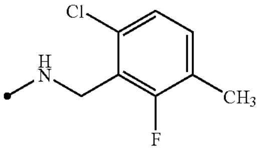 | 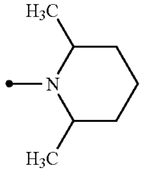 | MS m/z 598 $(M + H)^+$ |
| 9-268 | 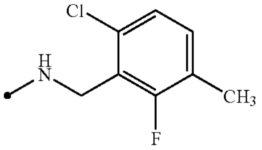 | 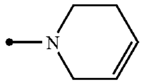 | MS m/z 568 $(M + H)^+$ |
| 9-269 | 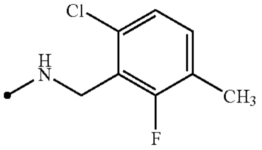 | 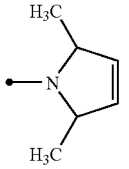 | MS m/z 582 $(M + H)^+$ |
| 9-270 | 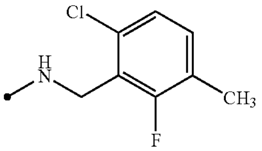 | 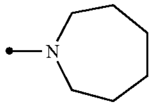 | MS m/z 584 $(M + H)^+$ |
| 9-271 | 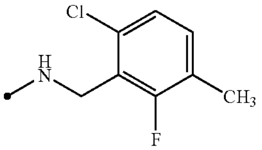 | 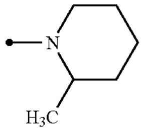 | MS m/z 584 $(M + H)^+$ |

TABLE 9-continued
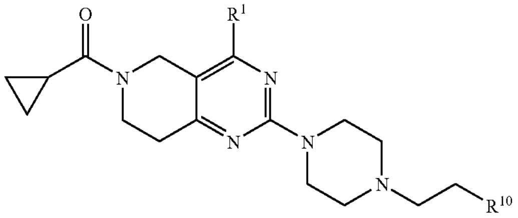
| Compound Number | •—$R^1$ | •—$R^{10}$ | Spectrum Data |
|---|---|---|---|
| 9-272 | 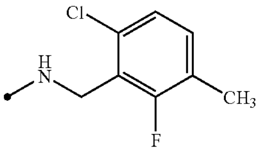 | 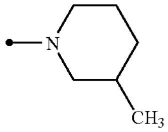 | MS m/z 584 $(M+H)^+$ |
| 9-273 | 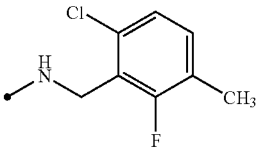 | 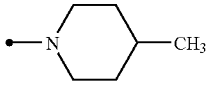 | MS m/z 584 $(M+H)^+$ |
| 9-274 | 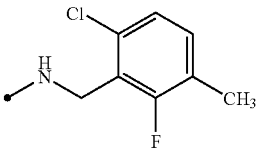 | 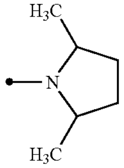 | MS m/z 584 $(M+H)^+$ |
| 9-275 | 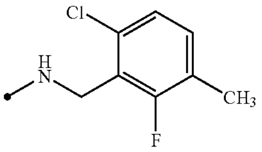 | 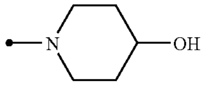 | MS m/z 586 $(M+H)^+$ |
| 9-276 | 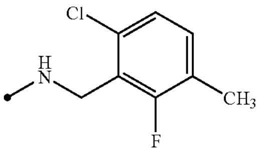 | 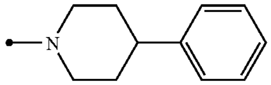 | MS m/z 646 $(M+H)^+$ |
| 9-277 | 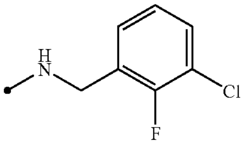 | 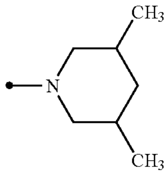 | MS m/z 584 $(M+H)^+$ |
| 9-278 | 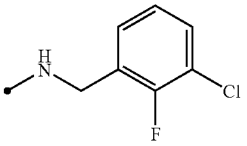 | 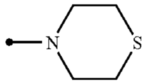 | MS m/z 574 $(M+H)^+$ |

TABLE 9-continued
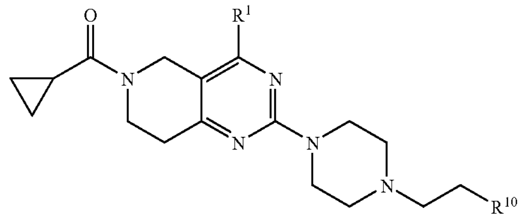
| Compound Number | •—$R^1$ | •—$R^{10}$ | Spectrum Data |
| --- | --- | --- | --- |
| 9-279 | 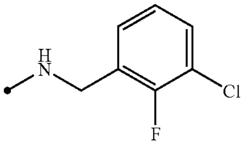 | 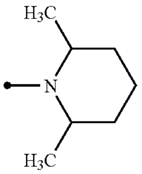 | MS m/z 584 $(M + H)^+$ |
| 9-280 | 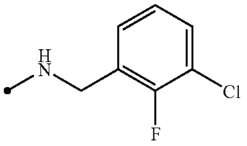 | 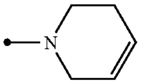 | MS m/z 584 $(M + H)^+$ |
| 9-281 | 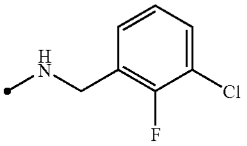 | 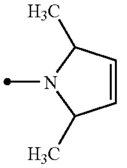 | MS m/z 568 $(M + H)^+$ |
| 9-282 | 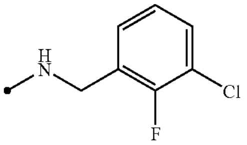 | 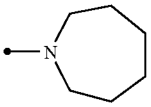 | MS m/z 570 $(M + H)^+$ |
| 9-283 | 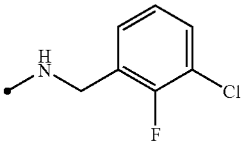 | 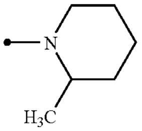 | MS m/z 570 $(M + H)^+$ |
| 9-284 | 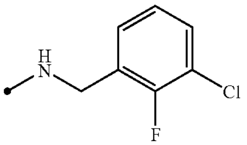 | 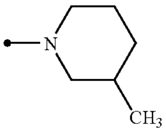 | MS m/z 570 $(M + H)^+$ |
| 9-285 | 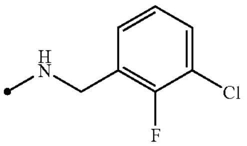 | 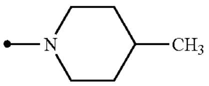 | MS m/z 570 $(M + H)^+$ |
| 9-286 | 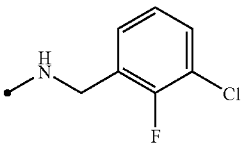 | 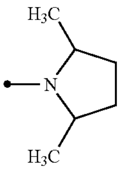 | MS m/z 570 $(M + H)^+$ |

TABLE 9-continued
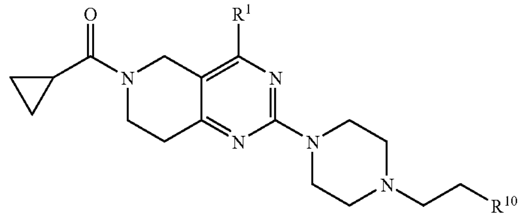
| Compound Number | •—$R^1$ | •—$R^{10}$ | Spectrum Data |
|---|---|---|---|
| 9-287 | 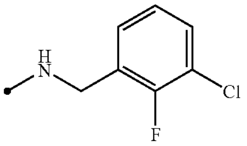 | 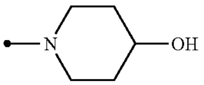 | MS m/z 572 $(M + H)^+$ |
| 9-288 | 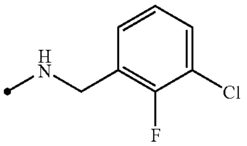 | 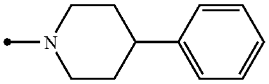 | MS m/z 632 $(M + H)^+$ |
| 9-289 | 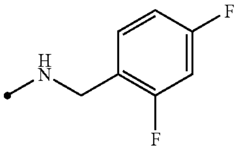 | 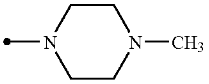 | MS m/z 555 $(M + H)^+$ |
| 9-290 | 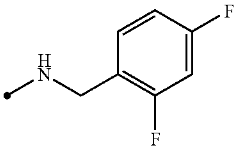 | 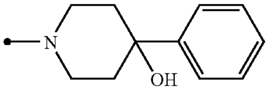 | MS m/z 632 $(M + H)^+$ |
| 9-291 | 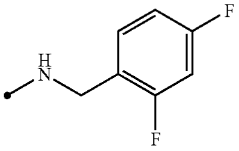 | 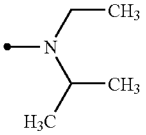 | MS m/z 542 $(M + H)^+$ |
| 9-292 | 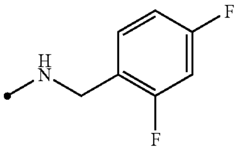 | 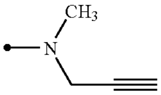 | MS m/z 524 $(M + H)^+$ |
| 9-293 | 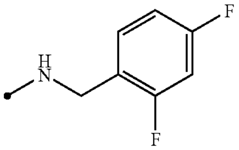 | 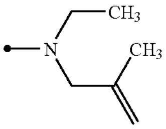 | MS m/z 554 $(M + H)^+$ |
| 9-294 | 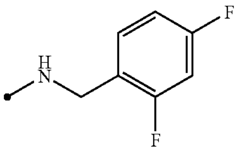 | 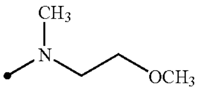 | MS m/z 544 $(M + H)^+$ |

TABLE 9-continued
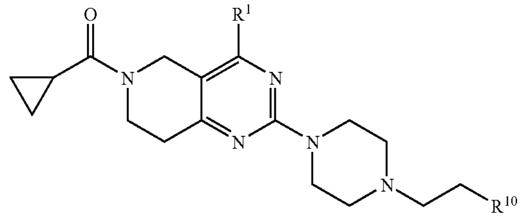
| Compound Number | •—R¹ | •—R¹⁰ | Spectrum Data |
|---|---|---|---|
| 9-295 | 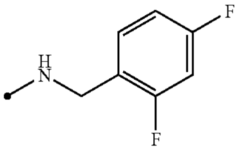 | 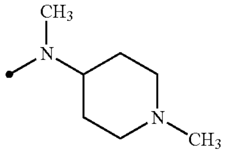 | MS m/z 583 (M + H)$^+$ |
| 9-296 | 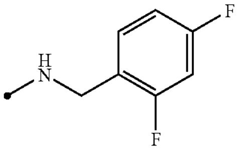 | 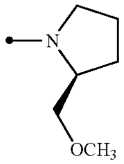 | MS m/z 570 (M + H)$^+$ |
| 9-297 | 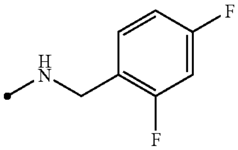 | 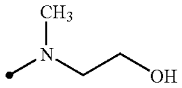 | MS m/z 530 (M + H)$^+$ |
| 9-298 | 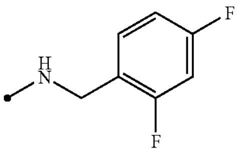 | 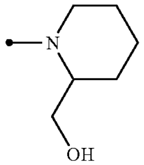 | MS m/z 570 (M + H)$^+$ |
| 9-299 | 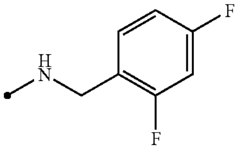 | 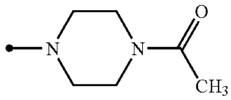 | MS m/z 583 (M + H)$^+$ |
| 9-300 | 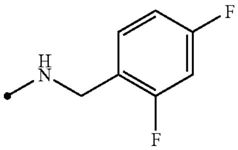 | 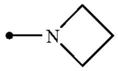 | MS m/z 512 (M + H)$^+$ |
| 9-301 | 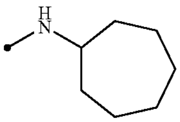 | 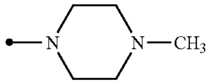 | MS m/z 525 (M + H)$^+$ |
| 9-302 | 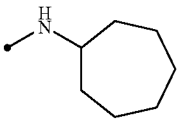 | 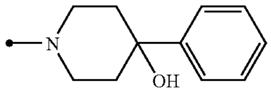 | MS m/z 602 (M + H)$^+$ |

TABLE 9-continued
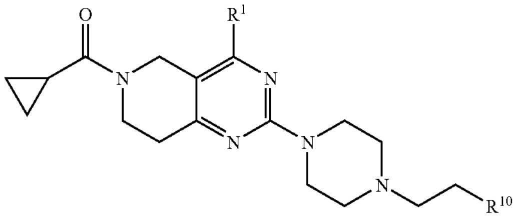
| Compound Number | •—$R^1$ | •—$R^{10}$ | Spectrum Data |
| --- | --- | --- | --- |
| 9-303 | 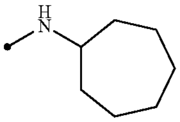 | 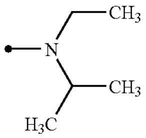 | MS m/z 512 $(M + H)^+$ |
| 9-304 | 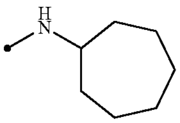 | 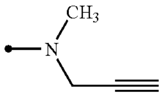 | MS m/z 494 $(M + H)^+$ |
| 9-305 | 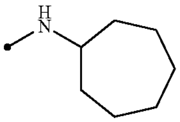 | 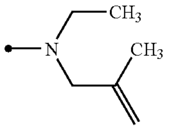 | MS m/z 524 $(M + H)^+$ |
| 9-306 | 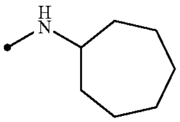 | 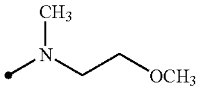 | MS m/z 514 $(M + H)^+$ |
| 9-307 | 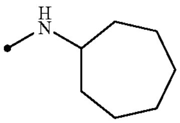 | 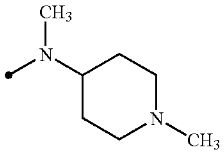 | MS m/z 553 $(M + H)^+$ |
| 9-308 | 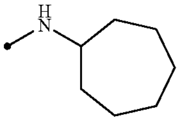 | 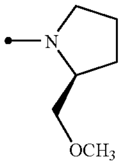 | MS m/z 540 $(M + H)^+$ |
| 9-309 | 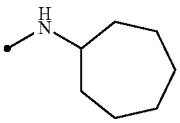 | 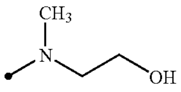 | MS m/z 500 $(M + H)^+$ |
| 9-310 | 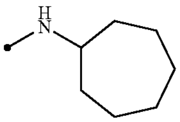 | 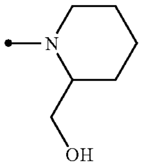 | MS m/z 540 $(M + H)^+$ |

TABLE 9-continued
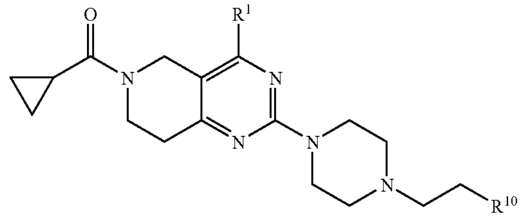
| Compound Number | •—$R^1$ | •—$R^{10}$ | Spectrum Data |
|---|---|---|---|
| 9-311 | 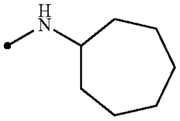 | 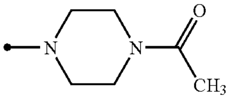 | MS m/z 553 $(M + H)^+$ |
| 9-312 | 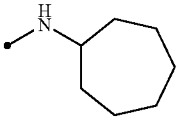 | 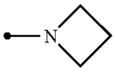 | MS m/z 482 $(M + H)^+$ |
| 9-313 | 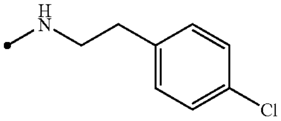 | 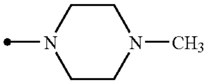 | MS m/z 567 $(M + H)^+$ |
| 9-314 | 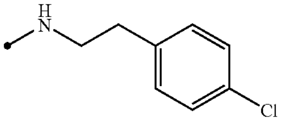 | 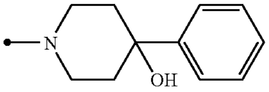 | MS m/z 644 $(M + H)^+$ |
| 9-315 | 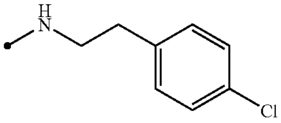 | 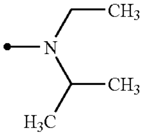 | MS m/z 554 $(M + H)^+$ |
| 9-316 | 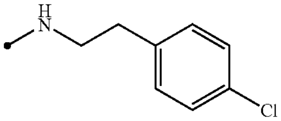 | 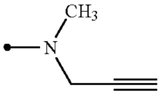 | MS m/z 536 $(M + H)^+$ |
| 9-317 | 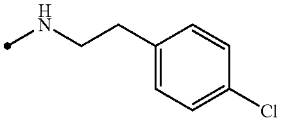 | 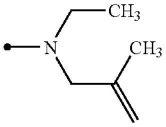 | MS m/z 566 $(M + H)^+$ |
| 9-318 | 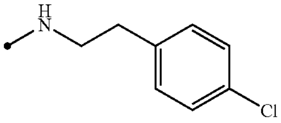 | 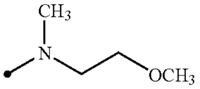 | MS m/z 556 $(M + H)^+$ |
| 9-319 | 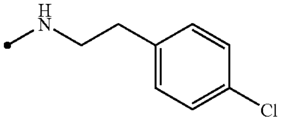 | 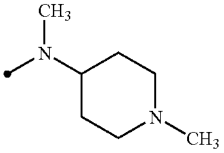 | MS m/z 595 $(M + H)^+$ |

TABLE 9-continued
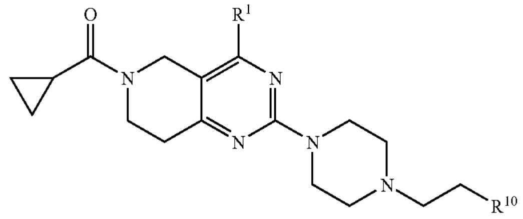
| Compound Number | •—$R^1$ | •—$R^{10}$ | Spectrum Data |
|---|---|---|---|
| 9-320 | 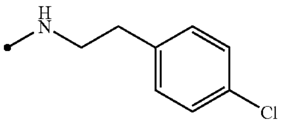 | 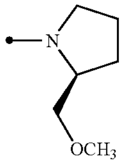 | MS m/z 582 $(M + H)^+$ |
| 9-321 | 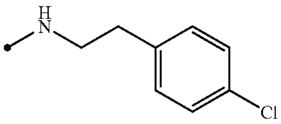 | 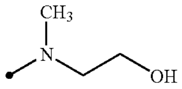 | MS m/z 542 $(M + H)^+$ |
| 9-322 | 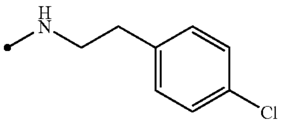 | 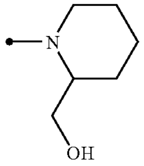 | MS m/z 582 $(M + H)^+$ |
| 9-323 | 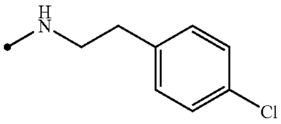 | 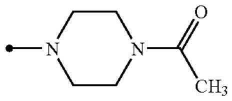 | MS m/z 595 $(M + H)^+$ |
| 9-324 | 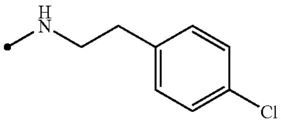 | 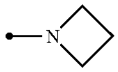 | MS m/z 524 $(M + H)^+$ |
| 9-325 | 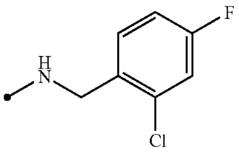 | 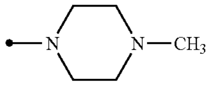 | MS m/z 571 $(M + H)^+$ |
| 9-326 | 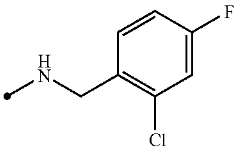 | 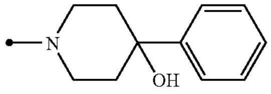 | MS m/z 648 $(M + H)^+$ |
| 9-327 | 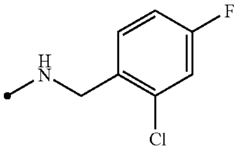 | 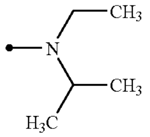 | MS m/z 558 $(M + H)^+$ |

TABLE 9-continued
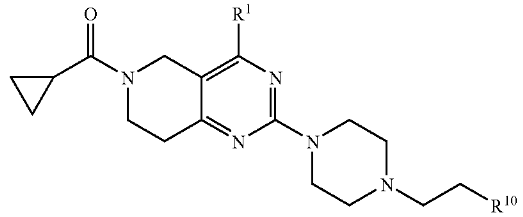
| Compound Number | •—$R^1$ | •—$R^{10}$ | Spectrum Data |
| --- | --- | --- | --- |
| 9-328 | 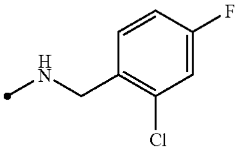 | 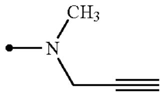 | MS m/z 540 $(M + H)^+$ |
| 9-329 | 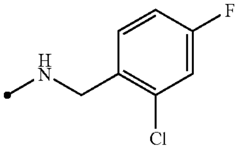 | 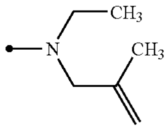 | MS m/z 570 $(M + H)^+$ |
| 9-330 | 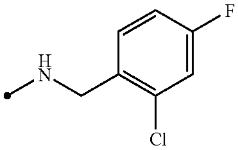 | 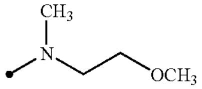 | MS m/z 560 $(M + H)^+$ |
| 9-331 | 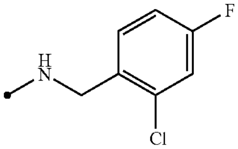 | 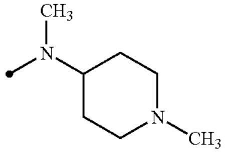 | MS m/z 599 $(M + H)^+$ |
| 9-332 | 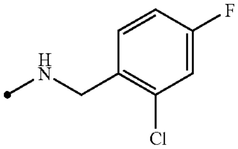 | 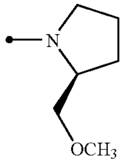 | MS m/z 586 $(M + H)^+$ |
| 9-333 | 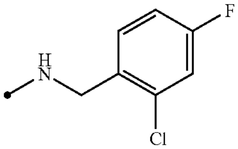 | 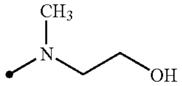 | MS m/z 546 $(M + H)^+$ |
| 9-334 | 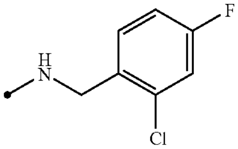 | 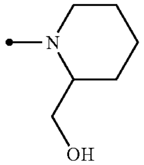 | MS m/z 586 $(M + H)^+$ |
| 9-335 | 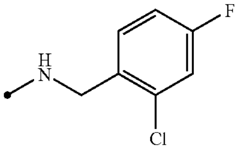 | 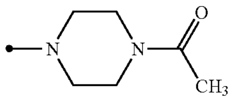 | MS m/z 599 $(M + H)^+$ |

TABLE 9-continued
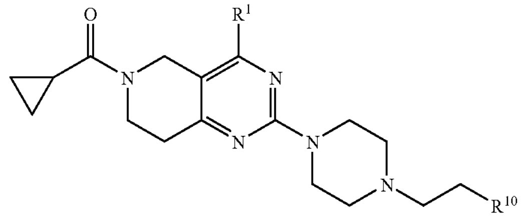
| Compound Number | •—$R^1$ | •—$R^{10}$ | Spectrum Data |
|---|---|---|---|
| 9-336 | 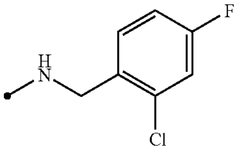 | 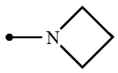 | MS m/z 528 $(M + H)^+$ |
| 9-337 | 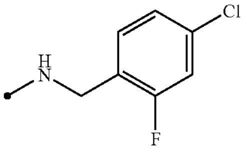 | 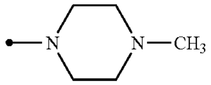 | MS m/z 571 $(M + H)^+$ |
| 9-338 | 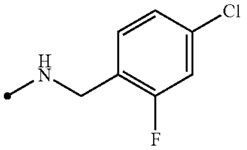 | 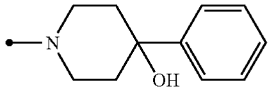 | MS m/z 648 $(M + H)^+$ |
| 9-339 | 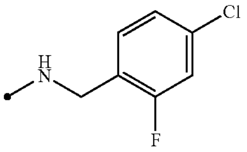 | 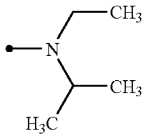 | MS m/z 558 $(M + H)^+$ |
| 9-340 | 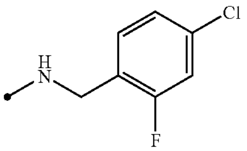 | 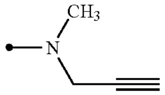 | MS m/z 540 $(M + H)^+$ |
| 9-341 | 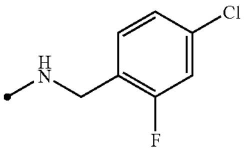 | 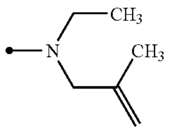 | MS m/z 570 $(M + H)^+$ |
| 9-342 | 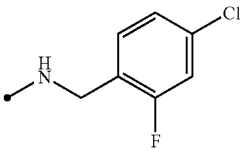 | 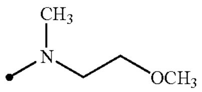 | MS m/z 560 $(M + H)^+$ |
| 9-343 | 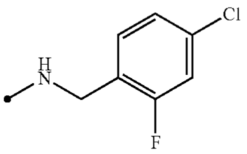 | 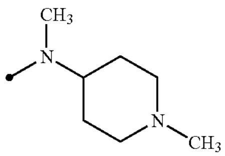 | MS m/z 599 $(M + H)^+$ |

TABLE 9-continued
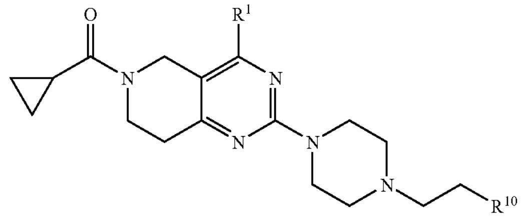
| Compound Number | •—$R^1$ | •—$R^{10}$ | Spectrum Data |
|---|---|---|---|
| 9-344 | 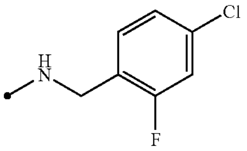 | 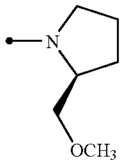 | MS m/z 586 $(M + H)^+$ |
| 9-345 | 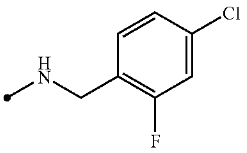 | 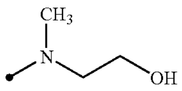 | MS m/z 546 $(M + H)^+$ |
| 9-346 | 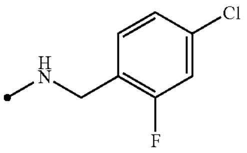 | 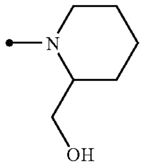 | MS m/z 586 $(M + H)^+$ |
| 9-347 | 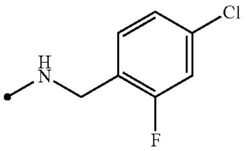 | 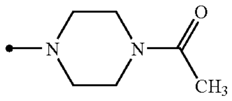 | MS m/z 599 $(M + H)^+$ |
| 9-348 | 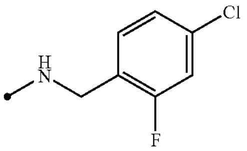 | 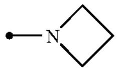 | MS m/z 528 $(M + H)^+$ |
| 9-349 | 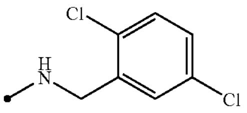 | 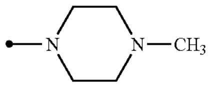 | MS m/z 587 $(M + H)^+$ |
| 9-350 | 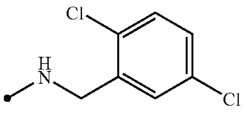 | 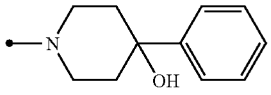 | MS m/z 664 $(M + H)^+$ |
| 9-351 | 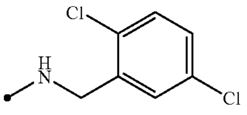 | 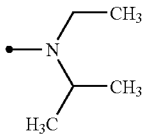 | MS m/z 574 $(M + H)^+$ |

TABLE 9-continued
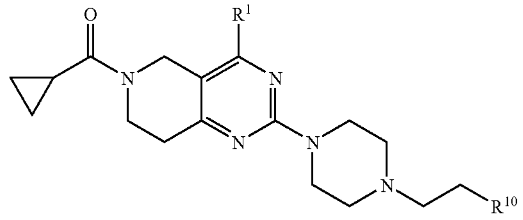
| Compound Number | •—R¹ | •—R¹⁰ | Spectrum Data |
|---|---|---|---|
| 9-352 | 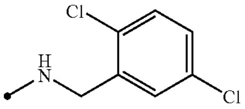 | 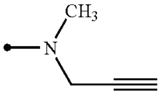 | MS m/z 556 $(M + H)^+$ |
| 9-353 | 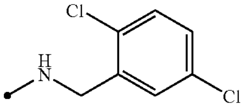 | 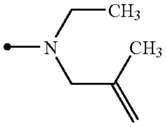 | MS m/z 586 $(M + H)^+$ |
| 9-354 | 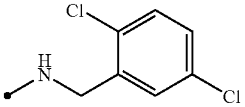 | 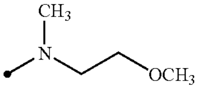 | MS m/z 576 $(M + H)^+$ |
| 9-355 | 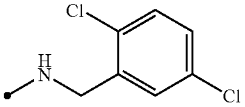 | 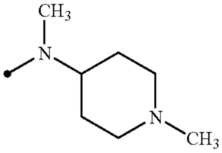 | MS m/z 615 $(M + H)^+$ |
| 9-356 | 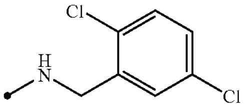 | 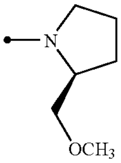 | MS m/z 602 $(M + H)^+$ |
| 9-357 | 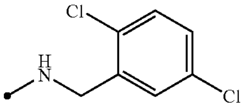 | 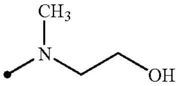 | MS m/z 562 $(M + H)^+$ |
| 9-358 | 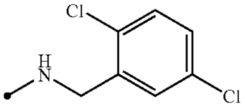 | 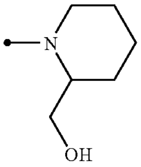 | MS m/z 602 $(M + H)^+$ |
| 9-359 | 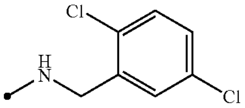 | 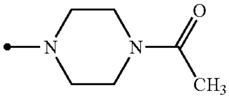 | MS m/z 615 $(M + H)^+$ |
| 9-360 | 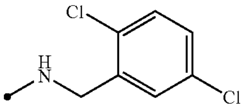 | 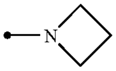 | MS m/z 544 $(M + H)^+$ |

TABLE 9-continued
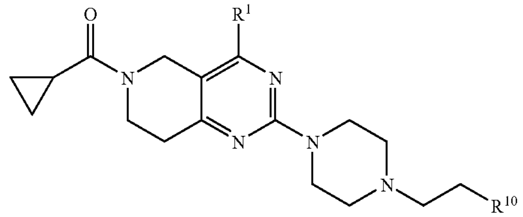
| Compound Number | •—$R^1$ | •—$R^{10}$ | Spectrum Data |
|---|---|---|---|
| 9-361 | 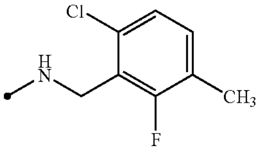 | 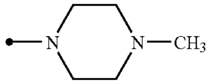 | MS m/z 585 $(M + H)^+$ |
| 9-362 | 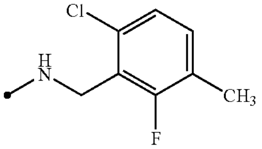 | 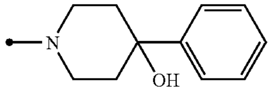 | MS m/z 662 $(M + H)^+$ |
| 9-363 | 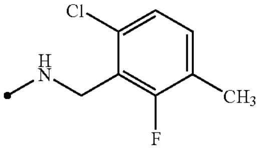 | 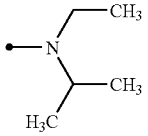 | MS m/z 572 $(M + H)^+$ |
| 9-364 | 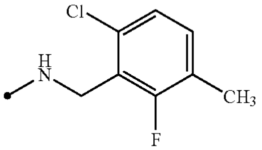 | 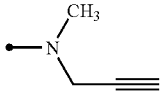 | MS m/z 554 $(M + H)^+$ |
| 9-365 | 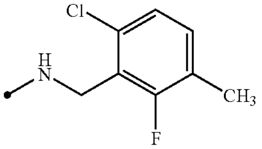 | 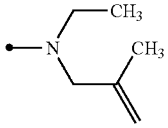 | MS m/z 584 $(M + H)^+$ |
| 9-366 | 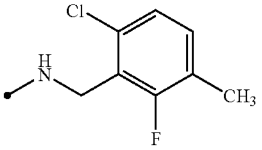 | 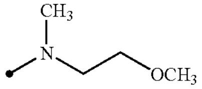 | MS m/z 574 $(M + H)^+$ |
| 9-367 | 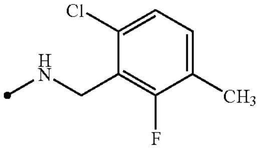 | 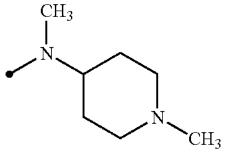 | MS m/z 613 $(M + H)^+$ |
| 9-368 | 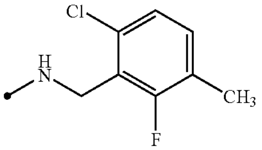 | 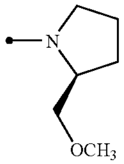 | MS m/z 600 $(M + H)^+$ |

TABLE 9-continued
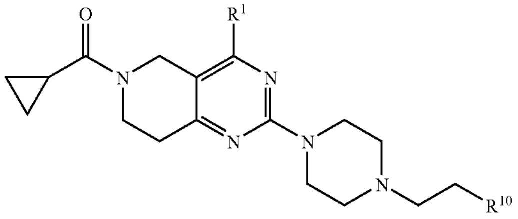
| Compound Number | •—$R^1$ | •—$R^{10}$ | Spectrum Data |
|---|---|---|---|
| 9-369 | 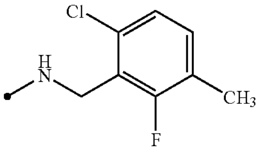 | 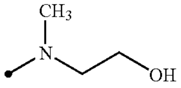 | MS m/z 560 $(M + H)^+$ |
| 9-370 | 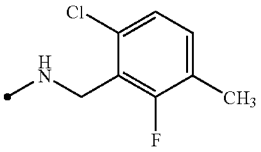 | 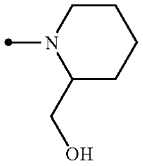 | MS m/z 600 $(M + H)^+$ |
| 9-371 | 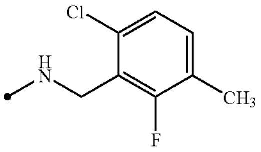 | 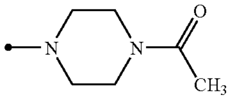 | MS m/z 613 $(M + H)^+$ |
| 9-372 | 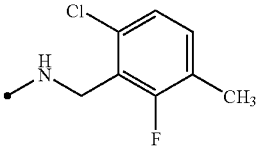 | 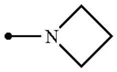 | MS m/z 542 $(M + H)^+$ |
| 9-373 | 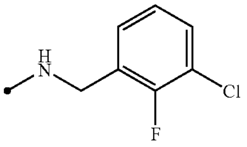 | 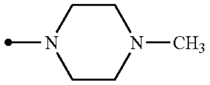 | MS m/z 571 $(M + H)^+$ |
| 9-374 | 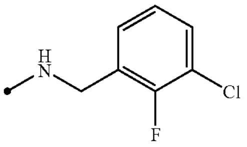 | 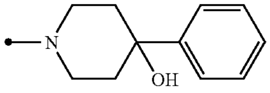 | MS m/z 648 $(M + H)^+$ |
| 9-375 | 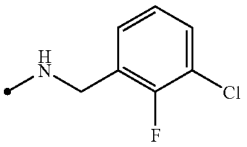 | 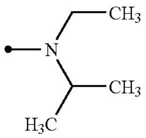 | MS m/z 558 $(M + H)^+$ |
| 9-376 | 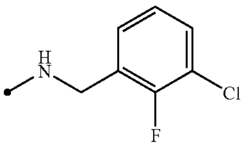 | 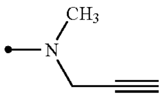 | MS m/z 540 $(M + H)^+$ |

TABLE 9-continued
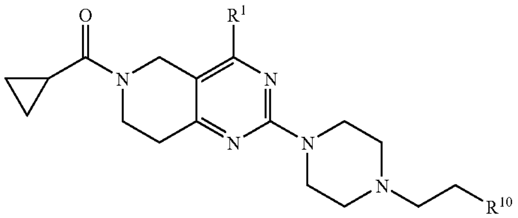
| Compound Number | •—R¹ | •—R¹⁰ | Spectrum Data |
|---|---|---|---|
| 9-377 | 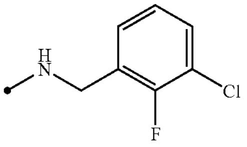 | 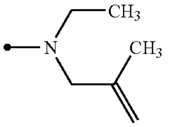 | MS m/z 570 (M + H)+ |
| 9-378 | 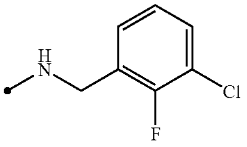 | 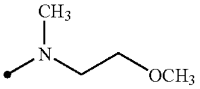 | MS m/z 560 (M + H)+ |
| 9-379 | 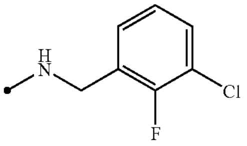 | 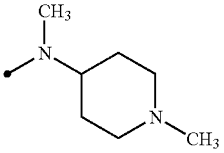 | MS m/z 599 (M + H)+ |
| 9-380 | 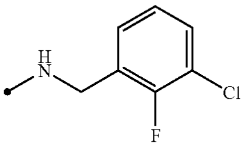 | 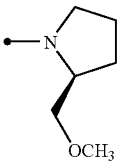 | MS m/z 586 (M + H)+ |
| 9-381 | 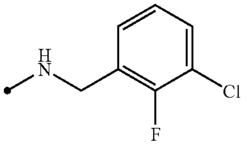 | 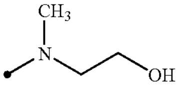 | MS m/z 546 (M + H)+ |
| 9-382 | 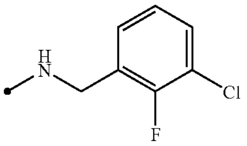 | 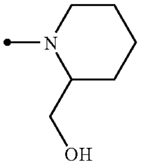 | MS m/z 586 (M + H)+ |
| 9-383 | 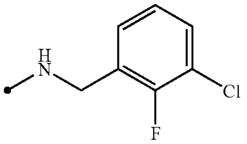 | 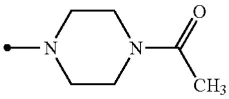 | MS m/z 599 (M + H)+ |
| 9-384 | 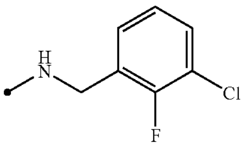 | 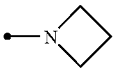 | MS m/z 528 (M + H)+ |

TABLE 10
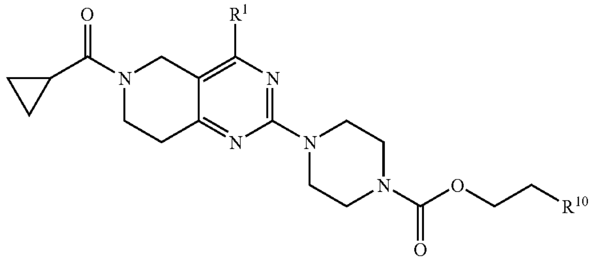
| Compound Number | •—$R^1$ | •—$R^{10}$ | Spectrum Data |
|---|---|---|---|
| 10-1 | 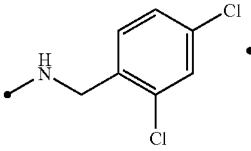 | 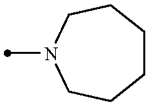 | MS m/z 630 $(M+H)^+$ |
| 10-2 | 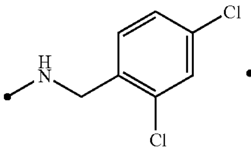 | 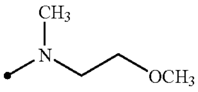 | MS m/z 620 $(M+H)^+$ |
| 10-3 | 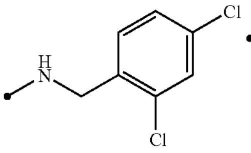 | 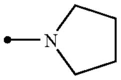 | MS m/z 602 $(M+H)^+$ |
| 10-4 | 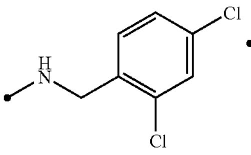 | 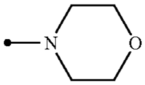 | MS m/z 618 $(M+H)^+$ |
| 10-5 | 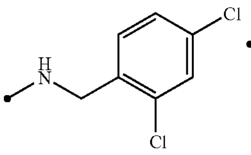 | 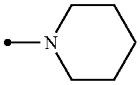 | MS m/z 616 $(M+H)^+$ |
| 10-6 | 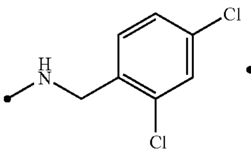 | 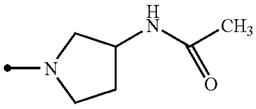 | MS m/z 659 $(M+H)^+$ |
| 10-7 | 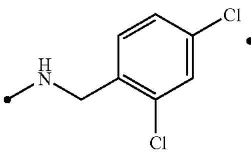 | 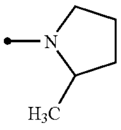 | MS m/z 616 $(M+H)^+$ |

TABLE 10-continued
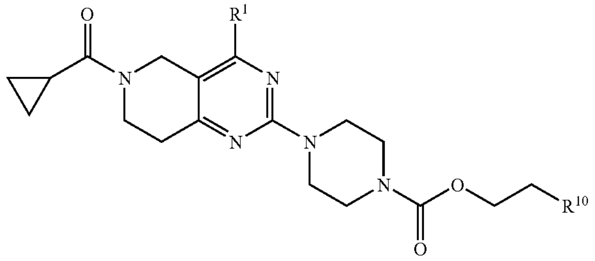
| Compound Number | •—$R^1$ | •—$R^{10}$ | Spectrum Data |
|---|---|---|---|
| 10-8 | 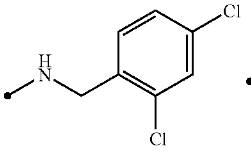 | 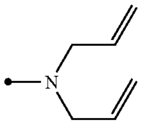 | MS m/z 628 $(M + H)^+$ |
| 10-9 | 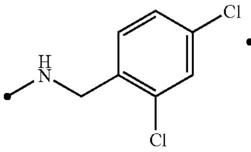 | 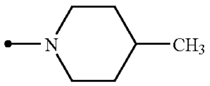 | MS m/z 630 $(M + H)^+$ |
| 10-10 | 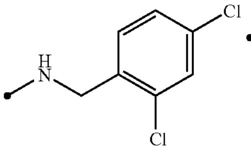 | 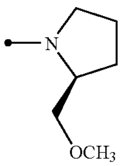 | MS m/z 646 $(M + H)^+$ |
| 10-11 | 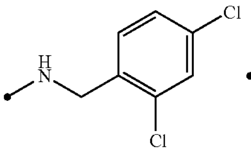 | 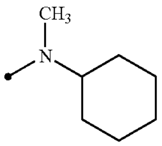 | MS m/z 644 $(M + H)^+$ |
| 10-12 | 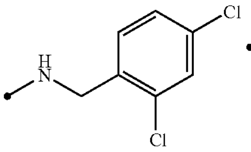 | 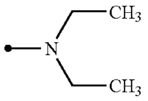 | MS m/z 604 $(M + H)^+$ |
| 10-13 | 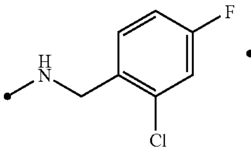 | 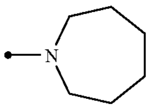 | MS m/z 614 $(M + H)^+$ |
| 10-14 | 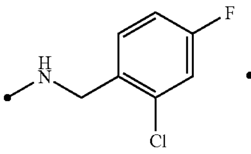 | 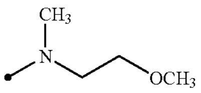 | MS m/z 604 $(M + H)^+$ |

TABLE 10-continued
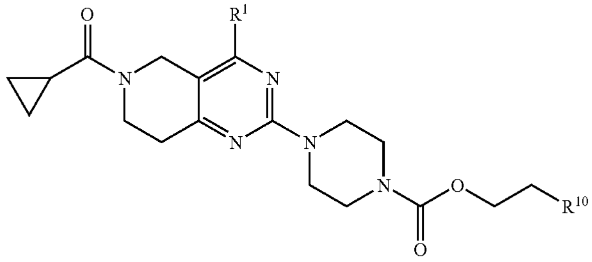
| Compound Number | •—$R^1$ | •—$R^{10}$ | Spectrum Data |
|---|---|---|---|
| 10-15 | 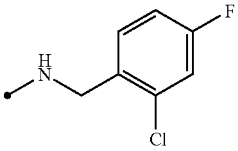 | 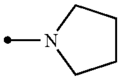 | MS m/z 586 $(M + H)^+$ |
| 10-16 | 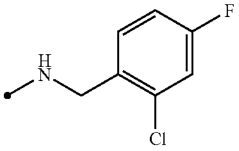 | 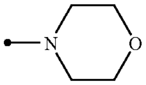 | MS m/z 602 $(M + H)^+$ |
| 10-17 | 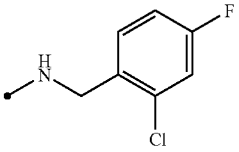 | 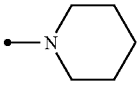 | MS m/z 600 $(M + H)^+$ |
| 10-18 | 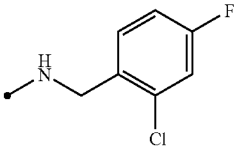 | 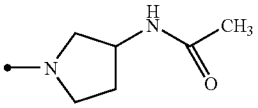 | MS m/z 643 $(M + H)^+$ |
| 10-19 | 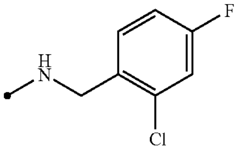 | 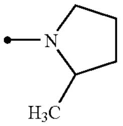 | MS m/z 600 $(M + H)^+$ |
| 10-20 | 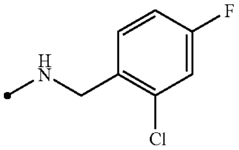 | 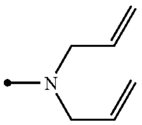 | MS m/z 612 $(M + H)^+$ |
| 10-21 | 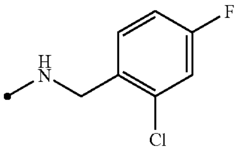 | 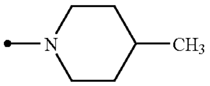 | MS m/z 614 $(M + H)^+$ |

TABLE 10-continued
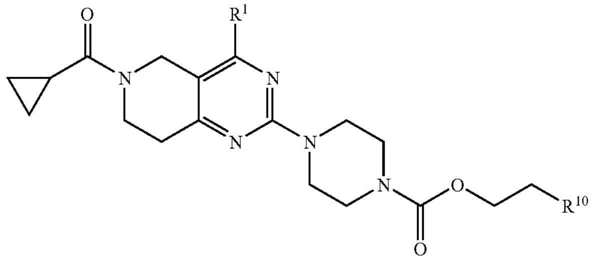
| Compound Number | •—$R^1$ | •—$R^{10}$ | Spectrum Data |
|---|---|---|---|
| 10-22 | 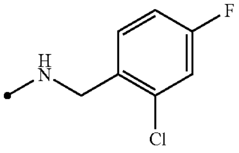 | 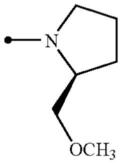 | MS m/z 630 $(M + H)^+$ |
| 10-23 | 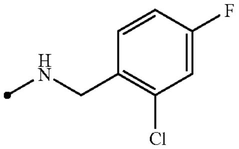 | 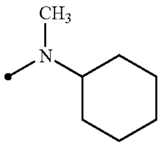 | MS m/z 628 $(M + H)^+$ |
| 10-24 | 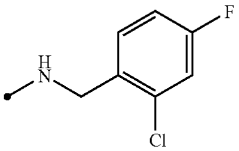 | 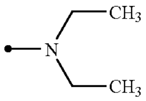 | MS m/z 588 $(M + H)^+$ |
| 10-25 | 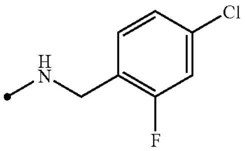 | 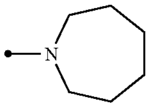 | MS m/z 614 $(M + H)^+$ |
| 10-26 | 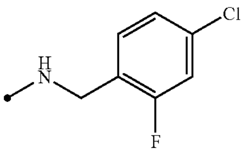 | 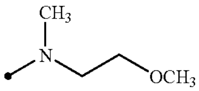 | MS m/z 604 $(M + H)^+$ |
| 10-27 | 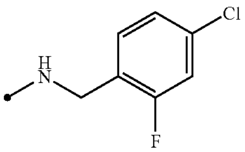 | 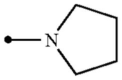 | MS m/z 586 $(M + H)^+$ |
| 10-28 | 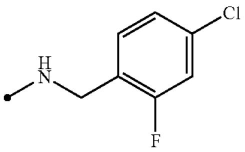 | 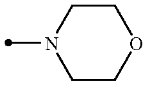 | MS m/z 602 $(M + H)^+$ |

TABLE 10-continued
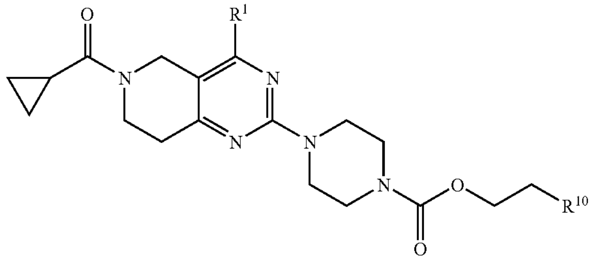
| Compound Number | •—$R^1$ | •—$R^{10}$ | Spectrum Data |
|---|---|---|---|
| 10-29 | 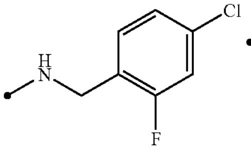 | 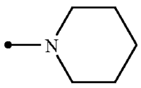 | MS m/z 600 $(M + H)^+$ |
| 10-30 | 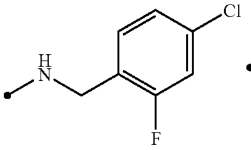 | 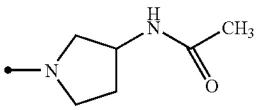 | MS m/z 643 $(M + H)^+$ |
| 10-31 | 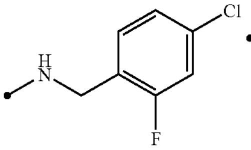 | 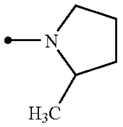 | MS m/z 600 $(M + H)^+$ |
| 10-32 | 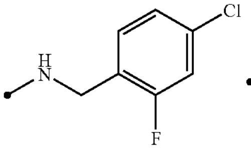 | 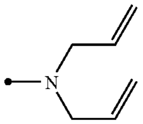 | MS m/z 612 $(M + H)^+$ |
| 10-33 | 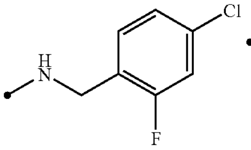 | 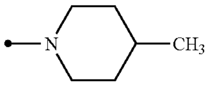 | MS m/z 614 $(M + H)^+$ |
| 10-34 | 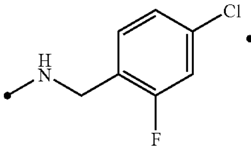 | 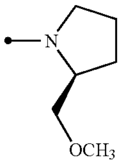 | MS m/z 630 $(M + H)^+$ |
| 10-35 | 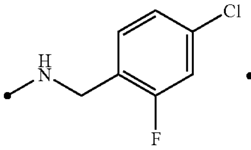 | 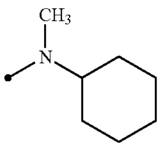 | MS m/z 628 $(M + H)^+$ |

TABLE 10-continued
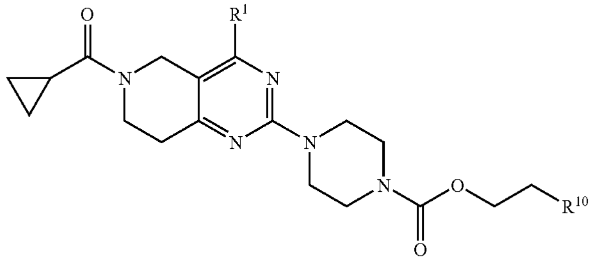
| Compound Number | •—R¹ | •—R¹⁰ | Spectrum Data |
|---|---|---|---|
| 10-36 | 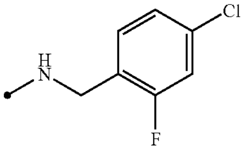 | 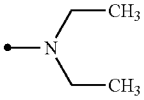 | MS m/z 588 $(M + H)^+$ |
| 10-37 | 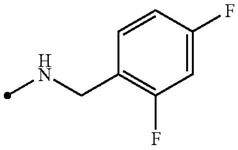 | 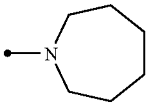 | MS m/z 598 $(M + H)^+$ |
| 10-38 | 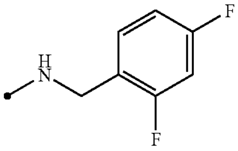 | 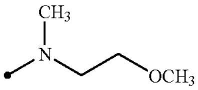 | MS m/z 588 $(M + H)^+$ |
| 10-39 | 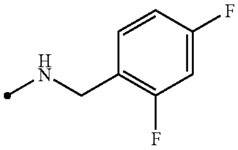 | 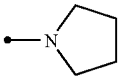 | MS m/z 570 $(M + H)^+$ |
| 10-40 | 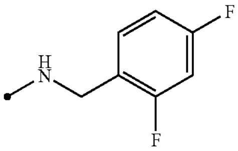 | 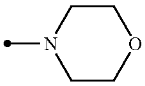 | MS m/z 586 $(M + H)^+$ |
| 10-41 | 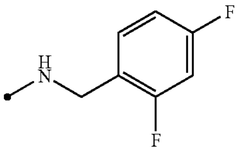 | 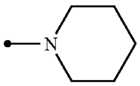 | MS m/z 584 $(M + H)^+$ |
| 10-42 | 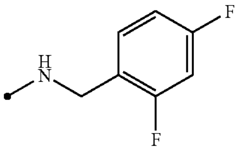 | 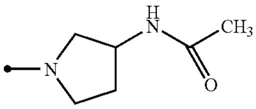 | MS m/z 627 $(M + H)^+$ |

TABLE 10-continued
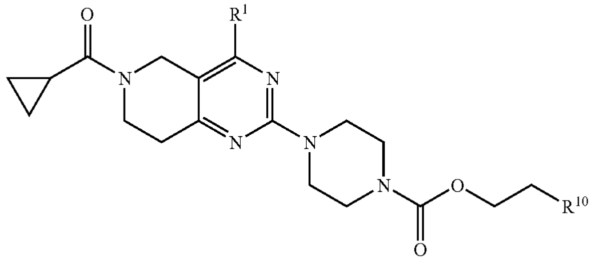
| Compound Number | •—$R^1$ | •—$R^{10}$ | Spectrum Data |
|---|---|---|---|
| 10-43 | 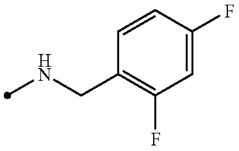 | 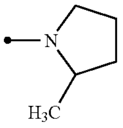 | MS m/z 584 $(M + H)^+$ |
| 10-44 | 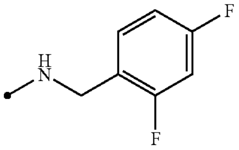 | 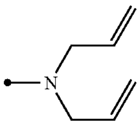 | MS m/z 596 $(M + H)^+$ |
| 10-45 | 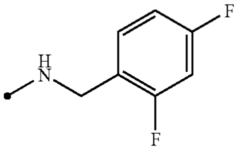 | 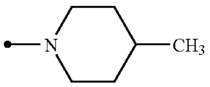 | MS m/z 598 $(M + H)^+$ |
| 10-46 | 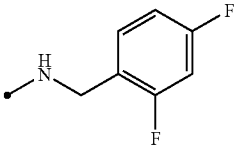 | 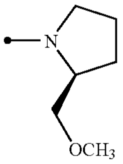 | MS m/z 614 $(M + H)^+$ |
| 10-47 | 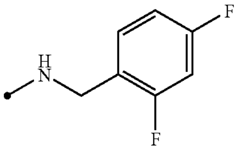 | 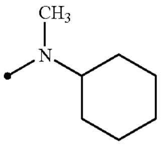 | MS m/z 612 $(M + H)^+$ |
| 10-48 | 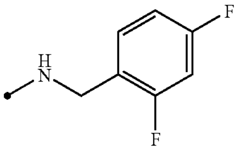 | 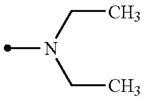 | MS m/z 572 $(M + H)^+$ |
| 10-49 | 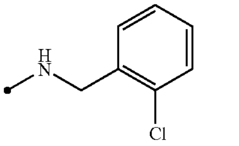 | 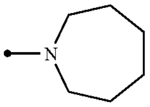 | MS m/z 596 $(M + H)^+$ |

TABLE 10-continued
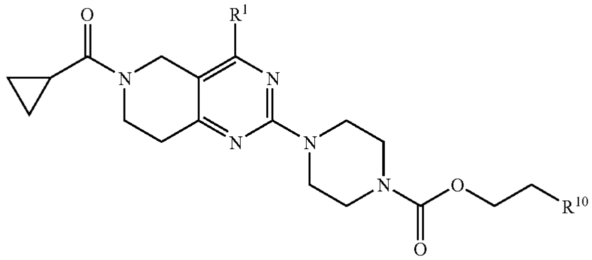
| Compound Number | •—$R^1$ | •—$R^{10}$ | Spectrum Data |
|---|---|---|---|
| 10-50 | 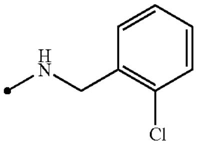 | 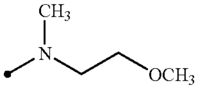 | MS m/z 586 $(M + H)^+$ |
| 10-51 | 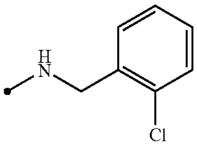 | 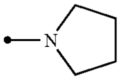 | MS m/z 568 $(M + H)^+$ |
| 10-52 | 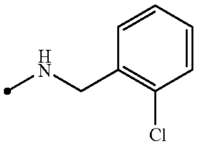 | 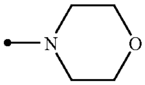 | MS m/z 584 $(M + H)^+$ |
| 10-53 | 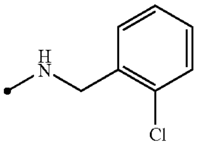 | 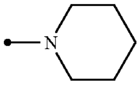 | MS m/z 582 $(M + H)^+$ |
| 10-54 | 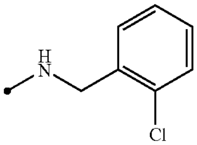 | 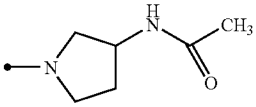 | MS m/z 625 $(M + H)^+$ |
| 10-55 | 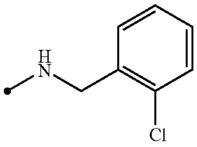 | 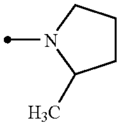 | MS m/z 582 $(M + H)^+$ |
| 10-56 | 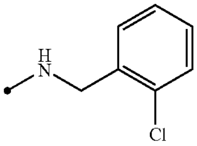 | 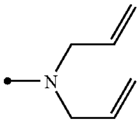 | MS m/z 594 $(M + H)^+$ |
| 10-57 | 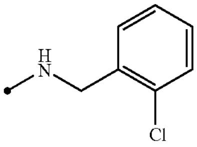 | 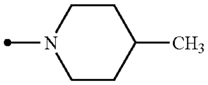 | MS m/z 596 $(M + H)^+$ |

TABLE 10-continued
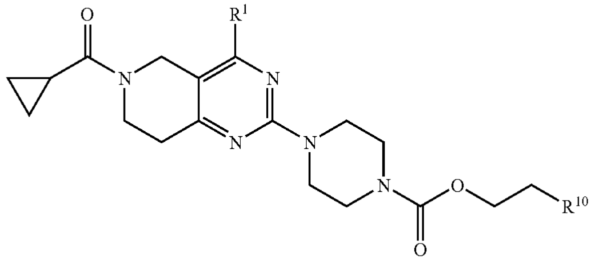
| Compound Number | •—$R^1$ | •—$R^{10}$ | Spectrum Data |
|---|---|---|---|
| 10-58 | 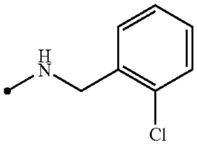 | 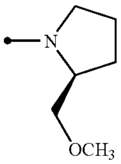 | MS m/z 612 $(M + H)^+$ |
| 10-59 | 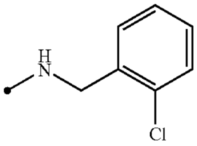 | 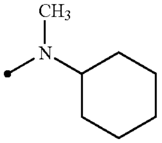 | MS m/z 610 $(M + H)^+$ |
| 10-60 | 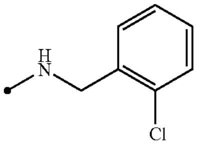 | 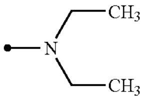 | MS m/z 570 $(M + H)^+$ |
| 10-61 | 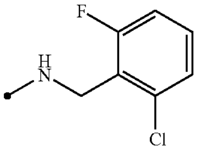 | 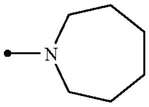 | MS m/z 614 $(M + H)^+$ |
| 10-62 | 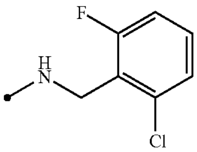 | 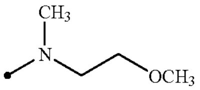 | MS m/z 604 $(M + H)^+$ |
| 10-63 | 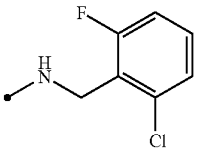 | 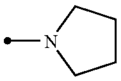 | MS m/z 586 $(M + H)^+$ |
| 10-64 | 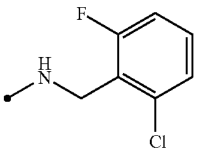 | 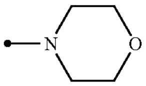 | MS m/z 602 $(M + H)^+$ |

TABLE 10-continued
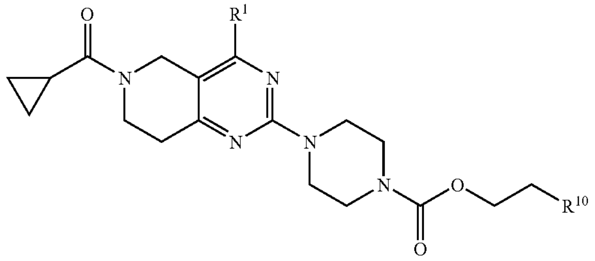
| Compound Number | •—$R^1$ | •—$R^{10}$ | Spectrum Data |
|---|---|---|---|
| 10-65 | 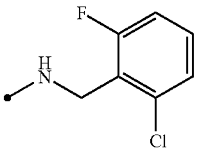 | 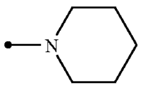 | MS m/z 600 $(M + H)^+$ |
| 10-66 | 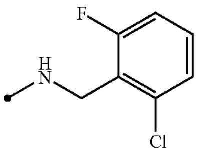 | 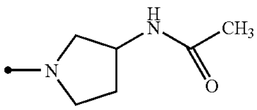 | MS m/z 643 $(M + H)^+$ |
| 10-67 | 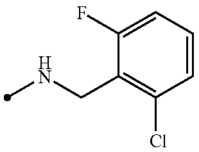 | 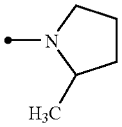 | MS m/z 600 $(M + H)^+$ |
| 10-68 | 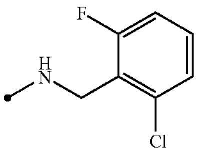 | 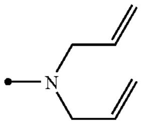 | MS m/z 612 $(M + H)^+$ |
| 10-69 | 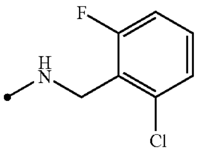 | 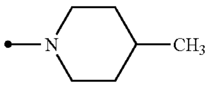 | MS m/z 614 $(M + H)^+$ |
| 10-70 | 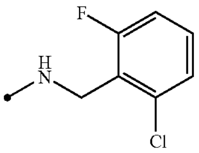 | 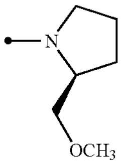 | MS m/z 630 $(M + H)^+$ |
| 10-71 | 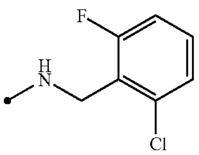 | 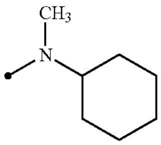 | MS m/z 628 $(M + H)^+$ |

TABLE 10-continued
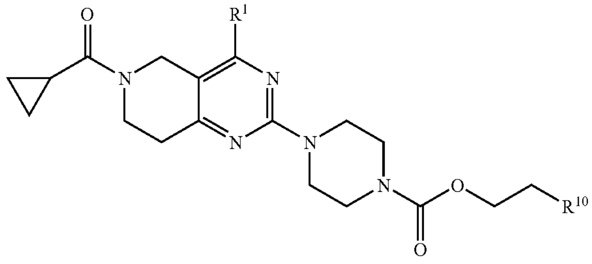
| Compound Number | •—R[1] | •—R[10] | Spectrum Data |
|---|---|---|---|
| 10-72 | 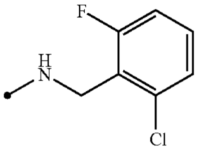 | 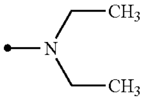 | MS m/z 588 (M + H)+ |
| 10-73 | 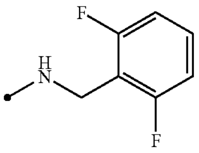 | 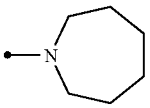 | MS m/z 598 (M + H)+ |
| 10-74 | 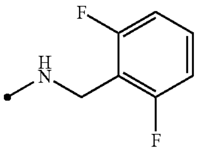 | 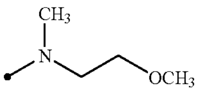 | MS m/z 588 (M + H)+ |
| 10-75 | 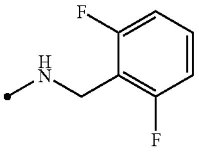 | 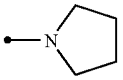 | MS m/z 570 (M + H)+ |
| 10-76 | 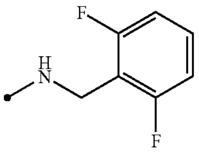 | 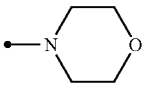 | MS m/z 586 (M + H)+ |
| 10-77 | 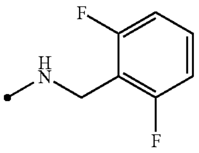 | 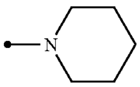 | MS m/z 584 (M + H)+ |
| 10-78 | 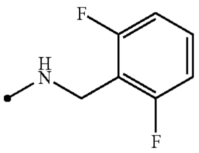 | 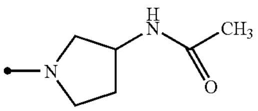 | MS m/z 627 (M + H)+ |

TABLE 10-continued
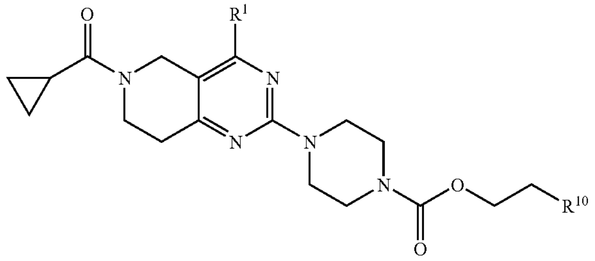
| Compound Number | •—$R^1$ | •—$R^{10}$ | Spectrum Data |
|---|---|---|---|
| 10-79 | 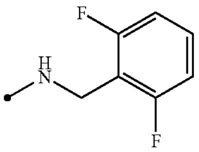 | 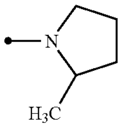 | MS m/z 584 $(M + H)^+$ |
| 10-80 | 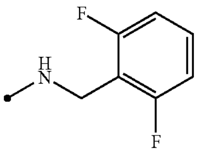 | 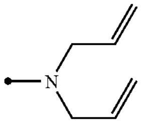 | MS m/z 596 $(M + H)^+$ |
| 10-81 | 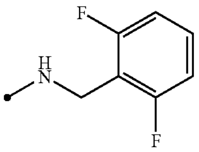 | 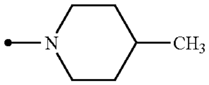 | MS m/z 598 $(M + H)^+$ |
| 10-82 | 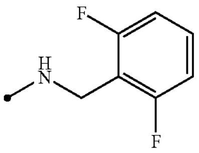 | 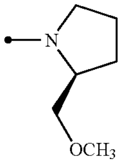 | MS m/z 614 $(M + H)^+$ |
| 10-83 | 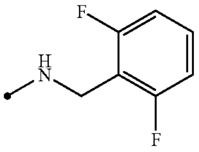 | 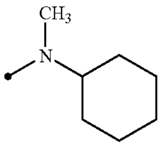 | MS m/z 612 $(M + H)^+$ |
| 10-84 | 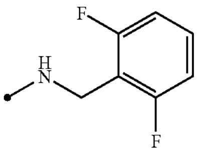 | 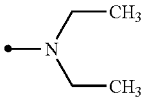 | MS m/z 572 $(M + H)^+$ |
| 10-85 | 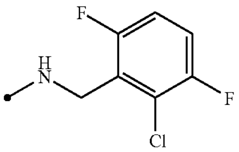 | 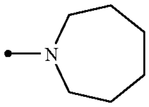 | MS m/z 632 $(M + H)^+$ |

TABLE 10-continued
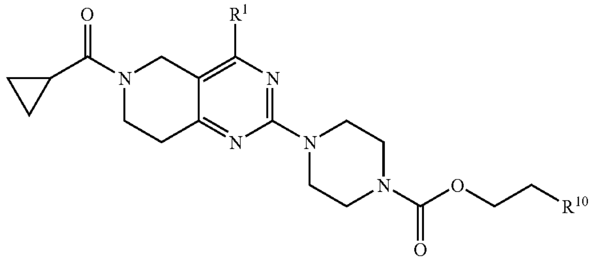
| Compound Number | •—$R^1$ | •—$R^{10}$ | Spectrum Data |
|---|---|---|---|
| 10-86 | 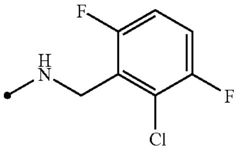 | 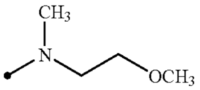 | MS m/z 622 $(M + H)^+$ |
| 10-87 | 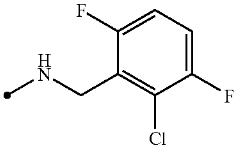 | 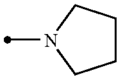 | MS m/z 604 $(M + H)^+$ |
| 10-88 | 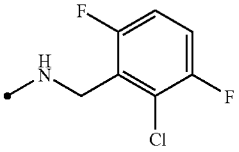 | 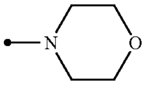 | MS m/z 620 $(M + H)^+$ |
| 10-89 | 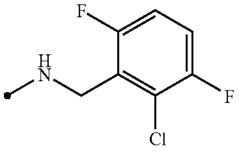 | 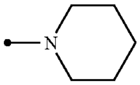 | MS m/z 618 $(M + H)^+$ |
| 10-90 | 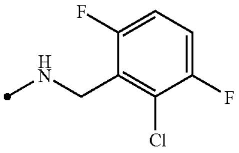 | 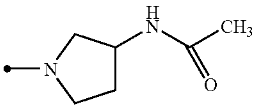 | MS m/z 661 $(M + H)^+$ |
| 10-91 | 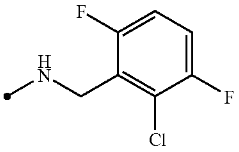 | 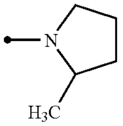 | MS m/z 618 $(M + H)^+$ |
| 10-92 | 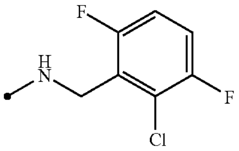 | 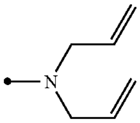 | MS m/z 630 $(M + H)^+$ |

TABLE 10-continued
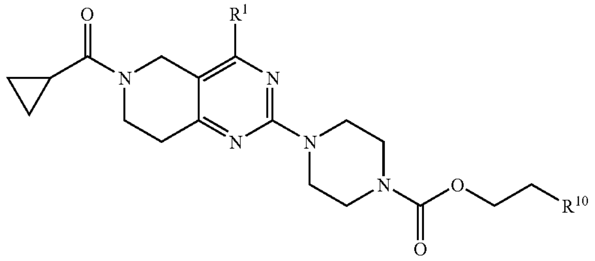
| Compound Number | •—$R^1$ | •—$R^{10}$ | Spectrum Data |
|---|---|---|---|
| 10-93 | 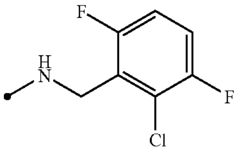 | 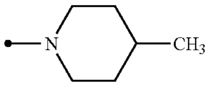 | MS m/z 632 $(M + H)^+$ |
| 10-94 | 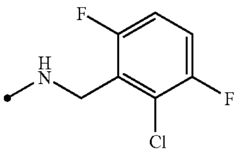 | 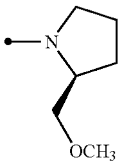 | MS m/z 648 $(M + H)^+$ |
| 10-95 | 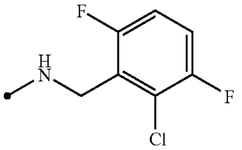 | 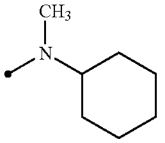 | MS m/z 646 $(M + H)^+$ |
| 10-96 | 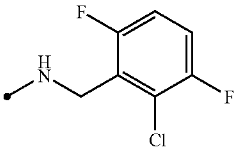 | 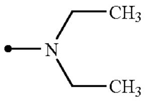 | MS m/z 606 $(M + H)^+$ |
| 10-97 | 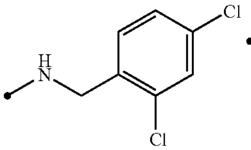 | 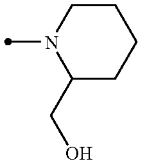 | MS m/z 646 $(M + H)^+$ |
| 10-98 | 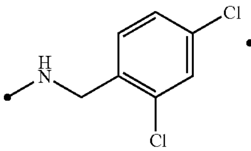 | 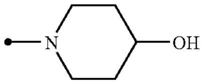 | MS m/z 632 $(M + H)^+$ |
| 10-99 | 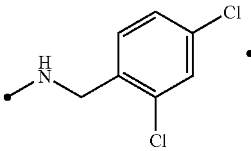 | 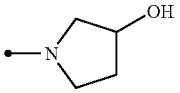 | MS m/z 618 $(M + H)^+$ |

TABLE 10-continued
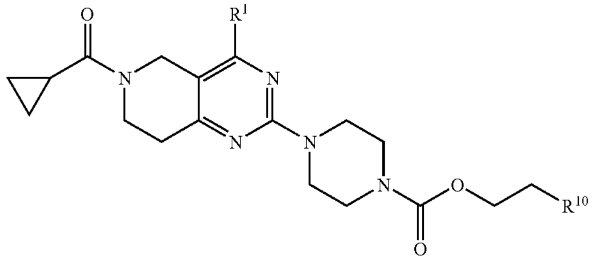
| Compound Number | •—$R^1$ | •—$R^{10}$ | Spectrum Data |
|---|---|---|---|
| 10-100 | 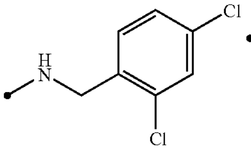 | 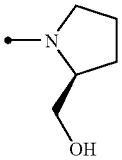 | MS m/z 632 $(M + H)^+$ |
| 10-101 | 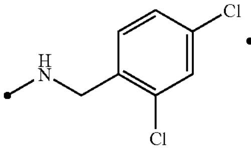 | 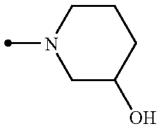 | MS m/z 632 $(M + H)^+$ |
| 10-102 | 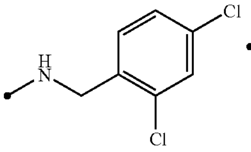 | 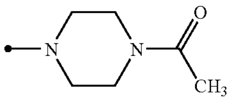 | MS m/z 659 $(M + H)^+$ |
| 10-103 | 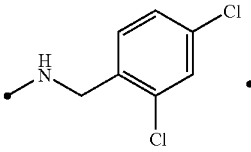 | 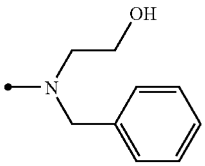 | MS m/z 682 $(M + H)^+$ |
| 10-104 | 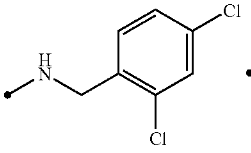 | 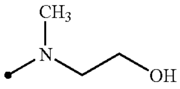 | MS m/z 606 $(M + H)^+$ |
| 10-105 | 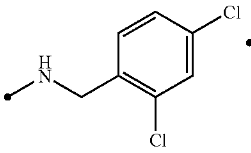 | 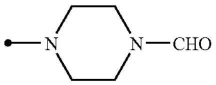 | MS m/z 645 $(M + H)^+$ |
| 10-106 | 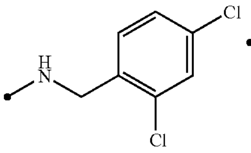 | 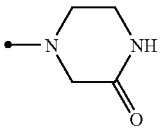 | MS m/z 631 $(M + H)^+$ |

TABLE 10-continued
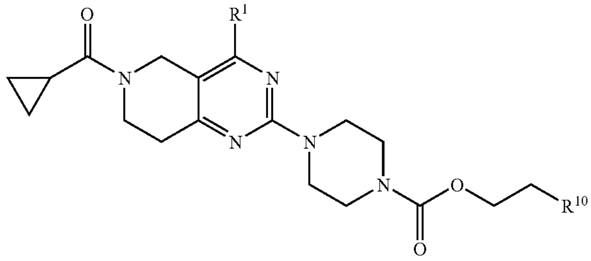
| Compound Number | •—$R^1$ | •—$R^{10}$ | Spectrum Data |
|---|---|---|---|
| 10-107 | 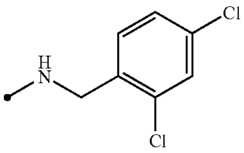 | 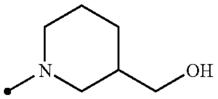 | MS m/z 646 $(M + H)^+$ |
| 10-108 | 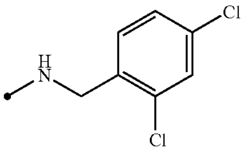 | 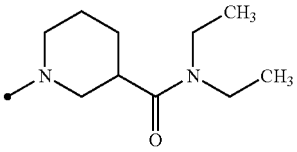 | MS m/z 715 $(M + H)^+$ |
| 10-109 | 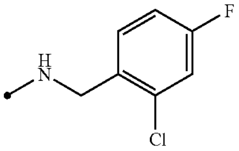 | 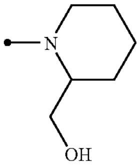 | MS m/z 630 $(M + H)^+$ |
| 10-110 | 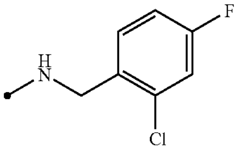 | 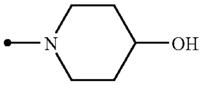 | MS m/z 630 $(M + H)^+$ |
| 10-111 | 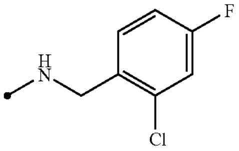 | 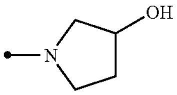 | MS m/z 602 $(M + H)^+$ |
| 10-112 | 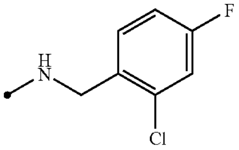 | 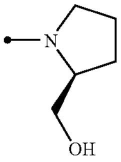 | MS m/z 616 $(M + H)^+$ |
| 10-113 | 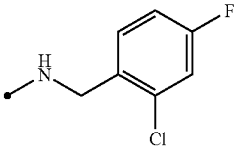 | 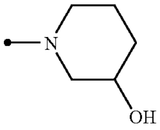 | MS m/z 616 $(M + H)^+$ |

TABLE 10-continued
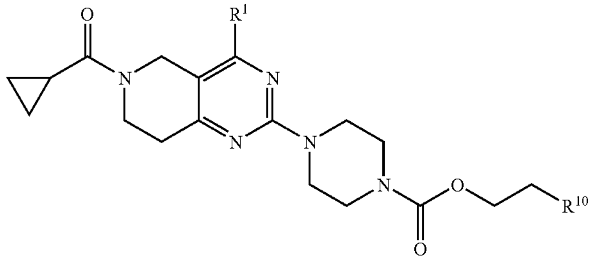
| Compound Number | •—$R^1$ | •—$R^{10}$ | Spectrum Data |
|---|---|---|---|
| 10-114 | 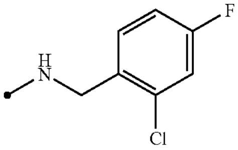 | 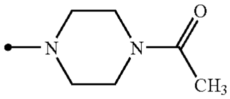 | MS m/z 643 $(M+H)^+$ |
| 10-115 | 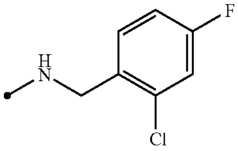 | 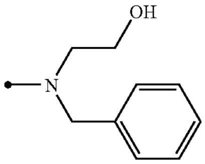 | MS m/z 666 $(M+H)^+$ |
| 10-116 | 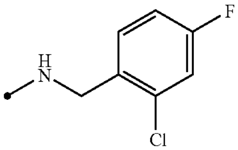 | 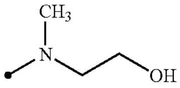 | MS m/z 590 $(M+H)^+$ |
| 10-117 | 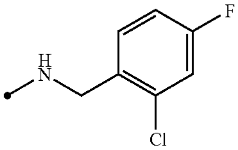 | 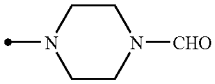 | MS m/z 629 $(M+H)^+$ |
| 10-118 | 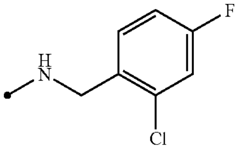 | 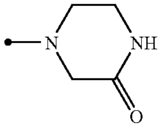 | MS m/z 615 $(M+H)^+$ |
| 10-119 | 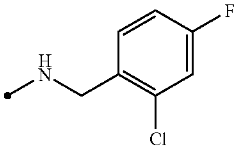 | 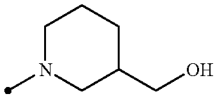 | MS m/z 630 $(M+H)^+$ |
| 10-120 | 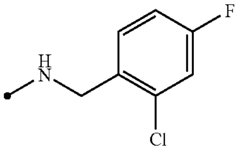 | 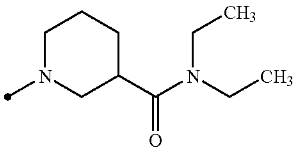 | MS m/z 699 $(M+H)^+$ |

TABLE 10-continued
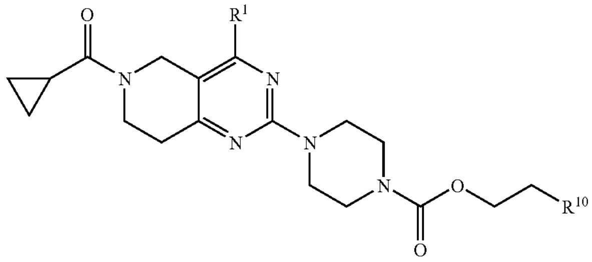
| Compound Number | •—$R^1$ | •—$R^{10}$ | Spectrum Data |
|---|---|---|---|
| 10-121 | 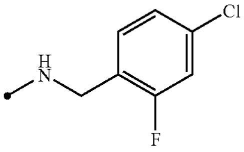 | 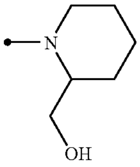 | MS m/z 630 $(M + H)^+$ |
| 10-122 | 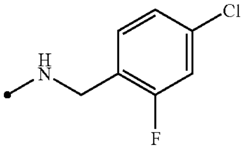 | 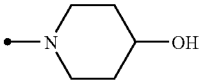 | MS m/z 616 $(M + H)^+$ |
| 10-123 | 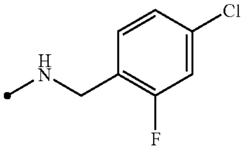 | 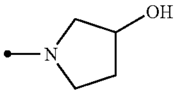 | MS m/z 602 $(M + H)^+$ |
| 10-124 | 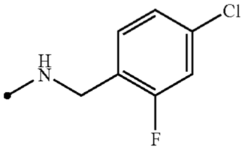 | 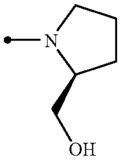 | MS m/z 616 $(M + H)^+$ |
| 10-125 | 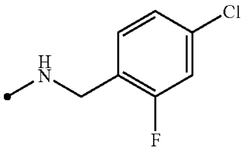 | 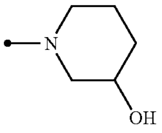 | MS m/z 616 $(M + H)^+$ |
| 10-126 | 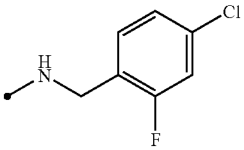 | 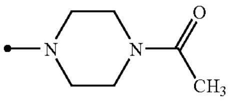 | MS m/z 643 $(M + H)^+$ |
| 10-127 | 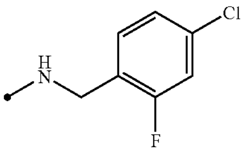 | 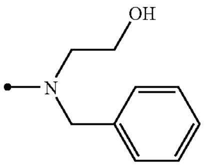 | MS m/z 666 $(M + H)^+$ |

TABLE 10-continued
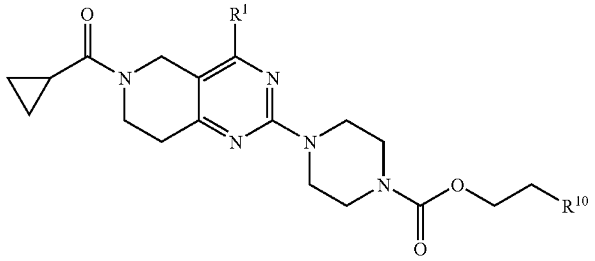
| Compound Number | •—$R^1$ | •—$R^{10}$ | Spectrum Data |
|---|---|---|---|
| 10-128 | 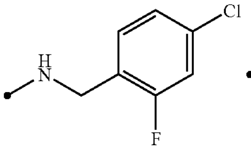 | 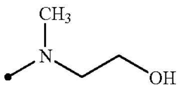 | MS m/z 590 $(M + H)^+$ |
| 10-129 | 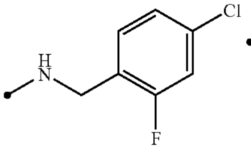 | 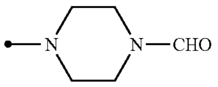 | MS m/z 629 $(M + H)^+$ |
| 10-130 | 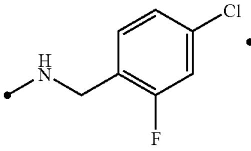 | 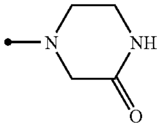 | MS m/z 615 $(M + H)^+$ |
| 10-131 | 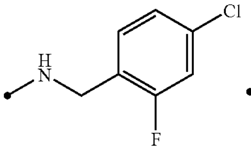 | 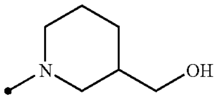 | MS m/z 630 $(M + H)^+$ |
| 10-132 | 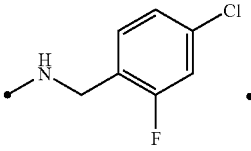 | 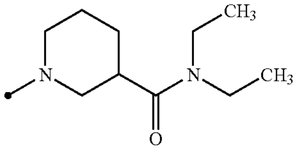 | MS m/z 699 $(M + H)^+$ |
| 10-133 | 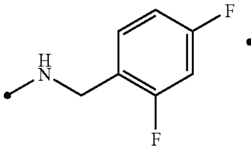 | 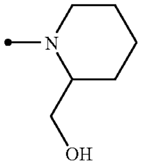 | MS m/z 614 $(M + H)^+$ |
| 10-134 | 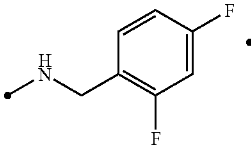 | 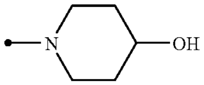 | MS m/z 600 $(M + H)^+$ |

TABLE 10-continued
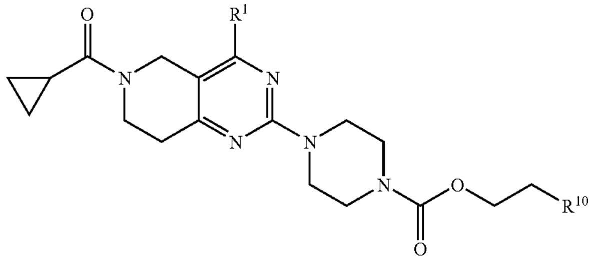
| Compound Number | •—$R^1$ | •—$R^{10}$ | Spectrum Data |
|---|---|---|---|
| 10-135 | 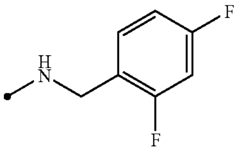 | 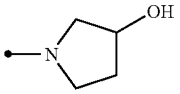 | MS m/z 586 $(M+H)^+$ |
| 10-136 | 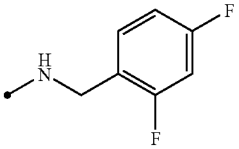 | 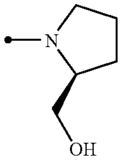 | MS m/z 600 $(M+H)^+$ |
| 10-137 | 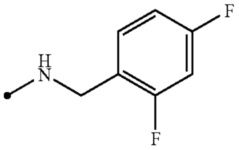 | 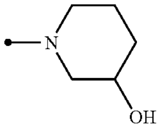 | MS m/z 600 $(M+H)^+$ |
| 10-138 | 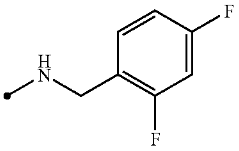 | 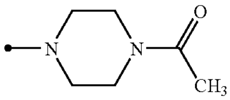 | MS m/z 627 $(M+H)^+$ |
| 10-139 | 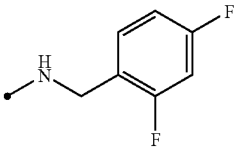 | 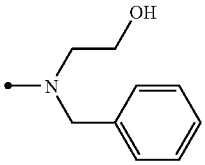 | MS m/z 650 $(M+H)^+$ |
| 10-140 | 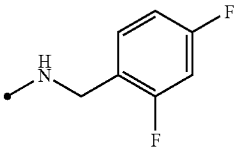 | 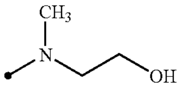 | MS m/z 574 $(M+H)^+$ |
| 10-141 | 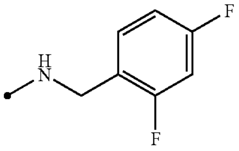 | 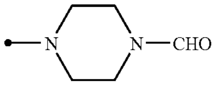 | MS m/z 613 $(M+H)^+$ |

TABLE 10-continued
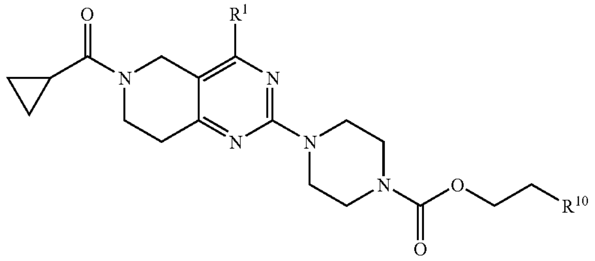
| Compound Number | •—$R^1$ | •—$R^{10}$ | Spectrum Data |
|---|---|---|---|
| 10-142 | 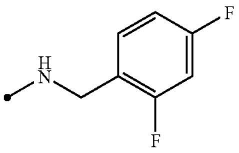 | 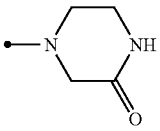 | MS m/z 599 $(M + H)^+$ |
| 10-143 | 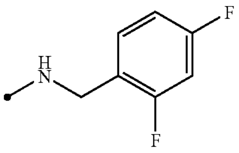 | 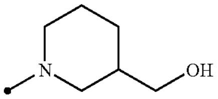 | MS m/z 614 $(M + H)^+$ |
| 10-144 | 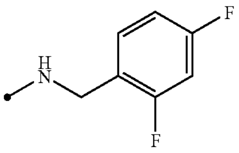 | 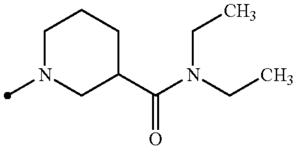 | MS m/z 683 $(M + H)^+$ |
| 10-145 | 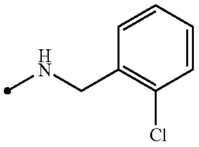 | 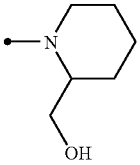 | MS m/z 612 $(M + H)^+$ |
| 10-146 | 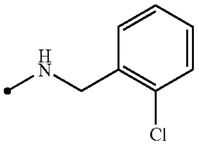 | 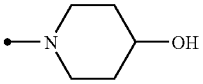 | MS m/z 598 $(M + H)^+$ |
| 10-147 | 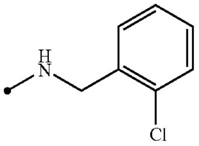 | 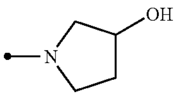 | MS m/z 584 $(M + H)^+$ |
| 10-148 | 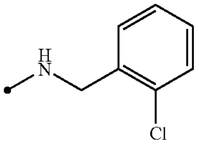 | 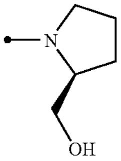 | MS m/z 598 $(M + H)^+$ |

TABLE 10-continued
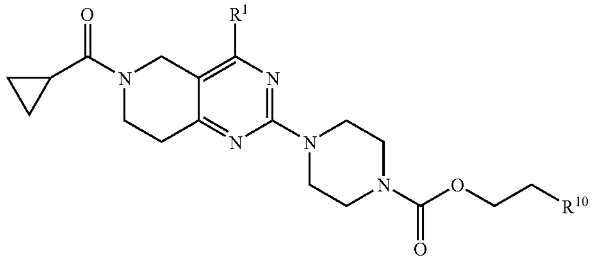
| Compound Number | •—$R^1$ | •—$R^{10}$ | Spectrum Data |
|---|---|---|---|
| 10-149 | 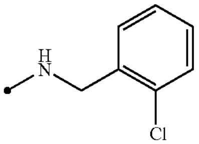 | 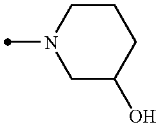 | MS m/z 598 $(M + H)^+$ |
| 10-150 | 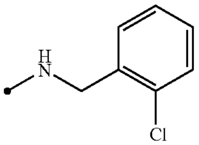 | 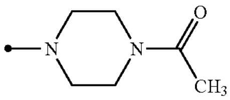 | MS m/z 625 $(M + H)^+$ |
| 10-151 | 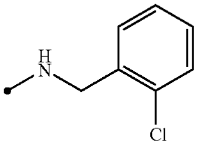 | 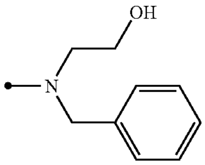 | MS m/z 648 $(M + H)^+$ |
| 10-152 | 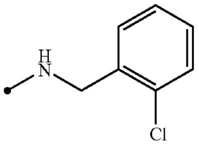 | 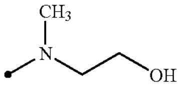 | MS m/z 572 $(M + H)^+$ |
| 10-153 | 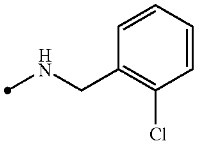 | 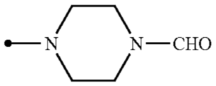 | MS m/z 611 $(M + H)^+$ |
| 10-154 | 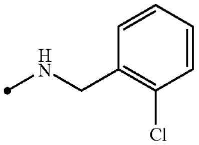 | 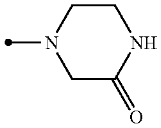 | MS m/z 597 $(M + H)^+$ |
| 10-155 | 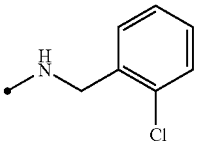 | 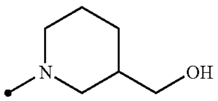 | MS m/z 612 $(M + H)^+$ |
| 10-156 | 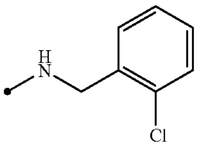 | 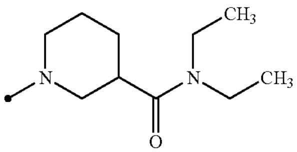 | MS m/z 681 $(M + H)^+$ |

TABLE 10-continued
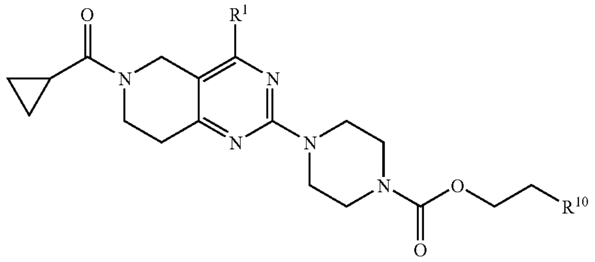
| Compound Number | •—$R^1$ | •—$R^{10}$ | Spectrum Data |
|---|---|---|---|
| 10-157 | 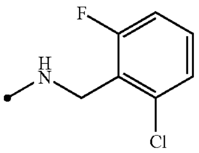 | 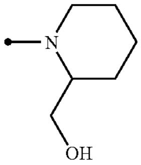 | MS m/z 630 $(M + H)^+$ |
| 10-158 | 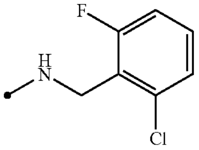 | 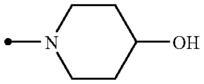 | MS m/z 616 $(M + H)^+$ |
| 10-159 | 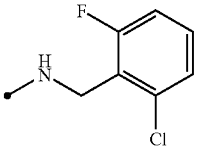 | 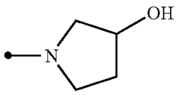 | MS m/z 602 $(M + H)^+$ |
| 10-160 | 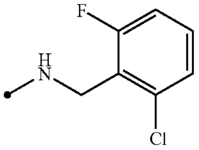 | 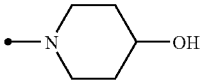 | MS m/z 616 $(M + H)^+$ |
| 10-161 | 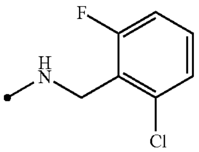 | 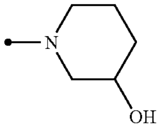 | MS m/z 616 $(M + H)^+$ |
| 10-162 | 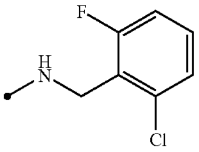 | 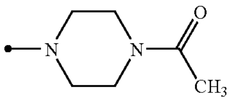 | MS m/z 643 $(M + H)^+$ |
| 10-163 | 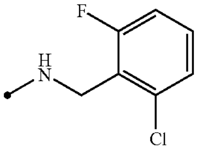 | 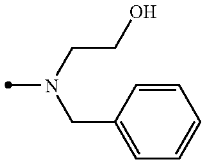 | MS m/z 666 $(M + H)^+$ |

TABLE 10-continued
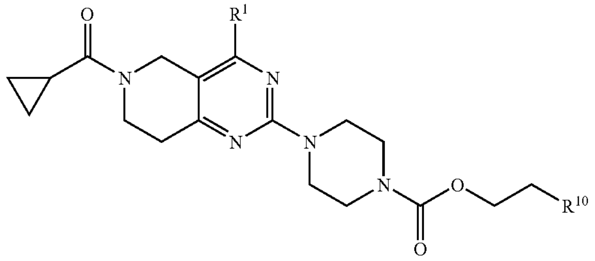
| Compound Number | •—$R^1$ | •—$R^{10}$ | Spectrum Data |
|---|---|---|---|
| 10-164 | 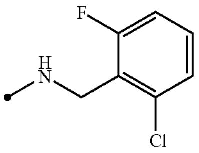 | 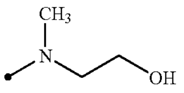 | MS m/z 590 $(M + H)^+$ |
| 10-165 | 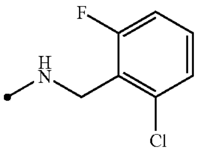 | 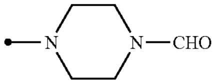 | MS m/z 629 $(M + H)^+$ |
| 10-166 | 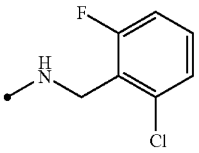 | 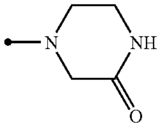 | MS m/z 615 $(M + H)^+$ |
| 10-167 | 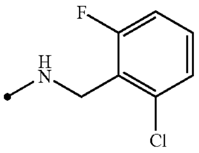 | 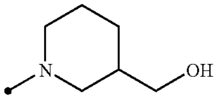 | MS m/z 630 $(M + H)^+$ |
| 10-168 | 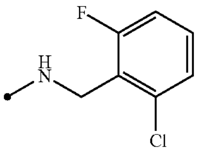 | 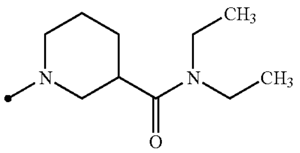 | MS m/z 699 $(M + H)^+$ |
| 10-169 | 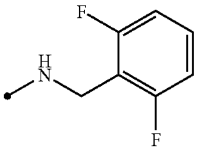 | 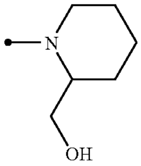 | MS m/z 614 $(M + H)^+$ |
| 10-170 | 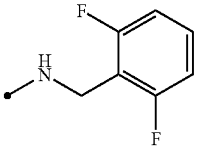 | 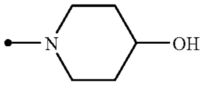 | MS m/z 600 $(M + H)^+$ |

TABLE 10-continued
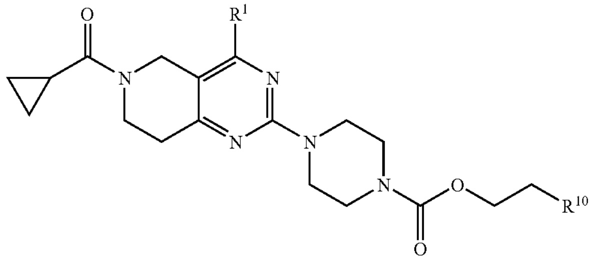
| Compound Number | •—R¹ | •—R¹⁰ | Spectrum Data |
|---|---|---|---|
| 10-171 | 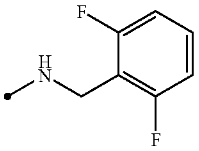 | 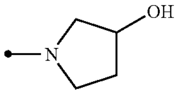 | MS m/z 586 (M + H)+ |
| 10-172 | 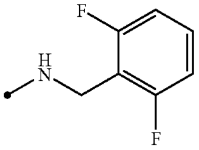 | 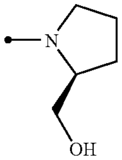 | MS m/z 600 (M + H)+ |
| 10-173 | 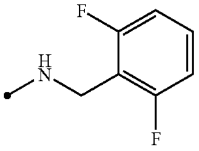 | 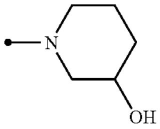 | MS m/z 600 (M + H)+ |
| 10-174 | 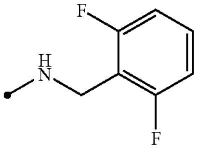 | 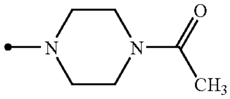 | MS m/z 627 (M + H)+ |
| 10-175 | 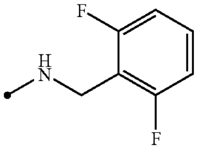 | 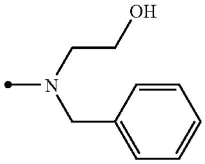 | MS m/z 650 (M + H)+ |
| 10-176 | 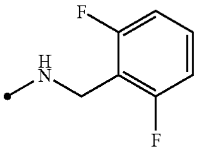 | 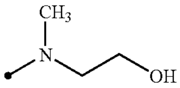 | MS m/z 574 (M + H)+ |
| 10-177 | 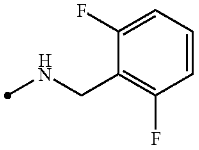 | 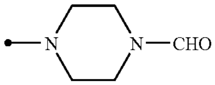 | MS m/z 613 (M + H)+ |

TABLE 10-continued
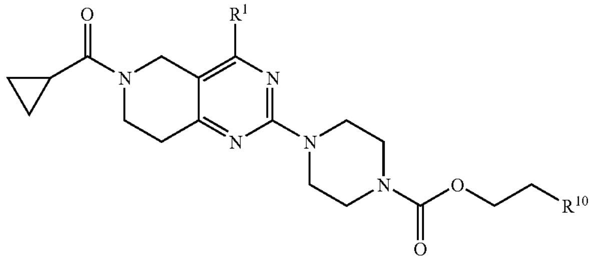
| Compound Number | •—$R^1$ | •—$R^{10}$ | Spectrum Data |
|---|---|---|---|
| 10-178 | 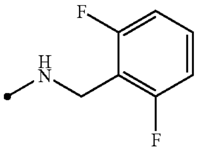 | 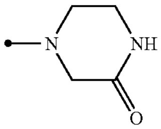 | MS m/z 599 $(M + H)^+$ |
| 10-179 | 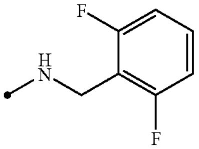 | 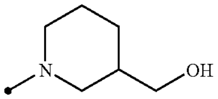 | MS m/z 614 $(M + H)^+$ |
| 10-180 | 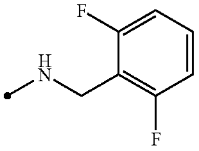 | 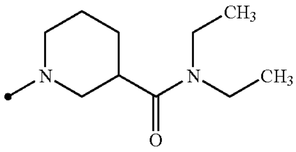 | MS m/z 683 $(M + H)^+$ |
| 10-181 | 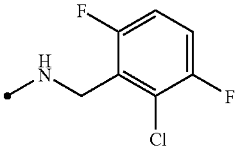 | 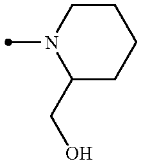 | MS m/z 648 $(M + H)^+$ |
| 10-182 | 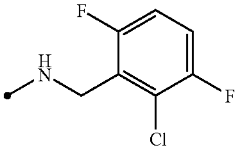 | 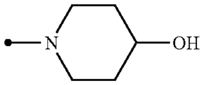 | MS m/z 634 $(M + H)^+$ |
| 10-183 | 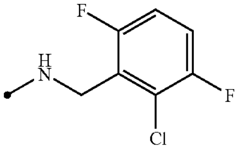 | 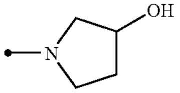 | MS m/z 620 $(M + H)^+$ |
| 10-184 | 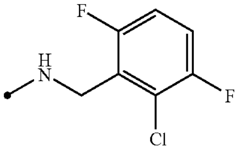 | 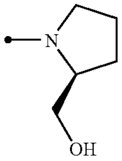 | MS m/z 634 $(M + H)^+$ |

TABLE 10-continued
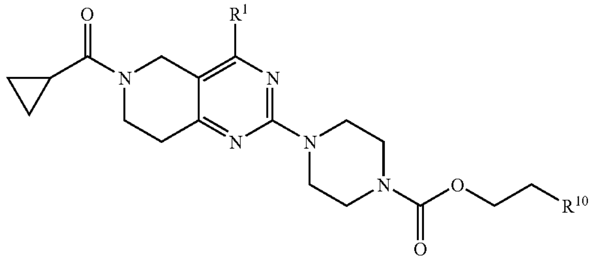
| Compound Number | •—$R^1$ | •—$R^{10}$ | Spectrum Data |
|---|---|---|---|
| 10-185 | 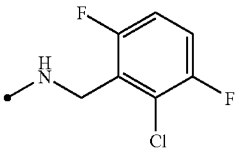 | 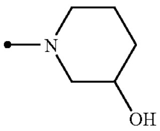 | MS m/z 634 $(M + H)^+$ |
| 10-186 | 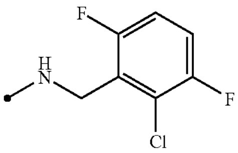 | 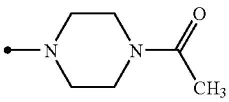 | MS m/z 661 $(M + H)^+$ |
| 10-187 | 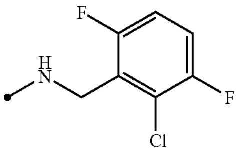 | 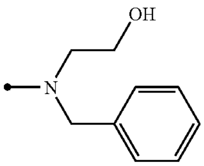 | MS m/z 684 $(M + H)^+$ |
| 10-188 | 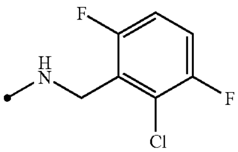 | 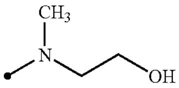 | MS m/z 608 $(M + H)^+$ |
| 10-189 | 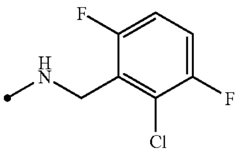 | 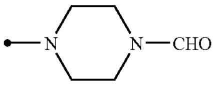 | MS m/z 647 $(M + H)^+$ |
| 10-190 | 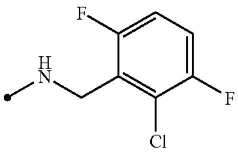 | 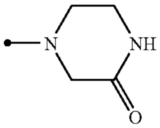 | MS m/z 633 $(M + H)^+$ |
| 10-191 | 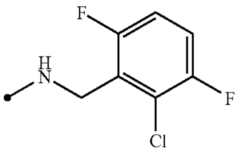 | 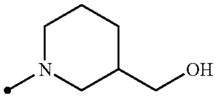 | MS m/z 648 $(M + H)^+$ |

TABLE 10-continued
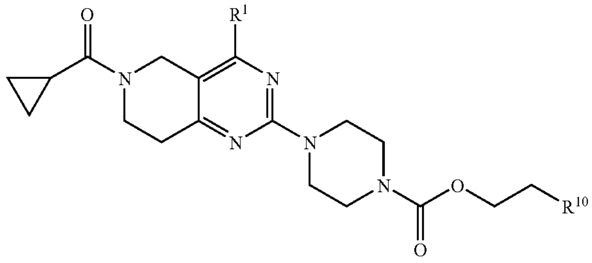
| Compound Number | •—$R^1$ | •—$R^{10}$ | Spectrum Data |
|---|---|---|---|
| 10-192 | 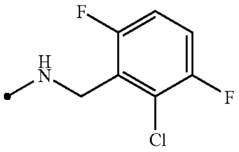 | 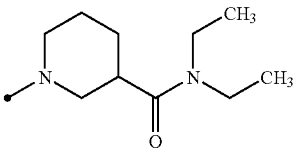 | MS m/z 717 $(M + H)^+$ |
TABLE 11
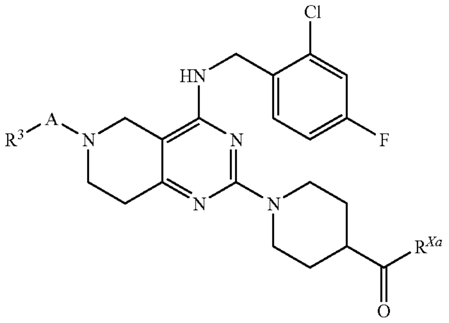
| Compound Number | •—A—$R^3$ | •—$R^{Xa}$ | Spectrum Data |
|---|---|---|---|
| 11-1 | 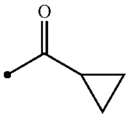 | 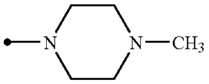 | MS m/z 570 $(M + H)^+$ |
| 11-2 | 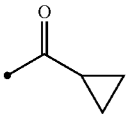 | 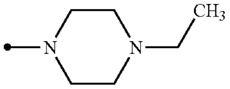 | MS m/z 584 $(M + H)^+$ |
| 11-3 | 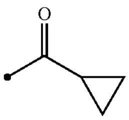 | 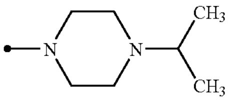 | MS m/z 598 $(M + H)^+$ |
| 11-4 | 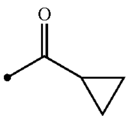 | 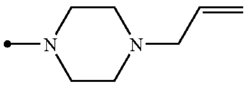 | MS m/z 596 $(M + H)^+$ |

TABLE 11-continued
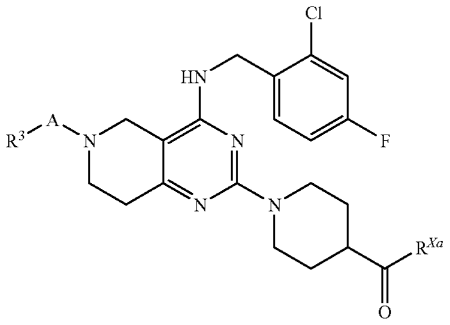
| Compound Number | •—A—$R^3$ | •—$R^{Xa}$ | Spectrum Data |
|---|---|---|---|
| 11-5 | 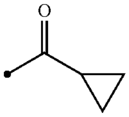 | 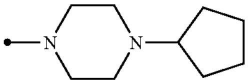 | MS m/z 624 $(M + H)^+$ |
| 11-6 | 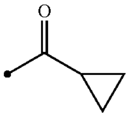 | 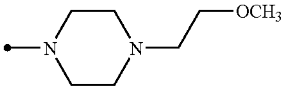 | MS m/z 614 $(M + H)^+$ |
| 11-7 | 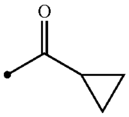 | 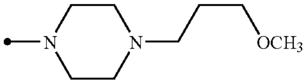 | MS m/z 628 $(M + H)^+$ |
| 11-8 | 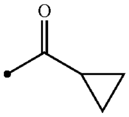 | 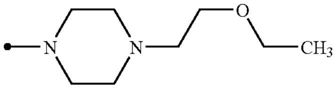 | MS m/z 628 $(M + H)^+$ |
| 11-9 | 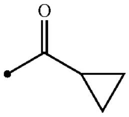 | 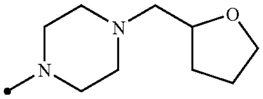 | MS m/z 640 $(M + H)^+$ |
| 11-10 | 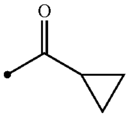 | 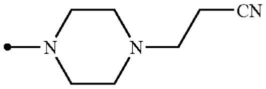 | MS m/z 609 $(M + H)^+$ |
| 11-11 | 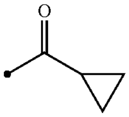 | 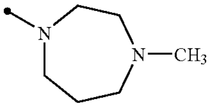 | MS m/z 584 $(M + H)^+$ |
| 11-12 | 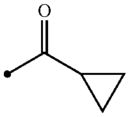 | 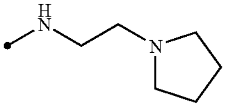 | MS m/z 584 $(M + H)^+$ |
| 11-13 | 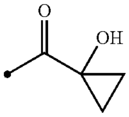 | 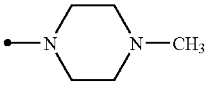 | MS m/z 586 $(M + H)^+$ |

TABLE 11-continued
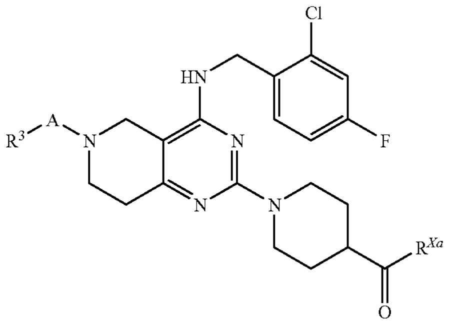
| Compound Number | •—A—$R^3$ | •—$R^{Xa}$ | Spectrum Data |
|---|---|---|---|
| 11-14 | 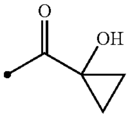 | 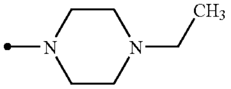 | MS m/z 600 $(M + H)^+$ |
| 11-15 | 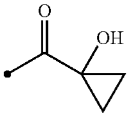 | 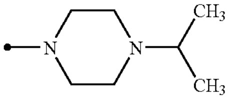 | MS m/z 614 $(M + H)^+$ |
| 11-16 | 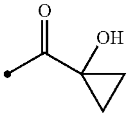 | 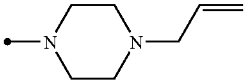 | MS m/z 612 $(M + H)^+$ |
| 11-17 | 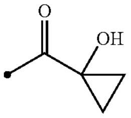 | 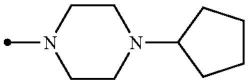 | MS m/z 640 $(M + H)^+$ |
| 11-18 | 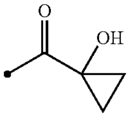 | 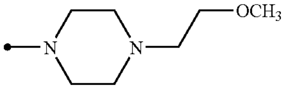 | MS m/z 630 $(M + H)^+$ |
| 11-19 | 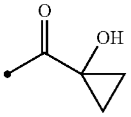 | 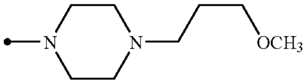 | MS m/z 644 $(M + H)^+$ |
| 11-20 | 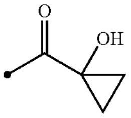 | 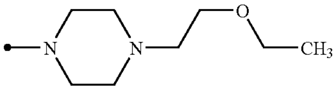 | MS m/z 644 $(M + H)^+$ |
| 11-21 | 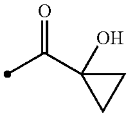 | 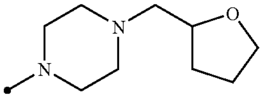 | MS m/z 656 $(M + H)^+$ |
| 11-22 | 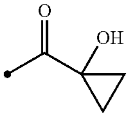 | 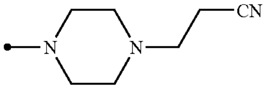 | MS m/z 625 $(M + H)^+$ |

TABLE 11-continued
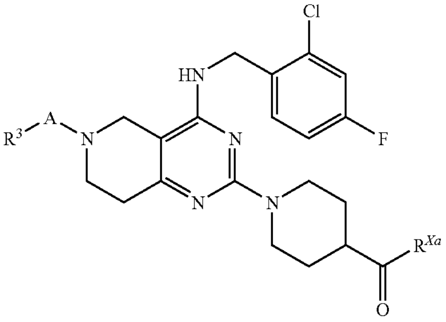
| Compound Number | •—A—$R^3$ | •—$R^{Xa}$ | Spectrum Data |
|---|---|---|---|
| 11-23 | 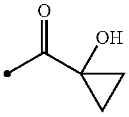 | 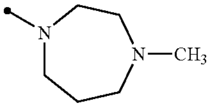 | MS m/z 600 $(M + H)^+$ |
| 11-24 | 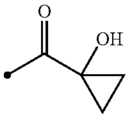 | 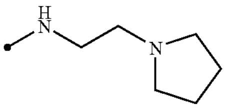 | MS m/z 600 $(M + H)^+$ |
| 11-25 | 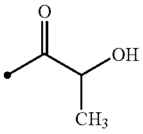 | 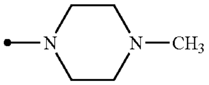 | MS m/z 574 $(M + H)^+$ |
| 11-26 | 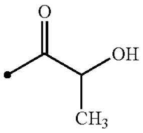 | 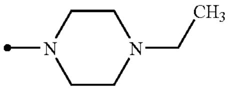 | MS m/z 588 $(M + H)^+$ |
| 11-27 | 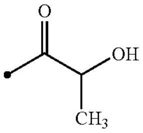 | 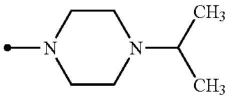 | MS m/z 602 $(M + H)^+$ |
| 11-28 | 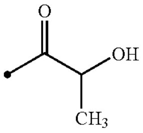 | 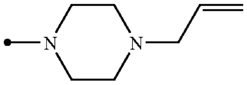 | MS m/z 600 $(M + H)^+$ |
| 11-29 | 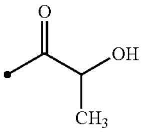 | 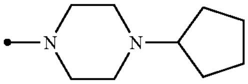 | MS m/z 628 $(M + H)^+$ |
| 11-30 | 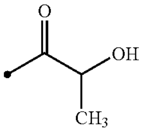 | 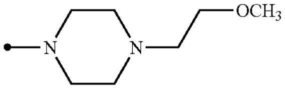 | MS m/z 618 $(M + H)^+$ |

TABLE 11-continued
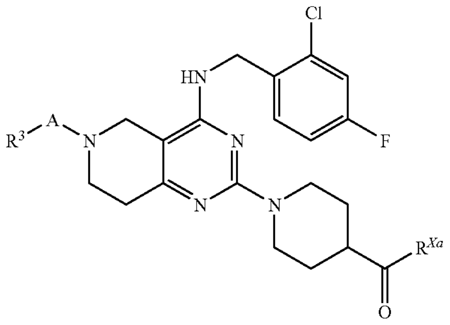
| Compound Number | •—A—$R^3$ | •—$R^{Xa}$ | Spectrum Data |
|---|---|---|---|
| 11-31 | 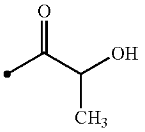 | 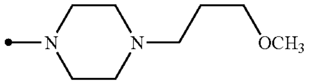 | MS m/z 632 $(M + H)^+$ |
| 11-32 | 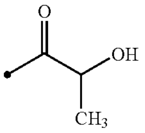 | 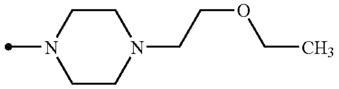 | MS m/z 632 $(M + H)^+$ |
| 11-33 | 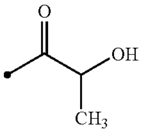 | 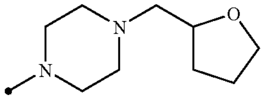 | MS m/z 644 $(M + H)^+$ |
| 11-34 | 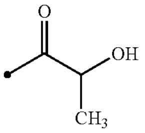 | 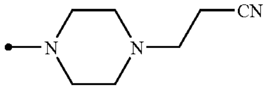 | MS m/z 613 $(M + H)^+$ |
| 11-35 | 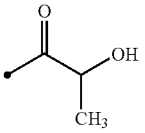 | 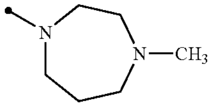 | MS m/z 588 $(M + H)^+$ |
| 11-36 | 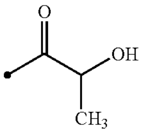 | 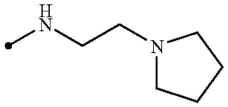 | MS m/z 588 $(M + H)^+$ |
| 11-37 | 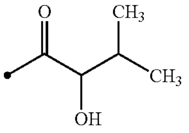 | 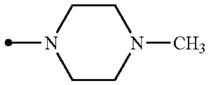 | MS m/z 602 $(M + H)^+$ |
| 11-38 | 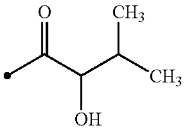 | 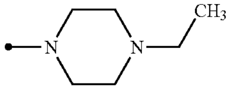 | MS m/z 616 $(M + H)^+$ |

TABLE 11-continued
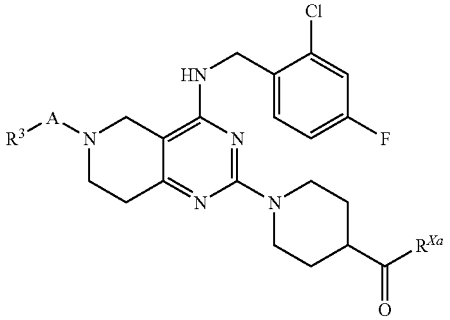
| Compound Number | •—A—$R^3$ | •—$R^{Xa}$ | Spectrum Data |
|---|---|---|---|
| 11-39 | 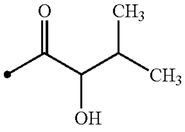 | 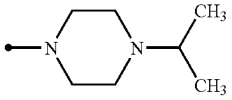 | MS m/z 630 $(M + H)^+$ |
| 11-40 | 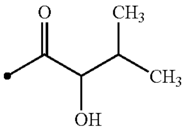 | 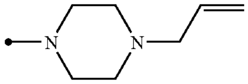 | MS m/z 628 $(M + H)^+$ |
| 11-41 | 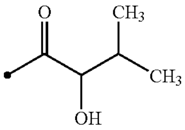 | 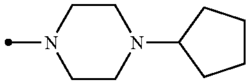 | MS m/z 656 $(M + H)^+$ |
| 11-42 | 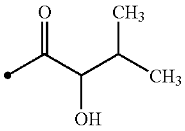 | 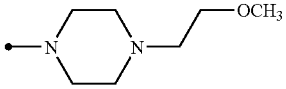 | MS m/z 646 $(M + H)^+$ |
| 11-43 | 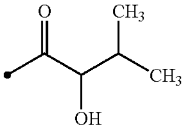 | 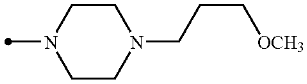 | MS m/z 660 $(M + H)^+$ |
| 11-44 | 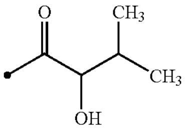 | 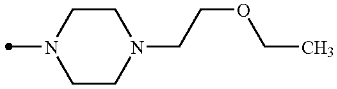 | MS m/z 660 $(M + H)^+$ |
| 11-45 | 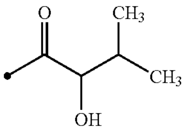 | 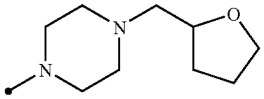 | MS m/z 672 $(M + H)^+$ |
| 11-46 | 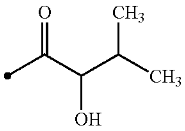 | 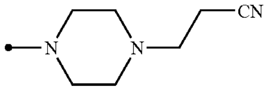 | MS m/z 641 $(M + H)^+$ |

TABLE 11-continued
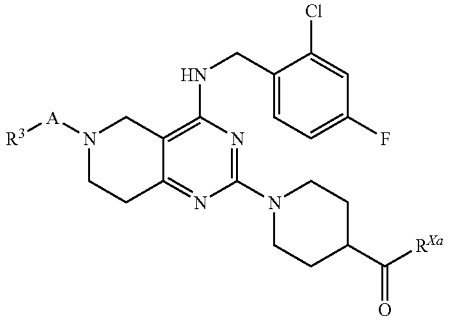
| Compound Number | •—A—$R^3$ | •—$R^{Xa}$ | Spectrum Data |
|---|---|---|---|
| 11-47 | 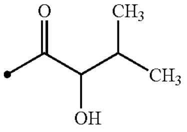 | 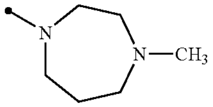 | MS m/z 616 (M + H)$^+$ |
| 11-48 | 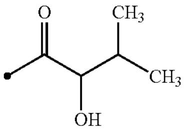 | 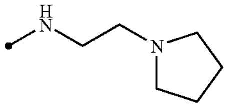 | MS m/z 616 (M + H)$^+$ |
| 11-49 | 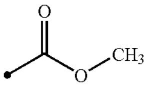 | 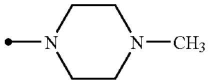 | MS m/z 560 (M + H)$^+$ |
| 11-50 | 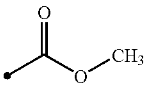 | 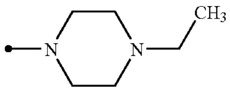 | MS m/z 574 (M + H)$^+$ |
| 11-51 | 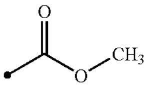 | 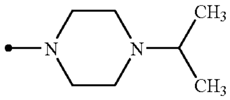 | MS m/z 588 (M + H)$^+$ |
| 11-52 | 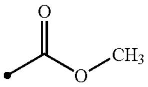 | 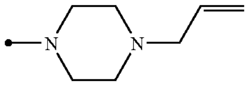 | MS m/z 586 (M + H)$^+$ |
| 11-53 | 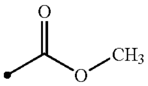 | 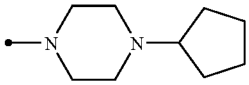 | MS m/z 614 (M + H)$^+$ |
| 11-54 | 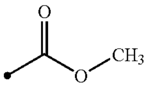 | 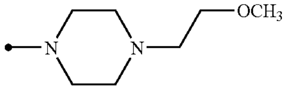 | MS m/z 604 (M + H)$^+$ |
| 11-55 | 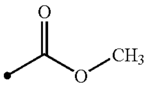 | 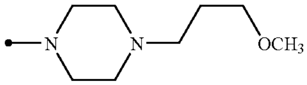 | MS m/z 618 (M + H)$^+$ |
| 11-56 | 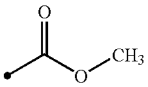 | 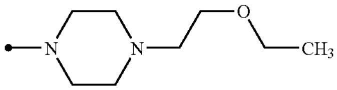 | MS m/z 618 (M + H)$^+$ |

TABLE 11-continued
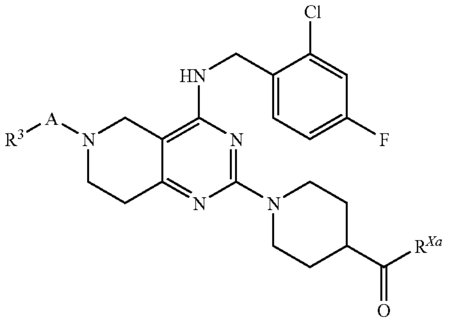
| Compound Number | •—A—$R^3$ | •—$R^{Xa}$ | Spectrum Data |
|---|---|---|---|
| 11-57 | 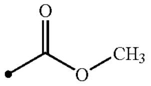 | 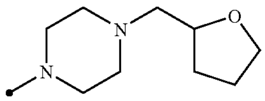 | MS m/z 630 $(M + H)^+$ |
| 11-58 | 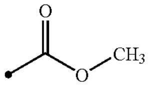 | 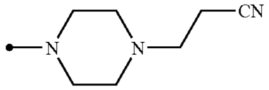 | MS m/z 599 $(M + H)^+$ |
| 11-59 | 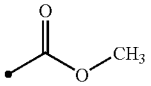 | 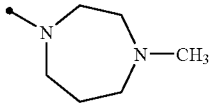 | MS m/z 574 $(M + H)^+$ |
| 11-60 | 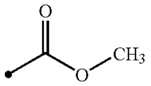 | 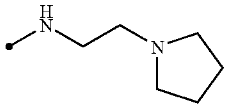 | MS m/z 574 $(M + H)^+$ |
| 11-61 | 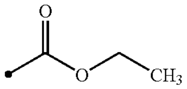 | 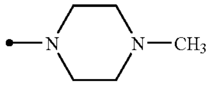 | MS m/z 574 $(M + H)^+$ |
| 11-62 | 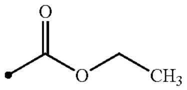 | 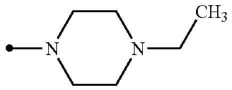 | MS m/z 588 $(M + H)^+$ |
| 11-63 | 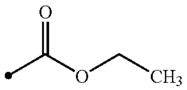 | 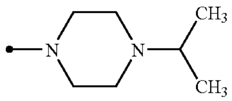 | MS m/z 602 $(M + H)^+$ |
| 11-64 | 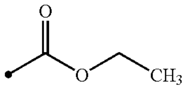 | 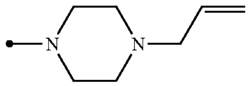 | MS m/z 600 $(M + H)^+$ |
| 11-65 | 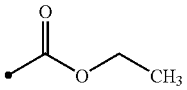 | 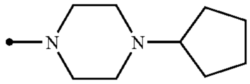 | MS m/z 628 $(M + H)^+$ |
| 11-66 | 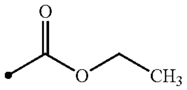 | 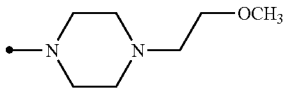 | MS m/z 618 $(M + H)^+$ |
| 11-67 | 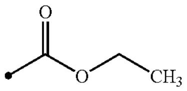 | 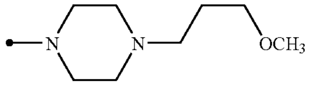 | MS m/z 632 $(M + H)^+$ |

TABLE 11-continued
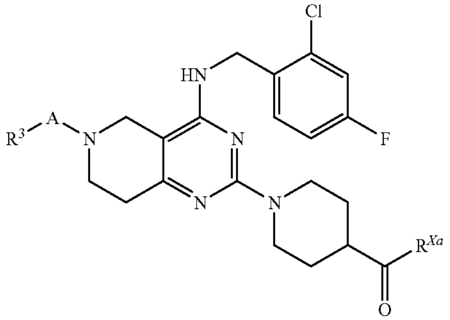
| Compound Number | •—A—$R^3$ | •—$R^{Xa}$ | Spectrum Data |
|---|---|---|---|
| 11-68 | 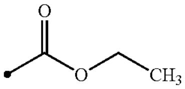 | 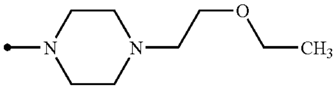 | MS m/z 632 $(M + H)^+$ |
| 11-69 | 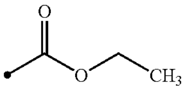 | 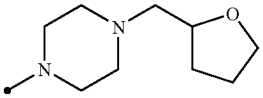 | MS m/z 644 $(M + H)^+$ |
| 11-70 | 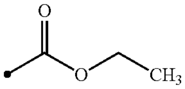 | 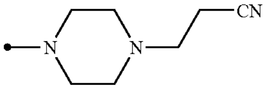 | MS m/z 613 $(M + H)^+$ |
| 11-71 | 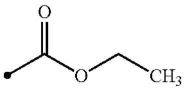 | 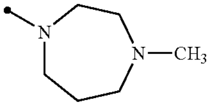 | MS m/z 588 $(M + H)^+$ |
| 11-72 | 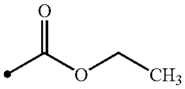 | 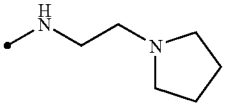 | MS m/z 588 $(M + H)^+$ |
| 11-73 | 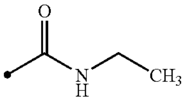 | 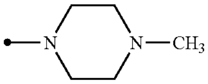 | MS m/z 573 $(M + H)^+$ |
| 11-74 | 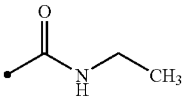 | 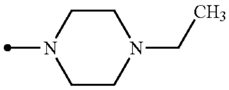 | MS m/z 587 $(M + H)^+$ |
| 11-75 | 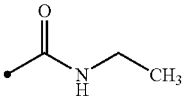 | 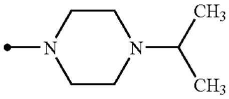 | MS m/z 601 $(M + H)^+$ |
| 11-76 | 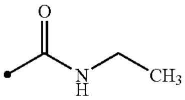 | 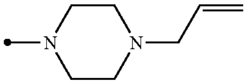 | MS m/z 599 $(M + H)^+$ |
| 11-77 | 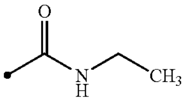 | 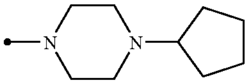 | MS m/z 627 $(M + H)^+$ |

TABLE 11-continued
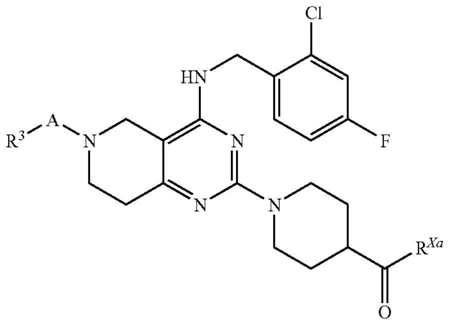
| Compound Number | •—A—$R^3$ | •—$R^{Xa}$ | Spectrum Data |
|---|---|---|---|
| 11-78 | 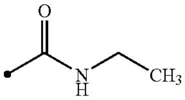 | 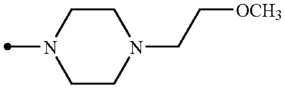 | MS m/z 617 $(M + H)^+$ |
| 11-79 | 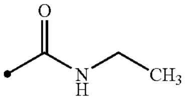 | 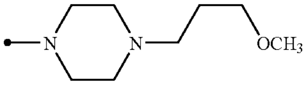 | MS m/z 631 $(M + H)^+$ |
| 11-80 | 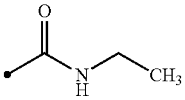 | 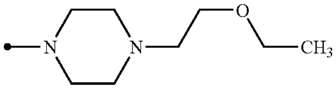 | MS m/z 631 $(M + H)^+$ |
| 11-81 | 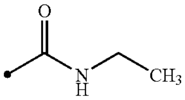 | 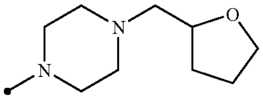 | MS m/z 643 $(M + H)^+$ |
| 11-82 | 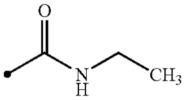 | 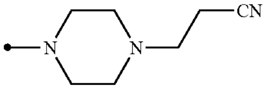 | MS m/z 612 $(M + H)^+$ |
| 11-83 | 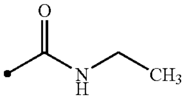 | 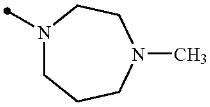 | MS m/z 587 $(M + H)^+$ |
| 11-84 | 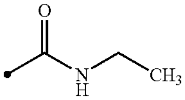 | 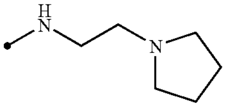 | MS m/z 587 $(M + H)^+$ |
| 11-85 | 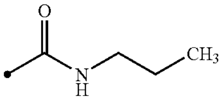 | 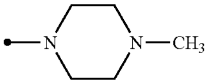 | MS m/z 587 $(M + H)^+$ |
| 11-86 | 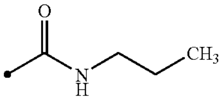 | 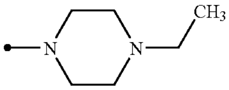 | MS m/z 601 $(M + H)^+$ |
| 11-87 | 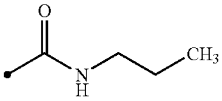 | 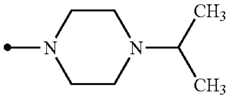 | MS m/z 615 $(M + H)^+$ |

TABLE 11-continued
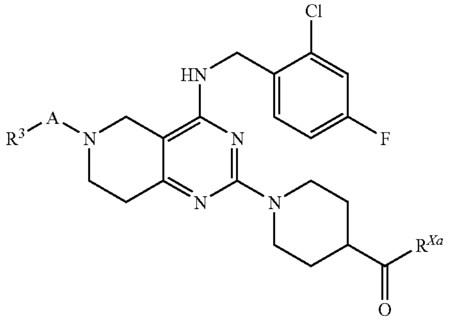
| Compound Number | •—A—$R^3$ | •—$R^{Xa}$ | Spectrum Data |
|---|---|---|---|
| 11-88 | 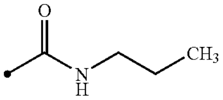 | 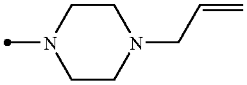 | MS m/z 613 $(M + H)^+$ |
| 11-89 | 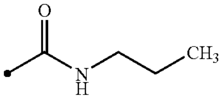 | 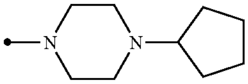 | MS m/z 641 $(M + H)^+$ |
| 11-90 | 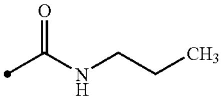 | 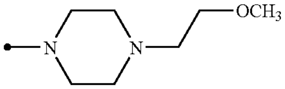 | MS m/z 631 $(M + H)^+$ |
| 11-91 | 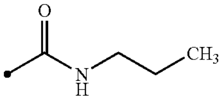 | 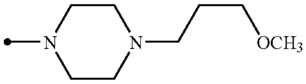 | MS m/z 645 $(M + H)^+$ |
| 11-92 | 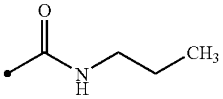 | 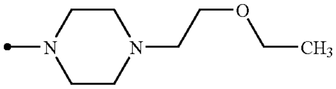 | MS m/z 645 $(M + H)^+$ |
| 11-93 | 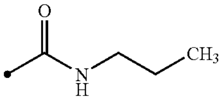 | 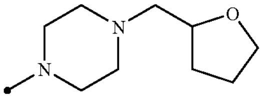 | MS m/z 657 $(M + H)^+$ |
| 11-94 | 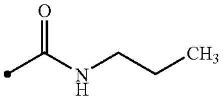 | 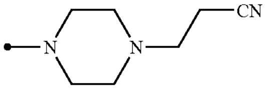 | MS m/z 626 $(M + H)^+$ |
| 11-95 | 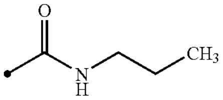 | 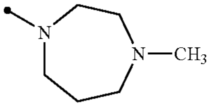 | MS m/z 601 $(M + H)^+$ |
| 11-96 | 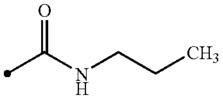 | 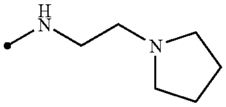 | MS m/z 601 $(M + H)^+$ |
| 11-97 | 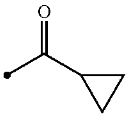 | 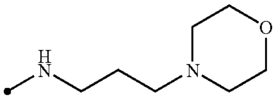 | MS m/z 614 $(M + H)^+$ |

TABLE 11-continued
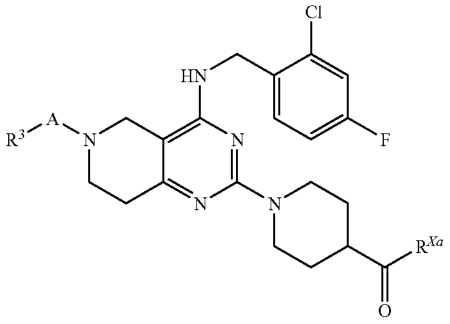
| Compound Number | •—A—$R^3$ | •—$R^{Xa}$ | Spectrum Data |
|---|---|---|---|
| 11-98 | 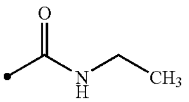 | 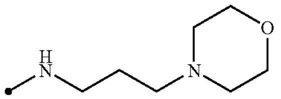 | MS m/z 617 $(M + H)^+$ |
TABLE 12
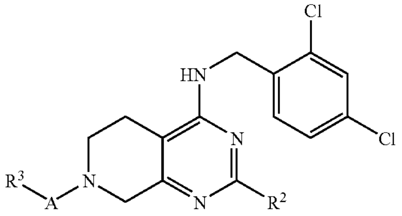
| Compound Number | •—A—$R^3$ | •—$R^2$ | Spectrum Data |
|---|---|---|---|
| 12-1 | 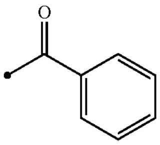 | 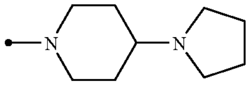 | MS m/z 565 $(M + H)^+$ |
| 12-2 | 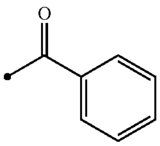 | 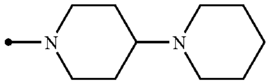 | MS m/z 579 $(M + H)^+$ |
| 12-3 | 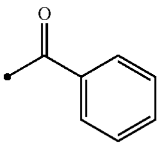 | 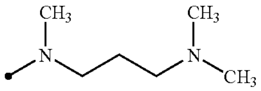 | MS m/z 527 $(M + H)^+$ |
| 12-4 | 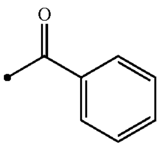 | 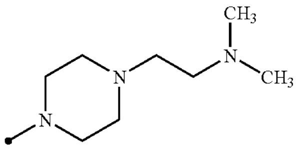 | MS m/z 568 $(M + H)^+$ |

TABLE 12-continued
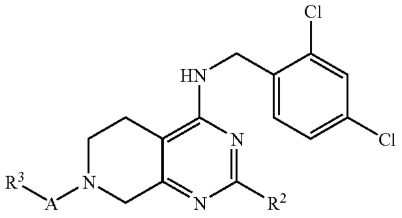
| Compound Number | •—A—$R^3$ | •—$R^2$ | Spectrum Data |
|---|---|---|---|
| 12-5 | 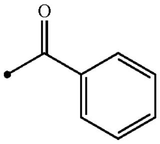 | 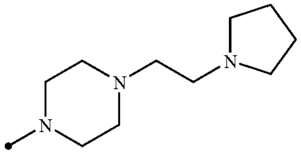 | MS m/z 594 $(M + H)^+$ |
| 12-6 | 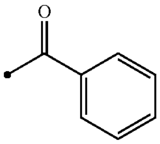 | 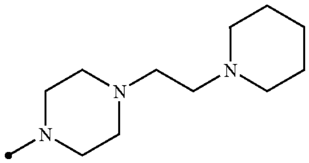 | MS m/z 608 $(M + H)^+$ |
| 12-7 | 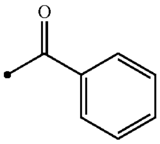 | 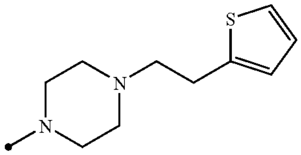 | MS m/z 607 $(M + H)^+$ |
| 12-8 | 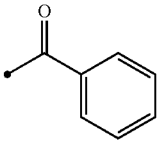 | 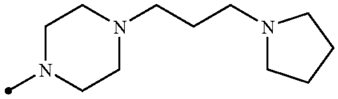 | MS m/z 608 $(M + H)^+$ |
| 12-9 | 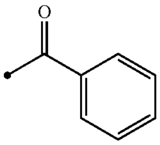 | 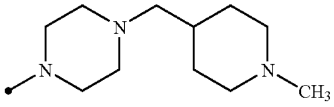 | MS m/z 608 $(M + H)^+$ |
| 12-10 | 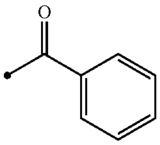 | 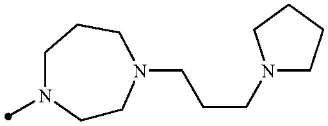 | MS m/z 622 $(M + H)^+$ |
| 12-11 | 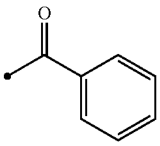 | 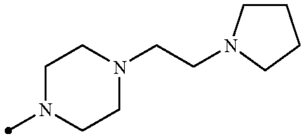 | MS m/z 593 $(M + H)^+$ |
| 12-12 | 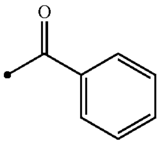 | 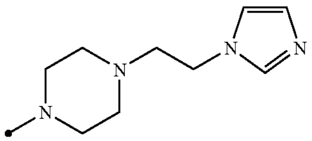 | MS m/z 591 $(M + H)^+$ |

TABLE 12-continued
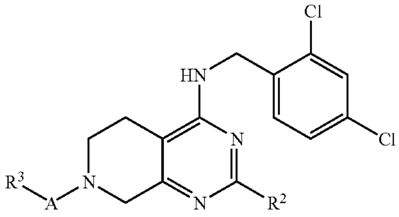
| Compound Number | •—A—$R^3$ | •—$R^2$ | Spectrum Data |
|---|---|---|---|
| 12-13 | 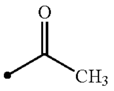 | 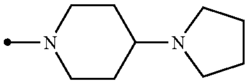 | MS m/z 503 $(M + H)^+$ |
| 12-14 | 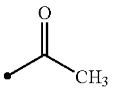 | 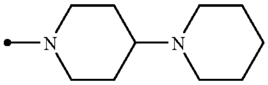 | MS m/z 517 $(M + H)^+$ |
| 12-15 | 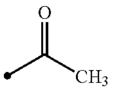 | 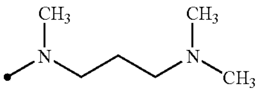 | MS m/z 465 $(M + H)^+$ |
| 12-16 | 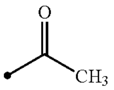 | 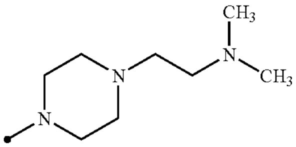 | MS m/z 506 $(M + H)^+$ |
| 12-17 | 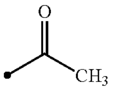 | 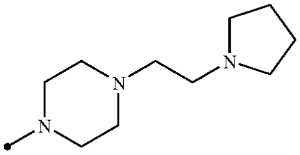 | MS m/z 532 $(M + H)^+$ |
| 12-18 | 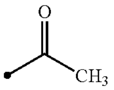 | 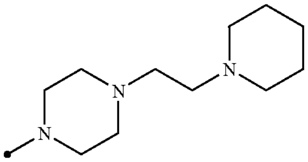 | MS m/z 546 $(M + H)^+$ |
| 12-19 | 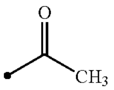 | 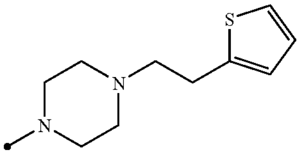 | MS m/z 545 $(M + H)^+$ |
| 12-20 | 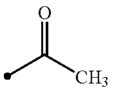 | 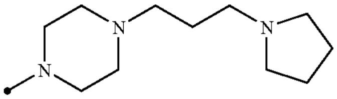 | MS m/z 546 $(M + H)^+$ |
| 12-21 | 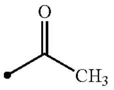 | 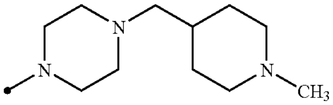 | MS m/z 546 $(M + H)^+$ |

TABLE 12-continued
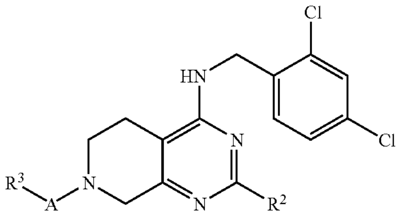
| Compound Number | •—A—$R^3$ | •—$R^2$ | Spectrum Data |
|---|---|---|---|
| 12-22 | 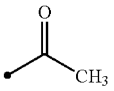 | 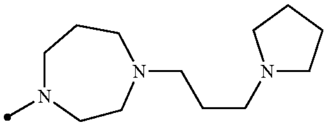 | MS m/z 560 $(M + H)^+$ |
| 12-23 | 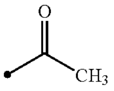 | 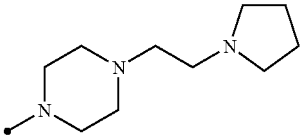 | MS m/z 531 $(M + H)^+$ |
| 12-24 | 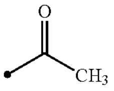 | 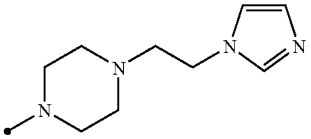 | MS m/z 529 $(M + H)^+$ |
| 12-25 | 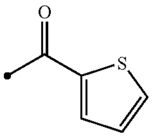 | 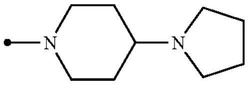 | MS m/z 571 $(M + H)^+$ |
| 12-26 | 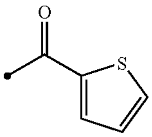 | 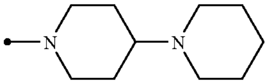 | MS m/z 585 $(M + H)^+$ |
| 12-27 | 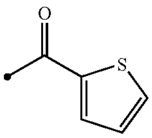 | 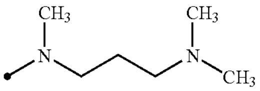 | MS m/z 533 $(M + H)^+$ |
| 12-28 | 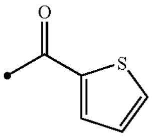 | 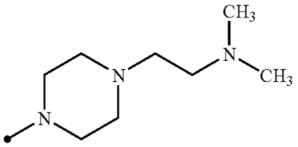 | MS m/z 574 $(M + H)^+$ |
| 12-29 | 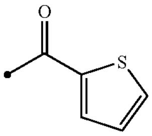 | 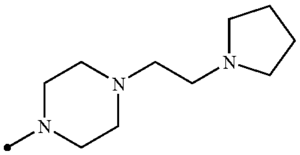 | MS m/z 600 $(M + H)^+$ |

TABLE 12-continued
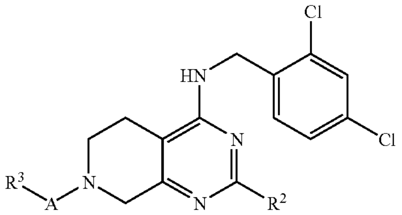
| Compound Number | •—A—$R^3$ | •—$R^2$ | Spectrum Data |
|---|---|---|---|
| 12-30 | 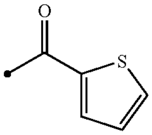 | 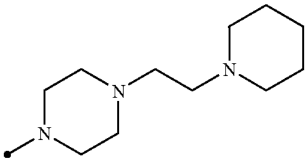 | MS m/z 614 $(M + H)^+$ |
| 12-31 | 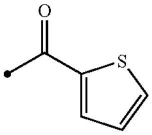 | 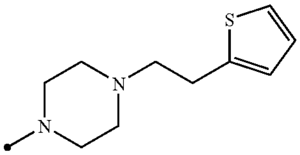 | MS m/z 613 $(M + H)^+$ |
| 12-32 | 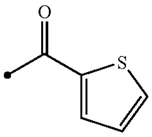 | 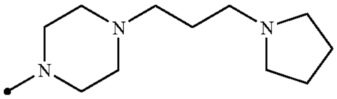 | MS m/z 614 $(M + H)^+$ |
| 12-33 | 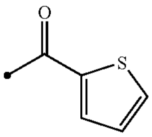 | 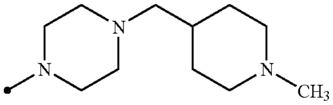 | MS m/z 614 $(M + H)^+$ |
| 12-34 | 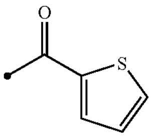 | 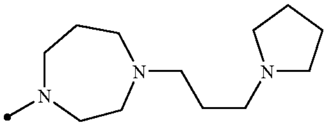 | MS m/z 628 $(M + H)^+$ |
| 12-35 | 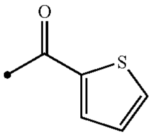 | 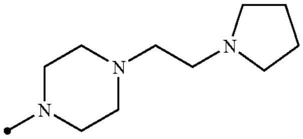 | MS m/z 599 $(M + H)^+$ |
| 12-36 | 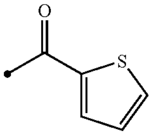 | 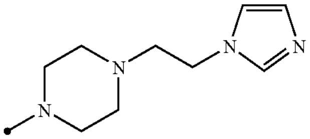 | MS m/z 597 $(M + H)^+$ |
| 12-37 | 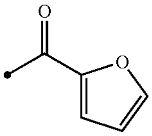 | 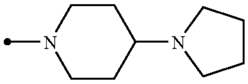 | MS m/z 555 $(M + H)^+$ |

TABLE 12-continued
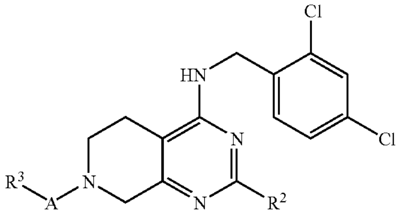
| Compound Number | •—A—$R^3$ | •—$R^2$ | Spectrum Data |
|---|---|---|---|
| 12-38 | 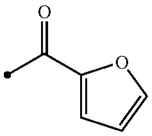 | 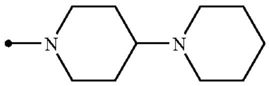 | MS m/z 569 $(M + H)^+$ |
| 12-39 | 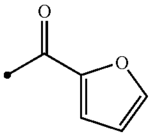 | 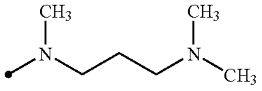 | MS m/z 517 $(M + H)^+$ |
| 12-40 | 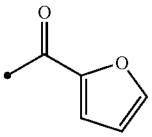 | 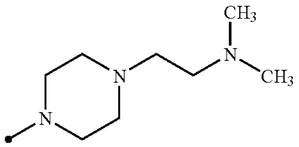 | MS m/z 558 $(M + H)^+$ |
| 12-41 | 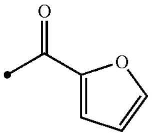 | 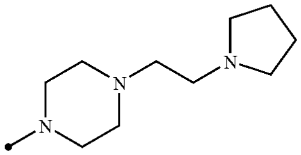 | MS m/z 584 $(M + H)^+$ |
| 12-42 | 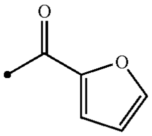 | 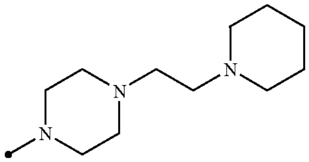 | MS m/z 598 $(M + H)^+$ |
| 12-43 | 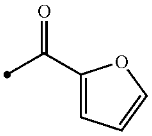 | 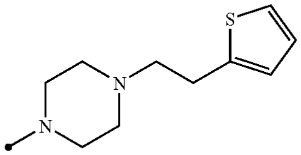 | MS m/z 597 $(M + H)^+$ |
| 12-44 | 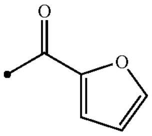 | 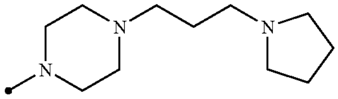 | MS m/z 598 $(M + H)^+$ |
| 12-45 | 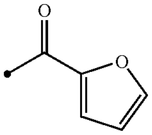 | 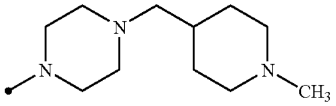 | MS m/z 598 $(M + H)^+$ |

TABLE 12-continued
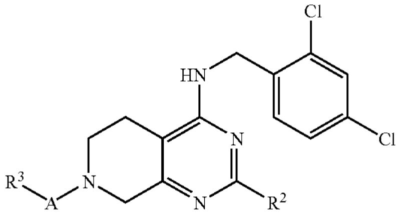
| Compound Number | •—A—$R^3$ | •—$R^2$ | Spectrum Data |
|---|---|---|---|
| 12-46 | 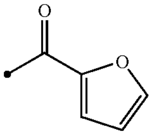 | 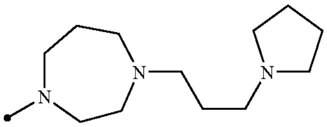 | MS m/z 612 $(M + H)^+$ |
| 12-47 | 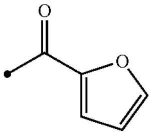 | 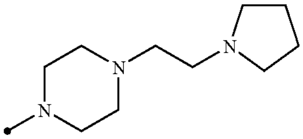 | MS m/z 583 $(M + H)^+$ |
| 12-48 | 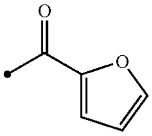 | 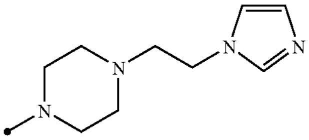 | MS m/z 581 $(M + H)^+$ |
| 12-49 | 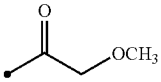 | 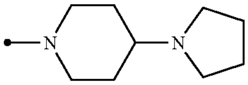 | MS m/z 533 $(M + H)^+$ |
| 12-50 | 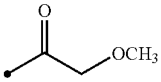 | 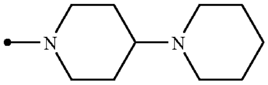 | MS m/z 547 $(M + H)^+$ |
| 12-51 | 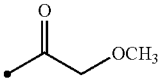 | 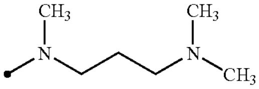 | MS m/z 495 $(M + H)^+$ |
| 12-52 | 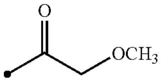 | 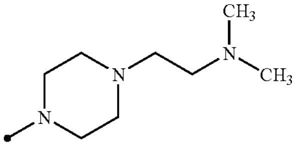 | MS m/z 536 $(M + H)^+$ |
| 12-53 | 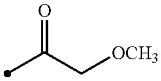 | 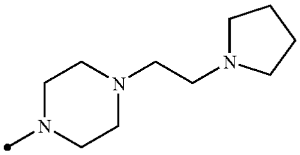 | MS m/z 562 $(M + H)^+$ |
| 12-54 | 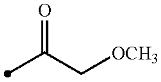 | 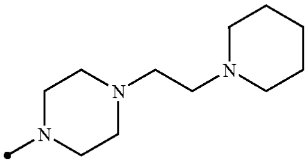 | MS m/z 576 $(M + H)^+$ |

TABLE 12-continued
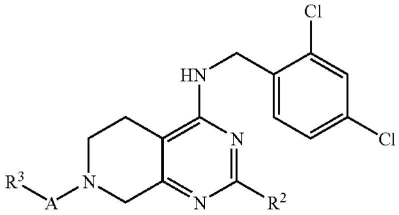
| Compound Number | •—A—$R^3$ | •—$R^2$ | Spectrum Data |
|---|---|---|---|
| 12-55 | 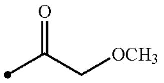 | 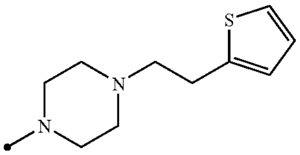 | MS m/z 575 $(M + H)^+$ |
| 12-56 | 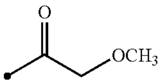 | 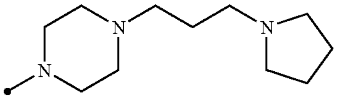 | MS m/z 576 $(M + H)^+$ |
| 12-57 | 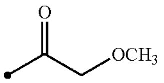 | 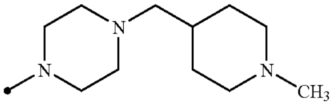 | MS m/z 576 $(M + H)^+$ |
| 12-58 | 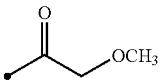 | 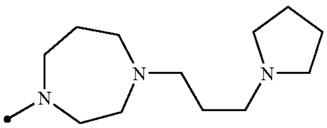 | MS m/z 590 $(M + H)^+$ |
| 12-59 | 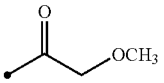 | 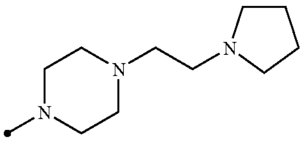 | MS m/z 561 $(M + H)^+$ |
| 12-60 | 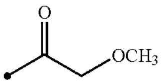 | 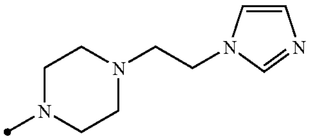 | MS m/z 559 $(M + H)^+$ |
| 12-61 | 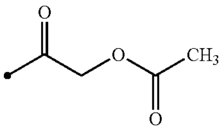 | 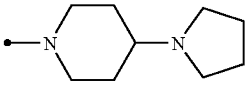 | MS m/z 561 $(M + H)^+$ |
| 12-62 | 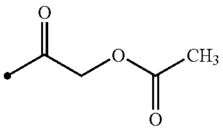 | 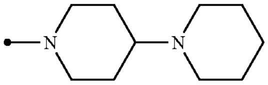 | MS m/z 575 $(M + H)^+$ |
| 12-63 | 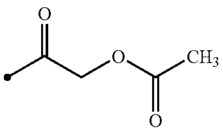 | 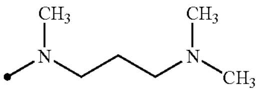 | MS m/z 523 $(M + H)^+$ |

TABLE 12-continued
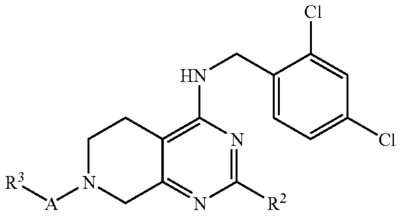
| Compound Number | •—A—$R^3$ | •—$R^2$ | Spectrum Data |
|---|---|---|---|
| 12-64 | 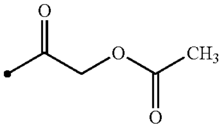 | 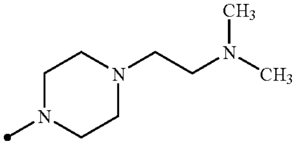 | MS m/z 564 $(M + H)^+$ |
| 12-65 | 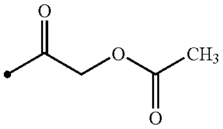 | 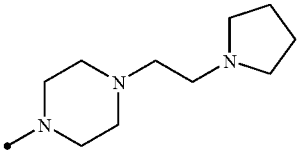 | MS m/z 561 $(M + H)^+$ |
| 12-66 | 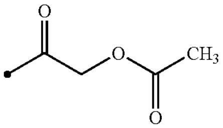 | 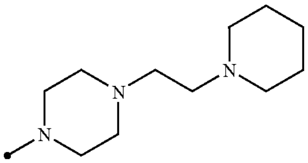 | MS m/z 604 $(M + H)^+$ |
| 12-67 | 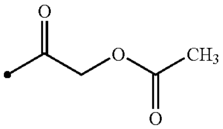 | 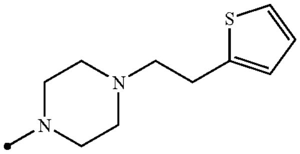 | MS m/z 603 $(M + H)^+$ |
| 12-68 | 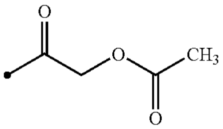 | 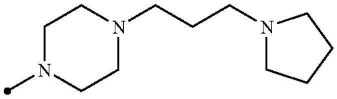 | MS m/z 604 $(M + H)^+$ |
| 12-69 | 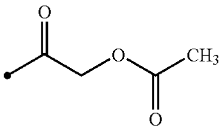 | 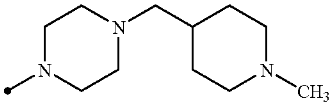 | MS m/z 604 $(M + H)^+$ |
| 12-70 | 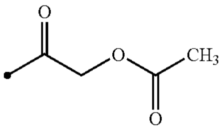 | 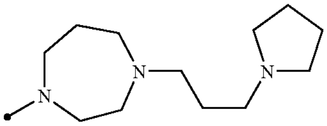 | MS m/z 618 $(M + H)^+$ |
| 12-71 | 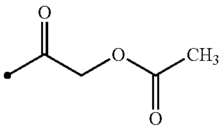 | 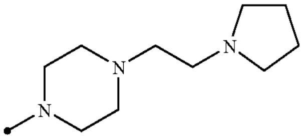 | MS m/z 589 $(M + H)^+$ |

TABLE 12-continued
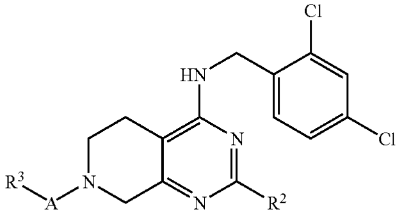
| Compound Number | •—A—$R^3$ | •—$R^2$ | Spectrum Data |
|---|---|---|---|
| 12-72 | 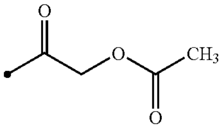 | 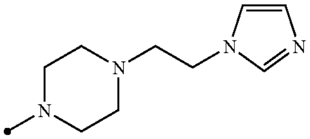 | MS m/z 587 $(M + H)^+$ |
| 12-73 | 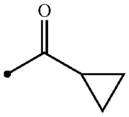 | 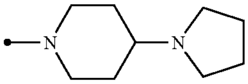 | MS m/z 529 $(M + H)^+$ |
| 12-74 | 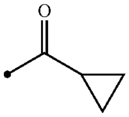 | 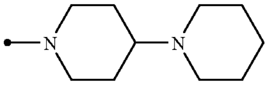 | MS m/z 543 $(M + H)^+$ |
| 12-75 | 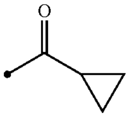 | 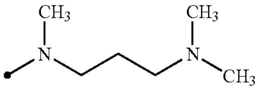 | MS m/z 491 $(M + H)^+$ |
| 12-76 | 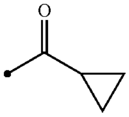 | 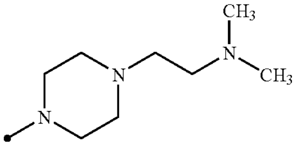 | MS m/z 532 $(M + H)^+$ |
| 12-77 | 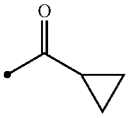 | 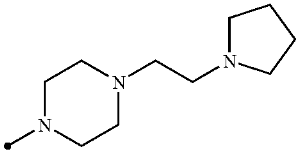 | MS m/z 558 $(M + H)^+$ |
| 12-78 | 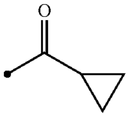 | 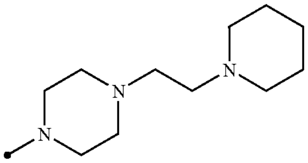 | MS m/z 572 $(M + H)^+$ |
| 12-79 | 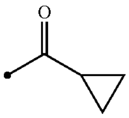 | 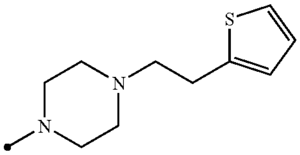 | MS m/z 571 $(M + H)^+$ |

TABLE 12-continued
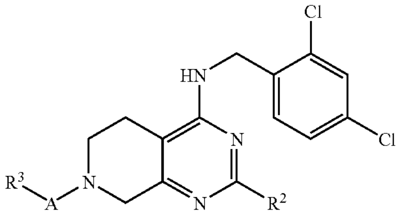
| Compound Number | •—A—$R^3$ | •—$R^2$ | Spectrum Data |
|---|---|---|---|
| 12-80 | 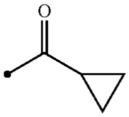 | 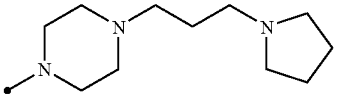 | MS m/z 572 $(M + H)^+$ |
| 12-81 | 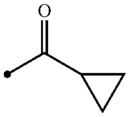 | 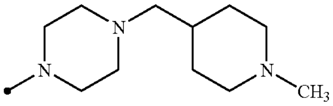 | MS m/z 572 $(M + H)^+$ |
| 12-82 | 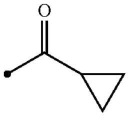 | 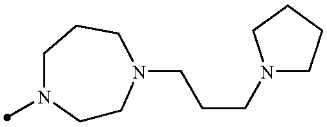 | MS m/z 586 $(M + H)^+$ |
| 12-83 | 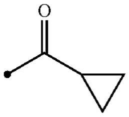 | 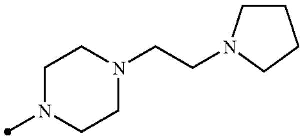 | MS m/z 557 $(M + H)^+$ |
| 12-84 | 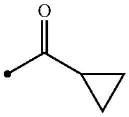 | 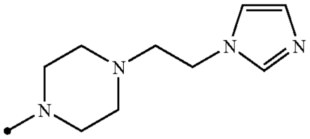 | MS m/z 555 $(M + H)^+$ |
| 12-85 | 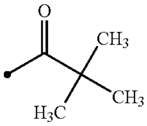 | 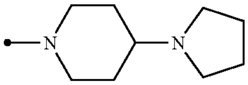 | MS m/z 545 $(M + H)^+$ |
| 12-86 | 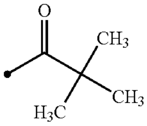 | 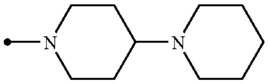 | MS m/z 559 $(M + H)^+$ |
| 12-87 | 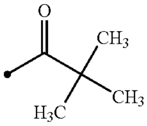 | 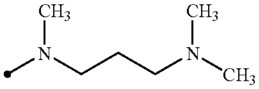 | MS m/z 507 $(M + H)^+$ |
| 12-88 | 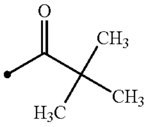 | 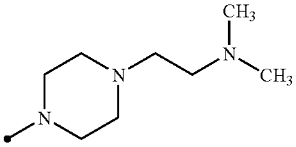 | MS m/z 548 $(M + H)^+$ |

TABLE 12-continued
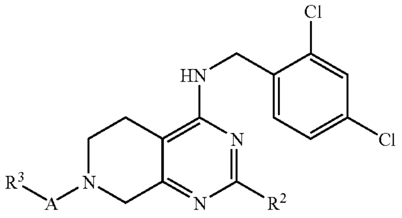
| Compound Number | •—A—$R^3$ | •—$R^2$ | Spectrum Data |
|---|---|---|---|
| 12-89 | 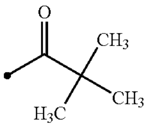 | 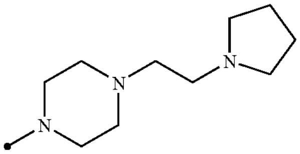 | MS m/z 574 $(M + H)^+$ |
| 12-90 | 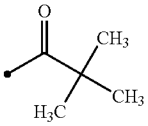 | 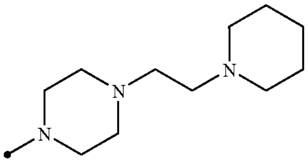 | MS m/z 588 $(M + H)^+$ |
| 12-91 | 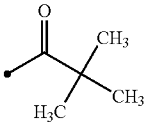 | 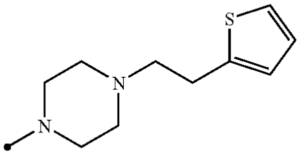 | MS m/z 587 $(M + H)^+$ |
| 12-92 | 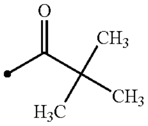 | 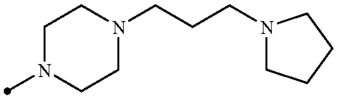 | MS m/z 588 $(M + H)^+$ |
| 12-93 | 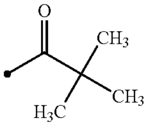 | 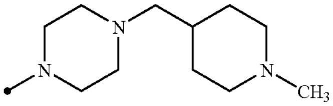 | MS m/z 588 $(M + H)^+$ |
| 12-94 | 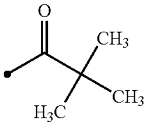 | 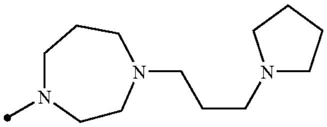 | MS m/z 602 $(M + H)^+$ |
| 12-95 | 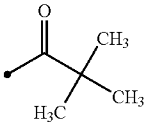 | 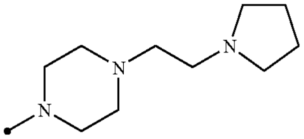 | MS m/z 573 $(M + H)^+$ |
| 12-96 | 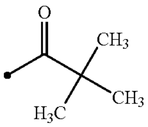 | 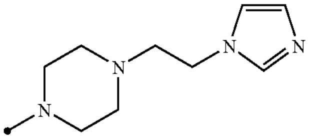 | MS m/z 571 $(M + H)^+$ |
| 12-97 | 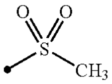 | 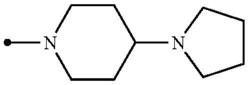 | MS m/z 539 $(M + H)^+$ |

TABLE 12-continued
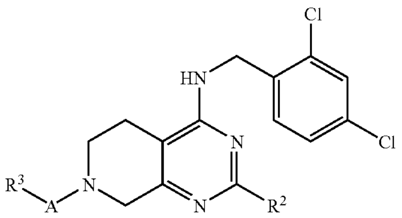
| Compound Number | •—A—$R^3$ | •—$R^2$ | Spectrum Data |
|---|---|---|---|
| 12-98 | 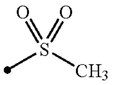 | 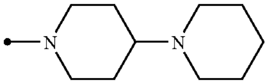 | MS m/z 553 $(M + H)^+$ |
| 12-99 | 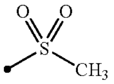 | 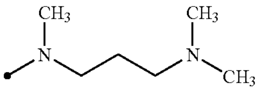 | MS m/z 501 $(M + H)^+$ |
| 12-100 | 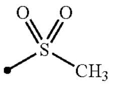 | 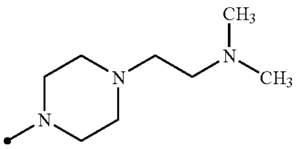 | MS m/z 542 $(M + H)^+$ |
| 12-101 | 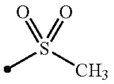 | 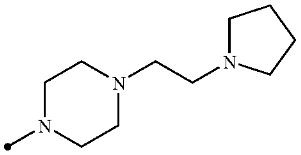 | MS m/z 568 $(M + H)^+$ |
| 12-102 | 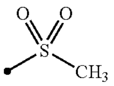 | 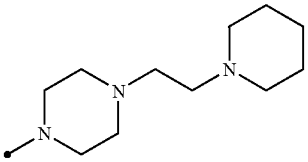 | MS m/z 582 $(M + H)^+$ |
| 12-103 | 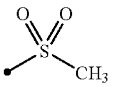 | 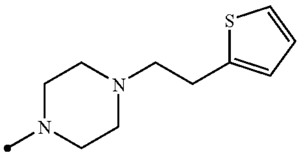 | MS m/z 581 $(M + H)^+$ |
| 12-104 | 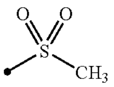 | 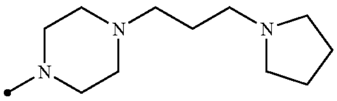 | MS m/z 582 $(M + H)^+$ |
| 12-105 | 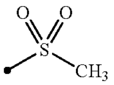 | 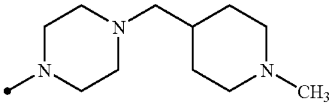 | MS m/z 582 $(M + H)^+$ |
| 12-106 | 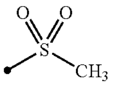 | 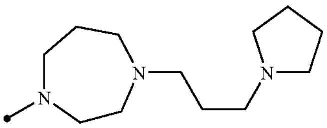 | MS m/z 596 $(M + H)^+$ |

TABLE 12-continued
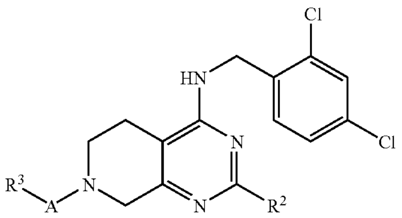
| Compound Number | •—A—$R^3$ | •—$R^2$ | Spectrum Data |
|---|---|---|---|
| 12-107 | 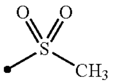 | 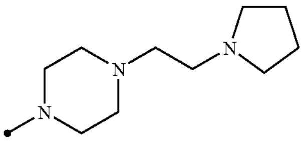 | MS m/z 567 $(M + H)^+$ |
| 12-108 | 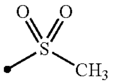 | 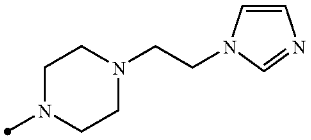 | MS m/z 565 $(M + H)^+$ |
| 12-109 | 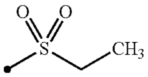 | 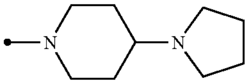 | MS m/z 553 $(M + H)^+$ |
| 12-110 | 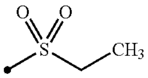 | 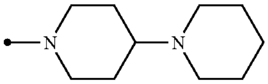 | MS m/z 567 $(M + H)^+$ |
| 12-111 | 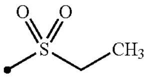 | 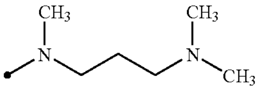 | MS m/z 515 $(M + H)^+$ |
| 12-112 | 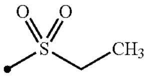 | 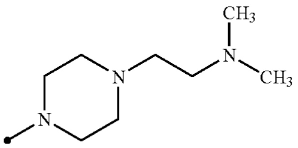 | MS m/z 556 $(M + H)^+$ |
| 12-113 | 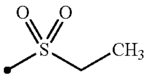 | 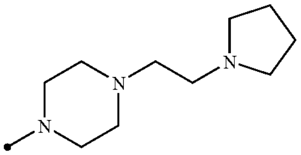 | MS m/z 582 $(M + H)^+$ |
| 12-114 | 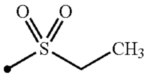 | 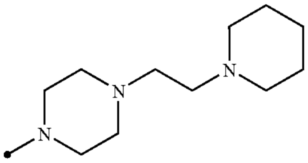 | MS m/z 596 $(M + H)^+$ |
| 12-115 | 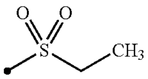 | 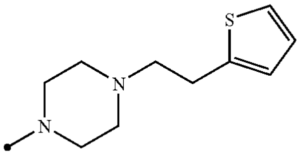 | MS m/z 595 $(M + H)^+$ |

TABLE 12-continued
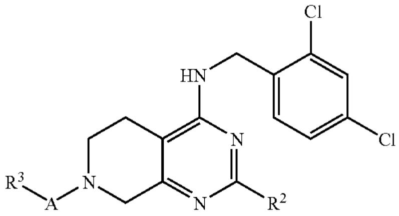
| Compound Number | •—A—$R^3$ | •—$R^2$ | Spectrum Data |
|---|---|---|---|
| 12-116 | 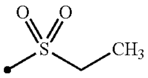 | 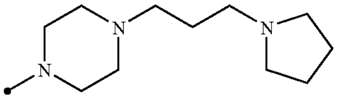 | MS m/z 596 (M + H)$^+$ |
| 12-117 | 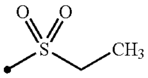 | 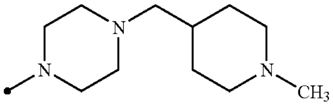 | MS m/z 596 (M + H)$^+$ |
| 12-118 | 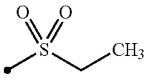 | 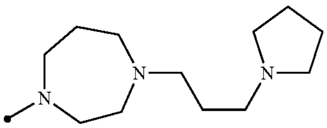 | MS m/z 610 (M + H)$^+$ |
| 12-119 | 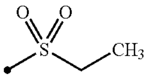 | 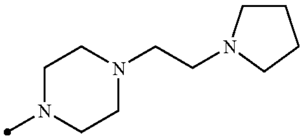 | MS m/z 581 (M + H)$^+$ |
| 12-120 | 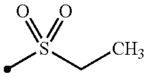 | 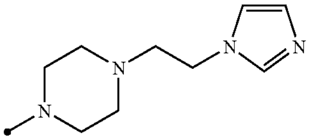 | MS m/z 579 (M + H)$^+$ |
| 12-121 | 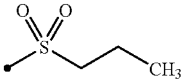 | 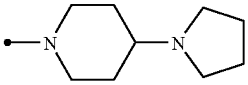 | MS m/z 567 (M + H)$^+$ |
| 12-122 | 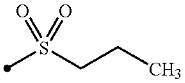 | 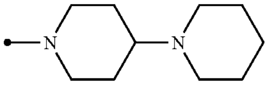 | MS m/z 581 (M + H)$^+$ |
| 12-123 | 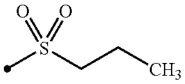 | 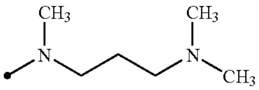 | MS m/z 529 (M + H)$^+$ |
| 12-124 | 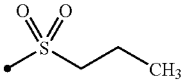 | 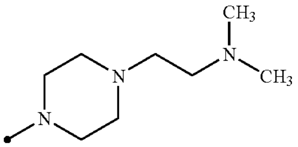 | MS m/z 570 (M + H)$^+$ |
| 12-125 | 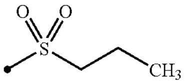 | 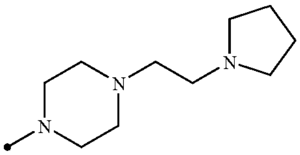 | MS m/z 596 (M + H)$^+$ |

TABLE 12-continued
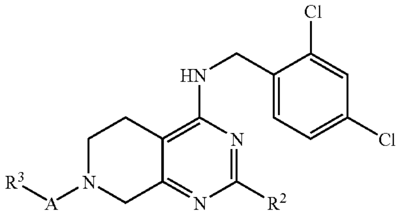
| Compound Number | •—A—$R^3$ | •—$R^2$ | Spectrum Data |
|---|---|---|---|
| 12-126 | 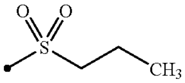 | 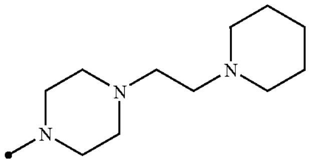 | MS m/z 610 $(M + H)^+$ |
| 12-127 | 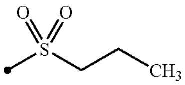 | 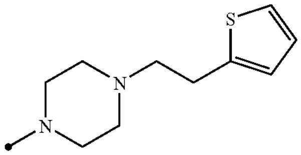 | MS m/z 609 $(M + H)^+$ |
| 12-128 | 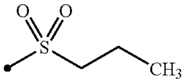 | 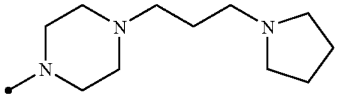 | MS m/z 610 $(M + H)^+$ |
| 12-129 | 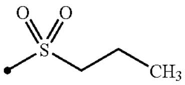 | 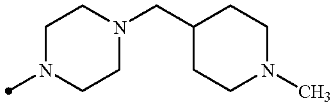 | MS m/z 610 $(M + H)^+$ |
| 12-130 | 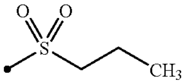 | 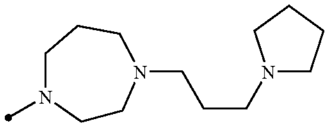 | MS m/z 624 $(M + H)^+$ |
| 12-131 | 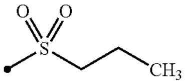 | 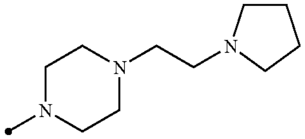 | MS m/z 593 $(M + H)^+$ |
| 12-132 | 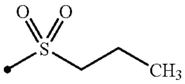 | 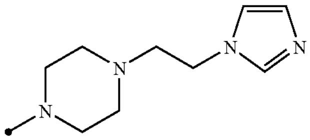 | MS m/z 593 $(M + H)^+$ |
| 12-133 | 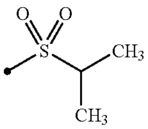 | 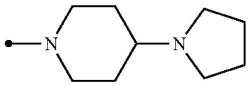 | MS m/z 567 $(M + H)^+$ |
| 12-134 | 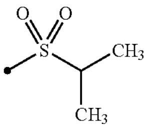 | 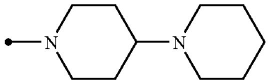 | MS m/z 581 $(M + H)^+$ |

TABLE 12-continued
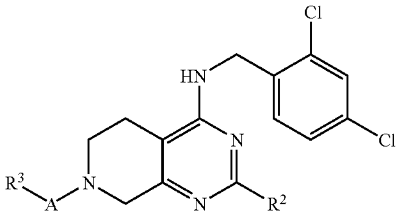
| Compound Number | •—A—$R^3$ | •—$R^2$ | Spectrum Data |
|---|---|---|---|
| 12-135 | 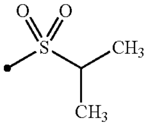 | 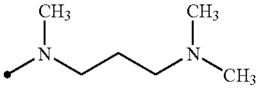 | MS m/z 529 $(M + H)^+$ |
| 12-136 | 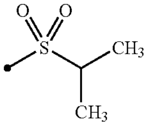 | 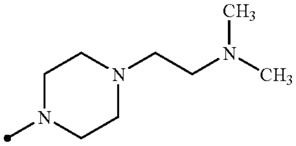 | MS m/z 570 $(M + H)^+$ |
| 12-137 | 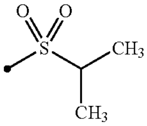 | 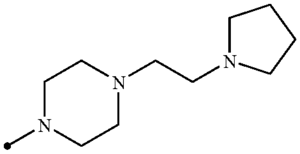 | MS m/z 596 $(M + H)^+$ |
| 12-138 | 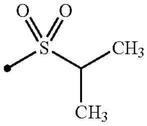 | 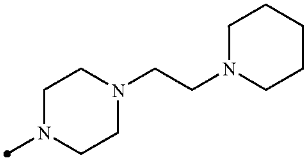 | MS m/z 610 $(M + H)^+$ |
| 12-139 | 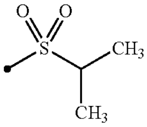 | 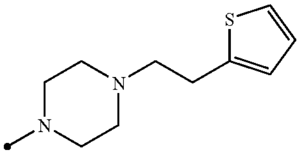 | MS m/z 609 $(M + H)^+$ |
| 12-140 | 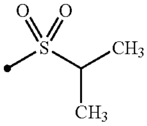 | 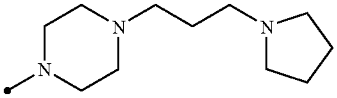 | MS m/z 610 $(M + H)^+$ |
| 12-141 | 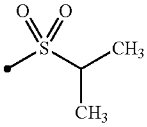 | 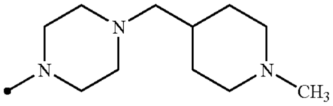 | MS m/z 610 $(M + H)^+$ |
| 12-142 | 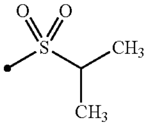 | 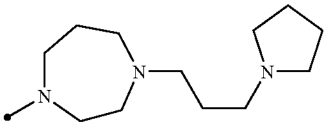 | MS m/z 624 $(M + H)^+$ |

TABLE 12-continued
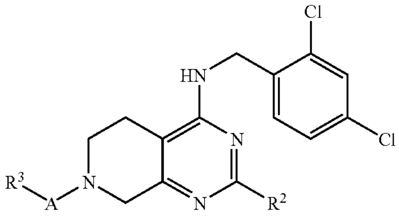
| Compound Number | •—A—$R^3$ | •—$R^2$ | Spectrum Data |
|---|---|---|---|
| 12-143 | 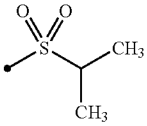 | 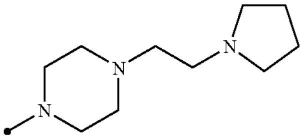 | MS m/z 595 $(M + H)^+$ |
| 12-144 | 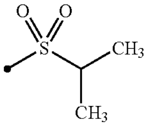 | 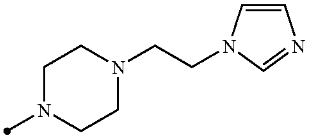 | MS m/z 593 $(M + H)^+$ |
| 12-145 | 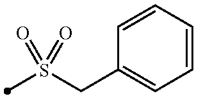 | 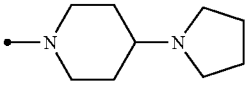 | MS m/z 615 $(M + H)^+$ |
| 12-146 | 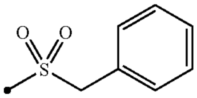 | 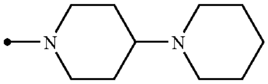 | MS m/z 629 $(M + H)^+$ |
| 12-147 | 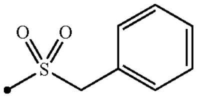 | 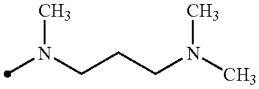 | MS m/z 577 $(M + H)^+$ |
| 12-148 | 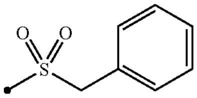 | 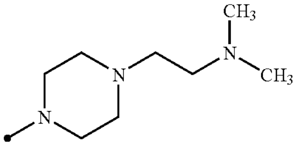 | MS m/z 618 $(M + H)^+$ |
| 12-149 | 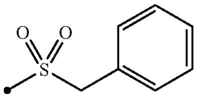 | 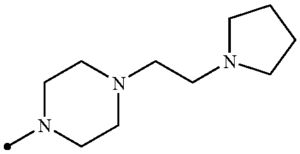 | MS m/z 644 $(M + H)^+$ |
| 12-150 | 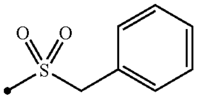 | 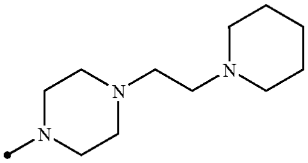 | MS m/z 658 $(M + H)^+$ |
| 12-151 | 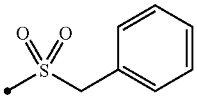 | 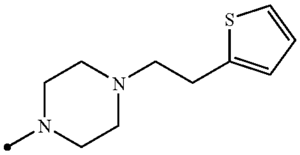 | MS m/z 657 $(M + H)^+$ |

TABLE 12-continued
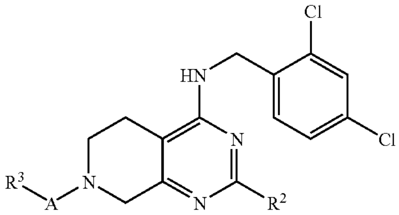
| Compound Number | •—A—$R^3$ | •—$R^2$ | Spectrum Data |
|---|---|---|---|
| 12-152 | 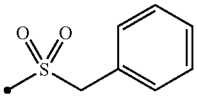 | 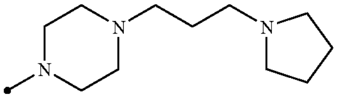 | MS m/z 658 (M + H)$^+$ |
| 12-153 | 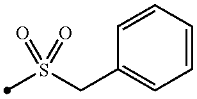 | 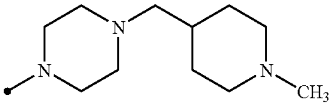 | MS m/z 658 (M + H)$^+$ |
| 12-154 | 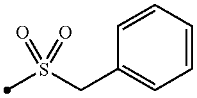 | 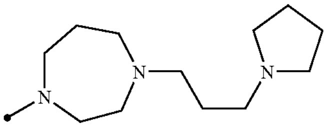 | MS m/z 672 (M + H)$^+$ |
| 12-155 | 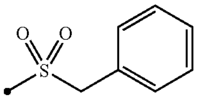 | 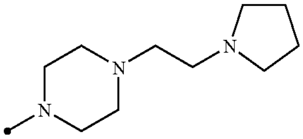 | MS m/z 643 (M + H)$^+$ |
| 12-156 | 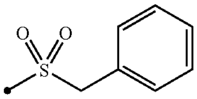 | 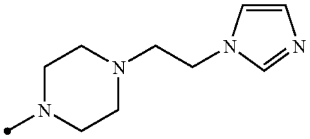 | MS m/z 641 (M + H)$^+$ |
| 12-157 | 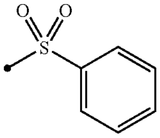 | 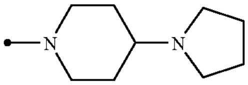 | MS m/z 601 (M + H)$^+$ |
| 12-158 | 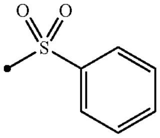 | 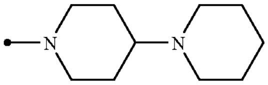 | MS m/z 615 (M + H)$^+$ |
| 12-159 | 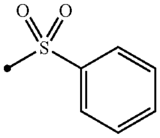 | 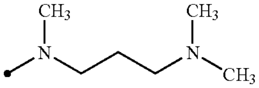 | MS m/z 563 (M + H)$^+$ |
| 12-160 | 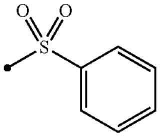 | 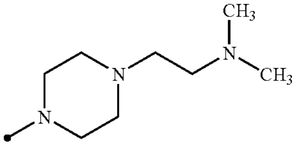 | MS m/z 604 (M + H)$^+$ |

TABLE 12-continued
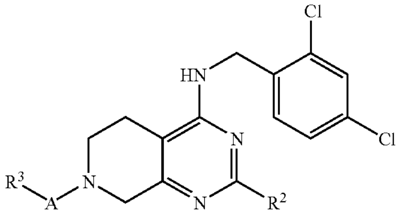
| Compound Number | •—A—$R^3$ | •—$R^2$ | Spectrum Data |
|---|---|---|---|
| 12-161 | 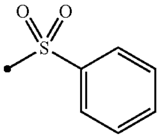 | 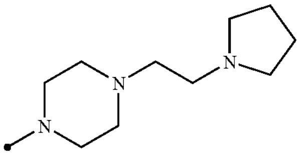 | MS m/z 630 $(M + H)^+$ |
| 12-162 | 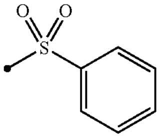 | 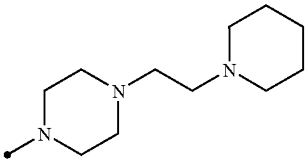 | MS m/z 644 $(M + H)^+$ |
| 12-163 | 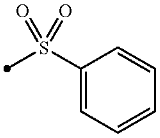 | 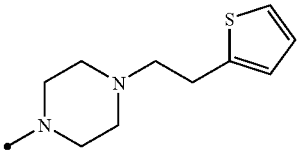 | MS m/z 643 $(M + H)^+$ |
| 12-164 | 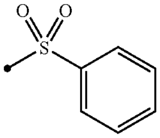 | 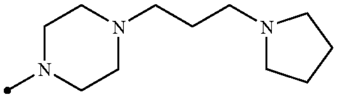 | MS m/z 644 $(M + H)^+$ |
| 12-165 | 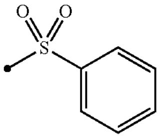 | 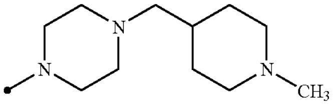 | MS m/z 644 $(M + H)^+$ |
| 12-166 | 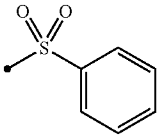 | 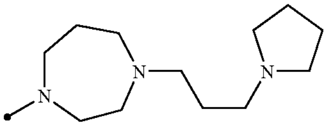 | MS m/z 658 $(M + H)^+$ |
| 12-167 | 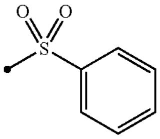 | 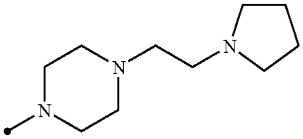 | MS m/z 629 $(M + H)^+$ |
| 12-168 | 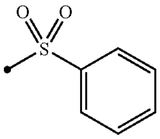 | 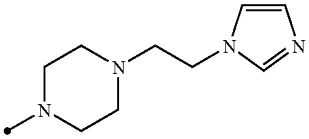 | MS m/z 627 $(M + H)^+$ |

TABLE 12-continued
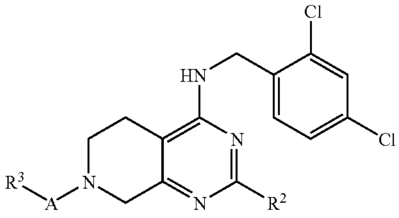
| Compound Number | •—A—$R^3$ | •—$R^2$ | Spectrum Data |
|---|---|---|---|
| 12-169 | 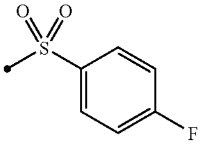 | 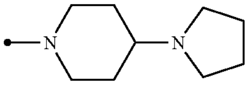 | MS m/z 619 $(M + H)^+$ |
| 12-170 | 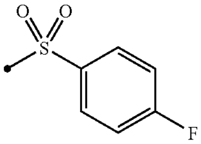 | 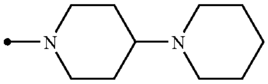 | MS m/z 633 $(M + H)^+$ |
| 12-171 | 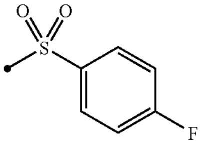 | 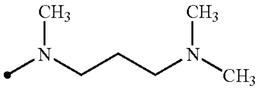 | MS m/z 581 $(M + H)^+$ |
| 12-172 | 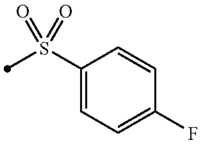 | 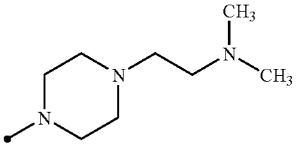 | MS m/z 622 $(M + H)^+$ |
| 12-173 | 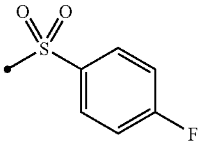 | 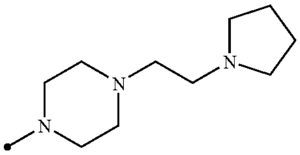 | MS m/z 648 $(M + H)^+$ |
| 12-174 | 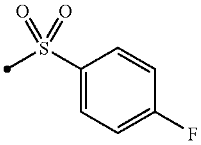 | 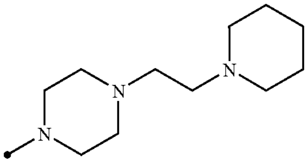 | MS m/z 662 $(M + H)^+$ |
| 12-175 | 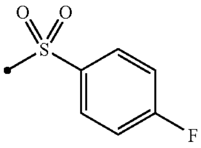 | 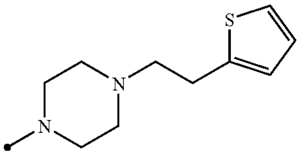 | MS m/z 661 $(M + H)^+$ |
| 12-176 | 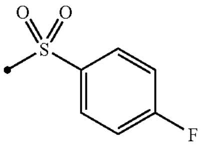 | 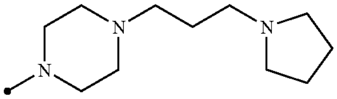 | MS m/z 662 $(M + H)^+$ |

TABLE 12-continued
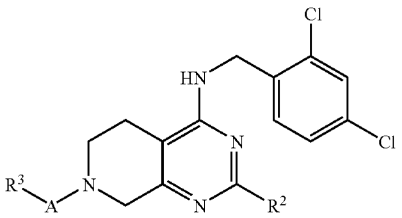
| Compound Number | •—A—$R^3$ | •—$R^2$ | Spectrum Data |
|---|---|---|---|
| 12-177 | 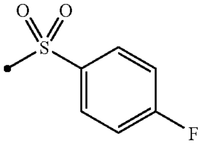 | 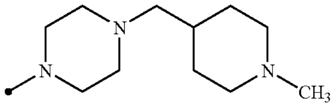 | MS m/z 662 $(M + H)^+$ |
| 12-178 | 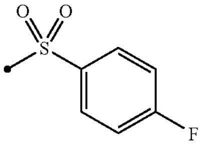 | 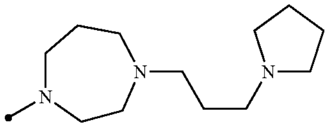 | MS m/z 676 $(M + H)^+$ |
| 12-179 | 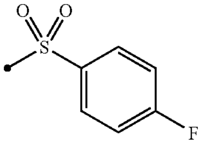 | 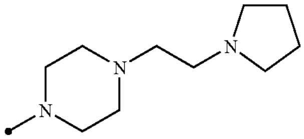 | MS m/z 647 $(M + H)^+$ |
| 12-180 | 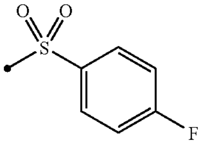 | 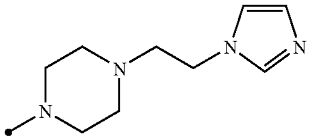 | MS m/z 645 $(M + H)^+$ |
| 12-181 | 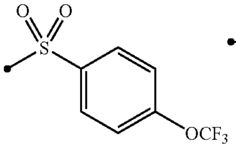 | 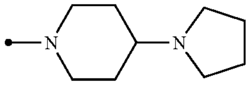 | MS m/z 685 $(M + H)^+$ |
| 12-182 | 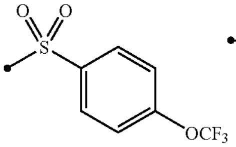 | 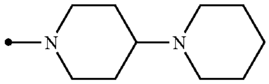 | MS m/z 699 $(M + H)^+$ |
| 12-183 | 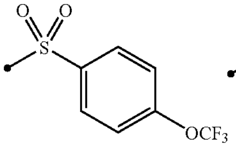 | 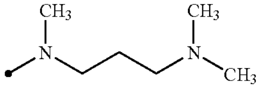 | MS m/z 647 $(M + H)^+$ |
| 12-184 | 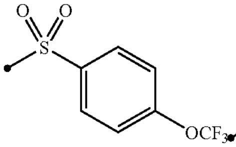 | 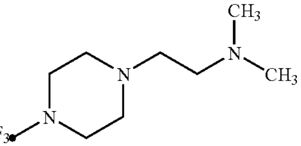 | MS m/z 688 $(M + H)^+$ |

TABLE 12-continued
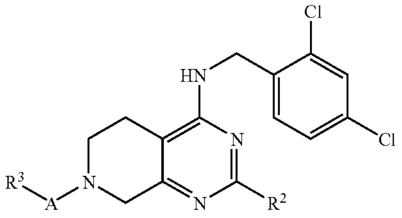
| Compound Number | •—A—$R^3$ | •—$R^2$ | Spectrum Data |
|---|---|---|---|
| 12-185 | 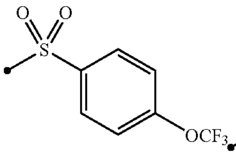 | 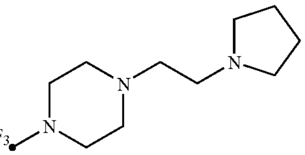 | MS m/z 714 $(M + H)^+$ |
| 12-186 | 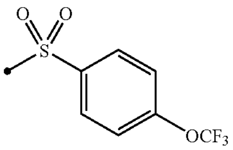 | 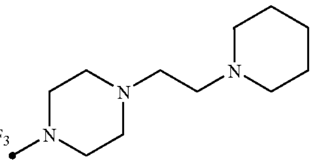 | MS m/z 728 $(M + H)^+$ |
| 12-187 | 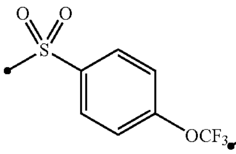 | 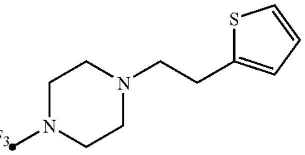 | MS m/z 727 $(M + H)^+$ |
| 12-188 | 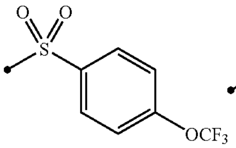 | 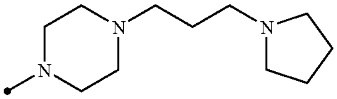 | MS m/z 728 $(M + H)^+$ |
| 12-189 | 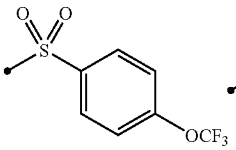 | 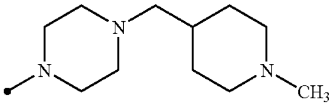 | MS m/z 728 $(M + H)^+$ |
| 12-190 | 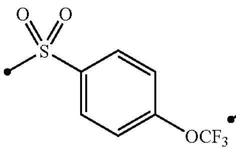 | 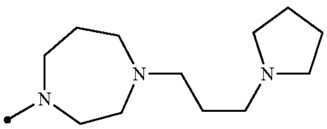 | MS m/z 742 $(M + H)^+$ |
| 12-191 | 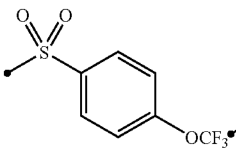 | 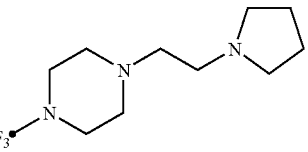 | MS m/z 713 $(M + H)^+$ |
| 12-192 | 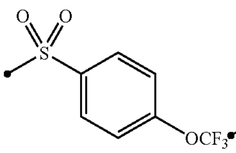 | 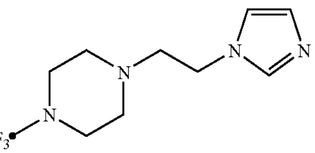 | MS m/z 711 $(M + H)^+$ |

TABLE 13
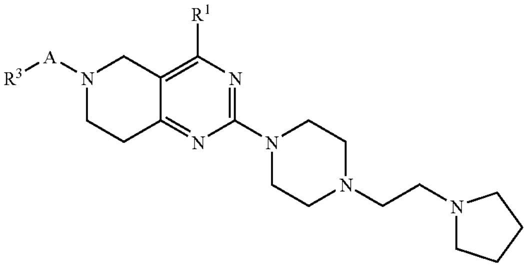
| Compound Number | •—A—$R^3$ | —$R^1$ | Spectrum Data |
|---|---|---|---|
| 13-1 | 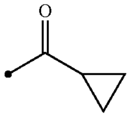 | 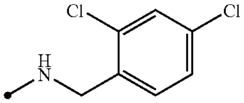 | MS m/z 559 $(M + H)^+$ |
| 13-2 | 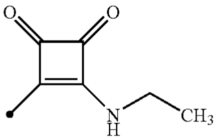 | 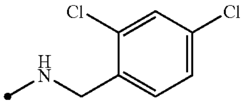 | MS m/z 613 $(M + H)^+$ |
| 13-3 | 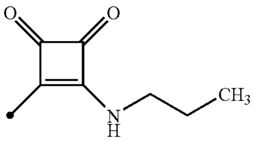 | 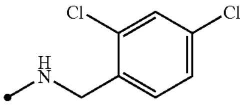 | MS m/z 627 $(M + H)^+$ |
| 13-4 | 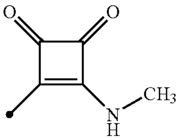 | 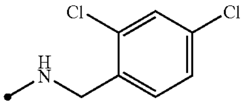 | MS m/z 599 $(M + H)^+$ |
| 13-5 | 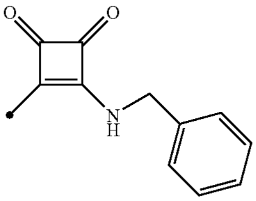 | 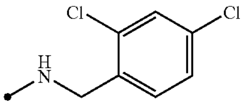 | MS m/z 675 $(M + H)^+$ |
| 13-6 | 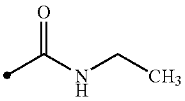 | 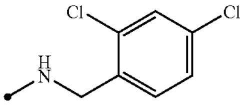 | MS m/z 561 $(M + H)^+$ |
| 13-7 | 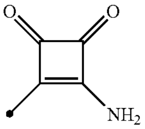 | 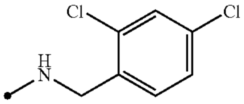 | MS m/z 585 $(M + H)^+$ |
| 13-8 | 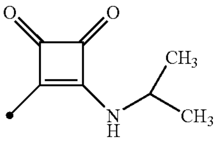 | 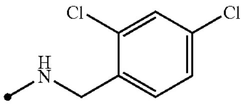 | MS m/z 627 $(M + H)^+$ |

TABLE 13-continued
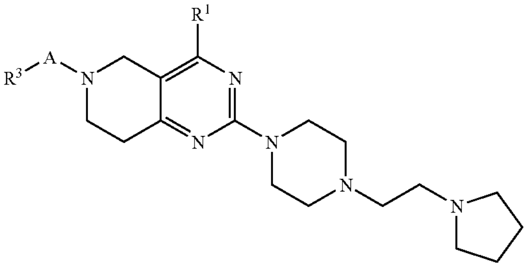
| Compound Number | •—A—R$^3$ | —R$^1$ | Spectrum Data |
|---|---|---|---|
| 13-9 | 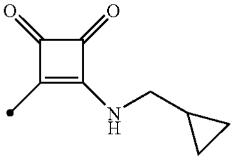 | 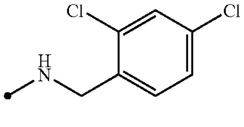 | MS m/z 639 (M + H)$^+$ |
| 13-10 | 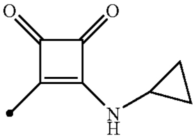 | 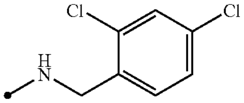 | MS m/z 625 (M + H)$^+$ |
| 13-11 | 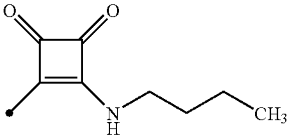 | 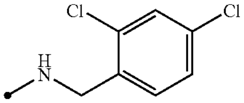 | MS m/z 641 (M + H)$^+$ |
| 13-12 | 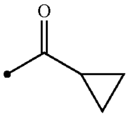 | 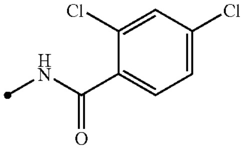 | MS m/z 572 (M + H)$^+$ |
TABLE 14
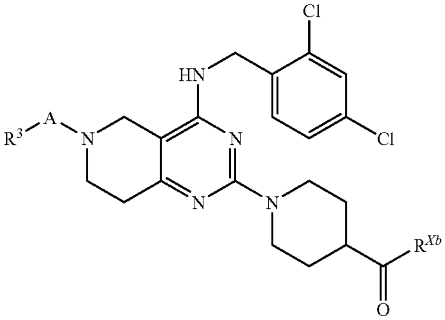
| Compound Number | •—A—R$^3$ | •—R$^{Xb}$ | Spectrum Data |
|---|---|---|---|
| 14-1 | 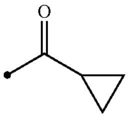 | 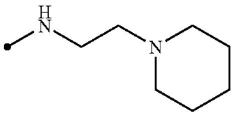 | MS m/z 614 (M + H)$^+$ |

TABLE 14-continued
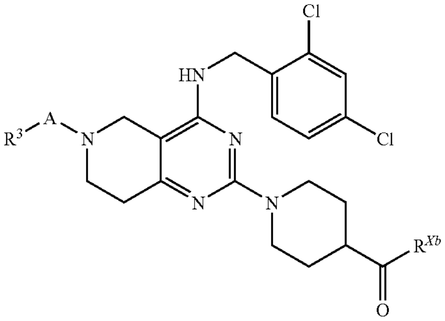
| Compound Number | •—A—$R^3$ | •—$R^{Xb}$ | Spectrum Data |
|---|---|---|---|
| 14-2 | 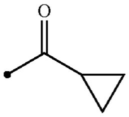 | 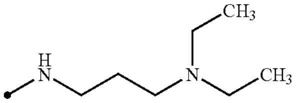 | MS m/z 616 (M + H)$^+$ |
| 14-3 | 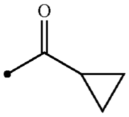 | 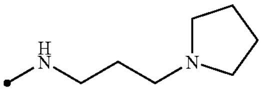 | MS m/z 614 (M + H)$^+$ |
| 14-4 | 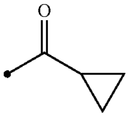 | 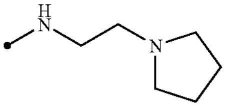 | MS m/z 600 (M + H)$^+$ |
| 14-5 | 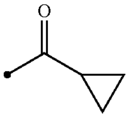 | 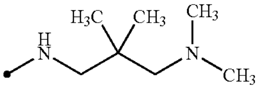 | MS m/z 616 (M + H)$^+$ |
| 14-6 | 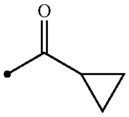 | 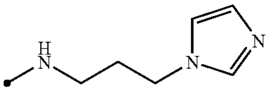 | MS m/z 611 (M + H)$^+$ |
| 14-7 | 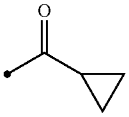 | 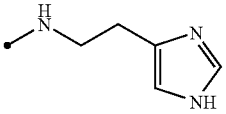 | MS m/z 597 (M + H)$^+$ |
| 14-8 | 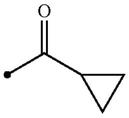 | 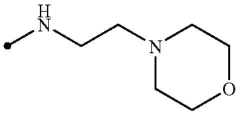 | MS m/z 616 (M + H)$^+$ |
| 14-9 | 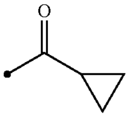 | 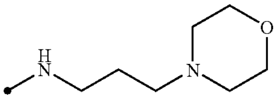 | MS m/z 630 (M + H)$^+$ |
| 14-10 | 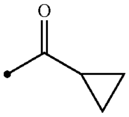 | 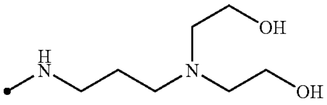 | MS m/z 648 (M + H)$^+$ |

TABLE 14-continued
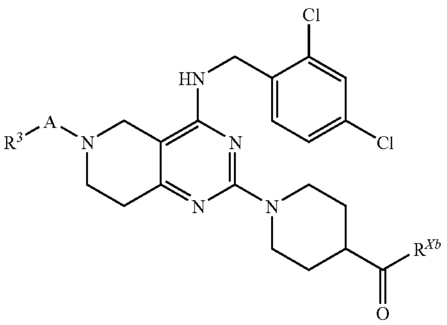
| Compound Number | •—A—$R^3$ | •—$R^{Xb}$ | Spectrum Data |
|---|---|---|---|
| 14-11 | 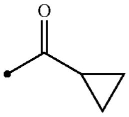 | 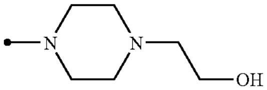 | MS m/z 616 (M + H)$^+$ |
| 14-12 | 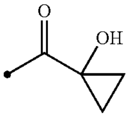 | 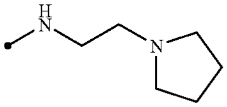 | MS m/z 616 (M + H)$^+$ |
| 14-13 | 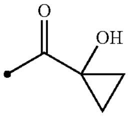 | 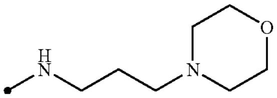 | MS m/z 646 (M + H)$^+$ |
| 14-14 | 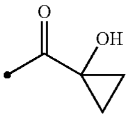 | 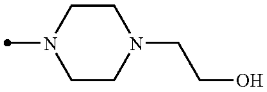 | MS m/z 632 (M + H)$^+$ |
TABLE 15
| Compound Number | •—A—$R^3$ | •—$R^{Xc}$ | Spectrum Data |
|---|---|---|---|
| 15-1 | 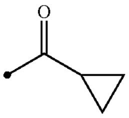 | 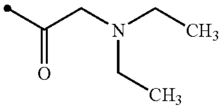 | MS m/z 574 (M + H)$^+$ |
| 15-2 | 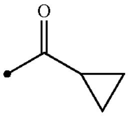 | 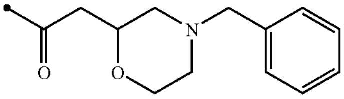 | MS m/z 678 (M + H)$^+$ |
| 15-3 | 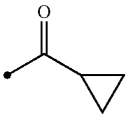 | 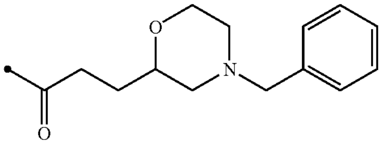 | MS m/z 692 (M + H)$^+$ |
| 15-4 | 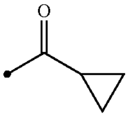 | 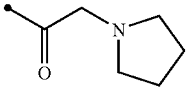 | MS m/z 572 (M + H)$^+$ |

TABLE 15-continued
| Compound Number | •—A—$R^3$ | •—$R^{Xc}$ | Spectrum Data |
|---|---|---|---|
| 15-5 | 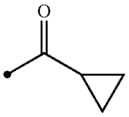 | 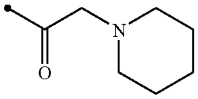 | MS m/z 586 $(M + H)^+$ |
| 15-6 | 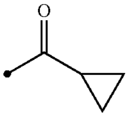 | 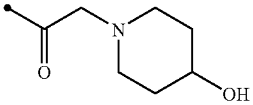 | MS m/z 602 $(M + H)^+$ |
| 15-7 | 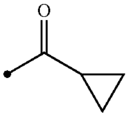 | 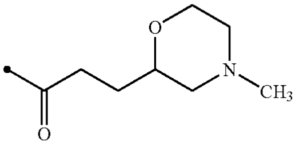 | MS m/z 616 $(M + H)^+$ |
| 15-8 | 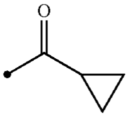 | 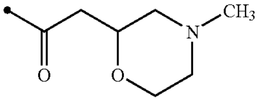 | MS m/z 602 $(M + H)^+$ |
| 15-9 | 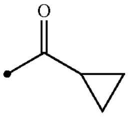 | 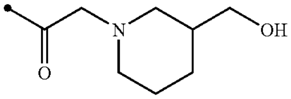 | MS m/z 616 $(M + H)^+$ |
| 15-10 | 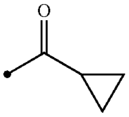 | 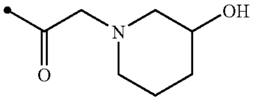 | MS m/z 602 $(M + H)^+$ |
| 15-11 | 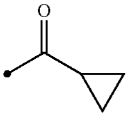 | 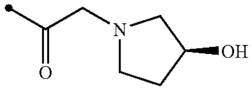 | MS m/z 587 $(M + H)^+$ |
| 15-12 | 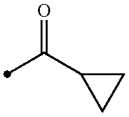 | 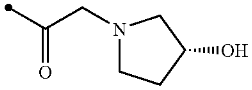 | MS m/z 587 $(M + H)^+$ |
| 15-13 | 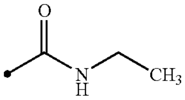 | 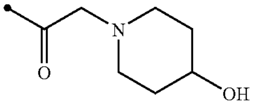 | MS m/z 605 $(M + H)^+$ |
| 15-14 | 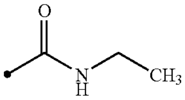 | 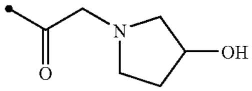 | MS m/z 591 $(M + H)^+$ |
| 15-15 | 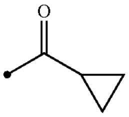 | 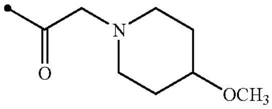 | MS m/z 616 $(M + H)^+$ |

TABLE 15-continued
| Compound Number | •—A—$R^3$ | •—$R^{Xc}$ | Spectrum Data |
|---|---|---|---|
| 15-16 | 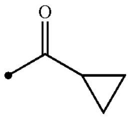 | 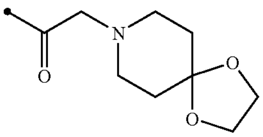 | MS m/z 643 $(M + H)^+$ |
| 15-17 | 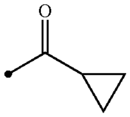 | 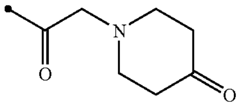 | MS m/z 600 $(M + H)^+$ |
| 15-18 | 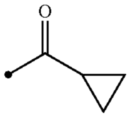 | 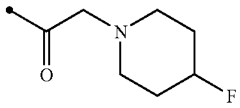 | MS m/z 604 $(M + H)^+$ |
| 15-19 | 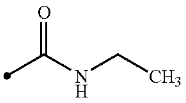 | 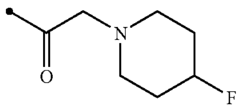 | MS m/z 605 $(M + H)^+$ |
| 15-20 | 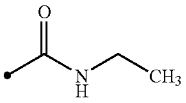 | 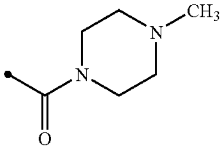 | MS m/z 590 $(M + H)^+$ |
| 15-21 | 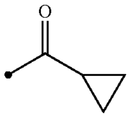 | 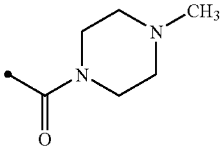 | MS m/z 587 $(M + H)^+$ |
| 15-22 | 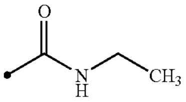 | 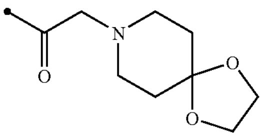 | MS m/z 647 $(M + H)^+$ |
| 15-23 | 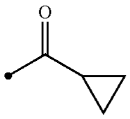 | 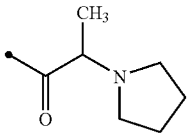 | MS m/z 586 $(M + H)^+$ |
| 15-24 | 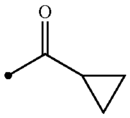 | 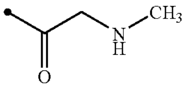 | MS m/z 532 $(M + H)^+$ |
| 15-25 | 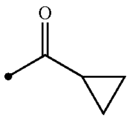 | 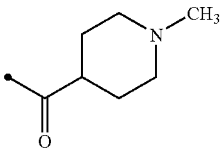 | MS m/z 586 $(M + H)^+$ |

TABLE 15-continued
| Compound Number | •—A—$R^3$ | •—$R^{Xc}$ | Spectrum Data |
|---|---|---|---|
| 15-26 | 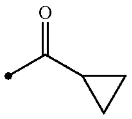 | 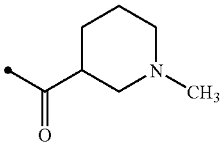 | MS m/z 586 $(M + H)^+$ |
| 15-27 | 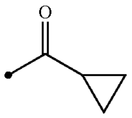 | 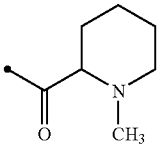 | MS m/z 586 $(M + H)^+$ |
| 15-28 | 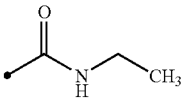 | 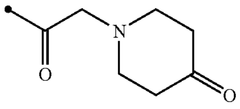 | MS m/z 603 $(M + H)^+$ |
| 15-29 | 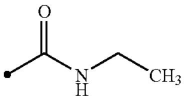 | 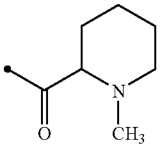 | MS m/z 589 $(M + H)^+$ |
| 15-30 | 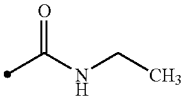 | 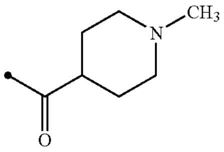 | MS m/z 589 $(M + H)^+$ |
| 15-31 | 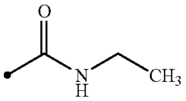 | 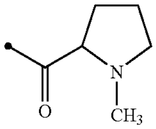 | MS m/z 575 $(M + H)^+$ |
| 15-32 | 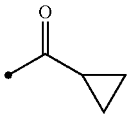 | 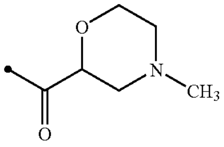 | MS m/z 588 $(M + H)^+$ |
| 15-33 | 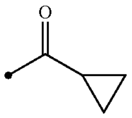 | 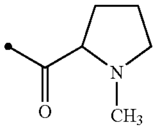 | MS m/z 572 $(M + H)^+$ |
| 15-34 | 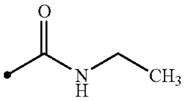 | 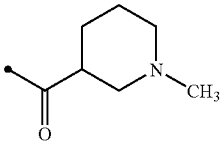 | MS m/z 589 $(M + H)^+$ |
| 15-35 | 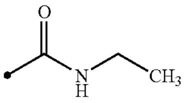 | 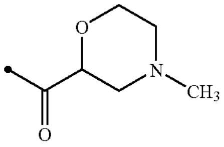 | MS m/z 591 $(M + H)^+$ |

TABLE 15-continued
| Compound Number | •—A—$R^3$ | •—$R^{Xc}$ | Spectrum Data |
|---|---|---|---|
| 15-36 | 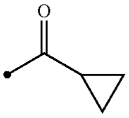 | 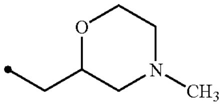 | MS m/z 574 $(M + H)^+$ |
| 15-37 | 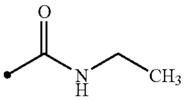 | 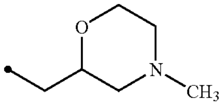 | MS m/z 577 $(M + H)^+$ |
| 15-38 | 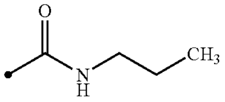 | 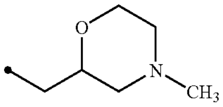 | MS m/z 591 $(M + H)^+$ |
| 15-39 | 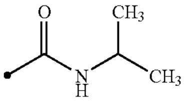 | 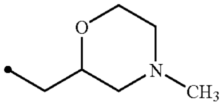 | MS m/z 591 $(M + H)^+$ |
| 15-40 | 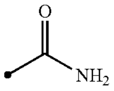 | 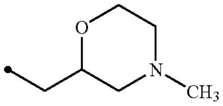 | MS m/z 549 $(M + H)^+$ |
| 15-41 | 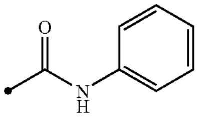 | 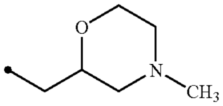 | MS m/z 625 $(M + H)^+$ |
| 15-42 | 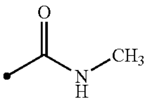 | 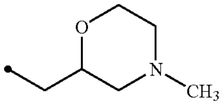 | MS m/z 563 $(M + H)^+$ |
| 15-43 | 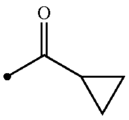 | 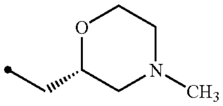 | MS m/z 573 $(M + H)^+$ |
| 15-44 | 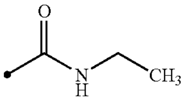 | 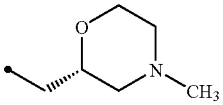 | MS m/z 577 $(M + H)^+$ |
| 15-45 | 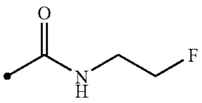 | 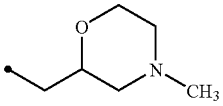 | MS m/z 595 $(M + H)^+$ |
| 15-46 | 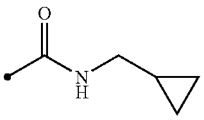 | 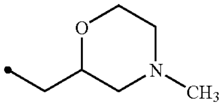 | MS m/z 603 $(M + H)^+$ |
| 15-47 | 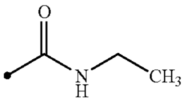 | 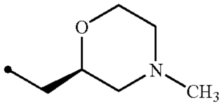 | MS m/z 577 $(M + H)^+$ |

TABLE 15-continued
| Compound Number | •—A—$R^3$ | •—$R^{Xc}$ | Spectrum Data |
|---|---|---|---|
| 15-48 | 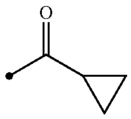 | 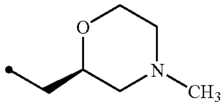 | MS m/z 574 $(M + H)^+$ |
| 15-49 | 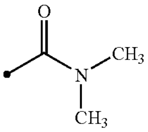 | 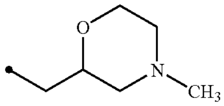 | MS m/z 577 $(M + H)^+$ |
| 15-50 | 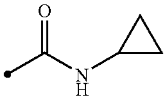 | 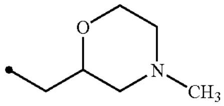 | MS m/z 589 $(M + H)^+$ |
| 15-51 | 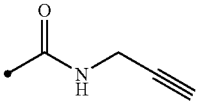 | 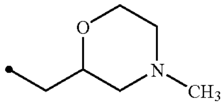 | MS m/z 587 $(M + H)^+$ |
| 15-52 | 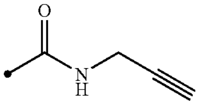 | 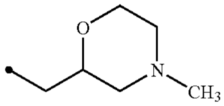 | MS m/z 625 $(M + H)^+$ |
| 15-53 | 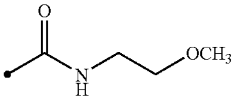 | 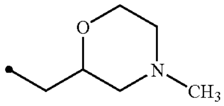 | MS m/z 607 $(M + H)^+$ |
| 15-54 | 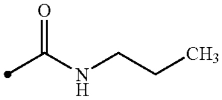 | 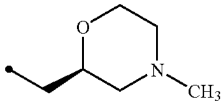 | MS m/z 591 $(M + H)^+$ |
| 15-55 | 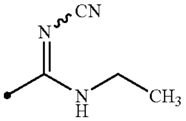 | 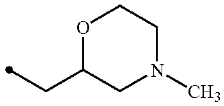 | MS m/z 601 $(M + H)^+$ |
| 15-56 | 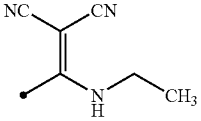 | 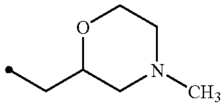 | MS m/z 625 $(M + H)^+$ |
| 15-57 | 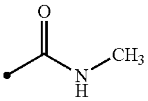 | 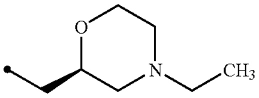 | MS m/z 577 $(M + H)^+$ |
| 15-58 | 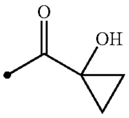 | 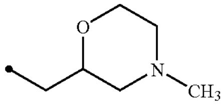 | MS m/z 590 $(M + H)^+$ |
| 15-59 | 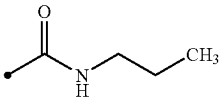 | 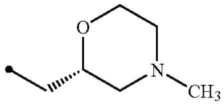 | MS m/z 591 $(M + H)^+$ |

TABLE 15-continued
| Compound Number | •—A—$R^3$ | •—$R^{Xc}$ | Spectrum Data |
|---|---|---|---|
| 15-60 | 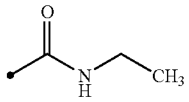 | 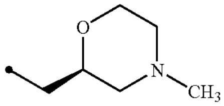 | MS m/z 591 $(M + H)^+$ |
| 15-61 | 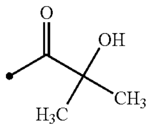 | 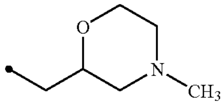 | MS m/z 592 $(M + H)^+$ |
| 15-62 | 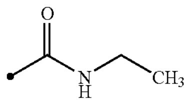 | 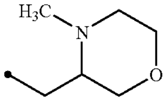 | MS m/z 577 $(M + H)^+$ |
| 15-63 | 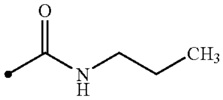 | 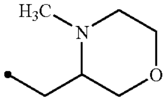 | MS m/z 591 $(M + H)^+$ |
| 15-64 | 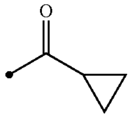 | 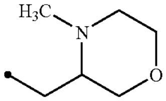 | MS m/z 574 $(M + H)^+$ |
| 15-65 | 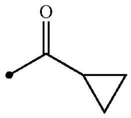 | 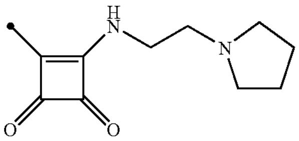 | MS m/z 653 $(M + H)^+$ |
| 15-66 | 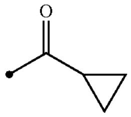 | 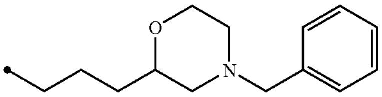 | MS m/z 678 $(M + H)^+$ |
| 15-67 | 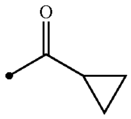 | 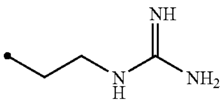 | MS m/z 546 $(M + H)^+$ |
| 15-68 | 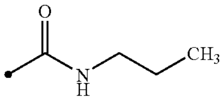 | •—H | MS m/z 464 $(M + H)^+$ |
| 15-69 | 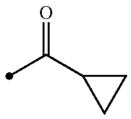 | 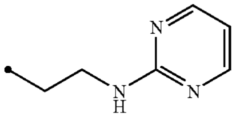 | MS m/z 582 $(M + H)^+$ |
| 15-70 | 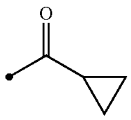 | 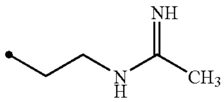 | MS m/z 545 $(M + H)^+$ |
| 15-71 | 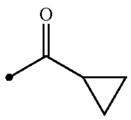 | 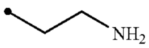 | MS m/z 504 $(M + H)^+$ |

TABLE 15-continued
| Compound Number | •—A—$R^3$ | •—$R^{Xc}$ | Spectrum Data |
|---|---|---|---|
| 15-72 | 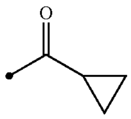 | 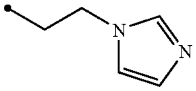 | MS m/z 555 $(M + H)^+$ |
| 15-73 | 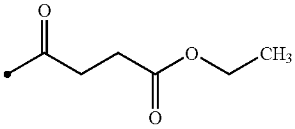 | 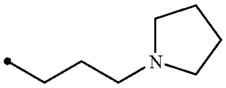 | MS m/z 618 $(M + H)^+$ |
| 15-74 | 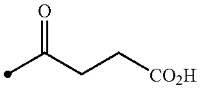 | 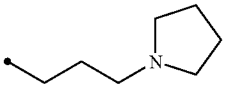 | MS m/z 604 $(M + H)^+$ |
| 15-75 | 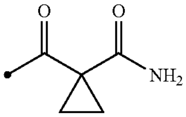 | 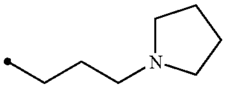 | MS m/z 615 $(M + H)^+$ |
| 15-76 | 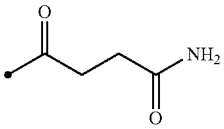 | 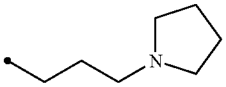 | MS m/z 603 $(M + H)^+$ |
| 15-77 | 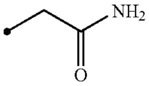 | 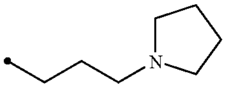 | MS m/z 561 $(M + H)^+$ |
| 15-78 | 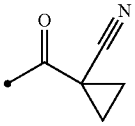 | 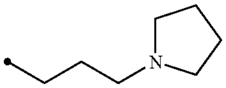 | MS m/z 597 $(M + H)^+$ |
| 15-79 | 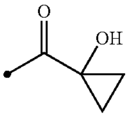 | 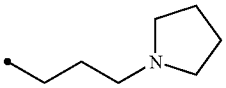 | MS m/z 588 $(M + H)^+$ |
| 15-80 | 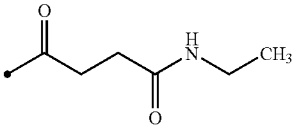 | 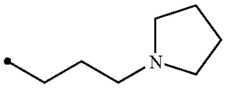 | MS m/z 631 $(M + H)^+$ |
| 15-81 | 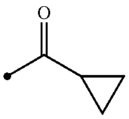 | 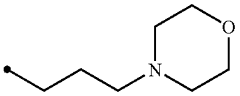 | MS m/z 588 $(M + H)^+$ |
| 15-82 | 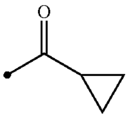 | 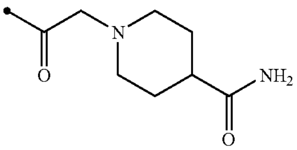 | MS m/z 629 $(M + H)^+$ |

TABLE 16
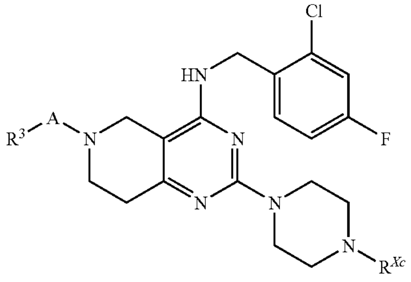
| Compound Number | •—A—$R^3$ | •—$R^{Xc}$ | Spectrum Data |
|---|---|---|---|
| 16-1 | 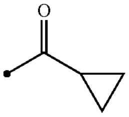 | 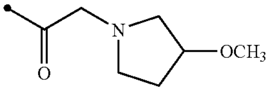 | MS m/z 586 $(M + H)^+$ |
| 16-2 | 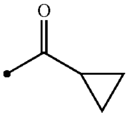 | 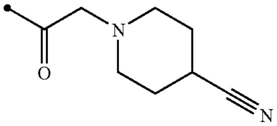 | MS m/z 595 $(M + H)^+$ |
| 16-3 | 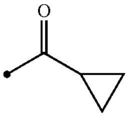 | 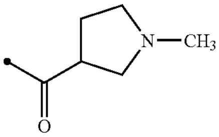 | MS m/z 556 $(M + H)^+$ |
| 16-4 | 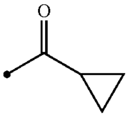 | 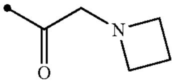 | MS m/z 542 $(M + H)^+$ |
| 16-5 | 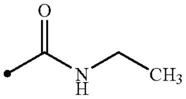 | 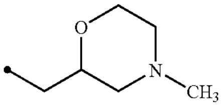 | MS m/z 561 $(M + H)^+$ |
| 16-6 | 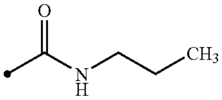 | 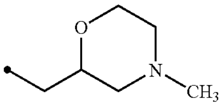 | MS m/z 575 $(M + H)^+$ |
| 16-7 | 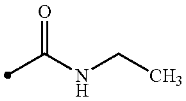 | 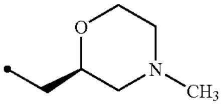 | MS m/z 561 $(M + H)^+$ |
| 16-8 | 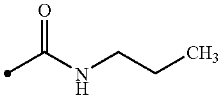 | 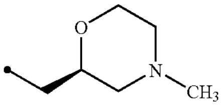 | MS m/z 575 $(M + H)^+$ |

TABLE 16-continued
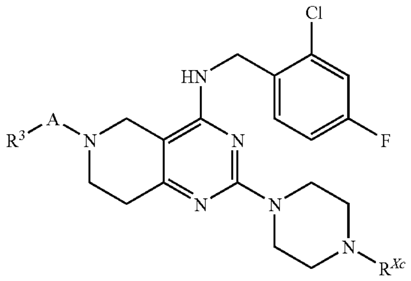
| Compound Number | •—A—$R^3$ | •—$R^{Xc}$ | Spectrum Data |
|---|---|---|---|
| 16-9 | 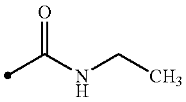 | 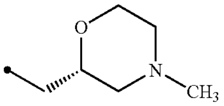 | MS m/z 561 $(M + H)^+$ |
| 16-10 | 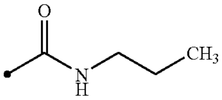 | 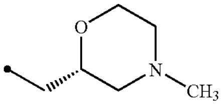 | MS m/z 575 $(M + H)^+$ |
| 16-11 | 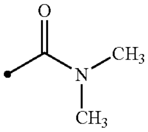 | 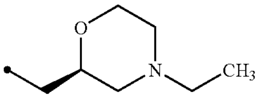 | MS m/z 561 $(M + H)^+$ |
| 16-12 | 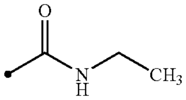 | 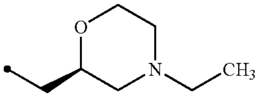 | MS m/z 575 $(M + H)^+$ |
| 16-13 | 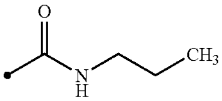 | 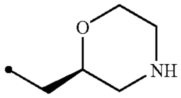 | MS m/z 561 $(M + H)^+$ |
| 16-14 | 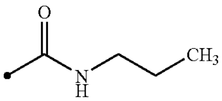 | 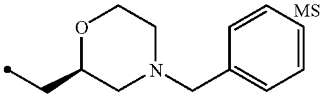 | MS m/z 651 $(M + H)^+$ |
| 16-15 | 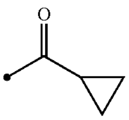 | 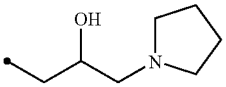 | MS m/z 572 $(M + H)^+$ |

TABLE 17
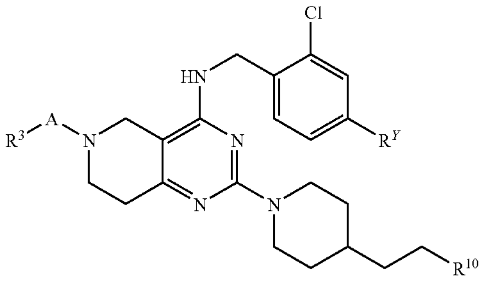
| Compound Number | •—A—$R^3$ | •—$R^{10}$ | •—$R^Y$ | Spectrum Data |
|---|---|---|---|---|
| 17-1 | 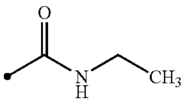 | 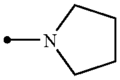 | Cl | MS m/z 560 $(M + H)^+$ |
| 17-2 | 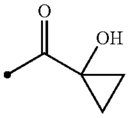 | 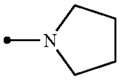 | Cl | MS m/z 573 $(M + H)^+$ |
| 17-3 | 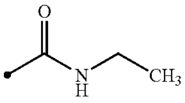 | 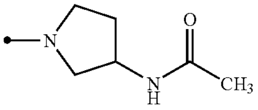 | Cl | MS m/z 617 $(M + H)^+$ |
| 17-4 | 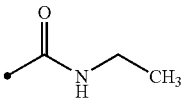 | 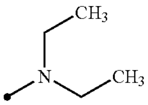 | Cl | MS m/z 562 $(M + H)^+$ |
| 17-5 | 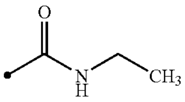 | 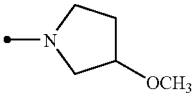 | Cl | MS m/z 590 $(M + H)^+$ |
| 17-6 | 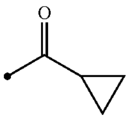 | 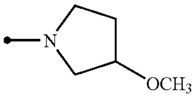 | Cl | MS m/z 587 $(M + H)^+$ |
| 17-7 | 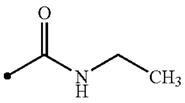 | 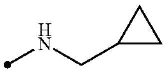 | Cl | MS m/z 560 $(M + H)^+$ |
| 17-8 | 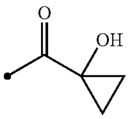 | 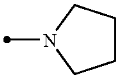 | F | MS m/z 557 $(M + H)^+$ |

TABLE 18
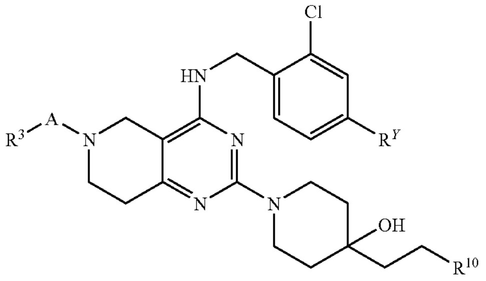
| Compound Number | •—A—$R^3$ | •—$R^{10}$ | •—$R^Y$ | Spectrum Data |
|---|---|---|---|---|
| 18-1 | 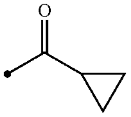 | 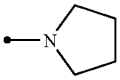 | Cl | MS m/z 573 $(M + H)^+$ |
| 18-2 | 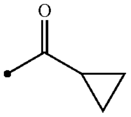 | 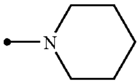 | Cl | MS m/z 587 $(M + H)^+$ |
| 18-3 | 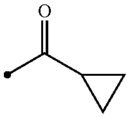 | 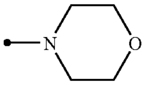 | Cl | MS m/z 589 $(M + H)^+$ |
| 18-4 | 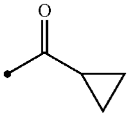 | 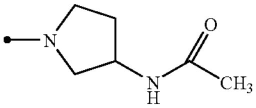 | Cl | MS m/z 630 $(M + H)^+$ |
| 18-5 | 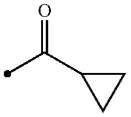 | 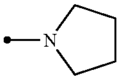 | F | MS m/z 557 $(M + H)^+$ |
| 18-6 | 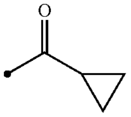 | 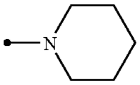 | F | MS m/z 571 $(M + H)^+$ |
| 18-7 | 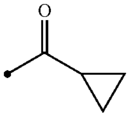 | 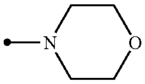 | F | MS m/z 573 $(M + H)^+$ |
| 18-8 | 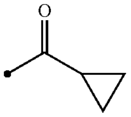 | 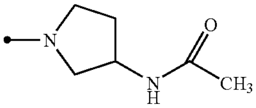 | F | MS m/z 614 $(M + H)^+$ |
| 18-9 | 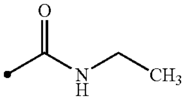 | 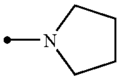 | Cl | MS m/z 576 $(M + H)^+$ |

TABLE 18-continued
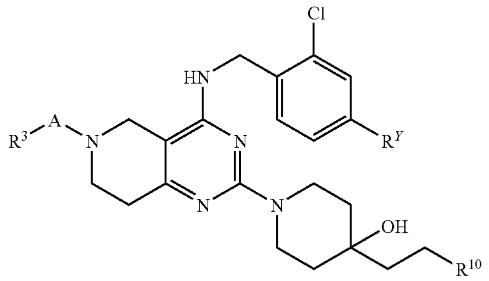
| Compound Number | •—A—$R^3$ | •—$R^{10}$ | •—$R^Y$ | Spectrum Data |
|---|---|---|---|---|
| 18-10 | 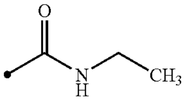 | 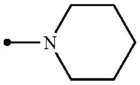 | Cl | MS m/z 590 $(M + H)^+$ |
| 18-11 | 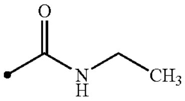 | 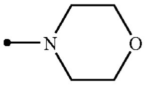 | Cl | MS m/z 592 $(M + H)^+$ |
| 18-12 | 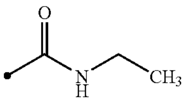 | 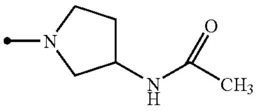 | Cl | MS m/z 633 $(M + H)^+$ |
| 18-13 | 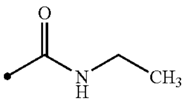 | 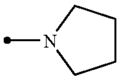 | F | MS m/z 560 $(M + H)^+$ |
| 18-14 | 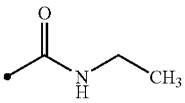 | 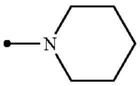 | F | MS m/z 574 $(M + H)^+$ |
| 18-15 | 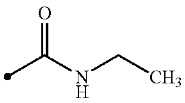 | 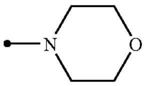 | F | MS m/z 576 $(M + H)^+$ |
| 18-16 | 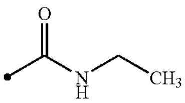 | 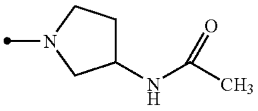 | F | MS m/z 617 $(M + H)^+$ |

TABLE 19
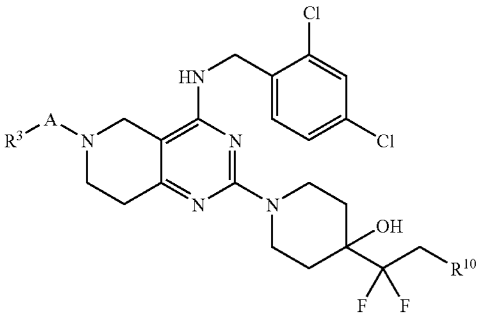
| Compound Number | •—A—$R^3$ | •—$R^{10}$ | Spectrum Data |
|---|---|---|---|
| 19-1 | 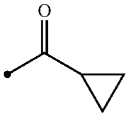 | 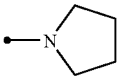 | MS m/z 609 $(M + H)^+$ |
| 19-2 | 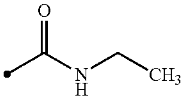 | 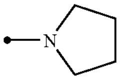 | MS m/z 612 $(M + H)^+$ |
TABLE 19-continued
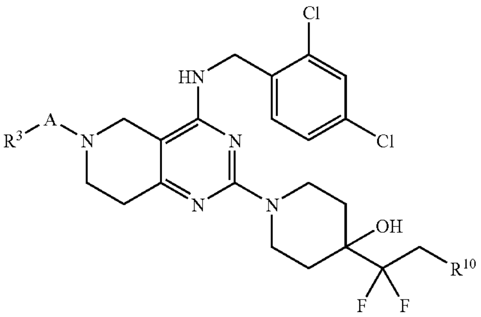
| Compound Number | •—A—$R^3$ | •—$R^{10}$ | Spectrum Data |
|---|---|---|---|
| 19-3 | 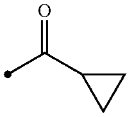 | 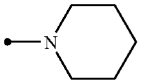 | MS m/z 623 $(M + H)^+$ |
| 19-4 | 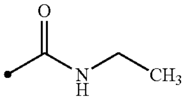 | 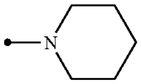 | MS m/z 626 $(M + H)^+$ |
TABLE 20
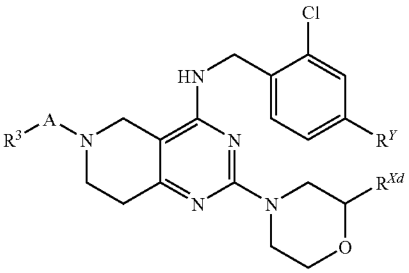
| Compound Number | •—A—$R^3$ | •—$R^{Xd}$ | •—$R^Y$ | Spectrum Data |
|---|---|---|---|---|
| 20-1 | 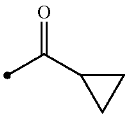 | 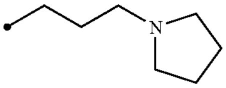 | Cl | MS m/z 573 $(M + H)^+$ |
| 20-2 | 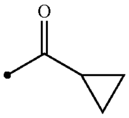 | 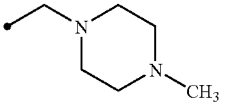 | F | MS m/z 558 $(M + H)^+$ |
| 20-3 | 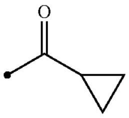 | 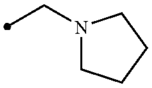 | F | MS m/z 529 $(M + H)^+$ |
| 20-4 | 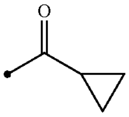 | 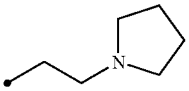 | F | MS m/z 543 $(M + H)^+$ |

TABLE 20-continued
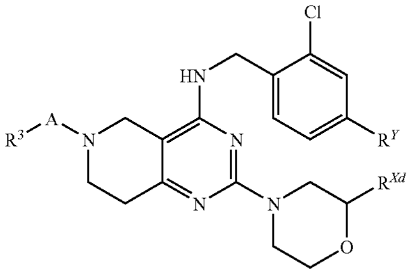
| Compound Number | •—A—$R^3$ | •—$R^{Xd}$ | •—$R^Y$ | Spectrum Data |
|---|---|---|---|---|
| 20-5 | 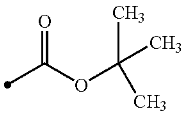 | 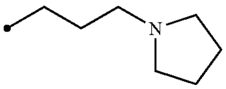 | Cl | MS m/z 605 $(M + H)^+$ |
| 20-6 | 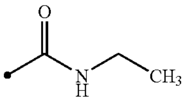 | 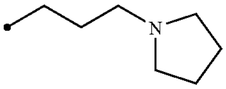 | Cl | MS m/z 576 $(M + H)^+$ |
| 20-7 | 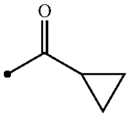 | 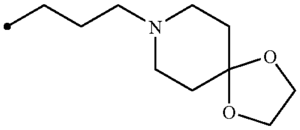 | Cl | MS m/z 645 $(M + H)^+$ |
| 20-8 | 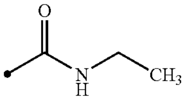 | 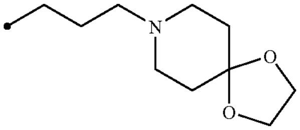 | Cl | MS m/z 648 $(M + H)^+$ |
| 20-10 | 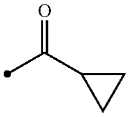 | 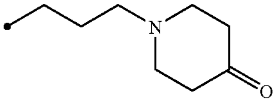 | Cl | MS m/z 601 $(M + H)^+$ |
| 20-11 | 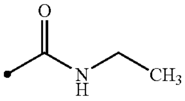 | 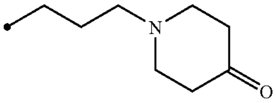 | Cl | MS m/z 604 $(M + H)^+$ |
| 20-12 | 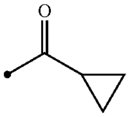 | 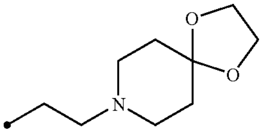 | Cl | MS m/z 631 $(M + H)^+$ |
| 20-13 | 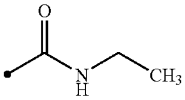 | 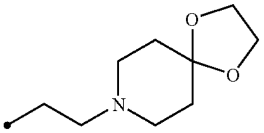 | Cl | MS m/z 634 $(M + H)^+$ |

TABLE 20-continued
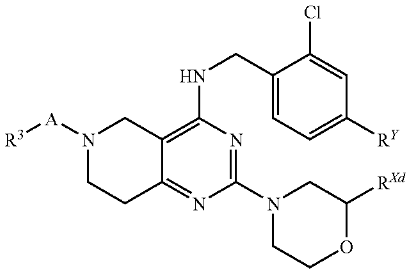
| Compound Number | •—A—$R^3$ | •—$R^{Xd}$ | •—$R^Y$ | Spectrum Data |
|---|---|---|---|---|
| 20-14 | 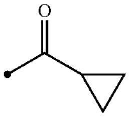 | 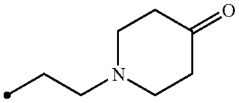 | Cl | MS m/z 587 $(M + H)^+$ |
| 20-15 | 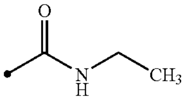 | 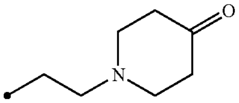 | Cl | MS m/z 590 $(M + H)^+$ |
| 20-16 | 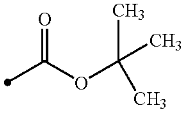 | 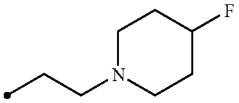 | Cl | MS m/z 623 $(M + H)^+$ |
| 20-17 | 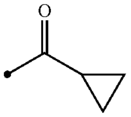 | 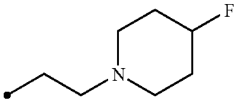 | Cl | MS m/z 591 $(M + H)^+$ |
| 20-18 | 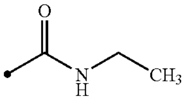 | 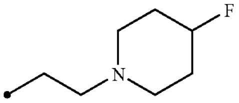 | Cl | MS m/z 594 $(M + H)^+$ |
| 20-19 | 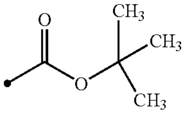 | 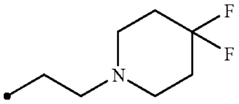 | Cl | MS m/z 641 $(M + H)^+$ |
| 20-20 | 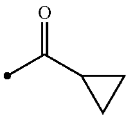 | 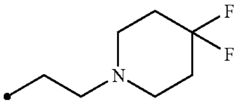 | Cl | MS m/z 609 $(M + H)^+$ |
| 20-21 | 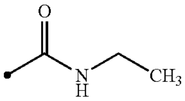 | 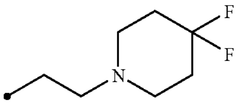 | Cl | MS m/z 612 $(M + H)^+$ |

TABLE 21
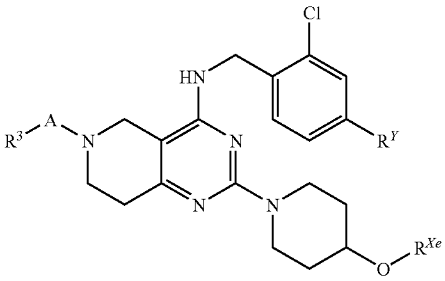
| Compound Number | •—A—$R^3$ | •—$R^{Xe}$ | •—$R^Y$ | Spectrum Data |
|---|---|---|---|---|
| 21-1 | 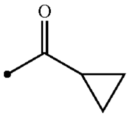 | 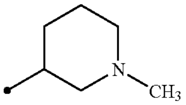 | Cl | MS m/z 573 $(M + H)^+$ |
| 21-2 | 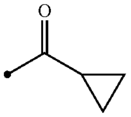 | 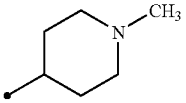 | Cl | MS m/z 573 $(M + H)^+$ |
| 21-3 | 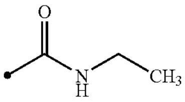 | 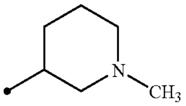 | Cl | MS m/z 576 $(M + H)^+$ |
| 21-4 | 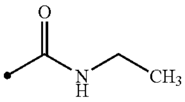 | 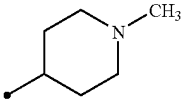 | Cl | MS m/z 576 $(M + H)^+$ |
TABLE 22
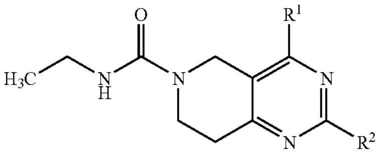
| Compound Number | •—$R^1$ | •—$R^2$ | Spectrum Data |
|---|---|---|---|
| 22-1 | 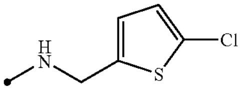 | 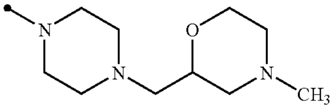 | MS m/z 549 $(M + H)^+$ |
| 22-2 | 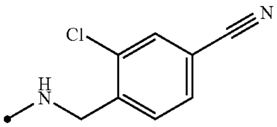 | 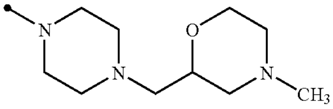 | MS m/z 568 $(M + H)^+$ |
| 22-3 | 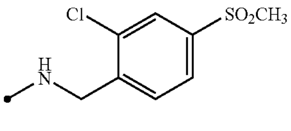 | 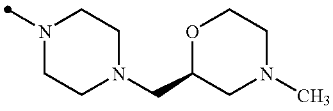 | MS m/z 621 $(M + H)^+$ |

TABLE 22-continued
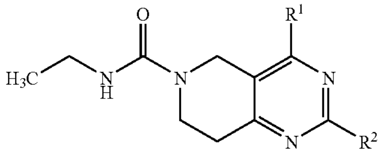
| Compound Number | •—$R^1$ | •—$R^2$ | Spectrum Data |
|---|---|---|---|
| 22-4 | 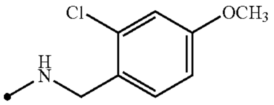 | 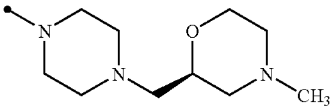 | MS m/z 573 $(M + H)^+$ |
TABLE 23
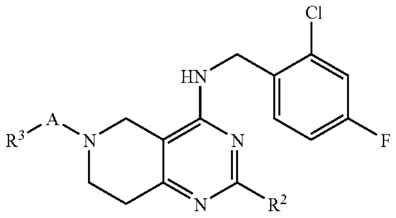
| Compound Number | •—A—$R^3$ | •—$R^2$ | Spectrum Data |
|---|---|---|---|
| 23-1 | 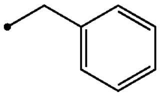 | 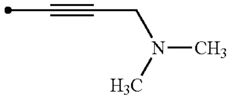 | MS m/z 464 $(M + H)^+$ |
| 23-2 | 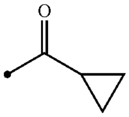 | 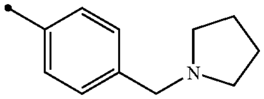 | MS m/z 520 $(M + H)^+$ |
| 23-3 | 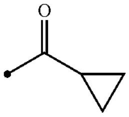 | 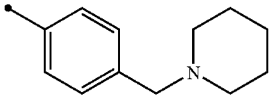 | MS m/z 534 $(M + H)^+$ |
| 23-4 | 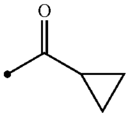 | 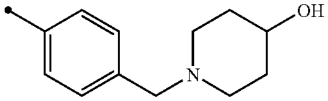 | MS m/z 550 $(M + H)^+$ |
| 23-5 | 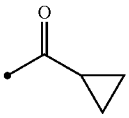 | 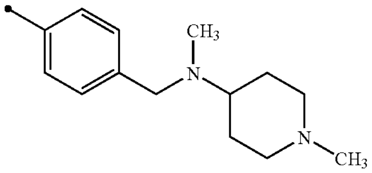 | MS m/z 577 $(M + H)^+$ |

TABLE 24
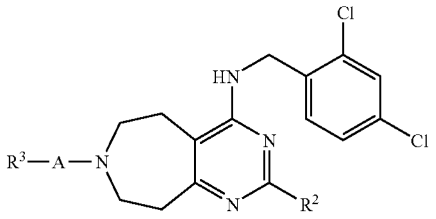
| Compound Number | •—A—$R^3$ | •—$R^2$ | Spectrum Data |
|---|---|---|---|
| 24-1 | 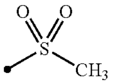 | 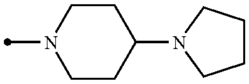 | MS m/z 553 $(M + H)^+$ |
| 24-2 | 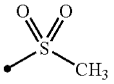 | 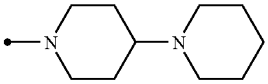 | MS m/z 567 $(M + H)^+$ |
| 24-3 | 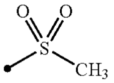 | 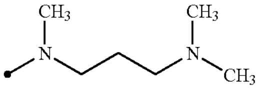 | MS m/z 515 $(M + H)^+$ |
| 24-4 | 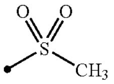 | 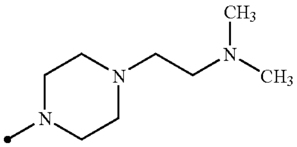 | MS m/z 556 $(M + H)^+$ |
| 24-5 | 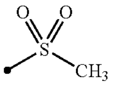 | 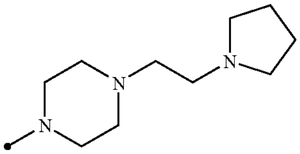 | MS m/z 582 $(M + H)^+$ |
| 24-6 | 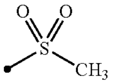 | 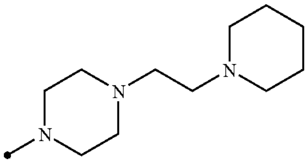 | MS m/z 596 $(M + H)^+$ |
| 24-7 | 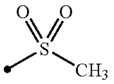 | 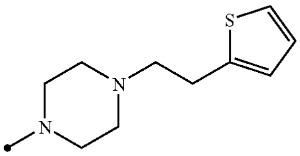 | MS m/z 595 $(M + H)^+$ |
| 24-8 | 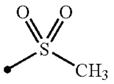 | 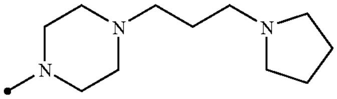 | MS m/z 596 $(M + H)^+$ |
| 24-9 | 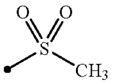 | 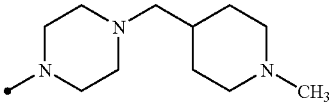 | MS m/z 596 $(M + H)^+$ |

TABLE 24-continued
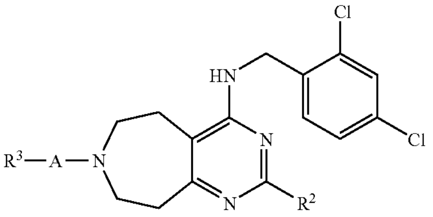
| Compound Number | •—A—$R^3$ | •—$R^2$ | Spectrum Data |
|---|---|---|---|
| 24-10 | 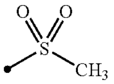 | 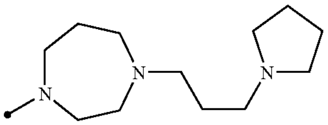 | MS m/z 610 $(M + H)^+$ |
| 24-11 | 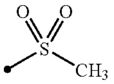 | 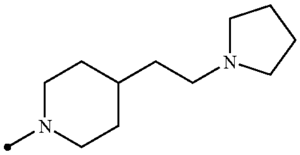 | MS m/z 581 $(M + H)^+$ |
| 24-12 | 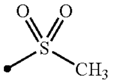 | 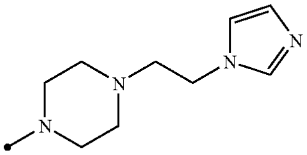 | MS m/z 579 $(M + H)^+$ |
| 24-13 | 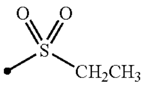 | 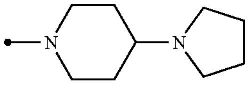 | MS m/z 567 $(M + H)^+$ |
| 24-14 | 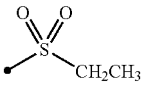 | 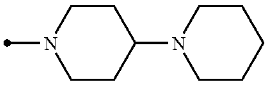 | MS m/z 581 $(M + H)^+$ |
| 24-15 | 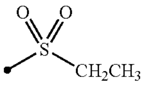 | 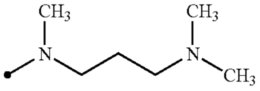 | MS m/z 529 $(M + H)^+$ |
| 24-16 | 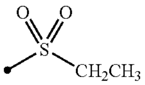 | 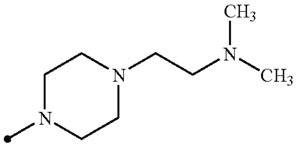 | MS m/z 570 $(M + H)^+$ |
| 24-17 | 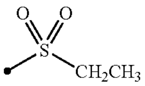 | 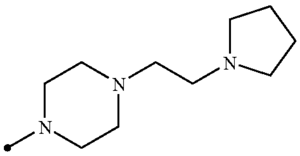 | MS m/z 596 $(M + H)^+$ |
| 24-18 | 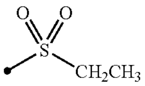 | 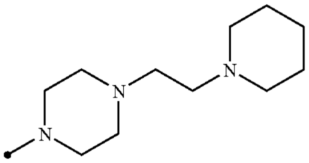 | MS m/z 610 $(M + H)^+$ |

TABLE 24-continued
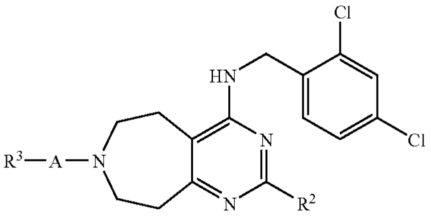
| Compound Number | •—A—$R^3$ | •—$R^2$ | Spectrum Data |
|---|---|---|---|
| 24-19 | 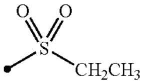 | 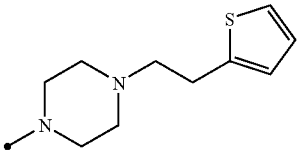 | MS m/z 609 $(M + H)^+$ |
| 24-20 | 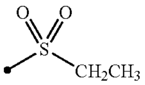 | 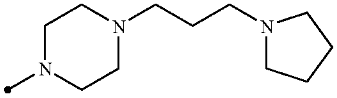 | MS m/z 610 $(M + H)^+$ |
| 24-21 | 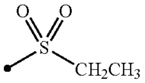 | 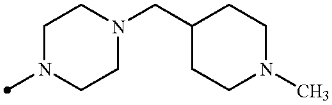 | MS m/z 610 $(M + H)^+$ |
| 24-22 | 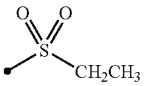 | 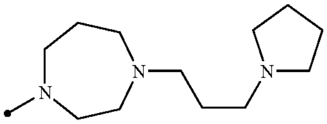 | MS m/z 624 $(M + H)^+$ |
| 24-23 | 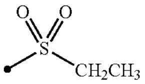 | 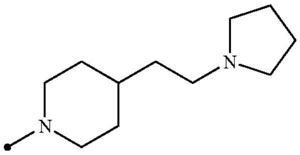 | MS m/z 595 $(M + H)^+$ |
| 24-24 | 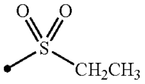 | 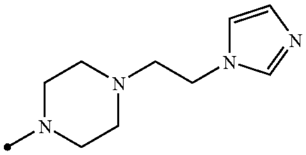 | MS m/z 593 $(M + H)^+$ |
| 24-25 | 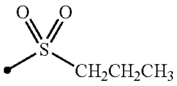 | 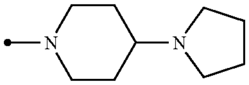 | MS m/z 581 $(M + H)^+$ |
| 24-26 | 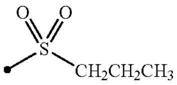 | 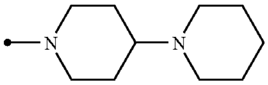 | MS m/z 595 $(M + H)^+$ |
| 24-27 | 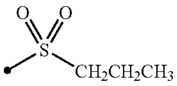 | 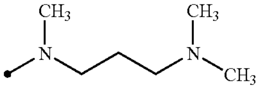 | MS m/z 543 $(M + H)^+$ |
| 24-28 | 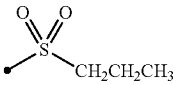 | 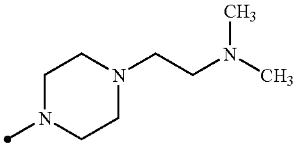 | MS m/z 584 $(M + H)^+$ |

TABLE 24-continued
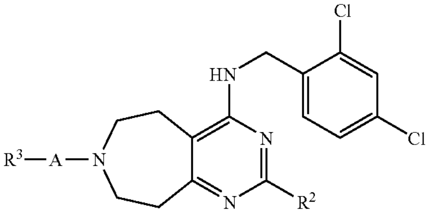
| Compound Number | •—A—$R^3$ | •—$R^2$ | Spectrum Data |
|---|---|---|---|
| 24-29 | 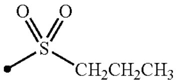 | 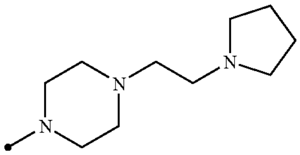 | MS m/z 610 $(M + H)^+$ |
| 24-30 | 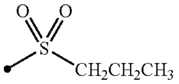 | 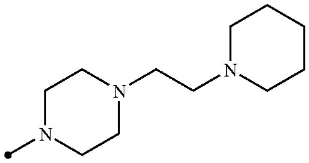 | MS m/z 624 $(M + H)^+$ |
| 24-31 | 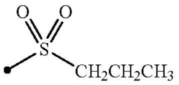 | 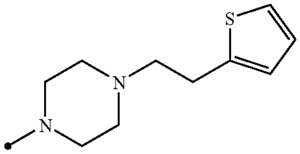 | MS m/z 623 $(M + H)^+$ |
| 24-32 | 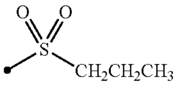 | 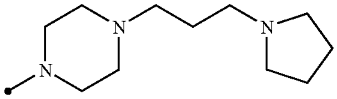 | MS m/z 624 $(M + H)^+$ |
| 24-33 | 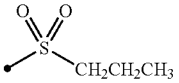 | 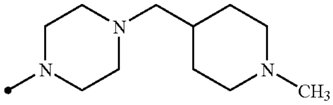 | MS m/z 624 $(M + H)^+$ |
| 24-34 | 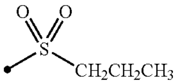 | 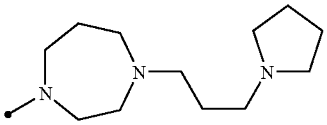 | MS m/z 638 $(M + H)^+$ |
| 24-35 | 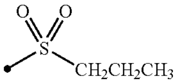 | 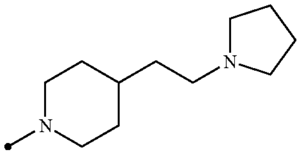 | MS m/z 609 $(M + H)^+$ |
| 24-36 | 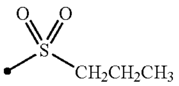 | 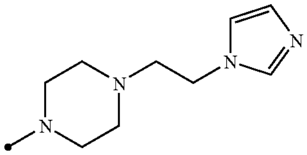 | MS m/z 607 $(M + H)^+$ |

TABLE 24-continued
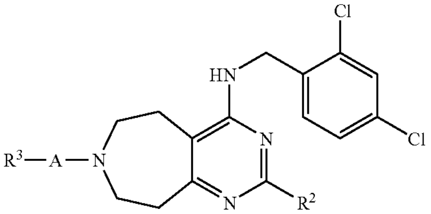
| Compound Number | •—A—$R^3$ | •—$R^2$ | Spectrum Data |
|---|---|---|---|
| 24-37 | 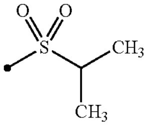 | 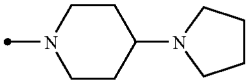 | MS m/z 581 $(M + H)^+$ |
| 24-38 | 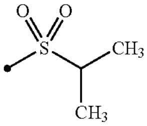 | 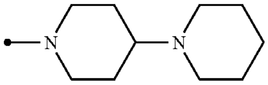 | MS m/z 595 $(M + H)^+$ |
| 24-39 | 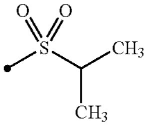 | 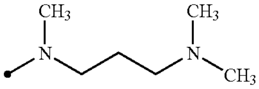 | MS m/z 543 $(M + H)^+$ |
| 24-40 | 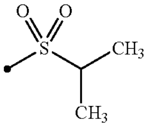 | 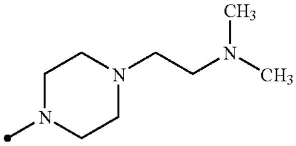 | MS m/z 584 $(M + H)^+$ |
| 24-41 | 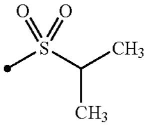 | 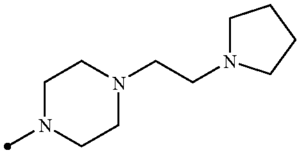 | MS m/z 610 $(M + H)^+$ |
| 24-42 | 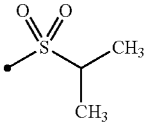 | 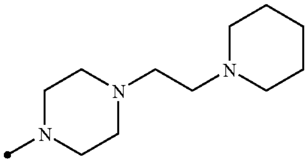 | MS m/z 624 $(M + H)^+$ |
| 24-43 | 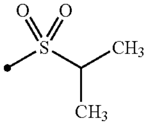 | 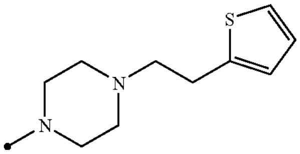 | MS m/z 623 $(M + H)^+$ |
| 24-44 | 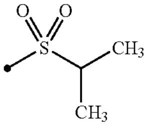 | 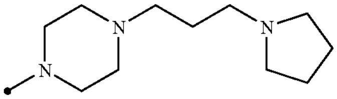 | MS m/z 624 $(M + H)^+$ |

TABLE 24-continued
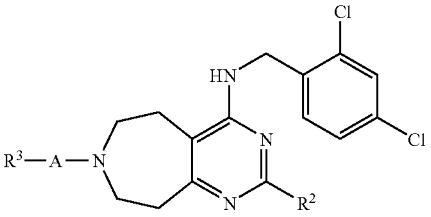
| Compound Number | •—A—$R^3$ | •—$R^2$ | Spectrum Data |
|---|---|---|---|
| 24-45 | 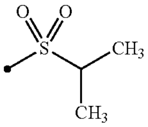 | 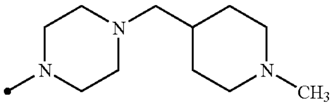 | MS m/z 624 $(M + H)^+$ |
| 24-46 | 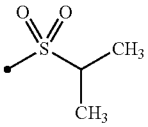 | 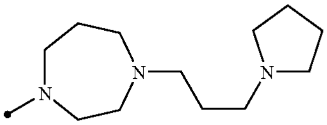 | MS m/z 638 $(M + H)^+$ |
| 24-47 | 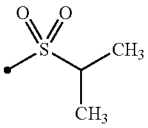 | 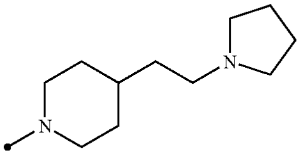 | MS m/z 609 $(M + H)^+$ |
| 24-48 | 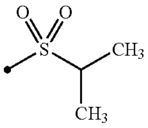 | 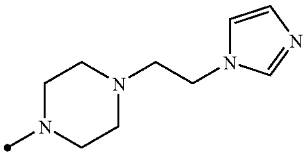 | MS m/z 607 $(M + H)^+$ |
| 24-49 | 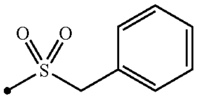 | 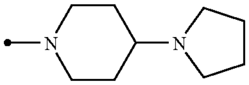 | MS m/z 629 $(M + H)^+$ |
| 24-50 | 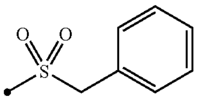 | 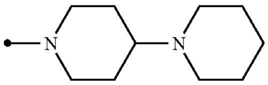 | MS m/z 643 $(M + H)^+$ |
| 24-51 | 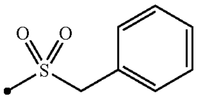 | 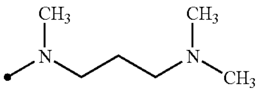 | MS m/z 591 $(M + H)^+$ |
| 24-52 | 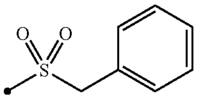 | 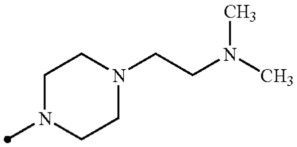 | MS m/z 632 $(M + H)^+$ |
| 24-53 | 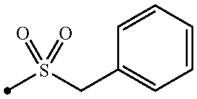 | 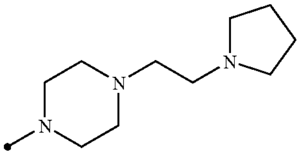 | MS m/z 658 $(M + H)^+$ |

TABLE 24-continued
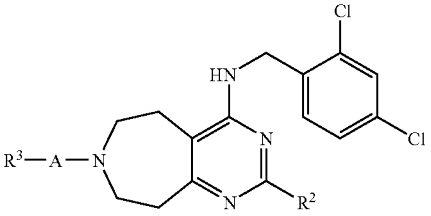
| Compound Number | •—A—$R^3$ | •—$R^2$ | Spectrum Data |
|---|---|---|---|
| 24-54 | 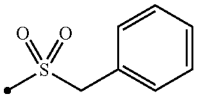 | 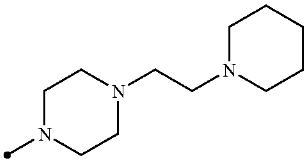 | MS m/z 672 $(M + H)^+$ |
| 24-55 | 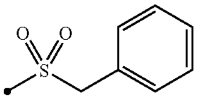 | 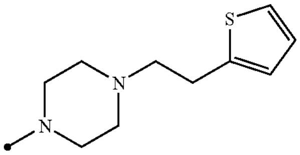 | MS m/z 671 $(M + H)^+$ |
| 24-56 | 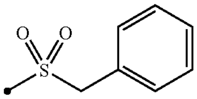 | 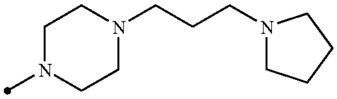 | MS m/z 672 $(M + H)^+$ |
| 24-57 | 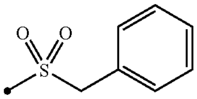 | 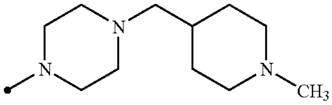 | MS m/z 672 $(M + H)^+$ |
| 24-58 | 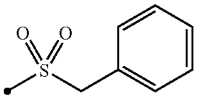 | 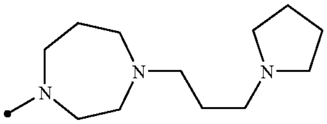 | MS m/z 686 $(M + H)^+$ |
| 24-59 | 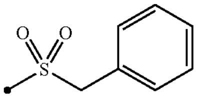 | 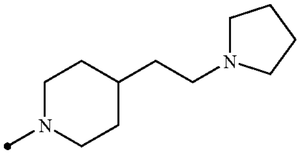 | MS m/z 657 $(M + H)^+$ |
| 24-60 | 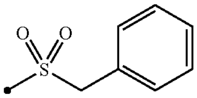 | 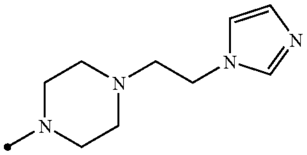 | MS m/z 655 $(M + H)^+$ |
| 24-61 | 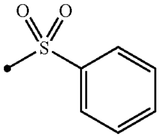 | 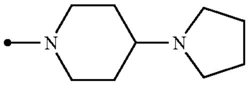 | MS m/z 615 $(M + H)^+$ |

TABLE 24-continued
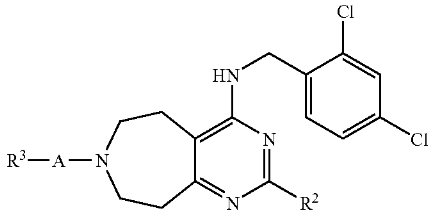
| Compound Number | •—A—$R^3$ | •—$R^2$ | Spectrum Data |
|---|---|---|---|
| 24-62 | 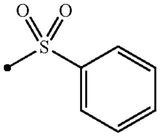 | 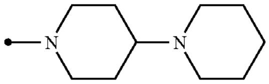 | MS m/z 629 (M + H)$^+$ |
| 24-63 | 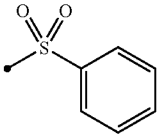 | 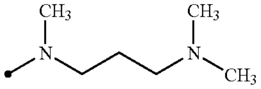 | MS m/z 577 (M + H)$^+$ |
| 24-64 | 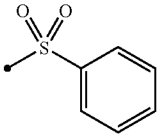 | 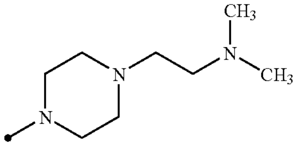 | MS m/z 618 (M + H)$^+$ |
| 24-65 | 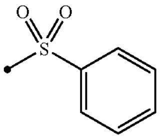 | 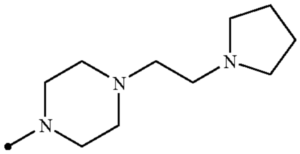 | MS m/z 644 (M + H)$^+$ |
| 24-66 | 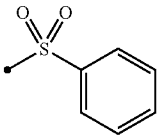 | 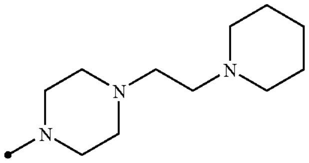 | MS m/z 658 (M + H)$^+$ |
| 24-67 | 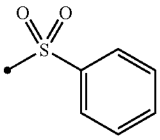 | 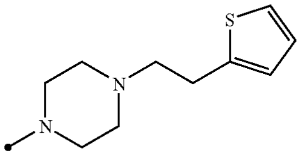 | MS m/z 657 (M + H)$^+$ |
| 24-68 | 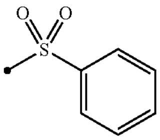 | 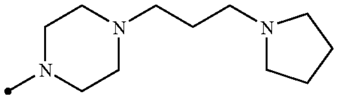 | MS m/z 658 (M + H)$^+$ |
| 24-69 | 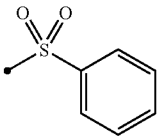 | 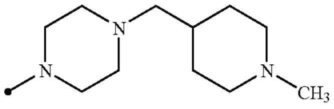 | MS m/z 658 (M + H)$^+$ |

TABLE 24-continued
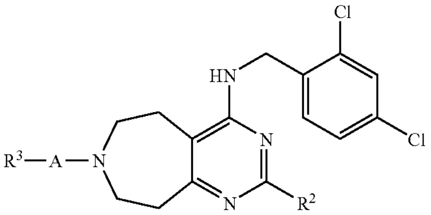
| Compound Number | •—A—$R^3$ | •—$R^2$ | Spectrum Data |
|---|---|---|---|
| 24-70 | 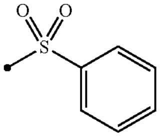 | 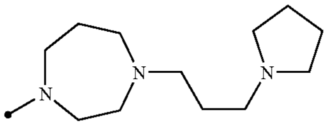 | MS m/z 672 $(M + H)^+$ |
| 24-71 | 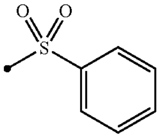 | 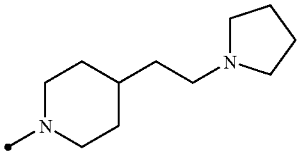 | MS m/z 643 $(M + H)^+$ |
| 24-72 | 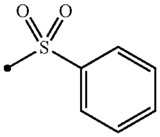 | 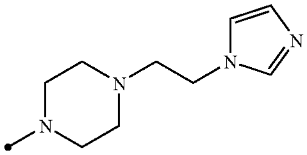 | MS m/z 641 $(M + H)^+$ |
| 24-73 | 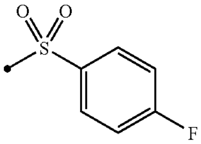 | 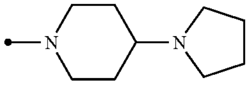 | MS m/z 633 $(M + H)^+$ |
| 24-74 | 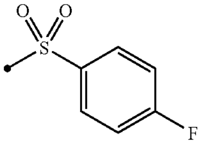 | 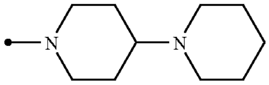 | MS m/z 647 $(M + H)^+$ |
| 24-75 | 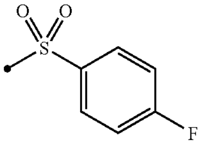 | 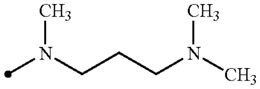 | MS m/z 595 $(M + H)^+$ |
| 24-76 | 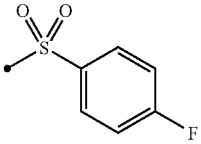 | 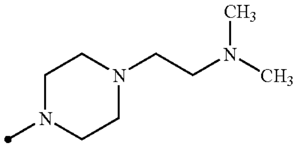 | MS m/z 636 $(M + H)^+$ |
| 24-77 | 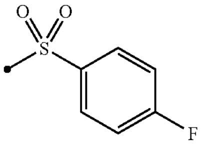 | 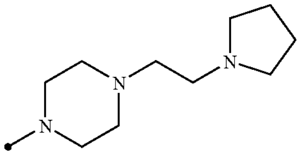 | MS m/z 662 $(M + H)^+$ |

TABLE 24-continued
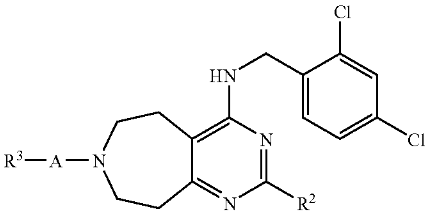
| Compound Number | •—A—$R^3$ | •—$R^2$ | Spectrum Data |
| --- | --- | --- | --- |
| 24-78 | 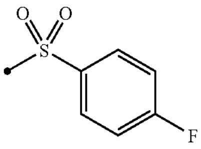 | 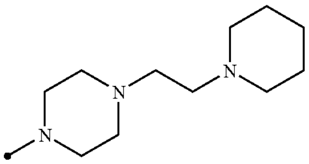 | MS m/z 676 $(M + H)^+$ |
| 24-79 | 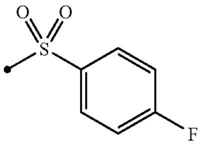 | 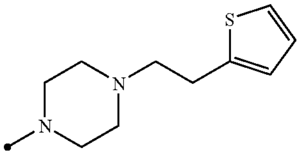 | MS m/z 675 $(M + H)^+$ |
| 24-80 | 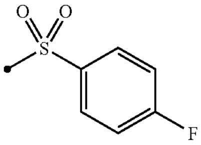 | 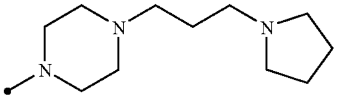 | MS m/z 676 $(M + H)^+$ |
| 24-81 | 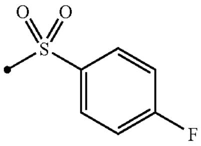 | 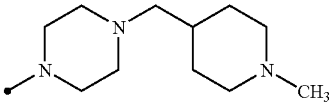 | MS m/z 676 $(M + H)^+$ |
| 24-82 | 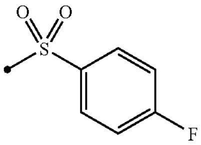 | 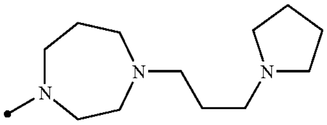 | MS m/z 690 $(M + H)^+$ |
| 24-83 | 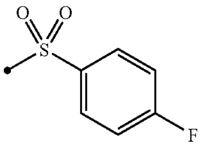 | 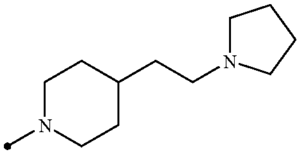 | MS m/z 661 $(M + H)^+$ |
| 24-84 | 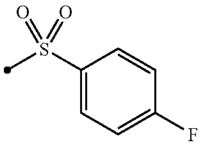 | 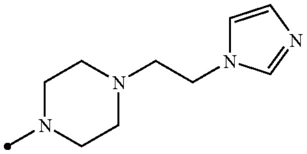 | MS m/z 659 $(M + H)^+$ |
| 24-85 | 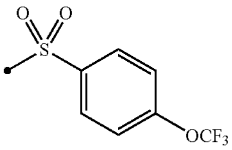 | 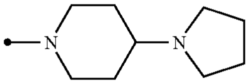 | MS m/z 699 $(M + H)^+$ |

TABLE 24-continued
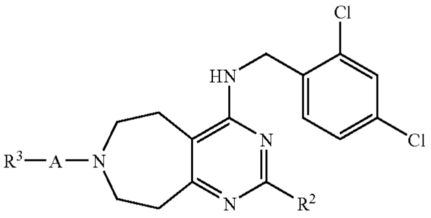
| Compound Number | •—A—$R^3$ | •—$R^2$ | Spectrum Data |
|---|---|---|---|
| 24-86 | 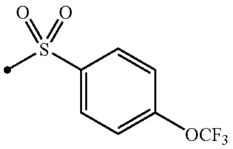 | 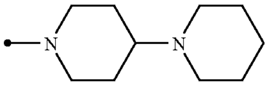 | MS m/z 713 $(M + H)^+$ |
| 24-87 | 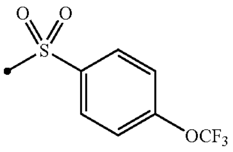 | 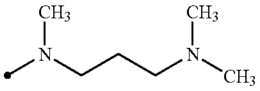 | MS m/z 661 $(M + H)^+$ |
| 24-88 | 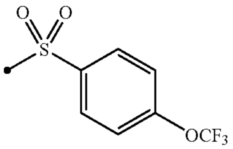 | 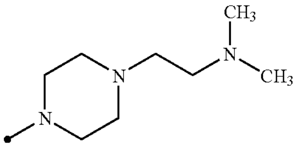 | MS m/z 702 $(M + H)^+$ |
| 24-89 | 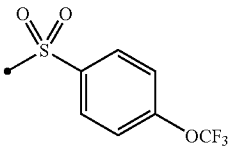 | 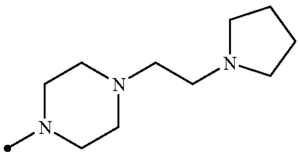 | MS m/z 728 $(M + H)^+$ |
| 24-90 | 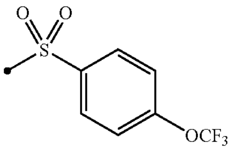 | 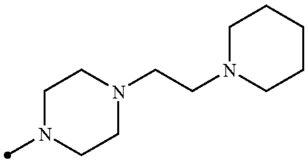 | MS m/z 742 $(M + H)^+$ |
| 24-91 | 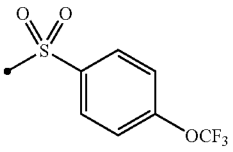 | 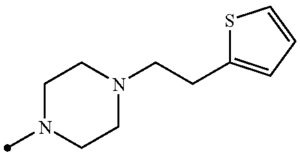 | MS m/z 741 $(M + H)^+$ |
| 24-92 | 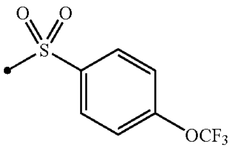 | 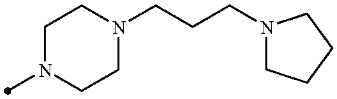 | MS m/z 742 $(M + H)^+$ |
| 24-93 | 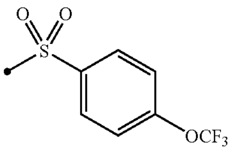 | 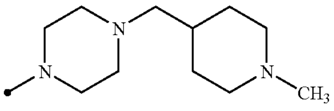 | MS m/z 742 $(M + H)^+$ |

TABLE 24-continued
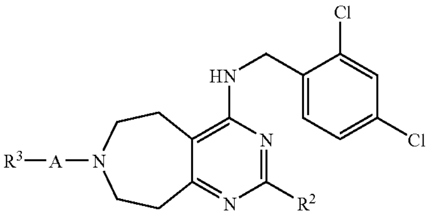
| Compound Number | •—A—$R^3$ | •—$R^2$ | Spectrum Data |
|---|---|---|---|
| 24-94 | 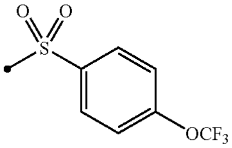 | 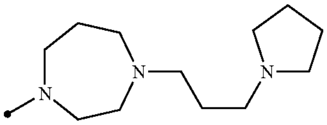 | MS m/z 756 $(M + H)^+$ |
| 24-95 | 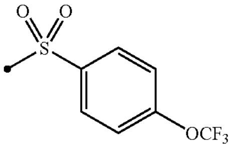 | 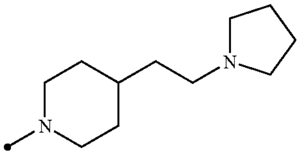 | MS m/z 727 $(M + H)^+$ |
| 24-96 | 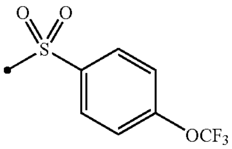 | 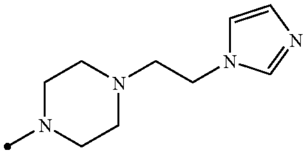 | MS m/z 725 $(M + H)^+$ |
| 24-97 | 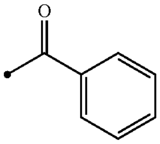 | 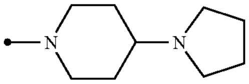 | MS m/z 579 $(M + H)^+$ |
| 24-98 | 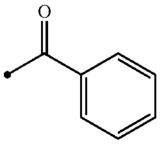 | 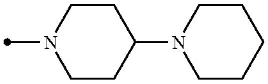 | MS m/z 593 $(M + H)^+$ |
| 24-99 | 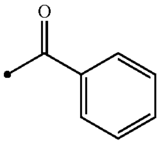 | 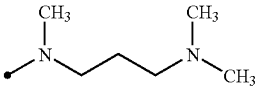 | MS m/z 541 $(M + H)^+$ |
| 24-100 | 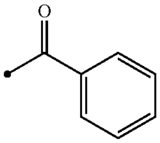 | 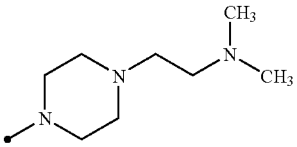 | MS m/z 582 $(M + H)^+$ |
| 24-101 | 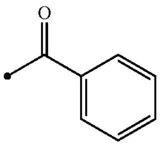 | 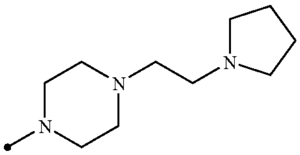 | MS m/z 608 $(M + H)^+$ |

TABLE 24-continued
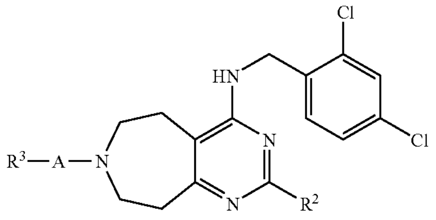
| Compound Number | •—A—$R^3$ | •—$R^2$ | Spectrum Data |
|---|---|---|---|
| 24-102 | 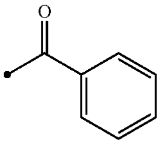 | 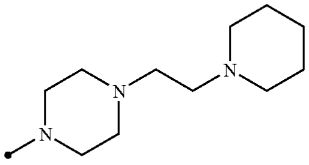 | MS m/z 622 $(M + H)^+$ |
| 24-103 | 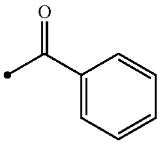 | 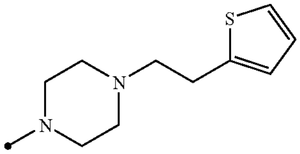 | MS m/z 621 $(M + H)^+$ |
| 24-104 | 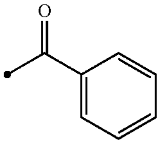 | 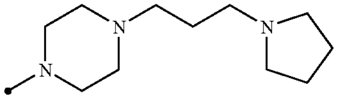 | MS m/z 622 $(M + H)^+$ |
| 24-105 | 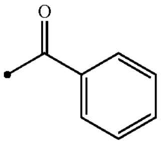 | 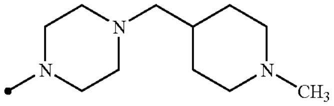 | MS m/z 622 $(M + H)^+$ |
| 24-106 | 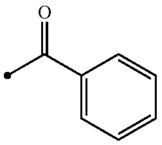 | 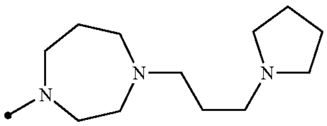 | MS m/z 636 $(M + H)^+$ |
| 24-107 | 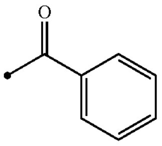 | 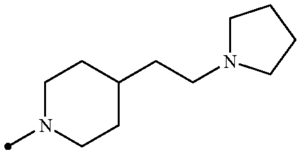 | MS m/z 607 $(M + H)^+$ |
| 24-108 | 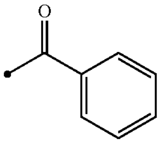 | 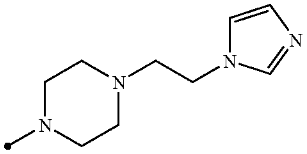 | MS m/z 605 $(M + H)^+$ |
| 24-109 | 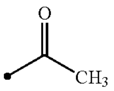 | 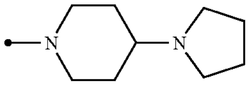 | MS m/z 517 $(M + H)^+$ |

TABLE 24-continued
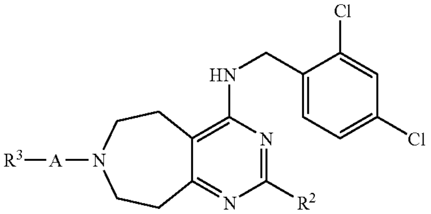
| Compound Number | •—A—R$^3$ | •—R$^2$ | Spectrum Data |
|---|---|---|---|
| 24-110 | 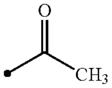 | 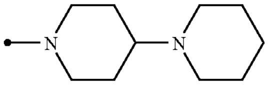 | MS m/z 531 $(M + H)^+$ |
| 24-111 | 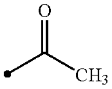 | 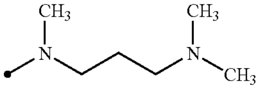 | MS m/z 479 $(M + H)^+$ |
| 24-112 | 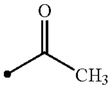 | 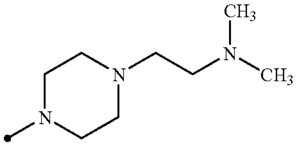 | MS m/z 520 $(M + H)^+$ |
| 24-113 | 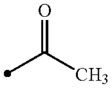 | 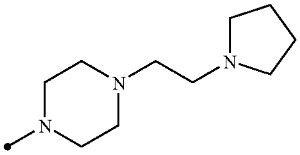 | MS m/z 546 $(M + H)^+$ |
| 24-114 | 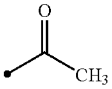 | 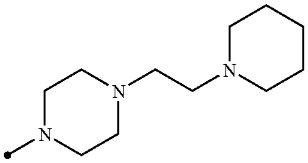 | MS m/z 560 $(M + H)^+$ |
| 24-115 | 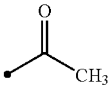 | 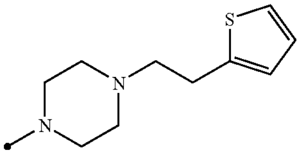 | MS m/z 559 $(M + H)^+$ |
| 24-116 | 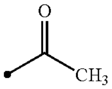 | 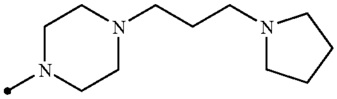 | MS m/z 560 $(M + H)^+$ |
| 24-117 | 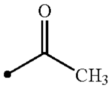 | 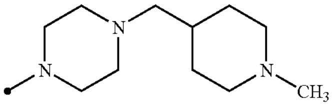 | MS m/z 560 $(M + H)^+$ |
| 24-118 | 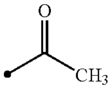 | 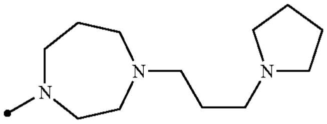 | MS m/z 574 $(M + H)^+$ |

TABLE 24-continued
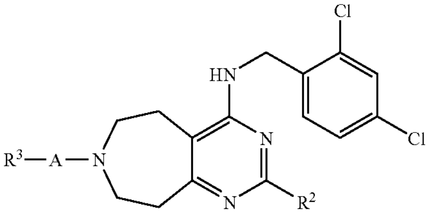
| Compound Number | •—A—$R^3$ | •—$R^2$ | Spectrum Data |
|---|---|---|---|
| 24-119 | 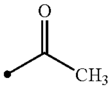 | 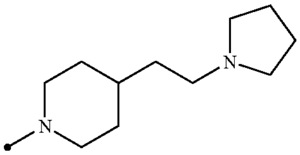 | MS m/z 545 $(M + H)^+$ |
| 24-120 | 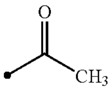 | 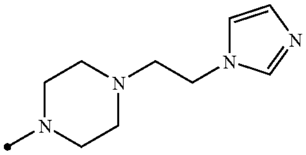 | MS m/z 543 $(M + H)^+$ |
| 24-121 | 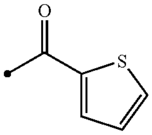 | 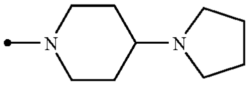 | MS m/z 585 $(M + H)^+$ |
| 24-122 | 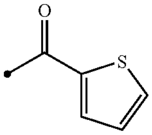 | 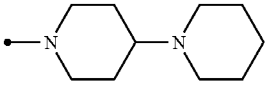 | MS m/z 599 $(M + H)^+$ |
| 24-123 | 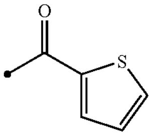 | 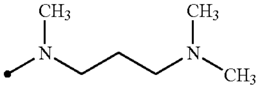 | MS m/z 547 $(M + H)^+$ |
| 24-124 | 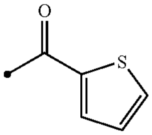 | 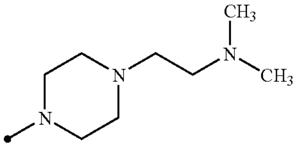 | MS m/z 588 $(M + H)^+$ |
| 24-125 | 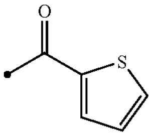 | 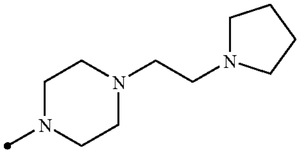 | MS m/z 614 $(M + H)^+$ |
| 24-126 | 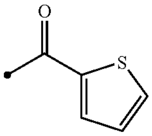 | 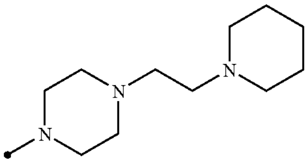 | MS m/z 628 $(M + H)^+$ |

TABLE 24-continued
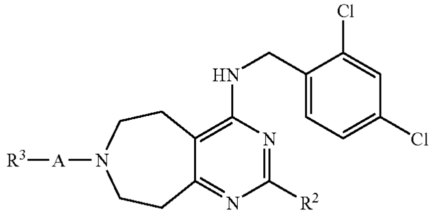
| Compound Number | •—A—$R^3$ | •—$R^2$ | Spectrum Data |
|---|---|---|---|
| 24-127 | 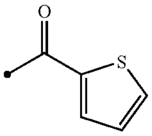 | 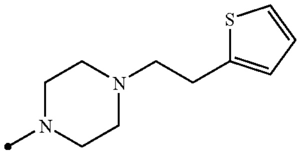 | MS m/z 627 $(M + H)^+$ |
| 24-128 | 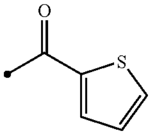 | 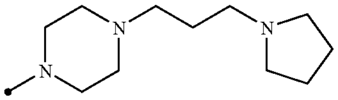 | MS m/z 628 $(M + H)^+$ |
| 24-129 | 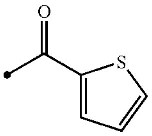 | 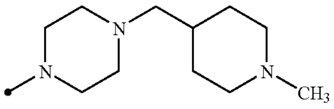 | MS m/z 628 $(M + H)^+$ |
| 24-130 | 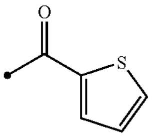 | 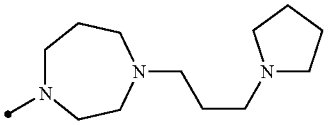 | MS m/z 642 $(M + H)^+$ |
| 24-131 | 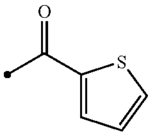 | 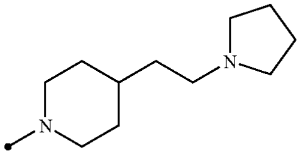 | MS m/z 613 $(M + H)^+$ |
| 24-132 | 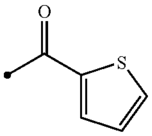 | 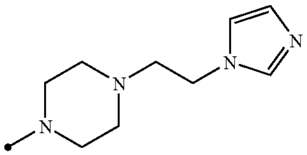 | MS m/z 611 $(M + H)^+$ |
| 24-133 | 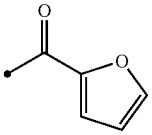 | 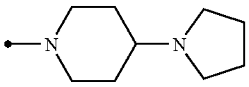 | MS m/z 569 $(M + H)^+$ |
| 24-134 | 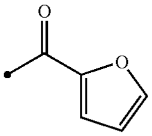 | 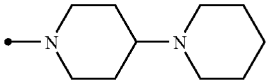 | MS m/z 583 $(M + H)^+$ |

TABLE 24-continued
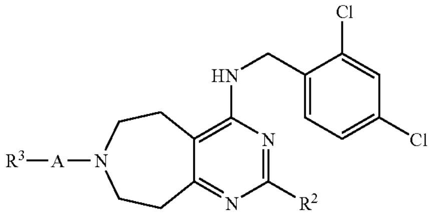
| Compound Number | •—A—$R^3$ | •—$R^2$ | Spectrum Data |
|---|---|---|---|
| 24-135 | 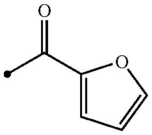 | 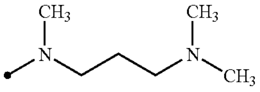 | MS m/z 531 $(M + H)^+$ |
| 24-136 | 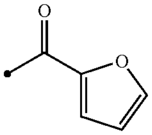 | 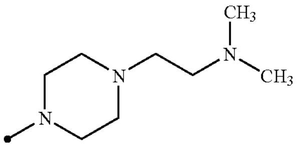 | MS m/z 572 $(M + H)^+$ |
| 24-137 | 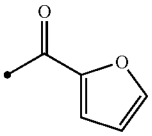 | 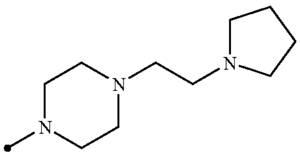 | MS m/z 598 $(M + H)^+$ |
| 24-138 | 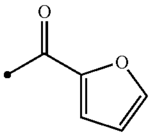 | 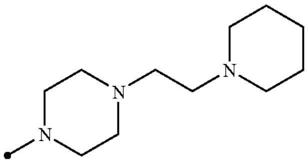 | MS m/z 612 $(M + H)^+$ |
| 24-139 | 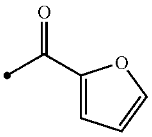 | 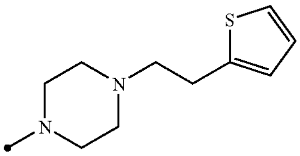 | MS m/z 611 $(M + H)^+$ |
| 24-140 | 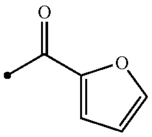 | 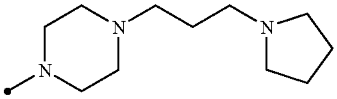 | MS m/z 612 $(M + H)^+$ |
| 24-141 | 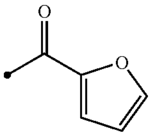 | 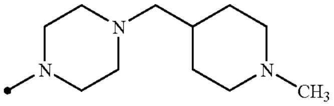 | MS m/z 612 $(M + H)^+$ |
| 24-142 | 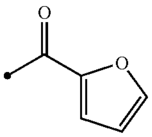 | 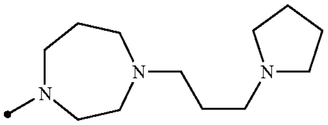 | MS m/z 626 $(M + H)^+$ |

TABLE 24-continued
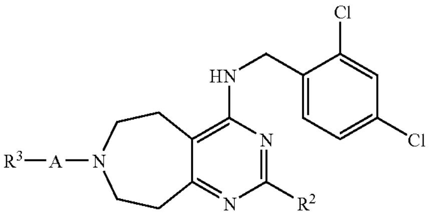
| Compound Number | •—A—$R^3$ | •—$R^2$ | Spectrum Data |
|---|---|---|---|
| 24-143 | 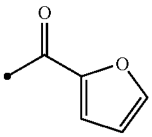 | 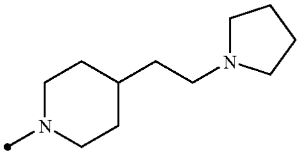 | MS m/z 597 $(M + H)^+$ |
| 24-144 | 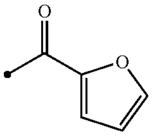 | 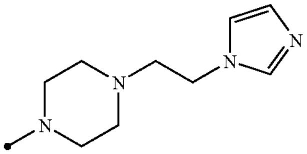 | MS m/z 595 $(M + H)^+$ |
| 24-145 | 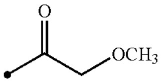 | 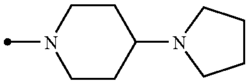 | MS m/z 547 $(M + H)^+$ |
| 24-146 | 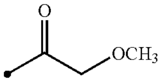 | 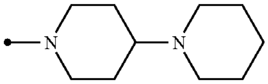 | MS m/z 561 $(M + H)^+$ |
| 24-147 | 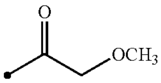 | 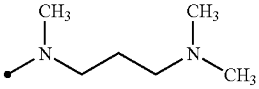 | MS m/z 509 $(M + H)^+$ |
| 24-148 | 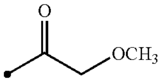 | 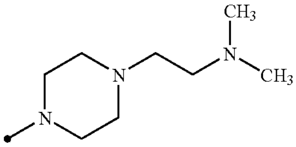 | MS m/z 550 $(M + H)^+$ |
| 24-149 | 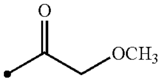 | 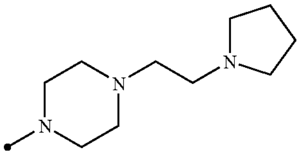 | MS m/z 576 $(M + H)^+$ |
| 24-150 | 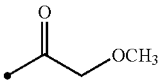 | 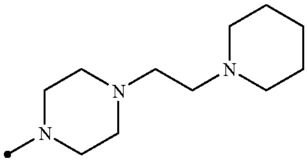 | MS m/z 590 $(M + H)^+$ |
| 24-151 | 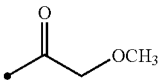 | 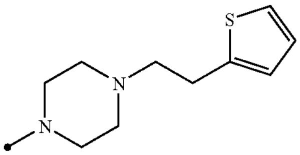 | MS m/z 589 $(M + H)^+$ |

TABLE 24-continued
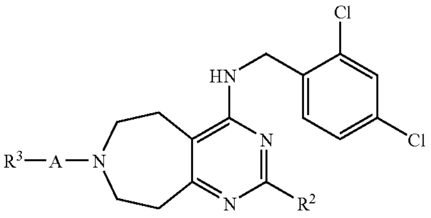
| Compound Number | •—A—R³ | •—R² | Spectrum Data |
|---|---|---|---|
| 24-152 | 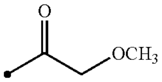 | 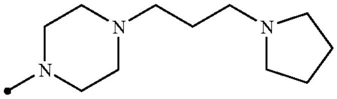 | MS m/z 590 (M + H)+ |
| 24-153 | 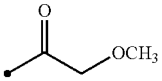 | 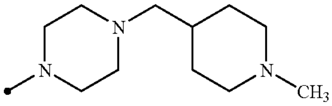 | MS m/z 590 (M + H)+ |
| 24-154 | 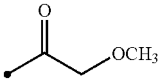 | 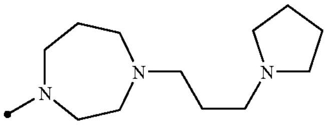 | MS m/z 604 (M + H)+ |
| 24-155 | 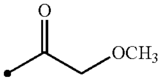 | 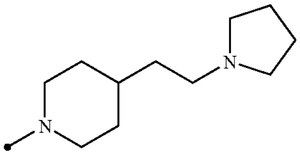 | MS m/z 575 (M + H)+ |
| 24-156 | 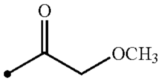 | 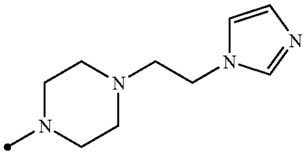 | MS m/z 573 (M + H)+ |
| 24-157 | 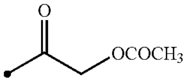 | 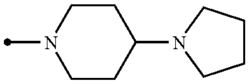 | MS m/z 575 (M + H)+ |
| 24-158 | 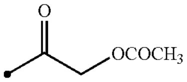 | 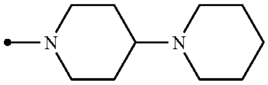 | MS m/z 589 (M + H)+ |
| 24-159 | 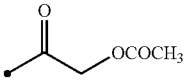 | 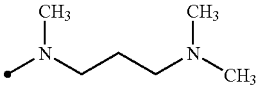 | MS m/z 537 (M + H)+ |
| 24-160 | 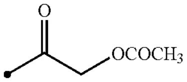 | 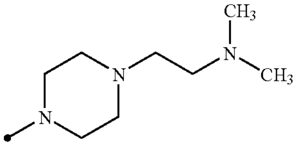 | MS m/z 578 (M + H)+ |
| 24-161 | 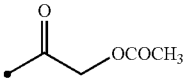 | 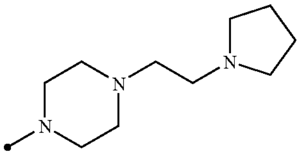 | MS m/z 604 (M + H)+ |

TABLE 24-continued
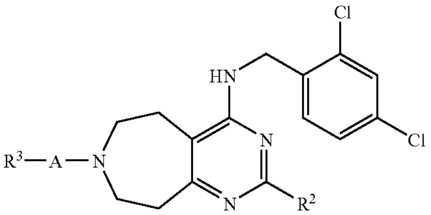
| Compound Number | •—A—$R^3$ | •—$R^2$ | Spectrum Data |
|---|---|---|---|
| 24-162 | 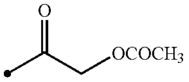 | 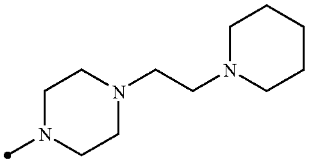 | MS m/z 618 $(M + H)^+$ |
| 24-163 | 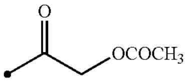 | 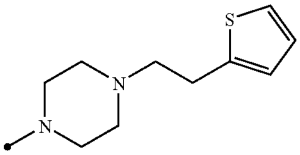 | MS m/z 617 $(M + H)^+$ |
| 24-164 | 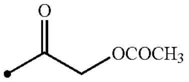 | 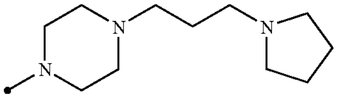 | MS m/z 618 $(M + H)^+$ |
| 24-165 | 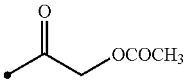 | 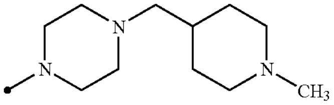 | MS m/z 618 $(M + H)^+$ |
| 24-166 | 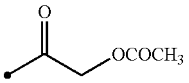 | 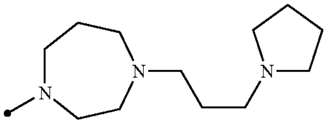 | MS m/z 632 $(M + H)^+$ |
| 24-167 | 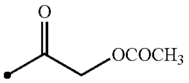 | 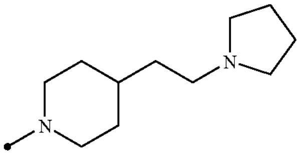 | MS m/z 603 $(M + H)^+$ |
| 24-168 | 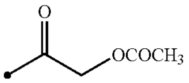 | 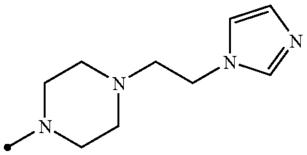 | MS m/z 601 $(M + H)^+$ |
| 24-169 | 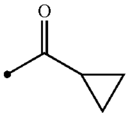 | 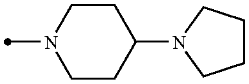 | MS m/z 543 $(M + H)^+$ |
| 24-170 | 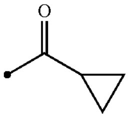 | 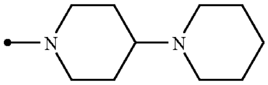 | MS m/z 557 $(M + H)^+$ |

TABLE 24-continued
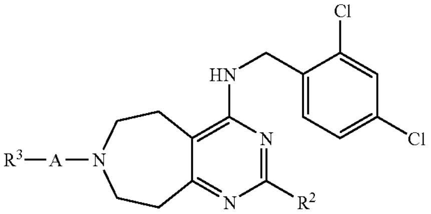
| Compound Number | •—A—$R^3$ | •—$R^2$ | Spectrum Data |
|---|---|---|---|
| 24-171 | 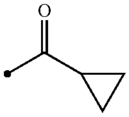 | 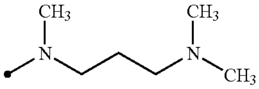 | MS m/z 505 $(M + H)^+$ |
| 24-172 | 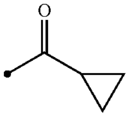 | 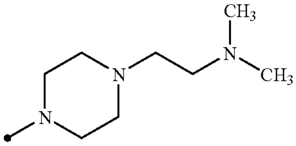 | MS m/z 546 $(M + H)^+$ |
| 24-173 | 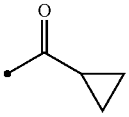 | 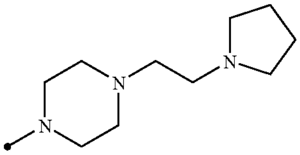 | MS m/z 572 $(M + H)^+$ |
| 24-174 | 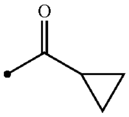 | 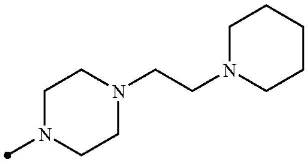 | MS m/z 586 $(M + H)^+$ |
| 24-175 | 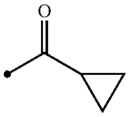 | 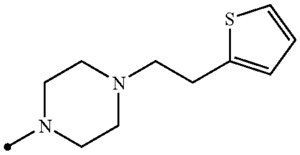 | MS m/z 585 $(M + H)^+$ |
| 24-176 | 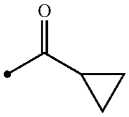 | 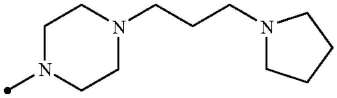 | MS m/z 586 $(M + H)^+$ |
| 24-177 | 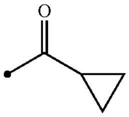 | 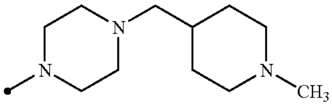 | MS m/z 586 $(M + H)^+$ |
| 24-178 | 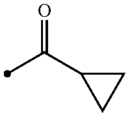 | 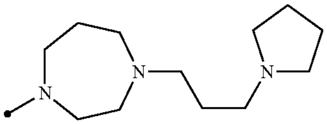 | MS m/z 600 $(M + H)^+$ |

TABLE 24-continued
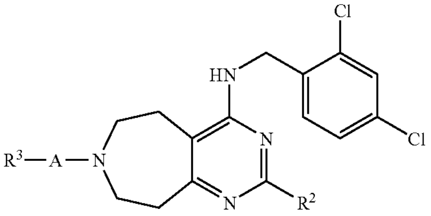
| Compound Number | •—A—$R^3$ | •—$R^2$ | Spectrum Data |
|---|---|---|---|
| 24-179 | 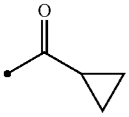 | 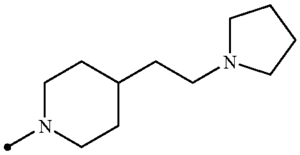 | MS m/z 571 $(M + H)^+$ |
| 24-180 | 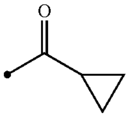 | 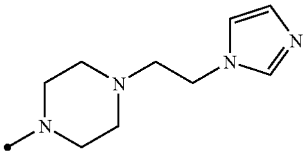 | MS m/z 569 $(M + H)^+$ |
| 24-181 | 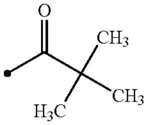 | 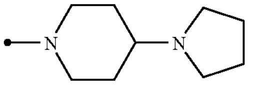 | MS m/z 559 $(M + H)^+$ |
| 24-182 | 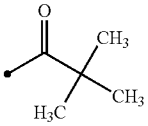 | 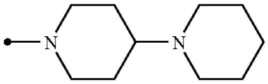 | MS m/z 573 $(M + H)^+$ |
| 24-183 | 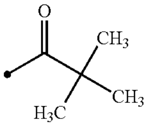 | 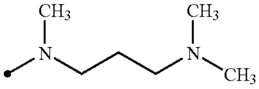 | MS m/z 521 $(M + H)^+$ |
| 24-184 | 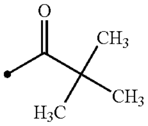 | 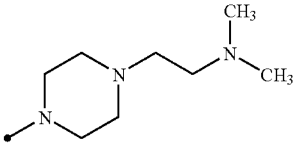 | MS m/z 562 $(M + H)^+$ |
| 24-185 | 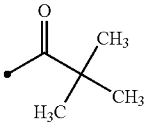 | 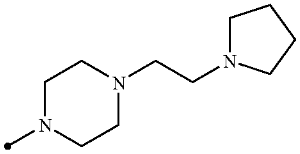 | MS m/z 588 $(M + H)^+$ |
| 24-186 | 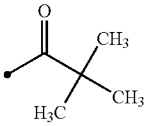 | 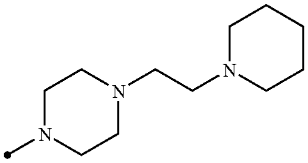 | MS m/z 602 $(M + H)^+$ |

TABLE 24-continued
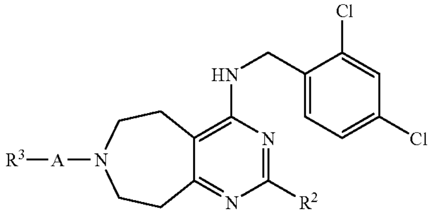
| Compound Number | •—A—$R^3$ | •—$R^2$ | Spectrum Data |
|---|---|---|---|
| 24-187 | 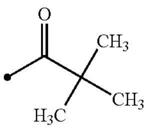 | 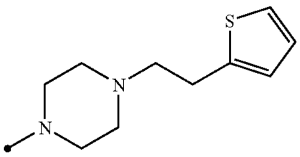 | MS m/z 601 $(M + H)^+$ |
| 24-188 | 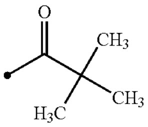 | 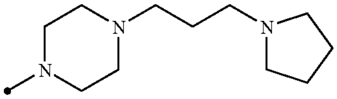 | MS m/z 602 $(M + H)^+$ |
| 24-189 | 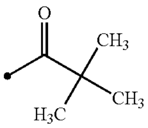 | 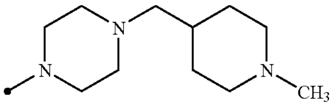 | MS m/z 602 $(M + H)^+$ |
| 24-190 | 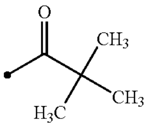 | 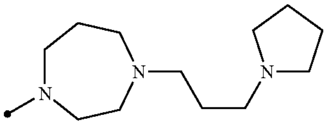 | MS m/z 616 $(M + H)^+$ |
| 24-191 | 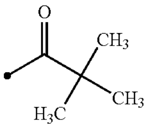 | 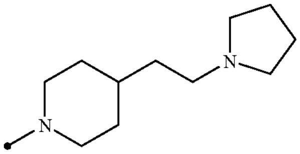 | MS m/z 587 $(M + H)^+$ |
| 24-192 | 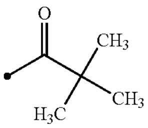 | 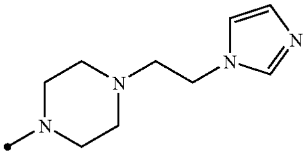 | MS m/z 585 $(M + H)^+$ |

TABLE 25
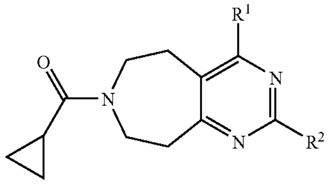
| Compound Number | •—R¹ | •—R² | Spectrum Data |
| --- | --- | --- | --- |
| 25-1 | 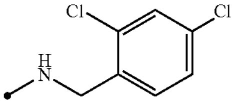 | 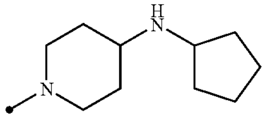 | MS m/z 557 $(M + H)^+$ |
| 25-2 | 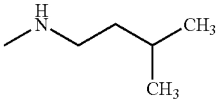 | 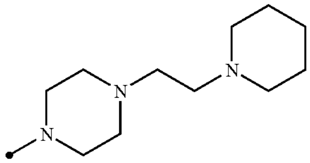 | MS m/z 498 $(M + H)^+$ |
| 25-3 | 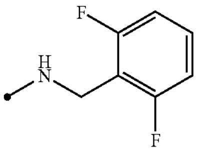 | 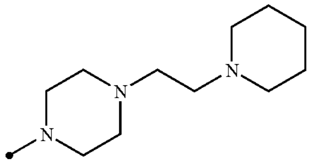 | MS m/z 554 $(M + H)^+$ |
| 25-4 | 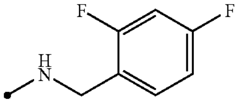 | 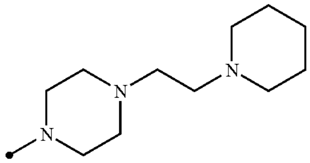 | MS m/z 554 $(M + H)^+$ |
| 25-5 | 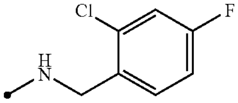 | 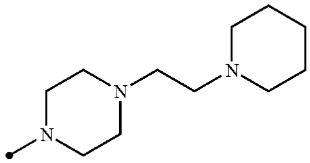 | MS m/z 570 $(M + H)^+$ |
| 25-6 | 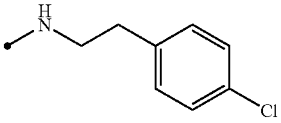 | 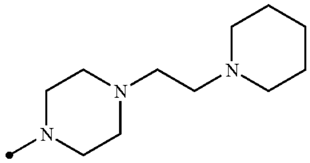 | MS m/z 566 $(M + H)^+$ |
| 25-7 | 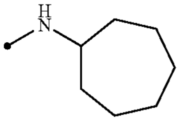 | 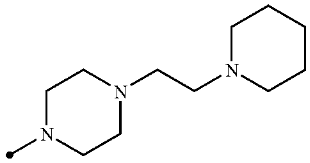 | MS m/z 524 $(M + H)^+$ |
| 25-8 | 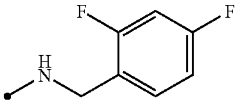 | 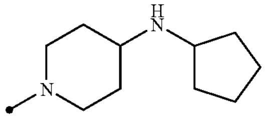 | MS m/z 525 $(M + H)^+$ |

TABLE 25-continued

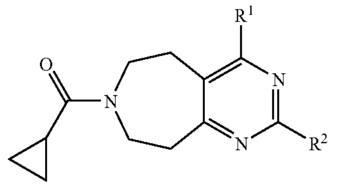

| Compound Number | •—$R^1$ | •—$R^2$ | Spectrum Data |
|---|---|---|---|
| 25-9 | 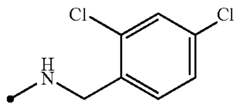 | 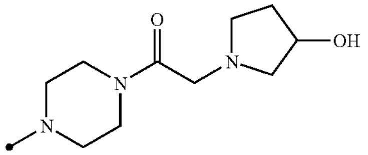 | MS m/z 602 $(M + H)^+$ |
| 25-10 | 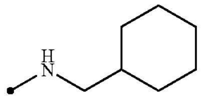 | 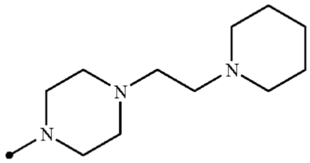 | MS m/z 524 $(M + H)^+$ |

Representative pharmacological activities of Compounds (I) will be illustrated below with reference to several test examples.

TEST EXAMPLE 1

Inhibitory Activity on Binding of [$^{125}$I]-TARC to Hut78 Cells

The RPMI-1640 medium (Sigma-Aldrich Japan) containing 20 mmol/L HEPES [4-(2-hydroxyethyl)-1-piperazinylethanesulfonic acid; HEPES, Nacalai Tesque, Inc.] and 0.1 w/v % bovine serum albumin (SEIKAGAKU CORPORATION) was adjusted to pH 7.0 with sodium hydrogen carbonate (Wako Pure Chemical Industries, Ltd.) to yield a binding/wash buffer. In a 96-well round-bottomed plate (Corning Costar Corporation) were placed 60 μL of a suspension of Hut78 cells (ATCC No. TIB-161) (3×10 cells) in the binding/wash buffer, 20 μL of a solution of a test compound and 20 μL of a solution of 810 Bq of [$^{125}$I]-TARC (Amersham Biosciences K.K.) diluted with the binding/wash buffer up to the total aliquot of 100 μL, followed by reaction at room temperature for two hours. The solution of the test compound had been prepared by dissolving the test compound in dimethyl sulfoxide (Nacalai Tesque, Inc.) to a concentration of 10 mmol/L, and diluting the solution with the binding/wash buffer to a series of concentrations. The nonspecific binding was determined by a binding assay in the presence of a sufficient amount of unlabeled TARC. The total binding was defined as a binding in the case where dimethyl sulfoxide (Nacalai Tesque, Inc.) was added, instead of the test compound, in the same concentration (0.1 v/v %). After binding [$^{125}$I]-TARC to Hut78 cells, 50 μL of a polyethyleneimine solution (Nacalai Tesque, Inc.) diluted to 0.3 w/v % with the binding/wash buffer was added each of wells of a glass filter (Unifilter GF/B96, Packard BioScience Company), was rapidly filtrated using Filtermate 196 (Packard BioScience Company) and washed with the binding/wash buffer at 4° C. to thereby separate the radioactive ligand which is not bound to the cells. Microscinti 20 (Packard BioScience Company) was placed in each well at 50 μL/well, and the radioactivity on the glass filter was determined using Topcount NXT™ (Packard BioScience Company). The binding inhibitory rates of the test compounds at 1 μmol/L are shown in Table 26. The binding inhibitory rates (%) of the test compounds were determined by calculation according to the following equation:

$$\text{Binding inhibitory rate (\%)} = \frac{(\text{Total binding}) - \left(\begin{array}{c}\text{Binding upon addition}\\ \text{of test compound}\end{array}\right)}{(\text{Total binding}) - (\text{Nonspecific binding})} \times 100$$

Total binding: [$^{125}$I]-TARC binding radioactivity without addition of the test compound Binding upon addition of test compound: [$^{125}$I]-TARC binding radioactivity at respective concentration upon addition of test compound Nonspecific binding: [$^{125}$I]-TARC binding radioactivity upon addition of unlabeled TARC

TABLE 26

| Compound Number | The Binding Inhibitory Rates at 1 μmol/L |
|---|---|
| 3-1 | 81 |
| 3-11 | 96 |
| 3-14 | 94 |
| 3-21 | 84 |
| 3-29 | 88 |
| 3-30 | 85 |
| 3-31 | 98 |
| 3-32 | 87 |
| 3-33 | 90 |
| 4-6 | 95 |
| 4-43 | 93 |

TABLE 26-continued

| Compound Number | The Binding Inhibitory Rates at 1 μmol/L |
|---|---|
| 4-86 | 91 |
| 4-653 | 89 |
| 5-389 | 77 |
| 5-401 | 82 |
| 5-407 | 92 |
| 5-423 | 81 |
| 6-33 | 85 |
| 6-36 | 91 |
| 8-121 | 94 |
| 8-402 | 94 |
| 9-30 | 95 |
| 10-12 | 90 |
| 13-1 | 96 |
| 13-9 | 91 |
| 14-4 | 99 |
| 14-12 | 86 |
| 15-4 | 96 |
| 15-12 | 88 |
| 15-20 | 89 |
| 15-23 | 86 |
| 15-24 | 92 |
| 15-25 | 92 |
| 15-30 | 92 |
| 15-34 | 94 |
| 15-44 | 78 |
| 15-47 | 96 |
| 15-48 | 93 |
| 15-51 | 91 |
| 15-54 | 97 |
| 15-59 | 90 |
| 15-60 | 100 |
| 15-73 | 83 |
| 15-79 | 86 |
| 16-4 | 95 |
| 16-8 | 93 |
| 16-13 | 95 |
| 16-15 | 82 |
| 17-1 | 100 |
| 17-4 | 98 |
| 17-5 | 93 |
| 17-7 | 99 |
| 17-8 | 90 |
| 18-1 | 99 |
| 18-9 | 100 |
| 20-1 | 97 |
| 20-5 | 96 |
| 20-6 | 99 |
| 20-18 | 88 |
| 21-3 | 97 |

These results show that Compound (I) of the present application have satisfactory inhibitory activities on the binding of TARC to Hut78 cells.

The inhibitory activities on the binding of [$^{125}$I]-MDC to Hut78 cells were determined in the same way as the above-mentioned method, except for using [$^{125}$I]-MDC (The Perkin-Elmer Corporation) instead of [$^{125}$I]-TARC. As a result, Compounds 4-6 and Compound 16-6, for example, each exhibited a binding inhibitory rate of 50% or more at a concentration of the test compound of 1 μmol/L.

These results show that Compounds (I) of the present application have satisfactory inhibitory activities on the binding of TARC and/or MDC to Hut78 cells.

Chemotaxing cells by TARC and/or MDC are known to have high IL-4 productivity and low IFN-γ productivity [International Immunology, vol. 11, p. 81 (1999)]. More specifically, Th2 T cells are considered to play an important role on allergic reactions, and CCR4 as well as TARC and MDC as ligands thereof are considered to be significantly involved in allergic pathoses [Molecular Immunology, vol. 38, p. 881 (2002); and Allergy, vol. 57, p. 180 (2002)].

It has been reported, for example, that invasion of CCR4-positive cells and production of TARC and/or MDC in the lung are involved in onset of asthmatic patients [Journal of Clinical Investigation, vol. 107, p. 1357 (2001)]. In addition, there are reports on increase of CCR4-positive T cells in the peripheral blood [American Journal of Respiratory and Critical Care Medicine, vol. 164, p. 754 (2001)], increase of TARC in the peripheral blood and sputum [Allergy, vol. 57, p. 173 (2002)], and invasion of CCR4-positive T cells in the lung tissues by antigenic stimulation [Journal of Clinical Investigation, vol. 107, p. 1357 (2001)]. Asthmatic pathosis is strongly prevented in mice administered with an antibody against TARC [Journal of Immunology, vol. 166, p. 2055 (2001)], and an anti-MDC antibody shows inhibitory activities on asthmatic pathosis in a murine asthma model [Journal of Immunology, vol. 163, p. 403 (1999)].

Eosinophilic pneumonia patients show increase in TARC in the peripheral blood and the bronchoalveolar lavage [American Journal of Respiratory and Critical Care Medicine, vol. 165, p. 1125 (2002)].

Atopic dermatitis patients have been reported to show an increasing TARC level in the peripheral blood according with an disease severity [Journal of Allergy Clinical Immunology, vol. 107, p. 535 (2001)] and an increasing MDC level in the peripheral blood with an increasing severity [Clinical and Experimental Immunology, vol. 127, p. 270 (2002)]. Further, atopic dermatitis patients have been reported to show an increased proportion of CCR4-positive cells in CD4-positive T cells in the peripheral blood [Journal of Investigative Dermatology, vol. 117, p. 188 (2001)].

Rhinitis patients are known to show increase in TARC level in the peripheral blood [Allergy, vol. 57, p. 180 (2002)], and a CCR4 ligand TARC is known to be produced form the human nasal mucosa [Clinical and Experimental Allergy, vol. 31, p. 1923 (2001)]. It has been reported that TARC in the nasal mucosa decreases and rhinitis symptoms are mitigated after treatment of applying trichloroacetic acid to the inferior concha in allergic rhinitis [American Journal of Rhinology, vol. 15, p. 395 (2001)].

It has been reported that the production of TARC is increased by stimulating the corneal fibroblasts with a Th2 cytokine such as IL-4 or TNF-α, indicating that CCR4-positive cells may participate in allergic conjunctivitis [Biochemical and Biophysical Research Communications, vol. 279, p. 1 (2000)]. It has been reported in psoriasis that CCR4-positive cells increasingly invade around the cutaneous blood vessel in lesions [Laboratory Investigation, vol. 81, p. 335 (2001)]. Inpatients infected by *Candida albicans* in the intraoral skin, it has been reported that CCR4-positive T cells and MDC producing dendritic cells increase in the epidermis and dermis in regions of inflammation caused by infection [American Journal of Pathology, vol. 158, p. 1263 (2000)]. It has also been reported that CCR4-positive cells invade the synovial membrane tissue in rheumatoid arthritis [Arthritis and Rheumatism, vol. 44, p. 2750 (2001)], and that CCR4-positive cells increase in the peripheral blood of systemic lupus erythematosus patients in stages with high disease activity [Journal of Leukocyte Biology, vol. 70, p. 749 (2001)].

CCR4 is expressed in the nerve cells, particularly in substance P neurons in the dorsal root ganglion, and the stimulation of the nerve cells by MDC increases an intracellular calcium level to thereby release substance P serving as a pain producing substance [Journal of Neuroscience, vol. 21, p. 5027 (2001)]. CCR4 knockout mice become resistant against sepsis [Journal of Experimental Medicine, vol. 191, p. 1755 (2000)]. Further, cells in which CCR4 is expressed were known in leukemia [Blood, vol. 96, p. 685 (2000)], and CCR4 is significantly expressed in leukemia cells particuraly in adult T cell leukemia (ATL) [Blood, vol. 99, p. 1505 (2002)].

TARC has been reported to participate in pathoses in mycosis fungoides [Journal of American Academy of Dermatology, vol. 48, p. 23 (2003)].

It has been reported that an anti-mouse MDC antibody inhibits the onset of diabetes mellitus in a murine insulin-dependent diabetes mellitus model (NOD mice) [Journal of Clinical Investigation, vol. 110, p. 1675 (2002)].

Compounds (I) of the present application regulate or control the functions of TARC and/or MDC, namely, inhibit or antagonize the binding of TARC and/or MDC to T cells, and more specifically, for example, inhibit or antagonize the binding of TARC and/or MDC to CCR4 (i.e., have CCR4 antagonistic actions). Based on the above-mentioned findings, Compounds (I) of the present application are considered to be promising agents for treating, for example, allergic diseases and to be particularly efficacious for treating, for example, asthma, rhinitis and allergic conjunctivitis. Compounds (I) of the present application are considered to be efficacious for treating, for example, eosinophilic pneumonia, psoriasis, rheumatoid arthritis, systemic lupus erythematosus, sepsis and leukemia. In addition, Compounds (I) of the present application are expected to effectively inhibit pain and/or neuralgia by inhibiting the liberation of pain producing substances.

TEST EXAMPLE 2-1

Inhibitory Activities on Antigen-Induced Cellular Infiltration

BALB/c mice were sensitized by intraperitoneally administering 50 μg of ovalbumin (Sigma-Aldrich Japan) and 1 mg of aluminum hydroxide (Wako Pure Chemical Industries, Ltd.) and were then sensitized in the same manner seven days later. After 24 days, 26 days and 28 days from the first sensitization, the mice were allowed to inhale 1% ovalbumin physiological saline solution (prepared by dissolving ovalbumin in physiological saline (Otsuka Pharmaceutical Co., Ltd.) to a concentration of 1%) using a DeVilbiss 2000 (DeVilbiss Mfg Co.) for thirty minutes (antigen nebulization), respectively. After 3 days from the third antigen nebulization, a suspension of a test compound in water containing 0.5% of methylcellulose (Wako Pure Chemical Industries, Ltd.) was orally administered at a dose of 30 mg/kg (test compound treatment group). To a control group, only the water containing 0.5% of methylcellulose for use in the preparation of a suspension of the test compound was orally administered. After 20 minutes from the administration of the suspension of the test compound or the water containing 0.5% of methylcellulose, a fourth antigen nebulization was carried out. Thereafter the suspension of the test compound or the water containing 0.5% of methylcellulose was orally administered to the mice twice at interval of eight hours. Separately from these groups, the water containing 0.5% of methylcellulose was administered at intervals of eight hours without the fourth antigen nebulization in an untreated group. After twenty-four hours from the fourth antigen nebulization, the bronchoalveolar lavage was performed, and the number of total cells in the recovered bronchoalveolar lavage fluid was counted. The numbers of CD4-positive T cells and CD11b-positive cells were determined using a flow cytometer EPICS XL-MCL System II (Beckman Coulter, Inc.). Each seven mice in the test compound treatment group and the control group, and six mice in the untreated group were subjected to the test.

The number of CD4-positive T cells in the bronchoalveolar lavage in the untreated group was $7.8\pm1.0\times10^4$ [mean±(standard error)] per mouse, but that in the control group increased to $19.2\pm1.8\times10^4$ [mean±(standard error)]. In the Compound 4-6 treated group, the number of CD4-positive T cells in the bronchoalveolar lavage was $9.7\pm2.0\times10^4$ [mean±(standard error)]per mouse, and the invasion of CD4-positive T cells into the pulmonary alveolus was inhibited by a factor of 84% (P=0.0066, Student's-t test) as compared with the control group.

The number of CD11b-positive cells in the bronchoalveolar lavage in the untreated group was $4.6\pm1.0\times10^5$ [mean±(standard error)] per mouse, but that in the control group increased to $10.7\pm1.6\times10^5$ [mean±(standard error)]. In the Compound 4-6 treated group, the number of CD11b-positive cells in the bronchoalveolar lavage was $7.8\pm1.7\times10^5$ [mean±(standard error)]per mouse, and the invasion of CD11b-positive cells into the pulmonary alveolus was inhibited by a factor of 48% as compared with the control group.

TEST EXAMPLE 2-2

Inhibitory Activities on Antigen-Induced Celular Infiltration

BALB/c mice were sensitized by intraperitoneally administering 50 μg of ovalbumin (Sigma-Aldrich Japan) and 1 mg of aluminum hydroxide (Wako Pure Chemical Industries, Ltd.) and were then sensitized in the same manner seven days later. After 23 days, 25 days and 27 days from the first sensitization, the mice were allowed to inhale 1% ovalbumin physiological saline solution (prepared by dissolving ovalbumin in physiological saline (Otsuka Pharmaceutical Co., Ltd.) to a concentration of 1%) using an Ultrasound Nebulizer (OMRON Corporation) for thirty minutes (antigen nebulization), respectively. After 3 days from the third antigen nebulization, a suspension of a test compound in water containing 0.5% of methylcellulose (Wako Pure Chemical Industries, Ltd.) was orally administered at a dose of 30 mg/kg (test compound treatment group). To a control group, only the water containing 0.5% of methylcellulose for use in the preparation of a suspension of the test compound was orally administered. After 1 hour from the administration of the suspension of the test compound or the water containing 0.5% of methylcellulose, a fourth antigen nebulization was carried out. Separately from these groups, in an untreated group, the mice were allowed to inhale physiological saline using an Ultrasound Nebulizer NE-U12 after 23 days, 25 days and 27 days from the first sensitization, respectively (physiological saline nebulization), were administered with water containing 0.5% of methylcellulose alone after 3 days from the third physiological saline nebulization and were nebulized with physiological saline 1 hour later.

After eight hours from the fourth antigen nebulization or physiological saline nebulization, the bronchoalveolar lavage was performed, and the number of total cells in the recovered bronchoalveolar lavage fluid was counted. The numbers of CD4-positive T cells were determined using a flow cytometer EPICS XL-MCL System II (Beckman Coulter, Inc.). Each ten mice in the test compound treatment group and the control group, and ten mice in the untreated group were subjected to the test.

The number of CD4-positive T cells in the bronchoalveolar lavage fluid in the untreated group was $0.2\pm0.1\times10^4$ [mean±(standard error)] per mouse, but that in the control group increased to $3.6\pm0.7\times10^4$ [mean±(standard error)]. In the Compound 16-6 treated group, the number of CD4-positive T cells in the bronchoalveolar lavage was $2.2 \pm 0.4 \times 10^4$ [mean±(standard error)] per mouse, and the invasion of CD4-positive T cells into the pulmonary alveolus was reduced by a factor of 41% as compared with the control group.

TEST EXAMPLE 3

Inhibitory Activities on Antigen-Induced Airway Hypersensitivity and Inflammatory Cell Infiltration BALB/c mice were sensitized by intraperitoneally administering a mixture of 50 μg of ovalbumin (Sigma-Aldrich Japan) and 1 mg of aluminum hydroxide (Wako Pure Chemical Industries, Ltd.) twice at an interval of 1 week. After 14 days, 16 days, 18 days, 20 days and 22 days from the final sensitization, the mice were allowed to inhale 1% ovalbumin physiological saline solution (prepared by dissolving ovalbumin in physiological saline (Otsuka Pharmaceutical Co., Ltd.) to a concentration of 1%) or physiological saline (negative control group), respectively, for thirty minutes to thereby induce an antigen-antibody reaction (antigen nebulization). A suspension of a test compound in water containing 0.5% of methylcellulose (test compound suspension) was orally administered to the mice at a dose of 30 mg/kg in a total of 19 times from 1 hour before the first antigen inhalation at intervals of twelve hours (test compound treatment group). In a positive control group, water containing 0.5% of methylcellulose was administered instead of the test compound suspension. Airway hypersensitivity and inflammation cell infiltration in the bronchoalveolar lavage fluid were evaluated after twenty-four hours from the finial antigen inhalation.

As an airway hypersensitivity test, the mice were allowed to inhale 1.5 to 25 mg/mL of methacholine for 3 minutes, the airway responsiveness was determined using a murine respiratory function analyzer (BioSystem XA; Buxco Electronics, Inc., Sharon, Conn., USA). Airway hypersensitivity was determined by the area under the curve (AUC) which calculated by a methacholine dose dependent-airway responsiveness.

The inflammatory cell infiltration was evaluated in the following manner. The total cell count in the recovered bronchoalveolar lavage was determined using an automatic blood cell counter (Celltac a MEK-6158; Nihon Kohden, Tokyo), and a smear preparation was prepared using a Cytospin 3 (Shandon, Inc., Pittsburgh, Pa., US) and was observed under a microscope to classify cells morphologically as macrophages, neutrophils, eosinophils and lymphocytes. The cell counts of the respective cells were determined by multiplying the total cell count by percentages of the respective cells. Each ten mice per group were subjected to the test.

AUC [237.6±31.9, mean±(standard error)] of the airway responsiveness in the positive control group significantly increased (P=0.0137, Student's t-test) as compared with the AUC (132.7±21.5) in the negative control group.

The AUC in the test compound treatment group was 140.7±17.7, indicating that respiratory anaphylaxis was inhibited by a factor of 92% as compared with the positive control group (P=0.0161, Student's t-test).

The total cell count, eosinophil count and lymphocyte count in the bronchoalveolar lavage in the negative control group were $0.60 \pm 0.07 \times 10^5$, $0.00 \pm 0.00 \times 10^5$ and $0.00 \pm 0.00 \times 10^5$ per mouse, respectively, and those in the positive control group were $5.36 \pm 0.63 \times 10^5$, $3.89 \pm 0.62 \times 10^5$ and $0.22 \pm 0.03 \times 10^5$ per mouse, indicating significant increase (P<0.0001, Student's t-test) in the each cells.

The total cell count, eosinophil count and lymphocyte count in the test compound treatment group were $3.38 \pm 0.46 \times 10^5$, $1.84 \pm 0.31 \times 10^5$ and $0.10 \pm 0.02 \times 10^5$ per mouse, respectively. In other words, the total cell count, eosinophil count and lymphocyte count in the test compound treatment group were significantly reduced by factors of 42% (P=0.0207, Student's t-test), 53% (P=0.0086, Student's t-test), and 58% (P=0.0058, Student's t-test), respectively, as compared with the positive control group.

The excellent pharmacological activities of the compounds of the present invention can also be shown, in addition to the above test examples, by evaluation models generally used for determining anti-inflammatory activities, such as a guinea pig asthma model described in Journal of Pharmacology and Experimental Therapeutics, vol. 278, p. 847 (1996); a murine respiratory anaphylaxis model described in Journal of Immunology, vol. 163, p. 403 (1999); a delayed type hypersensitivity model described in Journal of Immunology, vol. 167, p. 3980 (2001); and a collagen arthritis model described in Journal of Immunology, vol. 167, p. 1004 (2001).

Each of Compounds (I) or pharmacologically acceptable salts thereof can be administered alone as intact but is preferably administered as a pharmaceutical preparation in general. Such pharmaceutical preparations can be used for animals or humans.

The pharmaceutical preparations according to the present invention may comprise, as an active ingredient, Compound (I) or a pharmaceutically acceptable salt thereof alone or optionally as a mixture with any other active ingredient for treatment. Such pharmaceutical preparations are produced by mixing the active ingredient with one or more pharmaceutically acceptable carries and formulating them according to any procedure known in the technical field of pharmaceutics.

The administration route is preferably most efficacious one in the treatment and includes oral administration or parenteral administration such as intravenous administration.

The dosage form includes, for example, tablets and injections.

The carrier for the pharmaceutical preparations includes, for example, lactose, mannitol, glucose, hydroxypropylcellulose, starch, magnesium stearate, sorbitan fatty acid esters, glyceric acid esters, polyvinyl alcohol, distilled water for injection, physiological saline, propylene glycol, polyethylene glycol and ethanol. The pharmaceutical preparations according to the present invention may further comprise, for example, any of various excipients, lubricants, binders, disintegrators, isotonizing agents and emulsifiers.

Compound (I) or a pharmaceutically acceptable salt thereof is generally administered systemically or locally, orally or parenterally when is used for the above-mentioned purpose. The dose and frequency of administration vary depending typically on the dosage form, age and body weight of the patient, and properties or severity of the symptom to be treated, but the compound or a pharmaceutically acceptable salt thereof is preferably administered at a dose of 0.1 to 100 mg/kg and preferably 1 to 50 mg/kg per day per one adult in three to four installments. However, these dose and frequency of administration vary depending of the various conditions.

BEST MODE FOR CARRYING OUT THE INVENTION

The present invention will be illustrated in further detail with reference to several Examples and Reference Examples below, which are never intended to limit the scope of the present invention. The numbers of compounds in the following examples and Reference examples correspond to the numbers of compounds listed as specific Examples in Tables 1 to 25, respectively.

The physico-chemical data of the compounds in the examples were determined using the following devices.

$^1$H NMR: JEOL JNM-EX270 (270 MHz) or JEOL JNM-GX270 (270 MHz) MS: Micromass LCT or Micromass Quatro (according to APCI, ESI or FAB)

REFERENCE EXAMPLE 1

Synthesis of 2,4-dichloro-5,6,7,8-tetrahydropyrido[4,3-d]pyrimidine hydrochloride Process Step 1

Commercially available ethyl 1-benzyl-4-oxo-3-piperidinecarboxylate hydrochloride (100 g, 0.335 mol) was dissolved in ethanol (1,500 mL), and the solution was mixed with urea (100 g, 1.67 mol) and sodium methoxide (227 g, 1.18 mol), followed by a reaction under reflux for twenty-four hours. After checking the completion of the reaction by thin layer chromatography, the reaction mixture was cooled, and the precipitated crystals were collected by filtration. The crystals were suspended in water, and the pH of the suspension was adjusted to 6.0 by the addition of diluted hydrochloric acid (6 mol/L). The mixture was stirred at room temperature for one hour, and the precipitated crystals were collected by filtration. The crystals were dried under reduced pressure and thereby yielded 6-benzyl-5,6,7,8-tetrahydropyrido[4,3-d]pyrimidine-2,4(1H,3H)-dione (60 g, in a yield of 70%).

Process Step 2

6-Benzyl-5,6,7,8-tetrahydropyrido-[4,3-d]pyrimidine-2,4(1H,3H)-dione (30.0 g, 0.116 mol) prepared according to Process Step 1 was mixed with phosphorus oxychloride (300 mL), followed by stirring with heating for five hours. After checking the completion of the reaction by thin layer chromatography, excess phosphorus oxychloride was distilled off under reduced pressure. The residue was mixed with isopropyl alcohol (300 mL) for crystallization. The suspension containing the precipitated crystals was stirred under reflux for one hour and was further stirred at room temperature for one hour. The precipitated crystals were collected by filtration, were dried under reduced pressure and thereby yielded 6-benzyl-2,4-dichloro-5,6,7,8-tetrahydropyrido[4,3-d]pyrimidine hydrochloride (33 g, in a yield of 85%).

Process Step 3

6-Benzyl-2,4-dichloro-5,6,7,8-tetrahydropyrido[4,3-d]pyrimidine hydrochloride (35.0 g, 0.106 mol) prepared according to Process Step 2 was dissolved in 1,2-dichloroethane (850 mL), and the solution was mixed with triethylamine (14.9 mL, 0.107 mol) and 1-chloroethyl chloroformate (34.1 mL, 0.316 mol), followed by stirring under reflux for five hours. After checking the completion of the reaction by thin layer chromatography, the reaction mixture was cooled and was mixed with water, followed by separation. The organic layer was washed with brine, was dried over anhydrous magnesium sulfate and was concentrated. The residue was purified by silica gel column chromatography (n-hexane:ethyl acetate=3:1) and thereby yielded a 2,4-dichloro-6-(1-chloroethoxycarbonyl)-5,6,7,8-tetrahydropyrido[4,3-d]pyrimidine fraction. After distilling off the solvent, the residue was dissolved in methanol (850 mL), followed by stirring under reflux for one hour. After checking the completion of the reaction by thin layer chromatography, the reaction mixture was concentrated and thereby yielded 2,4-dichloro-5,6,7,8-tetrahydropyrido[4,3-d]pyrimidine hydrochloride (23.5 g, in a total yield from 6-benzyl-2,4-dichloro-5,6,7,8-tetrahydropyrido[4,3-d]pyrimidine hydrochloride of 95%).

REFERENCE EXAMPLE 2

Synthesis of ethyl 1-benzyl-4-oxopyrrolidine-3-carboxylate

Commercially available ethyl 3-benzylaminopropionate (10.0 g, 0.0482 mol) was dissolved in 2-butanone (100 mL), and the solution was mixed with potassium carbonate (10.0 g, 0.0724 mol) and sodium iodide (10.9 g, 0.0724 mol). Ethyl bromoacetate (8.47 g, 0.0507 mol) was added dropwise to the resulting suspension, and the suspension was stirred under reflux over night. After filtrating the reaction mixture, the filtrate was mixed with water (200 mL) and chloroform (100 mL), followed by shaking and separation. After drying the organic layer over magnesium sulfate, the solvent was distilled off under reduced pressure, to thereby yield ethyl 3-[N-benzyl-N-(ethoxycarbonylmethyl)amino]propionate (14.0 g, in a yield of 99%).

Above-prepared ethyl 3-[N-benzyl-N-(ethoxycarbonylmethyl)amino]propionate (14.0 g, 0.0479 mol) was dissolved in toluene (100 mL), and the solution was mixed with potassium tert-butoxide (5.9 g, 0.0525 mol) gradually added under ice-cooling, followed by stirring under ice-cooling for two hours. The reaction mixture was mixed with diluted hydrochloric acid (about 1 mol/L, 100 mL) under ice-cooling, followed by shaking and separation, to yield an aqueous layer. Saturated aqueous sodium bicarbonate solution (300 mL) was added dropwise to the aqueous layer, and ethyl acetate (400 mL) was further added thereto, followed by shaking and separation. After drying the organic layer over anhydrous magnesium sulfate, the solvent was distilled off under reduced pressure, to thereby yield ethyl 1-benzyl-4-oxopyrrolidine-3-carboxylate (9.23 g, in a yield of 78%).

REFERENCE EXAMPLE 3

Synthesis of 2,4-dichloro-6,7-dihydro-5H-pyrrolo[3,4-d]pyrimidine hydrochloride

Process Step 1

Ethyl 1-benzyl-4-oxopyrrolidine-3-carboxylate (9.23 g, 0.0372 mol) prepared according to Reference Example 2 was dissolved in ethanol (170 mL), and the solution was mixed with urea (11.2 g, 0.186 mol) and a solution of sodium methoxide in methanol (about 28%, 25 g), followed by stirring under reflux for twenty-four hours. The reaction mixture was mixed with water (100 mL), followed by stirring at room temperature. Diluted hydrochloric acid (about 1 mol/L, 100 mL) was added dropwise to the reaction mixture. The precipitated crystals were collected by filtration, and the collected crystals were washed with water (100 mL). The crystals were dried under reduced pressure and thereby yielded 6-benzyl-6,7-dihydro-5H-pyrrolo[3,4-d]pyrimidine-2,4(1H,3H)-dione (3.93 g, in a yield of 43%).

Process Step 2

6-Benzyl-6,7-dihydro-5H-pyrrolo[3,4-d]pyrimidine-2,4(1H,3H)-dione (1.0 g, 0.0041 mol) prepared according to Process Step 1 was mixed with phosphorus oxychloride (10 mL), followed by stirring under reflux for eight hours. After standing to cool, the reaction mixture was mixed with water (50 mL) gradually added dropwise under ice-cooling. The reaction mixture was mixed with an aqueous sodium hydroxide solution (30 mL) added dropwise under ice-cooling and was then mixed with ethyl acetate (200 mL), followed by shaking and separation. The organic layer was dried and was concentrated under reduced pressure. The residue was dissolved in ethyl acetate (10 mL), and a solution of hydrogen chloride in ethyl acetate (4 mol/L, 2 mL) was added dropwise thereto. The reaction mixture was crystallized from diethyl ether (10 mL), the precipitated crystals were collected by filtration and were washed with diethylether (20 mL). The crystals were dried under reduced pressure and thereby yielded 6-benzyl-2,4-dichloro-6,7-dihydro-5H-pyrrolo[3,4-d]pyrimidine hydrochloride (0.50 g, in a yield of 39%).

Process Step 3

6-Benzyl-2,4-dichloro-6,7-dihydro-5H-pyrrolo[3,4-d]pyrimidine hydrochloride (0.500 g, 0.00158 mol) prepared according to Process Step 2 was dissolved in 1,2-dichloroethane (15 mL), and the solution was mixed with triethylamine (0.160 g, 0.00158 mol) added dropwise under ice-cooling. The resulting solution was mixed with 1-chloroethyl chloroformate (0.680 g, 0.00478 mol) added dropwise at room temperature, followed by stirring under reflux for three hours. The reaction mixture was mixed with water (20 mL), followed by shaking and separation. The organic layer was dried over anhydrous magnesium sulfate, and was concentrated under reduced pressure. The residue was dissolved in methanol (15 mL), followed by reflux of the solution for one hour. After standing the reaction mixture to cool, methanol was distilled off under reduced pressure, to thereby yield 2,4-dichloro-6,7-dihydro-5H-pyrrolo[3,4-d]pyrimidine hydrochloride (0.19 g, in a yield of 54%).

REFERENCE EXAMPLE 4

Synthesis of 4-(2,4-dichlorobenzylamino)-2-(4-toluenesulfonyloxy)-5,6,7,8-tetrahydropyrido[3,4-d]pyrimidine hydrochloride Process Step 1

Commercially available ethyl 1-benzyl-3-oxo-4-piperidinecarboxylate hydrochloride (25.0 g, 84.0 mmol) was dissolved in ethanol (350 mL), and the solution was mixed with urea (25.0 g, 416 mmol) and sodium methoxide (56.7 g), followed by a reaction under reflux for seventeen hours. After checking the completion of the reaction by thin layer chromatography, the reaction mixture was cooled to yield a suspension, and the pH of the suspension was adjusted to 6.0 by the addition of diluted hydrochloric acid (4 mol/L). The mixture was stirred at room temperature for one hour, and the precipitated crystals were collected by filtration. The crystals were reslurried with ethanol, were collected by filtration, were dried under reduced pressure and thereby yielded 7-benzyl-5,6,7,8-tetrahydropyrido[3,4-d]pyrimidine-2,4(1H,3H)-dione (17.2 g, in a yield of 80%).

Process Step 2

7-Benzyl-5,6,7,8-tetrahydro-(1H,3H)-pyrido[3,4-d]pyrimidine-2,4-dione (18.7 g, 72.7 mmol) prepared according to Process Step 1 was dissolved in dimethylformamide (180 mL), and the solution was mixed with sodium hydride (40% oily suspension, 7.3 g) added under ice-cooling, followed by stirring at room temperature for one and half hour. The reaction mixture was mixed with 4-toluenesulfonyl chloride (34.7 g), followed by stirring for further one hour and fifteen minutes. After checking the completion of the reaction by thin layer chromatography, the reaction mixture was diluted with water, was stirred and was extracted with ethyl acetate. The organic layer was washed with brine, was dried over anhydrous magnesium sulfate, and the solvent was distilled off. The whole quantity of the residue was dissolved in tetrahydrofuran (400 mL), and the solution was mixed with 2,4-dichlorobenzylamine (14.7 mL) and triethylamine (30.4 mL), followed by stirring at room temperature for twenty-four hours. After checking the completion of the reaction by thin layer chromatography, the reaction mixture was subjected to work-up in the same way as above. The residue was purified by silica gel column chromatography (n-hexane:ethyl acetate=1:1) and thereby yielded 7-benzyl-4-(2,4-dichlorobenzylamino)-2-(4-toluenesulfonyloxy)-5,6,7,8-tetrahydropyrido[3,4-d]pyrimidine (19.4 g, in a yield of 46%).

Process Step 3

7-Benzyl-4-(2,4-dichlorobenzylamino)-2-(4-toluenesulfonyloxy)-5,6,7,8-tetrahydropyrido[3,4-d]pyrimidine (18.7 g, 31.9 mmol) prepared according to Process Step 2 was dissolved in 1,2-dichloroethane (110 mL), and the solution was mixed with 1-chloroethyl chloroformate (14.1 mL), followed by stirring at room temperature for 40 minutes. After checking the completion of the reaction by thin layer chromatography, the reaction mixture was diluted with water, was stirred and was extracted with ethyl acetate. The organic layer was washed with brine, was dried over anhydrous magnesium sulfate, and the solvent was distilled off. The residue was purified by silica gel column chromatography (n-hexane: ethyl acetate=1:1) and thereby yielded a 4-(2,4-dichlorobenzylamino)-7-(1-chloroethoxycarbonyl)-2-(4-toluenesulfonyloxy)-5,6,7,8-tetrahydropyrido[3,4-d]pyrimidine fraction. After distilling off the solvent, the residue was dissolved in methanol (150 mL), followed by stirring at room temperature for two hours. After concentrating the reaction mixture, the residue was mixed with diethyl ether for crystallization. The precipitated crystals were collected by filtration, were dried and thereby yielded 4-(2,4-dichlorobenzylamino)-2-(4-toluenesulfonyloxy)-5,6,7,8-tetrahydropyrido[3,4-d]pyrimidine hydrochloride (7.86 g, in a yield of 53%).

REFERENCE EXAMPLE 5

Synthesis of ethyl 1-benzyl-5-oxoperhydroazepine-4-carboxylate

Commercially available 1-benzylpiperidin-4-one (78.5 g, 0.415 mol) was dissolved in tetrahydrofuran (300 mL) and the solution was cooled to −25° C. Ethyl diazoacetate (56.8 g) and boron trifluoride diethyl ether complex (128 mL) were simultaneously added dropwise to the solution over one hour, followed by stirring for one hour while elevating the temperature from −25° C. to 0° C. The reaction mixture was mixed with a saturated aqueous sodium bicarbonate solution and was extracted with ethyl acetate. The organic layer was washed with brine and was dried over anhydrous sodium sulfate. After distilling off the solvent, the residue was purified by silica gel column chromatography (n-hexane:ethyl acetate=4:1) and thereby yielded ethyl 1-benzyl-5-oxoperhydroazepine-4-carboxylate (30.6 g, in a yield of 27%).

REFERENCE EXAMPLE 6

Synthesis of 2,4-dichloro-6,7,8,9-tetrahydro-5H-pyrimido[4,5-d]azepine hydrochloride Process Step 1

Ethyl 1-benzyl-5-oxoperhydroazepine-4-carboxylate (30.6 g) prepared according to Reference Example 5 was dissolved in ethanol (500 mL), and the solution was mixed with urea (128 g) and sodium methoxide (75 g), followed by stirring under reflux for sixteen hours. The reaction mixture was mixed with water to yield a suspension, and the suspension was adjusted to a pH of 8 by adding diluted hydrochloric acid (6 mol/L) and was extracted with ethyl acetate. The organic layer was sequentially washed with water and brine, was dried over anhydrous sodium sulfate, and the solvent was distilled off. The residue was mixed with a mixture of acetone and diethyl ether for crystallization. The precipitated crystals were collected by filtration, were dried and thereby yielded 7-benzyl-6,7,8,9-tetrahydro-5H-pyrimido[4,5-d]azepine-2,4(1H,3H)-dione (4.15 g, in a yield of 17%).

Process Step 2

7-Benzyl-6,7,8,9-tetrahydro-5H-pyrimido[4,5-d]azepine-2,4(1H,3H)-dione (17.0 g, 62.7 mmol) prepared according to Process Step 1 was mixed with N,N-diisopropylethylamine (17mL) and phosphorus oxychloride (300 mL), followed by stirring at room temperature for thirteen hours. After concentrating the reaction mixture, the residue was dissolved in ethyl acetate, and the solution was mixed with a saturated aqueous sodium bicarbonate solution under ice-cooling. The solution was extracted with ethyl acetate, the organic layer was washed with brine and was dried over anhydrous magnesium sulfate. After distilling off the solvent, the residue was dried and thereby yielded 7-benzyl-2,4-dichloro-6,7,8,9-tetrahydro-5H-pyrimido[4,5-d]azepine (19.8 g, in a quantitative yield).

Process Step 3

7-Benzyl-2,4-dichloro-6,7,8,9-tetrahydro-5H-pyrimido[4,5-d]azepine (19.8 g, 64.1 mmol) prepared according to Process Step 2 was subjected to the procedure of Process Step 3 of Reference Example 4 and thereby yielded 2,4-dichloro-6,7,8,9-tetrahydro-5H-pyrimido[4,5-d]azepine hydrochloride (8.49 g, in a yield of 51%).

REFERENCE EXAMPLE 7

Synthesis of 2-chloro-4-(2,4-dichlorobenzylamino)-6,7,8,9-tetrahydro-5H-pyrimido4,5-d]azepine hydrochloride Process Step 1

2,4-Dichloro-6,7,8,9-tetrahydro-5H-pyrimido[4,5-d]azepine hydrochloride (4.79 g, 18.4 mmol) was suspended in dichloromethane (50 mL), and the suspension was mixed with di-tert-butyl dicarbonate (6.0 g) and triethylamine (7.7 mL), followed by stirring at room temperature for thirty minutes. The reaction mixture was mixed with a saturated aqueous sodium bicarbonate solution, was stirred for a while and was separated. The organic layer was washed with brine and was dried over anhydrous sodium sulfate. After distilling off the solvent, the whole quantity of the residue was dissolved in tetrahydrofuran (50 mL), and the solution was mixed with 2,4-dichlorobenzylamine (4.2 mL) and triethylamine (11.5 mL), followed by stirring at 40° C. for 21.5 hours. The reaction mixture was diluted with water and was extracted with ethyl acetate. The organic layer was washed with brine, was dried over anhydrous sodium sulfate, and the solvent was distilled off. The residue was mixed with ethyl acetate for crystallization. The precipitated crystals were collected by filtration, were dried and thereby yielded tert-butyl 2-chloro-4-(2,4-dichlorobenzylamino)-6,7,8,9-tetrahydro-5H-pyrimido[4,5-d]azepine-7-carboxylate (4.27 g). After concentrating the filtrate, the residue was purified by silica gel column chromatography (n-hexane:ethyl acetate=3:1) and thereby yielded the target compound (0.76 g, 5.03 g in total with the above-mentioned crystals, in a yield of 60%).

Process Step 2

Tert-butyl 2-chloro-4-(2,4-dichlorobenzylamino)-6,7,8,9-tetrahydro-5H-pyrimido[4,5-d]azepine-7-carboxylate (5.0 g) prepared according to Process Step 1 was dissolved in methanol (100 mL), and the solution was mixed with a solution of hydrogen chloride in ethyl acetate (4 mol/L, 30 mL), followed by stirring at room temperature for sixteen hours. After concentrating the reaction mixture, the residue was mixed with diethyl ether for crystallization. The precipitated crystals were collected by filtration, were dried and thereby yielded 2-chloro-4-(2,4-dichlorobenzylamino)-6,7,8,9-tetrahydro-5H-pyrimido[4,5-d]azepine hydrochloride (4.89 g, in a quantitative yield).

REFERENCE EXAMPLE 8

Synthesis of 1-[6-tert-butoxycarbonyl-4-(2-chloro-4-fluorobenzylamino)-5,6,7,8-tetrahydropyrido[4,3-d]pyrimidin-2-yl]piperidine-4-carboxylic acid Process Step 1

2,4-Dichloro-5,6,7,8-tetrahydropyrido[4,3-d]pyrimidine hydrochloride (20.0 g, 83.2 mmol) prepared according to Reference Example 1 was dissolved in acetonitrile (200 mL), and the solution was mixed with dimethylaminopyridine (752 mg), di-tert-butyl dicarbonate (20.9 g) and triethylamine (11.6 mL), followed by stirring at room temperature for sixteen hours. After checking the completion of the reaction by thin layer chromatography, the reaction mixture was concentrated, and the residue was dissolved in ethyl acetate. The solution was sequentially washed with a 5% aqueous citric acid solution, water, a saturated aqueous sodium bicarbonate solution and brine, was dried over anhydrous magnesium sulfate, and the solvent was distilled off under reduced pressure. The residue was purified by silica gel column chromatography (n-hexane:ethyl acetate=5:1) and thereby yielded tert-butyl 2,4-dichloro-5,6,7,8-tetrahydropyrido[4,3-d]pyrimidine-6-carboxylate (22.2 g, in a yield of 88%).

Process Step 2

Tert-butyl 2,4-dichloro-5,6,7,8-tetrahydropyrido[4,3-d]pyrimidine-6-carboxylate (8.30 g, 27.2 mmol) prepared according to Process Step 1 was dissolved in tetrahydrofuran (80 mL), and the solution was mixed with 2-chloro-4-fluorobenzylamine (8.69 g, 54.4 mmol) and triethylamine (11.4 mL), followed by stirring at 40° C. for 15.5 hours. Crystals precipitated in the reaction mixture were separated by filtration, and the solvent was distilled off from the filtrate. The precipitated crystals were reslurried from a 3:1 mixture of hexane and ethyl acetate and thereby yielded tert-butyl 2-chloro-4-(2-chloro-4-fluorobenzylamino)-5,6,7,8-tetrahydro pyrido[4,3-d]pyrimidine-6-carboxylate (9.99 g, 23.4 mmol, in a yield of 86%).

Process Step 3

Tert-butyl 2-chloro-4-(2-chloro-4-fluorobenzylamino)-5,6,7,8-tetrahydro pyrido[4,3-d]pyrimidine-6-carboxylate (7.88 g, 18.4 mmol) prepared according to Process Step 2 was dissolved in dioxane (140 mL), and the solution was mixed with ethyl 4-piperidinecarboxylate (5.8 g) and sodium carbonate (19.5 g), followed by stirring at 90° C. for 16.5 hours. After checking the completion of the reaction by thin layer chromatography, the reaction mixture was diluted with water and was extracted with ethyl acetate. The organic layer was sequentially washed with water and brine, was dried over anhydrous magnesium sulfate, and the solvent was distilled off under reduced pressure. The residue was purified by silica gel column chromatography (n-hexane:ethyl acetate=5:1) and thereby yielded ethyl 1-[6-tert-butoxycarbonyl-4-(2-chloro-4-fluorobenzylamino)-5,6,7,8-tetrahydropyrido[4,3-d]pyrimidin-2-yl]piperidine-4-carboxylate (9.16 g, 16.1 mmol, in a yield of 88%).

Process Step 4

Ethyl 1-[6-tert-butoxycarbonyl-4-(2-chloro-4-fluorobenzylamino)-5,6,7,8-tetrahydropyrido[4,3-d]pyrimidin-2-yl]piperidine-4-carboxylate (9.16 g, 16.1 mmol) prepared according to Process Step 3 was dissolved in ethanol (300 mL), and the solution was mixed with an aqueous sodium hydroxide solution (1 mol/L, 32 mL), followed by stirring at 65° C. for sixteen hours. After checking the completion of the reaction by thin layer chromatography, the reaction mixture was mixed with water and washed with diethyl ether. The aqueous layer was neutralized with diluted hydrochloric acid (1 mol/L, 35 mL), the precipitated crystals were collected by filtration and thereby yielded 1-[6-tert-butoxycarbonyl-4-(2-chloro-4-fluorobenzylamino)-5,6,7,8-tetrahydropyrido[4,3-d]pyrimidin-2-yl]piperidine-4-carboxylic acid (3.94 g). The filtrate was extracted with dichloromethane, the organic layer was washed with brine, was dried over anhydrous magnesium sulfate, and the solvent was distilled off. The residue was mixed with diethyl ether for crystallization. The precipitated crystals were collected by filtration and thereby yielded crystals of the target compound (1.07 g, 5.01 g in total with the above-mentioned crystals, in a yield of 62%).

REFERENCE EXAMPLE 9

Synthesis of 2,4-dichloro-5,6,7,8-tetrahydropyrido[4,3-d]pyrimidin-6-yl-N-ethylcarboxamide 2,4-Dichloro-5,6,7,8-tetrahydropyrido[4,3-d]pyrimidine hydrochloride (2.0 g, 8.3 mmol) prepared according to Reference Example 1 was dissolved in ethyl acetate (20 mL), and the solution was mixed with triethylamine (1.4 mL) and ethyl isocyanate (0.89 mL), followed by stirring at room temperature for twelve hours. After checking the completion of the reaction by thin layer chromatography, the reaction mixture was diluted with water and was extracted with ethyl acetate. The organic layer was washed with brine, was dried over anhydrous magnesium sulfate, and the solvent was distilled off under reduced pressure, to thereby yield 2,4-dichloro-5,6,7,8-tetrahydropyrido[4,3-d]pyrimidin-6-yl-N-ethylcarboxamide (2.3 g, in a quantitative yield).

REFERENCE EXAMPLE 10

Synthesis of 6-benzyl-2,4-dibromo-5,6,7,8-tetrahydropyrido[4,3-d]pyrimidine

6-Benzyl-5,6,7,8-tetrahydropyrido[4,3-d]pyrimidine-2,4(1H,3H)-dione (5.00 g, 19.4 mmol) prepared according to Process Step 1 of Reference Example 1 was mixed with phosphorus oxybromide (30.9 g, 108 mmol) and phosphorus tribromide (39 mL), and the mixture was heated at 120° C. for fifteen hours. The reaction mixture was cooled to room temperature, was poured onto ice water and was adjusted to a pH 7 by adding a 1 mol/L sodium hydroxide solution. The solution was extracted with ethyl acetate, the organic layer was washed with brine, was dried over anhydrous sodium sulfate, and the solvent was distilled off. The residue was purified by silica gel column chromatography (hexane:ethyl acetate=92:8 to 20:80) and thereby yielded 6-benzyl-2,4-dibromo-5,6,7,8-tetrahydropyrido[4,3-d]pyrimidine (1.86 g, in a yield of 25%).

REFERENCE EXAMPLE 11

Synthesis of 1-(tert-butoxycarbonyl)-4-(3-pyrrolidin-1-ylpropyl)piperidin e-4-carboxylic acid for use in the synthesis of Compound 3-28

Process Step 1

Commercially available ethyl 1-(tert-butoxycarbonyl)piperidine-4-carboxylate (2.5 g, 9.7 mmol) was dissolved in tetrahydrofuran (25 mL), and the solution was mixed with a solution of lithium diisopropylamide in tetrahydrofuran (1.0 mol/L, 15 mL, 15 mmol) added dropwise at 78° C., followed by stirring for 30 minute. Further, the reaction mixture was mixed with 1,3-dibromopropane (4.9 mL, 49 mmol) added dropwise, and the temperature was raised to −20° C. over two hours. The reaction mixture was further mixed with diluted hydrochloric acid (0.5 mol/L, 75 mL) and was extracted with ethyl acetate. The organic layer was washed with brine, was dried over anhydrous magnesium sulfate, and the solvent was distilled off. The residue was purified by silica gel chromatography (hexane:ethyl acetate=10:1) and thereby yielded ethyl 4-(3-bromopropyl)-1-(tert-butoxycarbonyl)piperidine-4-carboxylate (2.5 g, 68%).

FAB-MS m/z: 378 $[M+H]^+$ $^1$H NMR ($CDCl_3$) δ (ppm): 1.11-2.22 (m, 20H), 2.75-3.03 (m, 2H), 3.35 (t, J=6.2 Hz, 2H), 3.70-4.00 (m, 2H), 4.18 (q, J=7.0 Hz, 2H)

Process Step 2

Ethyl 4-(3-bromopropyl)-1-(tert-butoxycarbonyl)piperidine-4-carboxylate (0.75 g, 2.0 mmol) prepared according to Process Step 1 was dissolved in methanol (7.5 mL), and the solution was mixed with pyrrolidine (1.0 mL, 12 mmol) and triethylamine (0.56 mL, 4.0 mmol), followed by stirring under reflux for two hours. After standing the reaction mixture to cool, the solvent was distilled off. After adding diluted hydrochloric acid (0.5 mol/L, 20 mL), the aqueous solution was washed with ethyl acetate. By adding an aqueous potassium hydroxide solution (2.0 mol/L) under ice-cooling, the solution was adjusted to be basic and was extracted with ethyl acetate. The organic layer was washed with brine and was dried over anhydrous sodium sulfate. After distilling off the solvent, the residue was dried under reduced pressure and thereby yielded ethyl 1-(tert-butoxycarbonyl)-4-(3-pyrrolidin-1-ylpropyl)piperidine-4-carboxylate (0.51 g, 68%).

ESI-MS m/z: 369 $[M+H]^+$ $^1$H NMR ($CDCl_3$) δ (ppm): 1.11-1.90 (m, 18H), 2.00-2.23 (m, 2H), 2.30-2.58 (m, 6H), 2.75-3.02 (m, 2H), 3.70-4.00 (m, 2H), 4.17 (q, J=7.3 Hz, 2H)

Process Step 3

Ethyl 1-(tert-butoxycarbonyl)-4-(3-pyrrolidin-1-ylpropyl)piperidine-4-carboxylate (0.12 g, 0.33 mmol) prepared according to Process Step 2 was mixed with ethanol (1.8 mL) and aqueous sodium hydroxide solution (2.0 mol/L, 1.6 mL, 3.3 mmol), followed by stirring under reflux for fifteen hours. After adjusting the pH to 7.8 by adding diluted hydrochloric acid (6.0 mol/L) added under ice-cooling, the reaction mixture was extracted with n-butanol. The organic layer was dried over anhydrous sodium sulfate. After distilling off the solvent, the residue was dried under reduced pressure and thereby yielded 1-(tert-butoxycarbonyl)-4-(3-pyrrolidin-1-ylpropyl)piperidine-4-carboxylic acid (0.10 g, 91%).

APCI-MS m/z: 341 $[M+H]^+$ $^1$H NMR ($CD_3OD$) δ (ppm): 1.11-1.85 (m, 15H), 1.90-2.21 (m, 6H), 2.85-3.38 (m, 8H), 3.72-3.92 (m, 2H)

REFERENCE EXAMPLE 12

Synthesis of tert-butyl 4-(2-pyrrolidin-1-ylacetyl)piperidinecarboxylate for use in the synthesis of Compound 3-30

Tert-butyl 4-(2-bromoacetyl)piperidinecarboxylate (0.85 g, 2.8 mmol) was dissolved in tetrahydrofuran (8.5 mL), and the solution was mixed with pyrrolidine (0.46 mL, 5.6 mmol) and triethylamine (0.78 mL, 5.6 mmol) with stirring at room temperature, followed by stirring for twenty-four hours. The reaction mixture was mixed with diluted hydrochloric acid (0.5 mol/L, 27 mL) and washed with ethyl acetate. The aqueous layer was adjusted to be basic with an aqueous potassium hydroxide solution added under ice-cooling and was extracted with ethyl acetate. The organic layer was washed with brine, was dried over anhydrous sodium sulfate, and the solvent was distilled off. The residue was dried under reduced pressure and thereby yielded tert-butyl 4-(2-pyrrolidin-1-ylacetyl)piperidinecarboxylate (0.72 g, 87%).

APCI-MS m/z: 297 $[M+H]^+$ $^1H$ NMR ($CDCl_3$) δ (ppm): 1.30-1.95 (m, 18H), 2.45-2.90 (m, 6H), 3.42 (s, 2H), 4.00-4.21 (m, 2H)

REFERENCE EXAMPLE 13

Synthesis of tert-butyl 4-(1-hydroxy-2-pyrrolidin-1-ylethyl)piperidinecarboxylate for use in the synthesis of Compound 3-29

Tert-butyl 4-(2-pyrrolidin-1-ylacetyl)piperidinecarboxylate (0.33 g, 1.1 mmol) prepared according to Reference Example 12 was dissolved in methanol (5.0 mL), and was mixed with sodium borohydride (0.13 g, 3.3 mmol) added with stirring under ice-cooling, followed by stirring at room temperature for one hour. Diluted hydrochloric acid (1.0 mol/L, 0.5 mL) was added dropwise to the reaction mixture under ice-cooling, and the solvent was distilled off. The residue was diluted with water and was extracted with ethyl acetate. The organic layer was washed with brine, was dried over anhydrous sodium sulfate, and the solvent was distilled off. The residue was dried under reduced pressure and thereby yielded tert-butyl 4-(1-hydroxy-2-pyrrolidin-1-ylethyl)piperidinecarboxylate (0.24 g, 73%).

APCI-MS m/z: 299 $[M+H]^+$ $^1H$ NMR ($CDCl_3$) δ (ppm): 1.11-1.95 (m, 18H), 2.25-2.80 (m, 8H), 3.33-3.50 (m, 1H), 4.00-4.30 (m, 2H)

REFERENCE EXAMPLE 14

Synthesis of tert-butyl 3-oxo-4-(3-pyrrolidin-1-yl-propyl)piperazinecarboxylate for use in the synthesis of Compound 3-31

Tert-butyl 3-oxo-piperazinecarboxylate (1.5 g, 7.5 mmol) was dissolved in tetrahydrofuran (15 mL), and the solution was mixed with sodium bis(trimethylsilyl)amide (1.0 mol/L, 15 mL, 15 mmol) added dropwise with stirring under ice-cooling. After ten minutes, 1,3-dibromopropane (3.0 mL, 30 mmol) was added dropwise. The reaction mixture was heated to 50° C., was stirred for three hours, was poured onto water and was extracted with ethyl acetate. The organic layer was washed with brine, was dried over anhydrous sodium sulfate, and the solvent was distilled off. The residue was purified by silica gel chromatography (hexane:ethyl acetate=1:2) to thereby remove residual raw materials, and the solvent was distilled off. The residue was dissolved in dimethylformamide (12 mL), and the solution was mixed with pyrrolidine (1.6 mL, 19 mmol) and potassium carbonate (0.57 g, 4.1 mmol), followed by stirring at 80° C. for eight hours. The reaction mixture was diluted with water and was extracted with ethyl acetate. The organic layer was mixed with diluted hydrochloric acid (1.0 mol/L, 30 mL), and the organic layer and the aqueous layer were separated. The aqueous layer was adjusted to be basic with an aqueous sodium hydroxide solution (2.0 mol/L) and was extracted with ethyl acetate. The organic layer was washed with brine, was dried over anhydrous sodium sulfate, and the solvent was distilled off. The residue was purified by silica gel chromatography (chloroform:7.0 mol/L ammonia methanol solution=30:1) and thereby yielded tert-butyl 3-oxo-4-(3-pyrrolidin-1-yl-propyl)piperazinecarboxylate (0.16 g, 6.8%).

APCI-MS m/z: 312 $[M+H]^+$ $^1H$ NMR ($CDCl_3$) δ (ppm): 1.46 (s, 9H), 1.67-1.95 (m, 6H), 2.33-2.69 (m, 6H), 3.31-3.73 (m, 6H), 4.05 (s, 2H)

REFERENCE EXAMPLE 15

Synthesis of Compound (XXII-b-i) for use in Example 22

(XXII-b-i)

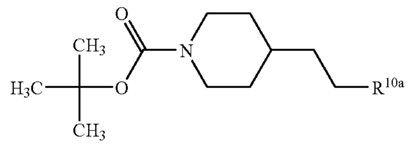

(wherein $R^{10a}$ has the same meaning as defined above)

Commercially available tert-butyl 4-(2-methanesulfonyloxyethyl)-piperidine-1-carboxylate (0.100 mmol) was dissolved in dioxane (0.200 mL), and the solution was mixed with a solution of $R^{10a}$—H, wherein $R^{10a}$ is as defined above, in chloroform (1.00 mol/L, 0.200 mL, 0.200 mmol) and sodium carbonate (70.0 mg), followed by stirring at 90° C. for eighteen hours. The reaction mixture was filtrated, and the filtrate was concentrated under reduced pressure. The residue was dissolved in chloroform (0.500 mL), and the solution was mixed with N-methylisatoic anhydride polystyrene (2% divinylbenzene copolymer, about 2.60 mmol/g, 100 mg, available from Nova biochem), followed by stirring at room temperature for twelve hours. The resin was separated from the reaction mixture by filtration, the filtrate was concentrated and thereby yielded Compound (XXII-b-i).

REFERENCE EXAMPLE 16

Synthesis of Compound (XXII-b-ii) for use in Example 23

(XXII-b-ii)

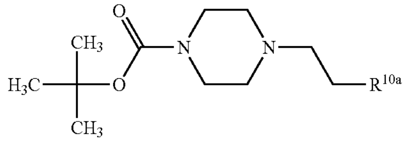

(wherein $R^{10a}$ has the same meaning as defined above)

Commercially available tert-butyl 4-(2-chloroethyl)-piperazine-1-carboxylate (0.120 mmol) was dissolved in dioxane (0.240 mL), and the solution was mixed with a solution of $R^{10a}$—H, wherein $R^{10a}$ is as defined above, in chloroform (1.00 mol/L, 0.200 mL, 0.200 mmol), a solution of potassium iodide in dimethylformamide (1.00 mol/L, 0.200 mL, 0.200 mmol) and sodium carbonate (70.0 mg), followed by stirring at 90° C. for two days. The reaction mixture was filtrated, and the filtrate was concentrated under reduced pressure. The residue was dissolved in chloroform and washed with water. The organic layer was dried over anhydrous magnesium sulfate and was concentrated under reduced pressure. The residue was dissolved in chloroform, and the solution was mixed with N-methylisatoic anhydride polystyrene (2% divinylbenzene copolymer, about 2.60 mmol/g, 100 mg, available from Novabiochem), followed by stirring at room temperature for fourteen hours. The resin was separated from the reaction mixture by filtration, the filtrate was concentrated and thereby yielded Compound (XXII-b-ii).

REFERENCE EXAMPLE 17

Synthesis of Compound (XXII-b-iii) for use in Example 24

(XXII-b-iii)

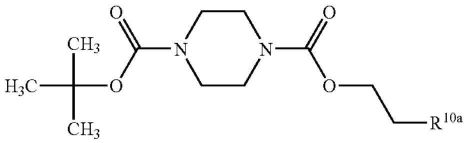

(wherein $R^{10a}$ has the same meaning as defined above)

Commercially available tert-butyl 4-(2-bromoethoxycarbonyl)-piperazine-1-carboxylate (0.100 mmol) was dissolved in dioxane (0.400 mL), and the solution was mixed with a solution of $R^{1a}$—H (wherein $R^{10a}$ is as defined above) in chloroform-(1.00 mol/L, 0.200 mL, 0.200 mmol) and sodium carbonate (70.0 mg), followed by stirring at 90° C. for two days. The reaction mixture was filtrated, and the filtrate was concentrated under reduced pressure. The residue was dissolved in chloroform (0.500 mL), and the solution was mixed with N-methylisatoic anhydride polystyrene (2% divinylbenzene copolymer, about 2.60 mmol/g, 100 mg, available from Novabiochem), followed by stirring at room temperature for fourteen hours. The resin was separated from the reaction mixture by filtration, the filtrate was concentrated and thereby yielded Compound (XXII-b-iii).

REFERENCE EXAMPLE 18

Synthesis of 4-methylmorpholine-2-carboxylic acid for use in the syntheses of Compound 15-32 and 15-35

The title compound was prepared from 2-chloroacrylonitrile through two process steps in the same way as Tetrahedron Letters, vol. 32, p. 2281 (1991).

REFERENCE EXAMPLE 19

Synthesis of 4-methyl-2-piperazin-1-ylmethylmorpholine for use in the syntheses of Compounds 15-36 to 15-56, 15-58, 15-59, 15-61, 16-5 through 16-10 and 22-1 to 22-4

Process Step 1

4-Benzyl-2-(chloromethyl)morpholine (9.40 g, 42.0 mmol) described in Journal of Medicinal Chemistry, vol. 33, p. 1406 (1990) was dissolved in dimethylformamide (180 mL), and the solution was mixed with tert-butyl 1-piperazinecarboxylate (13.2 g, 71.0 mmol), potassium carbonate (9.80 g, 71.0 mmol) and sodium iodide (10.6 g, 71.0 mmol), followed by stirring at 100° C. for twenty-four hours. After standing to cool, the reaction mixture was mixed with chloroform (300 mL) and water (300 mL) and was separated. The organic layer was washed with brine (300 mL), was dried over anhydrous magnesium sulfate, and the solvent was distilled off under reduced pressure. The resulting brown oil was purified by silica gel column chromatography (hexane:ethyl acetate=1:2) and thereby yielded tert-butyl 4-(4-benzylmorpholin-2-ylmethyl)piperazinecarboxylate (10.1 g, 64%).

Process Step 2

Tert-butyl 4-(4-benzylmorpholin-2-ylmethyl)piperazinecarboxylate (10.1 g, 27.0 mmol) prepared according to Process Step 1 was dissolved in ethanol (100 mL), and the solution was mixed with 10% palladium hydroxide-carbon (3.80 g), followed by stirring at room temperature under the hydrogen gas atmosphere for twelve hours. The reaction mixture was mixed with Celite (registered trademark: about 5 g), was filtrated under reduced pressure, and the filtrate was concentrated under reduced pressure. The solid was dissolved in methanol (100 mL). The solution was mixed with 37% aqueous formaldehyde solution (5.50 mL, 61.0 mmol) added dropwise and was further mixed with sodium cyanoborohydride (3.90 g, 61.0 mmol) added under ice-cooling, followed by stirring at room temperature for one hour. The reaction mixture was mixed with chloroform (50 mL) and a saturated aqueous sodium bicarbonate solution (50 mL), followed by separation. The organic layer was washed with brine (100 mL), was dried over anhydrous magnesium sulfate, and the solvent was distilled off under reduced pressure. The resulting pale yellow oil was purified by silica gel column chromatography (chloroform:methanol=10:1) and thereby yielded tert-butyl 4-(4-methylmorpholin-2-ylmethyl)piperazine-1-carboxylate (5.70 g, 71%).

Process Step 3

Tert-butyl 4-(4-methylmorpholin-2-ylmethyl)piperazine-1-carboxylate (5.00 g, 17.0 mmol) prepared according to Process Step 2 was dissolved in dichloromethane (60 mL), and the solution was mixed with trifluoroacetic acid (20 mL) added dropwise under ice-cooling. After stirring at room temperature for one hour, the solvent was distilled off under reduced pressure. The resulting yellow oil was dissolved in dioxane (100 mL), and the solution was mixed with triethylamine (20 mL) to thereby yield 4-methyl-2-piperazin-1-ylmethylmorpholine.

Optically active substances relating to the 2-position of the morpholine ring were synthetically prepared by the above procedure, except for using corresponding optically active isomers of 4-benzyl-2-chloromethylmorpholine as starting materials, respectively.

REFERENCE EXAMPLE 20

Synthesis of (2R)-4-ethyl-2-(piperazinylmethyl)morpholine for use in the syntheses of Compounds 15-57, 15-60, 16-11 and 16-12

Process Step 1

A solution of tert-butyl 4-((2R)-4-benzylmorpholin-2-ylmethyl)piperazinecarboxylate (2.00 g, 5.32 mmol) prepared in the same way as Process Step 1 of Reference Example 19 in ethanol (20 mL) was mixed with 10% palladium hydroxide-carbon (0.75 g), followed by stirring at room temperature under the hydrogen gas atmosphere for twelve hours. The reaction mixture was mixed with Celite (registered trademark: about 5 g), was filtrated under reduced pressure, and the filtrate was concentrated under reduced pressure. The solid was dissolved in ethanol (20 mL), and the solution was mixed with acetaldehyde (0.60 mL, 10.6 mmol) added dropwise and was further mixed with sodium cyanoborohydride (0.67 g, 10.6 mmol) added under ice-cooling, followed by stirring at room temperature for one hour. The reaction mixture was mixed with chloroform (20 mL) and a saturated aqueous sodium bicarbonate solution (20 mL), followed by separation. The organic layer was washed with brine (50 mL), was dried over anhydrous magnesium sulfate, and the solvent was distilled off under reduced pressure. The resulting pale yellow oil was purified by silica gel column chromatography (chloroform:methanol=10:1) and thereby yielded tert-butyl 4-((2R)-4-ethylmorpholin-2-ylmethyl)piperazinecarboxylate (0.50 g, 30%).

Process Step 2

Tert-butyl 4-((2R)-4-ethylmorpholin-2-ylmethyl)piperazinecarboxylate (0.50 g, 1.60 mmol) prepared according to Process Step 1 was dissolved in dichloromethane (5 mL), and the solution was mixed with trifluoroacetic acid (2 mL) added dropwise under ice-cooling. After stirring at room temperature for one hour, the solvent was distilled off under reduced pressure. The resulting yellow oil was dissolved in dioxane (6 mL), and the solution was mixed with triethylamine (3 mL) to thereby yield (2R)-4-ethyl-2-(piperazinylmethyl)morpholine.

REFERENCE EXAMPLE 21

Synthesis of 4-methyl-3-(piperazinylmethyl)morpholine for use in the syntheses of Compounds 15-62 to 15-64 Process Step 1

(4-Benzylmorpholin-3-yl)methanol (3.00 g, 22.9 mmol) described in Journal of Chemical Society, Perkin Transactions 1, p. 2577 (1985) was dissolved in tetrahydrofuran (5 mL), and the solution was mixed with triethylamine (6.30 mL, 49.2 mmol) and methanesulfonic anhydride (3.20 g, 18.5 mmol), followed by stirring at room temperature for two hours. After checking the completion of the reaction by thin layer chromatography, the reaction mixture was mixed with chloroform (50 mL) and a saturated aqueous sodium bicarbonate solution (50 mL), followed by separation. The organic layer was washed with brine (100 mL), was dried over anhydrous magnesium sulfate, and the solvent was distilled off under reduced pressure. The resulting pale yellow oil was dissolved in dioxane (50 mL), and the solution was mixed with tert-butyl 1-piperazinecarboxylate (3.44 g, 18.5 mmol) and sodium carbonate (19.6 g, 185 mmol), followed by stirring at 80° C. for eighteen hours. After standing to cool, the reaction mixture was mixed with chloroform (50 mL) and water (50 mL), followed by separation. The organic layer was washed with brine (100 mL), was dried over anhydrous magnesium sulfate, and the solvent was distilled off under reduced pressure. The resulting brown oil was purified by silica gel column chromatography (hexane:ethyl acetate=1:1) and thereby yielded tert-butyl 4-(4-benzylmorpholin-3-ylmethyl)piperazinecarboxylate (2.79 g, 60%).

Process Step 2

Tert-butyl 4-(4-benzylmorpholin-3-ylmethyl)piperazinecarboxylate (2.17 g, 5.77 mmol) prepared according to Process Step 1 was dissolved in ethanol (20 mL), and the solution was mixed with 10% palladium hydroxide-carbon (1.62 g), followed by stirring at room temperature under the hydrogen gas atmosphere for twelve hours. The reaction mixture was mixed with Celite (registered trademark: about 5 g), was filtrated under reduced pressure, and the filtrate was concentrated under reduced pressure. The solid was dissolved in methanol (20 mL), and the solution was mixed with 37% aqueous formaldehyde solution (1.03 mL, 11.5 mmol) added dropwise and was further mixed with sodium cyanoborohydride (0.73 g, 11.5 mmol) added under ice-cooling, followed by stirring at room temperature for one hour. The reaction mixture was mixed with chloroform (50 mL) and a saturated aqueous sodium bicarbonate solution (50 mL), followed by separation. The organic layer was washed with brine (100 mL), was dried over anhydrous magnesium sulfate, and the solvent was distilled off under reduced pressure. The resulting pale yellow oil was purified by silica gel column chromatography (n-hexane:ethyl acetate=3:2) and thereby yielded tert-butyl 4-(4-methylmorpholin-3-ylmethyl)piperazinecarboxylate (1.05 g, 61%).

Process Step 3

Tert-butyl 4-(4-methylmorpholin-3-ylmethyl)piperazinecarboxylate (5.00 g, 16.7 mmol) prepared according to Process Step 2 was dissolved in dichloromethane (60 mL), and the solution was mixed with trifluoroacetic acid (20 mL) added dropwise under ice-cooling. After stirring the reaction mixture at room temperature for one hour, the solvent was distilled off under reduced pressure. The resulting yellow oil was dissolved in dioxane (100 mL), the solution was mixed with triethylamine (20 mL) and thereby yielded 4-methyl-3-(piperazinylmethyl)morpholine.

REFERENCE EXAMPLE 22

Synthesis of 4-benzyl-2-(3-piperazin-1-ylpropyl)morpholine for use in the synthesis of Compound 15-66

Process Step 1

3-(4-Benzylmorpholin-2-yl)propan-1-ol (1.30 g, 5.52 mmol, Journal of Medicinal Chemistry, vol. 33, p. 1406 (1990)) was dissolved in dichloromethane (20 mL), and the solution was mixed with triethylamine (1.53 mL, 11.0 mmol) and methanesulfonyl chloride (0.640 mL, 8.28 mmol) added dropwise under ice-cooling, followed by stirring at room temperature for thirty minutes. The reaction mixture was mixed with a saturated aqueous sodium bicarbonate solution (50 mL) and chloroform (200 mL), followed by separation. The organic layer was dried over anhydrous magnesium sulfate, and the solvent was distilled off under reduced pressure, to thereby yield 3-(4-benzylmorpholin-2-yl)propyl methanesulfonate (1.72 g, in a yield of 99%).

Process Step 2

3-(4-Benzylmorpholin-2-yl)propyl methanesulfonate (1.30 g, 4.15 mmol) prepared according to Process Step 1 was dissolved in dioxane (20 mL), and the solution was mixed with tert-butyl 1-piperazinecarboxylate (1.55 g, 8.30 mmol) and sodium carbonate (6.60 g, 62.3 mmol), followed by stirring at 90° C. for two days. The reaction mixture was cooled and was mixed with water (100 mL) and chloroform (300 mL), followed by separation. The organic layer was dried over anhydrous magnesium sulfate, and the solvent was distilled off under reduced pressure, to thereby yield tert-butyl 4-[3-(4-benzylmorpholin-2-yl)propyl]piperazinecarboxylate (1.67 g, in a yield of 100%).

Process Step 3

Tert-butyl 4-[3-(4-benzylmorpholin-2-yl)propyl]piperazinecarboxylate prepared according to Process Step 2 was dissolved in dichloromethane, the solution was treated with trifluoroacetic acid and thereby yielded 4-benzyl-2-(3-piperazin-1-ylpropyl)morpholine (in a quantitative yield).

REFERENCE EXAMPLE 23

Synthesis of Compound (XIV-j-i) for use in the syntheses of Compounds 18-1 through 18-16

(XIV-j-i)

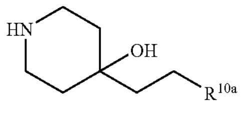

(wherein $R^{10a}$ has the same meaning as defined above)

Process Step 1

Powdered zinc (2.82 g, 0.043 mol) was suspended in tetrahydrofuran (50.0 mL) under the argon gas flow, and the suspension was mixed with ethyl bromoacetate (6.01 g, 0.036 mol) at room temperature. After stirring under reflux for five minutes, the mixture was further mixed with a solution of tert-butyl 4-oxopiperidinecarboxylate in tetrahydrofuran (3.00 mol/L, 10.0 mL, 0.030 mol), followed by stirring under reflux for two hours. After checking the completion of the reaction by thin layer chromatography, the reaction mixture was mixed with ethyl acetate and diluted hydrochloric acid (1.00 mol/L), followed by separation. The organic layer was sequentially washed with a saturated aqueous sodium bicarbonate solution and brine, was dried over anhydrous magnesium sulfate, and the solvent was distilled off under reduced pressure. The residue was purified by silica gel column chromatography (hexane:ethyl acetate=6:1) and thereby yielded tert-butyl 4-ethoxycarbonylmethyl-4-hydroxypiperidinecarboxylate (5.38 g, 62%).

Process Step 2

Lithium aluminum hydride (0.314 g, 8.27 mmol) was suspended in tetrahydrofuran (15.0 mL) underice-cooling, and the suspension was mixed with a solution of tert-butyl 4-ethoxycarbonylmethyl-4-hydroxypiperidinecarboxylate prepared according to Process Step 1 in tetrahydrofuran (0.420 mol/L, 20.0 mL, 8.40 mmol), followed by stirring under reflux for two hours. After checking the completion of the reaction by thin layer chromatography, the reaction mixture was mixed with sodium sulfate decahydrate (2.67 g, 8.29 mmol), followed by stirring at room temperature for one hour. The precipitate in the reaction mixture was separated by filtration, and the filtrate was concentrated under reduced pressure. The residue was purified by silica gel chromatography (hexane:ethyl acetate=2:1) and thereby yielded tert-butyl 4-hydroxy-4-(2-hydroxyethyl)piperidinecarboxylate (1.77 g, 86%).

Process Step 3

Tert-butyl 4-hydroxy-4-(2-hydroxyethyl)piperidinecarboxylate (1.67 g, 6.81 mmol) prepared according to Process Step 2 was dissolved in tetrahydrofuran (50.0 mL), and the solution was sequentially mixed with triethylamine (0.891 g, 8.81 mmol) and methanesulfonic anhydride (1.53 g, 8.78 mmol) added under ice-cooling, followed by stirring at room temperature for two hours. After checking the completion of the reaction by thin layer chromatography, the reaction mixture was diluted with ethyl acetate and was mixed with a saturated aqueous sodium bicarbonate solution, followed by separation. The organic layer was washed with brine, was dried over anhydrous magnesium sulfate, and the solvent was distilled off under reduced pressure, to thereby yield tert-butyl 4-hydroxy-4-(2-methanesulfonyloxyethyl)-piperidinecarboxylate (2.20 g, in a quantitative yield). This compound was subjected to a subsequent reaction without further purification.

Process Step 4

A solution of tert-butyl 4-hydroxy-4-(2-methanesulfonyloxyethyl)-piperidinecarboxylate prepared according to Process Step 3 in dioxane (0.200 mol/L, 0.300 mL, 0.060 mmol) was mixed with a solution of $R^{10a}$—H (wherein $R^{10a}$ has the same meaning as defined above) in chloroform (1.00 mol/L, 0.120 mL, 0.120 mmol) and sodium carbonate (70.0 mg), followed by stirring at 90° C. for twelve hours. The reaction mixture was filtrated, and the filtrate was mixed with N-methylisatoic anhydride polystyrene (2% divinylbenzene copolymer, about 2.60 mmol/g, 100 mg, available from Nova biochem), followed by stirring at room temperature for twelve hours. The resin was separated from the reaction mixture by filtration, and the filtrate was concentrated. The resulting solid was mixed with a solution of trifluoroacetic acid in dichloromethane (20%, 0.500 mL), followed by stirring at room temperature for four hours. The reaction mixture was concentrated under reduced pressure and thereby yielded title Compound (XIV-j-i).

REFERENCE EXAMPLE 24

Synthesis of tert-butyl 4-(ethoxycarbonyldifluoromethyl)-4-hydroxypiperidinecarboxylate for use in the syntheses of Compounds 19-1 through 19-4

Powdered zinc (2.82 g, 0.043 mol) was suspended in tetrahydrofuran (50.0 mL) under flow of argon gas, and the suspension was mixed with ethyl bromodifluoroacetate (7.31 g, 0.036 mol) at room temperature, followed by stirring under reflux for five minutes. The mixture was further mixed with a solution of tert-butyl 4-oxopiperidinecarboxylate in tetrahydrofuran (3.00 mol/L, 10.0 mL, 0.030 mol), followed by stirring under reflux for two hours. After checking the completion of the reaction by thin layer chromatography, the reaction mixture was mixed with ethyl acetate and diluted hydrochloric acid (1.00 mol/L), followed by separation. The organic layer was sequentially washed with a saturated aqueous sodium bicarbonate solution and brine, was dried over anhydrous magnesium sulfate, and the solvent was distilled off under reduced pressure. The residue was purified by silica gel column chromatography (hexane: chloroform=1:9) and thereby yielded tert-butyl 4-(ethoxycarbonyldifluoromethyl)-4-hydroxy-piperidinecarboxylate (7.39 g, 76%).

REFERENCE EXAMPLE 25

Synthesis of 2-(3-pyrrolidin-1-ylpropyl)morpholine hydrochloride for use in the syntheses of Compounds 20-1, 20-5 and 20-6

Process Step 1

3-(4-Benzylmorpholin-2-yl)propylmethanesulfonate (400 mg, 1.28 mmol) prepared according to Process Step 1 of Reference Example 22 was dissolved in dioxane (8 mL), and the solution was mixed with pyrrolidine (0.535 mL, 6.38 mmol) and sodium carbonate (2.0 g, 19.2 mmol), followed by stirring at 90° C. for twenty hours. The reaction mixture was cooled and was mixed with water (50 mL) and chloroform (100 mL), followed by separation. The organic layer was dried over anhydrous magnesium sulfate, and the solvent was distilled off under reduced pressure. The residue was purified by silica gel column chromatography (chloroform:methanol=5:1) and thereby yielded 4-benzyl-2-(3-pyrrolidin-1-yl-propyl)morpholine (190 mg, in a yield of 52%).

Process Step 2

4-Benzyl-2-(3-pyrrolidin-1-yl-propyl)morpholine (180 mg, 0.62 mmol) prepared according to Process Step 1 was dissolved in 1,2-dichloroethane (5 mL), and the solution was mixed with triethylamine (0.086 mL, 0.62 mmol) and 1-chloroethyl chloroformate (0.20 mL, 1.87 mmol), followed by stirring under reflux for three hours. The reaction mixture was cooled and was mixed with 1,2-dichloroethane (50 mL) and water (50 mL), followed by separation. The organic layer was washed with brine (50 mL), was dried over anhydrous magnesium sulfate, and the solvent was distilled off under reduced pressure. The residue was dissolved in methanol (5 mL), followed by stirring under reflux for one hour. After distilling off the solvent under reduced pressure, diethyl ether (5 mL) was added for crystallization, and the precipitated crystals were collected by filtration. The crystals were dried under reduced pressure and thereby yielded 2-(3-pyrrolidin-1-ylpropyl)morpholine hydrochloride (135 mg, in a yield of 93%).

REFERENCE EXAMPLE 26

Synthesis of 2-(4-methylpiperazin-1-ylmethyl)morpholine for use in the synthesis of Compound 20-2

Lithium aluminum hydride (150 mg, 4.10 mmol) was suspended in tetrahydrofuran (5 mL), and the suspension was mixed with a solution of tert-butyl 4-morpholin-2-ylmethylpiperazinecarboxylate (390 mg, 1.37 mmol) prepared as an intermediate according to Process Step 2 of Reference Example 19 in tetrahydrofuran (5 mL) added dropwise under ice-cooling, followed by heating at 60° C. under reflux for two hours. An aqueous sodium hydroxide solution (2 mol/L, 10 mL) and chloroform (50 mL) were added under ice-cooling, followed by separation. The organic layer was dried over anhydrous magnesium sulfate, and the solvent was distilled off under reduced pressure, to thereby yield the title compound (180 mg, in a yield of 66%).

REFERENCE EXAMPLE 27

Synthesis of 2-(pyrrolidin-1-ylmethyl)morpholine for use in the synthesis of Compound 20-3

Process Step 1

4-Benzyl-2-chloromethylmorpholine (500 mg, 2.22 mmol, Journal of Medicinal Chemistry, vol. 33, p. 1406 (1990)) was dissolved in dioxane (10 mL), and the solution was mixed with pyrrolidine (0.930 mL, 11.0 mmol) and sodium carbonate (2.0 g, 19.2 mmol), followed by stirring at 90° C. for twenty hours. The reaction mixture was cooled and was mixed with water (50 mL) and chloroform (100 mL), followed by separation. The organic layer was dried over anhydrous magnesium sulfate, and the solvent was distilled off under reduced pressure. The residue was purified by silica gel column chromatography (chloroform:methanol=5:1) and thereby yielded 4-benzyl-2-(pyrrolidin-1-ylmethyl)morpholine (460 mg, in a yield of 80%).

Process Step 2

4-Benzyl-2-(pyrrolidin-1-ylmethyl)morpholine (450 mg, 1.73 mmol) prepared according to Process Step 1 was dissolved in ethanol (10 mL), and 20% palladium hydroxide-carbon (200 mg, 0.285 mmol) was suspended therein, followed by stirring under the hydrogen gas atmosphere for two days. Celite (registered trademark: 2.0 g) was suspended in the reaction mixture, the solid was separated by filtration, and the solvent was distilled off under reduced pressure from the filtrate. The residue was purified by silica gel column chromatography (chloroform:methanol=5:1) and thereby yielded 2-(pyrrolidin-1-ylmethyl)morpholine (280 mg, in a yield of 95%).

REFERENCE EXAMPLE 28

Synthesis of 2-(2-pyrrolidin-1-ylethyl)morpholine hydrochloride for use in the synthesis of Compound 20-4

Process Step 1

2-(4-Benzylmorpholin-2-yl)acetate (400 mg, 1.70 mmol, Journal of Medicinal Chemistry, vol. 36, p. 1356 (1993)) was dissolved in dimethylformamide (5 mL), and the solution was mixed with 1-hydroxybenzotriazole monohydrate (520 mg, 3.40 mmol), N-ethyl-N'-(3-dimethylaminopropyl)carbodiimide hydrochloride (652 mg. 3.40 mmol), triethylamine (472 mL, 3.40 mmol) and pyrrolidine (0.285 mL, 3.40 mmol), followed by stirring at 60° C. for one hour. The reaction mixture was cooled and was mixed with water (50 mL) and chloroform (200 mL), followed by separation. The organic layer was dried over anhydrous magnesium sulfate, and the solvent was distilled off under reduced pressure. The residue was purified by silica gel column chromatography (chloroform:methanol=10:1) and thereby yielded 2-(4-benzylmorpholin-2-yl)-1-pyrrolidinylethanone (420 mg, in a yield of 86%).

Process Step 2

Lithium aluminum hydride (85 mg, 2.29 mmol) was suspended in tetrahydrofuran (5 mL), and the suspension was mixed with a solution of 2-(4-benzylmorpholin-2-yl)-1-pyrrolidin-1-ylethanone prepared according to Process Step 2 (330 mg, 1.14 mmol) in tetrahydrofuran (5 mL) added dropwise under ice-cooling, followed by stirring at 60° C. for thirty minutes. An aqueous sodium hydroxide solution (2 mol/L, 10 mL) and chloroform (50 mL) were added under ice-cooling, followed by separation. The organic layer was dried over anhydrous magnesium sulfate, and the solvent was distilled off under reduced pressure, to thereby yield 4-benzyl-2-(2-pyrrolidin-1-ylethyl)morpholine (290 mg, in a yield of 92%).

Process Step 3

4-Benzyl-2-(2-pyrrolidin-1-ylethyl)morpholine prepared according to Process Step 2 was treated in the same way as Process Step 2 of Reference Example 25, to thereby yield 2-(2-pyrrolidin-1-ylethyl)morpholine hydrochloride (213 mg, in a yield of 83%).

REFERENCE EXAMPLE 29

Synthesis of 8-(3-morpholin-2-ylpropyl)-1,4-dioxa-8-azaspiro[4,5]decane hydrochloride for use in the syntheses of Compounds 20-7 and 20-8

In the same way as Reference Example 25, 8-(3-morpholin-2-ylpropyl)-1,4-dioxa-8-azaspiro[4,5]decane hydrochloride (400 mg, in a yield of 90%) was prepared from 3-(4-benzylmorpholin-2-yl)propyl methanesulfonate and 1,4-dioxa-8-azaspiro[4,5]decane.

REFERENCE EXAMPLE 30

8-(2-Morpholin-2-ylethyl)-1,4-dioxa-8-azaspiro[4,5]decane hydrochloride for use in the syntheses of Compounds 20-12 and 20-13

In the same way as Reference Example 28, 8-(2-morpholin-2-ylethyl)-1,4-dioxa-8-azaspiro[4,5]decane hydrochloride was prepared from 2-(4-benzylmorpholin-2-yl)acetate and 1,4-dioxa-8-azaspiro[4,5]decane.

REFERENCE EXAMPLE 31

Syntheses of 2-[2-(4-fluoropiperdino)ethyl]morpholine hydrochloride and 2-[2-(4,4-difluoropiperdino)ethyl]morpholine hydrochloride for use in the syntheses of Compounds 20-16 through 20-21

In the same way as Reference Example 28, 2-[2-(4-fluoropiperdino)ethyl]morpholine hydrochloride and 2-[2-(4,4-difluoropiperdino)ethyl]morpholine hydrochloride were prepared from 2-(4-benzylmorpholin-2-yl)acetate, and 4-fluoropiperidine and 4,4-difluoropiperidine, respectively.

REFERENCE EXAMPLE 32

Synthesis of 1-methyl-3-(4-piperidyloxy)piperidine dihydrochloride for use in the syntheses of Compounds 21-1 and 21-3

Process Step 1

Commercially available 4-chloropyridine (4.00 g, 26.7 mmol) was dissolved in dimethyl sulfoxide (107 mL), and the solution was mixed with potassium tert-butoxide (6.59 g, 58.7 mmol) and 3-hydroxy-1-methylpiperidine (3.80 mL, 32.0 mmol), followed by stirring at room temperature for twenty-one hours. The reaction mixture was mixed with diluted hydrochloric acid (0.1 mol/L, 100 mL) and ethyl acetate, followed by separation. The aqueous layer was adjusted to be basic with an aqueous sodium hydroxide solution (0.1 mol/L) and was extracted with chloroform. The organic layer was sequentially washed with water and brine, was dried over anhydrous sodium sulfate, and the solvent was distilled off. The residue was purified by silica gel column chromatography (chloroform:methanol=95:5 to 85:15) and thereby yielded 4-(1-methylpiperidin-3-yloxy)pyridine (4.77 g, in a yield of 93%).

Process Step 2

4-(1-Methylpiperidin-3-yloxy)pyridine prepared in Process Step 1 (2.01 g, 7.58 mmol) was mixed with rhodium-carbon (0.80 g), acetic acid (4.34 mL) and ethanol (15 mL), followed by hydrogenation at 0.47 MPa. The reaction was quenched twenty-four hours later, the rhodium-carbon was separated by filtration through Celite (registered trademark), and the filtrate was concentrated. The residue was mixed with an excess of a 4 mol/L solution of hydrogen chloride in ethyl acetate. After distilling off the solvent, the residue was mixed with toluene, from which the solvent was distilled off again, to thereby yield 1-methyl-3-(4-piperidyloxy)piperidine dihydrochloride (1.83 g, in a yield of 89%). The resulting crystals were used as intact in a subsequent reaction.

REFERENCE EXAMPLE 33

Synthesis of 1-methyl-4-(4-piperidyloxy)piperidine dihydrochloride for use in the syntheses of Compounds 21-2 and 21-4

In the same way as Process Step 1 of Reference Example 32, 4-(1-methylpiperidin-4-yloxy)pyridine (3.68 g, in a yield of 72%) was prepared from 4-chloropyridine and 4-hydroxy-1-methylpiperidine (3.69 g, 32.0 mmol). Further, 1-methyl-4-(4-piperidyloxy)piperidine dihydrochloride (1.32 g, in a yield of 86%) was prepared from 4-(1-methylpiperidin-4-yloxy)pyridine (1.50 g, 5.66 mmol) in the same way as Process Step 2 of Reference Example 32.

EXAMPLE 1

Synthesis of Compound (IA-b) wherein A is —C(═O)—, —OC(═O)— or —$SO_2$—, of the compounds shown in Tables 1 to 25

Process Step 1

2,4-Dichloro-5,6,7,8-tetrahydropyrido[4,3-d]pyrimidine hydrochloride prepared according to Reference Example 1 or 2,4-dichloro-6,7-dihydro-5H-pyrrolo[3,4-d]pyrimidine hydrochloride prepared according to Reference Example 3 (0.0500 mmol) was dissolved in dichloromethane (0.500 mL) and triethylamine (0.021 mL), and the solution was mixed with a solution of $R^{3a}$—C(═O)Cl (wherein $R^{3a}$ is as defined above), $R^{3a}$—C(═O)Cl (wherein $R^3$a is as defined above), ($R^{3a}$—OCO)$_2$ (wherein $R^{3a}$ is defined above) O$R^{3a}$—$SO_2$Cl (wherein $R^{3a}$ is as defined above) in chloroform (1.00 mol/L, 0.060 mL, 0.060 mol) and morpholinomethyl polystyrene (2% divinylbenzene copolymer, about 3.2 mmol/g, 93 mg, available from Fluka), followed by sealing and stirring at room temperature for twenty hours. After checking the completion of the reaction by thin layer chromatography, the resin was separated from the reaction mixture by filtration, and the solvent was distilled off. The residue was dissolved in chloroform (0.60 mL), and the solution was mixed with benzoyl chloride polymer-bound (1% divinylbenzene copolymer, about 2.5 mmol/g, 38 mg, Canadian Journal of Chemistry, vol. 55, p. 3351 (1977)) and tris(2-aminomethyl)amine polystyrene (1% divinylbenzene copolymer, about 3 mmol/g, 38 mg, available from Novabiochem), followed by sealing and stirring at room temperature for twenty hours. After separating the resin by filtration, the filtrate was concentrated and thereby yielded Compound (XI-A) [of Compounds (XI), a compound wherein $A^a$ is —C(═O)—, —OC(═O)— or —$SO_2$—]

Process Step 2

The whole quantity of Compound (XI-A) prepared according to Process Step 1 was dissolved in tetrahydrofuran (0.50 mL) and triethylamine (0.020 mL, 0.15 mmol), and the solution was mixed with a chloroform solution of $R^4R^5NH$ (wherein $R^4$ and $R^5$ are as defined above, respectively) (1.00 mol/L, 0.100 mL, 0.100 mmol), followed by sealing and stirring at 40° C. for twenty hours. After checking the completion of the reaction by thin layer chromatography, the reaction mixture was filtrated, and the solvent was distilled off. The residue was dissolved in a mixture of chloroform and methanol (3:1, 0.60 mL), and the solution was mixed with formyl polystyrene (1% divinylbenzene copolymer, about 1.5 mmol/g, 89 mg, Canadian Journal of Chemistry, vol. 55, p. 3351 (1977)), followed by sealing and stirring at room temperature for twenty hours. After separating the resin by filtration, the filtrate was concentrated and thereby yielded Compound (XIII-A) [of Compounds (XIII), a compound wherein $A^a$ is —C(═O)—, —OC(═O)— or —$SO_2$—].

Process Step 3

The whole quantity of Compound (XIII-A) prepared according to Process Step 2 was dissolved in dioxane (0.40 mL), and the solution was mixed with a solution of $R^2$—H (wherein $R^2$ is as defined above) in chloroform (1.00 mmol/L, 0.100 mL, 0.100 mmol) and sodium carbonate (80 mg), followed by sealing and stirring at 90° C. for three days. The reaction mixture was mixed with chloroform (0.40 mL) and benzoyl chloride polymer-bound (1% divinylbenzene copolymer, about 2.5 mmol/g, 38 mg, Canadian Journal of Chemistry, vol. 55, p. 3351 (1977)), followed by sealing and stirring at room temperature for twenty hours. The solid was separated from the reaction mixture by filtration, and the solvent was distilled off from the filtrate. The residue was dissolved in a mixture of chloroform and methanol (3:1, 0.50 mL), was subjected to solid phase extraction using a column filled with Bondesil SCX (registered trademark) (0.18 g, available from Varian Inc.), and the solvent was distilled off, to thereby yield Compound (IA-b) in a total yield of 40% to 60% through three process steps.

Compounds not specifically shown in the following examples were prepared in the same way as Example 1, respectively.

EXAMPLE 2

Synthesis of Compound (IB-a), wherein A is a single bond, of the compounds shown in Table 5

Process Step 1

2,4-Dichloro-5,6,7,8-tetrahydropyrido[4,3-d]pyrimidine hydrochloride prepared according to Reference Example 1 or 2,4-dichloro-6,7-dihydro-5H-pyrrolo[3,4-d]pyrimidine hydrochloride prepared according to Reference Example 3 (0.0500 mmol) was suspended in 1,2-dichloroethane (0.20 mL), and the suspension was mixed with a solution of $R^{3b\text{-}i}$—CHO (wherein $R^{3b\text{-}i}$ is as defined above) in chloroform (1.00 mol/L, 0.060 mL, 0.060 mol) and a suspension of sodium triacetoxyborohydride in 1,2-dichloroethane (0.30 mmol/L, 0.500 mL, 0.150 mmol), followed by stirring at room temperature for twelve hours. After checking the completion of the reaction by thin layer chromatography, the reaction mixture was mixed with water (0.30 mL), followed by stirring for a while. The reaction mixture was separated, the organic layer was dried over anhydrous sodium sulfate, and the solvent was distilled off, to thereby yield Compound (XVI).

Process Step 2

The whole quantity of Compound (XVI) prepared according to Process Step 1 was dissolved in tetrahydrofuran (0.50 mL) and triethylamine (0.020 mL), and the solution was mixed with a solution of $R^4R^5NH$ (wherein $R^4$ and $R^5$ are as defined above, respectively) in chloroform (1.00 mmol/L, 0.100 mL, 0.100 mmol), followed by sealing and stirring at 40° C. for twenty hours. After checking the completion of the reaction by thin layer chromatography, the solvent was distilled off, and the residue was dissolved in a mixture of chloroform and methanol (3:1, 0.60 mL). The solution was mixed with formyl polystyrene (1% divinylbenzene copolymer, about 1.5 mmol/g, 89 mg, Canadian Journal of Chemistry, vol. 55, p. 3351 (1977)), followed by sealing and stirring at room temperature for twelve hours. The resin was separated from the reaction mixture by filtration, the filtrate was concentrated and thereby yielded Compound (XVII).

Process Step 3

The whole quantity of Compound (XVII) prepared according to Process Step 2 was dissolved in dioxane (0.30 mL), and the solution was mixed with a solution of $R^2$—H (wherein $R^2$ is as defined above) in chloroform (1.00 mmol/L, 0.100 mL, 0.100 mmol) and sodium carbonate (80 mg), followed by sealing and stirring at 90° C. for three days. After checking the completion of the reaction by thin layer chromatography, chloroform (0.40 mL) and benzoyl chloride polymer-bound (1% divinylbenzene copolymer, about 2.5 mmol/g, 38 mg, Canadian Journal of Chemistry, vol. 55, p. 3351 (1977)) were added, followed by sealing again and stirring at room temperature for twelve hours. The solid was separated from the reaction mixture by filtration, the filtrate was concentrated, and the residue was dissolved again in a mixture of chloroform and methanol (3:1, 0.50 mL). The solution was subjected to solid phase extraction using a column filled with Bondesil SCX (registered trademark) (0.18 g, available from Varian Inc.), and the solvent was distilled off, to thereby yield Compound (IB-a) in a total yield of 40% to 60% through the three process steps.

EXAMPLE 3

Synthesis of Compound 5-455

Compound 5-451 (0.174 g, 0.0031 mol) prepared according to Example 1 was dissolved in ethanol (2 mL), and the solution was mixed with an aqueous sodium hydroxide solution (5 mol/L, 1 mL), followed by stirring at room temperature for thirty minutes. After the completion of the reaction, the solvent was distilled off under reduced pressure. The residue was dissolved in water (2 mL), and diluted hydrochloric acid (2 mol/L, 2 mL) was added dropwise. The reaction mixture was mixed with chloroform (5 mL), followed by shaking and separation. The organic layer was dried over magnesium sulfate, and the solvent was distilled off under reduced pressure. The resulting crystals were washed with isopropyl ether (10 mL), were dried under reduced pressure and thereby yielded Compound 5-455 (0.112 mg, 68%).

EXAMPLE 4

Synthesis of Compound 6-21

Process Step 1

2,4-Dichloro-5,6,7,8-tetrahydropyrido[4,3-d]pyrimidine hydrochloride prepared according to Reference Example 1 (2.00 g) and triethylamine (2.80 mL, 2.4 equivalents) were dissolved in dichloromethane (40 mL), and the solution was mixed with di-tert-butyl dicarbonate (2.29 mL, 1.2 equivalents), followed by stirring at room temperature for twenty minutes. The reaction mixture was sequentially washed with water, a saturated aqueous sodium bicarbonate solution and brine, followed by extraction with chloroform. The organic layer was dried over anhydrous magnesium sulfate, and the solvent was distilled off, to thereby yield tert-butyl 2,4-dichloro-5,6,7,8-tetrahydropyrido[4;3-d]pyrimidine-6-carboxylate (3.0 g, in a quantitative yield).

Process Step 2

Tert-butyl 2,4-dichloro-5,6,7,8-tetrahydropyrido[4,3-d]pyrimidine-6-carboxylate prepared according to Process Step 1 (1.26 g) was dissolved in tetrahydrofuran (12 mL), and the solution was mixed with triethylamine (2.60 mL, 4.5 equivalents) and 2,4-dichlorobenzylamine (1.70 mL, 3 equivalents), followed by stirring at 40° C. for six hours. The reaction mixture was sequentially washed with water, a saturated aqueous sodium bicarbonate solution and brine, followed by extraction with chloroform. The organic layer was dried over magnesium sulfate, and the solvent was distilled off. The residue was mixed with diisopropyl ether, followed by stirring for one hour or more. The precipitated crystals were collected by filtration, were dried under reduced pressure and thereby yielded tert-butyl 2-chloro-4-(2,4-dichlorobenzylamino)-5,6,7,8-tetrahydropyrido[4,3-d]pyrimidine-6-carboxylate (1.54 g, in a yield of 83%).

Process Step 3

Tert-butyl 2-chloro-4-(2,4-dichlorobenzylamino)-5,6,7,8-tetrahydropyrido [4,3-d]pyrimidine-6-carboxylate prepared according to Process Step 2 (0.75 g) was dissolved in dioxane (15 mL), and the solution was mixed with 1-(2-piperidinoethyl)piperazine (0.50 g, 1.5 equivalents) and sodium carbonate (2.70 g, 15 equivalents), followed by stirring at 90° C. for three days. The reaction mixture was filtrated to remove sodium carbonate, and the filtrate was mixed with water and was extracted with chloroform. The organic layer was dried over magnesium sulfate, and the solvent was distilled off. The residue was purified by silica gel column chromatography (n-hexane:ethyl acetate=3:1 to 1:2), the target fraction was concentrated and thereby yielded tert-butyl 4-(2,4-dichlorobenzylamino)-2-[4-(2-piperidinoethyl)piperazin-1-yl]-5,6,7,8-tetrahydropyrido[4,3-d]pyrimidine-6-carboxylate (0.69 g, in a yield of 68%).

Process Step 4

Tert-butyl 4-(2,4-dichlorobenzylamino)-2-[4-(2-piperidinoethyl)piperazin-1-yl]-5,6,7,8-tetrahydropyrido[4,3-d]pyrimidine-6-carboxylate prepared according to Process Step 3 (0.67 g) was dissolved in dichloromethane (6.7 mL), and the solution was mixed with trifluoroacetic acid (2.00 mL, 3 equivalents), followed by stirring at room temperature for three hours. The reaction mixture was mixed with a saturated aqueous sodium bicarbonate solution, followed by extraction with chloroform. The organic layer was dried over magnesium sulfate, and the solvent was distilled off. The residue was mixed with diisopropyl ether, followed by stirring for one hour or more. The precipitated crystals were collected by filtration, were dried under reduced pressure and thereby yielded Compound 6-21 (0.44 g, in a yield of 78%).

EXAMPLE 5

Synthesis of Compound 6-30

Compound 6-21 prepared according to Example 4 (0.042 g) was dissolved in dimethylformamide (10 mL), the solution was mixed with potassium carbonate (0.035 g, 3 equivalents) and was cooled to 0° C. The mixture was mixed with tert-butyl bromoacetate (0.014 mL, 1.1 equivalents), followed by stirring at room temperature for one hour. The reaction mixture was diluted with water and was extracted with ethyl acetate. The organic layer was dried over magnesium sulfate, and the solvent was distilled off. The residue was purified by silica gel column chromatography (n-hexane:ethyl acetate=1:3), the target fraction was concentrated and thereby yielded Compound 6-30 (0.035 g, in a yield of 68%).

EXAMPLE 6

Synthesis of Compound 6-31

Compound 6-30 prepared according to Example 5 (0.035 g) was mixed with a solution of trifluoroacetic acid in dichloromethane (20%, 10 mL), followed by stirring at room temperature for three hours. After distilling off the solvent from the reaction mixture, the residue was mixed with a solution of hydrochloric acid in ethyl acetate (4 mol/L, 10 mL) and the mixture was concentrated. The residue was mixed with ethyl acetate for crystallization, and the suspension was stirred for one hour or more. The precipitated crystals were collected by filtration, were dried under reduced pressure and thereby yielded Compound 6-31 (0.027 g, in a yield of 80%).

EXAMPLE 7

Synthesis of Compound 5-395

Compound 5-395 was prepared in the same way as Example 6, except for using Compound 5-394 prepared according to Example 1.

EXAMPLE 8

Synthesis of Compound 5-421

Compound 5-421 was prepared in the same way as Example 3, except for using Compound 5-417 prepared according to Example 1.

EXAMPLE 9

Synthesis of Compound 5-450

Compound 5-450 was prepared in the same way as Example 3, except for using Compound 5-447 prepared according to Example 1.

EXAMPLE 10

Synthesis of Compound 5-456

Compound 5-456 was prepared in the same way as Example 3, except for using Compound 5-452 prepared according to Example 1.

EXAMPLE 11

Synthesis of Compound 6-9

Compound 6-9 was prepared through three process steps in the same way as Process Steps 2 to 4 of Example 4, except for using tert-butyl 2,4-dichloro-5,6,7,8-tetrahydropyrido[4,3-d]pyrimidine-6-carboxylate and 2,4-difluorobenzylamine.

EXAMPLE 12

Synthesis of Compound 3-21

Process Step 1

From 2,4-dichloro-5,6,7,8-tetrahydropyrido[4,3-d]pyrimidine hydrochloride prepared according to Reference Example 1 and cyclopropylcarbonyl chloride, 2,4-dichloro-6-cyclopropylcarbonyl-5,6,7,8-tetrahydropyrido[4,3-d]pyrimidine was prepared in the same way as Process Step 1 of Example 1. Further, 2,4-dichloro-6-cyclopropylcarbonyl-5,6,7,8-tetrahydropyrido[4,3-d]pyrimidine was allowed to sequentially react with 2-chloro-4-fluorobenzylamine and N-(2-aminoethyl)(tert-butoxy)carboxamide in the same way as Process Steps 2 and 3 of Example 1, to yield 4-(2-chloro-4-fluorobenzylamino)-6-cyclopropylcarbonyl-2-(2-tert-butoxycarbonylaminoethylamino)-5,6,7,8-tetrahydropyrido[4,3-d]pyrimidine.

APCI-MS m/z: 517 $[M-H]^-$ $^1H$ NMR ($CDCl_3$) (ppm): 0.72-1.12 (m, 4H), 1.42 (s, 9H), 1.71-1.95 (m, 1H), 2.54-2.84 (m, 2H), 3.15-3.59 (m, 4H), 3.78-4.00 (m, 2H), 4.25-4.51 (m, 2H), 4.57-5.04 (m, 4H), 5.18-5.51 (m, 1H), 6.83-7.20 (m, 2H), 7.27-7.50 (m, 1H)

Process Step 2

In the same way as Process Step 4 of Example 4, 4-(2-chloro-4-fluorobenzylamino)-6-cyclopropylcarbonyl-2-(2-aminoethylamino)-5,6,7,8-tetrahydropyrido[4,3-d]pyrimidine was prepared from 4-(2-chloro-4-fluorobenzylamino)-6-cyclopropylcarbonyl-2-(2-tert-butoxycarbonylaminoethylamino)-5,6,7,8-tetrahydropyrido[4,3-d]pyrimidine prepared according to Process Step 1.

APCI-MS m/z: 419 $[M+H]^+$ $^1H$ NMR ($CDCl_3$) δ (ppm): 0.72-1.12 (m, 4H), 1.70-1.95 (m, 1H), 2.49-2.96 (m, 4H), 3.30-3.59 (m, 2H), 3.75-4.00 (m, 2H), 4.22-4.51 (m, 2H), 4.57-4.81 (m, 2H), 4.89-5.11 (m, 1H), 5.29-5.55 (m, 1H), 6.80-7.20 (m, 2H), 7.27-7.50 (m, 1H)

Process Step 3

1-(2-Aminoethyl)pyrrolidine (23 mg, 0.20 mmol) was dissolved in dimethylformamide (0.23 mL), and the solution was mixed with carbonyldiimidazole (32 mg, 0.20 mmol) with stirring at room temperature. After stirring for one hour, the reaction mixture was mixed with a solution of 4-(2-chloro-4-fluorobenzylamino)-6-cyclopropylcarbonyl-2-(2-aminoethylamino)-5,6,7,8-tetrahydropyrido[4,3-d]pyrimidine prepared according to Process Step 2 (43 mg) in dimethylformamide (0.43 mL) added dropwise, followed by stirring for three hours. The reaction mixture was mixed with water and was extracted with ethyl acetate. The organic layer was washed with brine, was dried over anhydrous sodium sulfate, and the solvent was distilled off. The residue was purified by silica gel chromatography (chloroform:7.0 mol/L ammonia methanol solution=10:1) and thereby yielded Compound 3-21 (35 mg, 63%).

EXAMPLE 13

Syntheses of Compounds 3-22 and 3-23

Compound 3-22 and Compound 3-23 were prepared in the same way as Process Step 3 of Example 12 from 4-(2-chloro-4-fluorobenzylamino)-6-cyclopropylcarbonyl-2-(2-aminoethylamino)-5,6,7,8-tetrahydropyrido[4,3-d]pyrimidine prepared according to Process Step 2 of Example 12, except for using 2-pyrrolidinylethanol and 1-methylpiperazine, respectively.

EXAMPLE 14

Syntheses of Compounds 3-24, 3-25 and 3-26

Compounds 3-24, 3-25 and 3-26 were prepared in the same way as Process Steps 2 and 3 of Example 1, except for allowing 2,4-dichloro-6-(cyclopropylcarbonyl)-5,6,7,8-tetrahydropyrido[4,3-d]pyrimidine prepared according to Process Step 1 of Example 12 to sequentially react with 4-chloro-2-fluorobenzylamine and 2-(1-pyrrolidinyl)ethanol, with 2,4-dichlorobenzylamine and 2-(1-pyrrolidinyl)ethanol, or with 2,4-dichlorobenzylamine and 2-(1-methylpyrrolidin-2-yl)ethanol, respectively.

EXAMPLE 15

Synthesis of Compound 3-27

1-Methyl-2-piperidinemethanol (0.261 g, 2.02 mmol) was dissolved in 1,2-dimethoxyethane (6.00 mL), and the solution was mixed with a solution of n-butyllithium in hexane (1.60 mol/L, 1.30 mL, 2.08 mmol) added dropwise under ice-cooling. After stirring for fifteen minutes, the reaction mixture was mixed with 2-chloro-4-(2,4-dichlorobenzylamino)-6-(cyclopropylcarbonyl)-5,6,7,8-tetrahydropyrido[4,3-d]pyrimidine prepared according to Process Steps 1 and 2 of Example 1 (0.205 g, 0.498 mmol), followed by stirring at 100° C. for three days. After checking the completion of the reaction by thin layer chromatography, the reaction mixture was concentrated under reduced pressure. The residue was purified by silica gel column chromatography (ethyl acetate: triethylamine=10:1) and thereby yielded Compound 3-27 (0.190 g, 76%).

EXAMPLE 16

Synthesis of Compound 3-30

Process Step 1

2-Chloro-4-(2-chloro-4-fluorobenzylamino)-6-cyclopropyl carbonyl-5,6,7,8-tetrahydropyrido[4,3-d]pyrimidine prepared according to Process Steps 1 and 2 of Example 1 (0.35 g, 0.89 mmol) was dissolved in tetrahydrofuran (7.0 mL), and the solution was mixed with di-tert-butyl dicarbonate (0.29 g, 1.3 mmol) and 4-dimethylaminopyridine (54 mg, 0.45 mmol), followed by stirring at room temperature for twenty-four hours. The reaction mixture was mixed with 1.0 mol/L hydrochloric acid (21 mL) and was extracted with ethyl acetate. The organic layer was sequentially washed with water and brine, was dried over anhydrous magnesium sulfate, and the solvent was distilled off. The residue was purified by silica gel chromatography (hexane:ethyl acetate=2:1) and thereby yielded 4-(N-tert-butoxycarbonyl-2-chloro-4-fluorobenzylamino)-2-chloro-6'-cyclopropylcarbonyl-5,6,7,8-tetrahydropyrido[4,3-d]pyrimidine (0.40 g, 91%).

APCI-MS m/z: 495 $[M+H]^+$ $^1H$ NMR ($CDCl_3$) δ (ppm): 0.67-1.10 (m, 4H), 1.28-1.90 (m, 10H), 2.88-3.20 (m, 2H), 3.79-4.10 (m, 2H), 4.45-4.70 (m, 2H), 5.00-5.20 (s, 2H), 6.87-7.17 (m, 2H), 7.34-7.51 (m, 1H)

Process Step 2

In the same way as Example 92 mentioned later, 4-(N-tert-butoxycarbonyl-2-chloro-4-fluorobenzylamino)-6-cyclopropylcarbonyl-2-[4-(2-pyrrolidin-1-ylacetyl)piperidino]-5,6,7,8-tetrahydropyrido[4,3-d]pyrimidine was prepared from 4-(N-tert-butoxycarbonyl-2-chloro-4-fluorobenzylamino)-2-chloro-6-cyclopropylcarbonyl-5,6,7,8-tetrahydropyrido[4,3-d]pyrimidine prepared according to Process Step 1 and tert-butyl 4-(2-pyrrolidin-1-ylacetyl)piperidinecarboxylate prepared according to Reference Example 12.

APCI-MS m/z: 655 $[M+H]^+$ $^1H$ NMR ($CDCl_3$) δ (ppm): 0.60-1.10 (m, 4H), 1.20-2.05 (m, 19H), 2.45-3.05 (m, 8H), 3.42 (s, 2H), 3.69-4.05 (m, 2H), 4.35-4.75 (m, 4H), 4.85-5.15 (m, 2H), 6.80-7.12 (m, 2H), 7.32-7.61 (m, 1H)

Process Step 3

Compound 3-30 (0.14 g, in a yield of 23%) was prepared in the same way as Process Step 4 of Example 4, except for using 4-(N-tert-butoxycarbonyl-2-chloro-4-fluorobenzylamino)-6-cyclopropylcarbonyl-2-[4-(2-pyrrolidin-1-ylacetyl)piperidino]-5,6,7,8-tetrahydropyrido[4,3-d]pyrimidine prepared according to Process Step 2 (0.47 g).

EXAMPLE 17

Synthesis of Compound 3-32

Compound 4-7 prepared according to Example 1 (50.0 mg, 0.087 mmol) was dissolved in dichloromethane, and the solution was mixed with methyl iodide (38.0 mg, 0.268 mmol), followed by stirring at 40° C. for twenty hours. After checking the completion of the reaction by thin layer chromatography, the reaction mixture was concentrated under reduced pressure and was mixed with diethyl ether for crystallization. The precipitated crystals were collected by filtration, were dried under reduced pressure and thereby yielded Compound 3-32 (50.0 mg, 70%).

EXAMPLE 18

Syntheses of Compounds 3-20 and 3-33

Compounds 3-20 and 3-33 were prepared in the same way as Example 12, except for using Compounds 4-6 and 5-10 prepared according to Example 1, respectively.

EXAMPLE 19

Synthesis of Compound 6-34

Process Step 1

4-(2,4-Dichlorobenzylamino)-2-[4-(2-piperid-1-ylethyl) piperazin-1-yl]-5,6,7,8-tetrahydropyrido[4,3-d]pyrimidine (1.18 g, 2.34 mmol) prepared in the same way as Example 4 was dissolved in 2-propanol (20 mL), and the solution was mixed with diisopropyl squarate (0.56 g, 2.81 mmol), followed by stirring at room temperature for two hours. After checking the completion of the reaction by thin layer chromatography, the reaction mixture was concentrated. The residue was purified by silica gel column chromatography (chloroform:methanol=5:1) and thereby yielded 3-{4-(2,4-dichlorobenzylamino)-2-[4-(2-piperidinoethyl)piperazin-1-yl]-5,6,7,8-tetrahydropyrido[4,3-d]pyrimidin-6-yl}-4-isopropoxy-3-cyclobutene-1,2-dione (1.11 g, 73%).

Process Step 2

3-(4-(2,4-Dichlorobenzylamino)-2-[4-(2-piperidinoethyl) piperazin-1-yl]-5,6,7,8-tetrahydro-pyrido[4,3-d]pyrimidin-6-yl}-4-isopropoxy-3-cyclobutene-1,2-dione prepared according to Process Step 1 (200 mg, 0.31 mmol) was dissolved in 2-propanol, and the solution was mixed with pyrrolidine (0.05 mL, 0.62 mmol) added dropwise, followed by stirring at room temperature for twelve hours. After checking the completion of the reaction by thin layer chromatography, the reaction mixture was concentrated, the resulting solid was washed with 2-propanol and thereby yielded Compound 6-34 (159 mg, 78%).

EXAMPLE 20

Synthesis of Compound 6-35

Compound 6-35 was prepared in the same way as Process Step 2 of Example 19, except for using 3-(4-(2,4-dichlorobenzylamino)-2-[4-(2-piperidinoethyl)piperazin-1-yl]-5,6,7,8-tetrahydro-pyrido[4,3-d]pyrimidin-6-yl)-4-isopropoxy-3-cyclobutene-1,2-dione and a solution of methylamine in tetrahydrofuran (2 mol/L).

EXAMPLE 21

Syntheses of Compounds 8-385 through 8-576 shown in Table 8

Process Step 1

2,4-Dichloro-5,6,7,8-tetrahydropyrido[4,3-d]pyrimidine hydrochloride prepared according to Reference Example 1 (10.9 g, 45.4 mmol) was dissolved in dichloromethane (280 mL), and the solution was mixed with cyclopropylcarbonyl chloride (4.98 mL) and triethylamine (19.0 mL) added under ice-cooling, followed by stirring at room temperature for one hour. After checking the completion of the reaction by thin layer chromatography, the reaction mixture was mixed with water, followed by separation. The organic layer was washed with a saturated aqueous sodium bicarbonate solution, was dried over anhydrous magnesium sulfate, and the solvent was distilled off. The residue was mixed with diisopropyl ether for crystallization. The precipitated crystals were collected by filtration, were dried under reduced pressure and thereby yielded 2,4-dichloro-6-cyclopropylcarbonyl-5,6,7,8-tetrahydropyrido[4,3-d]pyrimidine (10.8 g, in a yield of 87%).

Process Step 2

2,4-Dichloro-6-cyclopropylcarbonyl-5,6,7,8-tetrahydropyrido[4,3-d]pyrimidine prepared according to Process Step 1 (0.0800 mmol) was dissolved in tetrahydrofuran (0.400 mL) and triethylamine (0.040 mL), and the solution was mixed with a solution of $R^4R^5NH$ (wherein $R^4$ and $R^5$ are as defined above, respectively) in chloroform (1.00 mol/L, 0.150 mL, 0.150 mmol), followed by sealing and stirring at 40° C. for twenty hours. After checking the completion of the reaction by thin layer chromatography, the reaction mixture was filtrated, and the solvent was distilled off from the filtrate. The residue was treated in the same way as Process Step 2 of Example 1 and thereby yielded Compound (XIII-B) [of Compounds (XIII), a compound wherein $R^{3a}$ is cyclopropyl; and $A^a$ is —C(=O)—].

Process Step 3

Compound (XIII-B) prepared according to Process Step 2 was dissolved in dioxane (0.200 mL), and the solution was mixed with a solution of 4-hydroxyethylpiperidine in dioxane (0.400 mol/L, 0.400 mL, 0.160 mmol) and sodium carbonate (70.0 mg), followed by stirring at 90° C. for two days. After checking the completion of the reaction by thin layer chromatography, the reaction mixture was filtrated, and the solvent was distilled off from the filtrate under reduced pressure. The residue was mixed with chloroform (0.500 mL) and N-methylisatoic anhydride polystyrene (2% divinylbenzene copolymer, about 2.60 mmol/g, 100 mg, available from Novabiochem), followed by stirring at room temperature for twelve hours. The resin was separated from the reaction mixture by filtration, the filtrate was concentrated and thereby yielded Compound (A-A) [of Compounds (A), a compound wherein $R^1$ is —$NR^4R^5$ (wherein $R^4$ and $R^5$ are as defined above, respectively); $R^3$ is cyclopropyl; A is —C(═O)—; and $R^{2A}$ is 4-(2-hydroxyethyl)piperidyl group]. Compound (A-A) was mixed with a solution of methanesulfonic anhydride in tetrahydrofuran (0.80 mol/L, 0.400 mL, 0.320 mmol) and morpholinomethyl polystyrene (2% divinylbenzene copolymer, about 3.20 mmol/g, 93.0 mg, available from Fluka), followed by stirring at 60° C. for twelve hours. After checking the completion of the reaction by thin layer chromatography, the resin was separated from the reaction mixture by filtration, and the filtrate was concentrated. The residue was dissolved in chloroform (0.800 mL), and the solution was mixed with tris(2-aminoethyl)amine polystyrene (1% divinylbenzene copolymer, about 3.40 mmol/g, 176 mg, available from Novabiochem), followed by stirring at room temperature for twelve hours. The resin was separated from the reaction mixture by filtration, the filtrate was concentrated and thereby yielded Compound (A-B) [of Compounds (A), a compound wherein $R^1$ is —$NR^4R^5$ (wherein $R^4$ and $R^5$ are as defined above, respectively); $R^3$ is cyclopropyl; A is —C(═O)—; and $R^{2A}$ is 4-(2-methanesulfonyloxyethyl)piperidyl group].

Process Step 4

Compound (A-B) prepared according to Process Step 3 was dissolved in 1,3-dimethyl-2-imidazolidinone (0.300 mL), and the solution was mixed with a solution of $R^{10a}$—H (wherein $R^{10a}$ is as defined above) in 1,3-dimethyl-2-imidazolidinone (1.00 mol/L, 0.300 mL, 0.300 mmol) and morpholinomethyl polystyrene (2% divinylbenzene copolymer, about 3.20 mmol/g, 93.0 mg, available from Fluka), followed by stirring at 90° C. for eighteen hours. After checking the completion of the reaction by thin layer chromatography, the resin was separated from the reaction mixture by filtration. The filtrate was subjected to solid phase extraction using a column filled with Bondesil SCX (0.180 g, available from Varian Inc.), and the solvent was distilled off. The residue was dissolved in a mixture of chloroform and methanol (3:1, 0.900 mL), and the solution was mixed with formyl polystyrene (1% divinylbenzene copolymer, about 1.50 mmol/g, 190 mg, Canadian Journal of Chemistry, vol. 55, p. 3351 (1977)), followed by sealing and stirring at room temperature for twelve hours. The resin was separated from the reaction mixture by filtration, the filtrate was subjected to solid phase extraction using a column filled with Bondesil SCX (registered trademark) (0.180 g, available from Varian Inc.), and the solvent was distilled off, to thereby yield Compounds 8-385 through 8-576 (in total yields from 2,4-dichloro-6-cyclopropylcarbonyl-5,6,7,8-tetrahydropyrido[4,3-d]pyrimidine of 15% to 30%), respectively.

EXAMPLE 22

Syntheses of Compounds 8-1 through 8-384 shown in Table 8

Compound (XXII-b-i) prepared according to Reference Example 15 was mixed with a solution of trifluoroacetic acid in dichloromethane (20%, 0.500 mL), followed by stirring at room temperature for four hours. The reaction mixture was concentrated under reduced pressure, and the residue was suspended in dioxane (0.300 mL). The suspension was mixed with Compound (XIII-B) and sodium carbonate (70.0 mg), followed by stirring at 90° C. for two days. Compound (XIII-B) had been prepared in the same way as Process Step 2 of Example 21, except for using 2,4-dichloro-6-cyclopropylcarbonyl-5,6,7,8-tetrahydropyrido[4,3-d]pyrimidine prepared according to Process Step 1 of Example 21 (0.040 mmol). After checking the completion of the reaction by thin layer chromatography, the reaction mixture was filtrated, and the solvent was distilled off from the filtrate under reduced pressure. The residue was mixed with chloroform (0.500 mL) and N-methylisatoic anhydride polystyrene (2% divinylbenzene copolymer, about 2.60 mmol/g, 100 mg, available from Novabiochem), followed by stirring at room temperature for twelve hours. The resin was separated from the reaction mixture by filtration, and the filtrate was concentrated. The residue was dissolved in a mixture of chloroform and methanol (3:1, 0.500 mL). The solution was subjected to solid phase extraction using a column filled with Bondesil SCX (registered trademark) (available from Varian Inc., 0.180 g), and the solvent was distilled off, to thereby yield Compounds 8-1 through 8-384 (in total yields from 2,4-dichloro-6-cyclopropylcarbonyl-5,6,7,8-tetrahydropyrido[4,3-d]pyrimidine of 30% to 50%), respectively.

EXAMPLE 23

Syntheses of the Compounds Shown in Table 9 (Compounds 9-1 through 9-384)

Compound (XXII-b-ii) prepared according to Reference Example 16 was mixed with a solution of trifluoroacetic acid in dichloromethane (20%, 0.500 mL), followed by stirring at room temperature for four hours. The reaction mixture was concentrated under reduced pressure, and the residue was suspended in dioxane (0.300 mL). The suspension was mixed with Compound (XIII-B) and sodium carbonate (70.0 mg), followed by stirring at 90° C. for two days. Compound (XIII-B) had been prepared in the same way as Process Step 2 of Example 21, except for using 2,4-dichloro-6-cyclopropylcarbonyl-5,6,7,8-tetrahydropyrido [4,3-d]pyrimidine prepared according to Process Step 1 of Example 21 (0.050 mmol). After checking the completion of the reaction by thin layer chromatography, the reaction mixture was mixed with chloroform and benzoyl chloride polymer-bound (1% divinylbenzene copolymer, about 2.50 mmol/g, 76.0 mg, Canadian Journal of Chemistry, vol. 55, p. 3351 (1977)), followed by stirring at room temperature for twelve hours. The resin was separated from the reaction mixture by filtration, and the filtrate was concentrated. The residue was dissolved in a mixture of chloroform and methanol (3:1, 0.500 mL), the solution was subjected to solid phase extraction using a column filled with Bondesil SCX (registered trademark) (0.180 g, available from Varian Inc.), and the solvent was distilled off, to thereby yield Compounds 9-1 through 9-384 (in total yields from 2,4-dichloro-6-cyclopropylcarbonyl-5,6,7,8-tetrahydropyrido[4,3-d]pyrimidine of 40% to 60%), respectively.

EXAMPLE 24

Syntheses of the Compounds Shown in Table 10 (Compounds 10-1 through 10-192)

Compound (XXII-b-iii) prepared according to Reference Example 17 was mixed with a solution of trifluoroacetic acid in dichloromethane (20%, 0.500 mL), followed by stirring at room temperature for four hours. The reaction mixture was concentrated under reduced pressure, and the residue was suspended in dioxane (0.300 mL). The suspension was mixed with Compound (XIII-B) and sodium carbonate (70.0 mg), followed by stirring at 90° C. for two days. Compound (XIII-B) had been prepared in the same way as Process Step 2 of Example 21, except for using 2,4-dichloro-6-cyclopropylcarbonyl-5,6,7,8-tetrahydropyrido[4,3-d]pyrimidine prepared according to Process Step 1 of Example 21 (0.040 mmol). After checking the completion of the reaction by thin layer chromatography, the reaction mixture was filtrated, and the solvent was distilled off from the filtrate under reduced pressure. The residue was mixed with chloroform (0.500 mL) and N-methylisatoic anhydride polystyrene (2% divinylbenzene copolymer, about 2.60 mmol/g, 100 mg, available from Nova biochem), the mixture was stirred at room temperature for twelve hours, the resin was separated from the reaction mixture by filtration, and the filtrate was concentrated. The residue was dissolved in a mixture of chloroform and methanol (3:1, 0.500 mL), was subjected to solid phase extraction using a column filled with Bondesil SCX (registered trademark) (0.180 g, available from Varian Inc.), and the solvent was distilled off, to thereby yield Compounds 10-1 through 10-192 (in total yields from 2,4-dichloro-6-cyclopropylcarbonyl-5,6,7,8-tetrahydropyrido[4,3-d]pyrimidine of 30% to 50%), respectively.

EXAMPLE 25

Syntheses of the Compounds Shown in Table 11 (Compounds 11-1 through 11-98)

Process Step 1

1-[6-tert-Butoxycarbonyl-4-(2-chloro-4-fluorobenzylamino)-5,6,7,8-tetrahydropyrido[4,3-d]pyrimidin-2-yl]piperidine-4-carboxylic acid prepared according to Reference Example 8 (0.0500 mmol) was suspended in chloroform (0.50 mL), and the suspension was mixed with a suspension of 1-hydroxybenzotriazole in chloroform-tetrahydrofuran (3:1) (0.25 mol/L, 0.200 mL), a solution of $R^{10a}$—H (wherein $R^{10a}$ is as defined above) or $R^{10}$—$(CH_2)_{ra}$—$NH_2$ (wherein $R^{10}$ and ra are as defined above, respectively) in chloroform (1.00 mol/L, 0.080 mL) and N-ethyl-N'-(3-dimethylaminopropyl)carbodiimide polymer-bound (70 mg), followed by sealing and stirring at 55° C. for twenty hours. After checking the completion of the reaction by thin layer chromatography, the solid was separated from the reaction mixture by filtration, and the filtrate was concentrated. The residue was dissolved in chloroform (0.70 mL), and the solution was mixed with benzoyl chloride polymer-bound (1% divinylbenzene copolymer, 23 mg, Canadian Journal of Chemistry, vol. 55, p. 3351 (1977)) and polyvinylpyridine (23 mg), followed by stirring at room temperature for twelve hours. The resin was separated from the reaction mixture by filtration, and the filtrate was concentrated. The residue was mixed with a solution of trifluoroacetic acid in dichloromethane (20 v/v %, 0.30 mL), followed by sealing and stirring at room temperature for one hour. The reaction mixture was mixed with dichloromethane (0.50 mL) and an aqueous sodium hydroxide solution (1 mol/L), followed by separation. The organic layer was dried over anhydrous sodium sulfate, was concentrated and thereby yielded Compound (IC-a) [Of Compounds (I), a compound wherein A is a single bond; $R^3$ is hydrogen atom; $R^1$ is 2-chloro-4-fluorobenzylamino; $R^2$ is

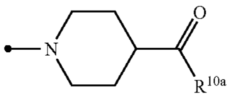

(wherein $R^{10a}$ has the same meaning as defined above), or

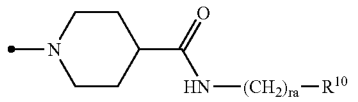

(wherein $R^{10}$ and ra have the same meanings as defined above, respectively)].

Process Step 2

Compound (IC-a) prepared according to Process Step 1 was dissolved in dichloromethane (0.50 mL), and the solution was mixed with triethylamine (0.021 mL), a solution of $R^{3a}$—W (wherein $R^{3a}$ and W are as defined above, respectively) in chloroform (1.00 mol/L, 0.0600 mL) and morpholinomethyl polystyrene (0.075 mL, available from Novabiochem), followed by sealing and stirring at room temperature for twenty hours. After checking the completion of the reaction by thin layer chromatography, the resin was separated from the reaction mixture by filtration, and the filtrate was concentrated. The residue was dissolved in chloroform (0.80 mL), and the solution was mixed with benzoyl chloride polymer-bound (1% divinylbenzene copolymer, 23 mg, Canadian Journal of Chemistry, vol. 55, p. 3351 (1977) and tris(2-aminoethyl)amine polystyrene (25 mg, available from Novabiochem), followed by sealing and stirring at room temperature for twenty hours. The resin was separated from the reaction mixture by filtration, and the filtrate was concentrated. The residue was dissolved in a mixture of chloroform and methanol (3:1), the solution was subjected to solid phase extraction by adsorbing using a column filled with Bondesil SCX (registered trademark) (0.18 g, available from Varian Inc.) and eluting with a ammonia methanol solution (2 mol/L) and thereby yielded Compounds 11-1 through 11-98 (average total yield: about 20%), respectively.

EXAMPLE 26

Syntheses of the Compounds Shown in Table 12 (Compounds 12-1 through 12-192) and the Compounds Shown in Table 24 (Compounds 24-1 through 24-192)

Process Step 1

4-(2,4-Dichlorobenzylamino)-2-(4-toluenesulfonyloxy)-5,6,7,8-tetrahydropyrido[3,4-d]pyrimidine hydrochloride prepared according to Reference Example 4 (0.0400 mmol) or 2-chloro-4-(2,4-dichlorobenzylamino)-6,7,8,9-tetrahydro-5H-pyrimido[4,5-d]azepine hydrochloride prepared according to Reference Example 7 (0.0400 mmol) was dissolved in dichloromethane (0.40 mL) and triethylamine (0.017 mL), and the solution was mixed with a solution of $R^{3a}$—W (wherein $R^{3a}$ and W are as defined above, respectively) in chloroform (1.00 mol/L, 0.050 mL, 0.050 mmol) and morpholinomethyl polystyrene (0.075 mL, available from Novabiochem), followed by sealing and stirring at room temperature for twenty hours. After checking the completion of the reaction by thin layer chromatography, the solid was separated from the reaction mixture by filtration, and the filtrate was concentrated. The residue was dissolved in chloroform (0.80 mL), and the solution was mixed with benzoyl chloride polymer-bound (1% divinylbenzene copolymer, 23 mg, Canadian Journal of Chemistry, vol. 55, p. 3351 (1977) and tris(2-aminoethyl)amine polystyrene (25 mg, available from Novabiochem), followed by sealing and stirring at room temperature for twenty hours. The resin was separated from the reaction mixture by filtration, the filtrate was concentrated and thereby yielded:

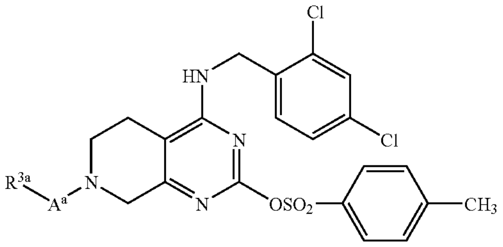

(wherein $R^{3a}$ and $A^{a}$ have the same meanings as defined above, respectively), or

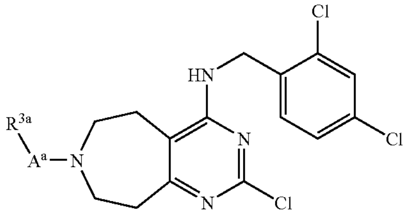

(wherein $R^{3a}$ and $A^{a}$ have the same meanings as defined above, respectively).

Process Step 2

Each of the compounds prepared according to Process Step 1 was dissolved in dioxane (0.30 mL), and the solution was mixed with a solution of $R^2$—H (wherein $R^2$ is as defined above) in chloroform (1.00 mmol/L, 0.100 mL) and sodium carbonate (80 mg), followed by sealing and stirring at 90° C. for three days. After checking the completion of the reaction by thin layer chromatography, the reaction mixture was treated in the same way as the work-up in Process Step 3 of Example 1 and thereby yielded Compounds 12-1 through 12-192 and Compounds 24-1 through 24-192, respectively.

EXAMPLE 27

Synthesis of Compound 13-2

Compound 13-2 was prepared in the same way as Process Step 2 of Example 19, except for using 3-{4-(2,4-dichlorobenzylamino)-2-[4-(2-pyrrolidin-1-ylethyl) piperazin-1-yl]-5,6,7,8-tetrahydropyrido[4,3-d]pyrimidin-6-yl}-4-isopropoxy-3-cyclobutene-1,2-dione and a solution of ethylamine in tetrahydrofuran (2 mol/L).

EXAMPLE 28

Synthesis of Compound 13-3

Compound 13-3 was prepared in the same way as Process Step 2 of Example 19, except for using 3-{4-(2,4-dichlorobenzylamino)-2-[4-(2-pyrrolidin-1-ylethyl)piperazin-1-yl]-5,6,7,8-tetrahydropyrido[4,3-d]pyrimidin-6-yl}-4-isopropoxy-3-cyclobutene-1,2-dione and n-propylamine.

EXAMPLE 29

Synthesis of Compound 13-4

Compound 13-4 was prepared in the same way as Process Step 2 of Example 19, except for using 3-{4-(2,4-dichlorobenzylamino)-2-[4-(2-pyrrolidin-1-ylethyl)piperazin-1-yl]-5,6,7,8-tetrahydropyrido[4,3-d]pyrimidin-6-yl}-4-isopropoxy-3-cyclobutene-1,2-dione and a solution of methylamine in tetrahydrofuran (2 mol/L).

EXAMPLE 30

Synthesis of Compound 13-5

Compound 13-5 was prepared in the same way as Process Step 2 of Example 19, except for using 3-{4-(2,4-dichlorobenzylamino)-2-[4-(2-pyrrolidin-1-ylethyl)piperazin-1-yl]-5,6,7,8-tetrahydropyrido[4,3-d]pyrimidin-6-yl}-4-isopropoxy-3-cyclobutene-1,2-dione and benzylamine.

EXAMPLE 31

Synthesis of Compound 13-6

4-(2,4-dichlorobenzylamino)-2-[4-(2-pyrrolidin-1-ylethyl)piperazin-1-yl]-5,6,7,8-tetrahydropyrido[4,3-d]pyrimidine prepared in the same way as Example 4 (150 mg, 0.31 mmol) was dissolved in toluene (3 mL), and the solution was mixed with ethyl isocyanate (0.03 mL, 0.37 mmol) added dropwise, followed by stirring at room temperature for two hours. After checking the completion of the reaction by thin layer chromatography, the reaction mixture was concentrated and thereby yielded Compound 13-6 (124 mg, 71%).

EXAMPLE 32

Synthesis of Compound 13-7

Compound 13-7 was prepared in the same way as Process Step 2 of Example 19, except for using 3-{4-(2,4-dichlorobenzylamino)-2-[4-(2-pyrrolidin-1-ylethyl)piperazin-1-yl]-5,6,7,8-tetrahydropyrido[4,3-d]pyrimidin-6-yl}-4-isopropoxy-3-cyclobutene-1,2-dione and a ammonia methanol solution (2 mol/L).

EXAMPLE 33

Synthesis of Compound 13-8

Compound 13-8 was prepared in the same way as Process Step 2 of Example 19, except for using 3-{4-(2,4-dichlorobenzylamino)-2-[4-(2-pyrrolidin-1-ylethyl)piperazin-1-yl]-5,6,7,8-tetrahydropyrido[4,3-d]pyrimidin-6-yl}-4-isopropoxy-3-cyclobutene-1,2-dione and isopropylamine.

EXAMPLE 34

Synthesis of Compound 13-9

Compound 13-9 was prepared in the same way as Process Step 2 of Example 19, except for using 3-{4-(2,4-dichlorobenzylamino)-2-[4-(2-pyrrolidin-1-ylethyl)piperazin-1-yl]-5,6,7,8-tetrahydropyrido[4,3-d]pyrimidin-6-yl}-4-isopropoxy-3-cyclobutene-1,2-dione and cyclopropylmethylamine.

EXAMPLE 35

Synthesis of Compound 13-10

Compound 13-10 was prepared in the same way as Process Step 2 of Example 19, except for using 3-{4-(2,4-dichlorobenzylamino)-2-[4-(2-pyrrolidin-1-ylethyl)piperazin-1-yl]-5,6,7,8-tetrahydropyrido[4,3-d]pyrimidin-6-yl}-4-isopropoxy-3-cyclobutene-1,2-dione and cyclopropylamine.

EXAMPLE 36

Synthesis of Compound 13-11

Compound 13-11 was prepared in the same way as Process Step 2 of Example 19, except for using 3-{4-(2,4-dichlorobenzylamino)-2-[4-(2-pyrrolidin-1-ylethyl)piperazin-1-yl]-5,6,7,8-tetrahydropyrido[4,3-d]pyrimidin-6-yl}-4-isopropoxy-3-cyclobutene-1,2-dione and n-butylamine.

EXAMPLE 37

Syntheses of Compounds 14-1 through 14-11

Initially, 1-[6-tert-butoxycarbonyl-4-(2-chloro-4-fluorobenzylamino)-5,6,7,8-tetrahydropyrido[4,3-d]pyrimidin-2-yl]piperidine-4-carboxylic acid was prepared in the same way as Reference Example 8 from 2,4-dichloro-5,6,7,8-tetrahydropyrido[4,3-d]pyrimidine hydrochloride prepared according to Reference Example 1, except for using 2,4-dichlorobenzylamine instead of 2-chloro-4-fluorobenzylamine. Next, Compounds 14-1 through 14-11 were respectively prepared from 1-[6-tert-butoxycarbonyl-4-(2-chloro-4-fluorobenzylamino)-5,6,7,8-tetrahydropyrido[4,3-d]pyrimidin-2-yl]piperidine-4-carboxylic acid in the same way as Example 25 using 2,4-dichlorobenzylamine.

EXAMPLE 38

Synthesis of Compound 14-13

Process Step 1

Initially, 1-[6-tert-butoxycarbonyl-4-(2,4-dichlorobenzylamino)-5,6,7,8-tetrahydropyrido[4,3-d]pyrimidin-2-yl]piperidine-4-carboxylic acid (1.30 g, 2.50 mmol) was prepared in the same way as Reference Example 8 from 2,4-dichloro-5,6,7,8-tetrahydropyrido[4,3-d]pyrimidine hydrochloride prepared according to Reference Example 1, except for using 2,4-dichlorobenzylamine instead of 2-chloro-4-fluorobenzylamine. Next, 1-[6-tert-butoxycarbonyl-4-(2,4-dichlorobenzylamino)-5,6,7,8-tetrahydropyrido[4,3-d]pyrimidin-2-yl]piperidine-4-carboxylic acid was dissolved in chloroform (50 mL), and the solution was mixed with a solution of N-hydroxybenzotriazole in chloroform-tetrahydrofuran (2:1) (0.25 mol/L, 20 mL), a solution of 2-(4-morpholino)ethylamine in chloroform (1.00 mol/L, 8.0 mL) and N-ethyl-N'-(3-dimethylaminopropyl)carbodiimide polymer-bound (7.0 g), followed by stirring at 50° C. for eighteen hours. After checking the completion of the reaction by thin layer chromatography, the solid was separated from the reaction mixture by filtration, and the filtrate was concentrated. The residue was purified by silica gel column chromatography (ethyl acetate:n-hexane:triethylamine=10:10:1) and thereby yielded tert-butyl 4-(2,4-dichlorobenzylamino)-2-[4-(2-morpholin-4-ylethylcarbamoyl)piperidyl]-5,6,7,8-tetrahydropyrido[4,3-d]pyrimidine-6-carboxylate (0.80 g, in a yield of 50%).

Process Step 2

Tert-butyl 4-(2,4-dichlorobenzylamino)-2-[4-(2-morpholin-4-ylethylcarbamoyl)piperdino]-5,6,7,8-tetrahydropyrido[4,3-d]pyrimidine-6-carboxylate prepared according to Process Step 1 (0.80 g) was dissolved in dichloromethane (50 mL), and the solution was mixed with trifluoroacetic acid (10 mL), followed by stirring at room temperature for one hour. The reaction mixture was concentrated under reduced pressure, the residue was dissolved in ethyl acetate, and the solution was mixed with an aqueous sodium hydroxide solution (1.0 mol/L), followed by stirring. The reaction mixture was separated, and the aqueous layer was extracted with ethyl acetate. The combined organic layers were washed with brine, were dried over anhydrous magnesium sulfate, and the solvent was distilled off, to thereby yield 4-(2,4-dichlorobenzylamino)-2-[4-(2-morpholin-4-ylethylcarbamoyl)piperdino]-5,6,7,8-tetrahydropyrido[4,3-d]pyrimidine (0.56 g, in a yield of 84%).

Process Step 3

4-(2,4-Dichlorobenzylamino)-2-[4-(2-morpholin-4-ylethyl carbamoyl)piperdino]-5,6,7,8-tetrahydropyrido[4,3-d]pyrimidine prepared according to Process Step 2 (0.56 g, 1.1 mmol) was dissolved in chloroform, and the solution was mixed with N-hydroxybenzotriazole (161 mg), 1-hydroxycyclopropanecarboxylic acid (210 mg) and N-ethyl-N'-(3-dimethylaminopropyl)carbodiimide polymer-bound (2.9 g), followed by stirring at 50° C. for one hour. After checking the completion of the reaction by thin layer chromatography, the solid was separated from the reaction mixture by filtration, and the filtrate was concentrated. The residue was purified by silica gel column chromatography (ethyl acetate:triethylamine=10:1), and ethyl acetate was added for crystallization. The precipitated crystals were collected by filtration, were dried under reduced pressure and thereby yielded Compound 14-13 (298 mg, 44%).

EXAMPLE 39

Synthesis of Compound 14-12

Compound 14-12 was prepared by allowing 1-[6-tert-butoxycarbonyl-4-(2,4-dichlorobenzylamino)-5,6,7,8-tetrahydropyrido[4,3-d]pyrimidin-2-yl]piperidine-4-carboxylic acid to react with (2-pyrrolidinyl)ethylamine in the same way as Process Step 1 of Example 38 and treating the resulting compound in the same way as Process Steps 2 and 3 of Example 38.

EXAMPLE 40

Synthesis of Compound 14-14

Compound 14-14 was prepared by allowing 1-[6-tert-butoxycarbonyl-4-(2,4-dichlorobenzylamino)-5,6,7,8-tetrahydropyrido[4,3-d]pyrimidin-2-yl]piperidine-4-carboxylic acid to react with (2-piperazinyl)ethylamine in the same way as Process Step 1 of Example 38 and treating the resulting compound in the same way as Process Steps 2 and 3 of Example 38.

EXAMPLE 41

Syntheses of Compounds 15-1, 15-4 to 15-6, 15-9 to 15-12, 15-16, 15-23, 15-24 and 15-82

Process Step 1

Compound 3-10 prepared according to Example 1 (1.62 g, 3.50 mmol) and N,N-diisopropylethylamine (0.543 g, 4.20 mmol) were dissolved in tetrahydrofuran (20.0 mL), and the solution was mixed with bromoacetyl chloride (0.661 g, 4.20 mmol) added under ice-cooling, followed by stirring at room temperature for twenty minutes. The reaction mixture was mixed with water and was extracted with ethyl acetate. The organic layer was sequentially washed with a saturated aqueous sodium bicarbonate solution and brine, was dried over anhydrous magnesium sulfate, and the solvent was distilled off under reduced pressure, to thereby yield 2-(4-bromoacetylpiperazin-1-yl)-4-(2,4-dichlorobenzylamino)-6-(cyclopropylcarbonyl)-5,6,7,8-tetrahydropyrido[4,3-d]pyrimidine (1.82 g, 3.10 mmol, 89%). This compound was subjected to a subsequent step without further purification.

Process Step 2

(1) Compound 15-16

2-(4-Bromoacetylpiperazin-1-yl)-4-(2,4-dichlorobenzylamino)-6-(cyclopropylcarbonyl)-5,6,7,8-tetrahydropyrido [4,3-d]pyrimidine prepared according to Process Step 1 (0.478 g, 0.821 mmol) was dissolved in acetonitrile (7.00 mL), and the solution was mixed with 1,4-dioxa-8-azaspiro [4,5]decane (0.172 g, 1.20 mmol) and N,N-diisopropylethylamine (0.233 g, 1.80 mmol), followed by stirring at 60° C. for twelve hours. After checking the completion of the reaction by thin layer chromatography, the reaction mixture was purified by silica gel column chromatography (ethyl acetate: triethylamine=20:1) and thereby yielded Compound 15-16 (0.507 g, 96%).

(2) Compounds other than Compound 15-16

Compounds 15-1, 15-4 to 15-6, 15-9 to 15-12, 15-23, 15-24 and 15-82 were prepared from 2-(4-bromoacetylpiperazin-1-yl)-4-(2,4-dichlorobenzylamino)-6-(cyclopropylcarbonyl)-5,6,7,8-tetrahydropyrido[4,3-d]pyrimidine prepared according to Process Step 1 and corresponding amines, respectively, in the same way as above-mentioned (1).

EXAMPLE 42

Syntheses of Compounds 15-13, 15-14 and 15-22

Process Step 1

Initially, tert-butyl 4-(2,4-dichlorobenzylamino)-2-piperazinyl-5,6,7,8-tetrahydro pyrido[4,3-d]pyrimidine-6-carboxylate (1.06 g, 2.15 mmol) was prepared in the same way as Process Step 3 of Example 4 from tert-butyl 2-chloro-4-(2,4-dichlorobenzylamino)-5,6,7,8-tetrahydropyrido[4,3-d]pyrimidine-6-carboxylate prepared according to Process Step 2 of Example 4 and piperazine. The resulting compound was allowed to react with bromoacetyl chloride in the same way as Process Step 1 of Example 41 and thereby yielded tert-butyl 4-(2,4-dichlorobenzylamino)-2-(4-bromoacetylpiperazin-1-yl)-5,6,7,8-tetrahydropyrido[4,3-d]pyrimidine-6-carboxylate (1.27 g, in a quantitative yield).

Process Step 2

Tert-butyl 4-(2,4-dichlorobenzylamino)-2-(4-bromoacetylpiperazin-1-yl)-5,6,7,8-tetrahydropyrido[4,3-d]pyrimidine-6-carboxylate prepared according to Process Step 1 was allowed to react with 4-hydroxypiperidine, 3-hydroxypyrrolidine or 1,4-dioxa-8-azaspiro[4,5]decane, respectively, in the same way as Process Step 2 of Example 41, was then treated in the same way as Process Step 4 of Example 4 and thereby yielded 4-(2,4-dichlorobenzylamino)-2-(4-aminoacetylpiperazin-1-yl)-5,6,7,8-tetrahydropyrido[4,3-d]pyrimidine derivatives each having a corresponding 2-position side chain, respectively.

Process Step 3

Compounds 15-13, 15-14 and 15-22 were obtained in the same way as Example 31 from the corresponding 5,6,7,8-tetrahydropyrido[4,3-d]pyrimidine derivatives prepared according to Process Step 2, respectively, and ethyl isocyanate.

EXAMPLE 43

Synthesis of Compound 15-17

Compound 15-16 prepared according to Example 41 (0.322 g, 0.500 mmol) was dissolved in tetrahydrofuran (10.0 mL), and the solution was mixed with diluted hydrochloric acid (3.00 mol/L, 5.00 mL), followed by stirring at 80° C. for six hours. After checking the completion of the reaction by thin layer chromatography, the reaction mixture was neutralized with an aqueous sodium hydroxide solution (3.00 mol/L) and was extracted with ethyl acetate. The organic layer was dried over anhydrous magnesium sulfate, was concentrated under reduced pressure, and the residue was purified by silica gel column chromatography (ethyl acetate:triethylamine=20:1). The resulting oil was crystallized from a mixture of hexane and ethyl acetate (3:1) and thereby yielded Compound 15-17 (0.250 g, 83%).

EXAMPLE 44

Synthesis of Compound 15-19

Compound 15-19 was prepared in the same way as Example 31, except for using 4-(2,4-dichlorobenzylamino)-2-[4-(4-fluoropiperid-1-ylacetyl)piperazin-1-yl]-5,6,7,8-tetrahydropyrido[4,3-d]pyrimidine prepared in the same way as Example 4 and ethyl isocyanate.

EXAMPLE 45

Synthesis of Compound 15-20

Process Step 1

Tert-butyl 4-(2,4-dichlorobenzylamino)-2-piperazinyl-5,6,7,8-tetrahydro pyrido[4,3-d]pyrimidine-6-carboxylate prepared as an intermediate in Process Step 1 of Example 42 (0.665 g, 1.35 mmol) was dissolved in tetrahydrofuran (5.4 mL), and the solution was mixed with 4-methylpiperazine-1-carbonyl chloride (0.325 g) and N,N-diisopropylethylamine (0.59 mL), followed by stirring for eighteen hours. After checking the completion of the reaction by thin layer chromatography, the reaction mixture was mixed with a saturated aqueous sodium bicarbonate solution and was extracted with ethyl acetate. The organic layer was washed with brine, was dried over anhydrous sodium chloride, and the solvent was distilled off. The residue was purified by silica gel column chromatography (methanol:chloroform=3:97 to 10:90) and thereby yielded tert-butyl 4-(2,4-dichlorobenzylamino)-2-[4-(4-methylpiperazin-1-ylcarbonyl)piperazin-1-yl]-5,6,7,8-tetrahydropyrido[4,3-d]pyrimidine-6-carboxylate (0.797 g, in a yield of 96%).

Process Step 2

Tert-butyl 4-(2,4-dichlorobenzylamino)-2-[4-(4-methylpiperazin-1-ylcarbonyl)piperazin-1-yl]-5,6,7,8-tetrahydropyrido[4,3-d]pyrimidine-6-carboxylate prepared according to Process Step 1 was subjected to the procedure of Process Step 4 of Example 4 and then to the procedure of Example 31 and thereby yielded Compound 15-20.

EXAMPLE 46

Synthesis of Compound 15-21

Tert-butyl 4-(2,4-dichlorobenzylamino)-2-[4-(4-methylpiperazin-1-ylcarbonyl)piperazin-1-yl]-5,6,7,8-tetrahydropyrido[4,3-d]pyrimidine-6-carboxylate prepared according to Process Step 1 of Example 45 was subjected to the procedure of Process Step 4 of Example 4 and then to the procedure of Process Step 1 of Example 26 and thereby yielded Compound 15-21.

EXAMPLE 47

Synthesis of Compound 15-25

Compound 3-10 (0.306 g, 0.663 mmol) was dissolved in dimethylformamide (2.7 mL), and the solution was mixed with N-ethyl-N'-(3-dimethylaminopropylcarbodiimide hydrochloride (0.193 g, 0.995 mmol), 1-hydroxybenzotriazole monohydrate (0.158 g, 0.995 mmol), 1-methylpiperidine-4-carboxylic acid hydrochloride (0.181 g, 0.995 mmol) and triethylamine (0.369 mL), followed by stirring at 70° C. for four hours. The reaction mixture was cooled to room temperature and was mixed with an aqueous sodium bicarbonate solution, followed by extraction with chloroform. The organic layer was sequentially washed with diluted hydrochloric acid (0.1 mol/L), a saturated aqueous sodium bicarbonate solution and brine, was dried over anhydrous sodium sulfate, and the solvent was distilled off. The residue was purified by silica gel column chromatography (chloroform: 7 mol/L ammonia-methanol solution=97:3 to 95:5), and the solvent was distilled off. The residue was crystallized from isopropanol, the precipitated crystals were collected by filtration, were dried and thereby yielded Compound 15-25 (0.183 g, in a yield of 47%).

EXAMPLE 48

Syntheses of Compounds 15-26, 15-27, 15-32 and 15-33

Compounds 15-26, 15-27, 15-32 and 15-33 were prepared in the same way as Example 47, except for allowing Compound 3-10 to react with 1-methylpiperidine-3-carboxylic acid, 1-methylpiperidine-2-carboxylic acid, 4-methylmorpholine-2-carboxylic acid prepared according to Reference Example 18 or 1-methylpyrrolidine-2-carboxylic acid, respectively.

EXAMPLE 49

Syntheses of Compounds 15-28 to 15-31, 15-34 and 15-35

Compounds 15-28 to 15-31, 15-34 and 15-35 were prepared in the same way as Example 47, except for allowing Compound 15-68 prepared according to Example 67 mentioned later to react with 4-oxopiperidinoacetic acid, 1-methylpiperidine-2-carboxylic acid, 1-methylpiperidine-4-carboxylic acid, 1-methylpyrrolidine-2-carboxylic acid, 1-methylpiperidine-3-carboxylic acid or 4-methylmorpholine-2-carboxylic acid prepared according to Reference Example 18, respectively.

EXAMPLE 50

Syntheses of Compounds 15-37 to 15-39, 15-41, 15-42, 15-45, 15-46 and 15-50 to 15-53

Compounds 15-37 to 15-39, 15-41, 15-42, 15-45, 15-46, 15-50 to 15-53 were prepared in the same way as Example 31, except for allowing 4-(2,4-dichlorobenzylamino)-2-[4-(4-methylmorpholin-2-ylmethyl)piperazin-1-yl]-5,6,7,8-tetrahydropyrido[4,3-d]pyrimidine prepared in the same way as Example 4 to react with corresponding isocyanates, respectively.

EXAMPLE 51

Synthesis of Compound 15-40

Compound 15-40 was prepared in the same way as Example 31, except for allowing 4-(2,4-dichlorobenzylamino)-2-[4-(4-methylmorpholin-2-ylmethyl)piperazin-1-yl]-5,6,7,8-tetrahydropyrido[4,3-d]pyrimidine prepared in the same way as Example 4 to react with trimethylsilyl isocyanate.

EXAMPLE 52

Synthesis of Compound 15-44

Compound 15-44 was prepared in the same way as Example 31, except for allowing 4-(2,4-dichlorobenzylamino)-2-[4-((2R)-4-methylmorpholin-2-ylmethyl)piperazin-1-yl]-5,6,7,8-tetrahydropyrido[4,3-d]pyrimidine prepared in the same way as Example 4 to react with ethyl isocyanate.

EXAMPLE 53

Synthesis of Compound 15-47

Compound 15-47 was prepared in the same way as Example 31, except for allowing 4-(2,4-dichlorobenzylamino)-2-[4-((2S)-4-methylmorpholin-2-ylmethyl)piperazin-1-yl]-5,6,7,8-tetrahydropyrido[4,3-d]pyrimidine prepared in the same way as Example 4 to react with ethyl isocyanate.

EXAMPLE 54

Synthesis of Compound 15-49

4-(2,4-Dichlorobenzylamino)-2-[4-(4-methylmorpholin-2-ylmethyl)piperazin-1-yl]-5,6,7,8-tetrahydropyrido[4,3-d]pyrimidine prepared in the same way as Example 4 (0.14 g, 0.28 mmol) was dissolved in tetrahydrofuran (1.4 mL), and the solution was mixed with triethylamine (0.059 mL, 0.42 mmol) and dimethylcarbamoyl chloride (0.028 mL, 0.30 mmol) while stirring under ice-cooling, followed by stirring at room temperature for two hours. The reaction mixture was mixed with water and was extracted with ethyl acetate. The organic layer was washed with brine, was dried over anhydrous sodium sulfate, and the solvent was distilled off. The residue was purified by thin layer chromatography (chloroform:ammonia methanol solution (7.0 mol/L)=20:1) and thereby yielded Compound 15-49 (0.050 mg, 31%).

EXAMPLE 55

Synthesis of Compound 15-54

Compound 15-54 was prepared in the same way as Example 31, except for allowing 4-(2,4-dichlorobenzylamino)-2-[4-((2S)-4-methylmorpholin-2-ylmethyl)piperazin-1-yl]-5,6,7,8-tetrahydropyrido[4,3-d]pyrimidine prepared in the same way as Example 4 to react with n-propyl isocyanate.

EXAMPLE 56

Synthesis of Compound 15-55

Process Step 1

4-(2,4-Dichlorobenzylamino)-2-[4-(4-methylmorpholin-2-ylmethyl)piperazin-1-yl]-5,6,7,8-tetrahydropyrido[4,3-d]pyrimidine prepared in the same way as Example 4 (0.974 g, 1.92 mmol) was mixed with diphenyl cyanocarbonimidate (0.503 g, 2.11 mmol), triethylamine (0.348 mL), isopropanol (8.7 mL) and dimethylformamide (2.2 mL), followed by stirring for fourteen hours. The reaction mixture was mixed with water and was extracted with a mixture of chloroform and isopropanol (3:1). The organic layer was dried over anhydrous sodium sulfate, and the solvent was distilled off. The residue was reslurried with isopropyl ether and isopropyl alcohol, the crystals were collected by filtration, were dried and thereby yielded N-cyano-O-phenylisourea intermediate (0.862 g, in a yield of 69%).

Process Step 2

The N-cyano-O-phenylisourea intermediate (0.386 g, 0.594 mmol) prepared according to Process Step 1 was mixed with ethylamine hydrochloride (0.252 g, 3.09 mmol) and triethylamine (0.257 mL), followed by stirring at 70° C. for five hours. The reaction mixture was cooled to room temperature and was mixed with a saturated aqueous sodium bicarbonate solution, followed by extraction with chloroform. The organic layer was washed with brine, was dried over anhydrous sodium sulfate, and the solvent was distilled off. The residue was purified by silica gel column chromatography (chloroform:ammonia methanol solution (7 mol/L)=95:5 to 93:7) and thereby yielded Compound 15-55 (0.328 g, in a yield of 88%).

EXAMPLE 57

Synthesis of Compound 15-56

Process Step 1

4-(2,4-Dichlorobenzylamino)-2-[4-(4-methylmorpholin-2-ylmethyl)piperazin-1-yl]-5,6,7,8-tetrahydropyrido[4,3-d]pyrimidine prepared in the same way as Example 4 (0.802 g, 1.58 mmol) was mixed with [bis(methylthio)methylene]propanedinitrile (0.299 g, 1.74 mmol), ethanol (6.32 mL) and triethylamine (0.44 mL), followed by stirring at room temperature for fifteen hours. A saturated aqueous sodium bicarbonate solution and chloroform were added, followed by separation. The organic layer was washed with brine, was dried over anhydrous sodium sulfate, and the solvent was distilled off. The residue was reslurried with isopropanol and isopropyl ether, the resulting crystals were collected by filtration and thereby yielded 4-(2,4-dichlorobenzylamino)-6-(2,2-dicyanomethyl-1-sulfanylvinyl)-2-[4-(4-methylmorpholin-2-ylmethyl)piperazin-1-yl]-5,6,7,8-tetrahydropyrido[4,3-d]pyrimidine (0.763 g, in a yield of 77%).

Process Step 2

4-(2,4-Dichlorobenzylamino)-6-(2,2-dicyanomethyl-1-sulfanylvinyl)-2-[4-(4-methylmorpholin-2-ylmethyl)piperazin-1-yl ]-5,6,7,8-tetrahydropyrido[4,3-d]pyrimidine prepared according to Process Step 1 (0.408 g, 0.649 mmol) was mixed with a solution of ethylamine in tetrahydrofuran (2.0 mol/L, 0.625 mL, 1.25 mmol), triethylamine (0.174 mL), isopropanol (2.9 mL) and dimethylformamide (0.72 mL), followed by stirring at room temperature for one day. The reaction mixture was mixed with water and was extracted with chloroform. The organic layer was washed with brine, was dried over anhydrous sodium sulfate, and the solvent was distilled off. The residue was sequentially purified by silica gel column chromatography (chloroform:ammonia methanol solution (7 mol/L)=95:5 to 90:10), preparative thin layer chromatography (chloroform:methanol=90:10), and preparative thin layer chromatography (chloroform: ammonia methanol solution (7 mol/L)=90:10) and thereby yielded Compound 15-56 (0.165 g, in a yield of 41%).

EXAMPLE 58

Synthesis of Compound 15-57

Compound 15-57 was prepared in the same way as Example 31, except for allowing 4-(2,4-dichlorobenzylamino)-2-[4-((2R)-4-ethylmorpholin-2-yl methyl)piperazin-1-yl]-5,6,7,8-tetrahydropyrido[4,3-d]pyrimidine prepared in the same way as Example 4 to react with methyl isocyanate.

EXAMPLE 59

Synthesis of Compound 15-58

4-(2,4-Dichlorobenzylamino)-2-[4-(4-methylmorpholin-2-ylmethyl)piperazin-1-yl]-5,6,7,8-tetrahydropyrido[4,3-d]pyrimidine prepared in the same way as Example 4 (0.917 g, 1.81 mmol) was mixed with N-ethyl-N'-(3-dimethylaminopropylcarbodiimide hydrochloride (1.04 g, 5.43 mmol), 1-hydroxybenzotriazole monohydrate (0.837 g, 5.43 mmol), 1-hydroxy-1-cyclopropanecarboxylic acid (0.279 g, 2.72 mmol, triethylamine (1.01 mL) and dimethylformamide (7.24 mL), followed by stirring at room temperature for eleven hours. The reaction mixture was mixed with water and was extracted with a mixture of chloroform and isopropanol (4:1). The organic layer was dried over anhydrous sodium sulfate, and the solvent was distilled off. The residue was purified by silica gel column chromatography (chloroform: ammonia methanol solution (7 mol/L)=97:3 to 94:6) and was further purified twice by preparative thin layer chromatography (chloroform:ammonia methanol solution (7 mol/L)=90:10) and thereby yielded Compound 15-58 (0.362 g, in a yield of 34%).

EXAMPLE 60

Synthesis of Compound 15-59

Compound 15-59 was prepared in the same way as Example 31, except for allowing 4-(2,4-dichlorobenzylamino)-2-[4-((2R)-4-methylmorpholin-2-ylmethyl)piperazin-1-yl]-5,6,7,8-tetrahydropyrido[4,3-d]pyrimidine prepared in the same way as Example 4 to react with n-propyl isocyanate.

EXAMPLE 61

Synthesis of Compound 15-60

Compound 15-60 was prepared in the same way as Example 31, except for allowing 4-(2,4-dichlorobenzylamino)-2-[4-((2R)-4-methylmorpholin-2-ylmethyl)piperazin-1-yl]-5,6,7,8-tetrahydropyrido[4,3-d]pyrimidine prepared in the same way as Example 4 to react with ethyl isocyanate.

EXAMPLE 62

Synthesis of Compound 15-61

Compound 15-61 was prepared in the same way as Example 59, except for allowing 4-(2,4-dichlorobenzylamino)-2-[4-(4-methylmorpholin-2-ylmethyl)piperazin-1-yl]-5,6,7,8-tetrahydropyrido[4,3-d]pyrimidine prepared in the same way as Example 4 to react with 2-hydroxy-2-propionic acid.

EXAMPLE 63

Synthesis of Compound 15-62

Compound 15-62 was prepared in the same way as Example 31, except for allowing 4-(2,4-dichlorobenzylamino)-2-[4-(4-methylmorpholin-3-ylmethyl)piperazin-1-yl]-5,6,7,8-tetrahydropyrido[4,3-d]pyrimidine prepared in the same way as Example 4 to react with ethyl isocyanate.

EXAMPLE 64

Synthesis of Compound 15-63

Compound 15-63 was prepared in the same way as Example 31, except for allowing 4-(2,4-dichlorobenzylamino)-2-[4-(4-methylmorpholin-3-ylmethyl)piperazin-1-yl]-5,6,7,8-tetrahydropyrido[4,3-d]pyrimidine prepared in the same way as Example 4 to react with n-propyl isocyanate.

EXAMPLE 65

Synthesis of Compound 15-65

Compound 3-10 (82.1 mg, 0.18 mmol) prepared according to Example 1 was dissolved in 2-propanol (3 mL), and the solution was mixed with 3-isopropoxy-4-(2-pyrrolidin-1-ylethylamino)-3-cyclobutene-1,2-dione (49.0 mg, 0.20 mmol), followed by stirring at room temperature for three hours. After checking the completion of the reaction by thin layer chromatography, the reaction mixture was concentrated, the resulting solid was washed with 2-propanol and thereby yielded Compound 15-65 (59.6 mg, 52%).

EXAMPLE 66

Synthesis of Compound 15-67

Process Step 1

Compound 15-71 prepared according to Example 1 (0.23 g, 0.46 mmol) was dissolved in ethanol (2.3 mL), and the solution was mixed with N,N'-bis(tert-butoxycarbonyl)-S-methylisothiourea (0.15 g, 0.50 mmol), followed by stirring at room temperature for twenty-four hours. The solvent was distilled off, the residue was purified by silica gel chromatography (ethyl acetate:methanol=10:1), was triturated with ethyl acetate and thereby yielded 4-(2,4-dichlorobenzylamino)-6-cyclopropylcarbonyl-2-{4-[2-$N^2$,$N^3$-bis(tert-butoxycarbonyl)guanidinoethyl]piperazin-1-yl}-5,6,7,8-tetrahydropyrido[4,3-d]pyrimidine (20 mg, 5.9%).

ESI-MS m/z: 546 $[M+H]^+$ $^1H$ NMR ($CDCl_3$) δ (ppm): 0.71-1.12 (m, 4H), 1.50 (s, 9H), 1.52 (s, 9H), 1.65-1.99 (m, 1H), 2.40-2.92 (m, 8H), 3.41-4.00 (m, 8H), 4.28-4.45 (m, 2H), 4.62-4.99 (m, 3H), 7.11-7.42 (m, 3H), 8.70-8.90 (m, 1H), 11.3-11.6 (m, 1H)

Process Step 2

4-(2,4-Dichlorobenzylamino)-6-cyclopropylcarbonyl-2-{4-[2-$N^2$,$N^3$-bis(tert-butoxycarbonyl)guanidinoethyl]piperazin-1-yl}-5,6,7,8-tetrahydropyrido[4,3-d]pyrimidine prepared according to Process Step 1 (20 mg, 0.027 mmol) was mixed with a solution of hydrogen chloride in ethyl acetate (4.0 mol/L, 1.0 mL), followed by standing still at room temperature for four hours. The precipitated crystals were collected by filtration, were dried under reduced pressure and thereby yielded Compound 15-67 (13 mg, 76%).

EXAMPLE 67

Synthesis of Compound 15-68

Initially, 2-(4-tert-butoxycarbonylpiperazinyl)-4-(2,4-dichlorobenzylamino)-5,6,7,8-tetrahydropyrido[4,3-d]pyrimidin-6-yl-N-ethylcarboxamide was prepared in the same way as Process Steps 2 and 3 of Example 1, except for allowing 2,4-dichloro-5,6,7,8-tetrahydropyrido[4,3-d]pyrimidin-6-yl-N-ethylcarboxamide prepared according to Reference Example 9 to react sequentially with 2,4-dichlorobenzylamino and 1-tert-butoxycarbonylpiperazine. Above-prepared 2-(4-tert-butoxycarbonylpiperazinyl)-4-(2,4-dichlorobenzylamino)-5,6,7,8-tetrahydropyrido[4,3-d]pyrimidin-6-yl-N-ethylcarboxamide was treated in the same way as Process Step 4 of Example 4 and thereby yielded Compound 15-68.

EXAMPLE 68

Synthesis of Compound 15-69

Compound 15-71 (0.803 g, 1.59 mmol) prepared in the same way as Example 1 was mixed with 2-chloropyrimidine (0.547 g, 4.77 mmol), sodium carbonate (2.53 g, 424 mmol) and dioxane (6.36 mL), followed by stirring at 100° C. for two hours. The reaction mixture was mixed with water and was extracted with chloroform. The organic layer was washed with brine, was dried over anhydrous sodium sulfate, and the solvent was distilled off. The residue was purified by silica gel column chromatography (chloroform:methanol=97:3 to 92:8) and thereby yielded Compound 15-69 (0.586 g, in a yield of 64%).

EXAMPLE 69

Synthesis of Compound 15-70

Compound 15-70 was prepared in the same way as Example 68, except for using Compound 15-71 and ethylacetimidate hydrochloride.

EXAMPLE 70

Syntheses of Compounds 15-73 to 15-80

Compounds 15-73 to 15-80 were prepared in the same way as Example 59, except for allowing 4-(2,4-dichlorobenzylamino)-2-[4-(3-pyrrolidinylpropyl)piperazinyl]-5,6,7,8-tetrahydropyrido[4,3-d]pyrimidine prepared in the same way as Example 4 to react with corresponding carboxylic acids, respectively.

EXAMPLE 71

Syntheses of Compounds 16-1, 16-2 and 16-4

Process Step 1

Initially, 2-(4-bromoacetylpiperazin-1-yl)-4-(2-chloro-4-fluorobenzylamino)-6-(cyclopropylcarbonyl)-5,6,7,8-tetrahydropyrido[4,3-d]pyrimidine was prepared in the same way as Process Step 1 of Example 41, except for using 4-(2-chloro-4-fluorobenzylamino)-6-(cyclopropylcarbonyl)-2-piperazinyl-5,6,7,8-tetrahydropyrido[4,3-d]pyrimidine prepared in the same way as Example 1.

Process Step 2

Compounds 16-1, 16-2 and 16-4 were prepared in the same way as Process Step 2 of Example 41, except for allowing 2-(4-bromoacetylpiperazin-1-yl)-4-(2-chloro-4-fluorobenzylamino)-6-(cyclopropylcarbonyl)-5,6,7,8-tetrahydropyrido[4,3-d]pyrimidine prepared according to Process Step 1 to react with 3-methoxypyrrolidine, 4-cyanopiperidine or cyclobutylamine, respectively.

EXAMPLE 72

Synthesis of Compound 16-3

Tert-butyl methylpyrrolidine-3-carboxylate prepared according to a method described in Chemistry Letters, vol. 973 (1986) (186 mg, 1.00 mmol) was dissolved in dichloromethane (5.00 mL), and the solution was mixed with trifluoroacetic acid (2.00 mL), followed by stirring at room temperature for three hours. The reaction mixture was concentrated under reduced pressure, and the residue was suspended in tetrahydrofuran (3.00 mL). The suspension was mixed with 6-(cyclopropylcarbonyl)-4-(2-chloro-4-fluorobenzylamino)-2-piperazinyl-5,6,7,8-tetrahydropyrido[4,3-d]pyrimidine prepared in the same way as Example 1 (223 mg, 0.501 mmol), 1-ethyl-3-(3-dimethylaminopropyl)carbodiimide hydrochloride (0.192 g, 1.00 mmol), 1-hydroxybenzotriazole monohydrate (0.135 g, 0.999 mmol) and triethylamine (0.304 g, 3.00 mmol), followed by stirring at room temperature for ten hours. The reaction mixture was mixed with water and was extracted with ethyl acetate. The organic layer was washed with brine, was dried over anhydrous magnesium sulfate, and the solvent was distilled off under reduced pressure. The residue was purified by silica gel column chromatography (ethyl acetate:triethylamine=10:1) and thereby yielded Compound 16-3 (0.100 g, 36%).

EXAMPLE 73

Synthesis of Compound 16-5

Compound 16-5 was prepared in the same way as Example 31, except for allowing 4-(2-chloro-4-fluorobenzylamino)-2-[4-(4-methylmorpholin-2-ylmethyl)piperazin-1-yl]-5,6,7,8-tetrahydropyrido[4,3-d]pyrimidine prepared in the same way as Example 4 to react with ethyl isocyanate.

EXAMPLE 74

Synthesis of Compound 16-6

Compound 16-6 was prepared in the same way as Example 31, except for allowing 4-(2-chloro-4-fluorobenzylamino)-2-[4-(4-methylmorpholin-2-ylmethyl)piperazin-1-yl]-5,6,7,8-tetrahydropyrido[4,3-d]pyrimidine prepared in the same way as Example 4 to react with n-propyl isocyanate.

EXAMPLE 75

Synthesis of Compound 16-7

Compound 16-7 was prepared in the same way as Example 31, except for allowing 4-(2-chloro-4-fluorobenzylamino)-2-[4-((2S)-4-methylmorpholin-2-ylmethyl)piperazin-1-yl]-5,6,7,8-tetrahydropyrido[4,3-d]pyrimidine prepared in the same way as Example 4 to react with ethyl isocyanate.

EXAMPLE 76

Synthesis of Compound 16-8

Compound 16-8 was prepared in the same way as Example 31, except for allowing 4-(2-chloro-4-fluorobenzylamino)-2-[4-((2S)-4-methylmorpholin-2-ylmethyl)piperazin-1-yl]-5,6,7,8-tetrahydropyrido[4,3-d]pyrimidine prepared in the same way as Example 4 to react with n-propyl isocyanate.

EXAMPLE 77

Synthesis of Compound 16-9

Compound 16-9 was prepared in the same way as Example 31, except for allowing 4-(2-chloro-4-fluorobenzylamino)-2-[4-((2R)-4-methylmorpholin-2-ylmethyl)piperazin-1-yl]-5,6,7,8-tetrahydropyrido[4,3-d]pyrimidine prepared in the same way as Example 4 to react with ethyl isocyanate.

EXAMPLE 78

Synthesis of Compound 16-10

Compound 16-10 was prepared in the same way as Example 31, except for allowing 4-(2-chloro-4-fluorobenzylamino)-2-[4-((2R)-4-methylmorpholin-2-ylmethyl)piperazin-1-yl]-5,6,7,8-tetrahydropyrido[4,3-d]pyrimidine prepared in the same way as Example 4 to react with n-propyl isocyanate.

EXAMPLE 79

Synthesis of Compound 16-11

Compound 16-11 was prepared in the same way as Example 31, except for allowing 4-(2-chloro-4-fluorobenzylamino)-2-[4-((2R)-4-ethylmorpholin-2-ylmethyl)piperazin-1-yl]-5,6,7,8-tetrahydropyrido[4,3-d]pyrimidine prepared in the same way as Example 4 to react with methyl isocyanate.

EXAMPLE 80

Synthesis of Compound 16-12

Compound 16-12 was prepared in the same way as Example 31, except for allowing 4-(2-chloro-4-fluorobenzylamino)-2-[4-((2R)-4-ethylmorpholin-3-ylmethyl)piperazin-1-yl]-5,6,7,8-tetrahydropyrido[4,3-d]pyrimidine prepared in the same way as Example 4 to react with ethyl isocyanate.

EXAMPLE 81

Synthesis of Compound 16-13

Compound 16-14 (1.29 g, 1.98 mmol) prepared according to Example 82 mentioned later was dissolved in 1,2-dichloroethane (30 mL), and the solution was mixed with 1-chloroethyl chloroformate (0.43 mL, 3.96 mmol), followed by stirring under reflux for three hours. After checking the completion of the reaction by thin layer chromatography, the reaction mixture was cooled and was mixed with water, followed by separation. The organic layer was washed with brine, was dried over anhydrous magnesium sulfate, and the solvent was distilled off. The residue was purified by silica gel column chromatography (chloroform:methanol=15:1) and thereby yielded a 1-chloroethyl (2R)-2-{4-[4-(2-chloro-4-fluorobenzylamino)-6-(N-propylcarbamoyl)-5,6,7,8-tetrahydropyrido[4,3-d]pyrimidin-2-yl]piperazin-1-ylmethyl}morpholine-4-carboxylate fraction. After distilling off the solvent, the residue was dissolved in methanol (850 mL), followed by stirring under reflux for three hours. After checking the completion of the reaction by thin layer chromatography, the reaction mixture was concentrated, the residue was purified by silica gel column chromatography (chloroform:methanol:ammonia methanol solution (7 mol/L)=5:0.9:0.1) and thereby yielded Compound 16-13 (0.28 g, 25%).

EXAMPLE 82

Synthesis of Compound 16-14

Compound 16-14 was prepared in the same way as Example 31, except for allowing 2-[4-((2R)-4-benzylmorpholin-2-ylmethyl)piperazin-1-yl]-4-(2-chloro-4-fluorobenzylamino)-5,6,7,8-tetrahydropyrido[4,3-d]pyrimidine prepared in the same way as Example 4 to react with n-propyl isocyanate.

EXAMPLE 83

Synthesis of Compound 16-15

Process Step 1

6-(Cyclopropylcarbonyl)-4-(2-chloro-4-fluorobenzylamino)-2-piperazinyl-5,6,7,8-tetrahydropyrido[4,3-d]pyrimidine prepared in the same way as Example 1 (0.21 g, 0.47 mmol) was dissolved in dimethylformamide (2.1 mL), and the solution was mixed with triethylamine (0.20 mL, 1.4 mmol) and epibromohydrin (0.081 mL, 0.94 mmol), followed by stirring at room temperature for twenty-four hours. The reaction mixture was mixed with water and was extracted with ethylacetate. The organic layer was washed with brine, was dried over anhydrous sodium sulfate, and the solvent was distilled off. The residue was purified by silica gel chromatography (ethyl acetate:triethylamine=10:1) and thereby yielded 4-(2-chloro-4-fluorobenzylamino)-6-cyclopropylcarbonyl-2-[4-(oxiran-2-ylmethyl)piperazin-1-yl]-5,6,7,8-tetrahydropyrido[4,3-d]pyrimidine (0.22 g, 90%).

APCI-MS m/z: 501 $[M+H]^+$ $^1H$ NMR ($CDCl_3$) δ (ppm): 0.71-1.10 (m, 4H), 1.71-1.97 (m, 1H), 2.23-3.21 (m, 11H), 3.68-4.00 (m, 6H), 4.25-4.44 (m, 2H), 4.64-4.93 (m, 3H), 6.82-7.00 (m, 1H), 7.05-7.22 (m, 1H), 7.25-7.49 (m, 1H)

Process Step 2

4-(2-Chloro-4-fluorobenzylamino)-6-cyclopropylcarbonyl-2-[4-(oxiran-2-ylmethyl)piperazin-1-yl]-5,6,7,8-tetrahydropyrido[4,3-d]pyrimidine prepared according to Process Step 1 (0.20 g, 0.40 mmol) was dissolved in isopropanol (2.0 mL), the solution was mixed with pyrrolidine (0.067 mL, 0.80 mmol), followed by stirring under reflux for three hours. The solvent was distilled off, the residue was purified by silica gel chromatography (ethyl acetate:methanol:triethylamine=10:1:0.1) and thereby yielded Compound 16-15 (0.19 g, 83%).

EXAMPLE 84

Synthesis of Compound 17-1

Compound 17-1 was prepared in the same way as Example 31, except for allowing 4-(2,4-dichlorobenzylamino)-2-[4-(2-pyrrolidin-1-ylethyl)piperidino]-5,6,7,8-tetrahydropyrido[4,3-d]pyrimidine prepared in the same way as Example 4 to react with ethyl isocyanate.

EXAMPLE 85

Synthesis of Compound 17-2

Compound 17-2 was prepared in the same way as Example 59, except for allowing 4-(2,4-dichlorobenzylamino)-2-[4-(2-pyrrolidin-1-ylethyl)piperidino]-5,6,7,8-tetrahydropyrido[4,3-d]pyrimidine prepared in the same way as Example 4 to react with 1-hydroxy-1-cyclopropanecarboxylic acid.

EXAMPLE 86

Synthesis of Compound 17-3

Compound 17-3 was prepared in the same way as Example 31, except for allowing 2-{4-[2-(3-acetylaminopyrrolidin-1-yl)ethyl]piperidino}-4-(2,4-dichlorobenzylamino)-5,6,7,8-tetrahydropyrido[4,3-d]pyrimidine prepared in the same way as Example 4 to react with ethyl isocyanate.

EXAMPLE 87

Synthesis of Compound 17-4

Compound 17-4 was prepared in the same way as Example 31, except for allowing 4-(2,4-dichlorobenzylamino)-2-{4-

[(2-diethylamino)ethyl]piperidino}5,6,7,8-tetrahydropyrido [4,3-d]pyrimidine prepared in the same way as Example 4 to react with ethyl isocyanate.

EXAMPLE 88

Synthesis of Compound 17-5

Compound 17-5 was prepared in the same way as Example 31, except for allowing 4-(2,4-dichlorobenzylamino)-2-{4-[2-(3-methoxypyrrolidin-1-yl)ethyl]piperidino}-5,6,7,8-tetrahydropyrido[4,3-d]pyrimidine prepared in the same way as Example 4 to react with ethyl isocyanate.

EXAMPLE 89

Synthesis of Compound 17-6

Compound 17-6 was prepared in the same way as Example 59, except for allowing 4-(2,4-dichlorobenzylamino)-2-(4-[2-(3-methoxypyrrolidin-1-yl)ethyl]piperidino)-5,6,7,8-tetrahydropyrido[4,3-d]pyrimidine prepared in the same way as Example 4 to react with cyclopropanecarboxylic acid.

EXAMPLE 90

Synthesis of Compound 17-7

Compound 17-7 was prepared in the same way as Example 31, except for allowing 4-(2,4-dichlorobenzylamino)-2-(4-{2-[(cyclopropylmethyl)amino]ethyl)piperidino}-5,6,7,8-tetrahydropyrido[4,3-d]pyrimidine prepared in the same way as Example 4 to react with ethyl isocyanate.

EXAMPLE 91

Synthesis of Compound 17-8

Compound 17-8 was prepared in the same way as Example 59, except for allowing 4-(2-chloro-4-fluorobenzylamino)-2-[4-(2-pyrrolidin-1-ylethyl)piperidino]-5,6,7,8-tetrahydropyrido[4,3-d]pyrimidine prepared in the same way as Example 4 to react with 1-hydroxy-1-cyclopropanecarboxylic acid.

EXAMPLE 92

Synthesis of Compound 19-1

Process Step 1

Tert-butyl 4-(ethoxycarbonyldifluoromethyl)-4-hydroxypiperidinecarboxylate prepared according to Reference Example 24 (0.647 g, 2.00 mmol) was dissolved in dioxane (5.00 mL), and the solution was mixed with pyrrolidine (0.285 g, 4.00 mmol) and sodium carbonate (1.06 g, 10.0 mmol), followed by stirring at 80° C. for three hours. The reaction mixture was filtrated, and the filtrate was concentrated under reduced pressure. The residue was mixed with a solution of trifluoroacetic acid in dichloromethane (20%, 10.0 mL), followed by stirring at room temperature for two hours. The reaction mixture was concentrated under reduced pressure, was suspended in dioxane (5.00 mL), and the suspension was mixed with sodium carbonate (1.06 g, 10.0 mmol) and tert-butyl 4-[tert-butoxycarbonyl-(2,4-dichlorobenzyl)amino]-2-chloro-5,6,7,8-tetrahydropyrido[4,3-d] pyrimidine-6-carboxylate prepared in the same way as Process Step 1 of Example 16 (0.544 g, 1.00 mmol), followed by stirring at 90° C. for eight hours. After checking the completion of the reaction by thin layer chromatography, the reaction mixture was filtrated, and the filtrate was concentrated under reduced pressure. The residue was purified by silica gel column chromatography (hexane:ethyl acetate=1:1) and thereby yielded tert-butyl 4-[tert-butoxycarbonyl-(2,4-dichlorobenzyl)amino]-2-[4-(1,1-difluoro-2-oxo-2-pyrrolidin-1-yl-ethyl)-4-hydroxypiperidino]-5,6,7,8-tetrahydropyrido[4,3-d]pyrimidine-6-carboxylate (0.498 g, 66%).

Process Step 2

Tert-butyl 4-[tert-butoxycarbonyl-(2,4-dichlorobenzyl) amino]-2-[4-(1,1-difluoro-2-oxo-2-pyrrolidin-1-yl-ethyl)-4-hydroxypiperidino]-5,6,7,8-tetrahydropyrido[4,3-d]pyrimidine-6-carboxylate prepared according to Process Step 1 (0.351 g, 0.465 mmol) was dissolved in tetrahydrofuran (5.00 mL), and the solution was mixed with a solution of borane-tetrahydrofuran complex in tetrahydrofuran (1.20 mol/L, 1.70 mL, 2.04 mmol), followed by stirring at 70° C. for twelve hours. After checking the completion of the reaction by thin layer chromatography, the reaction mixture was mixed with methanol (5.00 mL), was concentrated under reduced pressure, and the residue was mixed with chloroform and water, followed by separation. The organic layer was dried over anhydrous magnesium sulfate, and the solvent was distilled off under reduced pressure. The residue was purified by silica gel column chromatography (hexane:ethyl acetate=3:1) and thereby yielded tert-butyl 4-[tert-butoxycarbonyl-(2,4-dichlorobenzyl)amino]-2-[4-(1,1-difluoro-2-pyrrolidin-1-ylethyl)-4-hydroxypiperidino]-5,6,7,8-tetrahydropyrido[4,3-d]pyrimidine-6-carboxylate (0.245 g, 71%). This compound was mixed with a solution of trifluoroacetic acid in dichloromethane (20%, 10.0 mL), followed by stirring at room temperature for three hours. The reaction mixture was concentrated under reduced pressure and was mixed with a saturated aqueous sodium bicarbonate solution, followed by extraction with chloroform. The organic layer was washed with brine, was dried over anhydrous magnesium sulfate, and the solvent was distilled off under reduced pressure, to thereby yield 4-(2,4-dichlorobenzylamino)-2-[4-(1,1-difluoro-2-pyrrolidin-1-ylethyl)-4-hydroxypiperidino]-5,6,7,8-tetrahydropyrido[4,3-d]pyrimidine (0.179 g, in a quantitative yield).

Process Step 3

4-(2,4-Dichlorobenzylamino)-2-[4-(1,1-difluoro-2-pyrrolidin-1-ylethyl)-4-hydroxypiperidino]-5,6,7,8-tetrahydropyrido[4,3-d]pyrimidine prepared according to Process Step 2 (0.067 g, 0.120 mmol) was dissolved in dichloromethane (2.00 mL), and the solution was mixed with cyclopropylcarbonyl chloride (0.016 g, 0.150 mmol) and triethylamine (0.015 g, 0.150 mmol), followed by stirring at room temperature for three hours. The reaction mixture was diluted with ethyl acetate and was sequentially washed with a saturated aqueous sodium bicarbonate solution and brine. The organic layer was dried over anhydrous magnesium sulfate, and the solvent was distilled off under reduced pressure. The residue was purified by silica gel column chromatography (chloroform:methanol=20:1) and thereby yielded Compound 19-1 (0.030 g, in a yield of 41%).

EXAMPLE 93

Synthesis of Compound 19-2

4-(2,4-Dichlorobenzylamino)-2-[4-(1,1-difluoro-2-pyrrolidin-1-ylethyl)-4-hydroxypiperidino]-5,6,7,8-tetrahydropyrido[4,3-d]pyrimidine prepared according to Process Step 2 of Example 92 (0.067 g, 0.120 mmol) was dissolved in toluene (3.00 mL), and the solution was mixed with ethylisocyanate (0.009 g, 0.130 mmol), followed by stirring at room temperature for three hours. The reaction mixture was concentrated under reduced pressure, the residue was purified by silica gel column chromatography (chloroform:methanol=20:1) and thereby yielded Compound 19-2 (0.026 g, 35%).

EXAMPLE 94

Synthesis of Compound 19-3

Compound 19-3 was prepared in the same way as Example 92, using piperidine instead of pyrrolidine in Process Step 1 of Example 92.

EXAMPLE 95

Synthesis of Compound 19-4

Initially, 4-(2,4-dichlorobenzylamino)-2-[4-(1,1-difluoro-2-pyrrolidin-1-ylethyl)-4-hydroxypiperazin-1-yl]-5,6,7,8-tetrahydropyrido [4,3-d]pyrimidine was prepared in the same way as Example 92 as an intermediate in Process Step 2 of Example 92, except for using piperidine instead of pyrrolidine in Process Step 1 of Example 92. Next, Compound 19-4 was prepared from the intermediate in the same way as Example 93.

EXAMPLE 96

Synthesis of Compound 20-6

Compound 20-6 was prepared in the same way as Example 31, except for allowing 4-(2,4-dichlorobenzylamino)-2-[2-(3-pyrrolidin-1-ylpropyl)morpholin-4-yl]-5,6,7,8-tetrahydropyrido[4,3-d]pyrimidine prepared in the same way as Example 4 to react with ethyl isocyanate.

EXAMPLE 97

Synthesis of Compound 20-8

Compound 20-8 was prepared in the same way as Example 31, except for allowing 4-(2,4-dichlorobenzylamino)-2-{2-[3-(1,4-dioxa-8-azaspiro[4.5]dec-8-yl)propyl]morpholin-4-yl}-5,6,7,8-tetrahydropyrido[4,3-d]pyrimidine prepared in the same way as Example 4 to react with ethyl isocyanate.

EXAMPLE 98

Synthesis of Compound 20-10

4-(2,4-Dichlorobenzylamino)-6-cyclopropylcarbonyl-2-{2-[3-(1,4-dioxa-8-azaspiro[4.5]dec-8-yl)propyl]morpholin-4-yl}-5,6,7,8-tetrahydropyrido[4,3-d]pyrimidine (Compound 20-7) prepared in the same way as Example 1 (146 mg, 0.226 mmol) was dissolved in tetrahydrofuran (5 mL), and the solution was mixed with hydrochloric acid (2 mol/L, 3 mL), followed by stirring under reflux for six hours. The reaction mixture was cooled, was mixed with a saturated aqueous sodium bicarbonate solution (10 mL) added dropwise, followed by addition of chloroform (50 mL) and separation. After drying the organic layer over anhydrous magnesium sulfate, the solvent was distilled off under reduced pressure, to thereby yield Compound 20-10 (100 mg, in a yield of 74%).

EXAMPLE 99

Synthesis of Compound 20-11

Compound 20-11 was prepared in the same way as Example 98, except for using Compound 20-8 prepared according to Example 97.

EXAMPLE 100

Synthesis of Compound 20-13

Compound 20-13 was prepared in the same way as Example 31, except for allowing 4-(2,4-dichlorobenzylamino)-2-{2-[2-(1,4-dioxa-8-azaspiro[4.5]dec-8-yl)ethyl]morpholin-4-yl}-5,6,7,8-tetrahydropyrido[4,3-d]pyrimidine prepared in the same way as Example 4 to react with ethyl isocyanate.

EXAMPLE 101

Synthesis of Compound 20-14

Compound 20-14 was prepared in the same way as Example 98, except for using 4-(2,4-dichlorobenzylamino)-6-cyclopropylcarbonyl-2-{2-[2-(1,4-dioxa-8-azaspiro[4.5]dec-8-yl)ethyl]morpholin-4-yl}-5,6,7,8-tetrahydropyrido[4,3-d]pyrimidine prepared in the same way as Example 1.

EXAMPLE 102

Synthesis of Compound 20-15

Compound 20-15 was prepared in the same way as Example 98, except for using Compound 20-13 prepared according to Example 100.

EXAMPLE 103

Synthesis of Compound 20-18

Compound 20-18 was prepared in the same way as Example 31, except for allowing 4-(2,4-dichlorobenzylamino)-2-{2-[2-(4-fluoropiperidino)ethyl]morpholin-4-yl}-5,6,7,8-tetrahydropyrido[4,3-d]pyrimidine prepared in the same way as Example 4 to react with ethyl isocyanate.

EXAMPLE 104

Synthesis of Compound 20-21

Compound 20-21 was prepared in the same way as Example 31, except for allowing 4-(2,4-dichlorobenzylamino)-2-{2-[2-(4,4-difluoropiperidino)ethyl]morpholin-4-yl}-5,6,7,8-tetrahydropyrido[4,3-d]pyrimidine prepared in the same way as Example 4 to react with ethyl isocyanate.

EXAMPLE 105

Synthesis of Compound 21-3

Compound 21-3 was prepared in the same way as Example 31, except for allowing 4-(2,4-dichlorobenzylamino)-2-[4-(1-methylpiperidin-3-yloxy)piperdino]-5,6,7,8-tetrahydropyrido[4,3-d]pyrimidine prepared in the same way as Example 4 to react with ethyl isocyanate.

EXAMPLE 106

Synthesis of Compound 21-4

Compound 21-4 was prepared in the same way as Example 31, except for allowing 4-(2,4-dichlorobenzylamino)-2-[4-(1-methylpiperidin-4-yloxy)piperdino]-5,6,7,8-tetrahydro-pyrido[4,3-d]pyrimidine prepared in the same way as Example 4 to react with ethyl isocyanate.

EXAMPLE 107

Syntheses of Compounds 22-1 through 22-4

Compounds 22-1 through 22-4 were prepared in the same way as Process Steps 2 and 3 of Example 1, except for using 2,4-dichloro-5,6,7,8-tetrahydropyrido[4,3-d]pyrimidin-6-yl-N-ethylcarboxamide prepared according to Reference Example 9, respectively.

EXAMPLE 108

Synthesis of Compound 23-1

Process Step 1

6-Benzyl-2,4-dibromo-5,6,7,8-tetrahydropyrido[4,3-d] pyrimidine prepared according to Reference Example 10 (0.964 g, 2.52 mmol) was mixed with 2-chloro-4-fluorobenzylamine (0.608 g, 3.78 mmol), triethylamine (1.05 mL, 7.56 mmol) and tetrahydrofuran (10 mL), followed by stirring at room temperature for ten hours. The reaction mixture was mixed with an aqueous sodium bicarbonate solution and was extracted with ethyl acetate. The organic layer was washed with brine, was dried over anhydrous sodium sulfate, and the solvent was distilled off. The residue was purified by silica gel column chromatography (chloroform:methanol=98:2 to 96.5:3.5), and the solvent was distilled off. The residue was reslurried with ether, the precipitated crystals were collected by filtration, were dried and thereby yielded 6-benzyl-2-bromo-4-(2-chloro-4-fluorobenzylamino)-5,6,7,8-tetrahydropyrido[4,3-d]pyrimidine (0.550 g, in a yield of 47%).

Process Step 2

6-Benzyl-2-bromo-4-(2-chloro-4-fluorobenzylamino)-5,6,7,8-tetrahydropyrido[4,3-d]pyrimidine prepared according to Process Step 1 (0.181 g, 0.393 mmol) was mixed with 1-dimethylamino-2-propyne (0.169 mL, 1.57 mmol), dichlorobis(triphenylphosphine)palladium(II) (28.2 mg, 0.0393 mmol), copper iodide (0.0135 g, 0.0668 mmol), triethylamine (82.2 μL, 0.590 mmol), tetrahydrofuran (1.97 mL) and triphenylphosphine (0.0400 g, 0.149 mmol), followed by stirring at 80° C. for sixteen hours. The reaction mixture was cooled to room temperature, was mixed with water and was extracted with chloroform. The organic layer was washed with diluted hydrochloric acid (0.2 mol/L), the aqueous layer was recovered and was adjusted to be basic with an aqueous sodium hydroxide solution (2 mol/L). The aqueous solution was extracted with chloroform, the organic layer was washed with brine, was dried over anhydrous sodium sulfate, and the solvent was distilled off. The residue was sequentially purified by preparative thin layer chromatography (chloroform: ammonia methanol solution (2 mol/L)=90:10) and silica gel column chromatography (ethyl acetate:hexane:triethylamine=80:20:10 to 100:0:10) and thereby yielded Compound 23-1 (0.0264 g, in a yield of 14%).

EXAMPLE 109

Synthesis of Compound 23-2

Process Step 1

6-(Cyclopropylcarbonyl)-2-chloro-4-(2-chloro-4-fluorobenzylamino)-5,6,7,8-tetrahydropyrido[4,3-d]pyrimidine prepared in the same way as Process Steps 1 and 2 of Example 1 (1.98 g, 5.01 mmol) was dissolved in a mixture of dimethoxyethane and water (5:1, 10.0 mL), and the solution was mixed with 4-formylphenylboronic acid (1.50 g, 10.0 mmol), cerium carbonate (3.26 g, 10.0 mmol) and bis(tri-o-tolylphosphine)palladium(II) dichloride (0.393 g, 0.500 mmol), followed by stirring at 100° C. for fifteen hours. The reaction mixture was concentrated under reduced pressure and was purified by silica gel column chromatography (chloroform:methanol=50:1). The resulting oil was recrystallized from a mixture of hexane and ethyl acetate (3:1) and thereby yielded 4-(2-chloro-4-fluorobenzylamino)-6-(cyclopropylcarbonyl)-2-(4-formylphen-1-yl)-5,6,7,8-tetrahydropyrido[4,3-d]pyrimidine (0.972 g, in a yield of 42%).

Process Step 2

4-(2-Chloro-4-fluorobenzylamino)-6-(cyclopropylcarbonyl)-2-(4-formylphen-1-yl)-5,6,7,8-tetrahydropyrido[4,3-d] pyrimidine prepared according to Process Step 1 (0.014 g, 0.030 mmol) was dissolved in 1,2-dichloroethane (0.150 mL); and the solution was mixed with a solution of pyrrolidine in chloroform (1.00 mol/L, 0.060 mL, 0.060 mmol) and a suspension of sodium triacetoxyborohydride in 1,2-dichloroethane (0.500 mol/L, 0.200 mL, 0.100 mmol), followed by stirring at room temperature for twelve hours. After checking the completion of the reaction by thin layer chromatography, an aqueous sodium hydroxide solution (2.00 mol/L, 0.300 mL) was added, and the mixture was stirred for fifteen minutes, followed by separation. The organic layer was dried over anhydrous magnesium sulfate and was mixed with N-methylisatoic anhydride polystyrene (2% divinylbenzene copolymer, about 2.60 mmol/g, 50.0 mg, available from Novabiochem), followed by sealing and stirring at room temperature for twelve hours. The resin was separated from the reaction mixture by filtration, the filtrate was concentrated and thereby yielded Compound 23-2.

EXAMPLE 110

Syntheses of Compounds 23-3 through 23-5

Compounds 23-3 through 23-5 were prepared in the same way as Process Step 2 of Example 109, except for allowing 4-(2-chloro-4-fluorobenzylamino)-6-(cyclopropylcarbonyl)-2-(4-formylphen-1-yl)-5,6,7,8-tetrahydropyrido[4,3-d] pyrimidine prepared according to Process Step 1 of Example 109 to react with piperidine, 4-hydroxypiperidine or 1-methyl-4-methylaminopiperidine, respectively, instead of pyrrolidine used in Process Step 2 of Example 109.

The compounds prepared according to the above examples were identified by mass spectrometry. The analyses data of the compounds are shown as equipment data in Tables 1 to 25.

The proton nuclear magnetic resonance spectra of representative compounds are shown below.

Compound 1-6

$^1$H NMR ($CDCl_3$) d (ppm): 1.45 (m, 4H), 1.61 (m, 4H), 1.86 (m, 2H), 1.9-2.4 (m, 6H), 2.52 (m, 5H), 2.60(m, 2H), 2.72 (m, 2H), 3.32 (m, 1H), 3.53 (m, 2H), 4.26 (s, 2H), 4.6-4.9 (1H, overlapping with other peak), 4.75 (d, J=6.0 Hz, 2H), 4.85 (m, 2H), 6.8-6.9 (m, 2H), 7.1-7.3 (m, 1H)

Compound 2-1

$^1$H NMR ($CDCl_3$) d (ppm): 1.3-1.9 (m, 18H), 2.51 (m, 5H), 2.66 (t, J=5.9 Hz, 2H), 2.72 (m, 2H), 2.96 (m, 1H), 3.71 (t, J=5.9 Hz, 2H), 4.28 (s, 2H), 4.69 (br t, J=5.6 Hz, 1H), 4.75 (d, J=5.6 Hz, 2H), 4.85 (m, 2H), 6.86 (m, 2H), 7.21 (m, 1H)

Compound 2-2

$^1$H NMR ($CDCl_3$) d (ppm): 1.44 (m, 2H), 1.5-1.9 (m, 12H), 2.3-2.6 (m, 12H), 2.66 (m, 2H), 2.96 (m, 1H), 3.71 (m, 2H), 3.80 (m, 4H), 4.28 (s, 2H), 4.7-4.8 (1H, overlapping with other peak), 4.74 (s, 2H), 6.8-6.9 (m, 2H), 7.1-7.3 (m, 1H)

Compound 2-3

$^1$H NMR ($CDCl_3$) d (ppm): 1.3-1.9 (m, 14H), 2.3-2.6 (m, 12H), 2.68 (m, 2H), 2.96 (m, 1H), 3.6-3.8 (m, 6H), 4.31 (s, 2H), 4.65 (d, J=6.0 Hz, 2H), 4.80 (br t, J=6.0 Hz, 1H), 6.7-6.9 (m, 2H), 7.2-7.4 (m, 1H)

Compound 2-4

$^1$H NMR ($CDCl_3$) d (ppm): 0.8-1.9 (m, 23H), 2.3-2.6 (m, 12H), 2.67 (m, 2H), 2.95 (m, 1H), 3.43 (m, 2H), 3.7-3.9 (m, 6H), 4.28 (s, 2H), 4.3 (1H, overlapping with other peak)

Compound 3-1

$^1$H NMR ($CDCl_3$) d (ppm): 0.80 (m, 2H), 1.01 (m, 2H), 1.44 (m, 2H), 1.58 (m, 4H), 1.81 (m, 1H), 2.3-2.6 (m, 12H), 2.71 (m, 2H), 3.7-3.9 (m, 6H), 4.28 (s, 2H), 4.74 (s, 2H), 4.7-4.8 (1, H, overlapping with other peak), 6.86 (m, 2H), 7.21 (m, 1 H)

Compound 3-2

$^1$H NMR ($CDCl_3$) d (ppm): 0.80 (m, 2H), 1.01 (m, 2H), 1.44 (m, 2H), 1.57 (m, 4H), 1.82 (m, 1H), 2.3-2.6 (m, 12H), 2.73 (m, 2H), 3.75 (m, 4H), 3.87 (m, 2H), 4.31 (s, 2H), 4.65 (br s, 2H), 4.77 (br s, 1H), 6.79 (m, 2H), 7.28 (m, 1H)

Compound 3-3

$^1$H NMR ($CDCl_3$) d (ppm): 0.80 (m, 2H), 0.91 (br t, J=about 7 Hz, 3H), 1.02 (m, 2H), 1.2-1.7 (m, 12H), 1.83 (m, 1H), 2.3-2.6 (m, 12H), 2.73 (m, 2H), 3.43 (m, 2H), 3.77 (m, 4H), 3.78 (m, 2H), 4.2-4.4 (1H, overlapping with other peak), 4.28 (s, 2H)

Compound 3-4 (2 Fumarate)

$^1$H NMR (DMSO-$d_6$) d (ppm): (major peaks) 0.76 (m, 4H), 1.05 (m, 4H), 1.47 (m, 2H), 2.06 (m, 1H), 2.3-2.6 (m, 14H), 3.58 (m, 4H), 3.69 (m, 1H), 3.88 (m, 1H), 4.28 (br s, 1H), 4.4-4.6 (m, 4H), 6.56 (s, 4H), 7.2-7.4 (m, 4H)

Compound 3-5

$^1$H NMR ($CDCl_3$) d (ppm): 0.80 (m, 2H), 1.00 (m, 2H), 1.44 (m, 2H), 1.58 (m, 4H), 1.81 (m, 1H), 2.3-2.6 (m, 12H), 2.73 (m, 2H), 3.73 (m, 4H), 3.87 (m, 2H), 4.33 (s, 2H), 4.69 (br s, 2H), 4.83 (br s, 1H), 6.90 (m, 1H), 7.11 (dd, J=8.3, 2.4 Hz, 1H), 7.34 (m, 1H)

Compound 3-6

$^1$H NMR ($CDCl_3$) d (ppm): 0.80 (m, 2H), 1.00 (m, 2H), 1.44 (m, 2H), 1.58 (m, 4H), 1.81 (m, 1H), 2.3-2.6 (m, 12H), 2.73 (m, 2H), 3.74 (m, 4H), 3.87 (m, 2H), 4.32 (s, 2H), 4.65 (d, J=4.5 Hz, 2H), 4.81 (br s, 1H), 7.0-7.1 (m, 2H), 7.2-7.3 (m, 1H)

Compound 3-7

$^1$H NMR ($CDCl_3$) d (ppm): 0.80 (m, 2H), 1.01 (m, 2H), 1.7-1.9 (m, 7H), 2.3-2.6 (m, 12H), 2.73 (m, 2H), 3.76 (m, 4H), 3.88 (m, 2H), 4.31 (s, 2, H), 4.5-4.7 (1H, overlapping with Other peak), 4.66 (br s, 2H), 6.79 (m, 2H), 7.30 (m, 1H)

Compound 3-8

$^1$H NMR ($CDCl_3$) d (ppm) 0.80 (m, 2H), 1.01 (m, 2H), 1.7-1.9 (m, 7H), 2.3-2.6 (m, 12H), 2.73 (m, 2H), 3.74 (m, 4H), 3.87 (m, 2H), 4.33 (s, 2H), 4.71 (br s, 2H), 4.83 (br s, 1H), 6.90 (m, 1H), 7.11 (dd, J=8.4, 2.3 Hz, 1H), 7.34 (m, 1H)

Compound 3-9

$^1$H NMR ($CDCl_3$) d (ppm): 0.80 (m, 2H), 1.00 (m, 2H), 1.7-1.9 (m, 7H), 2.3-2.6 (m, 12H), 2.73 (m, 2H), 3.74 (m, 4H), 3.87 (m, 2H), 4.33 (s, 2H), 4.66 (br s, 2H), 4.82 (br s, 1H), 7.0-7.1 (m, 2H), 7.2-7.3 (m, 1H)

Compound 3-10

$^1$H NMR ($CDCl_3$) d (ppm): 0.80 (m, 2H), 1.01 (m, 2H), 1.81 (m, 1H), 2.6-2.8 (1H, overlapping with other peak), 2.73 (m, 2H), 2.86 (m, 4H), 3.68 (m, 4H), 3.89 (m, 2H), 4.35 (s, 2H), 4.71 (br s, 2H), 4.89 (br s, 1H), 7.1-7.4 (m, 3H)

Compound 3-11

$^1$H NMR ($CDCl_3$) d (ppm): 0.80 (m, 2H), 1.00 (m, 2H), 1.6-1.9 (m, 7H), 2.3-2.6 (m, 6H), 2.70 (m, 2H), 3.38 (m, 2H), 3.89 (m, 2H), 4.35 (s, 2H), 4.70 (d, J=5.9 Hz, 2H), 4.95(br s, 1H), 5.08 (br s, 1H), 7.1-7.4 (m, 3H)

Compound 3-12

$^1$H NMR ($CDCl_3$) d (ppm): 0.80 (m, 2H), 1.01 (m, 2H), 1.68 (m, 2H), 1.82 (m, 1H), 2.1-2.3 (2H, overlapping with other peak), 2.19 (s, 6H), 2.74 (m, 2H), 3.06 (s, 3H), 3.52 (t, J=7.1 Hz, 2H), 3.89 (m, 2H), 4.37 (s, 2H), 4.70 (br s, 2H), 4.85 (br s, 1H), 7.1-7.4 (m, 3H)

Compound 3-14

$^1$H-NMR ($CDCl_3$) d (ppm): 0.77-0.84 (m, 2H), 1.01 (br s, 2H), 1.10-1.19 (m, 2H), 1.48 (t, J=7.4 Hz, 4H), 1.67-1.83 (m, 6H), 2.44-2.50 (m, 6H), 2.64-2.79 (m, 4H), 3.89 (br s, 2H), 4.34 (br s, 2H), 4.16-4.70 (m, 4H), 4.79 (br s, 1H), 7.16 (d, J=8.1 Hz, 1H), 7.30 (m, 1H), 7.37 (br s, 1H)

Compound 3-15

$^1$H-NMR ($CDCl_3$) d (ppm): 0.78-0.88 (m, 2H), 1.01 (br s, 2H), 1.78-1.86 (m, 1H), 2.77 (br s, 8H), 3.47-3.49 (m, 2H), 3.60-3.63 (m, 2H), 3.70 (s, 2H), 3.73-3.77 (m, 2H), 3.91 (br s, 2H), 4.38 (br s, 2H), 4.69 (d, J=5.4 Hz, 2H), 5.24 (br s, 1H), 7.18 (d, J=8.1 Hz, 1H), 7.25-7.26 (m, 1H), 7.40 (br s, 1H)

Compound 3-17

$^1$H NMR ($CDCl_3$) d (ppm): 0.79 (m, 2' H), 0.99 (m, 2H), 1.50 (m, 2H), 1.7-1.9 (m, 3H), 2.29 (s, 3H), 2.6-3.0 (m, 4H), 2.73 (m, 2H), 2.93 (s, 3H), 3.27 (m, 1H), 3.89 (m, 2H), 4.41 (br s, 2H), 4.67 (br s, 2H), 5.23 (br s, 1H), 7.0-7.4 (m, 3H)

Compound 3-18

$^1$H NMR ($CDCl_3$) d (ppm): 0.81 (m, 2H), 1.01 (m, 2H), 1.8-2.1 (m, 3H), 2.71 (m, 2H), 3.30 (m, 2H), 3.92 (m, 2H), 4.05 (m, 2H), 4.42 (s, 2H), 4.67 (d, J=5.6 Hz, 2H), 4.92 (br s, 1H), 5.73 (br s, 1H), 6.8-7.36 (m, 6H)

Compound 3-19

$^1$H NMR ($CDCl_3$) d (ppm): 0.80 (m, 2H), 1.00 (m, 2H), 1.6-1.9 (m, 5H), 2.48 (m, 4H), 2.60 (t, J=6.3 Hz, 2H), 2.71 (m, 2H), 3.43 (dt, J=5.6, 6.1 Hz, 2H), 3.89 (m, 2H), 4.36 (s, 2H), 4.71 (br d, J=5.6 Hz, 2H), 4.93 (br s, 1H), 5.19 (br s, 1H), 7.1-7.4 (m, 3H)

Compound 3-20

$^1$H NMR ($CDCl_3$) d (ppm): 0.80 (m, 2H), 1.00 (m, 2H), 1.4-2.0 (m, 7H), 2.4-3.0 (m, 8H), 3.4-4.0 (m, 12H), 3.47 (s, 3H), 4.36 (s, 2H), 4.71 (br s, 2H), 4.98 (br s, 1H), 7.1-7.4 (m, 3H)

Compound 3-21

$^1$H NMR ($CDCl_3$) d (ppm): 0.69-1.14 (m, 4H), 1.60-1.91 (m, 5H), 2.45-2.83(m, 8H), 3.15-3.58(m, 6H), 3.73-4.00(m, 2H), 4.21-4.50 (m, 2H), 4.56-5.29 (m, 5H), 5.38-5.70 (m, 1H), 6.79-7.60 (m, 3H)

Compound 3-22

$^1$H NMR ($CDCl_3$) d (ppm): 0.75-1.09 (m, 4H), 1.70-1.95 (m, 5H), 2.48-2.89 (m, 8H), 3.20-3.59 (m, 4H), 3.68-3.90 (m, 2H), 4.00-4.32 (m, 4H), 4.62-4.80 (s, 2H), 4.89-5.04 (m, 1H), 5.17-5.30 (m, 1H), 5.49-5.70 (m, 1H), 6.85-7.20 (m, 2H), 7.26-7.47 (m, 1H)

Compound 3-23

$^1$H NMR ($CDCl_3$) d (ppm): 0.71-1.12 (m, 4H), 1.71-1.98 (m, 1H), 2.20-2.50 (m, 7H), 2.67-2.89 (m, 2H), 3.24-3.63 (m, 8H), 3.78-4.00 (m, 2H), 4.34 (s, 2H), 4.70 (d, J=6.0 Hz, 2H), 5.20-5.58 (m, 3H), 6.84-7.21 (m, 2H), 7.24-7.49 (m, 1H)

Compound 3-24

$^1$H NMR ($CDCl_3$) d (ppm): 0.81 (m, 2H), 1.00 (m, 2H), 1.7-1.9 (m, 5H), 2.7-2.9 (m, 6H), 2.96 (br t, J=5.9 Hz, 2H), 3.8-4.0 (m, 2H), 4.37 (s, 2H), 4.48 (br t, J=5.9 Hz, 2H), 4.70 (d, J=5.3 Hz, 2H), 5.22 (br s, 1H), 7.0-7.4 (m, 3H)

Compound 3-25

$^1$H NMR ($CDCl_3$) d (ppm): 0.81 (m, 2H), 1.00 (m, 2H), 1.7-1.9 (m, 5H), 2.57 (m, 4H), 2.7-2.9 (m, 4H), 3.91 (m, 2H), 4.3-4.5 (m, 2H), 4.39 (s, 2H), 4.75 (d, J=5.4 Hz, 2H), 5.19 (br s, 1H), 7.1-7.4 (m, 3H)

Compound 3-26

$^1$H NMR ($CDCl_3$) d (ppm): 0.81 (m, 2H), 0.99 (m, 2H), 1.4-2.3 (m, 10H), 2.31 (s, 3H), 2.80 (m, 2H), 3.89 (m, 2H), 4.2-4.5 (m, 4H), 4.74 (br s, 2H), 5.13 (br s, 1H), 7.1-7.4 (m, 3H)

Compound 3-27

$^1$H NMR ($CDCl_3$) d (ppm): 0.81 (m, 2H), 1.01 (m, 2H), 1.4-2.4 (m, 7H), 2.33 (s, 3H), 2.7-2.9 (m, 5H), 3.91 (m, 2H), 4.16 (dd, J=107, 5.1 Hz, 1H), 4.3-4.5 (m, 1H), 4.40 (br s, 2H), 4.74 (d, J=5.6 Hz, 2H), 5.23 (m, 1H), 7.1-7.4 (m, 3H)

Compound 3-28

$^1$H NMR ($CD_3OD$) d (ppm): 0.65-0.99 (m, 4H), 1.00-1.18 (m, 2H), 1.25-1.49 (m, 2H), 1.50-1.82 (m, 2H), 1.85-2.20 (m, 7H), 2.58-2.78 (m, 1H), 2.80-3.09 (m, 4H), 3.11-3.38 (m, 4H), 3.69-3.85 (m, 1H), 3.85-4.03 (m, 1H), 4.04-4.28 (m, 2H), 4.29-4.46 (m, 1H), 4.50-4.72 (m, 4H), 6.85-7.03 (m, 1H), 7.05-7.21 (m, 1H), 7.21-7.41 (m, 1H)

Compound 3-29

$^1$H NMR ($CDCl_3$) d (ppm): 0.58-1.08 (m, 4H), 1.10-1.42 (m, 4H), 1.44-2.10 (m, 6H), 2.20-2.92 (m, 10H), 3.30-3.52 (m, 1H), 3.70-4.02 (m, 2H), 4.22-4.50 (m, 2H), 4.55-5.00 (m, 5H), 6.79-7.20 (m, 2H), 7.27-7.55 (m, 1H)

Compound 3-30

$^1$H NMR ($CDCl_3$) d (ppm): 0.69-0.91 (m, 2H), 0.95-1.12 (m, 2H), 1.39-2.01 (m, 10H), 2.39-3.08 (m, 8H), 3.43 (s, 2H), 3.73-4.02 (m, 2H), 4.23-4.52 (m, 2H), 4.59-5.05 (m, 5H), 6.81-7.21 (m, 2H), 7.24-52 (m, 1H)

Compound 3-31

$^1$H NMR ($CDCl_3$) d (ppm): 0.70-1.13 (m, 4H), 1.65-2.25 (m, 7H), 2.67-3.00 (m, 8H), 3.24-3.45 (m, 2H), 3.48 (t, J=6.9 Hz, 2H), 3.78-4.07 (m, 4H), 4.24-4.55 (m, 4H), 4.70 (d, J=5.8 Hz, 2H), 4.80-4.98 (m, 1H), 7.13-7.45 (m, 3H)

Compound 3-32

$^1$H NMR (DMSO-$d_6$) d (ppm): 0.78 (m, 4H), 1.8-2.6 (m, 15H), 2.99 (s, 3H), 3.3-3.6 (m, 10H), 3.70 (br s, 1H), 3.90 (m, 2H), 4.34 (br s, 2H), 4.57 (br s, 2H), 7.2-7.6 (m, 3H)

Compound 3-33

$^1$H NMR (DMSO-$d_6$) d (ppm): 0.78 (m, 4H), 1.33 (m, 2H), 1.54 (m, 2H), 1.80 (m, 4H), 1.97 (m, 2H), 2.09 (m, 1H), 2.5-2.9 (m, 4H), 2.78 (s, 3H), 3.6-3.9 (m, 5H), 3.92 (m, 2H), 4.36 (br s, 2H), 4.5-4.7 (m, 3H), 4.60 (br s, 2H), 7.2-7.7 (m, 3H)

Compound 4-2

$^1$H NMR ($CDCl_3$) d (ppm): 0.80 (m, 2H), 1.01 (m, 2H), 1.5-2.0 (m, 6H), 2.1-2.5 (m, 8H), 2.27 (s, 3H), 2.5-2.8 (m, 3H), 2.95 (m, 1H), 3.69 (m, 4H), 3.88 (m, 2H), 4.34 (br s, 2H), 4.70 (br s, 2H), 4.88 (br s, 1H), 7.1-7.4 (m, 3H)

Compound 4-6

$^1$H NMR ($CDCl_3$) d (ppm): 0.80 (m, 2H), 1.01 (m, 2H), 1.44 (m, 2H), 1.58 (m, 4H), 1.81 (m, 1H), 2.4-2.6 (m, 12H), 2.73 (m, 2H), 3.72 (m, 4H), 3.89 (m, 2H), 4.34 (s, 2H), 4.69 (br d, J=about 6 Hz, 2H), 4.88 (br s, 1H), 7.1-7.4 (m, 3H)

Compound 4-7

$^1$H NMR ($CDCl_3$) d (ppm): 0.80 (m, 2H), 1.01 (m, 2H), 1.7-1.9 (m, 7H), 2.3-2.6 (m, 12H), 2.73 (m, 2H), 3.73 (m, 4H), 3.87 (m, 2H), 4.34 (m, 2H), 4.69 (br d, J=about 6 Hz, 2H), 4.89 (br t, J=about 6 Hz, 1H), 7.1-7.4 (m, 3H)

Compound 4-9

$^1$H NMR ($CDCl_3$) d (ppm): 0.80 (m, 2H), 1.01 (m, 2H), 1.44 (m, 2H), 1.58 (m, 4H), 1.6-1.9 (m, 3H), 2.2-2.6 (m, 12H), 2.73 (m, 2H), 3.72 (m, 4H), 3.88 (m, 2H), 4.34 (s, 2H), 4.70 (br s, 2H), 4.87 (br s, 1H), 7.1-7.4 (m, 3H)

Compound 4-43

$^1$H NMR ($CDCl_3$) d (ppm): 1.77 (m, 6H), 2.3-2.6 (m, 14H), 3.6-3.8 (m, 6H), 3.82 (s, 2H), 4.37 (s, 2H), 4.68 (d, J=6.0 Hz, 2H), 4.89 (t, J=6.0 Hz, 1H), 7.1-7.4 (m, 8H)

Compound 4-67

$^1$H NMR ($CDCl_3$) d (ppm): 1.15 (d, J=7.0 Hz, 6H), 1.80 (m, 6H), 2.3-2.6 (m, 12H), 2.69 (m, 2H), 2.88 (septet, J=7.0 Hz, 1H), 3.6-3.8 (m, 6H), 4.34 (s, 2H), 4.70 (d, J=6.0 Hz, 2H), 4.90 (t, J=6.0 Hz, 1H), 7.1-7.4 (m, 3H)

Compound 4-86

$^1$H NMR ($CDCl_3$) d (ppm): 0.98 (t, J=7.0 Hz, 3H), 1.5-1.9 (m, 7H), 2.1-2.5 (m, 10H), 2.27 (s, 3H), 2.68 (m, 2H), 2.78 (m, 1H), 2.95 (m, 1H), 3.6-3.7 (m, 6H), 4.34 (s, 2H), 4.69 (d, J=6.0 Hz, 2H), 4.93 (t, J=6.0 Hz, 1H), 7.1-7.4 (m, 3H)

Compound 4-91

$^1$H NMR ($CDCl_3$) d (ppm): 0.98 (t, J=7.0 Hz, 3H), 1.6-1.8 (m, 8H), 2.3-2.6 (m, 14H), 2.68 (m, 2H), 3.6-3.8 (m, 6H), 4.34 (s, 2H), 4.70 (d, J=6.0 Hz, 2H), 4.90 (d, J=6.0 Hz, 1H), 7.1-7.4 (m, 3H)

Compound 4-93

$^1$H NMR ($CDCl_3$) d (ppm): 0.9.8 (t, J=7.0 Hz, 3H), 1.44 (m, 2H), 1.5-1.8 (m, 8H), 2.2-2.5 (m, 14H), 2.68 (m, 2H), 3.6-3.8 (m, 6H), 4.34 (s, 2H), 4.70 (d, J=6.0 Hz, 2H), 4.92 (t, J=6.0 Hz, 1H), 7.1-7.4 (m, 3H)

Compound 4-199

$^1$H NMR ($CDCl_3$) d (ppm): 0.81 (m, 2H), 0.9-1.1 (m, 8H), 1.70 (m, 2H), 1.82 (m, 1H), 2.3-2.7 (m, 12H), 2.73 (m, 2H), 3.73 (m, 4H), 3.89 (m, 2H), 4.35 (s, 2H), 4.71 (br s, 2H), 4.89 (br s, 1H), 7.1-7.4 (m, 3H)

Compound 4-235

$^1$H NMR ($CDCl_3$) d (ppm): 1.09 (t, J=7.2 Hz, 6H), 1.73 (m, 2H), 2.3-2.7 (m, 14H), 3.6-3.8 (m, 6H), 3.82 (s, 2H), 4.38 (s, 2H), 4.68 (d, J=5.8 Hz, 2H), 4.93 (t, J=5.8 Hz, 1H), 7.1-7.4 (m, 8H)

Compound 4-259

$^1$H NMR ($CDCl_3$) d (ppm): 1.02 (t, J=7.2 Hz, 6H), 1.15 (d, J=6.6 Hz, 6H), 1.68 (m, 2H), 2.3-2.6 (m, 12H), 2.69 (m, 2H), 2.88 (septet, J=6.6 Hz, 1H), 3.6-3.8 (m, 6H), 4.35 (s, 2H), 4.70 (d, J=5.6 Hz, 2H), 4.97 (br t, J=about 6 Hz, 1H), 7.1-7.4 (m, 3H)

Compound 4-283

$^1$H NMR ($CDCl_3$) d (ppm): 0.98 (t, J=7.4 Hz, 3H), 1.06 (t, J=7.1 Hz, 6H), 1.6-1.8 (m, 4H), 2.3-2.6 (m, 14H), 2.68 (m, 2H), 3.6-3.8 (m, 6H), 4.34 (s, 2H), 4.70 (d, J=5.8 Hz, 2H), 4.90 (t, J=5.8 Hz, 1H), 7.1-7.4 (m, 3H)

Compound 4-11

$^1$H NMR ($CDCl_3$) d (ppm): 0.81 (m, 2H), 1.01 (m, 2H), 1.81 (m, 1H), 2.4-2.6 (m, 12H), 2.73 (m, 2H), 3.6-3.8 (m, 8H), 3.89 (m, 2H), 4.34 (s, 2H), 4.69 (br d, J=5.3 Hz, 2H), 4.86 (br s, 1H), 7.1-7.4 (m, 3H)

Compound 4-584

$^1$H NMR ($CDCl_3$) d (ppm): 1.03 (t, J=7.2 Hz, 6H), 1.68 (m, 2H), 2.3-2.5 (m, 8H), 2.53 (q, J=7.1 Hz, 4H), 2.74 (m, 2H), 3.7-3.8 (m, 6H), 4.32 (s, 2H), 4.6-4.8 (br, 1H), 4.69 (br s, 2H), 7.0-7.4 (m, 8H)

Compound 4-641

$^1$H NMR ($CDCl_3$) d (ppm): 1.29 (t, J=7.1 Hz, 3H), 1.6-1.9 (m, 6H), 2.3-2.6 (m, 12H), 2.64 (m, 2H), 3.6-3.8 (m, 6H), 4.18 (q, J=7.1 Hz, 2H), 4.22 (s, 2H), 4.6-4.8 (br, 1H), 4.71 (s, 2H), 7.1-7.4 (m, 3H)

Compound 4-644

$^1$H NMR ($CDCl_3$) d (ppm): 1.02 (t, J=7.2 Hz, 6H), 1.29 (t, J=7.1 Hz, 3H), 1.68 (m, 2H), 2.3-2.5 (m, 8H), 2.53 (q, J=7.1 Hz, 4H), 2.64 (m, 2H), 3.6-3.8 (m, 6H), 4.18 (q, J=7.1 Hz, 2H), 4.22 (s, 2H), 4.71 (s, 2H), 4.6-4.8 (br s, 1H), 7.1-7.4 (m, 3H)

Compound 4-653

$^1$H NMR ($CDCl_3$) d (ppm): 0.96 (t, J=7.4 Hz, 3H), 1.68 (m, 2H), 1.7-1.9 (m, 6H), 2.3-2.6 (m, 12H), 2.64 (m, 2H), 3.6-3.8 (m, 6H), 4.08 (t, J=6.7 Hz, 2H), 4.22 (s, 2H), 4.6-4.8 (br s, 1H), 4.71 (br s, 2H), 7.1-7.4 (m, 3H)

Compound 5-1

$^1$H NMR ($CDCl_3$) d (ppm) 0.80 (m, 2H), 1.01 (m, 2H), 1.3-1.9 (m, 11H), 2.4-2.6 (m, 5H), 2.6-2.8 (m, 4H), 3.86 (m, 2H), 4.28 (s, 2H), 4.6-4.9 (1H, overlapping with other peak), 4.75 (br d, J=5.3 Hz, 2H), 4.85 (m, 2H), 6.8-6.9 (m, 2H), 7.1-7.3 (m, 1H)

Compound 5-2

$^1$H NMR ($CDCl_3$) d (ppm): 0.80 (m, 2H), 1.01 (m, 2H), 1.3-1.9 (m, 11H), 2.4-2.6 (m, 5H), 2.6-2.8 (m, 4H), 3.8-3.9 (m, 2H), 4.31 (s, 2H), 4.6-4.8 (1H, overlapping with other peak), 4.66 (br s, 2H), 4.77 (m, 2H), 6.79 (m, 2H), 7.31 (m, 1H)

Compound 5-10

$^1$H NMR ($CDCl_3$) d (ppm): 0.80 (m, 2H), 1.01 (m, 2H), 1.3-1.9 (m, 11H), 2.4-2.6 (m, 5H), 2.6-2.8 (m, 4H), 3.88 (m, 2H), 4.35 (s, 2H), 4.70 (s, 2H), 4.72 (m, 2H), 4.90 (br s, 1H), 7.1-7.4 (m, 3H)

Compound 5-218

$^1$H NMR ($CDCl_3$) d (ppm): 1.45 (m, 2H), 1.58 (m, 4H), 1.80 (m, 4H), 2.49 (m, 5H), 2.6-2.8 (m, 6H), 3.22 (s, 2H), 3.67 (s, 2H), 4.42 (t, J=5.9 Hz, 1H), 4.63 (d, J=5.9 Hz, 2H), 4.75 (m, 2H), 6.78 (m, 2H), 7.2-7.4 (m, 5H)

Compound 5-226

$^1$H NMR ($CDCl_3$) d (ppm): 1.3-1.9 (m, 10H), 2.49 (m, 5H), 2.6-2.8 (m, 6H), 3.24 (s, 2H), 3.67 (s, 2H), 4.55 (br t, J=about 6 Hz, 1H), 4.66 (d, J=5.8 Hz, 2H), 4.70 (m, 2H), 7.1-7.4 (m, 7H)

Compound 5-385

$^1$H NMR ($CDCl_3$) d (ppm): 1.2-1.9 (m, 10H), 2.52 (m, 5H), 2.64 (m, 2H), 2.74 (m, 2H), 3.53 (m, 2H), 4.47 (s, 2H), 4.71 (t, J=6.0 Hz, 1H), 4.78 (d, J=6.0 Hz, 2H), 4.86 (m, 2H), 6.7-6.9 (m, 2H), 7.0-7.5 (m, 5H)

Compound 5-386

$^1$H NMR ($CDCl_3$) d (ppm): 1.2-1.9 (m, 10H), 2.52 (m, 5H), 2.64 (m, 2H), 2.73 (m, 2H), 3.52 (m, 2H), 4.45 (s, 2H), 4.70 (t, J=6.0 Hz, 1H), 4.78 (d, J=6.0 Hz, 2H), 4.85 (m, 2H), 6.7-7.0 (m, 4H), 7.2-7.5 (m, 2H)

Compound 5-387

$^1$H NMR ($CDCl_3$) d (ppm): 1.38-1.62 (m, 8H), 1.81-1.85 (m, 2H), 2.53-2.75 (m, 9H), 3.34 (t, J=5.6 Hz, 2H), 3.89 (s, 2H), 4.52 (t, J=5.9 Hz, 1H), 4.63 (d, J=5.9 Hz, 1H), 4.71-4.76 (m, 2H), 6.81 (t, J=8.2 Hz, 2H), 7.30-7.36 (m, 1H), 7.51-7.64 (m, 3H), 7.83 (dd, J=1.3, 8.2 Hz, 2H)

Compound 5-388

$^1$H NMR ($CDCl_3$) d (ppm): 1.33-1.61 (m, 8H), 1.77-1.82 (m, 2H), 2.51-2.71 (m, 9H), 3.35 (t, J=5.6 Hz, 2H), 3.92 (s, 2H), 4.67-4.73 (m, 5H), 7.15 (dd, J=2.0, 8.2 Hz, 1H), 7.25-7.28 (m, 1H), 7.37 (d, J=2.3 Hz, 1H), 7.51-7.61 (m, 3H), 7.83 (dd, J=1.6, 8.6 Hz, 2H)

Compound 5-389

$^1$H NMR ($CDCl_3$) d (ppm): 1.20-1.29 (m, 4H), 1.44-1.62 (m, 14H), 1.83-1.88 (m, 2H), 1.97-2.00 (m, 2H), 2.54-2.75 (m, 9H), 3.34 (t, J=5.6 Hz, 2H), 3.85 (s, 2H), 3.96 (d, J=7.3 Hz, 1H), 4.08-4.13 (m, 1H), 4.72-4.77 (m, 2H), 7.52-7.61 (m, 3H), 7.84 (dd, J=1.6, 8.6 Hz, 2H)

Compound 5-390

$^1$H NMR ($CDCl_3$) d (ppm): 0.91-0.98 (m, 4H), 1.09-1.22 (m, 5H), 1.44-1.83 (m, 14H), 2.54-2.74 (m, 8H), 3.32-3.38 (m, 2H), 3.87 (d, J=13.6 Hz, 2H), 4.03-4.06 (m, 1H), 4.07-4.13 (m, 1H), 4.71-4.76 (m, 2H), 7.52-7.64 (m, 3H), 7.85 (dd, J=1.7, 8.3 Hz, 2H)

Compound 5-391

$^1$H NMR ($CDCl_3$) d (ppm): 1.41-1.63 (m, 8H), 1.82-1.87 (m, 2H), 2.56-2.76 (m, 9H), 3.41 (t, J=5.6 Hz, 2H), 3.93 (s, 2H), 4.51 (t, J=5.0 Hz, 1H), 4.64 (d, J=5.6 Hz, 2H), 4.72-4.77 (m, 2H), 6.81 (t, J=8.2 Hz, 2H), 7.25-7.32 (m, 1H), 7.49 (dd, J=5.0, 7.9 Hz, 1H), 8.09-8.13 (m, 1H), 8.82 (dd, J=1.6, 5.0 Hz, 1H), 9.06 (d, J=2.3 Hz, 1H)

Compound 5-392

$^1$H NMR ($CDCl_3$) d (ppm): 1.41-1.64 (m, 8H), 1.83-1.87 (m, 2H), 2.43 (s, 3H), 2.56-2.76 (m, 9H), 3.32 (t, J=5.6 Hz, 2H), 3.85 (s, 2H), 4.47 (t, J=5.6 Hz, 1H), 4.63 (d, J=6.3 Hz, 2H), 4.72-4.77 (m, 2H), 6.81 (t, J=8.6 Hz, 2H), 7.26-7.34 (m, 3H), 7.71 (d, J=8.2 Hz, 2H)

Compound 5-393

$^1$H NMR ($CDCl_3$) d (ppm): 1.40-1.59 (m, 8H), 1.79-1.84 (m, 2H), 2.59 (s, 3H), 2.49-2.76 (m, 9H), 3.44 (t, J=5.6 Hz, 2H), 4.04 (s, 2H), 4.51 (t, J=5.6 Hz 1H), 4.63 (d, J=5.6 Hz, 2H), 4.72-4.77 (m, 2H), 6.80 (t, J=9.7 Hz, 2H), 7.26-7.35 (m, 3H), 7.44-7.50 (m, 1H), 7.97 (d, J=8.3 Hz, 1H)

Compound 5-394

$^1$H NMR ($CDCl_3$) d (ppm): 1.38-1.59 (m, 17H), 1.80-1.85 (m, 2H), 2.44-2.76 (m, 9H), 3.62 (t, J=5.6 Hz, 2H), 4.13 (s, 2H), 4.60-4.65 (m, 3H), 4.75-4.79 (m, 2H), 6.80 (t, J=9.7 Hz, 2H), 7.29-7.37 (m, 1H)

Compound 5-395

$^1$H NMR ($CDCl_3$) d (ppm): (major peaks) 1.3-1.9 (m, 10H), 2.4-2.6 (m, 5H), 2.56 (t, J=5.9 Hz, 2H), 2.71 (m, 2H), 3.08 (t, J=5.9 Hz, 2H), 3.60 (s, 2H), 4.48 (br t, J=5.8 Hz, 1H), 4.65 (d, J=5.8 Hz, 2H), 4.76 (m, 2H), 6.80 (m, 2H), 7.34 (m, 1H)

Compound 5-396

$^1$H NMR ($CDCl_3$) d (ppm): 1.38-1.62 (m, 8H), 1.81-1.86 (m, 2H), 2.53-2.74 (m, 9H), 3.30 (t, J=5.9 Hz, 2H), 3.86 (s, 3H), 3.88 (s, 2H), 4.61-4.63 (m, 3H), 4.70-4.75 (m, 2H), 6.79 (t, J=8.3 Hz, 2H), 6.89 (d, J=13.8 Hz, 2H), 7.26-7.34 (m, 1H), 7.76 (d, J=8.9 Hz, 1H)

Compound 5-397

$^1$H NMR ($CDCl_3$) d (ppm): 1.40-1.62 (m, 8H), 1.81-1.86 (m, 2H), 2.53-2.75 (m, 9H), 3.35 (t, J=5.9 Hz, 2H), 3.88 (s, 2H), 4.48 (t, J=5.9 Hz, 1H), 4.64 (d, J=5.9 Hz, 2H), 4.71-4.76 (m, 2H), 6.81 (t, J=8.2 Hz, 2H), 7.26-7.33 (m, 1H), 7.50 (dd, J=1.9, 6.5 Hz, 2H), 7.76 (dd, J=1.9, 6.5 Hz, 2H)

Compound 5-398

$^1$H NMR ($CDCl_3$) d (ppm): 1.42-1.58 (m, 8H), 1.77-1.86 (m, 2H), 2.48-2.73 (m, 9H), 3.50 (t, J=5.9 Hz, 2H), 4.06 (s, 2H), 4.45 (t, J=5.6 Hz, 1H), 4.62 (d, J=5.6 Hz, 2H), 4.69-4.74 (m, 2H), 6.80 (t, J=8.6 Hz, 2H), 7.26-7.31 (m, 1H), 7.53-7.63 (m, 3H), 7.93 (d, J=9.9 Hz, 1H), 8.09 (d, J=8.3 Hz, 1H), 8.27 (d, J=6.3 Hz, 1H), 8.66 (d, J=7.9 Hz, 1H)

Compound 5-399

$^1$H NMR ($CDCl_3$) d (ppm): 1.42-1.59 (m, 8H), 1.79-1.86 (m, 2H), 2.47-2.72 (m, 9H), 3.72 (t, J=5.6 Hz, 2H), 4.44 (s, 2H), 4.59-4.72 (m, 5H), 6.82 (t, J=8.6 Hz, 2H), 7.26-7.35 (m, 1H), 7.44 (dd, J=4.3, 8.3 Hz, 1H), 7.62 (t, J=7.6 Hz, 1H), 8.01 (d, J=8.2 Hz, 1H), 8.19 (d, J=8.6 Hz, 1H), 8.52 (d, J=7.6 Hz, 1H), 8.88 (d, J=1.7 Hz, 1H)

Compound 5-400

$^1$H NMR ($CDCl_3$) d (ppm): 1.40-1.64 (m, 8H), 1.83-1.87 (m, 2H), 2.57-2.75 (m, 9H), 3.35 (t, J=5.6 Hz, 2H), 3.88 (s, 2H), 4.47 (t, J=5.6 Hz, 1H), 4.64 (d, J=5.6 Hz, 2H), 4.72-4.77 (m, 2H), 6.82 (t, J=9.5 Hz, 2H), 7.18-7.33 (m, 3H), 7.82-7.87 (m, 2H)

Compound 5-401

$^1$H NMR ($CDCl_3$) d (ppm): 1.43-1.63 (m, 8H), 1.84-1.88 (m, 2H), 2.54-2.77 (m, 9H), 3.36 (t, J=5.8 Hz, 2H), 3.87 (s, 2H), 4.27 (s, 2H), 4.27-4.31 (m, 1H), 4.60 (d, J=5.6 Hz, 2H), 4.74-4.79 (m, 2H), 6.82 (t, J=8.4 Hz, 2H), 7.26-7.36 (m, 6H)

Compound 5-402

$^1$H NMR ($CDCl_3$) d (ppm): 1.43-1.65 (m, 8H), 1.85-1.89 (m, 2H), 2.31 (s, 3H), 2.54-2.76 (m, 15H), 3.31 (t, J=5.8 Hz, 2H), 4.05 (s, 2H), 4.60-4.65 (m, 3H), 4.74-4.79 (m, 2H), 6.82 (t, J=9.9 Hz, 2H), 6.95 (s, 2H), 7.26-7.36 (m, 1H)

Compound 5-403

$^1$H NMR ($CDCl_3$) d (ppm): 1.44-1.69 (m, 8H), 1.84-1.94 (m, 2H), 2.62-2.77 (m, 9H), 3.59 (t, J=5.8 Hz, 2H), 4.15 (s, 2H), 4.50 (t, J=5.1 Hz, 1H), 4.65 (d, J=5.4 Hz, 2H), 4.75-4.80 (m, 2H), 6.82 (t, J=8.2 Hz, 2H), 7.26-7.36 (m, 1H), 7.44 (d, J=0.8 Hz, 2H), 8.12 (d, J=2.0 Hz, 1H)

Compound 5-404

$^1$H NMR ($CDCl_3$) d (ppm): 0.98 (dd, J=2.3, 9.6 Hz, 2H), 1.21 (dd, J=2.0, 4.6 Hz, 2H), 1.45-1.68 (m, 8H), 1.82-1.88 (m, 2H), 2.27-2.41 (m, 1H), 2.60-2.78 (m, 9H), 3.57 (t, J=5.6 Hz, 2H), 4.11 (s, 2H), 4.59-4.66 (m, 3H), 4.77-4.82 (m, 2H), 6.82 (t, J=8.1 Hz, 2H), 7.29-7.37 (m, 1H)

Compound 5-405

$^1$H NMR ($CDCl_3$) d (ppm): 1.45-1.61 (m, 8H), 1.81-1.85 (m, 2H), 2.52-2.75 (m, 9H), 3.53 (t, J=5.9 Hz, 2H), 4.06 (s, 2H), 4.48 (t, J=5.6 Hz, 1H), 4.64 (d, J=5.6 Hz, 2H), 4.72-4.77 (m, 2H), 6.81 (t, J=8.3 Hz, 2H), 7.16-7.36 (m, 3H), 7.53-7.61 (m, 1H), 7.92 (dt, J=2.0, 7.9 Hz, 1H)

Compound 5-406

$^1$H NMR ($CDCl_3$) d (ppm): 1.41-1.65 (m, 8H), 1.84-1.88 (m, 2H), 2.58-2.76 (m, 9H), 3.59 (t, J=5.9 Hz, 2H), 4.14 (s, 2H), 4.57 (t, J=5.6 Hz, 1H), 4.66 (d, J=5.6 Hz, 2H), 4.73-4.78 (m, 2H), 6.81 (t, J=8.6 Hz, 2H), 7.29-7.37 (m, 1H), 7.50-7.72 (m, 3H), 8.02-8.06 (m, 1H)

Compound 5-407

$^1$H NMR ($CDCl_3$) d (ppm) 1.41-1.61 (m, 8H), 1.82-1.87 (m, 2H), 2.53-2.76 (m, 9H), 3.57 (t, J=5.9 Hz, 2H), 4.15 (s, 2H), 4.50 (t, J=6.3 Hz, 1H), 4.64 (d, J=5.9 Hz, 2H), 4.73-4.77 (m, 2H), 6.81 (t, J=8.5 Hz, 2H), 7.30-7.49 (m, 2H), 7.50 (d, J=4.3 Hz, 2H), 8.12 (d, J=7.2 Hz, 1H)

Compound 5-408

$^1$H NMR ($CDCl_3$) d (ppm): 1.37-1.63 (m, 8H), 1.83-1.88 (m, 2H), 2.54-2.76 (m, 9H), 3.56 (t, J=5.6 Hz, 2H), 4.12 (s, 2H), 4.50 (t, J=6.0 Hz, 1H), 4.64 (d, J=5.6 Hz, 2H), 4.73-4.78 (m, 2H), 6.81 (t, J=8.2 Hz, 2H), 7.31 (d, J=6.6 Hz, 1H), 7.38 (dd, J=2.0, 8.6 Hz, 1H), 7.51 (d, J=7.2 Hz, 1H), 8.05 (d, J=8.6 Hz, 1H)

Compound 5-409

$^1$H NMR ($CDCl_3$) d (ppm): 1.41-1.62 (m, 8H), 1.82-1.86 (m, 2H), 2.53-2.76 (m, 9H), 3.55 (t, J=5.9 Hz, 2H), 4.09 (s, 2H), 4.48 (t, J=5.6 Hz, 1H), 4.64 (d, J=5.6 Hz, 2H), 4.73-4.78 (m, 2H), 6.81 (t, J=8.2 Hz, 2H), 7.27-7.36 (m, 1H), 7.67-7.73 (m, 2H), 7.89 (dd, J=3.0, 4.9 Hz, 1H), 8.16 (dd, J=4.3, 6.3 Hz, 1H)

Compound 5-410

$^1$H NMR ($CDCl_3$) d (ppm): 1.50-1.86 (m, 8H), 1.99-2.03 (m, 2H), 2.65-2.82 (m, 9H), 3.45 (t, J=5.6 Hz, 2H), 3.99 (s, 2H), 4.60-4.66 (m, 3H), 4.78-4.83 (m, 2H), 6.81 (t, J=8.6 Hz, 2H), 7.28-7.37 (m, 1H), 7.76 (t, J=7.9 Hz, 1H), 8.15 (dd, J=1.0, 7.9 Hz, 1H), 8.43-8.46 (m, 1H), 8.66 (t, J=2.0 Hz, 1H)

Compound 5-411

$^1$H NMR ($CDCl_3$) d (ppm): 1.40-1.62 (m, 8H), 1.82-1.86 (m, 2H), 2.54-2.75 (m, 9H), 3.43 (t, J=5.9 Hz, 2H), 3.96 (s, 2H), 4.51 (t, J=5.6 Hz, 1H), 4.64 (d, J=5.6 Hz, 2H), 4.71-4.76 (m, 2H), 6.81 (t, J=8.6 Hz, 2H), 7.28-7.36 (m, 1H), 8.01 (dd, J=2.0, 6.9 Hz, 2H), 8.36 (dd, J=1.7, 6.9 Hz, 2H)

Compound 5-412

$^1$H NMR ($CDCl_3$) d (ppm) 1.39-1.71 (m, 8H), 1.89-1.93 (m, 2H), 2.63-2.75 (m, 9H), 3.36 (t, J=5.9 Hz, 2H), 3.94 (s, 2H), 4.61-4.67 (m, 3H), 4.74-4.79 (m, 2H), 6.80 (t, J=8.6 Hz, 2H), 7.15 (t, J=4.6 Hz, 1H), 7.26-7.35 (m, 1H), 7.62 (d, J=4.3 Hz, 2H)

Compound 5-413

$^1$H NMR ($CDCl_3$) d (ppm): 0.99 (t, J=6.7 Hz, 6H), 1.44-1.62 (m, 8H), 1.84-2.00 (m, 3H), 2.54-2.77 (m, 9H), 3.28-3.44 (m, 3H), 3.63-3.70 (m, 1H), 3.81-3.86 (m, 1H), 3.92 (d, J=3.5 Hz, 2H), 3.98-4.04 (m, 1H), 4.20-4.23 (m, 1H), 4.65-4.70 (m, 2H), 7.26-7.64 (m, 3H), 7.85 (d, J=6.8 Hz, 2H)

Compound 5-414

$^1$H NMR ($CDCl_3$) d (ppm): 1.45-1.65 (m, 8H), 1.87-1.91 (m, 2H), 2.58-2.78 (m, 9H), 2.92 (d, J=6.6 Hz, 2H), 3.32 (t, J=5.7 Hz, 2H), 3.61-3.85 (m, 5H), 4.27-4.46 (m, 2H), 4.69-4.74 (m, 2H), 7.19-7.34 (m, 5H), 7.52-7.65 (m, 3H), 7.81 (d, J=6.9 Hz, 2H)

Compound 5-415

$^1$H NMR ($CDCl_3$) d (ppm): 1.25(d, J=6.3 Hz, 3H), 1.47-1.73 (m, 8H), 1.93-1.97 (m, 2H), 2.68-2.78 (m, 9H), 3.26-3.42 (m, 2H), 3.54-3.78 (m, 3H), 3.91 (d, J=4.6 Hz, 2H), 4.28-4.32 (m, 2H), 4.71-4.75 (m, 2H), 7.53-7.62 (m, 3H), 7.86 (d, J=6.8 Hz, 2H)

Compound 5-416

$^1$H NMR ($CDCl_3$) d (ppm): 1.46-1.63 (m, 8H), 1.84-1.88 (m, 2H), 2.55-2.76 (m, 9H), 3.33 (t, J=5.7 Hz, 2H), 3.88 (s, 2H), 4.57 (t, J=5.7 Hz, 1H), 4.80-4.83 (m, 4H), 6.98-7.03 (m, 1H), 7.20-7.27 (m, 2H), 7.52-7.60 (m, 3H), 7.81 (dd, J=1.4, 3.0 Hz, 2H)

Compound 5-417

$^1$H NMR ($CDCl_3$) d (ppm) 1.40-1.62 (m, 8H), 1.81-1.86 (m, 2H), 2.54-2.74 (m, 9H), 3.49 (t, J=5.6 Hz, 2H), 3.92 (s, 3H), 4.01 (s, 2H), 4.66-4.76 (m, 5H), 6.80 (t, J=8.6 Hz, 2H), 7.26-7.37 (m, 1H), 7.49(dd, J=1.6, 6.9 Hz, 1H), 7.55-7.64 (m, 2H), 7.88 (d, J=6.9 Hz, 1H)

Compound 5-418

$^1$H NMR ($CDCl_3$) d (ppm): 1.43-1.68 (m, 16H), 1.80-1.89 (m, 4H), 2.38-2.51 (m, 10H), 2.65-2.82 (m, 6H), 3.41 (t, J=5.9 Hz, 2H), 3.61-3.67(m, 2H), 3.98(s, 2H), 4.69-4.74 (m, 2H), 7.48-7.61 (m, 3H), 7.79 (d, J=6.6 Hz, 2H)

Compound 5-419

$^1$H NMR ($CDCl_3$) d (ppm): 0.93 (t, J=7.3 Hz, 3H), 1.39-1.60 (m, 10H), 1.73-1.84 (m, 4H), 2.48-2.51 (m, 5H), 2.70-2.74 (m, 4H), 2.97 (t, J=7.9 Hz, 2H), 3.54 (t, J=5.9 Hz, 2H), 4.06 (s, 2H), 4.57 (t, J=5.6 Hz, 1H), 4.65 (d, J=5.6 Hz, 2H), 4.68-4.72 (m, 2H), 6.81 (t, J=9.9 Hz, 2H), 7.28-7.34 (m, 1H)

Compound 5-420

$^1$H NMR ($CDCl_3$) d (ppm): 1.44-1.61 (m, 8H), 1.82-1.87 (m, 2H), 2.52-2.78 (m, 9H), 3.70-3.88 (m, 2H), 4.29-4.40 (m, 2H), 4.51-4.64 (m, 3H), 4.78-4.81 (m, 2H), 6.80 (t, J=8.6 Hz, 2H), 7.11 (d, J=7.3 Hz, 2H), 7.20-7.26 (m, 1H), 7.33-7.39 (m, 3H)

Compound 5-421

$^1$H NMR (DMSO-$d_6$) d (ppm): 1.23-1.46 (m, 8H), 1.71-1.88 (m, 2H), 2.49-2.83 (m, 9H), 3.37-3.42 (m, 2H), 4.07 (s, 2H), 4.49-4.61 (m, 5H), 7.00 (t, J=8.6 Hz, 1H), 7.13-7.43 (m, 4H), 7.55 (t, J=7.3 Hz, 1H), 7.78 (d, J=7.6 Hz, 1H)

Compound 5-422

$^1$H NMR ($CDCl_3$) d (ppm): 1.47-1.78 (m, 8H), 1.90-2.01 (m, 2H), 2.65-2.78 (m, 9H), 3.55 (t, J=6.0 Hz, 2H), 4.19 (s, 2H), 4.60-4.66 (m, 3H), 4.76-4.81 (m, 3H), 6.77-6.84 (m, 2H), 7.30-7.35 (m, 1H), 7.67-7.80 (m, 2H), 7.87 (dd, J=1.7, 7.6 Hz, 1H), 8.13 (dd, J=1.0, 7.6 Hz, 1H)

Compound 5-423

$^1$H NMR ($CDCl_3$) d (ppm): 1.15-1.89 (m, 18H), 2.01-2.05 (m, 2H), 2.55-2.74 (m, 9H), 3.34 (t, J=5.6 Hz, 2H), 3.86 (s, 2H), 3.90-3.94 (m, 2H), 4.71-4.76 (m, 2H), 6.77-6.84 (m, 2H), 7.51-7.64 (m, 3H), 7.85 (dd, J=2.0, 8.6 Hz, 2H)

Compound 5-424

$^1$H NMR ($CDCl_3$) d (ppm): 1.46-1.63 (m, 8H), 1.77-1.85 (m, 2H), 2.52-2.74 (m, 9H), 3.57 (t, J=5.6 Hz, 2H), 4.17 (s, 2H), 4.64-4.73 (m, 5H), 7.17 (dd, J=2.0, 8.2 Hz, 1H), 7.27-7.44 (m, 3H), 7.50 (dd, J=2.3, 5.6 Hz, 2H), 8.12 (d, J=7.2 Hz, 1H)

Compound 5-425

$^1$H NMR ($CDCl_3$) d (ppm): 1.18-2.11 (m, 19H), 2.69-2.79 (m, 9H), 3.21-3.26 (m, 1H), 3.39-3.49 (m, 2H), 3.80-3.85 (m, 2H), 3.95-4.00 (m, 1H), 4.13 (d, J=5.6 Hz, 1H), 4.64-4.77 (m, 2H), 7.52-7.63 (m, 3H), 7.85 (d, J=6.6 Hz, 2H)

Compound 5-426

$^1$H NMR ($CDCl_3$) d (ppm): 0.99 (dd, J=2.3, 9.6 Hz, 2H), 1.21 (dd, J=2.0, 4.6 Hz, 2H), 1.38-1.61 (m, 8H), 1.80-1.84 (m, 2H), 2.27-2.37 (m, 1H), 2.52-2.76 (m, 9H), 3.57 (t, J=5.6 Hz, 2H), 4.14 (s, 2H), 4.67-4.75 (m, 5H), 7.18 (dd, J=2.0, 8.3 Hz, 1H), 7.32 (d, J=8.3 Hz, 1H), 7.39 (d, J=2.0 Hz, 1H)

Compound 5-427

$^1$H NMR ($CDCl_3$) d (ppm): 1.52-2.23 (m, 10H), 2.68-2.77 (m, 9H), 3.37 (t, J=5.6 Hz, 2H), 3.95 (s, 2H), 4.62 (d, J=5.7 Hz, 2H), 4.83-4.92 (m, 3H), 6.72-6.84 (m, 2H), 7.25-7.30 (m, 1H), 7.49 (t, J=8.1 Hz, 1H), 7.58 (d, J=8.3 Hz, 1H), 7.75 (d, J=8.1 Hz, 1H), 7.84 (d, J=1.9 Hz, 1H)

Compound 5-428

$^1$H NMR ($CDCl_3$) d (ppm): 1.52-1.63 (m, 4H), 2.01-2.18 (m, 6H), 2.63-2.79 (m, 9H), 3.58 (t, J=5.6 Hz, 2H), 4.17 (s, 2H), 4.62 (d, J=5.6 Hz, 2H), 4.70 (t, J=5.7 Hz, 1H), 4.83-4.88 (m, 2H), 6.77-6.86 (m, 2H), 7.22-7.31 (m, 1H), 7.36 (t, J=8.1 Hz, 1H), 7.68 (dd, J=1.4, 8.1 Hz, 1H), 8.07 (dd, J=1.7, 8.1 Hz, 1H)

Compound 5-429

$^1$H NMR ($CDCl_3$) d (ppm): 1.20-1.81 (m, 10H), 2.48-2.70 (m, 9H), 3.28-3.44 (m, 2H), 3.90-3.97 (m, 5H), 4.57 (t, J=14.0 Hz, 2H), 4.79 (d, J=5.9 Hz, 1H), 5.20-5.25 (m, 1H), 7.28-7.38 (m, 5H), 7.51-7.64 (m, 3H), 7.86 (d, J=1.4, 8.1 Hz, 2H)

Compound 5-430

$^1$H NMR ($CDCl_3$) d (ppm): 1.54-2.23 (m, 15H), 2.69-2.78 (m, 4H), 3.36 (t, J=5.6 Hz, 2H), 3.94 (s, 2H), 4.61 (d, J=5.9 Hz, 2H), 4.83-4.94 (m, 3H), 6.76-6.84 (m, 2H), 7.24-7.38 (m, 2H), 7.50-7.58 (m, 2H), 7.67 (d, J=8.1 Hz, 1H)

Compound 5-431

$^1$H NMR ($CDCl_3$) d (ppm) 1.44-1.65 (m, 7H), 1.87-1.91 (m, 2H), 2.57-2.78 (m, 10H), 3.47 (t, J=5.9 Hz, 2H), 3.97 (s, 2H), 4.49 (t, J=5.7 Hz, 1H), 4.65 (d, J=5.6 Hz, 2H), 4.76-4.81 (m, 2H), 6.03 (d, J=9.6 Hz, 1H), 6.30 (d, J=16.5 Hz, 1H), 6.46 (dd, J=9.6, 16.5 Hz, 1H), 6.77-6.85 (m, 2H), 7.28-7.37 (m, 1H)

Compound 5-432

$^1$H NMR ($CDCl_3$) d (ppm): 1.39-1.69 (m, 8H), 1.87-1.92 (m, 2H), 2.64-2.77 (m, 9H), 3.53 (t, J=5.6 Hz, 2H), 4.05 (s, 2H), 4.50 (t, J=5.9 Hz, 1H), 4.64 (d, J=5.9 Hz, 2H), 4.74-4.79 (m, 2H), 6.77-7.03 (m, 4H), 7.30-7.35 (m, 1H), 7.90-7.98 (m, 1H)

Compound 5-433

$^1$H NMR ($CDCl_3$) d (ppm): 1.22 (d, J=5.6 Hz, 6H), 1.45-1.62 (m, 8H), 1.83-1.92 (m, 2H), 2.54-2.75 (m, 9H), 3.34 (t, J=5.7 Hz, 2H), 3.86 (s, 2H), 3.83-3.90 (m, 1H), 4.23-4.31 (m, 1H), 4.73-4.78 (m, 2H), 7.51-7.64 (m, 3H), 7.85 (dd, J=1.8, 8.4 Hz, 2H)

Compound 5-434

$^1$H NMR ($CDCl_3$) d (ppm): 0.92 (t, J=7.4 Hz, 3H), 1.19 (d, J=6.4 Hz, 3H), 1.45-1.62 (m, 10H), 1.83-1.87(m, 2H), 2.54-2.75 (m, 9H), 3.35 (t, J=5.8 Hz, 2H), 3.80-3.83 (m, 1H), 3.87 (s, 2H), 4.07-4.17 (m, 1H), 4.72-4.77 (m, 2H), 7.52-7.64 (m, 3H), 7.85 (dd, J=1.8, 8.4 Hz, 2H)

Compound 5-435

$^1H$ NMR ($CDCl_3$) d (ppm): 1.38-1.75 (m, 13H), 2.53-2.69 (m, 9H), 3.35 (t, J=5.9 Hz, 2H), 3.92 (s, 2H), 4.29 (d, J=5.6 Hz, 1H), 4.58-4.62 (m, 2H), 5.54(t, J=5.6 Hz, 1H), 6.98 (d, J=8.2 Hz, 2H), 7.26-7.30 (m, 3H), 7.52-7.64 (m, 3H), 7.86 (dd, J=1.6, 8.6 Hz, 2H)

Compound 5-436

$^1H$ NMR ($CDCl_3$) d (ppm): 1.38-1.64 (m, 13H), 2.53-2.69 (m, 9H), 3.35 (t, J=5.9 Hz, 2H), 3.92 (s, 2H), 4.29 (d, J=5.6 Hz, 1H), 4.60-4.64 (m, 2H), 5.19 (t, J=5.6 Hz, 1H), 6.98 (t, J=8.4 Hz, 2H), 7.24-7.30 (m, 2H), 7.52-7.62 (m, 3H), 7.85 (dd, J=1.6, 8.6 Hz, 2H)

Compound 5-437

$^1H$ NMR ($CDCl_3$) d (ppm): 1.34-1.62 (m, 8H), 1.81-1.86 (m, 2H), 2.52-2.75 (m, 9H), 3.47 (t, J=5.9 Hz, 2H), 4.00 (s, 2H), 4.62-4.75 (m, 5H), 6.03 (d, J=9.6 Hz, 1H), 6.30 (d, J=16.5 Hz, 1H), 6.46 (dd, J=9.6, 16.5 Hz, 1H), 7.18 (dd, J=2.3, 8.2 Hz, 1H), 7.30 (d, J=7.9 Hz, 1H), 7.39 (d, J=2.0 Hz, 1H)

Compound 5-438

$^1H$ NMR ($CDCl_3$) d (ppm): 1.48-1.81 (m, 8H), 2.01-2.15 (m, 2H), 2.56-2.83 (m, 9H), 3.54 (t, J=5.9 Hz, 2H), 3.81 (s, 3H), 3.86 (s, 2H), 3.88 (s, 3H), 4.53 (d, J=5.9 Hz, 2H), 4.67 (t, J=5.9 Hz, 1H), 4.86-4.91 (m, 2H), 6.44 (dt, J=2.7, 8.4 Hz, 2H), 7.16 (d, J=8.1 Hz, 1H), 7.48-7.64 (m, 3H), 7.82 (dd, J=1.6, 6.8 Hz, 2H)

Compound 5-439

$^1H$ NMR ($CDCl_3$) d (ppm): 1.49-1.70 (m, 8H), 1.88-1.96 (m, 2H), 2.63-2.79 (m, 9H), 3.57 (t, J=5.9 Hz, 2H), 3.76 (d, J=7.2 Hz, 2H), 4.10 (s, 2H), 4.52-4.56 (m, 1H), 4.64 (d, J=5.3 Hz, 2H), 4.78-4.82 (m, 2H), 5.34 (d, J=8.9 Hz, 1H), 5.40 (s, 1H), 5.85-5.95 (m, 1H), 6.82 (t, J=9.9 Hz, 2H), 7.28-7.37 (m, 1H)

Compound 5-440

$^1H$ NMR ($CDCl_3$) d (ppm): 1.46-1.68 (m, 8H), 1.85-1.90 (m, 2H), 2.61-2.80 (m, 9H), 3.58 (t, J=5.9 Hz, 2H), 3.76 (d, J=7.2 Hz, 2H), 4.12 (s, 2H), 4.65-4.78 (m, 5H), 5.35 (d, J=7.6 Hz, 1H), 5.40 (s, 1H), 5.86-5.96 (m, 1H), 7.19 (dd, J=2.0, 8.2 Hz, 1H), 7.30 (d, J=8.2 Hz, 1H), 7.39 (d, J=2.0 Hz, 1H)

Compound 5-441

$^1H$ NMR ($CDCl_3$) d (ppm): 1.26 (t, J=6.1 Hz, 3H), 1.42-1.94 (m, 16H), 2.12-2.19 (m, 2H), 2.63-2.75 (m, 9H), 2.88 (dd, J=4.6, 8.1 Hz, 1H), 3.31-3.37 (m, 2H), 3.82 (dd, J=14.5, 31.4 Hz, 2H), 4.09-4.22 (m, 2H), 4.28-4.33 (m, 1H), 4.72-4.77 (m, 2H), 5.17-5.20 (m, 1H), 7.51-7.60 (m, 3H), 7.85 (dd, J=1.8, 8.2 Hz, 2H)

Compound 5-442

$^1H$ NMR ($CDCl_3$) d (ppm): 0.93(t, J=7.6 Hz, 3H), 1.44-1.62 (m, 10H), 1.83-1.87 (m, 2H), 2.54-2.74 (m, 9H), 3.32-3.49 (m, 7H), 3.89 (s, 2H), 4.21-4.25 (m, 2H), 4.71-4.76 (m, 2H), 7.52-7.64 (m, 3H), 7.85 (dd, J=1.7, 8.2 Hz, 2H)

Compound 5-443

$^1H$ NMR ($CDCl_3$) d (ppm): 1.36 (t, J=7.6 Hz, 3H), 1.46-1.68 (m, 8H), 1.89-1.93 (m, 2H), 2.60-2.78 (m, 9H), 3.02 (dd, J=7.3, 14.8 Hz, 2H), 3.56 (t, J=5.9 Hz, 2H), 3.64 (s, 2H), 4.54 (t, J=5.9 Hz, 1H), 4.64 (d, J=5.6 Hz, 2H), 4.77-4.82 (m, 2H), 6.68-6.86 (m, 2H), 7.28-7.37 (m, 1H)

Compound 5-444

$^1H$ NMR ($CDCl_3$) d (ppm): 1.05 (t, J=7.4 Hz, 3H), 1.45-1.78 (m, 8H), 1.80-1.92 (m, 4H), 2.59-2.79 (m, 9H), 3.02 (dt, J=5.4, 7.9 Hz, 2H), 3.55 (t, J=5.8 Hz, 2H), 4.07 (s, 2H), 4.54 (t, J=5.3 Hz, 1H), 4.65 (d, J=5.4 Hz, 2H), 4.77-4.82 (m, 2H), 6.78-6.86 (m, 2H), 7.28-7.38 (m, 1H)

Compound 5-445

$^1H$ NMR ($CDCl_3$) d (ppm): 1.37 (t, J=7.4 Hz, 3H), 1.42-1.71 (m, 8H), 1.88-1.92 (m, 2H), 2.62-2.76 (m, 9H), 3.03 (dd, J=7.4, 14.8 Hz, 2H), 3.57 (t, J=5.7 Hz, 2H), 4.11 (s, 2H), 4.67-4.78 (m, 5H), 7.18 (dd, J=2.1, 8.4 Hz, 1H), 7.31 (d, J=8.4 Hz, 1H), 7.39 (d, J=2.1 Hz, 1H)

Compound 5-446

$^1H$ NMR ($CDCl_3$) d (ppm): 1.05 (t, J=7.4 Hz, 3H), 1.41-1.78 (m, 8H), 1.81-1.90 (m, 4H), 2.60-2.76 (m, 9H), 2.96 (dt, J=5.2, 7.9 Hz, 2H), 3.55 (t, J=5.8 Hz, 2H), 4.10 (s, 2H), 4.69-4.77 (m, 5H), 7.18 (d, J=8.2 Hz, 1H), 7.31 (d, J=8.2 Hz, 1H), 7.38(s, 1H)

Compound 5-447

$^1H$ NMR ($CDCl_3$) d (ppm): 1.14 (t, J=6.1 Hz, 3H), 1.44-1.82 (m, 12H), 1.98-2.04 (m, 4H), 2.53-2.75 (m, 9H), 3.05 (dd, J=7.2, 14.6 Hz, 1H), 3.26-3.28 (m, 1H), 3.40-3.42 (m, 1H), 3.83 (dd, J=13.5, 43.0 Hz, 2H), 3.98-4.05 (m, 2H), 4.64 (t, J=7.1 Hz, 1H), 4.72-4.77 (m, 2H), 4.86-4.89 (m, 1H), 7.54-7.60 (m, 3H), 7.85 (dd, J=1.8, 8.2 Hz, 2H)

Compound 5-448

$^1H$ NMR ($CDCl_3$) d (ppm): 1.44-1.59 (m, 10H), 1.82-1.87 (m, 2H), 2.00-2.04 (m, 2H), 2.53-2.75 (m, 9H), 3.35 (t, J=5.7 Hz, 2H), 3.51 (dt, J=2.0, 9.6 Hz, 2H), 3.87-4.02 (m, 5H), 4.11-4.17 (m, 1H), 4.69-4.74 (m, 2H), 7.53-7.62 (m, 3H), 7.85 (dd, J=1.6, 8.2 Hz, 2H)

Compound 5-449

$^1H$ NMR ($CDCl_3$) d (ppm): 1.46-1.64 (m, 3H), 1.85-1.90 (m, 2H), 2.57-2.78 (m, 9H), 3.34 (t, J=5.6 Hz, 2H), 3.87 (s, 2H), 4.35 (t, J=5.3 Hz, 1H), 4.83-4.88 (m, 2H), 4.95(d, J=5.2 Hz, 2H), 7.18-7.24 (m, 1H), 7.35 (d, J=7.9 Hz, 2H), 7.49-7.59 (m, 3H), 7.81 (d, J=7.3 Hz, 2H)

Compound 5-450

$^1H$ NMR (DMSO-$d_6$) d (ppm): 1.29-1.92 (m, 16H), 2.48-2.69 (m, 9H), 2.96-3.08 (m, 1H), 3.10-3.21 (m, 1H), 3.28-3.30 (m, 1H), 3.86 (dd, J=14.8, 30.0 Hz, 2H), 4.40-4.46 (m, 1H), 4.60-4.64 (m, 2H), 7.61-7.71 (m, 3H), 7.85 (d, J=6.9 Hz, 2H)

Compound 5-451

$^1H$ NMR ($CDCl_3$) d (ppm): 1.27 (t, J=7.1 Hz, 3H), 1.43-1.61 (m, 8H), 1.82-1.87 (m, 2H), 2.52-2.75 (m, 11H), 3.34 (t, J=5.8 Hz, 2H), 3.71 (dt, J=5.9, 11.9 Hz, 2H), 3.84 (s, 2H), 4.15 (dd, J=7.1, 14.2 Hz, 2H), 4.72-4.77 (m, 3H), 7.51-7.63 (m, 3H), 7.84 (dd, J=1.8, 8.4 Hz, 2H)

Compound 5-452

$^1H$ NMR ($CDCl_3$) d (ppm): 1.26 (t, J=7.2 Hz, 3H), 1.44-1.62 (m, 8H), 1.83-1.87 (m, 2H), 1.94 (t, J=6.8 Hz, 2H), 2.40 (t, J=6.9 Hz, 2H), 2.55-2.74 (m, 9H), 3.34 (t, J=5.8 Hz, 2H), 3.47 (dt, J=6.4, 12.0 Hz, 2H), 3.85 (s, 2H), 4.15 (dd, J=7.1, 14.2 Hz, 2H), 4.62 (t, J=5.8 Hz, 1H), 4.73-4.78 (m, 2H), 7.52-7.61 (m, 3H), 7.86 (dd, J=1.7, 8.3 Hz, 2H)

Compound 5-453

$^1H$ NMR ($CDCl_3$) d (ppm): 1.45-2.00 (m, 22H), 2.59-2.77 (m, 9H), 3.55 (t, J=5.8 Hz, 2H), 3.97-4.11 (m, 4H), 4.77-4.82 (m, 2H), 7.38-7.43 (m, 1H), 7.46-7.53 (m, 2H), 8.13 (dd, J=1.1, 8.1 Hz, 1H)

Compound 5-454

$^1H$ NMR ($CDCl_3$) d (ppm): 1.21-1.88 (m, 17H), 2.01-2.08 (m, 1H), 2.55-2.75 (m, 10H), 3.30-3.49 (m, 2H), 3.87 (s, 2H), 4.37-4.31 (m, 1H), 4.69-4.74 (m, 2H), 5.41-5.43 (m, 1H), 5.90 (br s, 2H), 7.52-7.60 (m, 3H), 7.85 (dd, J=1.9, 7.9 Hz, 2H)

Compound 5-455

$^1$H NMR (DMSO-$d_6$) d (ppm): 1.25-1.46 (m, 8H), 1.67-1.71 (m, 2H), 2.44-2.68 (m, 11H), 3.22 (t, J=5.4 Hz, 2H), 3.49 (br s, 2H), 3.77(s, 2H), 4.58-4.63 (m, 2H), 6.07 (br s, 1H), 7.62-7.74 (m, 3H), 7.84 (d, J=6.9 Hz, 2H)

Compound 5-456

$^1$H NMR (DMSO-$d_6$) d (ppm): 1.40-1.83 (m, 8H), 2.09-2.13 (m, 2H), 2.26 (t, J=7.2 Hz, 2H), 2.49-2.84 (m, 11H), 3.23-3.51 (m, 4H), 3.82 (s, 2H), 4.71-4.76 (m, 2H), 7.64-7.76 (m, 3H), 7.87 (d, J=6.7 Hz, 2H), 10.52 (br s, 1H), 12.09 (br, 1H)

Compound 5-457

$^1$H NMR (DMSO-$d_6$) d (ppm): 1.18-1.51 (m, 8H), 1.65-1.70 (m, 2H), 2.56-2.71 (m, 9H), 2.97 (t, J=6.3 Hz, 2H), 3.19 (s, 2H), 3.31 (t, J=6.6 Hz, 2H), 3.47 (br s, 2H), 4.09 (s, 2H), 4.50-4.56 (m, 5H), 7.01 (t, J=9.6 Hz, 1H), 7.12-7.40 (m, 2H)

Compound 5-458

$^1$H NMR (DMSO-$d_6$) d (ppm): 1.11-1.46 (m, 8H), 1.60-1.64 (m, 2H), 2.29 (t, J=7.6 Hz, 2H), 2.44-2.64 (m, 9H), 2.71 (t, J=6.6 Hz, 2H), 2.91 (t, J=6.9 Hz, 2H), 3.24 (t, J=6.6 Hz, 2H), 3.45 (t, J=5.3 Hz, 2H), 4.07 (s, 2H), 4.48-4.56 (m, 5H), 6.99 (dt, J=2.0, 8.6 Hz, 1H), 7.13-7.25 (m, 1H), 7.36 (dd, J=8.6, 15.8 Hz, 1H)

Compound 6-1

$^1$H NMR ($CDCl_3$) d (ppm) 1.44 (m, 2H), 1.59 (m, 4H), 2.3-2.6 (m, 12H), 2.71 (m, 2H), 3.53 (m, 2H), 3.81 (m, 4H), 4.47 (s, 2H), 4.6-4.8 (1H, overlapping with other peak), 4.7.7 (s, 2H), 6.7-7.5 (m, 7H)

Compound 6-2

$^1$H NMR ($CDCl_3$) d (ppm): 1.44 (m, 2H), 1.58 (m, 4H), 2.3-2.6 (m, 12H), 2.64 (m, 2H), 3.55 (m, 2H), 3.75(m, 4H), 4.48 (s, 2H), 4.64 (d, J=6.0 Hz, 2H), 4.98 (br t, J=6.0 Hz, 1H), 6.80 (m, 2H), 7.0-7.5 (m, 5H)

Compound 6-3

$^1$H NMR ($CDCl_3$) d (ppm): 0.92 (t, J=7.0 Hz, 3H), 1.2-1.7 (m, 12H), 2.3-2.6 (m, 12H), 2.65 (m, 2H), 3.45(m, 2H), 3.55 (m, 2H), 3.77 (m, 4H), 4.43 (t, J=6.0 Hz, 1H), 4.48 (s, 2H), 7.1-7.5 (m, 4H)

Compound 6-4

$^1$H NMR ($CDCl_3$) d (ppm): 1.44 (m, 2H), 1.59 (m, 4H), 2.3-2.6 (m, 12H), 2.64 (m, 2H), 3.53 (m, 2H), 3.80 (m, 4H), 4.45 (s, 2H), 4.6-4.8 (1H, overlapping with other peak), 4.77 (s, 2H), 6.8-7.0 (m, 4H), 7.2-7.5 (m, 2H)

Compound 6-5

$^1$H NMR ($CDCl_3$) d (ppm): 1.49 (m, 2H), 1.68 (m, 4H), 2.4-2.7 (m, 14H), 3.55 (m, 2H), 3.75 (m, 4H), 4.49 (s, 2H), 4.65 (d, J=6.0 Hz, 2H), 4.90 (t, J=6.0 Hz, 1H), 6.7-7.0 (m, 4H), 7.2-7.5 (m, 2H)

Compound 6-6

$^1$H NMR ($CDCl_3$) d (ppm): 0.92 (m, 3H), 1.2-1.8 (m, 12H), 2.3-2.7 (m, 14H), 3.44 (m, 2H), 3.54 (m, 2H), 3.76 (m, 4H), 4.3-4.5 (1H, overlapping with other peak), 4.44 (br s, 2H), 6.8-7.1 (m, 2H), 7.40 (m, 1H)

Compound 6-7

$^1$H NMR ($CDCl_3$) d (ppm): 1.43-1.60 (m, 6H), 2.45-2.54 (m, 12 H), 2.69 (t, J=5.6 Hz, 2H), 3.35 (t, J=5.6 Hz, 2H), 3.71 (t, J=4.9 Hz, 4H), 3.89 (s, 2H), 4.51 (t, J=5.6 Hz, 1H), 4.64 (d, J=5.6 Hz, 2H), 6.81 (t, J=2.3, 8.1 Hz, 2H), 7.29-7.32 (m, 1H), 7.51-7.61 (m, 3H), 7.83 (dd, J=1.7, 8.2 Hz, 2H)

Compound 6-8

$^1$H NMR ($CDCl_3$) d (ppm): 1.44-1.60 (m, 14H), 1.96-2.21 (m, 4H), 2.47-2.56 (m, 12H), 2.67 (t, J=5.8 Hz, 2H), 3.32 (t, J=5.8 Hz, 2H), 3.72 (t, J=4.9 Hz, 4H), 3.85 (s, 2H), 3.97-4.11 (m, 2H), 7.51-7.61 (m, 3H), 7.84 (dd, J=1.8, 8.4 Hz, 2H)

Compound 6-9

$^1$H NMR ($CDCl_3$) d (ppm): (major peaks) 1.44 (m, 2H), 1.59 (m, 4H), 2.4-2.6 (m, 14H), 3.08 (t, J=5.8 Hz, 2H), 3.60 (s, 2H), 3.74 (m, 4H), 4.49 (t, J=5.8 Hz, 1H), 4.65 (d, J=5.8 Hz, 2H), 6.80 (m, 2H), 7.32 (m, 1H)

Compound 6-10

$^1$H NMR ($CDCl_3$) d (ppm): 1.43-1.61 (m, 6H), 2.43-2.53 (m, 12H), 2.69 (t, J=5.6 Hz, 2H), 3.35 (t, J=5.6 Hz, 2H), 3.68 (t, J=4.9 Hz, 4H), 3.91 (s, 2H), 4.64-4.67 (m, 3H), 7.16 (dd, J=2.3, 7.3 Hz, 1H), 7.24-7.29 (m, 1H), 7.38 (d, J=2.0 Hz, 1H), 7.51-7.64 (m, 3H), 7.83 (dd, J=1.7, 8.2 Hz, 2H)

Compound 6-11

$^1$H NMR ($CDCl_3$) d (ppm): 1.44-1.65 (m, 6H), 2.47-2.56 (m, 12H), 2.66 (t, J=5.9 Hz, 2H), 3.34 (t, J=5.6 Hz, 2H), 3.77 (t, J=4.9 Hz, 4H), 3.99 (s, 2H), 4.57 (t, J=5.6 Hz, 1H), 4.81 (d, J=5.6 Hz, 2H), 6.96-7.03 (m, 2H), 7.16-7.24 (m, 2H), 7.49-7.62 (m, 3H), 7.82 (dd, J=1.4, 8.4 Hz, 2H)

Compound 6-14

$^1$H NMR ($CDCl_3$) d (ppm): 0.98 (dd, J=2.0, 7.3 Hz, 2H), 1.20-1.22 (m, 2H), 1.44-1.59 (m, 6H), 2.27-2.54 (m, 13H), 2.77 (t, J=5.6 Hz, 2H), 3.57 (t, J=5.6 Hz, 2H), 3.72 (t, J=4.6 Hz, 4H), 4.13 (s, 2H), 4.66-4.72 (m, 3H), 7.17 (dd, J=2.0, 8.2 Hz, 1H), 7.31 (d, J=8.2 Hz, 1H), 7.38 (d, J=2.0 Hz, 1H)

Compound 6-15

$^1$H NMR ($CDCl_3$) d (ppm): 0.92 (t, J=7.6 Hz, 3H), 1.18 (d, J=6.6 Hz, 3H), 1.44-1.59 (m, 8H), 2.47-2.55 (m, 12H), 2.67 (t, J=5.9 Hz, 2H), 3.35 (t, J=5.7 Hz, 2H), 3.71 (t, J=5.3 Hz, 4H), 3.81-3.87 (m, 3H), 4.07-4.17 (m; 1H), 7.51-7.64 (m, 3H), 7.85 (dd, J=1.5, 8.2 Hz, 2H)

Compound 6-16

$^1$H NMR ($CDCl_3$) d (ppm): 1.22 (d, J=6.4 Hz, 6H), 1.43-1.60 (m, 6H), 2.47-2.55 (m, 12H), 2.67 (t, J=5.6 Hz, 2H), 3.35 (t, J=5.9 Hz, 2H), 3.72 (t, J=5.0 Hz, 4H), 3.86 (s, 2H), 4.21-4.33 (m, 1H), 7.52-7.64 (m, 3H), 7.85 (d, J=6.8 Hz, 2H)

Compound 6-17

$^1$H NMR ($CDCl_3$) d (ppm): 0.98 (dd, J=2.0, 7.6 Hz, 2H), 1.20 (dd, J=2.0, 4.6 Hz, 2H), 1.45-1.63 (m, 6H), 2.27-2.36 (m, 1H), 2.48-2.58 (m, 12H), 2.74 (t, J=5.6 Hz, 2H), 3.56(t, J=6.0 Hz, 2H), 3.75 (t, J=4.6 Hz, 4H), 4.11 (s, 2H), 4.59-4.67 (m, 3H), 6.81 (t, J=2.0, 8.6 Hz, 2H), 7.28-7.37 (m, 1H)

Compound 6-18

$^1$H NMR ($CDCl_3$) d (ppm): 1.44-1.61 (m, 6H), 2.48-2.57 (m, 12H), 2.72 (t, J=5.9 Hz, 2H), 3.47 (t, J=5.9 Hz, 2H), 3.76 (t, J=2.3 Hz, 4H), 3.97 (s, 2H), 4.48 (t, J=5.6 Hz, 1H), 4.65 (d, J=5.6 Hz, 2H), 6.02 (d, J=9.9 Hz, 1H), 6.30 (d, J=16.5 Hz, 1H), 6.45 (dd, J=9.6, 16.5 Hz, 1H), 6.77-6.85 (m, 2H), 7.31-7.36 (m, 1H)

Compound 6-19

$^1$H NMR ($CDCl_3$) d (ppm): 1.45-1.64 (m, 6H), 2.46-2.56 (m, 12H), 2.72 (t, J=5.9 Hz, 2H), 3.47 (t, J=5.9 Hz, 2H), 3.72 (t, J=3.6 Hz, 4H), 4.00 (s, 2H), 4.59 (t, J=5.6 Hz, 1H), 4.69 (d, J=5.6 Hz, 2H), 6.02 (d, J=9.5 Hz, 1H), 6.30 (d, J=16.5 Hz, 1H), 6.46 (dd, J=9.6, 16.5 Hz, 1H), 7.20 (dd, J=8.2, 9.6 Hz, 1H), 7.30(d, J=8.3 Hz, 1H), 7.39 (d, J=2.3 Hz, 1H)

Compound 6-20

$^1$H NMR ($CDCl_3$) d (ppm): 1.57-1.90 (m, 6H), 2.52-2.87 (m, 14H), 3.34 (t, J=5.9 Hz, 2H), 3.76 (t, J=5.1 Hz, 4H), 3.81 (s, 3H), 3.84 (s, 2H), 3.86 (s, 3H), 4.54 (d, J=5.6 Hz, 2H), 4.62 (br s, 1H), 6.45 (dt, J=2.7, 8.4 Hz, 2H), 7.18 (d, J=8.1 Hz, 1H), 7.48-7.64 (m, 3H), 7.81 (dd, J=1.6, 6.8 Hz, 2H)

Compound 6-21

$^1$H NMR ($CDCl_3$) d (ppm): 1.55-1.81 (m, 6H), 2.47 (t, J=5.9 Hz, 2H), 2.60-2.71 (m, 4H), 2.87-2.91 (m, 6H), 3.15 (t, J=5.9 Hz, 2H), 3.60-3.71 (m, 6H), 4.66 (d, J=5.9 Hz, 2. H), 4.93 (t, J=5.6 Hz, 1H), 5.81 (br s, 1H), 7.15 (dd, J=2.3, 8.3 Hz, 1H), 7.28 (d, J=8.3 Hz, 1H), 7.36 (d, J=1.9 Hz, 1H)

Compound 6-22

$^1$H NMR ($CDCl_3$) d (ppm): 1.59-1.90 (m, 6H), 2.52 (t, J=4.9 Hz, 4H), 2.70 (t, J=5.9 Hz, 2H), 2.83-2.98 (m, 8H), 3.57 (t, J=5.8 Hz, 2H), 3.62-3.78 (m, 6H), 4.11 (s, 2H), 4.63-4.65 (m, 3H), 5.35 (d, J=16.6 Hz, 1H), 5.40 (s, 1H), 5.82-5.98 (m, 1H), 6.77-6.85 (m, 2H), 7.28-7.37 (m, 1H)

Compound 6-23

$^1$H NMR ($CDCl_3$) d (ppm): 1.52-1.76 (m, 6H), 2.48 (t, J=4.6 Hz, 4H), 2.70-2.92 (m, 10H), 3.58 (t, J=5.6 Hz, 2H), 3.64-3.78 (m, 6H), 4.13 (s, 2H), 4.66-4.72 (m, 3H), 5.34 (d, J=17.4 Hz, 1H), 5.40 (s, 1H), 5.83-5.95 (m, 1H), 7.19 (d, J=8.4 Hz, 1H), 7.30(d, J=8.3 Hz, 1H), 7.39 (s, 1H)

Compound 6-24

$^1$H NMR ($CDCl_3$) d (ppm): 0.93 (t, J=7.2 Hz, 3H), 1.43-1.70 (m, 10H), 2.46-2.54 (m, 12H), 2.68 (t, J=5.6 Hz, 2H), 3.33-3.52 (m, 6H), 3.70 (t, J=5.3 Hz, 4H), 3.89 (s, 2H), 4.22-4.26 (m, 1H), 7.52-7.64 (m, 3H), 7.85 (dd, J=1.7, 8.3 Hz, 2H)

Compound 6-25

$^1$H NMR ($CDCl_3$) d (ppm): 1.36 (t, J=7.4 Hz, 3H), 1.46-1.64 (m, 6H), 2.49-2.60 (m, 12H), 2.72 (t, J=5.6 Hz, 2H), 3.02 (dd, J=7.3, 14.7 Hz, 2H), 3.56 (t, J=5.9 Hz, 2H), 3.76 (t, J=5.1 Hz, 4H), 4.07 (s, 2H), 4.49 (t, J=5.4 Hz, 1H), 4.65 (d, J=5.4 Hz, 2H), 6.77-6.85 (m, 2H), 7.28-7.37 (m, 1H)

Compound 6-26

$^1$H NMR ($CDCl_3$) d (ppm): 1.05 (t, J=7.6 Hz, 3H), 1.46-1.65 (m, 6H), 1.81-1.92 (m, 2H), 2.48-2.60 (m, 12H), 2.72 (t, J=5.6 Hz, 2H), 2.95 (dt, J=5.3, 7.9 Hz, 2H, 3.54 (t, J=5.6 Hz, 2H), 3.76 (t, J=4.9 Hz, 4H), 4.06 (s, 2H), 4.51 (t, J=5.6 Hz, 1H), 4.65 (d, J=5.3 Hz, 2H), 6.78-6.85 (m, 2H), 7.28-7.37 (m, 1H)

Compound 6-27

$^1$H NMR ($CDCl_3$) d (ppm): 1.36 (t, J=7.3 Hz, 3H), 1.47-1.66 (m, 6H), 2.48-2.61 (m, 12H), 2.72 (t, J=5.9 Hz, 2H), 3.02 (dd, J=7.3, 14.9 Hz, 2H), 3.57 (t, J=5.9 Hz, 4H), 3.70-3.76 (m, 4H), 4.10 (s, 2H), 4.66-4.70 (m, 3H), 7.20 (dd, J=2.3, 8.6 Hz, 1H), 7.31 (d, J=8.5 Hz, 1H), 7.39 (d, J=2.0 Hz, 1H)

Compound 6-28

$^1$H NMR ($CDCl_3$) d (ppm): 1.05 (t, J=7.6 Hz, 3H), 1.50-1.89 (m, 8H), 2.49 (t, J=4.9 Hz, 3H), 2.70-2.74 (m, 10H), 2.96 (dt, J=5.3, 7.9 Hz, 2H), 3.55 (t, J=5.9 Hz, 2H), 3.72 (t, J=4.9 Hz, 4H), 4.09 (s, 2H), 4.68-4.72 (m, 3H), 7.18 (dd, J=2.4, 8.3 Hz, 1H), 7.30 (d, J=8.3 Hz, 1H), 7.38 (d, J=2.0 Hz, 1H)

Compound 6-29

$^1$H NMR ($CDCl_3$) d (ppm): 1.43-1.61 (m, 6H), 2.44-2.55 (m, 12H), 2.67 (t, J=5.9 Hz, 2H), 3.34 (t, J=5.9 Hz, 2H), 3.79 (t, J=5.0 Hz, 4H), 3.87 (s, 2H), 4.37 (t, J=5.3 Hz, 1H), 4.95 (d, J=5.4 Hz, 2H), 7.20 (dd, J=7.2, 8.9 Hz, 1H), 7.34 (d, J=8.3 Hz, 2H), 7.49-7.62 (m, 3H), 7.80 (dd, J=1.3, 8.3 Hz, 2H)

Compound 6-30 (4 hydrochloride)

$^1$H NMR (DMSO-$d_6$) d (ppm): (major peaks) 1.58 (br s, 2H), 1.82 (m, 4H), 2.4-2.6 (m, 14H), 3.06 (m, 2H), 3.57 (m, 4H), 4.22 (br s, 4H), 4.66 (d, J=4.8 Hz, 2H), 7.41 (s, 2H), 7.62 (s, 1H), 8.55 (br s, 1H)

Compound 6-31

$^1$H NMR ($CDCl_3$) d (ppm): 1.44 (m, 2H), 1.58 (m, 4H), 2.3-2.6 (m, 12H), 2.70 (m, 4H), 3.22 (s, 2H), 3.67 (s, 2H), 3.73 (m, 4H), 4.42 (t, J=5.9 Hz, 1H), 4.63 (d, J=5.9 Hz, 2-H), 6.79 (m, 2H), 7.2-7.4 (m, 5H)

Compound 6-32

$^1$H NMR ($CDCl_3$) d (ppm): 1.44 (m, 2H), 1.58 (m, 4H), 2.3-2.6 (m, 12H), 2.6-2.7 (m, 4H), 3.24 (s, 2H), 3.67 (s, 2H), 3.70 (m, 4H), 4.55 (t, J=5.9 Hz, 1H), 4.66 (d, J=5.9 Hz, 2H), 7.1-7.4 (m, 7H)

Compound 6-34

$^1$H NMR ($CDCl_3$) d (ppm): 1.43-1.61 (m, 2H), 1.55-1.62 (m, 4H), 1.97-2.01 (m, 4H), 2.42-2.57 (m, 12H), 2.76 (t, J=5.1 Hz, 2H), 3.72 (t, J=4.9 Hz, 4H), 3.78-3.88 (m, 6H), 4.61(s, 2H), 4.69 (d, J=5.7 Hz, 2H), 5.04 (t, J=5.7 Hz, 1H), 7.16 (dd, J=8.1, 1.8 Hz, 1H), 7.29 (d, J=8.4 Hz, 1H), 7.36 (d, J=2.1 Hz, 1H)

Compound 6-35

$^1$H NMR ($CDCl_3$) d (ppm): 1.45-1.61 (m, 6H), 2.45-2.55 (m, 12H), 2.75 (br s, 2H), 3.22 (s, 3H), 3.69 (t, J=5.4 Hz, 4H), 4.04 (br s, 2H), 4.56 (s, 2H), 4.65 (d, J=5.7 Hz, 2H), 4.66 (br s, 1H), 6.02 (br s, 1H), 7.10 (dd, J=8.4, 1.5 Hz, 1H), 7.22 (d, J=8.4 Hz, 1H), 7.29 (d, J=1.5 Hz, 1H)

Compound 6-36

$^1$H NMR (DMSO-$d_6$) d (ppm): 1.35-1.40 (m, 2H), 1.45-1.51 (m, 4H), 2.25-2.29 (m, 4H), 2.33-2.40 (m, 8H), 2.61 (t, J=5.6 Hz, 2H), 3.48-3.52 (m, 4H), 3.93-4.01 (m, 2H), 4.52 (s, 2H), 4.61 (d, J=5.6 Hz, 2H), 7.01-7.08 (br s, 1H), 7.32-7.38 (m, 2H), 7.57 (s, 1H), 7.69-7.78 (br s, 2H)

Compound 6-37

$^1$H NMR ($CDCl_3$) d (ppm): 1.40-1.48 (m, 2H), 1.55-1.66 (m, 4H), 2.41-2.58 (m, 12H), 2.76 (t, J=5.6 Hz, 2H), 3.26 (s, 6H), 3.65-3.74 (m, 6H), 4.55 (s, 2H), 4.70 (d, J=5.8 Hz, 2H), 5.00 (t, J=5.8 Hz, 1H), 7.17 (dd, J=8.2, 2.0 Hz, 1H), 7.30 (d, J=8.2 Hz, 1H), 7.38 (d, J=2.0 Hz, 1H)

Compound 7-1

$^1$H NMR ($CDCl_3$) d (ppm): 1.40-1.63 (m, 8H), 1.82-1.88 (m, 2H), 2.54-2.79 (m, 7H), 4.39 (t, J=2.2 Hz, 2H), 4.57 (t, J=2.2 Hz, 2H), 4.61 (d, J=5.9 Hz, 2H), 4.72-4.78 (m, 2H), 4.85 (t, J=5.6 Hz, 1H), 6.72-6.80 (m, 2H), 7.28-7.50 (m, 4H), 8.04 (dd, J=1.6, 7.4 Hz, 1H)

Compound 8-181

$^1$H-NMR ($CDCl_3$) d (ppm): 0.77-0.84 (m, 2H), 1.01 (br s, 2H), 1.06-1.20 (m, 2H), 1.40-1.15 (m, 2H), 1.66-1.72 (m, 5H), 1.78 (br s, 1H), 1.95 (s, 3H), 2.04-2.35 (m, 3H), 2.40-2.49 (m, 2H), 2.66-2.78 (m, 4H), 2.89-2.97 (m, 1H), 3.83-3.92 (m, 2H), 4.34 (br s, 2H), 4.42-4.47 (m, 1H), 4.61-4.70 (m, 4H), 4.84 (br s, 1H), 5.94 (br s, 1H), 7.16 (d, J=8.4 Hz, 1H), 7.29-7.32 (m, 1H), 7.38 (br s, 1H)

Compound 8-368

$^1$H-NMR ($CDCl_3$) d (ppm): 0.77-0.83 (m, 2H), 1.01 (br s, 2H), 1.05 (t, J=7.0 Hz, 6H), 1.40-1.72 (m, 7H), 1.83 (br s, 1H), 2.50-2.80 (m, 10H), 3.86-3.88 (m, 2H), 4.33 (br s, 2H), 4.66-4.75 (m, 5H), 7.16-7.23 (m, 3H), 7.37 (m, 1H)

Compound 8-398

$^1$H-NMR ($CDCl_3$) d (ppm): 0.77-0.83 (m, 2H), 1.01 (br s, 2H), 1.05-1.17(m, 2H), 1.41-1.71(m, 5H), 1.82-2.01(m, 5H), 2.61-2.79 (m, 9H), 3.71-3.88 (m, 4H), 3.96-4.05 (m, 1H), 4.32 (br s, 2H), 4.64-4.79 (m, 5H), 6.88-6.93 (m, 1H), 7.11 (dd, J=2.0, 8.7 Hz, 1H), 7.34-7.39 (m, 1H)

Compound 8-402

$^1$H-NMR ($CDCl_3$) d (ppm): 0.77-0.83 (m, 2H), 1.01 (br s, 2H), 1.04-1.18 (m, 2H), 1.27-1.46 (m, 2H), 1.58-1.70 (m, 7H), 1.83 (br s, 1H), 2.18-2.28 (m, 2H), 2.57 (t, J=7.5 Hz, 2H), 2.63-2.79 (m, 5H), 3.22-3.29 (m, 1H), 3.88 (br s, 2H), 4.33 (br s, 2H), 4.64-4.79 (m, 5H), 6.88-7.00 (m, 1H), 7.11 (dd, J=2.4, 8.7 Hz, 1H), 7.34-7.38 (m, 1H)

Compound 8-403

$^1$H-NMR ($CDCl_3$) d (ppm): 0.76-0.83 (m, 2H), 1.01 (br s, 2H), 1.06-1.20 (m, 2H), 1.26-1.71 (m, 11H), 1.80-1.91 (m, 3H), 2.61-2.79 (m, 7H), 3.06 (quintet, J=7.5 Hz, 1H), 3.88 (br s, 2H), 4.33 (br s, 2H), 4.70-4.80 (m, 5H), 6.88-6.91 (m, 1H), 7.10-7.13 (m, 1H), 7.36 (br s, 1H)

Compound 8-404

$^1$H-NMR ($CDCl_3$) d (ppm): 0.45-0.50 (m, 2H), 0.77-0.83 (m, 2H), 1.01 (br s, 2H), 1.06-1.20 (m, 2H), 1.41-1.82 (m, 9H), 2.47 (d, J=6.8 Hz, 2H), 2.63-2.75 (m, 7H), 3.88 (br s, 2H), 4.33 (br s, 2H), 4.64-4.81 (m, 5H), 6.88-6.90 (m, 1H), 7.09-7.12 (m, 1H), 7.36 (br s, 1H)

Compound 9-33

$^1$H-NMR ($CDCl_3$) d (ppm): 0.77-0.84 (m, 2H), 0.92 (d, J=5.9 Hz, 3H), 1.02 (br s, 2H), 1.18-1.31 (m, 4H), 1.60 (br s, 1H), 1.82 (br s, 1H), 1.93-2.02 (m, 2H), 2.46-2.53 (m, 8H), 2.73 (br s, 2H), 2.88-2.92 (m, 2H), 3.72 (br s, 4H), 3.89 (m, 2H), 4.34 (br s, 2H), 4.70 (d, J=5.4 Hz, 2H), 4.81 (br s, 1H), 7.17 (d, J=7.8 Hz, 1H), 7.28-7.31 (m, 1H), 7.38 (br s, 1H)

Compound 9-35

$^1$H-NMR ($CDCl_3$) d (ppm): 0.78-0.84 (m, 2H), 1.01 (br s, 2H), 1.54-1.65 (m, 4H), 1.80-1.93 (m, 1H), 2.16-2.23 (m, 2H), 2.46-2.54 (m, 8H), 2.71-2.81 (m, 4H), 3.67-3.85 (m, 5H), 3.88 (br s, 2H), 4.34 (br s, 2H), 4.70 (d, J=5.1 Hz, 2H), 4.87 (br s, 1H), 7.14-7.18 (m, 1H), 7.26-7.30 (m, 1H), 7.38 (d, J=1.8 Hz, 1H)

Compound 9-123

$^1$H-NMR ($CDCl_3$) d (ppm): 0.77-0.84 (m, 2H), 1.00 (d, J=6.5 Hz, 6H), 1.01 (br s, 2H), 1.04 (t, J=7.6 Hz, 3H), 1.83 (br s, 1H), 2.42-2.60 (m, 10H), 2.67-2.77 (m, 2H), 2.96 (septet, J=6.5 Hz, 1H), 3.73 (br s, 4H), 3.87-3.90 (m, 2H), 4.34 (br s, 2H), 4.70 (d, J=4.9 Hz, 2H), 4.80 (br s, 1H), 7.17 (d, J=8.1 Hz, 1H), 7.29-7.32 (m, 1H), 7.38 (br s, 1H)

Compound 10-3

$^1$H-NMR ($CDCl_3$) d (ppm): 0.78-0.84 (m, 2H), 1.02 (br s, 2H), 1.77-1.81(m, 5H), 2.56-2.61(m, 4H), 2.72-2.79(m, 4H), 3.46-3.50 (m, 4H), 3.71 (br s, 4H), 3.90 (br s, 2H), 4.26 (t, J=6.0 Hz, 2H), 4.35 (br s, 2H), 4.69 (d, J=5.7 Hz, 2H), 4.84 (br s, 1H), 7.18 (d, J=8.1 Hz, 1H), 7.28-7.30 (m, 1H), 7.39 (br s, 1H)

Compound 10-12

$^1$H-NMR ($CDCl_3$) d (ppm): 0.78-0.84 (m, 2H), 1.00-1.07 (m, 8H), 1.83 (br s, 1H), 2.59 (q, J=7.2 Hz, 4H), 2.71-2.76 (m, 4H), 3.70 (br s, 4H), 3.47 (br s, 4H), 3.90 (br s, 2H), 4.18 (t, J=6.3 Hz, 2H), 4.35 (br s, 2H), 4.69 (d, J=5.1 Hz, 2H), 4.88 (br s, 1H), 7.16 (d, J=8.7 Hz, 1H), 7.27-7.29 (m, 1H), 7.38 (br s, 1H)

Compound 11-12

$^1$H NMR ($CDCl_3$) d (ppm): 0.80 (m, 2H), 1.01 (m, 2H), 1.5-1.9 (m, 9H), 2.32 (m, 1H), 2.4-2.6 (m, 4H), 2.58 (t, J=6.0 Hz, 2H), 2.6-2.9 (m, 4H), 3.34 (dt, J=6.0, 6.0 Hz, 2H), 3.89 (m, 2H), 4.33 (s, 2H), 4.6-4.9 (m, 3H), 4.70 (s, 2H), 6.15 (br s, 1H), 6.91 (m, 1H), 7.11 (dd, J=8.4, 2.5 Hz, 1H), 7.35 (m, 1H)

Compound 11-97

$^1$H NMR ($CDCl_3$) d (ppm): 0.80 (m, 2H), 1.01 (m, 2H), 1.5-1.9 (m, 7H), 2.2-2.5 (m, 7H), 2.5-2.9 (m, 4H), 3.35 (dd, J=11.3, 6.0 Hz, 2H), 3.65 (m, 4H), 3.89 (m, 2H), 4.33 (s, 2H), 4.6-4.9 (m, 3H), 4.70 (br s, 2H), 6.91 (m, 1H), 7.0-7.4 (m, 3H)

Compound 11-98

$^1$H NMR ($CDCl_3$) d (ppm): 1.15 (t, J=7.2 Hz, 3H), 1.5-1.9 (m, 6H), 2.31 (m, 1H), 2.4-2.6 (m, 6H), 2.68 (m, 2H), 2.85 (m, 2H), 3.2-3.4 (m, 4H), 3.55 (m, 2H), 3.71 (m, 4H), 4.20 (s, 2H), 4.6-4.8 (m, 3H), 4.70 (br d, J=5.9 Hz, 2H), 5.28 (br s, 1H), 6.8-7.0 (m, 2H), 7.11 (dd, J=8.6, 2.6 Hz, 1H), 7.35 (dd, J=8.5, 6.1 Hz, 1H)

Compound 13-1

$^1$H-NMR ($CDCl_3$) d (ppm): 0.77-0.83 (m, 2H), 1.01 (br s, 2H), 1.77-1.78 (m, 5H), 2.47-2.73 (m, 14H), 3.73 (br s, 4H), 3.89 (br s, 2H), 4.34 (br s, 2H), 4.71 (br s, 2H), 4.79 (br s, 1H), 7.14-7.19 (m, 1H), 7.26-7.32 (m, 1H), 7.38 (br s, 1H)

Compound 13-2

$^1$H NMR ($CDCl_3$) d (ppm): 1.19 (t, J=7.2 Hz, 3H), 1.84 (br s, 4H), 2.40-2.47 (m, 4H), 2.54-2.59 (m, 2H), 2.70-2.76 (m, 8H), 3.49-3.67 (m, 6H), 4.05 (br s, 2H), 4.60-4.68 (m, 5H), 6.17 (br s, 1H), 7.08 (dd, J=8.1, 2.4 Hz, 1H), 7.22 (d, J=8.4 Hz, 1H), 7.27 (dd, J=5.7, 2.7 Hz, 1H)

Compound 13-3

$^1$H NMR ($CDCl_3$) d (ppm): 0.85-0.92 (m, 3H), 1.54-1.58 (m, 2H), 1.84 (br s, 4H), 2.41-2.47 (m, 4H), 2.54-2.59 (m, 2H), 2.70-2.76 (m, 8H), 3.52-3.57 (m, 2H), 3.65-3.67 (m, 4H), 4.01 (br s, 2H), 4.59-4.63 (m, 5H), 6.17 (br s, 1H), 7.09 (dd, J=8.1, 1.8 Hz, 1H), 7.23 (d, J=9.0 Hz, 1H), 7.28 (d, J=1.8 Hz, 1H)

Compound 13-4

$^1$H NMR ($CDCl_3$) d (ppm): 1.74-1.75 (m, 4H), 2.46-2.57 (m, 10H), 2.62-2.67 (m, 2H), 2.76-2.77 (m, 2H), 3.21 (s, 3H), 3.70-3.75 (m, 4H), 4.03 (br s, 2H), 4.57 (s, 2H), 4.67 (d, J=5.4 Hz, 2H), 5.73 (br s, 1H), 7.09 (br s, 1H), 7.12 (dd, J=5.4, 2.1 Hz, 1H), 7.25 (d, J=6.6 Hz, 1H), 7.32 (d, J=2.1 Hz, 1H)

Compound 13-5

$^1$H NMR ($CDCl_3$) d (ppm): 1.39-1.42 (m, 4H), 2.20-2.28 (m, 4H), 2.35-2.40 (m, 2H), 2.49-2.73 (m, 1H), 3.37-3.62 (m, 4H), 3.95 (br s, 2H), 4.58-4.59 (m, 3H), 4.86 (d, J=6.3 Hz, 2H), 7.13 (br s, 1H), 7.26-7.41 (m, 7H), 7.58 (d, J=2.1 Hz, 1H)

Compound 13-6

$^1$H NMR (DMSO-$d_6$) d (ppm): 1.03 (t, J=6.9 Hz, 3H), 1.66 (br s, 4H), 2.23-2.29 (m, 4H), 2.34-2.38 (m, 2H), 2.43-2.57 (m, 8H), 3.08 (dt, J=12.6, 6.9 Hz, 2H), 3.46-3.52 (m, 6H), 4.16 (s, 2H), 4.55 (d, J=6.0 Hz, 2H), 6.46 (br t, J=6.0 Hz, 1H), 7.09 (br t, J=6.0 Hz, 1H), 7.29 (d, J=8.1 Hz, 1H), 7.37 (dd, J=8.4, 2.1 Hz, 1H), 7.57 (d, J=2.1 Hz, 1H)

Compound 13-7

$^1$H NMR (DMSO-$d_6$) d (ppm): 1.78-1.83 (m, 4H), 2.46-2.47 (m, 4H), 2.53-2.78 (m, 10H), 2.94 (br t, 2H), 3.64-3.72 (m, 4H), 4.02 (br s, 2H), 4.54-4.57 (m, 3H), 4.70 (s, 2H), 7.17 (dd, J=8.1, 1.2 Hz, 1H), 7.28 (d, J=8.4 Hz, 1H), 7.38 (d, J=1.5 Hz, 1H)

Compound 13-8

$^1$H NMR (DMSO-$d_6$) d (ppm): 1.23 (d, J=6.6 Hz, 6H), 1.64-1.70 (m, 4H), 2.23-2.25 (m, 4H), 2.36 (t, J=6.0 Hz, 2H), 2.48-2.59 (m, 8H), 3.44-3.50 (m, 4H), 3.90 (br s, 2H), 4.40-

4.47 (m, 1H), 4.57-4.59(m, 4H), 7.23 (br s, 1H), 7.29-7.37 (m, 2H), 7.53 (br s, 1H), 7.57 (d, J=1.8 Hz, 1H)

Compound 13-9

$^1$H NMR (DMSO-$d_6$) d (ppm) 0.26-0.31 (m, 2H), 0.44-0.50 (m, 2H), 1.03-1.06 (m, 1H), 1.62 (m, 4H), 2.22-2.26 (m, 4H), 2.32-2.40 (m, 4H), 2.46-2.51 (m, 4H), 2.60-2.63 (m, 2H), 3.44-3.49 (m, 6H), 3.92 (br s, 2H), 4.55-4.62 (m, 4H), 7.15 (br s, 1H), 7.31-7.39 (m, 2H), 7.59 (d, J=1.8 Hz, 1H), 7.88 (br s, 1H)

Compound 13-10

$^1$H NMR (DMSO-$d_6$) d (ppm) 0.64-0.69 (m, 2H), 0.72-0.78 (m, 2H), 1.62-1.65 (m, 4H), 2.22-2.26 (m, 4H), 2.32-2.46 (m, 4H), 2.49-2.51 (m, 4H), 2.60 (t, J=5.7 Hz, 2H), 3.14 (br s, 1H), 3.45 (m, 4H), 3.90 (br s, 2H), 4.54-4.60 (m, 4H), 7.12 (br s, 1H), 7.30-7.39 (m, 2H), 7.59 (d, J=2.1 Hz, 1H), 7.75 (br s, 1H)

Compound 13-11

$^1$H NMR (DMSO-$d_6$) d (ppm): 0.90 (t, J=7.2 Hz, 3H), 1.28-1.40 (m, 2H), 1.51-1.60 (m, 2H), 1.62-1.66 (m, 4H), 2.21-2.27 (m, 4H), 2.32-2.40 (m, 4H), 2.46-2.51 (m, 4H), 2.61 (t, J=5.4 Hz, 2H), 3.44-3.50 (m, 4H), 3.58-3.65 (m, 2H), 3.90 (br s, 2H), 4.59-4.61 (m, 4H), 7.12 (br s, 1H), 7.30-7.39 (m, 2H), 7.59 (d, J=1.8 Hz, 1H), 7.73 (br s, 1H)

Compound 14-1

$^1$H NMR ($CDCl_3$) d (ppm): 0.80 (m, 2H), 1.01 (m, 2H), 1.4-1.9 (m, 11H), 2.3-2.5 (m, 5H), 2.43 (t, J=6.0 Hz, 2H), 2.6-2.9 (m, 4H), 3.32 (dt, J=5.3, 5.8 Hz, 2H), 3.89 (m, 2H), 4.35 (s, 2H), 4.70 (m, 4H), 4.87 (br s, 1H), 6.21 (br s, 1H), 7.1-7.4 (m, 3H)

Compound 14-2

$^1$H NMR ($CDCl_3$) d (ppm): 0.80 (m, 2H), 1.01 (t, J=7.1 Hz, 6H), 1.01 (m, 2H), 1.5-1.9 (m, 7H), 2.25 (m, 1H), 2.50 (q, J=7.1 Hz, 4H), 2.51 (t, J=7.1 Hz, 2H), 2.74 (m, 2H), 2.79 (m, 2H), 3.34 (dt, J=5.5, 5.5 Hz, 2H), 3.89 (m, 2H), 4.35 (br s, 2H), 4.6-4.8 (m, 2H), 4.70 (br s, 2H), 4.86 (br s, 1H), 7.1-7.4 (m, 3H), 7.55 (br s, 1H)

Compound 14-3

$^1$H NMR ($CDCl_3$) d (ppm): 0.82 (m, 2H), 1.01 (m, 2H), 1.51 (m, 2H), 1.6-1.9 (m, 9H), 2.23 (m, 1H), 2.48 (m, 4H), 2.58 (t, J=6.0 Hz, 2H), 2.73 (m, 2H), 2.79 (m, 2H), 3.35 (dt, J=6.0, 6.0 Hz, 2H), 3.88 (m, 2H), 4.35 (s, 2H), 4.6-4.8 (m, 4H), 4.89 (br s, 1H), 7.1-7.4 (m, 3H), 7.58 (br s, 1H)

Compound 14-4

$^1$H NMR ($CDCl_3$) d (ppm): 0.81 (m, 2H), 1.01 (m, 2H), 1.63 (m, 2H), 1.7-2.0 (m, 7H), 2.32 (m, 1H), 2.52 (m, 4H), 2.60 (t, J=6.0 Hz, 2H), 2.75 (m, 2H), 2.79 (m, 2H), 3.35 (dt, J=6.0, 6.0 Hz, 2H), 3.72 (m, 2H), 4.34 (s, 2H), 4.6-4.8 (m, 2H), 4.70 (br s, 2H), 4.86 (br s, 1H), 6.19 (br s, 1H), 7.1-7.4 (m, 3H)

Compound 14-5

$^1$H NMR ($CDCl_3$) d (ppm): 0.80 (m, 2H), 0.90 (s, 6H), 1.01 (m, 2H), 1.56 (m, 2H), 1.82 (m, 1H), 1.90 (m, 2H), 2.26 (s, 2H), 2.27 (s, 6H), 2.2-2.4 (m, 1H), 2.73 (m, 2H), 2.83 (m, 2H), 3.16 (d, J=4.6 Hz, 2H), 3.89 (m, 2H), 4.35 (s, 2H), 4.7-4.9 (m, 2H), 4.71 (br s, 2H), 4.87 (br s, 1H), 7.1-7.4 (m, 3H), 8.20 (br s, 1H)

Compound 14-6

$^1$H NMR (DMSO-$d_6$) d (ppm): 0.70 (m, 4H), 1.22 (m, 2H), 1.48 (m, 2H), 1.73 (m, 2H), 2.01 (m, 1H), 2.21 (m, 1H), 2.4-2.7 (m, 4H), 2.91 (m, 2H), 3.63 (m, 1H), 3.7-3.9 (m, 2H), 3.86 (m, 2H), 4.27 (br s, 2H), 4.38 (m, 2H), 4.4-4.6 (m, 1H), 4.49 (br s, 2H), 6.81 (s, 1H), 7.09 (s, 1H), 7.1-7.3 (m, 2H), 7.48 (s, 1H), 7.72 (m, 1H)

Compound 14-7

$^1$H NMR (DMSO-$d_6$) d (ppm): (major peaks) 0.75 (m, 4H), 1.25 (m, 2H), 1.53 (m, 2H), 2.05 (m, 1H), 2.25 (m, 1H), 2.5-2.7 (m, 6H), 3.2-3.5 (m, 2H), 3.72 (m, 1H), 3.90 (m, 2H), 4.3-4.6 (m, 7H), 6.72 (s, 1H), 7.1-7.3 (m, 2H), 7.50 (s, 1H), 7.75 (m, 1H)

Compound 14-8

$^1$H NMR ($CDCl_3$) d (ppm): 0.80 (m, 2H), 1.01 (m, 2H), 1.5-1.9 (m, 5H), 2.2-2.5 (m, 7H), 2.5-2.9 (m, 4H), 3.35 (dd, J=11.0, 5.6 Hz, 2H), 3.71 (m, 4H), 3.89 (m, 2H), 4.35 (s, 2H), 4.6-4.8 (m, 2H), 4.70 (br d, J=5.3 Hz, 2H), 4.90 (br s, 1H), 6.05 (m, 1H), 7.1-7.4 (m, 3H)

Compound 14-9

$^1$H NMR ($CDCl_3$) d (ppm): 0.81 (m, 2H), 1.01 (m, 2H), 1.5-1.9 (m, 7H), 2.2-2.5 (m, 7H), 2.5-2.8 (m, 4H), 3.34 (dd, J=11.5, 5.9 Hz, 2H), 3.65 (m, 4H), 3.89 (m, 2H), 4.35 (s, 2H), 4.6-4.8 (m, 2H), 4.72 (br d, J=10.5 Hz, 2H), 4.91 (br s, 1H), 6.89 (m, 1H), 7.1-7.4 (m, 3H)

Compound 14-10

$^1$H NMR ($CDCl_3$) d (ppm): (major peaks) 0.81 (m, 2H), 1.01 (m, 2H), 1.6-1.8 (m, 6H), 1.81 (m, 1H), 2.3-2.5 (m, 7H), 2.5-2.8 (m, 4H), 3.6-3.8 (m, 6H), 3.89 (m, 2H), 4.34 (m, 2H), 4.6-4.8 (m, 2H), 4.70 (d, J=5.1 Hz, 2H), 4.88 (br s, 1H), 7.1-7.4 (m, 3H).

Compound 14-11

$^1$H NMR ($CDCl_3$) d (ppm): (major peaks) 0.80 (m, 2H), 1.02 (m, 2H), 1.6-1.9 (m, 5H), 2.4-2.9 (m, 11H), 3.56 (m, 2H), 3.5-3.7 (m, 4H), 3.89 (m, 2H), 4.35 (s, 2H), 4.6-4.8 (m, 2H), 4.70 (br s, 2H), 4.87 (br s, 1H), 7.1-7.4 (m, 3H)

Compound 14-12

$^1$H NMR ($CDCl_3$) d (ppm): (major peaks) 0.98 (m, 2H), 1.12 (m, 2H), 1.5-1.9 (m, 8H), 2.31 (m, 1H), 2.4-2.8 (m, 8H), 2.59 (t, J=6.0 Hz, 2H), 3.35 (dt, J=6.0, 6.0 Hz, 2H), 3.94 (m, 2H), 4.33 (br s, 2H), 4.6-4.8 (m, 2H), 4.69 (d, J=5.4 Hz, 2H), 4.94 (br t, J=5 Hz, 1H), 6.23 (br t, J=6 Hz, 1H), 7.17 (dd, J=8.4, 2.1 Hz, 1H), 7.30 (d, J=8.4 Hz, 1H), 7.36 (d, J=2.1 Hz, 1H)

Compound 14-13

$^1$H NMR ($CDCl_3$) d (ppm): 0.99 (m, 2H), 1.15 (m, 2H), 1.4-1.7 (m, 4H), 1.82 (m, 2H), 2.30 (m, 1H), 2.3-2.6 (m, 6H), 2.70 (m, 2H), 2.79 (m, 2H), 3.34(dt, J=5.7, 5.7 Hz, 2H), 3.57 (m, 4H), 3.77 (br s, 1H), 3.95 (m, 2H), 4.35 (br s, 2H), 4.6-4.8 (m, 2H), 4.69 (d, J=5.6 Hz, 2H), 4.92 (t, J=5.6 Hz, 1H), 6.95 (m, 1H), 7.15 (dd, J=8.2, 2.0 Hz, 1H), 7.30 (d, J=8.2 Hz, 1H), 7.36 (d, J=2.0 Hz, 1H)

Compound 14-14

$^1$H NMR ($CDCl_3$) d (ppm): 0.99 (m, 2H), 1.14 (m, 2H), 1.6-1.9 (m, 4H), 2.4-2.9 (m, 11H), 3.5-3.8 (m, 6H), 3.95 (m, 2H), 4.33 (br s, 2H), 4.6-4.8 (m, 2H), 4.69 (d, J=5.9 Hz, 2H), 4.97 (br t, J=6 Hz, 1H), 7.1-7.4 (m, 3H)

Compound 15-1

$^1$H-NMR ($CDCl_3$) d (ppm): 0.79-0.88 (m, 2H), 1.01 (br s, 2H), 1.04 (t, J=7.0 Hz, 6H), 1.74 (br s, 1H), 2.57 (q, J=7.0 Hz, 4H), 2.83 (br s, 2H), 3.27 (br s, 6H), 3.61-3.74 (m, 4H), 3.92 (br s, 2H), 4.31-4.34 (m, 2H), 4.62 (br, s 2H), 4.88 (br s, 1H), 7.15-7.19 (m, 1H), 7.26-7.31 (m, 1H), 7.38 (br s, 1H)

Compound 15-2

$^1$H NMR ($CDCl_3$) d (ppm): 0.78-0.84 (m, 2H), 1.11 (br s, 2H), 1.84 (br s, 1H), 1.95 (t, J=10.8 Hz, 1H), 2.15 (dt, J=11.1, 3.6 Hz, 1H), 2.35 (dd, J=15.0, 6.0 Hz, 1H), 2.61-2.74 (m, 4H), 2.87 (d, J=10.8 Hz, 2H), 3.50 (d, J=4.5 Hz, 2H), 3.54-3.90 (m, 13H), 4.00-4.06 (m, 1H), 4.36 (s, 2H), 4.69 (d, J=5.4 Hz, 2H), 4.94 (br t, 1H), 7.18-7.32 (m, 7H), 7.39 (d, J=1.8 Hz, 1H)

Compound 15-3

$^1$H NMR ($CDCl_3$) d (ppm): 0.78-0.84 (m, 2H), 1.12 (br s, 2H), 1.65-1.93 (m, 4H), 2.14 (dt, J=11.1, 3.6 Hz, 1H), 2.41-2.53 (m, 2H), 2.63-2.76 (m, 4H), 3.49-3.70 (m, 12H), 3.81-3.90 (m, 3H), 4.36 (s, 2H), 4.69 (d, J=5.4 Hz, 2H), 4.94 (br s, 1H), 7.15-7.32 (m, 7H), 7.38 (d, J=1.5 Hz, 1H)

Compound 15-4

$^1$H NMR ($CDCl_3$) d (ppm): 0.78-0.84 (m, 2H), 0.99-1.06 (m, 2H), 1.76-1.86 (m, 5H), 2.55-2.63 (m, 4H), 2.74 (br s, 2H), 3.34 (s, 2H), 3.61 (m, 4H), 3.72 (m, 4H), 3.90 (m, 2H), 4.35 (s, 2H), 4.70 (d, J=5.7 Hz, 2H), 4.84 (br s, 1H), 7.14-7.40 (m, 3H)

Compound 15-5

$^1$H NMR ($CDCl_3$) d (ppm): 0.78-0.86 (m, 2H), 0.99-1.06 (m, 2H), 1.43 (m, 2H), 1.57 (m, 4H), 1.83 (m, 1H), 2.41 (br s, 4H), 2.65-2.77 (m, 2H), 3.15 (s, 2H), 3.61 (m, 4H), 3.71 (m, 4H), 3.89 (m, 2H), 4.36 (s, 2H), 4.70 (d, J=5.5 Hz, 2H), 4.87 (br s, 1H), 7.14-7.40 (m, 3H)

Compound 15-6

$^1$H NMR ($CDCl_3$) d (ppm): 0.78-0.86 (m, 2H), 0.99-1.06 (m, 2H), 1.55-1.66 (m, 2H), 1.80-1.96 (m, 3H), 2.26 (m, 2H), 1.70-1.82 (m, 4H), 3.20 (s, 2H), 3.59-3.78 (m, 9H), 3.91 (m, 2H), 4.36 (s, 2H), 4.71 (d, J=5.5 Hz, 2H), 4.84 (br s, 1H), 7.15-7.41 (m, 3H)

Compound 15-7

$^1$H NMR ($CDCl_3$) d (ppm): 0.79-0.85 (m, 2H), 0.97-1.06 (m, 2H), 1.68-1.87 (m, 4H), 2.09 (ddd, J=11.5, 11.5, 3.3 Hz, 1H), 2.27 (s, 3H), 2.36-2.76 (m, 6H), 3.45-3.77 (m, 10H), 3.82-3.90 (m, 3H), 4.36 (s, 2H), 4.69 (d, J=5.6 Hz, 2H), 4.86-4.94 (br m, 1H), 7.16-7.39 (m, 3H)

Compound 15-8

$^1$H NMR ($CDCl_3$) d (ppm): 0.77-0.85 (m, 2H), 0.99-1.05 (m, 2H), 1.79-1.86 (m, 1H), 1.87 (dd, J=10.9, 10.9 Hz, 1H), 2.10 (ddd, J=11.3, 11.3, 3.5 Hz, 1H), 2.28 (s, 3H), 2.40 (dd, J=14.7, 5.7 Hz, 1H), 2.61-2.78 (m, 4H), 2.84-2.88 (m, 1H), 3.48-4.04 (m, 13H), 4.35 (s, 2H), 4.69 (d, J=5.6 Hz, 2H), 4.83-5.01 (br m, 1H), 7.16-7.39 (m, 3H)

Compound 15-9

$^1$H NMR ($CDCl_3$) d (ppm): 0.78-0.86 (m, 2H), 0.99-1.06 (m, 2H), 1.60-1.86 (m, 6H), 2.08-2.28 (m, 2H), 2.61-2.79 (m, 2H), 3.17 (d, J=13.4 Hz, 1H), 3.19 (d, J=13.4 Hz, 1H), 3.55-3.65 (m, 6H), 3.72 (m, 4H), 3.90 (m, 4H), 4.36 (s, 2H), 4.70 (d, J=5.7 Hz, 2H), 7.14-7.40 (m, 3H)

Compound 15-10

$^1$H NMR ($CDCl_3$) d (ppm): 0.78-0.86 (m, 2H), 0.99-1.06 (m, 2H), 1.50-1.87 (m, 5H), 2.38-2.52 (m, 3H), 2.61-2.68 (m, 1H), 2.75 (m, 2H), 3.22 (s, 2H), 3.53-3.94 (m, 11H), 4.36 (s, 2H), 4.70 (d, J=5.5 Hz, 2H), 4.93 (br s, 1H), 7.14-7.40 (m, 3H)

Compound 15-11

$^1$H-NMR ($CDCl_3$) d (ppm): 0.79-0.85 (m, 2H), 1.02 (br s, 2H), 1.77-1.87 (m, 2H), 2.08-2.19 (m, 1H), 2.53-2.60 (m, 1H), 2.63 (br s, 1H), 2.74-2.88 (m, 4H), 2.98-3.06 (m, 1H), 3.46 (s, 2H), 3.49-3.65 (m, 4H), 3.73 (br s, 4H), 3.86-3.94 (m, 2H), 4.30-4.39 (m, 3H), 4.70 (d, J=5.7 Hz, 2H), 4.89 (br s, 1H), 7.17-7.19 (m, 1H), 7.25-7.30 (m, 1H), 7.40 (br s, 1H)

Compound 15-12

$^1$H-NMR ($CDCl_3$) d (ppm): 0.79-0.85 (m, 2H), 1.02 (br s, 2H), 1.78-1.87 (m, 2H), 2.07-2.18 (m, 1H), 2.52-2.59 (m, 1H), 2.63 (br s, 1H), 2.74-2.87 (m, 4H), 2.98-3.06 (m, 1H), 3.46 (s, 3H), 3.50-3.65 (m, 4H), 3.72 (br s, 4H), 3.87-3.95 (m, 2H), 4.33-4.36 (m, 3H), 4.70 (d, J=5.7 Hz, 1H), 4.97 (br s, 1H), 7.16-7.19 (m, 1H), 7.25-7.29 (m, 1H), 7.39 (br s, 1H)

Compound 15-13

$^1$H NMR ($CDCl_3$) d (ppm): 1.16 (t, J=7.2 Hz, 3H), 1.53-1.92 (m, 4H), 2.26-2.33 (m, 2H), 2.68 (br t, J=5.6 Hz, 2H), 2.77-2.83 (m, 2H), 3.22-3.35 (m, 4H), 3.53-3.73 (m, 11H), 4.22 (s, 2H), 4.62 (br t, J=5.1 Hz, 1H), 4.70 (d, J=14.0 Hz, 2H), 5.02-5.05 (m, 1H), 7.17 (dd, J=8.7, 2.1 Hz, 1H), 7.29 (d, J=8.7 Hz, 1H), 7.39 (d, J=2.1 Hz, 1H)

Compound 15-14

$^1$H NMR ($CDCl_3$) d (ppm) 1.13 (t, J=7.2 Hz, 3H), 1.76-1.84 (m, 1H), 2.06-2.17 (m, 1H), 2.49-3.04 (m, 6H), 3.22-3.31 (m, 2H), 3.39-3.70 (m, 13H), 4.24 (s, 2H), 4.31 (br s, 1H), 4.67 (d, J=5.4 Hz, 2H), 4.95 (br t, J=5.4 Hz, 1H), 5.43 (br t, J=5.8 Hz, 1H), 7.17 (dd, J=8.3, 2.0 Hz, 1H), 7.25 (d, J=8.3 Hz, 1H), 7.35 (d, J=2.0 Hz, 1H)

Compound 15-15

$^1$H NMR ($CDCl_3$) d (ppm): 0.78-0.84 (m, 2H), 0.96-1.04 (m, 2H), 1.54-1.64 (m, 1H), 1.82-1.94 (m, 4H), 2.26 (br t, J=8.7 Hz, 2H), 2.74-2.79 (m, 4H), 3.18-3.23 (m, 1H), 3.20 (s, 2H), 3.34 (s, 3H), 3.57-3.62 (m, 5H), 3.69-3.75 (m, 4H), 4.36 (s, 2H), 4.70 (d, J=5.4 Hz, 2H), 4.94 (br t, J=6.0 Hz, 1H), 7.17 (d, J=8.1 Hz, 1H), 7.24 (dd, J=8.4, 1.8 Hz, 1H), 7.39 (d, J=1.8 Hz, 1H)

Compound 15-16

$^1$H-NMR ($CDCl_3$) d (ppm): 0.78-0.85 (m, 2H), 1.02 (br s, 2H), 1.78-1.86(m, 5H), 2.61-2.75(m, 6H), 3.61-3.62(m, 4H), 3.66-3.78 (m, 4H), 3.88-3.98 (m, 6H), 4.36 (br s, 2H), 4.71 (d, J=5.4 Hz, 2H), 4.92 (br s, 1H), 7.19 (d, J=8.1 Hz, 1H), 7.26-7.30 (m, 1H), 7.39 (br s, 1H)

Compound 15-17

$^1$H-NMR ($CDCl_3$) d (ppm): 0.79-0.84 (m, 2H), 1.02 (br s, 2H), 1.83 (br s, 1H), 2.49 (t, J=6.0 Hz, 4H), 2.75 (br s, 2H), 2.86 (t, J=6.0 Hz, 4H), 3.36 (s, 2H), 3.74 (br s, 4H), 3.64-3.66 (m, 4H), 3.89-3.95 (m, 2H), 4.34 (br s, 2H), 4.70 (d, J=6.0 Hz, 2H), 4.92 (br s, 1H), 7.17 (d, J=8.1 Hz, 1H), 7.25-7.28 (m, 1H), 7.40 (br s, 1H)

Compound 15-18

$^1$H NMR ($CDCl_3$) d (ppm): 0.78-0.82 (m, 2H), 0.88-0.94 (m, 2H), 1.85-2.05 (m, 4H), 2.47-2.49 (m, 2H), 2.64-2.75 (m, 4H), 3.22 (s, 2H), 3.61-3.67 (m, 6H), 3.69-3.72 (m, 4H), 3.89-3.91 (m, 2H), 4.36 (s, 2H), 4.58-4.78 (m, 1H), 4.70 (d, J=4.0 Hz, 2H), 4.90 (br s, 1H), 7.17 (d, J=7.6 Hz, 1H), 7.27 (dd, J=7.6, 1.6 Hz, 1H), 7.39 (d, J=1.6 Hz, 1H)

Compound 15-19

$^1$H NMR ($CDCl_3$) d (ppm): 1.16 (t, J=7.2 Hz, 3H), 1.84-2.01 (m, 4H), 2.42-2.50 (m, 2H), 2.62-2.68 (m, 4H), 3.21 (s, 2H), 3.30 (dt, J=12.5, 6.9 Hz, 2H), 3.53-3.62 (m, 6H), 3.68-3.72 (m, 4H), 4.22 (s, 2H), 4.55-4.61 (m, 1H), 4.70 (d, J=5.6 Hz, 2H), 4.74-4.78 (m, 1H), 4.95 (br t, J=6.0 Hz, 1H), 7.29 (d, J=8.2 Hz, 1H), 7.27 (dd, J=8.2, 2.1 Hz, 1H), 7.39 (d, J=2.0 Hz, 1H)

Compound 15-20

$^1$H NMR ($CDCl_3$) d (ppm): 1.11 (t, J=7.2 Hz, 3H), 2.32 (s, 3H), 2.40-2.44 (m, 4H), 2.65 (br t, J=5.5 Hz, 2H), 3.23-3.31 (m, 10H), 3.57 (br t, J=5.8 Hz, 2H), 3.65-3.73 (m, 4H), 4.23 (s, 2H), 4.68 (d, J=5.6 Hz, 2H), 4.93-4.97 (m, 1H), 5.36-5.40 (m, 1H), 7.17 (dd, J=8.3, 2.0 Hz, 1H), 7.26 (d, J=8.3 Hz, 1H), 7.34 (d, J=2.0 Hz, 1H)

Compound 15-21

$^1$H NMR ($CDCl_3$) d (ppm): 0.78-0.85 (m, 2H), 0.98-1.06 (m, 2H), 1.76-1.87 (m, 1H), 2.33 (s, 3H), 2.42-2.46 (m, 4H), 2.72-2.76 (m, 2H), 3.24-3.35 (m, 8H), 3.67-3.79 (m, 4H), 3.88-3.92 (m, 2H), 4.35 (s, 2H), 4.69-4.71 (m, 2H), 4.85-4.87 (m, 1H), 7.16-7.19 (m, 1H), 7.26-7.29 (m, 1H), 7.39 (br s, 1H)

Compound 15-22

$^1$H NMR ($CDCl_3$) d (ppm): 1.17 (t, J=7.3 Hz, 3H), 1.75 (br t, J=5.5 Hz, 4H), 2.57-2.61 (m, 4H), 2.68 (t, J=5.7 Hz, 2H), 3.22 (s, 2H), 3.26-3.35 (m, 2H), 3.53-3.76 (m, 10H), 3.95 (s, 4H), 4.21 (s, 2H), 4.53 (br t, J=5.9 Hz, 1H), 4.71 (d, J=5.5 Hz, 2H), 4.85 (br t, J=5.5 Hz, 1H), 7.19 (dd, J=8.3, 2.1 Hz, 1H), 7.29 (d, J=8.3 Hz, 1H), 7.40 (d, J=2.1 Hz, 1H)

Compound 15-23

$^1$H-NMR ($CDCl_3$) d (ppm): 0.78-0.84 (m, 2H), 1.02 (br s, 2H), 1.30 (d, J=6.9 Hz, 3H), 1.70-1.83 (m, 8H), 2.59 (dt, J=6.0, 12.0 Hz, 4H), 2.74 (br s, 2H), 3.48 (q, J=6.7 Hz, 1H), 3.53-3.76 (m, 8H), 3.90 (br s, 2H), 4.36 (br s, 2H), 4.70 (d, J=6.0 Hz, 2H), 4.92 (br s, 1H), 7.17 (d, J=8.4 Hz, 1H), 7.26-7.29 (m, 1H), 7.39 (br s, 1H)

Compound 15-24

$^1$H-NMR ($CDCl_3$) d (ppm): 0.81-0.88 (m, 2H), 1.01 (br s, 2H), 1.90-2.02(m, 1H), 2.46 (s, 3H), 2.74 (br s, 3H), 3.42 (s, 2H), 3.65 (br s, 4H), 3.73 (br s, 4H), 3.91 (br s, 2H), 4.37 (br s, 2H), 4.70 (br s, 2H), 4.99 (br s, 1H), 7.15-7.18 (m, 1H), 7.23-7.26 (m, 1H), 7.39 (br s, 1H)

Compound 15-25

$^1$H NMR ($CDCl_3$) d (ppm): 0.78-0.85 (m, 2H), 1.00-1.02 (m, 2H), 1.78-2.30 (m, 7H), 2.37 (s, 3H), 2.49-2.76 (m, 3H), 2.97-3.04 (m, 2H), 3.47-3.72 (m, 8H), 3.88-3.92 (m, 2H), 4.37 (s, 2H), 4.69-4.71 (m, 2H), 4.95-4.99 (m, 1H), 7.15-7.39 (m, 2H), 7.39-7.41 (m, 1H)

Compound 15-26

$^1$H NMR ($CDCl_3$) d (ppm): 0.78-0.84 (m, 2H), 1.01 (br s, 2H), 1.65-2.17 (m, 9H), 2.26 (s, 3H), 2.67-2.81 (m, 2H), 2.83-3.18 (m, 1H), 3.60-3.92 (m, 10H), 4.47 (s, 2H), 4.67-4.81 (m, 2H), 4.88-5.03 (m, 1H), 7.15-7.36 (m, 2H), 7.39 (br s, 1H)

Compound 15-27

$^1$H NMR ($CDCl_3$) d (ppm): 0.78-0.84 (m, 2H), 0.95-1.08 (m, 2H), 1.50-1.59 (m, 1H), 1.62-1.83 (m, 3H), 2.01-2.32 (m, 3H), 2.38 (m, 3H), 2.68-2.80 (m, 2H), 2.88-2.98 (m, 3H), 3.46-3.72 (m, 8H), 3.80-4.00 (m, 2H), 4.36 (s, 2H), 4.68-4.70 (m, 2H), 4.96-5.00 (m, 1H), 7.15-7.35 (m, 2H), 7.39 (br s, 1H)

Compound 15-28

$^1$H NMR ($CDCl_3$) d (ppm): 1.10 (t, J=7.2 Hz, 3H), 2.47 (t, J=5.8 Hz, 4H), 2.65 (br t, J=5.2 Hz, 2H), 2.84 (t, J=5.8 Hz, 4H), 3.19-3.27 (m, 2H), 3.34 (s, 2H), 3.60-3.74 (m, 10H), 4.27 (s, 2H), 4.67 (s, 2H), 5.15 (t, J=5.1 Hz, 1H), 5.68 (t, J=5.4 Hz, 1H), 7.10 (dd, J=8.3, 2.0 Hz, 1H), 7.24 (d, J=8.3 Hz, 1H), 7.33 (d, J=2.0 Hz; 1H)

Compound 15-29

$^1$H NMR ($CDCl_3$) d (ppm): 1.16 (t, J=7.2 Hz, 3H), 1.47-1.90 (m, 6H), 2.25 (s, 3H), 2.67 (t, J=5.7 Hz, 2H), 2.81-3.15 (m, 2H), 3.26-3.35 (m, 2H), 3.55 (t, J=5.8 Hz, 2H), 3.62-3.82 (m, 8H), 3.84-4.02 (m, 1H), 4.21 (s, 2H), 4.50-4.60 (m, 1H), 4.70 (d, J=5.6 Hz, 2H), 4.87-4.95 (m, 1H), 7.18 (dd, J=8.4, 1.9 Hz, 1H), 7.28 (d, J=8.4 Hz, 1H), 7.39 (d, J=1.9 Hz, 1H)

Compound 15-30

$^1$H NMR ($CDCl_3$) d (ppm): 1.15 (t, J=7.2 Hz, 3H), 1.74-2.12 (m, 6H), 2.34 (s, 3H), 2.46-2.53 (m, 1H), 2.67 (t, J=5.8 Hz, 2H), 2.94-3.01 (m, 2H), 3.24-3.34 (m, 2H), 3.46-3.70 (m, 10H), 4.22 (s, 2H), 4.61 (t, J=5.3 Hz, 1H), 4.70 (d, J=5.7 Hz, 2H), 5.00 (t, J=5.7 Hz, 1H), 7.16 (dd, J=8.3, 2.1 Hz, 1H), 7.27 (d, J=8.3 Hz, 1H), 7.38 (d, J=2.1 Hz, 1H)

Compound 15-31

$^1$H NMR ($CDCl_3$) d (ppm): 1.15 (t, J=7.2 Hz, 3H), 1.76-2.34 (m, 4H), 2.37 (s, 3H), 2.67 (t, J=5.7 Hz, 2H), 3.12-3.34 (m, 4H), 3.54-3.80 (m, 11H), 4.23 (s, 2H), 4.61-4.65 (m, 1H), 4.69 (d, J=5.8 Hz, 2H), 5.02-5.06 (m, 1H), 7.16 (dd, J=8.3, 2.2 Hz, 1H), 7.27 (d, J=8.3 Hz, 1H), 7.38 (d, J=2.2 Hz, 1H)

Compound 15-32

$^1$H NMR ($CDCl_3$) d (ppm): 0.77-0.84 (m, 2H), 1.00 (br s, 2H), 1.75-1.90 (m, 1H), 2.25 (td, J=11.6, 3.5 Hz, 1H), 2.37 (s, 3H), 2.41-2.47 (m, 1H), 2.57-2.81 (m, 3H), 2.90 (d, J=12.1 Hz, 1H), 3.38-4.02 (m, 12H), 4.28 (dd, J=10.0, 2.4 Hz, 1H), 4.37 (br s, 2H), 4.69-4.70 (m, 2H), 5.02-5.06 (m, 1H), 7.13-7.27 (m, 2H), 7.39 (br s, 1H)

Compound 15-33

$^1$H NMR ($CDCl_3$) d (ppm): 0.77-0.84 (m, 2H), 0.99 (br s, 2H), 1.77-2.30 (m, 5H), 2.36 (s, 3H), 2.57-2.90 (m, 2H), 3.07-3.19 (m, 2H), 3.55-3.92 (m, 11H), 4.39 (br s, 2H), 4.68-4.70 (m, 2H), 5.18-5.22 (m, 1H), 7.12 (br d, J=8.0 Hz, 1H), 7.24 (br d, J=8.0 Hz, 1H), 7.37 (br s, 1H)

Compound 15-34

$^1$H NMR ($CDCl_3$) d (ppm): 1.15 (t, J=7.3 Hz, 3H), 1.45-1.81 (m, 4H), 1.99 (br t, J=11.2 Hz, 1H), 2.22 (br t, J=11.2 Hz, 1H), 2.35 (s, 3H), 2.67 (t, J=5.8 Hz; 2H), 2.83-2.93 (m, 3H), 3.24-3.34 (m, 2H), 3.50-3.71 (m, 10H), 4.22 (s, 2H), 4.61 (t, J=5.3 Hz, 1H), 4.69 (d, J=5.7 Hz, 2H), 5.01 (t, J=5.7 Hz, 1H), 7.21 (dd, J=8.3, 2.0 Hz, 1H), 7.27 (d, J=8.3 Hz, 1H), 7.38 (d, J=2.0 Hz, 1H)

Compound 15-35

$^1$H NMR ($CDCl_3$) d (ppm): 1.17 (t, J=7.2 Hz, 3H), 2.24 (td, J=11.5, 3.4 Hz, 1H), 2.36 (s, 3H), 2.41 (d, J=11.8 Hz, 1H), 2.66-2.69 (m, 3H), 2.89 (br d, J=11.8 Hz, 1H), 3.27-3.36 (m, 2H), 3.40-3.88 (m, 11H, 3.55 (t, J=5.7 Hz, 2H) を含む, 3.93-3.98 (m, 1H), 4.21 (s, 2H), 4.22-4.34 (m, 1H), 4.51 (br t, J=5.2 Hz, 1H), 4.70 (d, J=5.9 Hz, 2H), 4.85 (br t, J=5.9 Hz, 1H), 7.18 (dd, J=8.3, 2.1 Hz, 1H), 7.29 (d, J=8.3 Hz, 1H), 7.39 (d, J=2.1 Hz, 1H)

Compound 15-36

$^1$H NMR ($CDCl_3$) d (ppm): 0.77-0.84 (m, 2H), 0.98-1.04 (m, 2H), 1.78-1.85 (m, 1H), 1.81 (dd, J=10.8, 10.8 Hz, 1H), 2.11 (ddd, J=11.5, 11.5, 3.5 Hz, 1H), 2.27-2.32 (m, 1H), 2.30 (s, 3H), 2.47 (t, J=4.9 Hz, 4H), 2.55(dd, J=13.0, 7.4 Hz, 1H), 2.62-2.67 (m, 2H), 2.70-2.80 (m, 2H), 3.64-3.78 (m, 6H), 3.87-3.92 (m, 3H), 4.33 (s, 2H), 4.70 (d, J=5.0 Hz, 2H), 4.78-4.82 (br m, 1H), 7.16 (dd, J=8.1, 1.8 Hz; 1H), 7.28 (d, J=8.4 Hz, 1H), 7.37 (d, J=1.6 Hz, 1H)

Compound 15-39

$^1$H NMR ($CDCl_3$) d (ppm): 1.17 (d, J=6.4 Hz, 6H), 1.78-1.98 (m, 1H), 2.02-2.21 (m, 1H), 2.24-2.40 (m, 4H), 2.42-2.87 (m, 9H), 3.51 (t, J=5.8 Hz, 2H), 3.60-4.02 (m, 8H), 4.17 (s, 2H), 4.25-4.37 (m, 1H), 4.70 (d, J=5.6 Hz, 2H), 4.75-4.92, (m, 1H), 7.16 (dd, J=2.0, 8.2 Hz, 1H), 7.30 (d, J=8.2 Hz, 1H), 7.37 (d, J=2.0 Hz, 1H)

Compound 15-40

$^1$H NMR ($CDCl_3$) d (ppm): 1.79-1.95 (m, 1H), 2.06-2.85 (m, 14H), 3.43-3.95 (m, 9H), 4.21 (s, 2H), 4.66 (d, J=5.4 Hz, 2H), 4.86 (s, 2H), 5.17-5.30 (m, 1H), 7.13 (dd, J=1.9, 8.4 Hz, 1H), 7.27 (d, J=8.4 Hz, 1H), 7.34 (d, J=1.9 Hz, 1H)

Compound 15-41

$^1$H NMR ($CDCl_3$) d (ppm): 1.72-1.95 (m, 1H), 2.03-2.90 (m, 14H), 3.56-3.98(m, 9H), 4.29(s, 2H), 4.55-4.74(m, 2H), 4.79-5.00 (m, 1H), 6.46-6.68 (m, 1H), 6.97-7.46 (m, 8H)

Compound 15-43

$^1$H NMR ($CDCl_3$) d (ppm): 0.77-0.84 (m, 2H), 0.98-1.04 (m, 2H), 1.80-1.88 (m, 2H), 2.13 (br dt, J=10.8, 3.2 Hz, 1H), 2.27-2.32 (m, 1H), 2.32 (s, 3H), 2.49-2.59 (m, 5H), 2.67-2.82 (m, 4H), 3.64-3.79 (m, 6H), 3.88-3.93 (m, 3H), 4.34 (s, 2H), 4.69 (d, J=3.8 Hz, 2H), 4.88 (br s, 1H), 7.16 (dd, J=8.1, 1.8 Hz, 1H), 7.28 (d, J=8.4 Hz, 1H), 7.37 (d, J=1.6 Hz, 1H)

Compound 15-44

$^1$H NMR ($CDCl_3$) d (ppm): 1.16 (t, J=7.3 Hz, 3H), 1.81 (t, J=10.8 Hz, 1H), 2.10 (dt, J=10.8, 3.2 Hz, 1H), 2.24-2.36 (m, 1H), 2.29 (s, 3H), 2.45-2.58 (m, 5H), 2.64-2.68 (m, 2H), 2.77 (d, J=11.5 Hz, 1H), 3.26-3.36 (m, 3H), 3.54 (t, J=5.7 Hz, 2H), 3.62-3.75 (m, 6H), 3.90 (dd, J=11.3, 1.9 Hz, 1H), 4.18 (s, 2H), 4.49 (br t, J=3.3 Hz, 1H), 4.69-4.75 (m, 1H), 4.70 (d, J=3.3 Hz, 2H), 7.17 (dd, J=1.9, 8.1 Hz, 1H), 7.32 (d, J=8.4 Hz, 1H), 7.38 (d, J=2.2 Hz, 1H)

Compound 15-45

$^1$H NMR ($CDCl_3$) d (ppm): 1.72-1.92 (m, 1H), 2.02-2.22 (m, 1H), 2.27-2.38 (m, 4H), 2.41-2.85 (m, 9H), 3.46-3.96 (m, 11H), 4.19 (s, 2H), 4.43 (t, J=4.6 Hz, 1H), 4.61 (d, J=4.6 Hz, 1H), 4.65-4.80 (m, 3H), 4.87-5.03 (m, 1H), 7.17 (dd, J=1.6, 8.1 Hz, 1H), 7.31 (d, J=8.1 Hz, 1H), 7.38 (d, J=1.6 Hz, 1H)

Compound 15-46

$^1$H NMR ($CDCl_3$) d (ppm): 0.10-0.27 (m, 2H), 0.40-0.57 (m, 2H), 0.85-1.08 (m, 1H), 1.68-1.90 (m, 1H), 1.99-2.18 (m, 1H), 2.19-2.35 (m, 4H), 2.36-2.84 (m, 9H), 3.10 (dd, J=4.9, 7.0 Hz, 2H), 3.55 (t, J=5.7 Hz, 2H), 3.60-3.92 (m, 7H), 4.19 (s, 2H), 4.55-4.90 (m, 4H), 7.15 (dd, J=1.9, 8.4 Hz, 1H), 7.29 (d, J=8.4 Hz, 1H), 7.36 (d, J=1.9 Hz, 1H)

Compound 15-47

$^1$H NMR ($CDCl_3$) d (ppm): 1.16 (t, J=7.3 Hz, 3H), 1.81 (t, J=10.8 Hz, 1H), 2.10 (dt, J=10.8, 3.2 Hz, 1H), 2.24-2.36 (m, 1H), 2.29 (s, 3H), 2.45-2.58 (m, 5H), 2.64-2.68 (m, 2H), 2.77 (d, J=11.5 Hz, 1H), 3.26-3.36 (m, 3H), 3.54 (t, J=5.7 Hz, 2H), 3.62-3.75 (m, 6H), 3.90 (dd, J=11.3, 1.9 Hz, 1H), 4.18 (s, 2H), 4.49 (br t, J=3.3 Hz, 1H), 4.69-4.75 (m, 1H), 4.70 (d, J=3.3 Hz, 2H), 7.17 (dd, J=1.9, 8.1 Hz, 1H), 7.32 (d, J=8.4 Hz, 1H), 7.38 (d, J=2.2 Hz, 1H)

Compound 15-48

$^1$H NMR ($CDCl_3$) d (ppm): 0.77-0.84 (m, 2H), 0.98-1.04 (m, 2H), 1.80-1.88 (m, 2H), 2.13 (br dt, J=10.8, 3.2 Hz, 1H), 2.27-2.32 (m, 1H), 2.32 (s, 3H), 2.49-2.59 (m, 5H), 2.67-2.82 (m, 4H), 3.64-3.79 (m, 6(H), 3.88-3.93 (m, 3H), 4.34 (s, 2H), 4.69 (d, J=3.8 Hz, 2H), 4.88 (br s, 1H), 7.16 (dd, J=8.1, 1.8 Hz, 1H), 7.28 (d, J=8.4 Hz, 1H), 7.37 (d, J=1.6 Hz, 1H)

Compound 15-49

$^1$H NMR ($CDCl_3$) d (ppm): 1.72-1.89 (m, 1H), 2.00-2.18 (m, 1H), 2.22-2.35 (m, 4H), 2.36-3.00 (m, 15H), 3.41 (t, J=5.7 Hz, 2H), 3.57-4.06 (m, 9H), 4.65-4.87 (m, 3H), 7.17 (dd, J=1.9, 8.4 Hz, 1H), 7.31 (d, J=8.4 Hz, 1H), 7.38 (d, J=1.9 Hz, 1H)

Compound 15-50

$^1$H NMR ($CDCl_3$) d (ppm) 0.38-0.55 (m, 2H), 0.62-0.83 (m, 2H), 1.70-1.97 (m, 1H), 2.00-2.86 (m, 15H), 3.41-3.98 (m, 9H), 4.16 (s, 2H), 4.69 (d, J=5.9 Hz, 2H), 4.75-4.95 (m, 2H), 7.16 (dd, J=2.2, 8.1 Hz, 1H), 7.30 (d, J=8.1 Hz, 1H), 7.37 (d, J=2.2 Hz, 1H)

Compound 15-51

$^1$H NMR ($CDCl_3$) d (ppm): 0.70-0.90 (m, 1H), 2.01-2.87 (m, 15H), 3.47-4.10 (m, 11H), 4.19 (s, 2H), 4.62-4.85 (m, 4H), 7.16 (dd, J=2.2, 8.4 Hz, 1H), 7.31 (d, J=8.4 Hz, 1H), 7.38 (d, J=2.2 Hz, 1H)

Compound 15-52

$^1$H NMR ($CDCl_3$) d (ppm): 0.69-0.89 (m, 1H), 2.00-2.85 (m, 14H), 3.49-3.99 (m, 9H), 4.08-4.28 (m, 4H), 4.68 (d, J=5.4, Hz, 2H), 4.76-4.91 (m, 1H), 5.11-5.30 (m, 1H), 7.15 (dd, J=2.2, 8.4 Hz, 1H), 7.30 (d, J=8.4 Hz, 1H), 7.36 (d, J=2.2 Hz, 1H)

Compound 15-53

$^1$H NMR ($CDCl_3$) d (ppm): 0.72-0.89 (m, 1H), 2.00-2.82 (m, 14H), 3.30-3.98 (m, 16H), 4.18 (s, 2H), 4.65-4.82 (m, 3H), 4.86-5.02 (m, 1H), 7.17 (dd, J=2.0, 8.3 Hz, 1H), 7.32 (d, J=8.3 Hz, 1H), 7.38 (d, J=2.0 Hz, 1H)

Compound 15-54

$^1$H NMR ($CDCl_3$) d (ppm): 0.92 (t, J=7.3 Hz, 3H), 1.54 (dd, J=10.8, 3.2 Hz, 2H), 1.81 (t, J=10.8 Hz, 1H), 2.10 (dt, J=12.2 Hz, 1H), 2.24-2.31 (m, 1H), 2.29 (s, 3H), 2.45-2.55 (m, 5H), 2.58-2.66 (m, 3H), 2.72 (d, J=11.5 Hz, 1H), 3.18-3.25 (m, 2H), 3.54 (t, J=5.7 Hz, 2H), 3.62-3.77 (m, 6H), 3.90 (dd, J=11.3, 1.9 Hz, 1H), 4.19 (s, 2H), 4.58 (br s, 1H), 4.63 (d, J=3.3 Hz, 2H), 4.80 (br s, 1H), 7.16 (dd, J=8.1, 1.9 Hz, 1H), 7.31 (d, J=8.6 Hz, 1H), 7.37 (d, J=1.9 Hz, 1H)

Compound 15-55

$^1$H NMR ($CDCl_3$) d (ppm): 1.25 (t, J=7.2 Hz, 3-H), 1.81 (t, J=10.7 Hz, 1H), 2.11 (td, J=11.4, 3.3 Hz, 1H), 2.25-2.33 (m, 4H, The peak at 2.29 (s, 3H) is involved in this peak), 2.44-2.57 (m, 5H), 7.88 (br d, J=11.5 Hz, 1H), 2.71 (br d, J=5.5 Hz, 2H), 2.77 (br d, J=11.5 Hz, 1H), 3.49-3.55 (m, 2H), 3.62-3.76 (m, 8H), 3.87-3.91 (m, 1H), 4.21 (s, 2H), 4.70 (br d, J=5.1 Hz, 2H), 5.37-5.47 (m, 1H), 5.65-5.76 (m, 1H), 7.14 (dd, J 8.2, 2.0 Hz, 1H), 7.30 (d, J=8.2 Hz, 1H), 7.33 (d, J=2.0 Hz, 1H)

Compound 15-56

$^1$H NMR ($CDCl_3$) d (ppm): 1.29 (t, J=7.2 Hz, 3H), 1.81 (t, J=10.7 Hz, 1H), 2.10 (td, J=3.3, 11.5 Hz, 1H), 2.25-2.30 (m, 4H, The peak at 2.29 (s, 3H) is involved in this peak), 2.46 (br t, J=5.0 Hz, 4H), 2.54 (dd, J=13.0, 7.2 Hz, 1H), 2.65 (br d, J=10.8 Hz, 1H), 2.74-2.81 (m, 3H), 3.33-3.42 (m, 2H), 3.62-3.74 (m, 8H), 3.87-3.92 (m, 1H), 4.23 (s, 2H), 4.71 (d, J=5.3 Hz, 2H), 4.75 (br t, J=5.5 Hz, 1H), 4.88 (br t, J=5.8 Hz, 1H), 7.18 (dd, J=8.4, 2.1 Hz, 1H), 7.30 (d, J=8.4 Hz, 1H), 7.38 (d, J=2.1 Hz, 1H)

Compound 15-57

$^1$H NMR ($CDCl_3$) d (ppm): 1.11 (t, J=7.4 Hz, 3H), 1.83 (t, J=10.6 Hz, 1H), 2.12 (t, J=11.6 Hz, 1H), 2.29 (dd, J=12.4, 4.6 Hz, 1H), 2.44-2.59 (m, 7H), 2.66 (t, J=5.9 Hz, 2H), 2.76-2.89 (m, 2H), 2.84 (d, J=4.0 Hz, 3H), 3.54 (t, J=5.8 Hz, 2H), 3.65-3.85 (m, 6H), 3.93 (dd, J=11.3, 1.9 Hz, 1H), 4.19 (s, 2H), 4.54 (br s, 1H), 4.70 (d, J=5.3 Hz, 2H), 4.77 (br s, 1H), 7.17 (dd, J=8.3, 2.1 Hz, 1H), 7.31 (d, J=8;3 Hz, 1H), 7.38 (d, J=2.1 Hz, 1H)

Compound 15-58

$^1$H NMR ($CDCl_3$) d (ppm): 0.95-0.99 (m, 2H), 1.10-1.14 (m, 2H), 1.81 (t, J=10.7 Hz, 1H), 2.11 (td, J=11.4, 3.3 Hz, 1H), 2.23-2.35 (m, 4H, The peak at 2.29 (s, 3H) is involved in this peak), 2.45 (br t, J=4.8 Hz, 4H), 2.54 (dd, J=12.8, 7.2 Hz, 1H), 2.64-2.78 (m, 4H), 3.65 (td, J=11.6, 2.4 Hz, 2H), 3.71-3.74 (m, 4H), 3.88-3.95 (m, 3H), 4.10-4.43 (m, 2H), 4.69 (d, J=5.7 Hz, 2H), 4.90-4.98 (m, 1H), 7.15 (dd, J=8.3, 1.8 Hz, 1H), 7.30 (d, J=8.3 Hz, 1H), 7.36 (d, J=1.8 Hz, 1H)

Compound 15-59

$^1$H NMR ($CDCl_3$) d (ppm): 0.92 (t, J=7.3 Hz, 3H), 1.54 (dd, J=10.8, 3.2 Hz, 2H), 1.81 (t, J=10.8 Hz, 1H)—, 2.10 (dt, J=12.2 Hz, 1H), 2.24-2.31 (m, 1H), 2.29 (s, 3H), 2.45-2.55 (m, 5H), 2.58-2.66 (m, 3H), 2.72 (d, J=11.5 Hz, 1H), 3.18-3.25 (m, 2H), 3.54 (t, J=5.7 Hz, 2H), 3.62-3.77 (m, 6H), 3.90 (dd, J=11.3, 1.9 Hz, 1H), 4.19 (s, 2H), 4.58 (br s, 1H), 4.63 (d, J=3.3 Hz, 2H), 4.80 (br s, 1H), 7.16 (dd, J=8.1, 1.9 Hz, 1H), 7.31 (d, J=8.6 Hz, 1H), 7.37 (d, J=1.9 Hz, 1H)

Compound 15-60

$^1$H NMR ($CDCl_3$) d (ppm): 1.09-1.19 (m, 6H), 1.84 (t, J=10.3 Hz, 1H), 2.12 (dt, J=11.4, 3.7 Hz, 1H), 2.28 (dd, J=12.8, 4.4 Hz, 1H), 2.48-2.59 (m, 7H), 2.67 (t, J=5.4 Hz, 2H), 2.83 (dd, J=27.3, 10.8 Hz, 2H), 3.28-3.33 (m, 2H), 3.54 (t, J=5.1 Hz, 2H), 3.66-3.85 (m, 6H), 3.92 (dd, J=11.3, 1.9 Hz, 1H), 4.18 (s, 2H), 4.49 (br s, 1H), 4.70 (d, J=3.3 Hz, 2H), 4.75 (br s, 1H), 7.17 (dd, J=8.1, 2.2 Hz, 1H), 7.31 (d, J=8.3 Hz, 1H), 7.38 (d, J=2.0 Hz, 1H)

Compound 15-61

$^1$H NMR ($CDCl_3$) d (ppm): 1.50 (s, 6H), 1.80 (t, J=10.8 Hz, 1H), 2.10 (td, J=11.5, 3.2 Hz, 1H), 2.23-2.28 (m, 4H, The peak at 2.28 (s, 3H) is involved in this peak), 2.44-2.47 (m, 4H), 2.53 (dd, J=12.9, 7.2 Hz, 1H), 2.63-2.66 (m, 2H), 2.76 (br d, J=11.2 Hz, 2H), 3.61-3.73 (m, 6H), 3.88-3.91 (m, 3H), 4.18-4.50 (m, 2H), 4.69 (br d, J=5.5 Hz, 2H), 5.02-5.17 (m, 1H), 7.11 (br dd, J=8.3, 2.0 Hz, 1H), 7.27 (d, J=9.9 Hz, 1H), 7.34 (br d, J=2.0 Hz, 1H)

Compound 15-62

$^1$H NMR ($CDCl_3$) d (ppm): 1.15 (t, J=7.3 Hz, 3H), 2.18-2.23 (m, 1H), 2.30-2.57 (m, 7H), 2.35 (s, 3H), 2.64-2.70 (m, 3H), 3.25-3.33 (m, 2H), 3.54 (t, J=5.7 Hz, 2H), 3.60-3.69 (m, 6H), 3.80 (d, J=10.8 Hz, 1H), 3.98 (dd, J=11.6, 3 Hz, 1H), 4.19 (s, 2H), 4.54 (br s, 1H), 4.69 (d, J=5.4 Hz, 2H), 4.83 (br s, 1H), 7.16 (dd, J=8.1, 2.2 Hz, 1H), 7.29 (d, J=8.1 Hz, 1H), 7.37 (d, J=2.2 Hz, 1H)

Compound 15-63

$^1$H NMR ($CDCl_3$) d (ppm): 0.92 (t, J=7.3 Hz, 3H), 1.54 (dd, J=10.8, 3.2 Hz, 2H), 2.21-2.25 (m, 1H), 2.36-2.55 (m, 7H), 2.40 (s, 3H), 2.65-2.69 (m, 3H), 3.18-3.26 (m, 2H), 3.54 (t, J=5.7 Hz, 2H), 3.62-3.69 (m, 6H), 3.80 (d, J=10.8 Hz, 1H), 3.98 (dd, J=11.6, 3 Hz, 1H), 4.20 (s, 2H), 4.59 (br s, 1H), 4.69 (d, J=5.4 Hz, 2H), 4.81 (br s, 1H), 7.17 (dd, J=8.2, 2.2. Hz, 1H), 7.27 (d, J=8.1 Hz, 1H), 7.38 (d, J=2.2 Hz, 1H)

Compound 15-64

$^1$H NMR ($CDCl_3$) d (ppm): 0.77-0.84 (m, 2H), 0.97-1.01 (m, 2H), 1.83-1.85 (m, 1H), 2.16-2.23 (m, 1H), 2.31-2.58 (m, 7H), 2.35 (s, 3H), 2.66-2.73 (m, 3H), 3.29 (t, J=5.7 Hz, 2H), 3.60-4.00 (m, 8H), 4.34 (s, 2H), 4.69 (s, 2H), 4.82 (br s, 1H), 7.16 (dd, J=8.2, 1.9 Hz, 1H), 7.29 (d, J=8.1 Hz, 1H), 7.37 (d, J=2.2 Hz, 1H)

Compound 15-65

$^1$H NMR ($CDCl_3$) d (ppm): 0.83-0.86 (m, 2H), 0.94 (br s, 2H), 1.80-1.92(m, 5H), 2.54-2.66(m, 4H), 2.72-2.74(m, 4H), 3.54-4.00 (m, 12H), 4.34 (s, 2H), 4.51 (br s, 1H), 4.67 (s, 2H), 6.00 (br s, 1H), 7.18-7.25 (m, 2H), 7.37 (d, J=1.5 Hz, 1H)

Compound 15-66

$^1$H NMR ($CDCl_3$) d (ppm): 0.76-0.81 (m, 2H), 0.98-1.04 (m, 2H), 1.38-1.65(m, 4H), 1.80-1.86(m, 2H), 2.11-2.17(m, 1H), 2.34-2.48 (m, 6H), 2.63-2.74 (m, 4H), 3.49 (m, 2H), 3.61-3.72 (m, 6H), 3.82-3.89 (m, 3H), 4.33 (s, 2H), 4.67-4.71 (m, 2H), 4.78-4.82 (br m, 1H), 7.17 (dd, J=7.8, 1.8 Hz, 1H), 7.25-7.32 (m, 6H), 7.38 (d, J=1.8 Hz, 1H)

Compound 15-67

$^1$H NMR ($CDCl_3$) d (ppm): 0.71-1.12 (m, 4H), 1.71-1.98 (m, 1H), 2.40-2.82 (m, 8H), 3.20-3.40 (m, 2H), 3.58-4.00 (m, 6H), 4.36 (s, 2H), 4.68-4.95 (m, 3H), 7.10-7.49 (m, 3H)

Compound 15-68

$^1$H NMR ($CDCl_3$) d (ppm): 1.16 (t, J=7.2 Hz, 3H), 2.65 (t, J=5.8 Hz, 2H), 2.84-2.88 (m, 4H), 3.25-3.34 (m, 2H), 3.55 (t, J=5.8 Hz, 2H), 3.66-3.70 (m, 4H), 4.20 (s, 2H), 4.56 (t, J=5.1 Hz, 1H), 4.70 (d, J=5.7 Hz, 2H), 4.87 (t, J=5.7 Hz, 1H), 7.16 (dd, J=8.2, 2.0 Hz, 1H), 7.30 (d, J=8.2 Hz, 1H), 7.37 (d, J=2.0 Hz, 1H)

Compound 15-69

$^1$H NMR ($CDCl_3$) d (ppm): 0.77-0.84 (m, 2H), 0.99-1.05 (m, 2H), 1.75-1.89 (m, 1H), 2.48 (br t, J=4.8 Hz, 4H), 2.61 (t, J=5.8 Hz, 2H), 2.71-2.75 (m, 2H), 3.49-3.55 (m, 2H), 3.71-3.75 (m, 4H), 3.87-3.91 (m, 2H), 4.34 (s, 2H), 4.70 (br d, J=4.6 Hz, 2H), 4.75-4.85 (m, 1H), 5.70 (br t, J=5.0 Hz, 1H), 6.52 (t, J=4.8 Hz, 1H), 7.20 (d, J=9.2 Hz, 1H), 7.28-7.32 (m, 1H), 7.37-7.38 (m, 1H), 8.28 (d, J=5.0 Hz, 2H)

Compound 15-70

$^1$H NMR ($CDCl_3$) d (ppm): 0.77-0.83 (m, 2H), 0.94-1.03 (m, 2H), 1.79-1.85 (m, 1H), 2.43-2.46 (m, 4H), 2.56 (t, J=6.0 Hz, 2H), 2.71-2.75 (m, 2H), 3.30 (t, J=6.0 Hz, 2H), 3.45 (s, 3H), 3.66-3.73 (m, 4H), 3.73-3.91 (m, 2H), 4.37 (s, 2H), 4.68 (br d, J=4.3 Hz, 2H), 5.18-5.30 (m, 1H), 7.13 (br d, J=8.3 Hz, 1H), 7.26 (br d, J=8.3 Hz, 1H), 7.36 (br s, 1H)

Compound 15-71

$^1$H NMR ($CDCl_3$) d (ppm): 0.77-0.84 (m, 2H), 0.95-1.07 (m, 2H), 1.74-1.88 (m, 1H), 2.35-2.56 (m, 6H), 2.72-2.75 (m, 2H), 2.82 (t, J=6.1 Hz, 2H), 3.70-3.74 (m, 4H), 3.87-3.91 (m, 2H), 4.35 (s, 2H), 4.70 (d, J=5.0 Hz, 2H), 4.84-4.95 (m, 1H), 7.16 (d, J=7.9 Hz, 1H), 7.29 (d, J=7.9 Hz, 1H), 7.37 (s, 1H)

Compound 15-72

$^1$H NMR ($CDCl_3$) d (ppm): 0.81 (m, 2H), 1.01 (m, 2H), 1.82 (m, 1H), 2.46 (m, 4H), 2.6-2.8 (m, 2H), 2.70 (t, J=6.4 Hz, 2H), 3.72 (m, 4H), 3.89 (m, 2H), 4.06 (t, J=6.4 Hz, 2H), 4.37 (br s, 2H), 4.70 (br s, 2H), 5.01 (br s, 1H), 6.99 (t, J=1.1 Hz, 1H), 7.05 (t, J=1.1 Hz, 1H), 7.1-7.4 (m, 3H), 7.56 (t, J=1.1 Hz, 1H)

Compound 15-73

$^1$H NMR ($CDCl_3$) d (ppm): 1.78 (m, 6H), 2.3-2.6 (m, 12H), 2.6-2.8 (m, 6H), 3.6-3.8 (m, 6H), 3.69 (s, 3H), 4.33 (s, 2H), 4.69 (d, J=5.9 Hz, 2H), 4.80 (br t, J=5.9 Hz, 1H), 7.1-7.4 (m, 3H)

Compound 15-74

$^1$H NMR (DMSO-$d_6$) d (ppm): (major peaks) 1.5-1.7 (m, 6H), 2.1-2.7 (m, 18H), 3.48 (m, 4H), 3.70 (m, 1H), 3.8-4.0 (m, 2H), 4.33 (s, 2H), 4.5-4.6 (m, 2H), 7.2-7.6 (m, 3H)

Compound 15-75

$^1$H NMR ($CDCl_3$) d (ppm): 1.22 (m, 2H), 1.48 (m, 2H), 1.78 (m, 6H), 2.3-2.6 (m, 12H), 2.69 (br t, J=5.8 Hz, 2H), 3.72 (m, 4H), 3.83 (t, J=5.8 Hz, 2H), 4.35 (s, 2H), 4.70 (d, J=5.8 Hz, 2H), 4.95 (br t, J=5.8 Hz, 1H), 5.64 (br s, 1H), 5.93 (br s, 1H), 7.1-7.4 (m, 3H)

Compound 15-76

$^1$H NMR ($CDCl_3$) d (ppm): 1.78 (m, 6H), 2.3-2.8 (m, 18H), 3.6-3.8 (m, 6H), 4.32 (s, 2H), 4.69 (d, J=5.8 Hz, 2H), 4.98 (br t, J=5.8 Hz, 1H), 5.54 (br s, 1H), 6.05 (br s, 1H), 7.1-7.4 (m, 3H)

Compound 15-77

$^1$H NMR ($CDCl_3$) d (ppm): 1.6-1.8 (m, 6H), 2.3-2.6 (m, 12H), 2.70 (br t, J=5.4 Hz, 2H), 2.84 (br t, J=5.4 Hz, 2H), 3.21 (s, 2H), 3.34 (s, 2H), 3.6-3.8 (m, 4H), 4.60 (br t, J=5.8 Hz, 1H), 4.69 (d, J=5.8 Hz, 2H), 5.42 (br s, 1H), 7.00 (br s, 1H), 7.1-7.4 (m, 3H)

Compound 15-78

$^1$H NMR ($CDCl_3$) d (ppm): 1.58 (m, 2H), 1.62 (m, 2H), 1.6-1.9 (m, 6H), 2.3-2.6 (m, 12H), 2.91 (m, 2H), 3.74 (m, 4H), 4.01 (m, 2H), 4.29 (br s, 2H), 4.7-4.9 (br, 1H), 4.72 (br s, 2H), 7.17 (dd, J=8.2, 2.0 Hz, 1H), 7.31 (d, J=8.2 Hz, 1H), 7.38 (d, J=2.0 Hz, 1H)

Compound 15-79

$^1$H NMR ($CDCl_3$) d (ppm): (major peaks) 0.94 (m, 2H), 1.09 (m, 2H), 1.6-1.9 (m, 6H), 2.3-2.6 (m, 12H), 2.69 (m, 2H), 3.69 (m, 4H), 3.94 (m, 2H), 4.31 (br s, 2H), 4.68 (d, J=6.8 Hz, 2H), 5.01 (br t; J=7 Hz, 1H), 7.13 (dd, J=8.4, 2.1 Hz, 1H), 7.29 (d, J=8.4 Hz, 1H), 7.35 (d, J=2.1 Hz, 1H)

Compound 15-81

$^1$H NMR ($CDCl_3$) d (ppm): 0.80 (m, 2H), 1.01 (m, 2H), 1.6-1.9 (m, 3H), 2.3-2.5 (m, 12H), 2.73 (m, 2H), 3.6-3.8 (m, 8H), 3.87 (m, 2H), 4.35 (s, 2H), 4.70 (br d, J=4.9 Hz, 2H), 4.87 (br s, 1H), 7.1-7.4 (m, 3H)

Compound 15-82

$^1$H NMR ($CDCl_3$) d (ppm): 0.78-0.86 (m, 2H), 0.99-1.06 (m, 2H), 1.72-1.92 (m, 5H), 2.08-2.19 (m, 3H), 2.65-2.77 (m, 2H), 2.91-2.98 (m, 2H), 3.20 (s, 2H), 3.61 (m, 4H), 3.71 (m, 4H), 3.89 (m, 2H), 4.36 (s, 2H), 4.71 (d, J=5.5 Hz, 2H), 4.88 (br s, 1H), 5.30 (br s, 1H), 5.45 (br s, 1H), 7.15-7.41 (m, 3H)

Compound 16-1

$^1$H-NMR ($CDCl_3$) d (ppm): 0.78-0.84 (m, 2H), 1.02 (br s, 2H), 1.75-1.85 (m, 2H), 2.03-2.17 (m, 1H), 2.59-2.76 (m, 6H), 2.89-2.94 (m, 1H), 3.28 (s, 3H), 3.36 (s, 2H), 3.58-3.64 (m, 4H), 3.73 (br s, 4H), 3.90-3.97 (m, 2H), 4.34 (br s, 2H), 4.71 (br s, 2H), 4.79 (br s, 1H), 6.90-6.96 (m, 1H), 7.12-7.14 (m, 1H), 7.22-7.35 (m, 1H)

Compound 16-2

$^1$H-NMR ($CDCl_3$) d (ppm): 0.78-0.84 (m, 2H), 1.01 (br s, 2H), 1.82-2.01 (m, 5H), 2.40-2.46 (m, 2H), 2.63-2.74 (m, 5H), 3.22 (s, 2H), 3.56-3.61(m, 4H), 3.72 (br s, 4H), 3.89-3.91 (m, 2H), 4.36 (br s, 2H), 4.70 (d, J=5.4 Hz, 2H), 4.94 (br s, 1H), 6.89-6.94 (m, 1H), 7.13 (dd, J=2.4, 8.1 Hz, 1H), 7.29-7.34 (m, 1H)

Compound 16-3

$^1$H-NMR ($CDCl_3$) d (ppm): 0.78-0.85 (m, 2H), 1.02 (br s, 2H), 1.83 (br s, 1H), 2.08-2.16 (m, 1H), 2.41 (s, 3H), 2.49 (q, J=8.4 Hz, 1H), 2.64-2.75 (m, 4H), 2.83-2.90 (m, 1H), 3.00 (t, J=8.7 Hz, 1H), 3.29 (quintet, J=7.5 Hz, 1H), 3.47-3.51 (m, 2H), 3.64-3.66 (m, 2H), 3.73 (br s, 4H), 3.90 (br s, 2H), 4.34 (br s, 2H), 4.70 (d, J=4.8 Hz, 2H), 4.84 (br s, 1H), 6.84-6.95 (m, 1H), 7.14 (dd, J=2.7, 8.4 Hz, 1H), 7.29-7.35 (m, 1H)

Compound 16-4

$^1$H-NMR ($CDCl_3$) d (ppm) 0.77-0.84 (m, 2H), 1.01 (br s, 2H), 1.74 (br s, 1H), 2.10 (quintet, J=7.0 Hz, 2H), 2.74 (br s, 2H), 3.30 (d, J=6.2 Hz, 4H), 3.34 (s, 2H), 3.50-3.61 (m, 4H), 3.73 (br s, 4H), 3.90 (br s, 2H), 4.35 (br s, 2H), 4.69 (d, J=5.9 Hz, 2H), 4.88 (br s, 1H), 6.89-6.94 (m, 1H), 7.13 (dd, J=2.4, 8.4 Hz, 1H), 7.29-7.34 (m, 1H)

Compound 16-7

$^1$H NMR ($CDCl_3$) d (ppm): 1.16 (t, J=7.3 Hz, 3H), 1.88 (t, J=10.8 Hz, 1H), 2.17 (dt, J=3.2, 10.8 Hz, 1H), 2.24-2.36 (m, 1H), 2.31 (s, 3H), 2.50-2.59 (m, 5H), 2.64-2.68 (m, 3H), 2.80 (d, J=11.5 Hz, 1H), 3.25-3.35 (m, 2H), 3.54 (t, J=5.7 Hz, 2H), 3.63-3.75 (m, 6H), 3.90 (dd, J=11.3, 1.9 Hz, 1H), 4.17 (s, 2H), 4.49 (br s, 1H), 4.71 (br s, 1H), 4.71 (s, 2H), 6.92 (dt, J=8.4, 2.7 Hz, 1H), 7.11 (dd, J=8.4, 2.4 Hz, 1H), 7.36 (dd, J=2.7, 2.3 Hz, 1H)

Compound 16-8

$^1$H NMR ($CDCl_3$) d (ppm): 0.93 (t, J=7.3 Hz, 3H), 1.54 (dd, J=10.8, 3.2 Hz, 2H), 1.86 (t, J=10.8 Hz, 1H), 2.15 (t, J=12.2 Hz, 1H), 2.24-2.36 (m, 1H), 2.33 (s, 3H), 2.51-2.60 (m, 5H), 2.65-2.69 (m, 3H), 2.76 (d, J=11.5 Hz, 1H), 3.21-3.26 (m, 2H), 3.54 (t, J=5.7 Hz, 2H), 3.64-3.76 (m, 6H), 3.91 (dd, J=11.3, 1.9 Hz, 1H), 4.18 (s, 2H), 4.55 (br s, 1H), 4.70 (d, J=3.3 Hz, 2H), 4.75 (br s, 1H), 6.91 (dt, J=8.4, 2.7 Hz, 1H), 7.11 (dd, J=8.4, 2.4 Hz, 1H), 7.36 (dd, J=2.7, 2.3 Hz, 1H)

Compound 16-9

$^1$H NMR ($CDCl_3$) d (ppm): 1.16 (t, J=7.3 Hz, 3H), 1.88 (t, J=10.8 Hz, 1H), 2.17 (dt, J=3.2, 10.8 Hz, 1H), 2.24-2.36 (m, 1H), 2.31 (s, 3H), 2.50-2.59 (m, 5H), 2.64-2.68 (m, 3H), 2.80 (d, J=11.5 Hz, 1H), 3.25-3.35 (m, 2H), 3.54 (t, J=5.7 Hz, 2H), 3.63-3.75 (m, 6H), 3.90 (dd, J=11.3, 1.9 Hz, 1H), 4.17 (s, 2H), 4.49 (br s, 1H), 4.71 (br s, 1H), 4.71 (s, 2H), 6.92 (dt, J=2.7, 8.4 Hz, 1H), 7.11 (dd, J=8.4, 2.4 Hz, 1H), 7.36 (dd, J=2.7, 2.3 Hz, 1H)

Compound 16-10

$^1$H NMR ($CDCl_3$) d (ppm): 0.93 (t, J=7.3 Hz, 3H), 1.54 (dd, J=10.8, 3.2 Hz, 2H), 1.86 (t, J=10.8 Hz, 1H), 2.15 (t, J=12.2 Hz, 1H), 2.24-2.36 (m, 1H), 2.33 (s, 3H), 2.51-2.60 (m, 5H), 2.65-2.69 (m, 3H), 2.76 (d, J=11.5 Hz, 1H), 3.21-3.26 (m, 2H), 3.54 (t, J=5.7 Hz, 2H), 3.64-3.76 (m, 6H), 3.91 (dd, J=11.3, 1.9 Hz, 1H), 4.18 (s, 2H), 4.55 (br s, 1H), 4.70 (d, J=3.3 Hz, 2H), 4.75 (br s, 1H), 6.91 (dt, J=8.4, 2.7 Hz, 1H), 7.11 (dd, J=8.4, 2.4 Hz, 1H), 7.36 (dd, J=2.7, 2.3 Hz, 1H)

Compound 16-11

$^1$H NMR ($CDCl_3$) d (ppm): 1.09 (t, J=7.3 Hz, 3H), 1.80 (t, J=10.3 Hz, 1H), 2.08 (dt, J=11.4, 3.7 Hz, 1H), 2.28 (dd, J=12.8, 4.4 Hz, 1H), 2.40-2.52 (m, 7H), 2.66 (t, J=5.5 Hz, 2H), 2.75 (d, J=9.9 Hz, 1H), 2.81-2.87 (m, 1H), 2.85 (d, J=4.6 Hz, 3H), 3.54 (t, J=5.5 Hz, 2H), 3.67-3.8.1 (m, 6H), 3.92 (dd, J=11.4, 2.2 Hz, 1H), 4.17 (s, 2H), 4.49 (br s, 1H), 4.70 (s, 2H), 4.70 (br s, 1H), 6.92 (dt, J=8.1, 2.8 Hz, 1H), 7.12 (dd, J=8.3, 2.6 Hz, 1H), 7.37 (dd, J=8.6, 6.2 Hz, 1H)

Compound 16-12

$^1$H NMR ($CDCl_3$) d (ppm): 1.07-1.19 (m, 6H), 1.80 (t, J=10.3 Hz, 1H), 2.08 (dt, J=11.7, 3.1 Hz, 1H), 2.28 (dd, J=12.8, 3.9 Hz, 1H), 2.40-2.52 (m, 7H), 2.67 (t, J=5.3 Hz, 2H), 2.79 (dd, J=27.3, 10.8 Hz, 2H), 3.26-3.36 (m, 2H), 3.54 (t, J=5.7 Hz, 2H), 3.64-3.81(m, 6H), 3.92 (dd, J=11.6, 1.8 Hz, 1H), 4.17 (s, 2H), 4.47 (br s, 1H), 4.70 (d, J=3.3 Hz, 2H), 4.70 (br s, 1H), 6.92 (dt, J=8.6, 2.8 Hz, 1H), 7.12 (dd, J=8.6, 2.9 Hz, 1H), 7.37 (dd, J=8.6, 5.9 Hz, 1H)

Compound 16-13

$^1$H NMR ($CDCl_3$) d (ppm) 0.93 (t, J=7.7 Hz, 3H), 1.54 (dt, J=14.7, 7.3 Hz, 2H), 1.86 (br s, 1H), 2.25 (dd, J=12.8, 4.4 Hz, 1H), 2.45-2.60(m, 6H), 2.66(t, J=5.5 Hz, 2H), 2.79-2.95 (m, 3H), 3.19-3.25 (m, 2H), 3.52-3.76 (m, 8H), 3.89 (d, J=11.4 Hz, 1H), 4.18 (s, 2H), 4.57 (br s, 1H), 4.70 (d, J=5.1 Hz, 2H), 4.78 (br s, 1H), 6.91 (dt, J=8.1, 2.6 Hz, 1H), 7.11 (dd, J=8.8, 2.6 Hz, 1H), 7.36 (dd, J=8.4, 6.2 Hz, 1H)

Compound 16-14

$^1$H NMR ($CDCl_3$) d (ppm): 0.93 (t, J=7.7 Hz, 3H), 1.54 (dt, J=14.7, 7.7 Hz, 2H), 1.88 (t, J=10.4 Hz, 1H), 2.20-2.27 (m, 2H), 2.42-2.58 (m, 5. H), 2.66 (t, J=5.1 Hz, 2H), 2.64-2.78 (m, 2H), 3.18-3.26 (m, 2H), 3.50-3.56 (m, 4H), 3.62-3.90 (m, 7H), 4.18 (s, 2H), 4.56 (br s, 1H), 4.70 (d, J=4.3 Hz, 2H), 4.74 (br s, 1H), 6.91 (dt, J=8.6, 2.6 Hz, 1H), 7.12 (dd, J=8.4, 2.6 Hz, 1H), 7.28-7.38 (m, 6H)

Compound 16-15

$^1$H NMR ($CDCl_3$) d (ppm) 0.71-0.92 (m, 2H), 1.00-1.08 (m, 2H), 1.71-1.97 (m, 5H), 2.23-2.91 (m, 14H), 3.68-4.03 (m, 7H), 4.25-4.46 (m, 2H), 4.65-4.93 (m, 3H), 6.82-7.02 (m, 1H), 7.07-7.22 (m, 1H), 7.25-7.51 (m, 1H)

Compound 17-1

$^1$H NMR ($CDCl_3$) d (ppm): 1.08-1.48 (m, 2H), 1.15 (t, J=7.2 Hz, 3H), 1.26-1.68 (m, 5H), 1.85-1.94 (m, 4H), 2.63-2.80 (m, 10H), 3.25-3.35 (m, 2H), 3.55 (t, J=5.8 Hz, 2H), 4.19 (s, 2H), 4.61-4.70 (m, 5H), 4.90 (br t, 1H), 7.16 (dd, J=8.2, 1.6 Hz, 1H), 7.31 (d, J=8.4 Hz, 1H), 7.36 (d, J=1.8 Hz, 1H)

Compound 17-2

$^1$H NMR ($CDCl_3$) d (ppm): (major peaks) 0.96 (m, 2H), 1.11 (m, 2H), 1.4-1.8 (m, 11H), 2.4-2.5 (m, 6H), 2.6-2.8 (m, 4H), 3.94 (m, 2H), 4.32 (br s, 2H), 4.6-4.8 (m, 2H), 4.68 (d, J=5.8 Hz, 2H), 4.95 (t, J=5.8 Hz, 1H), 7.14 (dd, J=8.3, 2.1 Hz, 1H), 7.31 (d, J=8.3 Hz, 1H), 7.35 (d, J=2.1 Hz, 1H)

Compound 17-3

$^1$H-NMR ($CDCl_3$) d (ppm): 1.05-1.13 (m, 2H), 1.17 (t, J=7.2 Hz, 3H), 1.42-1.47 (m, 2H), 1.59-1.73 (m, 5H), 1.95 (s, 3H), 2.13-2.31 (m, 3H), 2.42-2.49 (m, 2H), 2.63-2.77 (m, 4H), 2.90-2.97 (m, 1H), 3.27-3.36 (m, 2H), 3.54 (t, J=6.0 Hz, 2H), 4.18 (s, 2H), 4.43-4.49 (m, 2H), 4.62-4.74 (m, 5H), 5.92 (br s, 1H), 7.17 (dd, J=2.0, 8.4 Hz, 1H), 7.32 (d, J=8.4 Hz, 1H), 7.38 (d, J=2.0 Hz, 1H)

Compound 17-4

$^1$H-NMR ($CDCl_3$) d (ppm): 1.03 (t, J=7.2 Hz, 6H), 1.07-1.17 (m, 5H), 1.38-1.43 (m, 1H), 1.67-1.89 (m, 4H), 2.46-2.58 (m, 6H), 2.64-2.78 (m, 4H), 3.27-3.35 (m, 2H), 3.54 (t, J=5.7 Hz, 2H), 4.18 (s, 2H), 4.47-4.50 (m, 1H), 4.61-4.73 (m, 5H), 7.17 (dd, J=2.1, 7.2 Hz, 1H), 7.33 (d, J=7.2 Hz, 1H), 7.38 (d, J=2.1 Hz, 1H)

Compound 17-5

$^1$H-NMR ($CDCl_3$) d (ppm): 1.05-1.13 (m, 2H), 1.17 (t, J=7.2 Hz, 3H), 1.44-1.49 (m, 2H), 1.64-1.70 (m, 4H), 1.73-1.85 (m, 1H), 1.73-1.85 (m, 1H), 2.43-2.77 (m, 10H), 3.26-3.36 (m, 5H), 3.54 (t, J=5.9 Hz, 2H), 3.87-3.96 (m, 1H), 4.18 (s, 2H), 4.47-4.50 (m, 1H), 4.61-4.65 (m, 2H), 4.69-4.72 (m, 3H), 7.17 (dd, J=2.2, 8.4 Hz, 1H), 7.33 (d, J=7.8 Hz, 1H), 7.38 (d, J=2.2 Hz, 1H)

Compound 17-6

$^1$H-NMR ($CDCl_3$) d (ppm): 0.77-0.84 (m, 2H), 1.02 (br s, 2H), 1.09-1.17 (m, 2H), 1.45-1.50 (m, 2H), 1.66-1.70 (m, 4H), 1.83 (br s, 1H), 2.47-2.78 (m, 10H), 3.29 (s, 3H), 3.87-3.96 (m, 4H), 4.33 (br s, 2H), 4.61-4.65 (m, 2H), 4.69 (d, J=5.1 Hz, 2H), 4.79 (br s, 1H), 7.16 (d, J=7.8 Hz, 1H), 7.30-7.33 (m, 1H), 7.37 (br s, 1H)

Compound 17-7

$^1$H-NMR ($CDCl_3$) d (ppm): 0.10-0.15 (m, 2H), 0.46-0.51 (m, 2H), 1.15 (t, J=7.2 Hz, 3H), 1.25-1.91 (m, 8H), 2.48 (d, J=6.9 Hz, 2H), 2.64-2.78 (m, 7H), 3.25-3.34 (m, 2H), 3.53-3.56 (m, 2H), 4.19 (s, 2H), 4.58-4.72 (m, 5H), 4.90-4.94 (m, 1H), 7.14 (dd, J=2.1, 8.1 Hz, 1H), 7.31 (d, J=8.1 Hz, 1H), 7.36 (d, J=2.1 Hz, 1H)

Compound 17-8

$^1$H NMR ($CDCl_3$) d (ppm):(major peaks) 0.96 (m, 2H), 1.11 (m, 2H), 1.4-1.8 (m, 11H), 2.4-2.5 (m, 6H), 2.6-2.8 (m, 4H), 3.94 (m, 2H), 4.31 (br s, 2H), 4.6-4.8 (m, 2H), 4.68 (d, J=5.8 Hz, 2H), 4.86 (t, J=5.8 Hz, 1H), 6.89 (dt, J=8.1, 2.6 Hz, 1H), 7.09 (dd, J=8.4, 2.6 Hz, 1H), 7.36 (dd, J=8.6, 6.1 Hz, 1H)

Compound 18-1

$^1$H-NMR ($CDCl_3$) d (ppm): 0.77-0.84 (m, 2H), 1.01 (br s, 2H), 1.35-1.45 (m, 2H), 1.57-1.82 (m, 10H), 2.00 (br, s, 1H), 2.59 (br s, 5H), 2.73-2.78 (m, 4H), 3.28-3.37 (m, 2H), 3.89 (br s, 2H), 4.30-4.45 (br s, 3H), 4.69 (d, J=5.1 Hz, 1H), 4.82 (br s, 1H), 7.14-7.17 (m, 1H), 7.31-7.37 (m, 2H)

Compound 18-2

$^1$H-NMR ($CDCl_3$) d (ppm): 0.77-0.84 (m, 2H), 1.02 (br s, 2H), 1.34-1.65 (m, 12H), 2.45-2.60 (m, 8H), 2.73 (br s, 2H), 3.30-3.34 (m, 2H), 3.88 (br s, 2H), 4.29-4.34 (m, 4H), 4.71 (br s, 2H), 4.79 (br s, 1H), 7.14-7.18 (m, 1H), 7.31-7.37 (m, 2H)

Compound 18-3

$^1$H-NMR ($CDCl_3$) d (ppm): 0.77-0.84 (m, 2H), 1.02 (br s, 2H), 1.35-1.65 (m, 6H), 1.83 (br s, 1H), 2.54-2.73 (m, 9H), 3.28-3.36 (m, 2H), 3.72 (t, J=4.3 Hz, 4H), 3.89 (br s, 2H), 4.28-4.34 (m, 4H), 4.70 (br s, 2H), 4.81 (br s, 1H), 7.14-7.17 (m, 1H), 7.30-7.33 (m, 1H), 7.37 (br s, 1H)

Compound 18-4

$^1$H-NMR ($CDCl_3$) d (ppm): 0.77-0.83 (m, 2H), 1.01 (br s, 2H), 1.23-1.48 (m, 4H), 1.63-1.81 (m, 5H), 1.97 (s, 3H), 2.34-2.47 (m, 2H), 2.66-2.74 (m, 3H), 2.92 (br s, 2H), 3.05-3.09 (m, 1H), 3.26-3.34 (m, 5H), 3.89 (br s, 2H), 4.30-4.70 (m, 8H), 4.95 (br s, 1H), 6.50 (br s, 1H), 7.14-7.17 (m, 1H), 7.28-7.32 (m, 1H), 7.37 (br s, 1H)

Compound 18-5

$^1$H-NMR ($CDCl_3$) d (ppm): 0.76-0.83 (m, 2H), 1.01 (br s, 2H), 1.21 (t, J=7.3 Hz, 2H), 1.37-1.48 (m, 2H), 1.59-1.78 (m, 9H), 2.62-2.87 (m, 7H), 3.30-3.38 (m, 2H), 3.88 (br s, 2H), 4.33 (br s, 4H), 4.69 (br s, 2H), 4.84 (br s, 1H), 6.88-6.92 (m, 1H), 7.09-7.13 (m, 1H), 7.34-7.39 (m, 1H)

Compound 18-6

$^1$H-NMR ($CDCl_3$) d (ppm): 0.77-0.83 (m, 2H), 1.01 (br s, 2H), 1.36-1.67 (m, 12H), 1.83 (br s, 1H), 2.46-2.73 (m, 8H), 3.32-3.40 (m, 2H), 3.89 (br s, 2H), 4.33-4.36 (m, 4H), 4.71 (br s, 3H), 6.88-6.93 (m, 1H), 7.10-7.13 (m, 1H), 7.35-7.40 (m, 1H)

Compound 18-7

$^1$H-NMR ($CDCl_3$) d (ppm): 0.76-0.83 (m, 2H), 1.00 (br s, 2H), 1.37-1.67 (m, 6H), 1.82 (br s, 1H), 2.55-2.75 (m, 9H), 3.30-3.38 (m, 2H), 3.71-3.74 (m, 4H), 3.88 (br s, 2H), 4.34-4.38 (m, 4H), 4.69 (br s, 2H), 4.95 (br s, 1H), 6.89-6.93 (m, 1H), 7.09-7.13 (m, 1H), 7.33-7.38 (m, 1H)

Compound 18-8

$^1$H-NMR ($CDCl_3$) d (ppm): 0.77-0.84 (m, 2H), 1.01 (br s, 2H), 1.39-1.68 (m, 6H), 1.83 (br, s, 1H), 1.96 (s, 3H), 1.98-2.06 (m, 3H), 2.27-2.34 (m, 2H), 2.78 (br s, 6H), 3.02-3.07 (m, 1H), 3.29-3.37 (m, 2H), 3.89 (br s, 2H), 4.34-4.44 (m, 4H), 4.71 (br s, 2H), 4.86 (br s, 1H), 5.78 (d, J=7.3 Hz, 1H), 6.88-6.92 (m, 1H), 7.11 (dd, J=2.4, 8.4 Hz, 1H), 7.32-7.36 (m, 1H)

Compound 18-9

$^1$H-NMR ($CDCl_3$) d (ppm): 1.16 (t, J=7.3 Hz, 3H), 1.39-1.45 (m, 2H), 1.57-1.77 (m, 8H), 2.04 (br s, 1H), 2.60-2.68 (m, 6H), 2.76-2.81 (m, 2H), 3.25-3.36 (m, 4H), 3.55 (t, J=5.7 Hz, 2H), 4.19 (s, 2H), 4.29-4.34 (m, 2H), 4.56 (br s, 1H), 4.70 (d, J=5.9 Hz, 2H), 4.83 (br s, 1H), 7.14-7.17 (m, 1H), 7.31-7.37 (m, 2H)

Compound 18-10

$^1$H-NMR ($CDCl_3$) d (ppm) 1.16 (t, J=7.3 Hz, 3H), 1.26-1.45 (m, 6H), 1.60-1.65 (m, 6H), 2.02 (br s, 1H), 2.48 (br s, 4H), 2.58-2.68 (m, 4H), 3.25-3.38 (m, 4H), 3.53-3.57 (m, 2H), 4.19 (s, 2H), 4.28-4.33 (br s, 2H), 4.55 (br s, 1H), 4.70 (d, J=5.7 Hz, 2H), 4.83 (br s, 1H), 7.14-7.17 (m, 1H), 7.31-7.37 (m, 2H)

Compound 18-11

$^1$H-NMR ($CDCl_3$) d (ppm) 1.16 (t, J=7.2 Hz, 3H), 1.34-1.43 (m, 2H), 1.57-1.64 (m, 4H), 2.01 (br s, 1H), 2.54 (br s, 4H), 2.64-2.66 (m, 4H), 3.26-3.35 (m, 4H), 3.52-3.57 (m, 2H), 3.70-3.72 (m, 4H), 4.19 (s, 2H), 4.30-4.34 (m, 2H), 4.54 (br s, 1H), 4.70 (d, J=5.7 Hz, 2H), 4.83 (br s, 1H), 7.14-7.17 (m, 1H), 7.26-7.37 (m, 2H)

Compound 18-12

$^1$H-NMR ($CDCl_3$) d (ppm): 1.16 (t, J=7.2 Hz, 3H), 1.35-1.66 (m, 2H), 1.57-1.66 (m, 4H), 1.95 (s, 3H), 2.02 (br s, 1H), 2.26-2.33 (m, 2H), 2.54-2.80 (m, 7H), 3.02-3.06 (m, 1H), 3.23-3.35 (m, 4H), 3.53-3.63 (m, 2H), 4.20 (s, 2H), 4.28-4.32 (m, 2H), 4.44 (br s, 1H), 4.59 (br s, 1H), 4.69 (d, J=6.0 Hz, 2H), 4.88 (br s, 1H), 5.79 (br s, 1H), 7.14-7.17 (m, 1H), 7.27-7.37 (m, 2H)

Compound 18-13

$^1$H-NMR ($CDCl_3$) d (ppm): 1.16 (t, J=7.3 Hz, 3H), 1.36-1.47 (m, 2H), 1.58-1.78 (m, 8H), 2.02 (br s, 1H), 2.61-2.68 (m, 6H), 2.77-2.81 (m, 2H), 3.25-3.38 (m, 4H), 3.54 (t, J=5.7 Hz, 2H), 4.17 (s, 2H), 4.31-4.36 (m, 2H), 4.52 (br s, 1H), 4.70 (d, J=5.4 Hz, 2H), 4.74-4.76 (m, 1H), 6.87-6.94 (m, 1H), 7.09-7.13 (m, 1H), 7.36-7.41 (m, 1H)

Compound 18-14

$^1$H-NMR ($CDCl_3$) d (ppm): 1.16 (t, J=7.2 Hz, 1H), 1.25-1.46 (m, 2H), 1.57-1.66 (m, 10H), 2.02 (br s, 1H), 2.46 (br s, 4H), 2.57-2.68 (m, 4H), 3.25-3.39 (m, 4H), 3.52-3.57 (m, 2H), 4.17 (s, 2H), 4.30-4.35 (m, 2H), 4.53 (br s, 1H), 4.69 (d, J=5.1 Hz, 2H), 4.76 (d, J=5.1 Hz, 1H), 6.87-6.94 (m, 1H), 7.11 (dd, J=2.4, 8.6 Hz, 1H), 7.36-7.41 (m, 1H)

Compound 18-15

$^1$H-NMR ($CDCl_3$) d (ppm): 1.16 (t, J=7.2 Hz, 3H), 1.38-1.48 (m, 2H), 1.58-1.66 (m, 4H), 1.98 (br s, 1H), 2.54 (br s, 4H), 2.66 (br s, 4H), 3.25-3.37 (m, 4H), 3.55 (t, J=6.0 Hz, 2H), 3.70-3.73 (m, 4H), 4.18 (s, 2H), 4.32-4.36 (m, 2H), 4.56 (br s, 1H), 4.69-4.71 (m, 2H), 4.82 (br s, 1H), 6.87-6.93 (m, 1H), 7.11 (dd, J=2.7, 8.1 Hz, 1H), 7.35-7.40 (m, 1H)

Compound 18-16

$^1$H-NMR ($CDCl_3$) d (ppm): 1.16 (t, J=7.2 Hz, 3H), 1.40-1.47 (m, 2H), 1.58-1.68 (m, 6H), 1.96 (s, 3H), 2.02 (br s, 1H), 2.27-2.31 (m, 2H), 2.54-2.82 (m, 7H), 3.01-3.3.10 (m, 1H), 3.25-3.36 (m, 3H), 3.53-3.57 (m, 2H), 4.19 (s, 2H), 4.30-4.34 (m, 2H), 4.44 (br s, 1H), 4.57 (br s, 1H), 4.71-4.81 (m, 2H), 4.83 (br s, 1H), 5.81-5.89 (m, 1H), 6.90-6.94 (m, 1H), 7.11 (dd, J=2.7, 8.4 Hz, 1H), 7.35-7.40 (m, 1H)

Compound 19-1

$^1$H-NMR ($CDCl_3$) d (ppm): 0.77-0.83 (m, 2H), 1.01 (br s, 2H), 1.58-1.87 (m, 9H), 2.01 (br, s 1H), 2.64-2.72 (m, 6H), 3.05 (t, J=13.5 Hz, 2H), 3.10-3.20 (m, 2H), 3.88 (br s, 2H), 4.37 (br s, 2H), 4.57-4.70 (m, 4H), 4.93 (br s, 1H), 7.15 (d, J=8.1 Hz, 1H), 7.28-7.31 (m, 1H), 7.37 (br s, 1H)

Compound 19-2

$^1$H-NMR ($CDCl_3$) d (ppm): 1.16 (t, J=7.2 Hz, 3H), 1.58-1.79 (m, 8H), 2.01 (br s, 1H), 2.65-2.72 (m, 6H), 3.05 (t, J=13.2 Hz, 2H), 3.14-3.18 (m, 2H), 3.25-3.34 (m, 2H), 3.53-3.57 (m, 2H), 4.20 (s, 2H), 4.57-4.61 (m, 3H), 4.68-4.70 (m, 2H), 4.70-4.88 (m, 1H), 7.14-7.17 (m, 1H), 7.29-7.37 (m, 2H)

Compound 19-3

$^1$H-NMR ($CDCl_3$) d (ppm): 0.77-0.83 (m, 2H), 1.01 (br s, 2H), 1.44-1.46 (m, 2H), 1.55-1.72 (m, 8H), 1.82 (br s, 1H), 2.00 (br s, 1H), 2.61-2.73 (m, 6H), 2.85 (t, J=13.2 Hz, 2H), 3.13-3.21 (m, 2H), 3.89 (br s, 2H), 4.36 (br s, 2H), 4.46-4.57 (m, 2H), 4.69 (d, J=5.4 Hz, 2H), 4.91 (br s, 1H), 7.14-7.16 (m, 1H), 7.26-7.37 (m, 2H)

Compound 19-4

$^1$H-NMR ($CDCl_3$) d (ppm): 1.15 (t, J=7.2 Hz, 3H), 1.44-1.72 (m, 10H), 1.98 (br s, 1H), 2.61-2.68 (m, 6H), 2.85 (t, J=13.2 Hz, 2H), 3.13-3.34 (m, 4H), 3.54-3.58 (m, 2H), 4.20 (s, 2H), 4.57-4.61 (m, 3H), 4.69 (d, J=5.4 Hz, 2H), 4.89 (br s, 1H), 7.13-7.17 (m, 1H), 7.29-7.37 (m, 2H)

Compound 20-1

$^1$H NMR ($CDCl_3$) d (ppm): 0.78-0.83 (m, 2H), 0.99-1.06 (m, 2H), 1.50-1.62 (m, 2H), 1.76-1.90 (m, 3H), 1.90-1.98 (m, 4H), 2.54-2.95 (m, 10H), 3.32-3.43 (m, 1H), 3.47-3.58 (m, 1H), 3.82-3.92 (m, 3H), 4.35 (s, 2H), 4.38-4.46 (m, 2H), 4.69-4.74 (m, 2H), 4.77-4.82 (m, 1H), 7.18 (dd, J=8.2, 2.0 Hz, 1H), 7.26 (d, J=8.2 Hz, 1H), 7.38 (d, J=2.0 Hz, 1H)

Compound 20-2

$^1$H NMR ($CDCl_3$) d (ppm): 0.81 (ddd, J=8.0, 4.8, 4.0 Hz, 2H), 0.99-1.05 (m, 2H), 1.75-1.88 (m, 1H), 2.28 (s, 3H), 2.33-2.69 (m, 11H), 2.69-2.77 (m, 2H), 2.87-3.00 (m, 1H), 3.50-3.68 (m, 2H), 3.85-4.00 (m, 3H), 4.33 (s, 2H), 4.39-4.51 (m, 2H), 4.70 (s, 2H), 4.75-4.85 (m, 1H), 6.87-6.96 (m, 1H), 7.12 (dd, J=8.6, 2.7 Hz, 1H), 7.30-7.40 (m, 1H)

Compound 20-3

$^1$H NMR ($CDCl_3$) d (ppm): 0.81 (ddd, J=8.0, 4.8, 4.0 Hz, 2H), 0.96-1.07 (m, 2H), 1.73-1.88(m, 5H), 2.40-2.80(m, 9H), 2.87-3.01 (m, 1H), 3.52-3.68 (m, 2H), 3.80-4.00 (m, 3H), 4.34 (s, 2H), 4.39-4.53 (m, 2H), 4.70 (s, 2H), 4.74-4.81 (m, 1H), 6.87-6.97 (m, 1H), 7.14 (dd, J=8.8, 2.3 Hz, 1H), 7.28-7.40 (m, 1H)

Compound 20-4

$^1$H NMR ($CDCl_3$) d (ppm): 0.81 (ddd, J=7.9, 3.9, 3.9 Hz, 2H), 0.98-1.03(m, 2H), 1.70-2.00(m, 4H), 2.00-2.15(m, 5H), 2.57-2.79 (m, 3H), 2.85-2.98 (m, 1H), 3.05-3.40 (m, 4H) 3.44-3.59 (m, 2H), 3.80-3.95 (m, 3H), 4.33 (s, 2H), 4.39-4.53 (m, 2H), 4.69 (s, 2H), 4.75-4.85 (m, 1H), 6.80-6.98 (m, 1H), 7.13 (dd, J=8.2, 2.3 Hz, 1H), 7.24-7.34 (m, 1H)

Compound 20-5

$^1$H NMR ($CDCl_3$) d (ppm): 1.49 (s, 9H), 1.50-1.60 (m, 2H) 1.75-1.90 (m, 2H), 1.95-2.05 (m, 4H), 2.50-2.65 (m, 3H), 2.80-3.20 (m, 7H), 3.32-3.43 (m, 1H), 3.48-3.58 (m, 1H), 3.60-3.68 (m, 2H), 3.88-3.94 (m, 1H), 4.18 (s, 2H), 4.35-4.43 (m, 2H), 4.70 (s, 3H), 7.19 (dd, J=8.2, 2.0 Hz, 1H), 7.26 (d, J=8.2 Hz, 1H), 7.39 (d, J=2.0 Hz, 1H)

Compound 20-6

$^1$H NMR ($CDCl_3$) d (ppm): 1.16 (t, J=7.0 Hz, 3H), 1.45-1.60 (m, 2H) 1.70-2.05 (m, 6H), 2.50-2.70 (m, 3H), 2.80-3.20 (m, 7H), 3.30-3.45 (m, 3H), 3.45-3.60 (m, 3H), 3.87-3.92 (m, 1H), 4.20 (s, 2H), 4.35-4.38 (m, 2H), 4.55 (t, J=5.3 Hz, 1H), 4.69 (d, J=5.5 Hz, 2H), 4.89 (t, J=5.5 Hz, 1H), 7.18 (dd, J=8.3, 2.4 Hz, 1H), 7.28 (d, J=8.3 Hz, 1H), 7.38 (d, J=2.4 Hz, 1H)

Compound 20-7

$^1$H NMR ($CDCl_3$) d (ppm): 0.75-0.85 (m, 2H), 0.95-1.05 (m, 2H), 1.45-1.70(m, 5H) 1.70-1.85(m, 4H), 2.35-2.45(m, 2H), 2.45-2.65 (m, 5H), 2.65-2.75 (m, 2H), 2.85-2.95 (m, 1H), 3.20-3.40 (m, 1H), 3.45-3.60 (m, 1H), 3.80-3.94 (m, 3H), 3.95 (s, 4H), 4.35 (s, 2H), 4.35-4.60 (m, 2H), 4.70 (d, J=4.0 Hz, 2H), 4.75-4.85 (m, 1H), 7.16 (dd, J=8.5 Hz, 1.8 Hz, 1H), 7.27 (d, J=8.0 Hz, 1H), 7.38 (d, J=1.8 Hz, 1H)

Compound 20-8

$^1$H NMR ($CDCl_3$) d (ppm): 1.17 (t, J=7.2 Hz, 3H), 1.45-1.60 (m, 2H) 1.80-2.20 (m, 6H), 2.50-2.65 (m, 1H), 2.65-2.75 (m, 2H), 2.80-3.00 (m, 7H), 3.25-3.35 (m, 2H), 3.30-3.40 (m, 1H), 3.40-3.55 (m, 1H), 3.50-3.60 (m, 2H), 3.80-3.92 (m, 1H), 3.97 (s, 4H), 4.25 (s, 2H), 4.30-4.45 (m, 2H), 4.70 (d, J=4.0 Hz, 2H), 4.75-4.85 (m, 1H), 7.17 (dd, J=8.4 Hz, 2.0 Hz, 1H), 7.29 (d, J=8.4 Hz, 1H), 7.37 (d, J=2.0 Hz, 1H)

Compound 20-10

$^1$H NMR ($CDCl_3$) d (ppm): 0.78-0.85 (m, 2H), 0.98-1.05 (m, 2H), 1.65-1.80 (m, 3H) 1.80-1.90 (m, 2H), 2.40-2.52 (m, 6H), 2.52-2.70 (m, 1H), 2.70-2.80 (m, 6H), 2.85-3.00 (m, 1H), 3.30-3.45 (m, 1H), 3.50-3.60 (m, 1H), 3.80-3.95 (m, 3H) 4.36 (s, 2H), 4.40-4.50 (m, 2H), 4.65-4.75 (m, 2H), 4.80-4.90 (m, 1H), 7.15-7.20 (m, 1H), 7.26 (d, J=9.0 Hz, 1H), 7.38 (d, J=1.6 Hz, 1H)

Compound 20-11

$^1$H NMR ($CDCl_3$) d (ppm): 1.16 (t, J=7.2 Hz, 3H), 1.50-1.65 (m, 2H) 1.65-1.80 (m, 2H), 2.40-2.52 (m, 6H), 2.52-2.65 (m, 1H), 2.65-2.80 (m, 6H), 2.85-2.98 (m, 1H), 3.25-3.35 (m, 2H), 3.35-3.45 (m, 1H), 3.50-3.60 (m, 3H), 3.88-3.95 (m, 1H), 4.22 (s, 2H), 4.33-4.47 (m, 2H), 4.50-4.56 (m, 1H), 4.70 (d, J=5.0 Hz, 2H), 4.83-4.92 (m, 1H), 7.17 (dd, J=8.2, 2.0 Hz, 1H), 7.28 (d, J=8.2 Hz, 1H), 7.38 (d, J=2.0 Hz, 1H)

Compound 20-12

$^1$H NMR ($CDCl_3$) d (ppm): 0.79-0.85 (m, 2H), 0.97-1.05 (m, 2H), 1.70-1.85 (m, 3H) 1.85-2.10(m, 4H), 2.55-2.80 (m, 4H), 2.80-3.20 (m, 6H), 3.40-3.55 (m, 2H), 3.80-3.95 (m, 3H), 3.98 (s, 4H), 4.35 (s, 2H), 4.35-4.50 (m, 2H), 4.69 (d, J=5.3 Hz, 2H), 4.85-4.95 (m, 1H), 7.16-7.22 (m, 1H), 7.27-7.30 (m, 1H), 7.39 (d, J=1.8 Hz, 1H)

Compound 20-13

$^1$H NMR ($CDCl_3$) d (ppm): 1.17 (t, J=7.2 Hz, 3H), 1.80-2.20 (m, 6H), 2.55-2.62 (m, 3H), 2.80-2.95 (m, 1H), 2.95-3.22 (m, 6H), 3.25-3.35 (m, 2H), 3.40-3.52 (m, 2H), 3.55-3.63 (m, 2H), 3.82-3.90 (m, 1H), 3.98 (s, 4H), 4.23 (s, 2H), 4.30-4.50 (m, 2H), 4.69 (d, J=5.1 Hz, 2H), 4.80-4.90 (m, 1H), 7.18 (dd, J=8.4, 2.0 Hz, 1H), 7.28 (d, J=8.4 Hz, 1H), 7.39 (d, J=2.0 Hz, 1H)

Compound 20-14

$^1$H NMR ($CDCl_3$) d (ppm): 0.78-0.85 (m, 2H), 0.98-1.07 (m, 2H), 1.65-1.90 (m, 3H), 2.40-2.52 (m, 4H), 2.52-2.80 (m, 9H), 2.85-3.00 (m, 1H), 3.40-3.60 (m, 2H), 3.80-3.95 (m, 3H), 4.36 (s, 2H), 4.40-4.50 (m, 2H), 4.65-4.75 (m, 2H), 4.80-4.90 (m, 1H), 7.15-7.20 (m, 1H), 7.25-7.30 (m, 1H), 7.38-7.40 (m, 1H)

Compound 20-15

$^1$H NMR ($CDCl_3$) d (ppm): 1.16 (t, J=7.1 Hz, 3H), 1.50-1.65 (m, 2H), 2.40-2.52 (m, 4H), 2.52-2.70 (m, 5H), 2.70-2.80 (m, 4H), 2.85-2.98 (m, 1H), 3.25-3.35 (m, 2H), 3.40-3.60 (m, 4H), 3.85-3.95 (m, 1H) 4.22 (s, 2H), 4.33-4.47 (m, 2H), 4.48-4.56 (m, 1H), 4.69 (d, J=5.6 Hz, 2H), 4.83-4.92 (m, 1H), 7.17 (dd, J=8.5, 2.0 Hz, 1H), 7.28 (d, J=8.5 Hz, 1H), 7.38 (d, J=2.0 Hz, 1H)

Compound 20-16

$^1$H NMR ($CDCl_3$) d (ppm): 1.49 (s, 9H), 1.60-1.75 (m, 2H), 1.80-2.00 (m, 4H), 2.40-2.80 (m, 9H), 2.85-2.98 (m, 1H), 3.35-3.60 (m, 2H), 3.60-3.67 (m, 2H), 3.88-3.95 (m, 1H), 4.19 (s, 2H), 4.33-4.47 (m, 2H), 4.50-4.80 (m, 4H), 7.18 (dd, J=8.2, 2.0 Hz, 1H), 7.28 (d, J=8.2 Hz, 1H), 7.38 (d, J=2.0 Hz, 1H)

Compound 20-17

$^1$H NMR ($CDCl_3$) d (ppm): 0.78-0.85 (m, 2H), 0.98-1.07 (m, 2H), 1.65-2.10 (m, 7H), 2.40-2.80 (m, 9H), 2.85-3.00 (m, 1H), 3.35-3.60 (m, 2H), 3.80-3.95 (m, 3H), 4.36 (s, 2H), 4.40-4.50 (m, 2H), 4.55-4.90 (m, 4H), 7.15-7.20 (m, 1H), 7.25-7.30 (m, 1H), 7.38-7.40 (m, 1H)

Compound 20-18

$^1$H NMR ($CDCl_3$) d (ppm): 1.17 (t, J=7.2 Hz, 3H), 1.60-1.80 (m, 2H), 1.80-2.10 (m, 4H), 2.40-2.75 (m, 9H), 2.85-3.00 (m, 1H), 3.35-3.45 (m, 2H), 3.45-3.60 (m, 4H), 3.86-3.95 (m, 1H), 4.20 (s, 2H), 4.33-4.48 (m, 2H), 4.48-4.55 (m, 1H), 4.55-4.85 (m, 2H), 4.69 (d, J=5.6 Hz, 2H), 7.16 (dd, J=8.4, 2.0 Hz, 1H), 7.28 (d, J=8.4 Hz, 1H), 7.39 (d, J=2.0 Hz, 1H)

Compound 20-19

$^1$H NMR ($CDCl_3$) d (ppm) 1.49 (s, 9H), 1.63-1.73 (m, 2H), 1.92-2.06 (m, 4H), 2.41-2.65 (m, 9H), 2.87-2.98 (m, 1H), 3.41-3.59 (m, 2H), 3.62-3.66 (m, 2H), 3.84-3.94 (m, 1H), 4.19 (s, 2H), 4.35-4.46 (m, 2H), 4.65-4.75 (br s, 1H), 4.70 (s, 2H), 7.18 (dd, J=8.2 Hz, 2.0 Hz, 1H), 7.28 (d, J=8.2 Hz, 1H), 7.39 (d, J=2.0 Hz, 1H)

Compound 20-20

$^1$H NMR ($CDCl_3$) d (ppm): 0.77-0.85 (m, 2H), 0.98-1.06 (m, 2H), 1.60-1.750 (m, 2H), 1.75-1.88 (m, 1H), 1.93-2.08 (m, 4H), 2.45-2.75 (m, 9H), 2.85-3.00 (m, 1H), 3.38-3.45 (m, 1H), 3.48-3.58 (m, 1H), 3.80-3.95 (m, 3H), 4.35-4.48 (m, 4H), 4.65-4.77 (m, 2H), 4.85-5.00 (br s, 1H), 7.14 (dd, J=8.4 Hz, 1.6 Hz, 1H), 7.26 (d, J=8.4 Hz, 1H), 7.38 (d, J=1.6 Hz, 1H)

Compound 20-21

$^1$H NMR ($CDCl_3$) d (ppm): 1.17 (t, J=7.2 Hz, 3H), 1.58-1.77 (m, 2H), 1.92-2.10 (m, 4H), 2.44-2.70 (m, 9H), 2.87-2.98 (m, 1H), 3.27-3.36 (m, 2H), 3.38-3.60 (m, 4H), 3.88-3.93 (m, 1H), 4.21 (s, 2H), 4.35-4.45 (m, 2H), 4.45-4.55 (m, 1H), 4.70 (d, J=4.4 Hz, 2H), 4.78-4.83 (m, 1H), 7.17 (dd, J=8.2 Hz, 2.0 Hz, 1H), 7.28 (d, J=8.2 Hz, 1H), 7.38 (d, J=2.0 Hz, 1H)

Compound 21-1

$^1$H NMR ($CDCl_3$) d (ppm): 0.77-0.83 (m, 2H), 0.90-1.10 (m, 2H), 1.15-1.29 (m, 1H), 1.39-2.05 (m, 10H), 2.28 (s, 3H), 2.61-2.74 (m, 3H), 2.86-2.90 (m, 1H), 3.16 (br t, J=10.4 Hz, 2H), 3.49-3.66 (m, 2H), 3.88(br t, J=5.3 Hz, 2H), 4.25-4.34 (m, 4H), 4.67-4.69 (m, 2H), 4.83-4.93 (m, 1H), 7.15 (br d, J=7.6 Hz, 1H), 7.29 (br d, J=7.6 Hz, 1H), 7.36 (br s, 1H)

Compound 21-2

$^1$H NMR ($CDCl_3$) d (ppm): 0.77-0.84 (m, 2H), 0.98-1.07 (m, 2H), 1.41-1.89 (m, 9H), 2.11 (br t, J=9.9 Hz, 2H), 2.26 (s, 3H), 2.58-2.81 (m, 4H), 3.17 (br t, J=10.4 Hz, 2H), 3.40-3.50 (m, 1H), 3.54-3.65 (m, 1H), 3.89 (br t, J=5.0 Hz, 2H), 4.24-4.34 (m, 4H), 4.68-4.70 (m, 2H), 4.77-4.87 (m, 1H), 7.16 (br d, J=7.9, 1H), 7.30 (br d, J=7.9, 1H), 7.37-7.39 (m, 1H)

Compound 21-3

$^1$H NMR ($CDCl_3$) d (ppm) 1.16 (t, J=7.2 Hz, 3H), 1.17-1.29 (m, 1H), 1.41-1.98 (m, 9H), 2.28 (s, 3H), 2.61-2.68 (m, 3H, The peak at 2.66 (t, J=5.8 Hz, 2H) is involved in this peak), 2.86-2.91 (m, 1H), 3.10-3.20 (m, 2H), 3.25-3.35 (m, 2H), 3.49-3.66 (m, 4H, The peak at 3.54 (t, J=5.8 Hz, 2H) is involved in this peak), 4.18 (s, 2H), 4.25 (br t, J=4.4 Hz, 1H), 4.30 (br t, J=4.5 Hz, 1H), 4.51-4.55 (m, 1H), 4.69 (d, J=5.8 Hz, 2H), 4.79-4.83 (m, 1H), 7.16 (dd, J=8.3, 2.0 Hz, 1H), 7.31 (d, J=8.3 Hz, 1H), 7.37 (d, J=2.0, 1H)

Compound 21-4

$^1H$ NMR ($CDCl_3$) d (ppm): 1.16 (t, J=7.3 Hz, 3H), 1.39-1.52 (m, 2H), 1.65-1.82 (m, 4H), 1.95-2.02 (m, 2H), 2.34-2.47 (m, 5H, The peak at 2.39 (s, 3H) is involved in this peak), 2.66 (t, J=5.7 Hz, 2H), 2.78-2.87 (m, 2H), 3.13-3.22 (m, 2H), 3.25-3.35 (m, 2H), 3.48-3.63 (m, 4H, The peak at 3.56 (t, J=5.7 Hz, 2H) is involved in this peak), 4.20 (s, 2H), 4.23-4.29 (m, 2H), 4.64-4.70 (m, 3H, The peak at 4.69 (d, J=5.6 Hz, 2H) is involved in this peak), 4.90-5.02 (m, 1H), 7.16 (dd, J=8.3, 2.1 Hz, 1H), 7.30 (d, J=8.3 Hz, 1H), 7.37 (d, J=2.1, 1H)

Compound 22-1

$^1H$ NMR ($CDCl_3$) d (ppm): 1.15 (t, J=7.3 Hz, 3H), 1.73-1.91 (m, 1H), 2.00-2.85 (m, 14H), 3.18-3.40 (m, 2H), 3.45-4.00 (m, 9H), 4.12 (s, 2H), 4.41-4.57 (m, 1H), 4.61-4.80 (m, 3H), 6.72 (d, J=3.5 Hz, 1H), 6.74 (d, J=3.5 Hz, 1H)

Compound 22-2

$^1H$ NMR ($CDCl_3$) d (ppm): 1.16 (t, J=7.3 Hz, 3H), 1.70-1.90 (m, 1H), 2.00-2.85 (m, 14H), 3.20-3.40 (m, 2H), 3.45-4.00 (m, 9H), 4.24 (s, 2H), 4.43-4.59 (m, 1H), 4.77 (d, J=4.3 Hz, 2H), 4.82-5.00 (m, 1H), 7.43-7.49 (m, 2H), 7.65 (s, 1H)

Compound 22-3

$^1H$ NMR ($CDCl_3$) d (ppm): 1.16 (t, J=7.3 Hz, 3H), 1.70-1.89 (m, 1H), 2.00-2.82 (m, 14H), 3.06 (s, 3H), 3.21-3.41 (m, 2H), 3.46-3.99 (m, 9H), 4.24 (s, 2H), 4.48-4.62 (m, 1H), 4.80 (d, J=5.1 Hz, 2H), 4.90-5.02 (m, 1H), 7.55 (d, J=5.1 Hz, 1H), 7.72 (dd, J=1.9, 5.1 Hz, 1H), 7.92 (d, J=1.9 Hz, 1H)

Compound 22-4

$^1H$ NMR ($CDCl_3$) d (ppm): 1.16 (t, J=7.3 Hz, 3H), 1.72-1.90 (m, 1H), 2.00-2.85 (m, 14H), 3.20-3.40 (m, 2H), 3.45-4.00 (m, 12H), 4.13 (s, 2H), 4.38-4.80 (m, 4H), 6.74 (dd, J=2.7, 8.4 Hz, 1H), 6.92 d, J=2.7 Hz, 1H), 7.31 (d, J=8.4 Hz, 1H)

Compound 23-1

$^1H$ NMR ($CDCl_3$) d (ppm): 2.39 (s, 6H), 2.74-2.81 (m, 4H), 3.30 (s, 2H), 3.50 (s, 2H), 3.72 (s, 2H), 4.73 (br d, J=5.7 Hz, 2H), 4.84 (br t, J=5.7 Hz, 1H), 6.92 (td, J=8.4, 2.6 Hz, 1H), 7.10 (td, J=8.4, 2.5 Hz, 1H), 7.24-7.35 (m, 5H), 7.46 (dd, J=8.4, 6.1 Hz, 1H)

Compound 23-2

$^1H$-NMR ($CDCl_3$) d (ppm): 0.80-0.87 (m, 2H), 1.03 (br s, 2H), 1.77-1.86 (m, 5H), 2.52-2.54 (m, 4H), 2.98 (br s, 2H), 3.68 (s, 2H), 3.96-3.98 (m, 2H), 4.47 (br s, 2H), 4.89 (d, J=5.7 Hz, 2H), 5.12 (br s, 1H), 6.88-6.94 (m, 1H), 7.14 (dd, J=2.4, 8.4 Hz, 1H), 7.41 (d, J=8.4 Hz, 2H), 7.45-7.50 (m, 1H), 8.29 (d, J=8.4 Hz, 2H)

Compound 23-3

$^1H$-NMR ($CDCl_3$) d (ppm): 0.80-0.87 (m, 2H), 1.03 (br s, 2H), 1.43-1.62 (m, 6H), 1.86 (br s, 1H), 2.40 (br s, 4H), 2.98 (br s, 2H), 3.53 (s, 2H), 3.96-4.00 (m, 2H), 4.47 (br s, 2H), 4.89 (d, J=5.7 Hz, 2H), 5.15 (br s, 1H), 6.88-6.94 (m, 1H), 7.14 (dd, J=2.4, 8.4 Hz, 1H), 7.39 (d, J=7.8 Hz, 2H), 7.45-7.50 (m, 1H), 8.28 (d, J=7.8 Hz, 2H)

Compound 23-4

$^1H$-NMR ($CDCl_3$) d (ppm): 0.81-0.87 (m, 2H), 1.03 (br s, 2H), 1.57-1.65 (m, 2H), 1.86 (br s, 4H), 2.14-2.17 (m, 2H), 2.75-2.79 (m, 2H), 2.98 (br s, 2H), 3.56 (s, 2H), 3.68-3.73 (m, 1H), 3.96-3.98 (m, 2H), 4.47 (br s, 2H), 4.89 (d, J=5.7 Hz, 2H), 4.90 (br s, 1H), 6.88-6.94 (m, 1H), 7.14 (dd, J=2.4, 8.1 Hz, 1H), 7.39 (d, J=7.8 Hz, 2H), 7.44-7.49 (m, 1H), 8.28 (d, J=7.8 Hz, 2H)

Compound 23-5

$^1H$-NMR ($CDCl_3$) d (ppm): 0.81-0.88 (m, 2H), 1.04 (br s, 2H), 1.72-1.86 (m, 5H), 1.98-2.05 (m, 2H), 2.23 (s, 3H), 2.31 (s, 3H), 2.43-2.51 (m, 1H), 2.86-2.99 (m, 4H), 3.64 (s, 2H), 3.98 (br s, 2H), 4.47 (br s, 2H), 4.90 (d, J=5.1 Hz, 2H), 5.06 (br s, 1H), 6.87-6.96 (m, 1H), 7.15 (dd, J=2.4, 8.4 Hz, 1H), 7.39 (d, J=8.1 Hz, 1H), 7.46-7.51 (m, 1H), 8.29 (d, J=8.4 Hz, 1H)

PREPARATION EXAMPLE 1

Tablet

Tablets having the following composition are prepared according to a conventional procedure.

| | | |
|---|---|---|
| Formulation | Compound 4-6 | 20 mg |
| | Lactose | 143.4 mg |
| | Potato starch | 30 mg |
| | Hydroxypropylcellulose | 6 mg |
| | Magnesium stearate | 0.6 mg |
| | | 200 mg |

PREPARATION EXAMPLE 2

Injection

An injection having the following composition is prepared according to a conventional procedure.

| | | |
|---|---|---|
| Formulation | Compound 5-407 | 2 mg |
| | Purified soybean oil | 200 mg |
| | Purified egg yolk lecithin | 24 mg |
| | Injectable glycerin | 50 mg |
| | Injectable distilled water | 1.72 mL |
| | | 2.00 mL |

INDUSTRIAL APPLICABILITY

The present invention provides bicyclic pyrimidine derivatives, or quaternary ammonium salts thereof, or pharmaceutically acceptable salts thereof, which have anti-inflammatory activities such as cellular infiltration inhibitory activities, modulating activities on the functions of TARC and/or MDC, such as inhibitory activities against binding of TARC and/or MDC to T cells, and are useful for treating and/or preventing, for example, a disease which is related to T cells, such as an allergic disease, an autoimmune disease or transplant rejection (graft rejection), as well as prevention of cancer metastasis. Examples of such diseases are asthma, allergic rhinitis, chronic rhinitis, eosinophilic sinusitis, rhinitis with eosinophilia, pollinosis, conjunctivitis, atopic dermatitis, contact dermatitis, urticaria, psoriasis, cutaneous candidiasis, mycotic stomatitis (oral candidiasis), rheumatoid arthritis, various connective tissue diseases, systemic lupus erythematosus, Sjögren syndrome, cellular rejection in organ transplantation, cancer or carcinoma, malignant lymphoma, leukemia, adult T cell leukemia (ATL), cutaneous T cell lymphoma, interstitial cystitis, endometriosis, insulin-dependent diabetes mellitus (IDDM), Churg-Strauss syndrome, mycosis fungoides, pain, neuralgia and cutaneous itching.

The invention claimed is:

1. A bicyclic pyrimidine represented by following Formula (I):

(I)

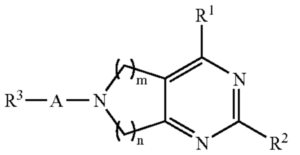

{wherein m represents 1, n represents 2, $R^1$ represents

—$NR^4R^5$ (wherein $R^4$ and $R^5$ independently represent a hydrogen atom, substituted or unsubstituted lower alkyl, substituted or unsubstituted cycloalkyl, substituted or unsubstituted lower alkenyl, substituted or unsubstituted lower alkynyl, substituted or unsubstituted aralkyl, substituted or unsubstituted arylcarbonyl, a substituted or unsubstituted heteroaromatic group, a substituted or unsubstituted heteroalicyclic group, substituted or unsubstituted heteroaromatic-substituted alkyl or substituted or unsubstituted heteroalicyclic-substituted alkyl, or $R^4$ and $R^5$ are combined together with the adjacent nitrogen atom to form a substituted or unsubstituted heteroalicyclic group, provided that $R^4$ and $R^5$ are not simultaneously hydrogen atoms, and that when one of $R^4$ and $R^5$ is a hydrogen atom, the other of $R^4$ and $R^5$ is neither a substituted or unsubstituted pyrazol-3-yl nor a substituted or unsubstituted 1,2,4-triazol-3-yl);

$R^2$ represents Formula (II):

(II)

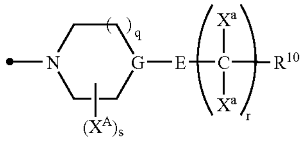

[wherein r represents an integer of 0 to 4;

s represents a number ranging from 0 to a substitutable number;

G represents a nitrogen atom, CH, C(OH), $C(CO_2H)$ or C(CN);

q represents an integer of 1 or 2 when G is a nitrogen atom, and q represents an integer of 0 to 2 when G is CH, C(OH), $C(CO_2H)$ or C(CN);

E represents a single bond, —C(═O)—, —O—, —CH(OH)—, —$CH_2$CH(OH)—, —C(═O)O—, —C(═O)$NR^6$— (wherein $R^6$ represents a hydrogen atom, substituted or unsubstituted lower alkyl or substituted or unsubstituted cycloalkyl) or

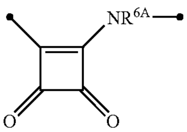

(wherein $R^{6A}$ has the same meaning as $R^6$ defined above), and E is bonded to G at the left side in each group;

$X^A$ represents substituted or unsubstituted lower alkyl or halogen, or two $X^A$s on the same carbon atom are combined together to form oxo, wherein respective $X^A$s may be the same or different when s is 2 or more;

$X^a$ has the same meaning as X defined above, where respective $X^a$s may be the same or different when r is 1 or more; and $R^{10}$ represents —$NR^{8A}R^{9A}$ (wherein $R^{8A}$ and $R^{9A}$ independently represent a hydrogen atom, substituted or unsubstituted lower alkyl, substituted or unsubstituted cycloalkyl, substituted or unsubstituted lower alkenyl, substituted or unsubstituted lower alkynyl, substituted or unsubstituted aralkyl, substituted or unsubstituted aryl, a substituted or unsubstituted heteroaromatic group, a substituted or unsubstituted heteroalicyclic group, substituted or unsubstituted heteroaromatic-substituted alkyl, substituted or unsubstituted heteroalicyclic-substituted alkyl, imino-(lower alkyl) or substituted or unsubstituted amidino), a hydrogen atom, substituted or unsubstituted lower alkyl, substituted or unsubstituted lower alkoxy, substituted or unsubstituted cycloalkyl, substituted or unsubstituted lower alkenyl, substituted or unsubstituted lower alkynyl, substituted or unsubstituted aryl, substituted or unsubstituted aralkyl, a substituted or unsubstituted heteroaromatic group, a substituted or unsubstituted heteroalicyclic group, substituted or unsubstituted heteroaromatic-substituted alkyl or substituted or unsubstituted heteroalicyclic-substituted alkyl];

A represents —C(═O)—, —$SO_2$—, —$NR^{6D}$C(═O)— (wherein $R^{6D}$ represents a hydrogen atom, substituted or unsubstituted lower alkyl or substituted or unsubstituted cycloalkyl, or is combined together with $R^3$ and the adjacent nitrogen atom to form a substituted or unsubstituted heterocyclic group), —$NR^{6D}$C(═S)—, —OC(═O)—, —OC(═S)—, —SC(═O)—, —SC(═S)—,

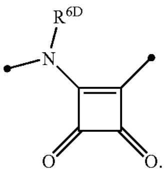

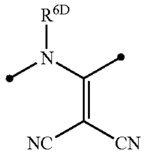

or

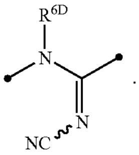

and A is bonded to $R^3$ at the left side in the each group; and with the provisio that (a) when A is a single bond,

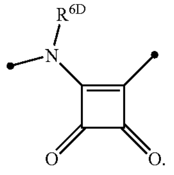

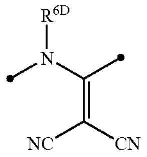

or

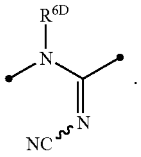

then $R^3$ represents a hydrogen atom, substituted or unsubstituted lower alkyl, substituted or unsubstituted cycloalkyl, substituted or unsubstituted lower alkenyl, substituted or unsubstituted lower alkynyl, substituted or unsubstituted aralkyl, substituted or unsubstituted aryl, a substituted or unsubstituted heteroaromatic group, a substituted or unsubstituted heteroalicyclic group, substituted or unsubstituted heteroaromatic-substituted alkyl or substituted or unsubstituted heteroalicyclic-substituted alkyl, and (b) when A is —C(═O)—, —$SO_2$—, —$NR^{6D}$C(═O)—, —$NR^{6D}$C(═S)—, —OC(═O)—, —OC(═S)—, —SC(═O)— or —SC(═S)—, then $R^3$ represents substituted or unsubstituted lower alkyl substituted or unsubstituted cycloalkyl, substituted or unsubstituted lower alkenyl, substituted or unsubstituted lower alkynyl, substituted or unsubstituted aralkyl, substituted or unsubstituted aryl, a substituted or unsubstituted heteroaromatic group, a substituted or unsubstituted heteroalicyclic group, substituted or unsubstituted heteroaromatic-substituted alkyl, substituted or unsubstituted heteroalicyclic-substituted alkyl or —$NR^{8B}R^{9B}$ (wherein $R^{8B}$ and $R^{9B}$ have the same meanings as $R^8$ and $R^9$ defined above, respectively)}, or a quaternary ammonium salt thereof, or a pharmaceutically acceptable salt thereof.

2. The bicyclic pyrimidine, or the quaternary ammonium salt thereof, or the pharmaceutically acceptable salt thereof according to claim 1, wherein $R^4$ is a hydrogen atom; and $R^5$ is substituted or unsubstituted aralkyl.

3. The bicyclic pyrimidine, or the quaternary ammonium salt thereof, or the pharmaceutically acceptable salt thereof according to claim 1, wherein $R^4$ is a hydrogen atom; and $R^5$ is substituted or unsubstituted cycloalkyl.

4. The bicyclic pyrimidine, or the quaternary ammonium salt thereof, or the pharmaceutically acceptable salt thereof according to any of claims 1, 2, or 3, wherein s is 0.

5. The bicyclic pyrimidine, or the quaternary ammonium salt thereof, or the pharmaceutically acceptable salt thereof according to claim 4, wherein q is 1 or 2.

6. The bicyclic pyrimidine, or the quaternary ammonium salt thereof, or the pharmaceutically acceptable salt thereof according to claim 5, wherein $X^a$ is a hydrogen atom.

7. The bicyclic pyrimidine, or the quaternary ammonium salt thereof, or the pharmaceutically acceptable salt thereof according to claim 6, wherein $R^{10}$ is —$NR^{8A}R^{9A}$, a substituted or unsubstituted heteroaromatic group or a substituted or unsubstituted heteroalicyclic group.

8. The bicyclic pyrimidine, or the quaternary ammonium salt thereof, or the pharmaceutically acceptable salt thereof according to claim 7, wherein $R^3$ is substituted or unsubstituted lower alkyl, substituted or unsubstituted cycloalkyl, substituted or unsubstituted aralkyl, substituted or unsubstituted aryl or a substituted or unsubstituted heteroaromatic group.

9. A pharmaceutical composition which comprises, as an active ingredient, the bicyclic pyrimidine, or the quaternary ammonium salt thereof, or the pharmaceutically acceptable salt thereof according to claim 4 and a pharmaceutically acceptable excipient.

10. The bicyclic pyrimidine, or the quaternary ammonium salt thereof, or the pharmaceutically acceptable salt thereof according to any of claims 1, 2, or 3, wherein A is —C(═O)—, and $R^3$ is substituted or unsubstituted lower alkyl, substituted or unsubstituted cyloalkyl, substituted or unsubstituted lower alkenyl, substituted or unsubstituted aralkyl or substituted or unsubstituted aryl.

11. The bicyclic pyrimidine, or the quaternary ammonium salt thereof, or the pharmaceutically acceptable salt thereof according to claim 4, wherein A is —C(═O)—, and $R^3$ is substituted or unsubstituted lower alkyl, substituted or unsubstituted cyloalkyl, substituted or unsubstituted lower alkenyl, substituted or unsubstituted aralkyl or substituted or unsubstituted aryl.

12. The bicyclic pyrimidine, or the quaternary ammonium salt thereof, or the pharmaceutically acceptable salt thereof according to claim 5, wherein A is —C(═O)—, and $R^3$ is substituted or unsubstituted lower alkyl, substituted or unsubstituted cyloalkyl, substituted or unsubstituted lower alkenyl, substituted or unsubstituted aralkyl or substituted or unsubstituted aryl.

13. The bicyclic pyrimidine, or the quaternary ammonium salt thereof, or the pharmaceutically acceptable salt thereof according to claim 7, wherein A is —C(═O)—, and $R^3$ is substituted or unsubstituted lower alkyl, substituted or unsubstituted cyloalkyl, substituted or unsubstituted lower alkenyl, substituted or unsubstituted aralkyl or substituted or unsubstituted aryl.

14. The bicyclic pyrimidine, or the quaternary ammonium salt thereof, or the pharmaceutically acceptable salt thereof according to claim 7, wherein A is —C(═O)—, and $R^3$ is substituted or unsubstituted lower alkyl, substituted or unsubstituted cyloalkyl, substituted or unsubstituted lower alkenyl, substituted or unsubstituted aralkyl or substituted or unsubstituted aryl.

15. The bicyclic pyrimidine, or the quaternary ammonium salt thereof, or the pharmaceutically acceptable salt thereof according to any of claims 1, 2, or 3, wherein A is —C(═O)—, and $R^3$ is —$NR^{8B}R^{9B}$ (wherein $R^{8B}$ and $R^{9B}$ have the same meaning as $R^8$ and $R^9$, respectively.

16. The bicyclic pyrimidine, or the quaternary ammonium salt thereof, or the pharmaceutically acceptable salt thereof according to claim 4, wherein A is —C(═O)—, and $R^3$ is —$NR^{8B}R^{9B}$ (wherein $R^{8B}$ and $R^{9B}$ have the same meaning as $R^8$ and $R^9$, respectively.

17. The bicyclic pyrimidine, or the quaternary ammonium salt thereof, or the pharmaceutically acceptable salt thereof according to claim 5, wherein A is —C(═O)—, and $R^3$ is —$NR^{8B}R^{9B}$ (wherein $R^{8B}$ and $R^{9B}$ have the same meaning as $R^8$ and $R^9$, respectively.

18. The bicyclic pyrimidine, or the quaternary ammonium salt thereof, or the pharmaceutically acceptable salt thereof according to claim 6, wherein A is —C(═O)—, and $R^3$ is —$NR^{8B}R^{9B}$ (wherein $R^{8B}$ and $R^{9B}$ have the same meaning as $R^8$ and $R^9$, respectively.

19. The bicyclic pyrimidine, or the quaternary ammonium salt thereof, or the pharmaceutically acceptable salt thereof according to claim 7, wherein A is —C(=O)—, and $R^3$ is —$NR^{8B}R^{9B}$ (wherein $R^{8B}$ and $R^{9B}$ have the same meaning as $R^8$ and $R^9$, respectively.

20. The bicyclic pyrimidine, or the quaternary ammonium salt thereof, or the pharmaceutically acceptable salt thereof according to any of claims 1, 2, or 3, wherein A is —$SO_2$, and $R^3$ is substituted or unsubstituted lower alkyl, substituted or unsubstituted lower alkenyl or substituted or unsubstituted aryl.

21. The bicyclic pyrimidine, or the quaternary ammonium salt thereof, or the pharmaceutically acceptable salt thereof according to claim 4, wherein A is —$SO_2$, and $R^3$ is substituted or unsubstituted lower alkyl, substituted or unsubstituted lower alkenyl or substituted or unsubstituted aryl.

22. The bicyclic pyrimidine, or the quaternary ammonium salt thereof, or the pharmaceutically acceptable salt thereof according to claim 5, wherein A is —$SO_2$, and $R^3$ is substituted or unsubstituted lower alkyl, substituted or unsubstituted lower alkenyl or substituted or unsubstituted aryl.

23. The bicyclic pyrimidine, or the quaternary ammonium salt thereof, or the pharmaceutically acceptable salt thereof according to claim 6, wherein A is —$SO_2$, and $R^3$ is substituted or unsubstituted lower alkyl, substituted or unsubstituted lower alkenyl or substituted or unsubstituted aryl.

24. The bicyclic pyrimidine, or the quaternary ammonium salt thereof, or the pharmaceutically acceptable salt thereof according to claim 7, wherein A is wherein A is —$SO_2$, and $R^3$ is substituted or unsubstituted lower alkyl, substituted or unsubstituted lower alkenyl or substituted or unsubstituted aryl.

25. A pharmaceutical composition which comprises, as an active ingredient, the bicyclic pyrimidine derivative, or the quaternary ammonium salt thereof, or the pharmaceutically acceptable salt thereof according to claim 10 and a pharmaceutical acceptable excipient.

26. A pharmaceutical composition which comprises, as an active ingredient, the bicyclic pyrimidine derivative, or the quaternary ammonium salt thereof, or the pharmaceutically acceptable salt thereof according to claim 11 and a pharmaceutical acceptable excipient.

27. A pharmaceutical composition which comprises, as an active ingredient, the bicyclic pyrimidine derivative, or the quaternary ammonium salt thereof, or the pharmaceutically acceptable salt thereof according to claim 12 and a pharmaceutical acceptable excipient.

28. A pharmaceutical composition which comprises, as an active ingredient, the bicyclic pyrimidine derivative, or the quaternary ammonium salt thereof, or the pharmaceutically acceptable salt thereof according to claim 13 and a pharmaceutical acceptable excipient.

29. A pharmaceutical composition which comprises, as an active ingredient, the bicyclic pyrimidine derivative, or the quaternary ammonium salt thereof, or the pharmaceutically acceptable salt thereof according to claim 14 and a pharmaceutical acceptable excipient.

30. A pharmaceutical composition which comprises, as an active ingredient, the bicyclic pyrimidine derivative, or the quaternary ammonium salt thereof, or the pharmaceutically acceptable salt thereof according to claim 15 and a pharmaceutical acceptable excipient.

31. A pharmaceutical composition which comprises, as an active ingredient, the bicyclic pyrimidine derivative, or the quaternary ammonium salt thereof, or the pharmaceutically acceptable salt thereof according to claim 16 and a pharmaceutical acceptable excipient.

32. A pharmaceutical composition which comprises, as an active ingredient, the bicyclic pyrimidine derivative, or the quaternary ammonium salt thereof, or the pharmaceutically acceptable salt thereof according to claim 17 and a pharmaceutical acceptable excipient.

33. A pharmaceutical composition which comprises, as an active ingredient, the bicyclic pyrimidine derivative, or the quaternary ammonium salt thereof, or the pharmaceutically acceptable salt thereof according to claim 18 and a pharmaceutical acceptable excipient.

34. A pharmaceutical composition which comprises, as an active ingredient, the bicyclic pyrimidine derivative, or the quaternary ammonium salt thereof, or the pharmaceutically acceptable salt thereof according to claim 19 and a pharmaceutical acceptable excipient.

35. A pharmaceutical composition which comprises, as an active ingredient, the bicyclic pyrimidine derivative, or the quaternary ammonium salt thereof, or the pharmaceutically acceptable salt thereof according to claim 20 and a pharmaceutical acceptable excipient.

36. A pharmaceutical composition which comprises, as an active ingredient, the bicyclic pyrimidine derivative, or the quaternary ammonium salt thereof, or the pharmaceutically acceptable salt thereof according to claim 21 and a pharmaceutical acceptable excipient.

37. A pharmaceutical composition which comprises, as an active ingredient, the bicyclic pyrimidine derivative, or the quaternary ammonium salt thereof, or the pharmaceutically acceptable salt thereof according to claim 22 and a pharmaceutical acceptable excipient.

38. A pharmaceutical composition which comprises, as an active ingredient, the bicyclic pyrimidine derivative, or the quaternary ammonium salt thereof, or the pharmaceutically acceptable salt thereof according to claim 23 and a pharmaceutical acceptable excipient.

39. A pharmaceutical composition which comprises, as an active ingredient, the bicyclic pyrimidine derivative, or the quaternary ammonium salt thereof, or the pharmaceutically acceptable salt thereof according to claim 24 and a pharmaceutical acceptable excipient.

* * * * *